(12) United States Patent
June et al.

(10) Patent No.: US 10,357,514 B2
(45) Date of Patent: Jul. 23, 2019

(54) TREATMENT OF CANCER USING ANTI-CD19 CHIMERIC ANTIGEN RECEPTOR

(71) Applicants: The Trustees of the University of Pennsylvania, Philadelphia, PA (US); Novartis AG, Basel (CH)

(72) Inventors: Carl H. June, Merion Station, PA (US); David L. Porter, Springfield, PA (US); Marcela Maus, Bryn Mawr, PA (US); Mariusz Wasik, Ardmore, PA (US); Saar Gill, Philadelphia, PA (US); Joseph Fraietta, Cherry Hill, NJ (US); Marco Ruella, Philadelphia, PA (US); John Byrd, Columbus, OH (US); Jason Dubovsky, Columbus, OH (US); Amy Johnson, Dublin, OH (US); Natarajan Muthusamy, Galloway, OH (US); Saad Kenderian, Philadelphia, PA (US); Joan Mannick, Cambridge, MA (US); David Glass, Cambridge, MA (US); Leon Murphy, Cambridge, MA (US); Jennifer Brogdon, Cambridge, MA (US); William Raj Sellers, Cambridge, MA (US)

(73) Assignees: The Trustees of the University of Pennsylvania, Philadelphia, PA (US); Novartis AG, Basel (CH)

( * ) Notice: Subject to any disclaimer, the term of this patent is extended or adjusted under 35 U.S.C. 154(b) by 0 days.

(21) Appl. No.: 14/680,860

(22) Filed: Apr. 7, 2015

(65) Prior Publication Data
US 2015/0283178 A1 Oct. 8, 2015

Related U.S. Application Data

(60) Provisional application No. 62/097,278, filed on Dec. 29, 2014, provisional application No. 62/087,888, filed on Dec. 5, 2014, provisional application No. 62/076,238, filed on Nov. 6, 2014, provisional application No. 62/036,493, filed on Aug. 12, 2014, provisional application No. 62/007,309, filed on Jun. 3, 2014, provisional application No. 61/976,396, filed on Apr. 7, 2014.

(51) Int. Cl.
| | |
|---|---|
| A61K 35/17 | (2015.01) |
| A61K 39/395 | (2006.01) |
| A61K 31/519 | (2006.01) |
| A61K 45/06 | (2006.01) |
| C07K 14/725 | (2006.01) |
| A61K 31/436 | (2006.01) |
| A61K 31/53 | (2006.01) |
| C12N 5/0783 | (2010.01) |
| C07K 16/28 | (2006.01) |
| A61K 39/00 | (2006.01) |

(52) U.S. Cl.
CPC ............ *A61K 35/17* (2013.01); *A61K 31/436* (2013.01); *A61K 31/519* (2013.01); *A61K 31/53* (2013.01); *A61K 39/3955* (2013.01); *A61K 39/39558* (2013.01); *A61K 45/06* (2013.01); *C07K 14/7051* (2013.01); *C07K 16/2803* (2013.01); *C12N 5/0636* (2013.01); *A61K 2039/505* (2013.01); *A61K 2039/5156* (2013.01); *A61K 2039/5158* (2013.01); *C07K 2317/14* (2013.01); *C07K 2317/24* (2013.01); *C07K 2317/565* (2013.01); *C07K 2317/622* (2013.01); *C07K 2317/73* (2013.01); *C07K 2319/03* (2013.01); *C12N 2501/599* (2013.01); *C12N 2501/727* (2013.01); *C12N 2510/00* (2013.01)

(58) Field of Classification Search
CPC .............. A61K 35/17; A61K 39/39558; A61K 2039/505; C07K 2317/565; C07K 2319/03
USPC ............................................ 424/133.1, 178.1
See application file for complete search history.

(56) References Cited

U.S. PATENT DOCUMENTS

| | | | |
|---|---|---|---|
| 5,359,046 A | 10/1994 | Capon et al. | |
| 5,686,281 A | 11/1997 | Roberts | |
| 5,712,149 A | 1/1998 | Roberts | |
| 5,786,464 A | 7/1998 | Seed | |
| 5,874,240 A | 2/1999 | Ni et al. | |
| 5,906,936 A | 5/1999 | Eshhar et al. | |
| 6,103,521 A | 8/2000 | Capon et al. | |
| 6,111,090 A | 8/2000 | Gorman et al. | |
| 6,114,148 A | 9/2000 | Seed et al. | |
| 6,319,494 B1 | 11/2001 | Capon et al. | |
| 6,355,779 B1 | 3/2002 | Goodwin et al. | |

(Continued)

FOREIGN PATENT DOCUMENTS

| | | |
|---|---|---|
| EP | 215576 A1 | 3/1987 |
| EP | 0574512 A1 | 12/1993 |

(Continued)

OTHER PUBLICATIONS

Voskoglou-Nomikos (Clin. Can. Res. 9:4227-4239 (2003)).*

(Continued)

*Primary Examiner* — Lynn A Bristol
(74) *Attorney, Agent, or Firm* — Lando & Anastasi, LLP

(57) ABSTRACT

The invention provides compositions and methods for treating diseases associated with expression of CD19, e.g., by administering a recombinant T cell comprising the CD19 CAR as described herein, in combination with a kinase inhibitor, e.g., a kinase inhibitor described herein. The invention also provides kits and compositions described herein.

45 Claims, 120 Drawing Sheets
Specification includes a Sequence Listing.

(56) References Cited

U.S. PATENT DOCUMENTS

| | | |
|---|---|---|
| 6,410,319 B1 | 6/2002 | Raubitschek et al. |
| 6,569,997 B1 | 5/2003 | Kwon |
| 7,049,136 B2 | 5/2006 | Seed et al. |
| 7,052,906 B1 | 5/2006 | Lawson et al. |
| 7,070,995 B2 | 7/2006 | Jensen |
| 7,132,255 B2 | 11/2006 | Blumberg |
| 7,265,209 B2 | 9/2007 | Jensen |
| 7,319,143 B2 | 1/2008 | Gross et al. |
| 7,320,787 B2 | 1/2008 | Seed et al. |
| 7,402,431 B2 | 7/2008 | Har-Noy |
| 7,446,190 B2 | 11/2008 | Sadelain et al. |
| 7,446,191 B2 | 11/2008 | Jensen |
| 7,514,537 B2 | 4/2009 | Jensen |
| 7,638,325 B2 | 12/2009 | June et al. |
| 7,638,326 B2 | 12/2009 | June et al. |
| 7,741,465 B1 | 6/2010 | Eshhar et al. |
| 7,745,140 B2 | 6/2010 | June et al. |
| 7,754,482 B2 | 7/2010 | Riley et al. |
| 7,994,298 B2 | 8/2011 | Zhang et al. |
| 8,008,449 B2 | 8/2011 | Korman et al. |
| 8,124,084 B2 | 2/2012 | Lefrancois et al. |
| 8,211,422 B2 | 7/2012 | Eshhar et al. |
| 8,252,914 B2 | 8/2012 | Zhang et al. |
| 8,383,778 B2 | 2/2013 | Hsieh et al. |
| 8,389,282 B2 | 3/2013 | Sadelain et al. |
| 8,399,645 B2 | 3/2013 | Campana et al. |
| 8,465,743 B2 | 6/2013 | Rosenberg et al. |
| 8,637,307 B2 | 1/2014 | June et al. |
| 8,722,400 B2 | 5/2014 | Riley et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,394,368 B2 | 7/2016 | Brogdon et al. |
| 9,464,140 B2 | 10/2016 | June et al. |
| 9,481,728 B2 | 11/2016 | June et al. |
| 9,499,629 B2 | 11/2016 | June et al. |
| 9,573,988 B2 | 2/2017 | Brogdon et al. |
| 9,745,368 B2 | 8/2017 | Milone et al. |
| 9,777,061 B2 | 10/2017 | Ebersbach et al. |
| 9,815,901 B2 | 11/2017 | Brogdon et al. |
| 2003/0060444 A1 | 3/2003 | Finney et al. |
| 2003/0077249 A1 | 4/2003 | Bebbington et al. |
| 2003/0148982 A1 | 8/2003 | Brenner et al. |
| 2003/0224520 A1 | 12/2003 | June et al. |
| 2004/0038886 A1 | 2/2004 | Finney et al. |
| 2004/0043401 A1 | 3/2004 | Sadelain et al. |
| 2005/0113564 A1 | 5/2005 | Campana et al. |
| 2005/0129671 A1 | 6/2005 | Cooper et al. |
| 2007/0036773 A1 | 2/2007 | Cooper et al. |
| 2008/0131415 A1 | 6/2008 | Riddell et al. |
| 2009/0082299 A1 | 3/2009 | Felber et al. |
| 2009/0257994 A1 | 10/2009 | Jensen |
| 2010/0233200 A1 | 9/2010 | Medin |
| 2010/0247521 A1 | 9/2010 | Jones et al. |
| 2011/0052554 A1 | 3/2011 | Zakrzewski et al. |
| 2011/0081311 A1 | 4/2011 | Pavlakis et al. |
| 2012/0141413 A1 | 6/2012 | Pavlakis et al. |
| 2012/0148552 A1 | 6/2012 | Jensen |
| 2012/0177598 A1 | 7/2012 | Lefrancois et al. |
| 2012/0321667 A1 | 12/2012 | Sentman |
| 2013/0071409 A1 | 3/2013 | Riley et al. |
| 2013/0071414 A1 | 3/2013 | Dotti et al. |
| 2013/0149337 A1 | 6/2013 | Cooper et al. |
| 2013/0155909 A1 | 6/2013 | Jackson et al. |
| 2013/0287748 A1 | 10/2013 | June et al. |
| 2014/0050708 A1 | 2/2014 | Powell |
| 2014/0099309 A1 | 4/2014 | Powell, Jr. et al. |
| 2014/0099340 A1 | 4/2014 | June et al. |
| 2014/0106449 A1 | 4/2014 | June et al. |
| 2014/0186947 A1 | 7/2014 | June et al. |
| 2014/0212446 A1 | 7/2014 | Riley et al. |
| 2014/0219975 A1 | 8/2014 | June et al. |
| 2014/0227237 A1 | 8/2014 | June et al. |
| 2014/0271635 A1 | 9/2014 | Brogdon et al. |
| 2014/0322169 A1 | 10/2014 | Harper et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0370017 A1 | 12/2014 | June et al. |
| 2014/0370045 A1 | 12/2014 | June et al. |
| 2015/0017141 A1 | 1/2015 | June et al. |
| 2015/0050729 A1 | 2/2015 | June et al. |
| 2015/0093822 A1 | 4/2015 | June et al. |
| 2015/0099299 A1 | 4/2015 | June et al. |
| 2015/0118202 A1 | 4/2015 | June et al. |
| 2015/0140019 A1 | 5/2015 | June et al. |
| 2015/0166661 A1* | 6/2015 | Chen ............... C07K 16/2809 424/135.1 |
| 2015/0190428 A1 | 7/2015 | June et al. |
| 2015/0202286 A1 | 7/2015 | June et al. |
| 2015/0238631 A1* | 8/2015 | Kim ............... C07K 16/2803 530/391.9 |
| 2015/0283178 A1 | 10/2015 | June et al. |
| 2015/0290207 A1* | 10/2015 | Kutok ............... A61K 31/506 424/134.1 |
| 2015/0290244 A1 | 10/2015 | June et al. |
| 2015/0342994 A1 | 12/2015 | Riley et al. |
| 2016/0046724 A1 | 2/2016 | Brogdon et al. |
| 2016/0051651 A1 | 2/2016 | Brogdon et al. |
| 2016/0068601 A1 | 3/2016 | Brogdon et al. |
| 2016/0096892 A1 | 4/2016 | Brogdon et al. |
| 2016/0130355 A1 | 5/2016 | June et al. |
| 2016/0159907 A1 | 6/2016 | June et al. |
| 2016/0185861 A1 | 6/2016 | Bedoya et al. |
| 2016/0194404 A1 | 7/2016 | June et al. |
| 2016/0208012 A1 | 7/2016 | June et al. |
| 2016/0311907 A1 | 10/2016 | Brogdon et al. |
| 2016/0311917 A1 | 10/2016 | Beatty et al. |
| 2016/0340406 A1 | 11/2016 | Zhao et al. |
| 2016/0362472 A1 | 12/2016 | Bitter et al. |
| 2017/0008963 A1 | 1/2017 | Brogdon et al. |
| 2017/0081411 A1 | 3/2017 | Engels et al. |
| 2017/0137783 A1 | 5/2017 | Bedoya et al. |
| 2017/0183415 A1 | 6/2017 | Brogdon et al. |
| 2017/0209492 A1 | 7/2017 | June et al. |
| 2017/0211055 A1 | 7/2017 | Brogdon et al. |
| 2017/0226495 A1 | 8/2017 | Guimaraes |
| 2017/0239294 A1 | 8/2017 | Thomas-Tikhonenko et al. |
| 2017/0260268 A1 | 9/2017 | Beatty et al. |
| 2017/0274074 A1 | 9/2017 | Brogdon et al. |
| 2017/0306416 A1 | 10/2017 | Bedoya et al. |
| 2017/0335281 A1 | 11/2017 | Loew et al. |
| 2018/0022795 A1 | 1/2018 | Milone et al. |
| 2018/0044423 A1 | 2/2018 | Ebersbach et al. |
| 2018/0044424 A1 | 2/2018 | June et al. |
| 2018/0118834 A1 | 5/2018 | Brogdon et al. |
| 2018/0125892 A1 | 5/2018 | Brannetti et al. |
| 2018/0133296 A1 | 5/2018 | Barrett et al. |
| 2018/0140602 A1 | 5/2018 | Angst et al. |
| 2018/0230193 A1 | 8/2018 | Loew et al. |
| 2018/0252727 A1 | 9/2018 | Garfall et al. |
| 2018/0258149 A1 | 9/2018 | Motz et al. |
| 2018/0298068 A1 | 10/2018 | Albelda |
| 2018/0312595 A1 | 11/2018 | Brogdon et al. |

FOREIGN PATENT DOCUMENTS

| | | |
|---|---|---|
| EP | 0871495 A1 | 10/1998 |
| EP | 1226244 A2 | 7/2002 |
| JP | 2003517301 A | 5/2003 |
| JP | 2004529636 A | 9/2004 |
| WO | 1992015322 A1 | 9/1992 |
| WO | 9507984 A1 | 3/1995 |
| WO | 199530014 A1 | 11/1995 |
| WO | 9623814 A1 | 8/1996 |
| WO | 9624671 A1 | 8/1996 |
| WO | 1997015669 A1 | 5/1997 |
| WO | 9723613 A2 | 7/1997 |
| WO | 9818809 A1 | 5/1998 |
| WO | 9900494 A2 | 1/1999 |

(56) References Cited

FOREIGN PATENT DOCUMENTS

| WO | 9921581 A1 | 5/1999 |
|---|---|---|
| WO | 9957268 A1 | 11/1999 |
| WO | 0014257 A1 | 3/2000 |
| WO | 200134843 A1 | 5/2001 |
| WO | 2002033101 A1 | 4/2002 |
| WO | 02077029 A2 | 10/2002 |
| WO | 02088334 A1 | 11/2002 |
| WO | 2003057171 A2 | 7/2003 |
| WO | 2004/003019 A2 | 1/2004 |
| WO | WO 2004/003019 * | 6/2004 |
| WO | 2005019429 A2 | 3/2005 |
| WO | 2005044996 A2 | 5/2005 |
| WO | 2005/118788 A2 | 12/2005 |
| WO | 2006060878 A1 | 6/2006 |
| WO | 2008045437 A2 | 4/2008 |
| WO | 2008049928 A1 | 5/2008 |
| WO | 2009091826 A2 | 7/2009 |
| WO | 2010019570 A2 | 2/2010 |
| WO | 2010085660 A2 | 7/2010 |
| WO | 2010095031 A2 | 8/2010 |
| WO | 2011059836 A2 | 5/2011 |
| WO | 2011097477 A1 | 8/2011 |
| WO | 2012058460 A2 | 5/2012 |
| WO | 2012079000 A1 | 6/2012 |
| WO | 2012082841 A2 | 6/2012 |
| WO | 2012/099973 A2 | 7/2012 |
| WO | 2012127464 A2 | 9/2012 |
| WO | 2012129514 A1 | 9/2012 |
| WO | 2012135854 A2 | 10/2012 |
| WO | 2012138858 A1 | 10/2012 |
| WO | 2013019615 A2 | 2/2013 |
| WO | 2013033626 A2 | 3/2013 |
| WO | 2013040371 A2 | 3/2013 |
| WO | 2013040557 A2 | 3/2013 |
| WO | 2013059593 A1 | 4/2013 |
| WO | 2013/126712 A1 | 8/2013 |
| WO | 2013126729 A1 | 8/2013 |
| WO | 2013126733 A1 | 8/2013 |
| WO | 2014/011984 A1 | 1/2014 |
| WO | 2014/011987 A1 | 1/2014 |
| WO | 2014/011993 A1 | 1/2014 |
| WO | 2014/012001 A2 | 1/2014 |
| WO | 2014011988 A2 | 1/2014 |
| WO | 2014011996 A1 | 1/2014 |
| WO | 2014031687 A1 | 2/2014 |
| WO | 2014039513 A2 | 3/2014 |
| WO | 2014/055442 A2 | 4/2014 |
| WO | 2014055657 A1 | 4/2014 |
| WO | 2014130635 A1 | 8/2014 |
| WO | 2014/145252 A2 | 9/2014 |
| WO | 2014153270 A1 | 9/2014 |
| WO | 2015079417 A1 | 6/2015 |
| WO | 2015090229 A1 | 6/2015 |
| WO | 2015090230 A1 | 6/2015 |
| WO | 2015112626 A1 | 7/2015 |
| WO | 2015/142661 A1 | 9/2015 |
| WO | 2015142675 A2 | 9/2015 |
| WO | 2015157252 A1 | 10/2015 |
| WO | 2016014501 A1 | 1/2016 |
| WO | 2016014530 A1 | 1/2016 |
| WO | 2016014535 A1 | 1/2016 |
| WO | 2016014553 A1 | 1/2016 |
| WO | 2016014565 A2 | 1/2016 |
| WO | 2016014576 A1 | 1/2016 |
| WO | 2016019300 A1 | 2/2016 |
| WO | 2016025880 A1 | 2/2016 |
| WO | 2016028896 A1 | 2/2016 |
| WO | 2016044605 A1 | 3/2016 |
| WO | 2016/164580 A1 | 10/2016 |

OTHER PUBLICATIONS

Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
MedChem Express PCI-32765 data sheet (pp. 1-3, Jul. 8, 2016).*
Jain et al. (South Asian Journal of Cancer 1(2): 84-89 (Oct.-Dec. 2012)).*
Smith-Gill et al. (J. Immunol. 139:4135-4144 (1987)).*
Ward et al. (Nature 341:544-546 (1989)).*
Kumar et al. (J. Biol. Chem. 275:35129-35136 (2000)).*
Song et al. (Biochem Biophys Res Comm 268:390-394 (2000)).*
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Hekele et al., "Growth Retardation of Tumors by Adoptive Transfer of Cytotoxic T Lymphocytes Reprogrammed by CD44V6-Specific SCFV:~—Chimera" Int J. Cancer (1996) vol. 68 pp. 232-238.
Henderson et al., "Comparison of the effects of FK-506, cyclosporin A and rapamycin on IL-2 production." Immunology (1991) No. 73 vol. 3 pp. 316-321.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD19 antigen for autologous adoptive cell therapy" J Immunother (2009) vol. 32 No. 2 pp. 169-180.
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Honigberg et al., "The Bruton tyrosine kinase inhibitor PCI-32765 blocks B-cell activation and is efficacious in models of autoimmune disease and B-cell malignancy." Proc Natl Acad Sci (2010) vol. 107 No. 29 pp. 13075-13080.
Huye E L et al: 'Combining mTor Inhibitors With Rapamycin-resistant T Cells: A Two-pronged Approach to Tumor Elimination',Molecular Therapy,vol. 19, No. 12,Aug. 30, 2011 (Aug. 30, 2011), pp. 2239-2248, XP055191016, GB, ISSN: 1525-0016, DOI: 10.1038/mt.2011.179 the whole document.
Imai et al., "Chimeric receptors with 4-1BB signaling capacity provoke potent cytotoxicity against acute lymphoblastic leukemia," Leukemia 18: 676-684 (2004).
Imai et al., "Genetic modification of primary natural killer cells overcomes inhibitory signals and induces specific killing of leukemic cells" Blood (2005) vol. 106 No. 1 pp. 376-383.
International Search Report and Written Opinion for International application No. PCT/US2015/024671, dated Jul. 31, 2015.
International Search Report from PCT/US2011/064191 dated Jan. 5, 2012.
Irvng et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets normal tissues expressing cognate antigen" Blood (2009) vol. 114 No. 3 pp. 535-545.
Jones et al., "Circulating clonotypic B cells in classic Hodgkin lymphoma." Blood (2009) vol. 113 No. 23 pp. 5920-5926.
Joo et al., "Targeted cancer therapy—are the days of systemic chemotherapy numbered?" Maturitas (2013) vol. 76 No. 4 pp. 308-314.
June et al., "Engineering lymphocyte subsets: tools, trials and tribulations" Nat Rev Immunol (2009) vol. 9 No. 10 pp. 704-716.

(56) References Cited

OTHER PUBLICATIONS

June, "Adoptive T cell therapy for cancer in the clinic" Journal of Clinical Investigation (2007) vol. 117 No. 6 pp. 1466-1476.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Kalos et al.,"T cells with chimeric antigen receptors have potent antitumor effects and can establish memory in patients with advanced leukemia." Science Translational Medicine (2011) vol. 3 No. 95 95ra73.
Kappos et al., "Ocrelizumab in relapsing-remitting multiple sclerosis: a phase 2, randomised, placebo-controlled, multicentre trial." Lancet (2011) vol. 378 No. 9805 pp. 1779-1787.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kim et al. "B-cell Depletion Using an Anti-CD20 Antibody Augments Antitumor Immune Responses and Immunotherapy in Nonhematopoetic Murine Tumor Models" Journal of Immunotherapy (2008) vol. 31 No. 5 pp. 446-457.
Kim et al., "Human 4-1BB regulates CD28 co-stimulation to promote Th1 cell responses" Eur. J. Immunol. (1998) vol. 28 pp. 881-890.
Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180 & 52nd Annual Meeting of the American-Society-of-Hematology (ASH), Orlando, FL, USA; Dec. 4-7, 2010 abstract.
Kochenderfer et al. "Construction and Pre-clinical Evaluation of an Anti-CD19 Chimeric Antigen Receptor", J Immunother (2009) vol. 32, No. 7, pp. 389-702.
Kochenderfer et al., "Eradication of B-lineage cells and regression of lymphoma in a patient treated with autologous T cells genetically-engineered to recognize CD19," Blood 116: 4099-4102 (2010).
Kohn et al., "CARs on Track in the Clinic—Workshop of the Blood and Marrow Transplant Clinical Trials Network Subcommittee on Cell and Gene Therapy" Meeting Report—Molecular Therapy (2011) vol. 19 No. 3.
Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp. 17372-17377.

Lim et al., "Anti-CD20 monoclonal antibodies: historical and future perspectives." Haematologica (2010) vol. 95 No. 1 pp. 135-143.
Liu et al., "Calcineurin is a common target of cyclophilin-cyclosporin A and FKBP-FK506 complexes." Cell (1991) vol. 66 No. 4 pp. 807-815.
MacAllan et al., "Measurement and modeling of human T cell kinetics" European Journal of Immunology (2003) vol. 33 pp. 2316-2326.
Maher et al., "Human T lymphocyte cytotoxicity and proliferation directed by a single chimeric TCRzeta/CD28 receptor," Nat. Biotechnol. 20: 70-75 (2002).
Marzec et al., "Mantle cell lymphoma cells express predominantly cyclin D1a isoform and are highly sensitive to selective inhibition of CDK4 kinase activity." Blood (2006) vol. 108 No. 5 pp. 1744-1750.
Mato et al., "Favorable Outcomes in CLL Pts with Alternate Kinase Inhibitors Following Ibrutinib or Idelalisib Discontinuation: Results from a Large Multi-Center Study" Blood (2015) vol. 126 No. 23.
Maude et al., "Chimeric Antigen Receptor T Cells for Sustained Remissions in Leukemia" The New England Journal of Medicine (2014) vol. 371 No. 16 pp. 1507-1517.
McGuinness et al., "Anti-tumor activity of human T cells expressing the CC49-zeta chimeric immune receptor," Hum. Gene Ther. 10: 165-173 (1999).
Milone et al, "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Moeini et al., "Emerging signaling pathways in hepatocellular carcinoma." Liver Cancer (2012) vol. 1 No. 2 pp. 83-93.
Molina, "A Decade of Rituximab: Improving Survival Outcomes in Non-Hodgkin's Lymphoma" Annu. Rev. Med. (2008) vol. 59 pp. 237-250.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.
Nicholson et al., "Construction and Characterisation of a Function CD19 Specific Single Chain Fv Fragment for Immunotherapy of B Lineage Leukaemia and Lymphoma," Molecular Immunology 34(16-17): 1157-1165 (1997).
Pardoll, "The blockade of immune checkpoints in cancer immunotherapy" Cancer (2012) vol. 12 pp. 252-264.
Parikh et al., "How we treat Richter syndrome." Blood (2014) vol. 123 No. 11 pp. 1647-1657.
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Patel et al., "Impact of chimeric immune receptor extracellular protein domains on T cell function" Gene Therapy (1999) vol. 6 pp. 412-419.
Ponader et al., "The Bruton tyrosine kinase inhibitor PCI-32765 thwarts chronic lymphocytic leukemia cell survival and tissue homing in vitro and in vivo" Blood (2012) vol. 119 No. 5 pp. 1182-1189.

(56) References Cited

OTHER PUBLICATIONS

Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric antigen receptor T cells persist and induce sustained remissions in relapsed refractory chronic lymphocytic leukemia" Science Translational Medicine (2015) vol. 7 No. 303 303ra139.
Porter et al., "Chimeric Antigen Receptor Therapy for B-cell Malignancies" Journal of Cancer (2011) vol. 2 pp. 331-332.
Porter et al., "Randomized, Phase II Dose Optimization Study of Chimeric Antigen Receptor Modified T Cells Directed Against CD19 (CTL019) in Patients with Relapsed, Refractory CLL" Blood (2014) vol. 124 No. 21.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Pyonteck et al., "CSF-1R inhibition alters macrophage polarization and blocks glioma progression." Natural Medicine (2013) vol. 19 No. 10 pp. 1264-1272.
Rapoport et al., "Restoration of immunity in lymphopenic individuals with cancer by vaccination and adoptive T-cell transfer" Nature Medicine (2005) vol. 11 No. 11 pp. 1230-1237.
Robak & Robak, "New Anti-CD20 Monoclonal Antibodies for the Treatment of B-Cell Lymphoid Malignancies" Biodrugs (2011) vol. 25 No. 1 pp. 13-25.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Romisher et al., "Bruton's Tyrosine Kinase Inhibition Is Associated with Manageable Cardiac Toxicity" Blood (2015) vol. 126 No. 23.
Ruella and Gill, "How to train your T cell: genetically engineered chimeric antigen receptor T cells versus bispecific T-cell engagers to target CD19 in B acute lymphoblastic leukemia." (2015) vol. 15 No. 6 pp. 761-766.
Ruella et al., "Combination of Ibrutinib and Anti-CD19 Chimeric Antigen Receptor T Cells for the Treatment of Relapsing/Refractory Mantle Cell Lymphoma (MCL)" Haematologica (2015) vol. 100 pp. 287-288.
Ruella et al., "The Addition of the BTK Ibrutinib to Anti-CD19 Chimeric Antigen Receptor T Cells (CART19) Improves Responses against Mantle Cell Lymphoma" Clinical Cancer Research (2016) 1-13.
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Salvadori, "Antineoplastic effects of mammalian target of rapamycine inhibitors." World Journal of Transplantation (2012) vol. 2 No. 5 pp. 74-83.
Santoni et al., "Role of natural and adaptive immunity in renal cell carcinoma response to VEGFR-TKIs and mTOR Inhibitor" International Journal of Cancer (2014) vol. 134 No. 12 pp. 2772-2777.
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Scott et al., "Monoclonal antibodies in cancer therapy" Cancer Immunity (2012) vol. 12 p. 14.
Sebestyen et al., "Human TCR That Incorporate CD3 Induce Highly Preferred Pairing between TCR and Chains following Gene Transfer" Journal of Immunology (2008) vol. 180 pp. 7736-7746.
Shirasu et al., "Functional Design of Chimeric T-Cell Antigen Receptors for Adoptive Immunotherapy of Cancer: Architecture and Outcomes," AntiCancer Res. 32: 2377-2384 (2012).
Sidaway, "Ibrutinib supercharges CAR T cells" Nature Reviews Clinical Oncology (2016) Abstract.
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Vinay & Kwon, "Role of 4-1BB in immune responses" Immunology (1998) vol. 10 pp. 481-489.
Wang et al., "Targeting BTK with ibrutinib in relapsed or refractory mantle-cell lymphoma." New England Journal of Medicine (2013) vol. 369 No. 6 pp. 507-516.
Wang et al., "Utilization of Next Generation Sequencing Identifies Potentially Actionable Mutations with Prognostic Significance in Chronic Lymphocytic Leukemia" Blood (2015) vol. 126 No. 23.
Willemsen et al., "Genetic Engineering of T Cell Specificity for Immunotherapy of Cancer" Human Immunology (2003) vol. 64 pp. 56-68.
Woyach et al., "Resistance mechanisms for the Bruton's tyrosine kinase inhibitor ibrutinib." New England Journal of Medicine (2014) vol. 370 No. 24 pp. 2286-2294.
Xu V et al: "Closely related T-memory stem cells correlate with in vivo expansion of CAR.CD19-T cells and are preserved by IL-7 and IL-15", Blood, vol. 123, No. 24, Apr. 29, 2014 (Apr. 29, 2014), pp. 3750-3759, XP055201372, ISSN: 0006-4971, DOI:10.1182/blood-2014-01-552174.
Younes et al., "Phase 2 study of rituximab plus ABVD in patients with newly diagnosed classical Hodgkin lymphoma." Blood (2012) vol. 119 No. 18 pp. 4123-4128.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zufferey et al., "Multiply attenuated lentiviral vector achieves efficient gene delivery in vivo" Nature Biotechnology (1997) vol. 15 pp. 871-876.
Mato et al., "Ibrutinib-induced pneumonitis in patients with chronic lymphocyticleukemia" Blood (2016) vol. 127 No. 8 pp. 1064-1067.
Grupp et al. "Chimeric Antigen Receptor-Modified T Cells for Acute Lymphoid Leukemia", New England Journal of Medicine (2013) vol. 368 No. 16 pp. 1509-1518.
Advani et al., "Bruton tyrosine kinase inhibitor ibrutinib (PCI-32765) has significant activity in patients with relapsed/refractory B-cell malignancies." Journal of Clinical Oncology (2013) vol. 31 No. 1 pp. 88-94.
Awan and Byrd, "New Strategies in Chronic Lymphocytic Leukemia: Shifting Treatment Paradigms" Clinical Cancer Research (2014) vol. 20 No. 23 pp. 5869-5874.
Baeksgaard & Sorensen, "Acute tumor lysis syndrome in solid tumors—a case report and review of the literature" Cancer Chemotherapy Pharmacology (2003) vol. 51 pp. 187-192.
Bierer et al., "Cyclosporin A and FK506: molecular mechanisms of immunosuppression and probes for transplantation biology" Current Opinion in Immunology (1992) vol. 5 pp. 763-773.
Bondanza et al. "Suicide gene therapy of graft-versus-host disease induced by central memory human T lymphocytes" Blood (2006) vol. 107 No. 5 pp. 1828-1836.
Brentjens et al. "Genetically Targeted T Cells Eradicate Systemic Acute Lymphoblastic Leukemia Xenografts", Clinical Cancer Research (2007) vol. 13, No. 18, pp. 5426-5435.

(56) References Cited

OTHER PUBLICATIONS

Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-1428.
Brocker and Karjalainen, "Signals through T Cell Receptor-Chain alone Are Insufficient to Prime Resting T Lymphocytes" J. Exp. Med. (1995) vol. 181 pp. 1653-1659.
Brown J R et al: "Novel Treatments for Chronic Lymphocytic Leukemia and Moving Forward",American Society of Clinical Oncology Educational Book,vol. 34, 2014, pp. e317-e325,XP05520 1368,ISSN: 1548-8748, DOI:10.14694/EdBook_AM.2014..34. e317 the whole document.
Byrd et al., "Targeting BTK with ibrutinib in relapsed chronic lymphocytic leukemia." New England Journal of Medicine (2013) vol. 369 No. 1 pp. 32-42.
Call & Wucherpfennig, "The T Cell Receptor: Critical Role of the Membrane Environment in Receptor Assembly and Function" Annu. Rev. Immunol. (2005) vol. 23 pp. 101-125.
Carpenito et al. "Control of large, established tumor xenografts with genetically retargeted human T cells containing 2,D28 and CD137 domains", Proc Natl Mad Sci USA (2009) vol. 106 pp. 3360-3365.
Casulo et al., "A phase I study of PRO131921, a novel anti-CD20 monoclonal antibody in patients with relapsed/refractory CD20+ indolent NHL: correlation between clinical responses and AUC pharmacokinetics." Clinical Immunology (2014) vol. 154 No. 1 pp. 37-46.
Cheson et al., "Report of an International Workshop to Standardize Response Criteria for Non-Hodgkin's Lynphomas" Journal of Clinical Oncology (1999) vol. 17 pp. 1244-1253.
Davila et al. "B Cell Aplasia in a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.
De Visser et al., "De novo carcinogenesis promoted by chronic inflammation is B lymphocyte dependent." Cancer Cell (2005) vol. 7 No. 5 pp. 411-423.
Di Stasi et al., "Inducing apoptosis as a safety switch for adoptive cell therapy" New England Journal of Medicine (2011) vol. 365 No. 18 pp. 1673-1683.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dropulic and June, "Gene-Based Immunotherapy for Human Immunodeficiency Virus Infection and Acquired Immunodeficiency Syndrome" Human Gene Therapy (2006) vol. 17 pp. 577-588.
Dubovsky et al., "Ibrutinib is an irreversible molecular inhibitor of ITK driving a Th1-selective pressure in T lymphocytes." Blood (2013) vol. 122 No. 15 pp. 2539-2549.
Dull et al, "A Third-Generation Lentivirus Vector with a Conditional Packaging System" Journal of Virology (1998) vol. 72 No. 11 pp. 8463-8471.

Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).
Evans et al., "Evolution to Plasmablastic Lymphoma (PBL) after CAR-T Cell Therapy in a Case of SLL/CLL with Richter's Transformation" Blood (2014) vol. 124 No. 21.
FDA: Highlights of Prescribing Information for Arzerra (2009).
FDA: Highlights of Prescribing Information for Gazyva (2013).
FDA: Highlights of Prescribing Information for Rituxan (2010).
Finn et al., "Current and Future Treatment Strategies for Patients with Advanced Hepatocellular Carcinoma: Role of mTOR Inhibition." Liver Cancer (2012) vol. 1 No. 3-4 pp. 247-256.
Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol. 161: 2791-2797 (1998).
Forero-Torres et al., "Results of a phase 1 study of AME-133v (LY2469298), an Fc-engineered humanized monoclonal anti-CD20 antibody, in Fc?RIIIa-genotyped patients with previously treated follicular lymphoma." Clinical Cancer Research (2012) vol. 18 No. 5 pp. 1395-1403.
Fraietta et al., "Ibrutinib enhances chimeric antigen receptor T-cell engraftment and efficacy in leukemia" Blood (2016) vol. 127 No. 9 pp. 1117-1127.
Fraietta et al., "P.D.14.19—Longitudinal Effects of Ibrutinib Therapy on T Lymphocytes: Implications for Combination Adoptive Cell Strategies to Treat Chronic Lymphocytic Leukemia (CLL)" The 4th European Congress of Immunology (2015) Presentation Abstract.
Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Friedmann-Morvinski et al., "Redirected primary T cells harboring a chimeric receptor require costimulation for their antigen-specific activation," Blood 105: 3087-3093 (2005).
Geiger & Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and costimulatory activity enhances signal transduction through single-chain chimeric receptors in T lymphocytes," Blood 98(8): 2364-2371 (2001).
GenBank Accession No. NP_000725.1 accessed on Jan. 7, 2016 from http://www.ncbi.nlm.nih.gov/protein/NIP_000725.
GenBank Accession No. NP_932170.1 accessed Jan. 7, 2016 from http://www.ncbi.nlm.nih.gov/protein/N1P_932170.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Goldenberg et al., "Veltuzuman (humanized anti-CD20 monoclonal antibody): characterization, current clinical results, and future prospects" Leukemia & Lymphoma (2010) vol. 51 No. 5 pp. 747-755.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 370-3378 (1992).
"Pilot study for Patients with chemotherapy resistant or refractory CD19 Leukemia and Lymphoma (CART-19)" ClinicalTrials.gov Identifier NCT00891215; Retrieved from the internet on Sep. 2, 2015 Found at http://web.archive.org/web/20090903002304/http://clinicaltrials.gov/ct2/show/study/NCT00891215.
A NCBI Direct Submission NP 000725 dated Nov. 21, 2010.

(56) References Cited

OTHER PUBLICATIONS

A NCBI Direct Submission NP 932170.1 dated Nov. 21, 2010.
AppliChem product sheet for RPMI-1640, 2 pages, downloaded Dec. 28, 2015.
Batzer et al. "Enhanced evolutionary PCR using oligonucleotides with inosine at the 3'-terminus" (1991) vol. 19, No. 18, pp. 5081.
Brentjens et al. "Novel cellular therapies for leukemia: CAR-modified T cells targeted to the CD19 antigen" Hematology (2012) pp. 143-151.
Campana et al., 2003 Blood 102(11); abstract #223.
Chothia et al. "Canonical structures for the hypervariable regions of immunoglobulins" Journal of Molecular Biology (1987) vol. 196, No. 4, pp. 901-917.
Cruz et al. "Adverse events following infusion of T cells for adoptive immunotherapy: a 10-year experience" Cytotherapy (2010) vol. 12, No. 6, pp. 743-749.
Davila et al, "T Cells Genetically Targeted to CD19 Eradicate B-All in a Novel Syngeneic Mouse Disease Model" 2010 ASH Abstract No. 171, presented Dec. 6, 2010 (poster abstract).
Dudley et al. "Malignancy Persisting After Allogeneic Hematopoietic Stem Cell Transplantation" Blood (2013) vol. 122, No. 21, pp. 151—Abstract Only.
Durie et al. "International uniform response criteria for multiple myeloma" Leukemia (2006) vol. 20, No. 9, pp. 1467-1473.
Hutchinson et al. "Breaking good: the inexorable rise of BTK inhibitors in the treatment of chronic lymphocytic eukaemia" British Journal of Haematology (2014) vol. 166, pp. 12-22.
International Preliminary Report on Patentability for International Application No. PCT/US2014/029943 dated Sep. 22, 2015.
International Search Report and Written Opinion for International Application No. PCT/US2014/029943 dated Jul. 17, 2014.
International Search Report and Written Opinion for International Application No. PCT/US2016/026437 dated Jun. 29, 2016.
Kochenderfer et al., "Novel Antigen-Specific Expansion of T Cells Transduced with a CD19 Chimeric Antigen Receptor" 2010 ASH Meeting Abstract No. 3262, presented Dec. 6, 2010 (poster abstract).
Kochenderfer, et al. "Adoptive transfer of syngeneic T cells transduced with a chimeric antigen receptor that ecognizes murine CD19 can eradicate lymphoma and normal B cells" Blood (2010) vol. 116, No. 9, pp. 3875-3886.
Martz et al. "Overcoming ibrutinib resistance" SciBX (2014) vol. 7, No. 33, pp. 1-3.
Maude, "217 Efficacy of Humanized CD19-Targeted Chimeric Antigen Receptor (CAR)-Modified T Cells in Children and Young Adults with Relapsed/Refractory Acute Lymphoblastic Leukemia" 58th Annual Meeting & Exposition—Dec. 3, 2016; Abstract.
Milone et al, Supplementary Materials and Methods, Mol. Ther (2009) vol. 17, 7 pages.
Ochoa et al, "Immune Defects in T Cells from Cancer Patients, Parallels in Infectious Diseases" Cancer Immunotherapy at the Crossroads: how tumors evade immunity and what can be done (current clinical oncology), edited by James H. Finke, Ronald M. Bukowski, 2004 edition.
Ohtsuka et al. "An Alternative Approach to Deoxyoligonucleotides as Hybridization Probes by Insertion of Deoxyinosine at Ambiguous Codon Positions" The Journal of Biological Chemistry (1985) vol. 260, No. 5, pp. 2605-2608.
Rossolini et al. "Use of deoxyinosine-containing primers vs degenerate primers for polymerase chain reaction based on ambiguous sequence information" Molecular and Cellular Probes (1994) vol. 8, No. 2, pp. 91-98.
Sagiv-Barfi, et al., "Ibrutinib enhances the antitumor immune response induced by intratumoral injection of a TLR9 ligand in mouse lymphoma" Blood, 125(13):2079-2086 (2015).
Sagiv-Barfi, et al., "Therapeutic antitumor immunity by checkpoint blockade is enhanced by ibrutinib, an inhibitor of both BTK and ITK" PNAS, 112(9):E966-E972 (2015).
Shi et al. "Chimeric antigen receptor for adoptive immunotherapy of cancer: latest research and future prospects" Molecular Cancer (2014) vol. 13, No. 219, pp. 1-8.

Song et al. "CD27 costimulation augments the survival and antitumor activity of redirected human T cells in vivo" Blood (2012) vol. 119, No. 3, pp. 696-706.
Tammana Syam et al., "4-1BB and CD28 Signaling plays a synergistic role in redirecting umbibical cord blood T cells against B-cell malignancies" Human Gene Therapy (2010) vol. 21, pp. 75-86.
Colman et al. "Effects of amino acid sequence changes on antibody-antigen interactions" Research in Immunology (1994) vol. 145, pp. 33-36.
Cooper et al. "Test-driving CARs" Blood (2008) vol. 112, No. 5, pp. 2172-2173.
Hombach et al. "0X40 costimulation by a chimeric antigen receptor abrogates CD28 and IL-2 induced IL-10 secretion by redirected CD4+ T cells" Oncolmmunology (2012) vol. 1, No. 4, pp. 458-466.
Kofler et al. "CD28 Costimulation Impairs the Efficacy of a Redirected T-cell Antitumor Attack in the Presence of Regulatory T cells Which Can Be Overcome by Preventing Lck Activation" Molecular Therapy (2001) vol. 19, No. 4, 760-767.
Lamers et al. "Immune responses to transgene and retroviral vector in patients treated with ex vivo-engineered T cells" Blood (2011) vol. 117, No. 1, pp. 72-82.
Rudikoff et al. "Single amino acid substitutuion altering antigen-binding specificity" Proc. Natl. Acad. Sci. (1982) vol. 79, pp. 1979-1983.
Shirasu et al. "Functional Design of Chimeric T-Cell Antigen Receptors for Adoptive Immunotherapy of Cancer: Architecture and Outcomes" Anticancer Research (2012) vol. 32, pp. 2377-2384.
Vajdos et al. "Comprehensive Functional Maps of the Antigen-binding Site of an Anti-ErbB2 Antibody Obtained with Shotgun Scanning Mutagenesis" Journal of Molecular Biology (2002) vol. 320, pp. 415-428.
Wang et al. "VISTA, a novel mouse Ig superfamily ligand that negatively regulates T cell responses" The Journal of Experimental Medicine (2011) vol. 208, No. 3, 577-592.
Acuto et al. "CD28-Mediated Co-Stimulation: A Quantitative Support for TCR Signalling" Nature Reviews Immunology (2003) vol. 3, pp. 939-951.
Diamond et al. "Somatic mutation of the T15 heavy chain gives rise to an antibody with autoantibody specificity" PNAS (1984) vol. 81, pp. 5841-5844.
Guest et al. "The Role of Extracellular Spacer Regions in the Optimal Design of Chimeric Immune Receptors valuation of Four Different scFvs and Antigens" J. Immunother. (2005) vol. 28, No. 3, pp. 203-211.
Intlekofer et al. "At the Bench: Preclinical rationale for CTLA-4 and PD-1 blockade as cancer immunotherapy" J Leukoc Biol (2013) vol. 94, No. 1, pp. 25-39.
Jena et al. "Chimeric Antigen Receptor (CAR)-Specific Monoclonal Antibody to Detect CD19-Specific T Cells in Clinical Trials" PLOS One (2013) vol. 8, No. 3, e57838, pp. 1-12.
Karlsson et al. "Combining CAR T cells and the Bcl-2 family apoptosis inhibitor ABT-737 for treating B-cell malignancy" Cancer Gene Therapy (2013) vol. 20, pp. 386-393.
Lee et al. "Xenograft models for the preclinical evaluation of new therapies in acute leukemia" Leukemia & Lymphoma (2007) vol. 48, No. 4, pp. 659-668.
Ohno, et al. "Antigen-binding specificities of antibodies are preimarily determined by seven residues of VH" PNAS (1985) vol. 82, pp. 2945-2949.
Parry et al. "CD28 and Inducible Costimulatory Protein Src Homology 2 Binding Domains Show Distinct Regulation of Phisphatidylinositol 3-Kinase, Bcl-xL, and IL-2 Expession in Primary Human CD4 T Lymphocytes" The Journal of Immunology (2003) vol. 171, pp. 166-174.
Singapore search report and written opinion for Singapore Application No. 11201506603P dated May 31, 2017.
Singapore Search Report and Written Opinion for Singapore Application No. 11201606909R dated Oct. 24, 2017.
Trinh et al. "Optimization of codon pair use within the (GGGGS)3 linker sequence results in enhanced protein expression" Molecular Immunology (2004) vol. 40, pp. 717-722.

(56) References Cited

OTHER PUBLICATIONS

Xu et al. "γc Cytokines IL7 and IL15 Expanded Chimeric Antigen Receptor-Redirected T Cells (CAR-T) with Superior Antitumor Activity in Vivo" Molecular Therapy (2013) vol. 21, pp. S20-S21.
Gill et al, "CD19 CAR-T cells combined with ibrutinib to induce complete remission in CLL" Journal of Clinical Oncologie (2017) vol. 35, No. 15_suppl, Abstract No. 7509.
Clinical Trials.Gov Identifier: NCT02640209, Last Updated Sep. 27, 2016, Retrieved on Nov. 9, 2016.
"Novartis next generation CAR-T cell therapy CTL119 combined with ibrutinib shows high rate of responses in CLL patients" Press Release from Novartis.com, dated May 30, 2017.
Akiba et al. "CD27, a Member of the Tumor Necrosis Factor Receptor Superfamily, Activates NF-kB and Stress-activated Protein Kinase/c-Jun N-terminal Kinase via TRAF2, TRAF5, and NF-kB-inducing Kinase" The Journal of Biological Chemistry (1998) vol. 273, No. 21, pp. 13353-13358.
Alabanza et al. "Function of Novel Anti-CD19 Chimeric Antigen Receptors with Human Variable Regions Is Affected by Hinge and Transmembrane Domains" Molecular Therapy (2017) vol. 25, No. 11, pp. 1-14.
Bridgeman et al. "The Optimal Antigen Response of Chimeric Antigen Receptors Harboring the CD3 Transmembrane Domain Is Dependent upon Incorporation of the Receptor into the Endogenous TCR/CD3 Complex" J. Immunol. (2010) vol. 184, pp. 6938-6949.
Cheadle et al "Natural Expression of the CD19 Antigen Impacts the Long-Term Engraftment but Not Antitumor Activity of CD19-Specific Engineered T Cells" The Journal of Immunology (2010) vol. 184, No. 4, pp. 1885-1896.
Chung et al. "All TRAFs are not created equal: common and distinct molecular mechanisms of TRAF-mediated signa transduction" Journal of Cell Science (2002) vol. 115, pp. 679-688.
GenBank Accession No. NM_000734 "*Homo sapiens* CD247 molecule (CD247), transcript variant 2, mRNA" Dec. 7, 2009.
Irving et al. "Functional Characterization of a Signal Transducing Motif Present in the T Cell Antigen Receptor Chain" Journal of Experimental Medicine (1993) vol. 177, pp. 1093-1103.
Jang et al. "Human 4-1BB (CD137) Signals Are Mediated by TRAF2 and Activate Nuclear Factor-kB" Biochemical and Biophysical Research Communications (1998)) vol. 242, pp. 613-620.
Kharfan-Dabaja et al. "Immunotherapy for chronic lymphocytic leukemia in the era of BTK inhibitors" Leukemia (2014) vol. 28, pp. 507-517.
Sadelain et al., "The Basic Principles of Chimeric Antigen Receptor Design" Cacner Discovery (2013) vol. 3 No. 4 pp. 388-398.
Yamamoto et al. "NF-kB Activation in CD27 Signaling: Involvement of TNF Receptor-Associated Factors in Its Signaling and Identification of Functional Region of CD27" The Journal of Immunology (1998) vol. 161, pp. 4753-4759.

* cited by examiner

CD138+ CD45 dim tumor cells stained for CD19 (x-axis) and CD38 (y-axis)

INTRA CYTOPLASMATIC IFNg PRODUCTION

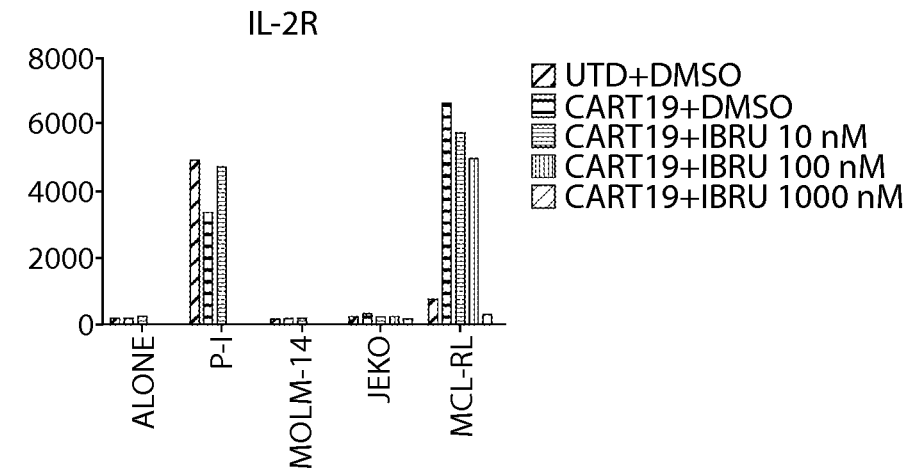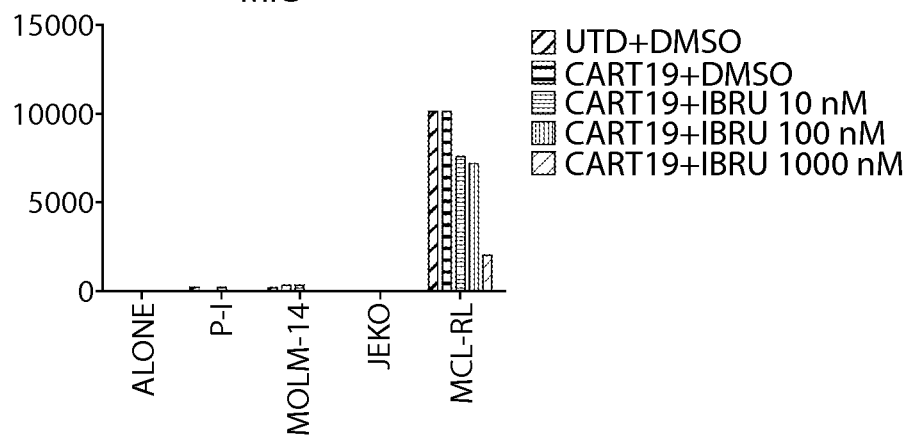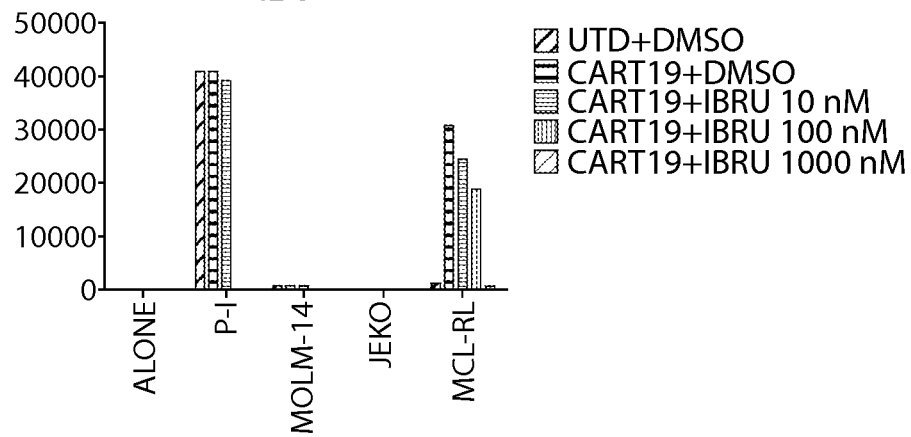
FIG. 15-10

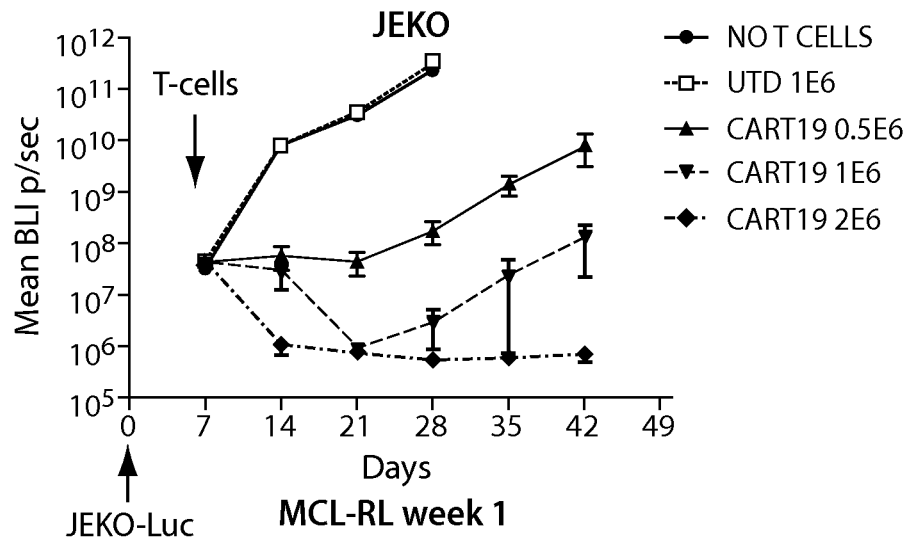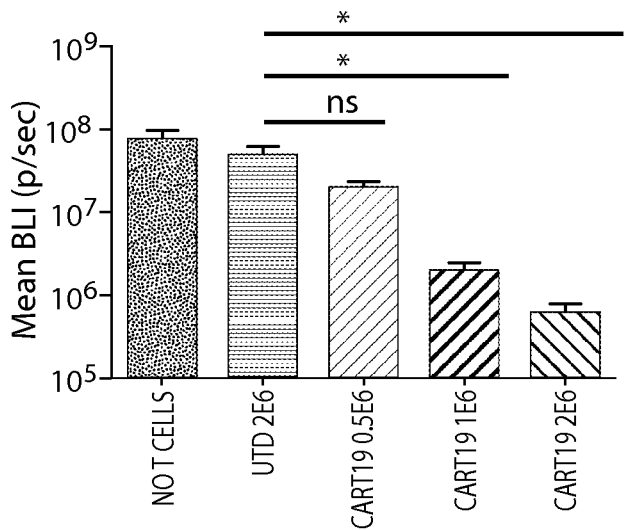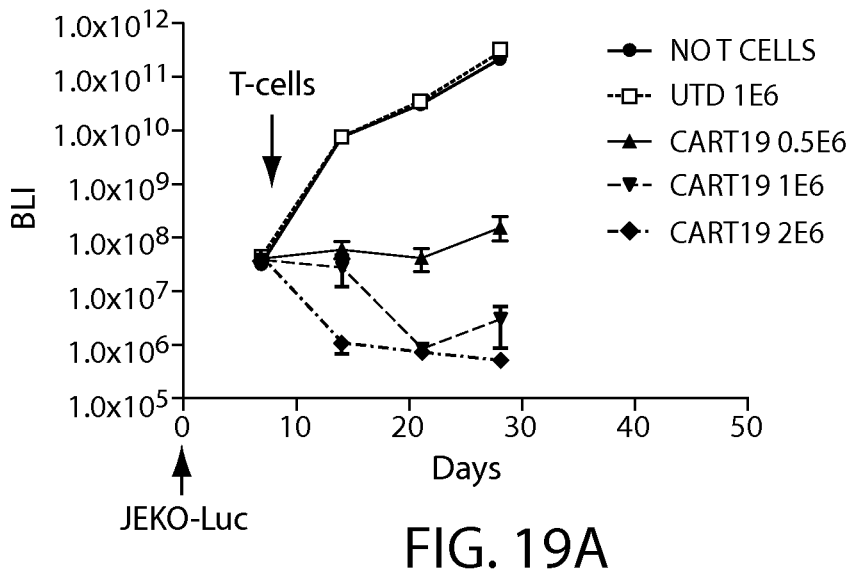
FIG. 19A

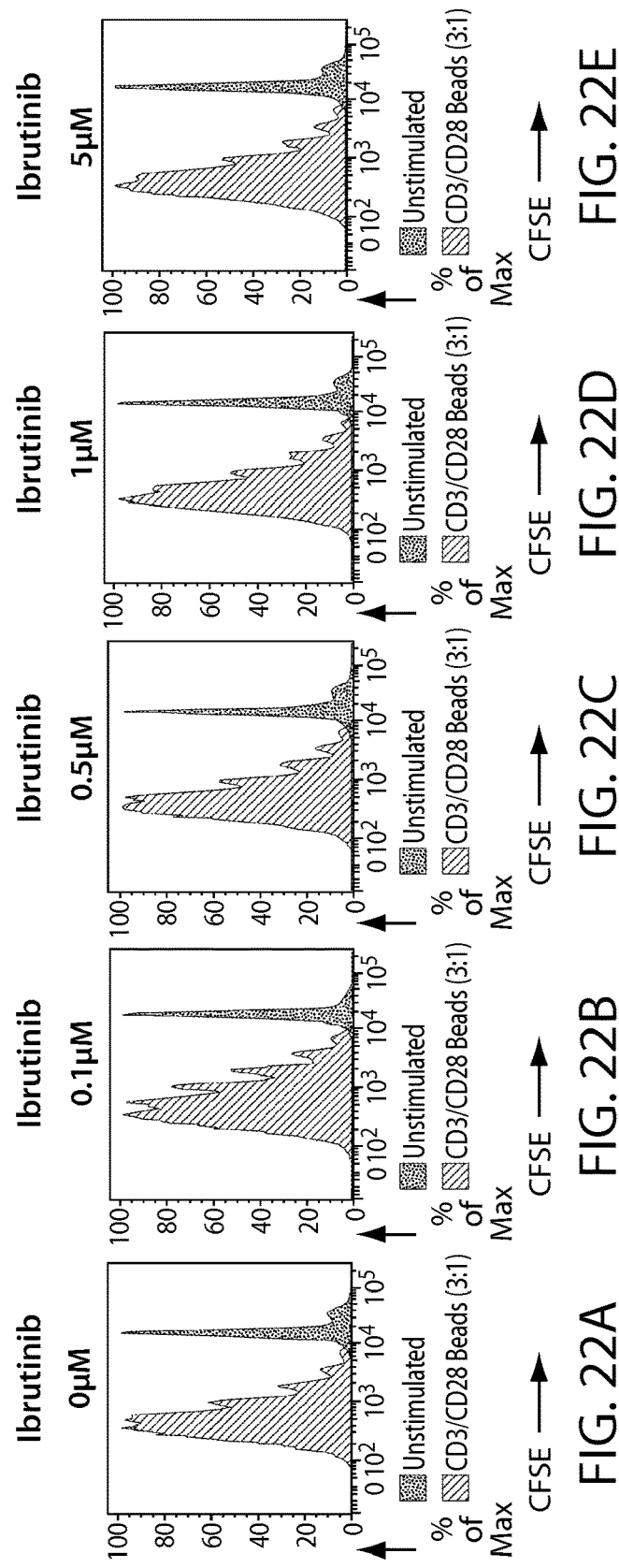

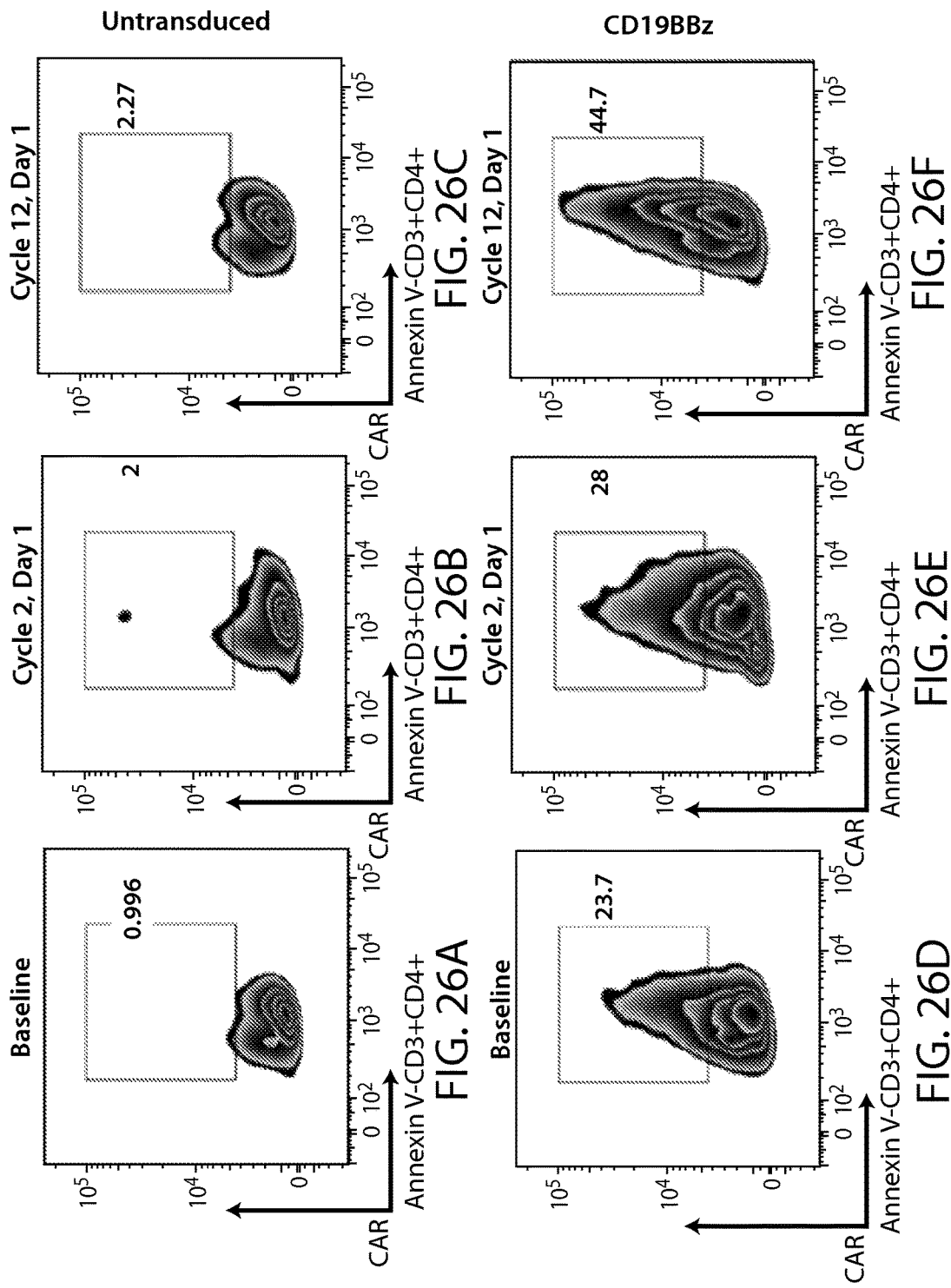

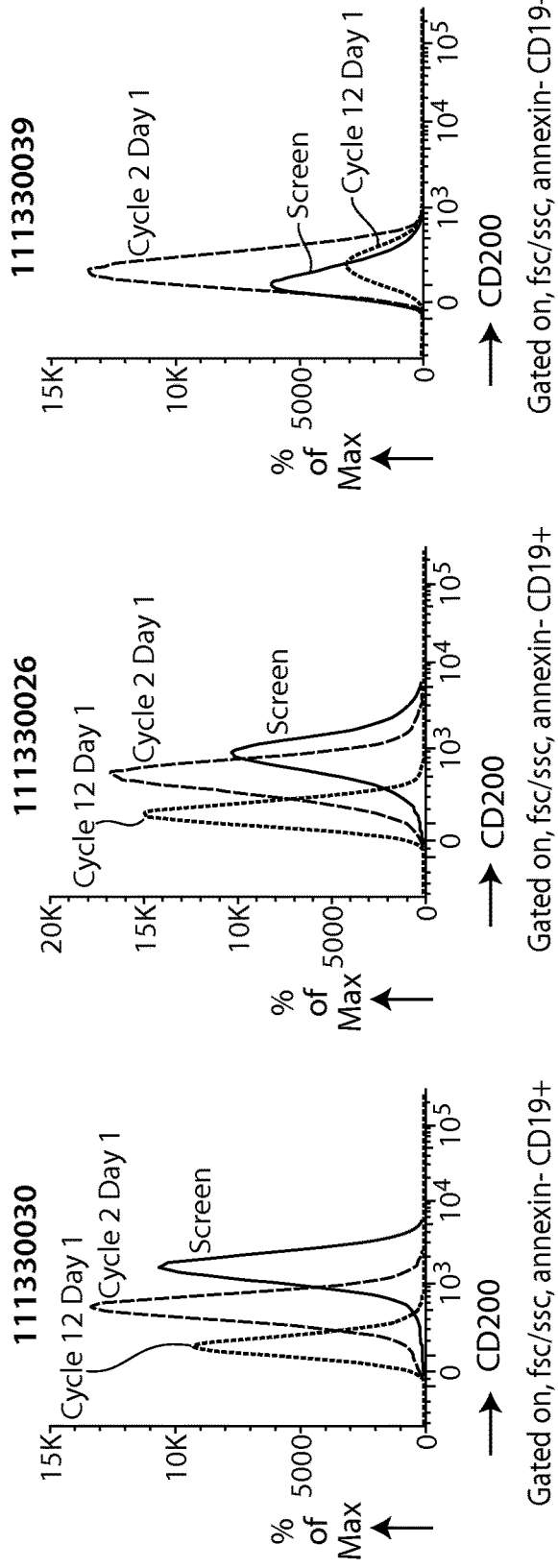

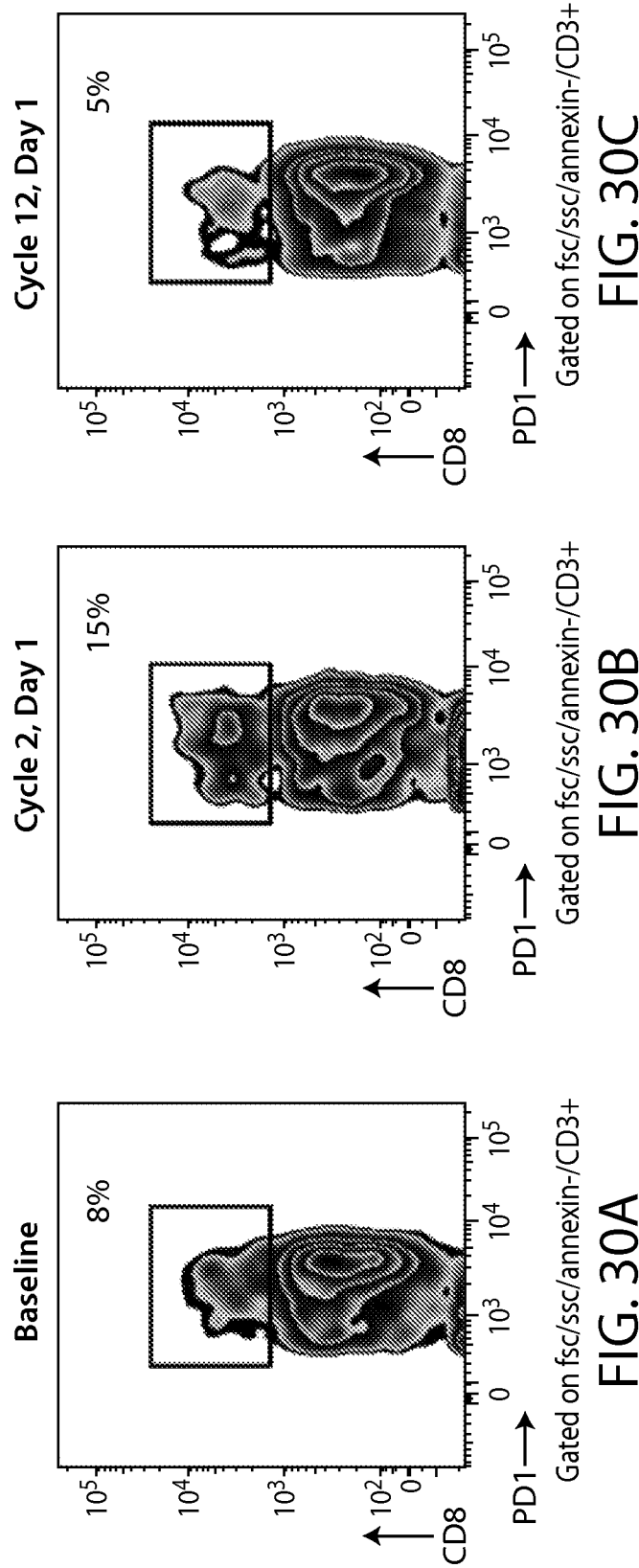

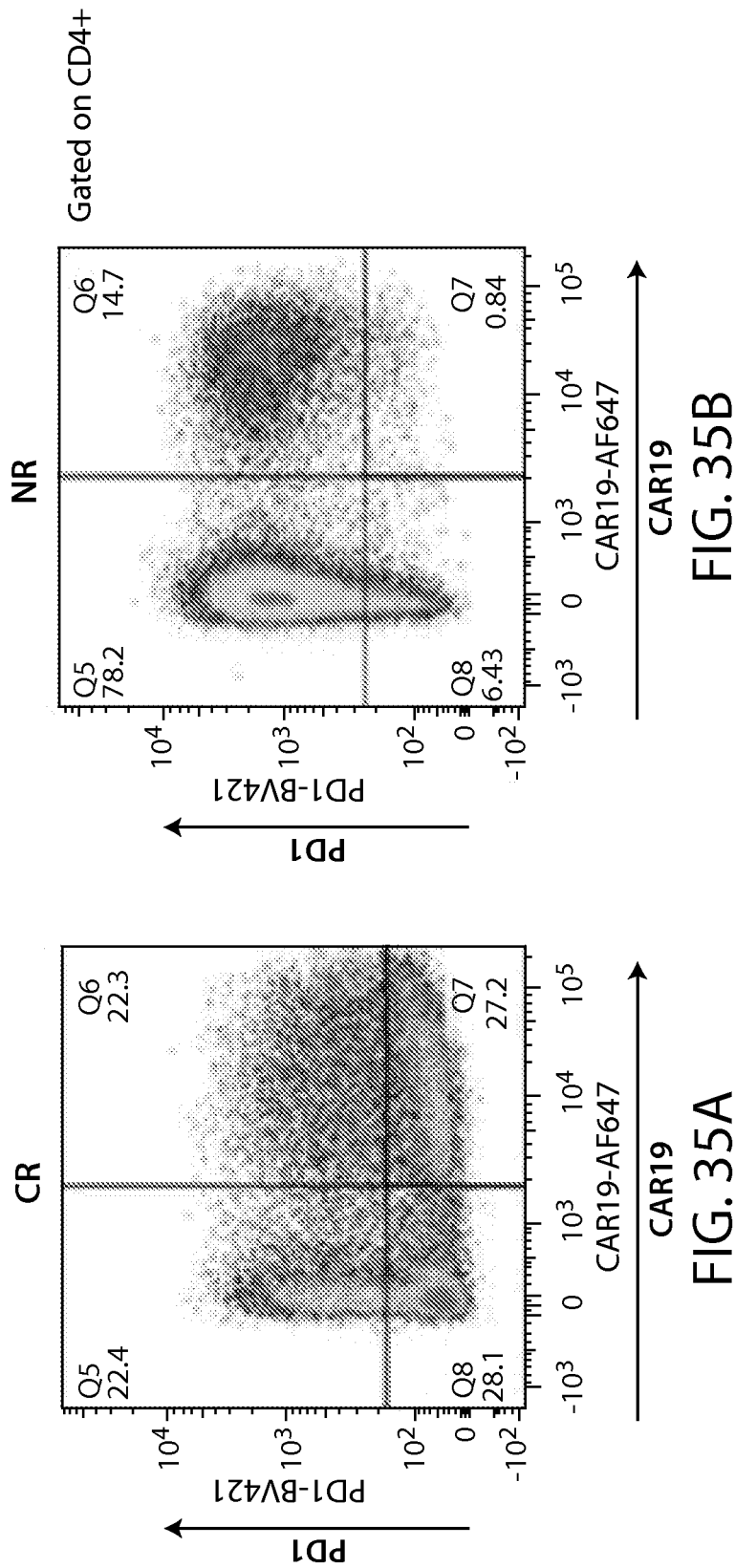

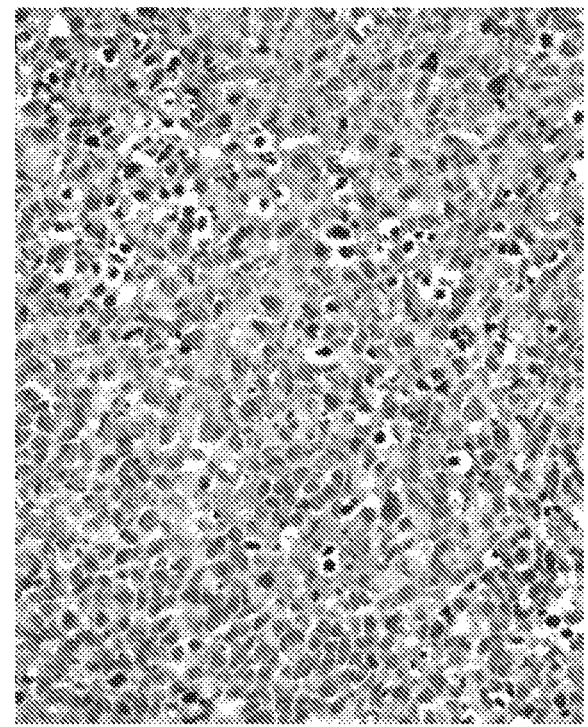
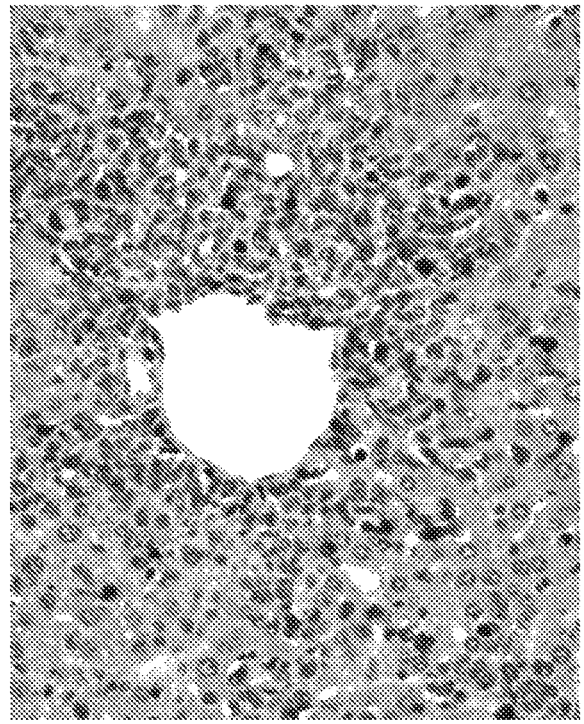
FIG. 52F

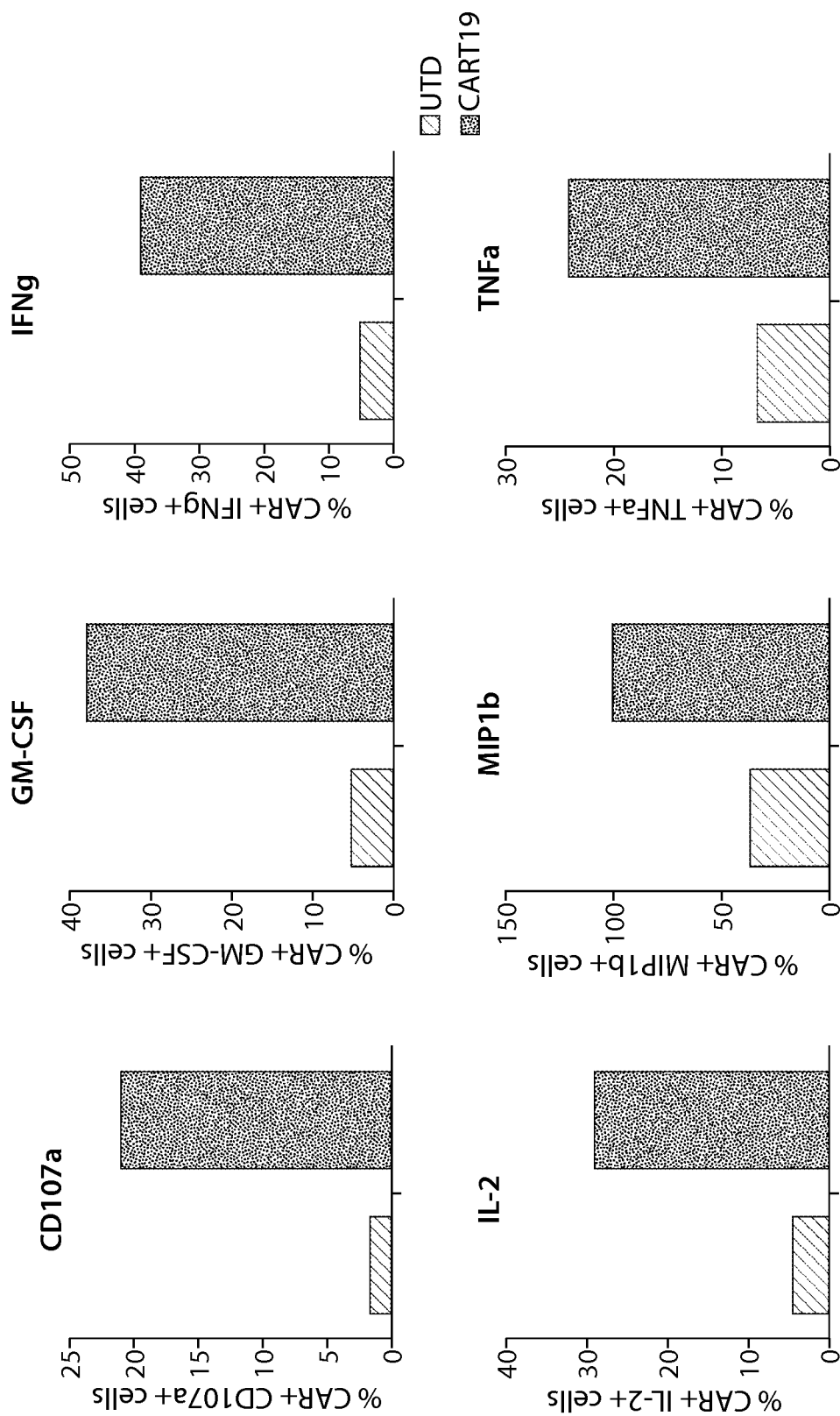

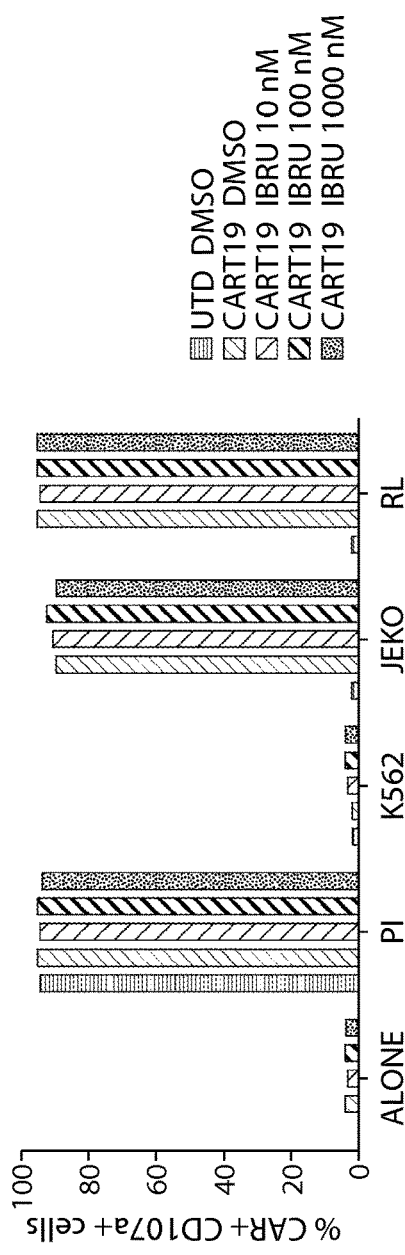
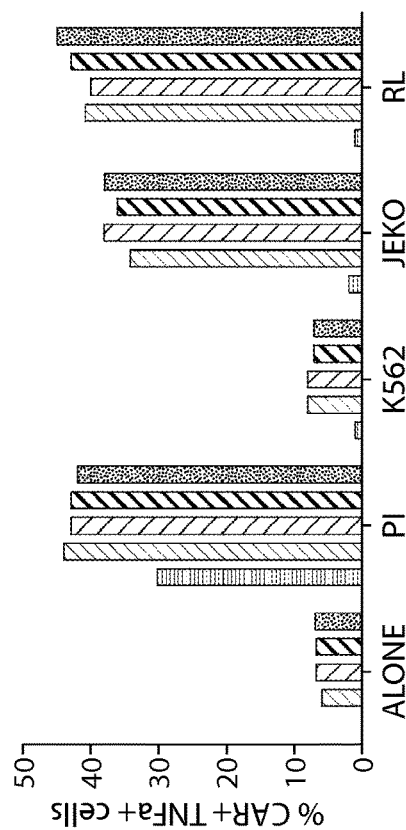
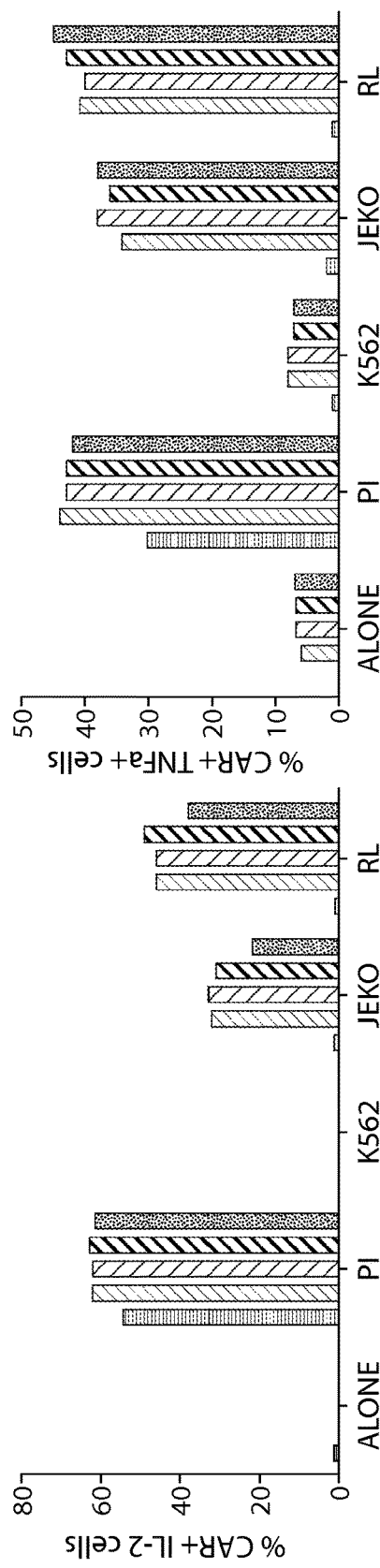
FIG. 54B

PB T cells, 1 week after infusion

SEQUENCE LISTING

```
<160> NUMBER OF SEQ ID NOS: 132

<210> SEQ ID NO 1
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45
```

```
Tyr His Thr Ser Arg Leu His Ser Gly Ile Pro Ala Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Val Tyr Phe Cys Gln Gln Gly Asn Thr Leu Pro Tyr
                 85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
        115                 120                 125

Ser Gly Pro Gly Leu Val Lys Pro Ser Glu Thr Leu Ser Leu Thr Cys
130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Ser Ser Leu Lys Ser Arg Val Thr Ile Ser
            180                 185                 190

Lys Asp Asn Ser Lys Asn Gln Val Ser Leu Lys Leu Ser Ser Val Thr
            195                 200                 205

Ala Ala Asp Thr Ala Val Tyr Tyr Cys Ala Lys His Tyr Tyr Tyr Gly
210                 215                 220

Gly Ser Tyr Ala Met Asp Tyr Trp Gly Gln Gly Thr Leu Val Thr Val
225                 230                 235                 240

Ser Ser

<210> SEQ ID NO 2
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Asp Ile Ser Lys Tyr
                20                  25                  30

Leu Asn Trp Tyr Gln Gln Lys Pro Gly Gln Ala Pro Arg Leu Leu Ile
            35                  40                  45

Tyr His Thr Ser Arg Leu His Ser Gly Ile Pro Ala Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Val Tyr Phe Cys Gln Gln Gly Asn Thr Leu Pro Tyr
                 85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
        115                 120                 125

Ser Gly Pro Gly Leu Val Lys Pro Ser Glu Thr Leu Ser Leu Thr Cys
130                 135                 140

Thr Val Ser Gly Val Ser Leu Pro Asp Tyr Gly Val Ser Trp Ile Arg
145                 150                 155                 160
```

Gln Pro Pro Gly Lys Gly Leu Glu Trp Ile Gly Val Ile Trp Gly Ser
            165                 170                 175

Glu Thr Thr Tyr Tyr Gln Ser Ser Leu Lys Ser Arg Val Thr Ile Ser
            180                 185                 190

Lys Asp Asn Ser Lys Asn Gln Val Ser Leu Lys Leu Ser Ser Val Thr
            195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser

<210> SEQ ID NO 3
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys

<210> SEQ ID NO 4

<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Val Ser Leu Pro Asp Tyr
            20                  25                  30
Gly Val Ser Trp Ile Arg Gln Pro Pro Gly Lys Gly Leu Glu Trp Ile
        35                  40                  45
Gly Val Ile Trp Gly Ser Glu Thr Thr Tyr Tyr Gln Ser Ser Leu Lys
    50                  55                  60
Ser Arg Val Thr Ile Ser Lys Asp Asn Ser Lys Asn Gln Val Ser Leu
65                  70                  75                  80
Lys Leu Ser Ser Val Thr Ala Ala Asp Thr Ala Val Tyr Tyr Cys Ala
                85                  90                  95
Lys His Tyr Tyr Tyr Gly Gly Ser Tyr Ala Met Asp Tyr Trp Gly Gln
            100                 105                 110
Gly Thr Leu Val Thr Val Ser Ser Gly Gly Gly Gly Ser Gly Gly Gly
        115                 120                 125
Gly Ser Gly Gly Gly Gly Ser Glu Ile Val Met Thr Gln Ser Pro Ala
    130                 135                 140
Thr Leu Ser Leu Ser Pro Gly Glu Arg Ala Thr Leu Ser Cys Arg Ala
145                 150                 155                 160
Ser Gln Asp Ile Ser Lys Tyr Leu Asn Trp Tyr Gln Gln Lys Pro Gly
                165                 170                 175
Gln Ala Pro Arg Leu Leu Ile Tyr His Thr Ser Arg Leu His Ser Gly
            180                 185                 190
Ile Pro Ala Arg Phe Ser Gly Ser Gly Ser Gly Thr Asp Tyr Thr Leu
        195                 200                 205
Thr Ile Ser Ser Leu Gln Pro Glu Asp Phe Ala Val Tyr Phe Cys Gln
    210                 215                 220
Gln Gly Asn Thr Leu Pro Tyr Thr Phe Gly Gln Gly Thr Lys Leu Glu
225                 230                 235                 240
Ile Lys
```

<210> SEQ ID NO 5
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

```
Glu Ile Val Met Thr Gln Ser Pro Ala Thr Leu Ser Leu Ser Pro Gly
1               5                   10                  15
Glu Arg Ala Thr Leu Ser Cys Arg Ala Ser Gln Asp Ile Ser Lys Tyr
            20                  25                  30
Leu Asn Trp Tyr Gln Gln Lys Pro Gly Gln Ala Pro Arg Leu Leu Ile
        35                  40                  45
Tyr His Thr Ser Arg Leu His Ser Gly Ile Pro Ala Arg Phe Ser Gly
```

```
                    50                  55                  60

Ser Gly Ser Gly Thr Asp Tyr Thr Leu Thr Ile Ser Ser Leu Gln Pro
 65                  70                  75                  80

Glu Asp Phe Ala Val Tyr Phe Cys Gln Gln Gly Asn Thr Leu Pro Tyr
                     85                  90                  95

Thr Phe Gly Gln Gly Thr Lys Leu Glu Ile Lys Gly Gly Gly Gly Ser
                100                 105                 110

Gly Gly Gly Gly Ser Gly Gly Gly Ser Gly Gly Gly Gly Ser Gln
                115                 120                 125

Val Gln Leu Gln Glu Ser Gly Pro Gly Leu Val Lys Pro Ser Glu Thr
                130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Ser Ser Ser Leu Lys Ser
                180                 185                 190

Arg Val Thr Ile Ser Lys Asp Asn Ser Lys Asn Gln Val Ser Leu Lys
                195                 200                 205

Leu Ser Ser Val Thr Ala Ala Asp Thr Ala Val Tyr Tyr Cys Ala Lys
210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245

<210> SEQ ID NO 6
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Asp Ile Ser Lys Tyr
                20                  25                  30

Leu Asn Trp Tyr Gln Gln Lys Pro Gly Gln Ala Pro Arg Leu Leu Ile
                35                  40                  45

Tyr His Thr Ser Arg Leu His Ser Gly Ile Pro Ala Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Val Tyr Phe Cys Gln Gln Gly Asn Thr Leu Pro Tyr
                     85                  90                  95

Thr Phe Gly Gln Gly Thr Lys Leu Glu Ile Lys Gly Gly Gly Gly Ser
                100                 105                 110

Gly Gly Gly Gly Ser Gly Gly Gly Gly Ser Gly Gly Gly Gly Ser Gln
                115                 120                 125

Val Gln Leu Gln Glu Ser Gly Pro Gly Leu Val Lys Pro Ser Glu Thr
                130                 135                 140

Leu Ser Leu Thr Cys Thr Val Ser Gly Val Ser Leu Pro Asp Tyr Gly
145                 150                 155                 160
```

```
Val Ser Trp Ile Arg Gln Pro Pro Gly Lys Gly Leu Glu Trp Ile Gly
            165                 170                 175

Val Ile Trp Gly Ser Glu Thr Thr Tyr Tyr Gln Ser Ser Leu Lys Ser
        180                 185                 190

Arg Val Thr Ile Ser Lys Asp Asn Ser Lys Asn Gln Val Ser Leu Lys
            195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245

<210> SEQ ID NO 7
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245
```

```
<210> SEQ ID NO 8
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Gly Gly Ser Tyr Ala Met Asp Tyr Trp Gly Gln Gly
            100                 105                 110

Gly Thr Leu Val Thr Val Ser Ser Gly Gly Gly Ser Gly Gly Gly
        115                 120                 125

Gly Ser Gly Gly Gly Gly Ser Gly Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245

<210> SEQ ID NO 9
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
```

```
                 35                  40                  45
Tyr His Thr Ser Arg Leu His Ser Gly Ile Pro Ala Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Val Tyr Phe Cys Gln Gln Gly Asn Thr Leu Pro Tyr
                 85                  90                  95

Thr Phe Gly Gln Gly Thr Lys Leu Glu Ile Lys Gly Gly Gly Gly Ser
                100                 105                 110

Gly Gly Gly Gly Ser Gly Gly Gly Ser Gly Gly Gly Ser Gln
                115                 120                 125

Val Gln Leu Gln Glu Ser Gly Pro Gly Leu Val Lys Pro Ser Glu Thr
130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Asn Ser Ser Leu Lys Ser
                180                 185                 190

Arg Val Thr Ile Ser Lys Asp Asn Ser Lys Asn Gln Val Ser Leu Lys
                195                 200                 205

Leu Ser Ser Val Thr Ala Ala Asp Thr Ala Val Tyr Tyr Cys Ala Lys
210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245

<210> SEQ ID NO 10
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gln Val Gln Leu Gln Glu Ser Gly Pro Gly Leu Val Lys Pro Ser Glu
  1               5                  10                  15

Thr Leu Ser Leu Thr Cys Thr Val Ser Gly Val Ser Leu Pro Asp Tyr
                 20                  25                  30

Gly Val Ser Trp Ile Arg Gln Pro Pro Gly Lys Gly Leu Glu Trp Ile
             35                  40                  45

Gly Val Ile Trp Gly Ser Glu Thr Thr Tyr Tyr Asn Ser Ser Leu Lys
         50                  55                  60

Ser Arg Val Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Lys His Tyr Tyr Tyr Gly Gly Ser Tyr Ala Met Asp Tyr Trp Gly Gln
                100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Gly Ser Glu Ile Val Met
        130                 135                 140
```

```
Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
            245
```

<210> SEQ ID NO 11
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Asn Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240
```

Ser Ser

<210> SEQ ID NO 12
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys

<210> SEQ ID NO 13
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Met Ala Leu Pro Val Thr Ala Leu Leu Leu Pro Leu Ala Leu Leu Leu
1               5                   10                  15

His Ala Ala Arg Pro
            20

<210> SEQ ID NO 14
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 15
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 15

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 16
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 17
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys

```
                35                  40                  45
Pro Arg Arg Lys Asn Pro Gln Glu Gly Leu Tyr Asn Glu Leu Gln Lys
        50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
            100                 105                 110

<210> SEQ ID NO 18
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gly Gly Gly Gly Ser
1               5

<210> SEQ ID NO 19
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly Val Ser Leu Pro Asp Tyr Gly Val Ser
1               5                   10

<210> SEQ ID NO 20
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Val Ile Trp Gly Ser Glu Thr Thr Tyr Tyr Asn Ser Ala Leu Lys Ser
1               5                   10                  15

<210> SEQ ID NO 21
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Val Ile Trp Gly Ser Glu Thr Thr Tyr Tyr Ser Ser Ser Leu Lys Ser
1               5                   10                  15

<210> SEQ ID NO 22
<211> LENGTH: 16
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 22

Val Ile Trp Gly Ser Glu Thr Thr Tyr Tyr Gln Ser Ser Leu Lys Ser
1               5                   10                  15

<210> SEQ ID NO 23
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Val Ile Trp Gly Ser Glu Thr Thr Tyr Tyr Asn Ser Ser Leu Lys Ser
1               5                   10                  15

<210> SEQ ID NO 24
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

His Tyr Tyr Tyr Gly Gly Ser Tyr Ala Met Asp Tyr
1               5                   10

<210> SEQ ID NO 25
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Arg Ala Ser Gln Asp Ile Ser Lys Tyr Leu Asn
1               5                   10

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

His Thr Ser Arg Leu His Ser
1               5

<210> SEQ ID NO 27
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<400> SEQUENCE: 27

Gln Gln Gly Asn Thr Leu Pro Tyr Thr
1               5

<210> SEQ ID NO 28
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Tyr Ser Ser Ser Leu
1               5

<210> SEQ ID NO 29
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Tyr Gln Ser Ser Leu
1               5

<210> SEQ ID NO 30
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Tyr Asn Ser Ser Leu
1               5

<210> SEQ ID NO 31
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
```

```
                85                  90                  95
Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
            115                 120                 125

Gly Gly Gly Ser Gly Gly Gly Gly Ser Gly Gly Gly Gly Ser Gln
            130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
                180                 185                 190

Val Ile Trp Gly Ser Glu Thr Thr Tyr Tyr Ser Ser Leu Lys Ser
            195                 200                 205

Arg Val Thr Ile Ser Lys Asp Asn Ser Lys Asn Gln Val Ser Leu Lys
            210                 215                 220

Leu Ser Ser Val Thr Ala Ala Asp Thr Ala Val Tyr Tyr Cys Ala Lys
225                 230                 235                 240

His Tyr Tyr Tyr Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
            370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
            450                 455                 460

Gln Gly Leu Ser Thr Ala Thr Lys Asp Thr Tyr Asp Ala Leu His Met
465                 470                 475                 480

Gln Ala Leu Pro Pro Arg
            485

<210> SEQ ID NO 32
```

-continued

```
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32
```

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Gln Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

```
Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
                435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 33
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Thr Val Ser Gly Val
            35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65              70                  75                  80

Ser Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
                100                 105                 110

Val Tyr Tyr Cys Ala Lys His Tyr Tyr Tyr Gly Gly Ser Tyr Ala Met
            115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr
            180                 185                 190

Gln Gln Lys Pro Gly Gln Ala Pro Arg Leu Leu Ile Tyr His Thr Ser
            195                 200                 205

Arg Leu His Ser Gly Ile Pro Ala Arg Phe Ser Gly Ser Gly Ser Gly
        210                 215                 220

Thr Asp Tyr Thr Leu Thr Ile Ser Ser Leu Gln Pro Glu Asp Phe Ala
```

```
                225                 230                 235                 240

Val Tyr Phe Cys Gln Gln Gly Asn Thr Leu Pro Tyr Thr Phe Gly Gln
                    245                 250                 255

Gly Thr Lys Leu Glu Ile Lys Thr Thr Thr Pro Ala Pro Arg Pro Pro
                260                 265                 270

Thr Pro Ala Pro Thr Ile Ala Ser Gln Pro Leu Ser Leu Arg Pro Glu
                275                 280                 285

Ala Cys Arg Pro Ala Ala Gly Gly Ala Val His Thr Arg Gly Leu Asp
                290                 295                 300

Phe Ala Cys Asp Ile Tyr Ile Trp Ala Pro Leu Ala Gly Thr Cys Gly
    305                 310                 315                 320

Val Leu Leu Leu Ser Leu Val Ile Thr Leu Tyr Cys Lys Arg Gly Arg
                    325                 330                 335

Lys Lys Leu Leu Tyr Ile Phe Lys Gln Pro Phe Met Arg Pro Val Gln
                    340                 345                 350

Thr Thr Gln Glu Glu Asp Gly Cys Ser Cys Arg Phe Pro Glu Glu Glu
                    355                 360                 365

Glu Gly Gly Cys Glu Leu Arg Val Lys Phe Ser Arg Ser Ala Asp Ala
                370                 375                 380

Pro Ala Tyr Lys Gln Gly Gln Asn Gln Leu Tyr Asn Glu Leu Asn Leu
    385                 390                 395                 400

Gly Arg Arg Glu Glu Tyr Asp Val Leu Asp Lys Arg Arg Gly Arg Asp
                    405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
                435                 440                 445

Gly Met Lys Gly Glu Arg Arg Arg Gly Lys Gly His Asp Gly Leu Tyr
                450                 455                 460

Gln Gly Leu Ser Thr Ala Thr Lys Asp Thr Tyr Asp Ala Leu His Met
    465                 470                 475                 480

Gln Ala Leu Pro Pro Arg
                485

<210> SEQ ID NO 34
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Thr Val Ser Gly Val
            35                  40                  45

Ser Leu Pro Asp Tyr Gly Val Ser Trp Ile Arg Gln Pro Pro Gly Lys
        50                  55                  60

Gly Leu Glu Trp Ile Gly Val Ile Trp Gly Ser Glu Thr Thr Tyr Tyr
65                  70                  75                  80

Gln Ser Ser Leu Lys Ser Arg Val Thr Ile Ser Lys Asp Asn Ser Lys
                85                  90                  95
```

Asn Gln Val Ser Leu Lys Leu Ser Ser Val Thr Ala Ala Asp Thr Ala
                100                 105                 110

Val Tyr Tyr Cys Ala Lys His Tyr Tyr Gly Gly Ser Tyr Ala Met
            115                 120                 125

Asp Tyr Trp Gly Gln Gly Thr Leu Val Thr Val Ser Ser Gly Gly Gly
130                 135                 140

Gly Ser Gly Gly Gly Ser Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr
            180                 185                 190

Gln Gln Lys Pro Gly Gln Ala Pro Arg Leu Leu Ile Tyr His Thr Ser
        195                 200                 205

Arg Leu His Ser Gly Ile Pro Ala Arg Phe Ser Gly Ser Gly Ser Gly
    210                 215                 220

Thr Asp Tyr Thr Leu Thr Ile Ser Ser Leu Gln Pro Glu Asp Phe Ala
225                 230                 235                 240

Val Tyr Phe Cys Gln Gln Gly Asn Thr Leu Pro Tyr Thr Phe Gly Gln
                245                 250                 255

Gly Thr Lys Leu Glu Ile Lys Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 35
<211> LENGTH: 491

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35
```

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gly
    130                 135                 140

Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Ser
        195                 200                 205

Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Gly Ser Tyr Ala Met Asp
                245                 250                 255

Tyr Trp Gly Gln Gly Thr Leu Val Thr Val Ser Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser

```
                370               375               380
Arg Ser Ala Asp Ala Pro Ala Tyr Lys Gln Gly Gln Asn Gln Leu Tyr
385               390               395               400

Asn Glu Leu Asn Leu Gly Arg Arg Glu Glu Tyr Asp Val Leu Asp Lys
            405               410               415

Arg Arg Gly Arg Asp Pro Glu Met Gly Gly Lys Pro Arg Arg Lys Asn
            420               425               430

Pro Gln Glu Gly Leu Tyr Asn Glu Leu Gln Lys Asp Lys Met Ala Glu
            435               440               445

Ala Tyr Ser Glu Ile Gly Met Lys Gly Glu Arg Arg Arg Gly Lys Gly
            450               455               460

His Asp Gly Leu Tyr Gln Gly Leu Ser Thr Ala Thr Lys Asp Thr Tyr
465               470               475               480

Asp Ala Leu His Met Gln Ala Leu Pro Pro Arg
            485               490

<210> SEQ ID NO 36
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Gly Ser Gly
    130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Gln
        195                 200                 205

Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240
```

```
Tyr Tyr Cys Ala Lys His Tyr Tyr Gly Gly Ser Tyr Ala Met Asp
                245                 250                 255

Tyr Trp Gly Gln Gly Thr Leu Val Thr Val Ser Ser Thr Thr Pro
                260                 265                 270

Ala Pro Arg Pro Pro Thr Pro Ala Pro Thr Ile Ala Ser Gln Pro Leu
                275                 280                 285

Ser Leu Arg Pro Glu Ala Cys Arg Pro Ala Ala Gly Gly Ala Val His
                290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
                340                 345                 350

Met Arg Pro Val Gln Thr Thr Gln Glu Glu Asp Gly Cys Ser Cys Arg
                355                 360                 365

Phe Pro Glu Glu Glu Glu Gly Gly Cys Glu Leu Arg Val Lys Phe Ser
                370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
                435                 440                 445

Ala Tyr Ser Glu Ile Gly Met Lys Gly Glu Arg Arg Arg Gly Lys Gly
                450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 37
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Thr Val Ser Gly Val
                35                  40                  45

Ser Leu Pro Asp Tyr Gly Val Ser Trp Ile Arg Gln Pro Pro Gly Lys
                50                  55                  60

Gly Leu Glu Trp Ile Gly Val Ile Trp Gly Ser Glu Thr Thr Tyr Tyr
65                  70                  75                  80

Ser Ser Ser Leu Lys Ser Arg Val Thr Ile Ser Lys Asp Asn Ser Lys
                85                  90                  95
```

```
Asn Gln Val Ser Leu Lys Leu Ser Ser Val Thr Ala Ala Asp Thr Ala
                100                 105                 110
Val Tyr Tyr Cys Ala Lys His Tyr Tyr Gly Gly Ser Tyr Ala Met
            115                 120                 125
Asp Tyr Trp Gly Gln Gly Thr Leu Val Thr Val Ser Ser Gly Gly Gly
        130                 135                 140
Gly Ser Gly Gly Gly Gly Ser Gly Gly Gly Gly Ser Gly Gly Gly Gly
145                 150                 155                 160
Ser Glu Ile Val Met Thr Gln Ser Pro Ala Thr Leu Ser Leu Ser Pro
                165                 170                 175
Gly Glu Arg Ala Thr Leu Ser Cys Arg Ala Ser Gln Asp Ile Ser Lys
            180                 185                 190
Tyr Leu Asn Trp Tyr Gln Gln Lys Pro Gly Gln Ala Pro Arg Leu Leu
        195                 200                 205
Ile Tyr His Thr Ser Arg Leu His Ser Gly Ile Pro Ala Arg Phe Ser
210                 215                 220
Gly Ser Gly Ser Gly Thr Asp Tyr Thr Leu Thr Ile Ser Ser Leu Gln
225                 230                 235                 240
Pro Glu Asp Phe Ala Val Tyr Phe Cys Gln Gln Gly Asn Thr Leu Pro
                245                 250                 255
Tyr Thr Phe Gly Gln Gly Thr Lys Leu Glu Ile Lys Thr Thr Thr Pro
            260                 265                 270
Ala Pro Arg Pro Pro Thr Pro Ala Pro Thr Ile Ala Ser Gln Pro Leu
        275                 280                 285
Ser Leu Arg Pro Glu Ala Cys Arg Pro Ala Ala Gly Gly Ala Val His
290                 295                 300
Thr Arg Gly Leu Asp Phe Ala Cys Asp Ile Tyr Ile Trp Ala Pro Leu
305                 310                 315                 320
Ala Gly Thr Cys Gly Val Leu Leu Leu Ser Leu Val Ile Thr Leu Tyr
                325                 330                 335
Cys Lys Arg Gly Arg Lys Lys Leu Leu Tyr Ile Phe Lys Gln Pro Phe
            340                 345                 350
Met Arg Pro Val Gln Thr Thr Gln Glu Glu Asp Gly Cys Ser Cys Arg
        355                 360                 365
Phe Pro Glu Glu Glu Glu Gly Gly Cys Glu Leu Arg Val Lys Phe Ser
370                 375                 380
Arg Ser Ala Asp Ala Pro Ala Tyr Lys Gln Gly Gln Asn Gln Leu Tyr
385                 390                 395                 400
Asn Glu Leu Asn Leu Gly Arg Arg Glu Glu Tyr Asp Val Leu Asp Lys
                405                 410                 415
Arg Arg Gly Arg Asp Pro Glu Met Gly Gly Lys Pro Arg Arg Lys Asn
            420                 425                 430
Pro Gln Glu Gly Leu Tyr Asn Glu Leu Gln Lys Asp Lys Met Ala Glu
        435                 440                 445
Ala Tyr Ser Glu Ile Gly Met Lys Gly Glu Arg Arg Arg Gly Lys Gly
450                 455                 460
His Asp Gly Leu Tyr Gln Gly Leu Ser Thr Ala Thr Lys Asp Thr Tyr
465                 470                 475                 480
Asp Ala Leu His Met Gln Ala Leu Pro Pro Arg
                485                 490

<210> SEQ ID NO 38
<211> LENGTH: 491
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 38

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Gln Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380
```

```
Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
            405                 410                 415

Arg Arg Gly Arg Asp Pro Glu Met Gly Gly Lys Pro Arg Arg Lys Asn
        420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
        450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 39
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gly
    130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Asn
        195                 200                 205

Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240
```

```
Tyr Tyr Cys Ala Lys His Tyr Tyr Tyr Gly Gly Ser Tyr Ala Met Asp
                245                 250                 255

Tyr Trp Gly Gln Gly Thr Leu Val Thr Val Ser Ser Thr Thr Thr Pro
            260                 265                 270

Ala Pro Arg Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
            325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
            355                 360                 365

Phe Pro Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
            405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
        450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 40
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
            85                  90                  95

Ser Ser Leu Gln Pro Glu Asp Phe Ala Val Tyr Phe Cys Gln Gln Gly
```

```
                    100              105                110
Asn Thr Leu Pro Tyr Thr Phe Gly Gln Gly Thr Lys Leu Glu Ile Lys
            115                 120                 125
Gly Gly Gly Gly Ser Gly Gly Gly Gly Ser Gly Gly Gly Ser Gly
        130                 135                 140
Gly Gly Gly Ser Gln Val Gln Leu Gln Glu Ser Gly Pro Gly Leu Val
145                 150                 155                 160
Lys Pro Ser Glu Thr Leu Ser Leu Thr Cys Thr Val Ser Gly Val Ser
                165                 170                 175
Leu Pro Asp Tyr Gly Val Ser Trp Ile Arg Gln Pro Pro Gly Lys Gly
            180                 185                 190
Leu Glu Trp Ile Gly Val Ile Trp Gly Ser Glu Thr Thr Tyr Tyr Asn
        195                 200                 205
Ser Ser Leu Lys Ser Arg Val Thr Ile Ser Lys Asp Asn Ser Lys Asn
    210                 215                 220
Gln Val Ser Leu Lys Leu Ser Ser Val Thr Ala Ala Asp Thr Ala Val
225                 230                 235                 240
Tyr Tyr Cys Ala Lys His Tyr Tyr Gly Gly Ser Tyr Ala Met Asp
                245                 250                 255
Tyr Trp Gly Gln Gly Thr Leu Val Thr Val Ser Ser Thr Thr Thr Pro
            260                 265                 270
Ala Pro Arg Pro Pro Thr Pro Ala Pro Thr Ile Ala Ser Gln Pro Leu
        275                 280                 285
Ser Leu Arg Pro Glu Ala Cys Arg Pro Ala Ala Gly Gly Ala Val His
    290                 295                 300
Thr Arg Gly Leu Asp Phe Ala Cys Asp Ile Tyr Ile Trp Ala Pro Leu
305                 310                 315                 320
Ala Gly Thr Cys Gly Val Leu Leu Leu Ser Leu Val Ile Thr Leu Tyr
                325                 330                 335
Cys Lys Arg Gly Arg Lys Lys Leu Leu Tyr Ile Phe Lys Gln Pro Phe
            340                 345                 350
Met Arg Pro Val Gln Thr Thr Gln Glu Glu Asp Gly Cys Ser Cys Arg
        355                 360                 365
Phe Pro Glu Glu Glu Glu Gly Gly Cys Glu Leu Arg Val Lys Phe Ser
    370                 375                 380
Arg Ser Ala Asp Ala Pro Ala Tyr Lys Gln Gly Gln Asn Gln Leu Tyr
385                 390                 395                 400
Asn Glu Leu Asn Leu Gly Arg Arg Glu Glu Tyr Asp Val Leu Asp Lys
                405                 410                 415
Arg Arg Gly Arg Asp Pro Glu Met Gly Gly Lys Pro Arg Arg Lys Asn
            420                 425                 430
Pro Gln Glu Gly Leu Tyr Asn Glu Leu Gln Lys Asp Lys Met Ala Glu
        435                 440                 445
Ala Tyr Ser Glu Ile Gly Met Lys Gly Glu Arg Arg Arg Gly Lys Gly
    450                 455                 460
His Asp Gly Leu Tyr Gln Gly Leu Ser Thr Ala Thr Lys Asp Thr Tyr
465                 470                 475                 480
Asp Ala Leu His Met Gln Ala Leu Pro Pro Arg
                485                 490

<210> SEQ ID NO 41
<211> LENGTH: 491
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 41

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Asn Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380
```

```
Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Tyr Asp Val Leu Asp Lys
            405                 410                 415

Arg Arg Gly Arg Asp Pro Glu Met Gly Gly Lys Pro Arg Arg Lys Asn
        420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 42
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Asn Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
```

```
                    245                 250                 255
Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
        370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
        450                 455                 460

Gln Gly Leu Ser Thr Ala Thr Lys Asp Thr Tyr Asp Ala Leu His Met
465                 470                 475                 480

Gln Ala Leu Pro Pro Arg
            485

<210> SEQ ID NO 43
<211> LENGTH: 112
<212> TYPE: PRT
<213> ORGANISM: Homo sapiens

<400> SEQUENCE: 43

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 44
<211> LENGTH: 336
```

<212> TYPE: DNA
<213> ORGANISM: Homo sapiens

<400> SEQUENCE: 44

```
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatggggg aaagccgaga aggaagaacc ctcaggaagg cctgtacaat    180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                             336
```

<210> SEQ ID NO 45
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 45

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
225                 230
```

<210> SEQ ID NO 46
<211> LENGTH: 690
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic polynucleotide"

<400> SEQUENCE: 46
gagagcaagt acggccctcc ctgccccct tgccctgccc ccgagttcct gggcggaccc      60
agcgtgttcc tgttccccc caagcccaag dacaccctga tgatcagccg acccccgag     120 gtgacctgtg tggtggtgga cgtgtcccag gaggaccccg aggtccagtt caactggtac    180
gtggacggcg tggaggtgca caacgccaag accaagcccc gggaggagca gttcaatagc    240
acctaccggg tggtgtccgt gctgaccgtg ctgcaccagg actggctgaa cggcaaggaa    300
tacaagtgta aggtgtccaa caagggcctg cccagcagca tcgagaaaac catcagcaag    360
gccaagggcc agcctcggga gccccaggtg tacaccctgc cccctagcca agaggagatg    420
accaagaacc aggtgtccct gacctgcctg gtgaagggct tctaccccag cgacatcgcc    480
gtggagtggg agagcaacgg ccagcccgag aacaactaca agaccacccc ccctgtgctg    540
gacagcgacg gcagcttctt cctgtacagc cggctgaccg tggacaagag ccggtggcag    600
gagggcaacg tctttagctg ctccgtgatg cacgaggccc tgcacaacca ctacacccag    660
aagagcctga gcctgtccct gggcaagatg                                    690

<210> SEQ ID NO 47
<211> LENGTH: 282
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Arg Trp Pro Glu Ser Pro Lys Ala Gln Ala Ser Val Pro Thr Ala
1               5                   10                  15

Gln Pro Gln Ala Glu Gly Ser Leu Ala Lys Ala Thr Thr Ala Pro Ala
                20                  25                  30

Thr Thr Arg Asn Thr Gly Arg Gly Gly Glu Glu Lys Lys Lys Glu Lys
            35                  40                  45

Glu Lys Glu Glu Gln Glu Glu Arg Glu Thr Lys Thr Pro Glu Cys Pro
        50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190
```

-continued

```
Trp Leu Leu Cys Glu Val Ser Gly Phe Ser Pro Asn Ile Leu Leu
            195                 200                 205
Met Trp Leu Glu Asp Gln Arg Glu Val Asn Thr Ser Gly Phe Ala Pro
210                 215                 220
Ala Arg Pro Pro Pro Gln Pro Gly Ser Thr Thr Phe Trp Ala Trp Ser
225                 230                 235                 240
Val Leu Arg Val Pro Ala Pro Pro Ser Pro Gln Pro Ala Thr Tyr Thr
                245                 250                 255
Cys Val Val Ser His Glu Asp Ser Arg Thr Leu Leu Asn Ala Ser Arg
                260                 265                 270
Ser Leu Glu Val Ser Tyr Val Thr Asp His
                275                 280
```

<210> SEQ ID NO 48
<211> LENGTH: 847
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 48

```
aggtggcccg aaagtcccaa ggcccaggca tctagtgttc ctactgcaca gccccaggca    60
gaaggcagcc tagccaaagc tactactgca cctgccacta cgcgcaatac tggccgtggc   120
ggggaggaga agaaaaagga gaaagagaaa gaagaacagg aagagaggga gaccaagacc   180
cctgaatgtc catcccatac ccagccgctg ggcgtctatc tcttgactcc cgcagtacag   240
gacttgtggc ttagagataa ggccaccttt acatgtttcg tcgtgggctc tgacctgaag   300
gatgcccatt tgacttggga ggttgccgga aaggtaccca ggggggggt tgaggaaggg   360
ttgctggagc gccattccaa tggctctcag agccagcact caagactcac ccttccgaga   420
tccctgtgga cgccgggac tctgtcaca tgtactctaa atcatcctag cctgccccca   480
cagcgtctga tggcccttag agagccagcc gcccaggcac cagttaagct tagcctgaat   540
ctgctcgcca gtagtgatcc cccagaggcc gccagctggc tcttatgcga agtgtccggc   600
tttagcccgc ccaacatctt gctcatgtgg ctggaggacc agcgagaagt gaacaccagc   660
ggcttcgctc cagcccggcc cccacccag ccgggttcta ccacattctg ggcctggagt   720
gtcttaaggg tcccagcacc acctagcccc cagccagcca catacacctg tgttgtgtcc   780
catgaagata gcaggaccct gctaaatgct tctaggagtc tggaggtttc ctacgtgact   840
gaccatt                                                             847
```

<210> SEQ ID NO 49
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 49

```
Gly Gly Gly Gly Ser Gly Gly Gly Gly Ser
1               5                   10
```

<210> SEQ ID NO 50
<211> LENGTH: 30
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Gly Gly Thr Gly Gly Cys Gly Gly Ala Gly Gly Thr Thr Cys Thr Gly
1               5                   10                  15

Gly Ala Gly Gly Thr Gly Gly Ala Gly Gly Thr Thr Cys Cys
            20                  25                  30

<210> SEQ ID NO 51
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 52
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                    123

<210> SEQ ID NO 53
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(30)
<223> OTHER INFORMATION: /note="This sequence may encompass 1-6
      repeating "Gly Gly Gly Gly Ser" repeating units"

<400> SEQUENCE: 53

Gly Gly Gly Gly Ser Gly Gly Gly Gly Ser Gly Gly Gly Gly Ser Gly
1               5                   10                  15

Gly Gly Ser Gly Gly Gly Gly Ser Gly Gly Gly Gly Ser
            20                  25                  30

<210> SEQ ID NO 54
<211> LENGTH: 63
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
atggccctgc ctgtgacagc cctgctgctg cctctggctc tgctgctgca tgccgctaga     60
ccc                                                                   63

<210> SEQ ID NO 55
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55
accacgacgc cagcgccgcg accaccaaca ccggcgccca ccatcgcgtc gcagcccctg     60
tccctgcgcc agaggcgtg ccggccagcg gcggggggcg cagtgcacac gaggggggctg   120 gacttcgcct gtgat                                                     135

<210> SEQ ID NO 56
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
atctacatct gggcgcsctt ggccgggact tgtggggtcc ttctcctgtc actggttatc     60 acccttact gc                                                         72

<210> SEQ ID NO 57
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Tyr Asn Ser Ala Leu
1               5

<210> SEQ ID NO 58
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Met Ala Leu Pro Val Thr Ala Leu Leu Leu Pro Leu Ala Leu Leu Leu
1               5                  10                  15

His Ala Ala Arg Pro Asp Ile Gln Met Thr Gln Thr Thr Ser Ser Leu
            20                  25                  30
```

Ser Ala Ser Leu Gly Asp Arg Val Thr Ile Ser Cys Arg Ala Ser Gln
             35                      40                      45

Asp Ile Ser Lys Tyr Leu Asn Trp Tyr Gln Gln Lys Pro Asp Gly Thr
         50                      55                  60

Val Lys Leu Leu Ile Tyr His Thr Ser Arg Leu His Ser Gly Val Pro
 65              70                      75                  80

Ser Arg Phe Ser Gly Ser Gly Ser Gly Thr Asp Tyr Ser Leu Thr Ile
                 85                  90                      95

Ser Asn Leu Glu Gln Glu Asp Ile Ala Thr Tyr Phe Cys Gln Gln Gly
             100                 105                 110

Asn Thr Leu Pro Tyr Thr Phe Gly Gly Gly Thr Lys Leu Glu Ile Thr
             115                 120                 125

Gly Gly Gly Gly Ser Gly Gly Gly Ser Gly Gly Gly Gly Ser Glu
             130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                 165                 170                 175

Val Ser Trp Ile Arg Gln Pro Pro Arg Lys Gly Leu Glu Trp Leu Gly
             180                 185                 190

Val Ile Trp Gly Ser Glu Thr Thr Tyr Tyr Asn Ser Ala Leu Lys Ser
             195                 200                 205

Arg Leu Thr Ile Ile Lys Asp Asn Ser Lys Ser Gln Val Phe Leu Lys
             210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                 245                 250                 255

Thr Ser Val Thr Val Ser Ser Thr Thr Thr Pro Ala Pro Arg Pro Pro
             260                 265                 270

Thr Pro Ala Pro Thr Ile Ala Ser Gln Pro Leu Ser Leu Arg Pro Glu
             275                 280                 285

Ala Cys Arg Pro Ala Ala Gly Gly Ala Val His Thr Arg Gly Leu Asp
             290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                 325                 330                 335

Lys Lys Leu Leu Tyr Ile Phe Lys Gln Pro Phe Met Arg Pro Val Gln
             340                 345                 350

Thr Thr Gln Glu Glu Asp Gly Cys Ser Cys Arg Phe Pro Glu Glu Glu
             355                 360                 365

Glu Gly Gly Cys Glu Leu Arg Val Lys Phe Ser Arg Ser Ala Asp Ala
             370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                 405                 410                 415

Pro Glu Met Gly Gly Lys Pro Arg Arg Lys Asn Pro Gln Glu Gly Leu
             420                 425                 430

Tyr Asn Glu Leu Gln Lys Asp Lys Met Ala Glu Ala Tyr Ser Glu Ile
             435                 440                 445

Gly Met Lys Gly Glu Arg Arg Gly Lys Gly His Asp Gly Leu Tyr
            450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 59
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 60
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 60

| | |
|---|---|
| aaacggggca gaaagaaact cctgtatata ttcaaacaac catttatgag accagtacaa | 60 |
| actactcaag aggaagatgg ctgtagctgc cgatttccag aagaagaaga aggaggatgt | 120 |
| gaactg | 126 |

<210> SEQ ID NO 61
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 61

| | |
|---|---|
| atggccctcc ctgtcaccgc cctgctgctt ccgctggctc ttctgctcca cgccgctcgg | 60 |
| cccgaaattg tgatgaccca gtcacccgcc actcttagcc tttcacccgg tgagcgcgca | 120 |
| accctgtctt gcagagcctc ccaagacatc tcaaaatacc ttaattggta tcaacagaag | 180 |
| cccggacagg ctcctcgcct tctgatctac cacaccagcc ggctccattc tggaatccct | 240 |
| gccaggttca gcgtagcgg atctgggacc gactacaccc tcactatcag ctcactgcag | 300 |
| ccagaggact cgctgtctta tttctgtcag caagggaaca ccctgcccta cacctttgga | 360 |
| cagggcacca agctcgagat taaaggtgga ggtggcagcg gaggaggtgg gtccggcggt | 420 |
| ggaggaagcc aggtccaact ccaagaaagc ggaccgggtc ttgtgaagcc atcagaaact | 480 |
| ctttcactga cttgtactgt gagcggagtg tctctcccg attacggggt gtcttggatc | 540 |
| agacagccac cggggaaggg tctggaatgg attggagtga tttggggctc tgagactact | 600 |
| tactactctt catccctcaa gtcacgcgtc accatctcaa aggacaactc taagaatcag | 660 |
| gtgtcactga aactgtcatc tgtgaccgca gccgacaccg ccgtgtacta ttgcgctaag | 720 |
| cattactatt atggcgggag ctacgcaatg gattactggg gacagggtac tctggtcacc | 780 |
| gtgtccagcc accaccatca tcaccatcac cat | 813 |

<210> SEQ ID NO 62
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 62

| | |
|---|---|
| atggccctcc ctgtcaccgc cctgctgctt ccgctggctc ttctgctcca cgccgctcgg | 60 |
| cccgaaattg tgatgaccca gtcacccgcc actcttagcc tttcacccgg tgagcgcgca | 120 |
| accctgtctt gcagagcctc ccaagacatc tcaaaatacc ttaattggta tcaacagaag | 180 |
| cccggacagg ctcctcgcct tctgatctac cacaccagcc ggctccattc tggaatccct | 240 |
| gccaggttca gcggtagcgg atctgggacc gactacaccc tcactatcag ctcactgcag | 300 |
| ccagaggact cgctgtctta tttctgtcag caagggaaca ccctgcccta cacctttgga | 360 |
| cagggcacca agctcgagat taaaggtgga ggtggcagcg gaggaggtgg gtccggcggt | 420 |
| ggaggaagcc aggtccaact ccaagaaagc ggaccgggtc ttgtgaagcc atcagaaact | 480 |
| ctttcactga cttgtactgt gagcggagtg tctctcccg attacggggt gtcttggatc | 540 |
| agacagccac cggggaaggg tctggaatgg attggagtga tttggggctc tgagactact | 600 |

```
tactaccaat catccctcaa gtcacgcgtc accatctcaa aggacaactc taagaatcag    660
gtgtcactga aactgtcatc tgtgaccgca gccgacaccg ccgtgtacta ttgcgctaag    720
cattactatt atggcgggag ctacgcaatg gattactggg gacagggtac tctggtcacc    780
gtgtccagcc accaccatca tcaccatcac cat                                813
```

<210> SEQ ID NO 63
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 63

```
atggctctgc ccgtgaccgc actcctcctg ccactggctc tgctgcttca cgccgctcgc     60
ccacaagtcc agcttcaaga atcagggcct ggtctggtga agccatctga gactctgtcc    120
ctcacttgca ccgtgagcgg agtgtccctc ccagactacg gagtgagctg gattagacag    180
cctcccggaa agggactgga gtggatcgga gtgatttggg gtagcgaaac cacttactat    240
tcatcttccc tgaagtcacg ggtcaccatt tcaaaggata actcaaagaa tcaagtgagc    300
ctcaagctct catcagtcac cgccgctgac accgccgtgt attactgtgc caagcattac    360
tactatggag gtcctacgc catggactac tggggccagg gaactctggt cactgtgtca    420
tctggtggag gaggtagcgg aggaggcggg agcggtggag gtggctccga aatcgtgatg    480
acccagagcc ctgcaaccct gtccctttct cccggggaac gggctaccct ttcttgtcgg    540
gcatcacaag atatctcaaa atacctcaat tggtatcaac agaagccggg acaggcccct    600
aggcttctta tctaccacac ctctcgcctg catagcggga ttcccgcacg ctttagcggg    660
tctggaagcg ggaccgacta cactctgacc atctcatctc tccagcccga ggacttcgcc    720
gtctacttct gccagcaggg taacaccctg ccgtacacct tcggccaggg caccaagctt    780
gagatcaaac atcaccacca tcatcaccat cac                                813
```

<210> SEQ ID NO 64
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 64

```
atggctctgc ccgtgaccgc actcctcctg ccactggctc tgctgcttca cgccgctcgc     60
ccacaagtcc agcttcaaga atcagggcct ggtctggtga agccatctga gactctgtcc    120
ctcacttgca ccgtgagcgg agtgtccctc ccagactacg gagtgagctg gattagacag    180
cctcccggaa agggactgga gtggatcgga gtgatttggg gtagcgaaac cacttactat    240
caatcttccc tgaagtcacg ggtcaccatt tcaaaggata actcaaagaa tcaagtgagc    300
ctcaagctct catcagtcac cgccgctgac accgccgtgt attactgtgc caagcattac    360
tactatggag gtcctacgc catggactac tggggccagg gaactctggt cactgtgtca    420
tctggtggag gaggtagcgg aggaggcggg agcggtggag gtggctccga aatcgtgatg    480
acccagagcc ctgcaaccct gtccctttct cccggggaac gggctaccct ttcttgtcgg    540
gcatcacaag atatctcaaa atacctcaat tggtatcaac agaagccggg acaggcccct    600
```

```
aggcttctta tctaccacac ctctcgcctg catagcggga ttcccgcacg ctttagcggg      660
tctggaagcg ggaccgacta cactctgacc atctcatctc tccagcccga ggacttcgcc      720
gtctacttct gccagcaggg taacaccctg ccgtacacct tcggccaggg caccaagctt      780
gagatcaaac atcaccacca tcatcaccat cac                                   813
```

<210> SEQ ID NO 65
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65

```
atggccctcc cagtgaccgc tctgctgctg cctctcgcac ttcttctcca tgccgctcgg       60
cctgagatcg tcatgaccca aagccccgct accctgtccc tgtcacccgg cgagagggca      120 acccttcat gcagggccag ccaggacatt tctaagtacc tcaactggta tcagcagaag      180
ccagggcagg ctcctcgcct gctgatctac acaccagcc gcctccacag cggtatcccc      240
gccagatttt ccgggagcgg gtctggaacc gactacaccc tcaccatctc ttctctgcag      300
cccgaggatt tcgccgtcta tttctgccag caggggaata tctgccgta caccttcggt      360 caaggtacca agctggaaat caagggaggc ggaggatcag gcggtggcgg aagcggagga      420
ggtggctccg gaggaggagg ttcccaagtg cagcttcaag aatcaggacc cggacttgtg      480
aagccatcag aaaccctctc cctgacttgt accgtgtccg gtgtgagcct ccccgactac      540
ggagtctctt ggattcgcca gcctccgggg aagggtcttg aatggattgg ggtgatttgg      600
ggatcagaga ctacttacta ctcttcatca cttaagtcac gggtcaccat cagcaaagat      660
aatagcaaga accaagtgtc acttaagctg tcatctgtga ccgccgctga caccgccgtg      720
tactattgtg ccaaacatta ctattacgga gggtcttatg ctatggacta ctggggacag      780
gggaccctgg tgactgtctc tagccatcac catcaccacc atcatcac                   828
```

<210> SEQ ID NO 66
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 66

```
atggccctcc cagtgaccgc tctgctgctg cctctcgcac ttcttctcca tgccgctcgg       60
cctgagatcg tcatgaccca aagccccgct accctgtccc tgtcacccgg cgagagggca      120 acccttcat gcagggccag ccaggacatt tctaagtacc tcaactggta tcagcagaag      180
ccagggcagg ctcctcgcct gctgatctac acaccagcc gcctccacag cggtatcccc      240
gccagatttt ccgggagcgg gtctggaacc gactacaccc tcaccatctc ttctctgcag      300
cccgaggatt tcgccgtcta tttctgccag caggggaata tctgccgta caccttcggt      360 caaggtacca agctggaaat caagggaggc ggaggatcag gcggtggcgg aagcggagga      420
ggtggctccg gaggaggagg ttcccaagtg cagcttcaag aatcaggacc cggacttgtg      480
aagccatcag aaaccctctc cctgacttgt accgtgtccg gtgtgagcct ccccgactac      540
```

```
ggagtctctt ggattcgcca gcctccgggg aagggtcttg aatggattgg ggtgatttgg      600
ggatcagaga ctacttacta ccagtcatca cttaagtcac gggtcaccat cagcaaagat      660
aatagcaaga accaagtgtc acttaagctg tcatctgtga ccgccgctga caccgccgtg      720
tactattgtg ccaaacatta ctattacgga gggtcttatg ctatggacta ctggggacag      780
gggaccctgg tgactgtctc tagccatcac catcaccacc atcatcac                   828
```

<210> SEQ ID NO 67
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67

```
atggcactgc ctgtcactgc cctcctgctg cctctggccc tccttctgca tgccgccagg       60
ccccaagtcc agctgcaaga gtcaggaccc ggactggtga agccgtctga gactctctca      120
ctgacttgta ccgtcagcgg cgtgtccctc cccgactacg gagtgtcatg gatccgccaa      180
cctcccggga aagggcttga atggattggt gtcatctggg gttctgaaac cacctactac      240
tcatcttccc tgaagtccag ggtgaccatc agcaaggata attccaagaa ccaggtcagc      300
cttaagctgt catctgtgac cgctgctgac accgccgtgt attactgcgc caagcactac      360
tattacggag gaagctacgc tatggactat tggggacagg gcactctcgt gactgtgagc      420
agcggcggtg gagggtctgg aggtggagga tccggtggtg gtgggtcagg cggaggaggg      480
agcgagattg tgatgactca gtcaccagcc acccttctc tttcacccgg cgagagagca      540 acctgagct gtagagccag ccaggacatt tctaagtacc tcaactggta tcagcaaaaa      600
ccggggcagg cccctcgcct cctgatctac catacctcac gccttcactc tggtatcccc      660
gctcggttta gcggatcagg atctggtacc gactacactc tgaccatttc agcctgcag      720 ccagaagatt tcgcagtgta tttctgccag cagggcaata cccttccta caccttcggt      780 cagggaacca agctcgaaat caagcaccat caccatcatc accaccat                   828
```

<210> SEQ ID NO 68
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 68

```
atggcactgc ctgtcactgc cctcctgctg cctctggccc tccttctgca tgccgccagg       60
ccccaagtcc agctgcaaga gtcaggaccc ggactggtga agccgtctga gactctctca      120
ctgacttgta ccgtcagcgg cgtgtccctc cccgactacg gagtgtcatg gatccgccaa      180
cctcccggga aagggcttga atggattggt gtcatctggg gttctgaaac cacctactac      240
cagtcttccc tgaagtccag ggtgaccatc agcaaggata attccaagaa ccaggtcagc      300
cttaagctgt catctgtgac cgctgctgac accgccgtgt attactgcgc caagcactac      360
tattacggag gaagctacgc tatggactat tggggacagg gcactctcgt gactgtgagc      420
agcggcggtg gagggtctgg aggtggagga tccggtggtg gtgggtcagg cggaggaggg      480
agcgagattg tgatgactca gtcaccagcc acccttctc tttcacccgg cgagagagca      540
```

```
acctgagct gtagagccag ccaggacatt tctaagtacc tcaactggta tcagcaaaaa      600
ccggggcagg cccctcgcct cctgatctac catacctcac gccttcactc tggtatcccc      660
gctcggttta gcggatcagg atctggtacc gactacactc tgaccatttc cagcctgcag      720
ccagaagatt tcgcagtgta tttctgccag cagggcaata cccttcctta caccttcggt      780
cagggaacca agctcgaaat caagcaccat caccatcatc atcaccac                   828
```

<210> SEQ ID NO 69
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69

```
atggccctcc cagtgaccgc tctgctgctg cctctcgcac ttcttctcca tgccgctcgg       60
cctgagatcg tcatgaccca agccccgct accctgtccc tgtcaccgg cgagagggca       120 acctttcat gcagggccag ccaggacatt tctaagtacc tcaactggta tcagcagaag      180
ccagggcagg ctcctcgcct gctgatctac cacaccagcc gcctccacag cggtatcccc      240
gccagatttt ccgggagcgg gtctggaacc gactacaccc tcaccatctc ttctctgcag      300
cccgaggatt tcgccgtcta tttctgccag cagggggaata ctctgccgta caccttcggt      360
caaggtacca agctggaaat caaggggaggc ggaggatcag gcggtggcgg aagcggagga      420
ggtggctccg gaggaggagg ttcccaagtg cagcttcaag aatcaggacc cggacttgtg      480
aagccatcag aaaccctctc cctgacttgt accgtgtccg gtgtgagcct ccccgactac      540
ggagtctctt ggattcgcca gcctccgggg aagggtcttg aatggattgg ggtgatttgg      600
ggatcagaga ctacttacta caattcatca cttaagtcac gggtcaccat cagcaaagat      660
aatagcaaga accaagtgtc acttaagctg tcatctgtga ccgccgctga caccgccgtg      720
tactattgtg ccaaacatta ctattacgga gggtcttatg ctatggacta ctggggacag      780
gggaccctgg tgactgtctc tagccatcac catcaccacc atcatcac                   828
```

<210> SEQ ID NO 70
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70

```
atggcactgc ctgtcactgc cctcctgctg cctctggccc tccttctgca tgccgccagg       60
ccccaagtcc agctgcaaga gtcaggaccc ggactggtga agccgtctga gactctctca      120
ctgacttgta ccgtcagcgg cgtgtccctc cccgactacg gagtgtcatg gatccgccaa      180
cctcccggga aagggcttga atggattggt gtcatctggg gttctgaaac cacctactac      240
aactcttccc tgaagtccag ggtgaccatc agcaaggata ttccaagaa ccaggtcagc      300 cttaagctgt catctgtgac cgctgctgac accgccgtgt attactgcgc caagcactac      360
tattacggag gaagctacgc tatggactat tggggacagg gcactctcgt gactgtgagc      420
agcggcggtg gagggtctgg aggtggagga tccggtggtg tgggtcagg cggaggaggg      480
```

| | |
|---|---|
| agcgagattg tgatgactca gtcaccagcc acccttttctc tttcacccgg cgagagagca | 540 |
| accctgagct gtagagccag ccaggacatt tctaagtacc tcaactggta tcagcaaaaa | 600 |
| ccggggcagg cccctcgcct cctgatctac catacctcac gccttcactc tggtatcccc | 660 |
| gctcggttta gcggatcagg atctggtacc gactacactc tgaccatttc agcctgcag | 720 |
| ccagaagatt tcgcagtgta tttctgccag cagggcaata cccttcctta caccttcggt | 780 |
| cagggaacca agctcgaaat caagcaccat caccatcatc accaccat | 828 |

```
<210> SEQ ID NO 71
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71
```

| | |
|---|---|
| atggccctcc ctgtcaccgc cctgctgctt ccgctggctc ttctgctcca cgccgctcgg | 60 |
| cccgaaattg tgatgaccca gtcacccgcc actcttagcc tttcacccgg tgagcgcgca | 120 |
| accctgtctt gcagagcctc ccaagacatc tcaaaatacc ttaattggta tcaacagaag | 180 |
| cccggacagg ctcctcgcct tctgatctac caccagcc ggctccattc tggaatccct | 240 |
| gccaggttca gcgtagcgg atctgggacc gactacaccc tcactatcag ctcactgcag | 300 |
| ccagaggact tcgctgtcta tttctgtcag caagggaaca ccctgcccta cacctttgga | 360 |
| cagggcacca agctcgagat taaaggtgga ggtggcagcg gaggaggtgg gtccggcggt | 420 |
| ggaggaagcc aggtccaact ccaagaaagc ggaccgggtc ttgtgaagcc atcagaaact | 480 |
| ctttcactga cttgtactgt gagcggagtg tctctccccg attacggggt gtcttggatc | 540 |
| agacagccac cggggaaggg tctggaatgg attggagtga tttggggctc tgagactact | 600 |
| tactacaatt catcccctcaa gtcacgcgtc accatctcaa aggacaactc taagaatcag | 660 |
| gtgtcactga aactgtcatc tgtgaccgca gccgacaccg ccgtgtacta ttgcgctaag | 720 |
| cattactatt atggcgggag ctacgcaatg gattactggg gacagggtac tctggtcacc | 780 |
| gtgtccagcc accaccatca tcaccatcac cat | 813 |

```
<210> SEQ ID NO 72
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 72
```

| | |
|---|---|
| atggctctgc ccgtgaccgc actcctcctg ccactggctc tgctgcttca cgccgctcgc | 60 |
| ccacaagtcc agcttcaaga atcagggcct ggtctggtga agccatctga gactctgtcc | 120 |
| ctcacttgca ccgtgagcgg agtgtccctc ccagactacg gagtgagctg gattagacag | 180 |
| cctcccggaa agggactgga gtggatcgga gtgatttggg gtagcgaaac cacttactat | 240 |
| aactcttccc tgaagtcacg ggtcaccatt tcaaaggata ctcaaagaa tcaagtgagc | 300 |
| ctcaagctct catcagtcac cgccgctgac accgccgtgt attactgtgc caagcattac | 360 |
| tactatggag gtcctacgc catggactac tggggccagg gaactctggt cactgtgtca | 420 |
| tctggtggag gaggtagcgg aggaggcggg agcggtggag gtggctccga aatcgtgatg | 480 |

```
acccagagcc ctgcaaccct gtcccttcct cccggggaac gggctaccct ttcttgtcgg    540
gcatcacaag atatctcaaa atacctcaat tggtatcaac agaagccggg acaggcccct    600
aggcttctta tctaccacac ctctcgcctg catagcggga ttcccgcacg ctttagcggg    660
tctggaagcg ggaccgacta cactctgacc atctcatctc tccagcccga ggacttcgcc    720
gtctacttct gccagcaggg taacaccctg ccgtacacct tcggccaggg caccaagctt    780
gagatcaaac atcaccacca tcatcaccat cac                                 813
```

```
<210> SEQ ID NO 73
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser His His His His His His
            260                 265                 270

<210> SEQ ID NO 74
<211> LENGTH: 271
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Gln Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser His His His His His His
            260                 265                 270

<210> SEQ ID NO 75
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
```

35                  40                  45
Ser Leu Pro Asp Tyr Gly Val Ser Trp Ile Arg Gln Pro Pro Gly Lys
            50                  55                  60
Gly Leu Glu Trp Ile Gly Val Ile Trp Gly Ser Glu Thr Thr Tyr Tyr
 65                  70                  75                  80
Ser Ser Ser Leu Lys Ser Arg Val Thr Ile Ser Lys Asp Asn Ser Lys
                 85                  90                  95
Asn Gln Val Ser Leu Lys Leu Ser Ser Val Thr Ala Ala Asp Thr Ala
            100                 105                 110
Val Tyr Tyr Cys Ala Lys His Tyr Tyr Gly Gly Ser Tyr Ala Met
        115                 120                 125
Asp Tyr Trp Gly Gln Gly Thr Leu Val Thr Val Ser Ser Gly Gly Gly
        130                 135                 140
Gly Ser Gly Gly Gly Gly Ser Gly Gly Gly Gly Ser Glu Ile Val Met
145                 150                 155                 160
Thr Gln Ser Pro Ala Thr Leu Ser Leu Ser Pro Gly Glu Arg Ala Thr
                165                 170                 175
Leu Ser Cys Arg Ala Ser Gln Asp Ile Ser Lys Tyr Leu Asn Trp Tyr
            180                 185                 190
Gln Gln Lys Pro Gly Gln Ala Pro Arg Leu Leu Ile Tyr His Thr Ser
            195                 200                 205
Arg Leu His Ser Gly Ile Pro Ala Arg Phe Ser Gly Ser Gly Ser Gly
        210                 215                 220
Thr Asp Tyr Thr Leu Thr Ile Ser Ser Leu Gln Pro Glu Asp Phe Ala
225                 230                 235                 240
Val Tyr Phe Cys Gln Gln Gly Asn Thr Leu Pro Tyr Thr Phe Gly Gln
                245                 250                 255
Gly Thr Lys Leu Glu Ile Lys His His His His His His His
            260                 265                 270

<210> SEQ ID NO 76
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Met Ala Leu Pro Val Thr Ala Leu Leu Leu Pro Leu Ala Leu Leu Leu
 1               5                  10                  15
His Ala Ala Arg Pro Gln Val Gln Leu Gln Glu Ser Gly Pro Gly Leu
             20                  25                  30
Val Lys Pro Ser Glu Thr Leu Ser Leu Thr Cys Thr Val Ser Gly Val
         35                  40                  45
Ser Leu Pro Asp Tyr Gly Val Ser Trp Ile Arg Gln Pro Pro Gly Lys
     50                  55                  60
Gly Leu Glu Trp Ile Gly Val Ile Trp Gly Ser Glu Thr Thr Tyr Tyr
 65                  70                  75                  80
Gln Ser Ser Leu Lys Ser Arg Val Thr Ile Ser Lys Asp Asn Ser Lys
                 85                  90                  95
Asn Gln Val Ser Leu Lys Leu Ser Ser Val Thr Ala Ala Asp Thr Ala
            100                 105                 110
Val Tyr Tyr Cys Ala Lys His Tyr Tyr Gly Gly Ser Tyr Ala Met
        115                 120                 125

Asp Tyr Trp Gly Gln Gly Thr Leu Val Thr Val Ser Ser Gly Gly Gly
            130                 135                 140

Gly Ser Gly Gly Gly Gly Ser Gly Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr
            180                 185                 190

Gln Gln Lys Pro Gly Gln Ala Pro Arg Leu Leu Ile Tyr His Thr Ser
        195                 200                 205

Arg Leu His Ser Gly Ile Pro Ala Arg Phe Ser Gly Ser Gly Ser Gly
210                 215                 220

Thr Asp Tyr Thr Leu Thr Ile Ser Ser Leu Gln Pro Glu Asp Phe Ala
225                 230                 235                 240

Val Tyr Phe Cys Gln Gln Gly Asn Thr Leu Pro Tyr Thr Phe Gly Gln
                245                 250                 255

Gly Thr Lys Leu Glu Ile Lys His His His His His His
            260                 265                 270

<210> SEQ ID NO 77
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gly
130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Ser
        195                 200                 205

```
Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Gly Gly Ser Tyr Ala Met Asp
                245                 250                 255

Tyr Trp Gly Gln Gly Thr Leu Val Thr Val Ser Ser His His His
                260                 265                 270

His His His His
        275

<210> SEQ ID NO 78
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln
            35                  40                  45

Asp Ile Ser Lys Tyr Leu Asn Trp Tyr Gln Gln Lys Pro Gly Gln Ala
50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Gly Ser Gly
    130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Gln
        195                 200                 205

Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Gly Gly Ser Tyr Ala Met Asp
                245                 250                 255

Tyr Trp Gly Gln Gly Thr Leu Val Thr Val Ser Ser His His His His
                260                 265                 270

His His His His
```

<210> SEQ ID NO 79
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 79

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Ser Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys His His His His
            260                 265                 270

His His His His
        275
```

<210> SEQ ID NO 80
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 80

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Thr Val Ser Gly Val
            35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Gln Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
                100                 105                 110

Val Tyr Tyr Cys Ala Lys His Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Ser Gly Gly Gly Ser Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys His His His His
            260                 265                 270

His His His His
        275

<210> SEQ ID NO 81
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60
```

```
Pro Arg Leu Leu Ile Tyr His Thr Ser Arg Leu His Ser Gly Ile Pro
 65                  70                  75                  80

Ala Arg Phe Ser Gly Ser Gly Ser Gly Thr Asp Tyr Thr Leu Thr Ile
                 85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Ser
130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Asn
        195                 200                 205

Ser Ser Leu Lys Ser Arg Val Thr Ile Ser Lys Asp Asn Ser Lys Asn
210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Gly Gly Ser Tyr Ala Met Asp
                245                 250                 255

Tyr Trp Gly Gln Gly Thr Leu Val Thr Val Ser Ser His His His His
            260                 265                 270

His His His His
        275

<210> SEQ ID NO 82
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Met Ala Leu Pro Val Thr Ala Leu Leu Leu Pro Leu Ala Leu Leu Leu
  1               5                  10                  15

His Ala Ala Arg Pro Gln Val Gln Leu Gln Glu Ser Gly Pro Gly Leu
             20                  25                  30

Val Lys Pro Ser Glu Thr Leu Ser Leu Thr Cys Thr Val Ser Gly Val
         35                  40                  45

Ser Leu Pro Asp Tyr Gly Val Ser Trp Ile Arg Gln Pro Pro Gly Lys
     50                  55                  60

Gly Leu Glu Trp Ile Gly Val Ile Trp Gly Ser Glu Thr Thr Tyr Tyr
 65                  70                  75                  80

Asn Ser Ser Leu Lys Ser Arg Val Thr Ile Ser Lys Asp Asn Ser Lys
                 85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Gly Gly Ser Tyr Ala Met
        115                 120                 125

Asp Tyr Trp Gly Gln Gly Thr Leu Val Thr Val Ser Ser Gly Gly Gly
```

```
                130                 135                 140
Gly Ser Gly Gly Gly Ser Gly Gly Gly Ser Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
                180                 185                 190

Tyr Leu Asn Trp Tyr Gln Gln Lys Pro Gly Gln Ala Pro Arg Leu Leu
                195                 200                 205

Ile Tyr His Thr Ser Arg Leu His Ser Gly Ile Pro Ala Arg Phe Ser
                210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys His His His His
                260                 265                 270

His His His His
        275

<210> SEQ ID NO 83
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln
            35                  40                  45

Asp Ile Ser Lys Tyr Leu Asn Trp Tyr Gln Gln Lys Pro Gly Gln Ala
        50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Ser Gln
            130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
                180                 185                 190

Val Ile Trp Gly Ser Glu Thr Thr Tyr Tyr Asn Ser Ser Leu Lys Ser
                195                 200                 205
```

Arg Val Thr Ile Ser Lys Asp Asn Ser Lys Asn Gln Val Ser Leu Lys
            210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
            245                 250                 255

Thr Leu Val Thr Val Ser Ser His His His His His His His
            260                 265                 270

<210> SEQ ID NO 84
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Asn Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr
            180                 185                 190

Gln Gln Lys Pro Gly Gln Ala Pro Arg Leu Leu Ile Tyr His Thr Ser
        195                 200                 205

Arg Leu His Ser Gly Ile Pro Ala Arg Phe Ser Gly Ser Gly Ser Gly
    210                 215                 220

Thr Asp Tyr Thr Leu Thr Ile Ser Ser Leu Gln Pro Glu Asp Phe Ala
225                 230                 235                 240

Val Tyr Phe Cys Gln Gln Gly Asn Thr Leu Pro Tyr Thr Phe Gly Gln
                245                 250                 255

Gly Thr Lys Leu Glu Ile Lys His His His His His His His
            260                 265                 270

<210> SEQ ID NO 85
<211> LENGTH: 1458

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85
atggccctcc ctgtcaccgc cctgctgctt ccgctggctc ttctgctcca cgccgctcgg      60
cccgaaattg tgatgaccca gtcacccgcc actcttagcc tttcacccgg tgagcgcgca     120
accctgtctt gcagagcctc ccaagacatc tcaaaatacc ttaattggta tcaacagaag     180
cccggacagg ctcctcgcct tctgatctac cacaccagcc ggctccattc tggaatccct     240
gccaggttca gcggtagcgg atctgggacc gactacaccc tcactatcag ctcactgcag     300
ccagaggact cgctgtctta tttctgtcag caagggaaca ccctgcccta cacctttgga     360
cagggcacca agctcgagat taaaggtgga ggtggcagcg gaggaggtgg gtccggcggt     420
ggaggaagcc aggtccaact ccaagaaagc ggacccggtc ttgtgaagcc atcagaaact     480
cttccactga cttgtactgt gagcggagtg tctctcccg attacgggt gtcttggatc      540 agacagccac cggggaaggg tctggaatgg attggagtga tttggggctc tgagactact     600
tactactctt catccctcaa gtcacgcgtc accatctcaa aggacaactc taagaatcag     660
gtgtcactga aactgtcatc tgtgaccgca gccgacaccg ccgtgtacta ttgcgctaag     720
cattactatt atggcgggag ctacgcaatg gattactggg gacagggtac tctggtcacc     780
gtgtccagca ccactacccc agcaccgagg ccacccaccc cggctcctac catcgcctcc     840
cagcctctgt ccctgcgtcc ggaggcatgt agacccgcag ctggtggggc cgtgcatacc     900
cggggtcttg acttcgcctg cgatatctac atttgggccc ctctggctgg tacttgcggg     960
gtcctgctgc tttcactcgt gatcactctt tactgtaagc gcggtcggaa gaagctgctg    1020
tacatcttta gcaaccctt catgaggcct gtgcagacta tcaagagga ggacggctgt     1080 tcatgccggt tcccagagga ggaggaaggc ggctgcgaac tgcgcgtgaa attcagccgc    1140
agcgcagatg ctccagccta caagcagggg cagaaccagc tctacaacga actcaatctt    1200
ggtcggagag aggagtacga cgtgctggac aagcggagag acgggaccc agaaatgggc    1260 gggaagccgc gcagaaagaa tccccaagag ggcctgtaca acgagctcca aaaggataag    1320
atggcagaag cctatagcga gattggtatg aaagggggaac gcagaagagg caaaggccac    1380
gacggactgt accagggact cagcaccgcc accaaggaca cctatgacgc tcttcacatg    1440
caggccctgc cgcctcgg                                                  1458

<210> SEQ ID NO 86
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 86
atggccctcc ctgtcaccgc cctgctgctt ccgctggctc ttctgctcca cgccgctcgg      60
cccgaaattg tgatgaccca gtcacccgcc actcttagcc tttcacccgg tgagcgcgca     120
accctgtctt gcagagcctc ccaagacatc tcaaaatacc ttaattggta tcaacagaag     180
cccggacagg ctcctcgcct tctgatctac cacaccagcc ggctccattc tggaatccct     240
```

| | |
|---|---|
| gccaggttca gcggtagcgg atctgggacc gactacaccc tcactatcag ctcactgcag | 300 |
| ccagaggact tcgctgtcta tttctgtcag caagggaaca ccctgcccta cacctttgga | 360 |
| cagggcacca agctcgagat taaaggtgga ggtggcagcg gaggaggtgg gtccggcggt | 420 |
| ggaggaagcc aggtccaact ccaagaaagc ggaccgggtc ttgtgaagcc atcagaaact | 480 |
| cttcactga cttgtactgt gagcggagtg tctctccccg attacggggt gtcttggatc | 540 |
| agacagccac cggggaaggg tctggaatgg attggagtga tttggggctc tgagactact | 600 |
| tactaccaat catccctcaa gtcacgcgtc accatctcaa aggacaactc taagaatcag | 660 |
| gtgtcactga aactgtcatc tgtgaccgca gccgacaccg ccgtgtacta ttgcgctaag | 720 |
| cattactatt atggcgggag ctacgcaatg gattactggg gacagggtac tctggtcacc | 780 |
| gtgtccagca ccactacccc agcaccgagg ccacccaccc cggctcctac catcgcctcc | 840 |
| cagcctctgt ccctgcgtcc ggaggcatgt agacccgcag ctggtggggc cgtgcatacc | 900 |
| cggggtcttg acttcgcctg cgatatctac atttgggccc ctctggctgg tacttgcggg | 960 |
| gtcctgctgc tttcactcgt gatcactctt tactgtaagc gcggtcggaa gaagctgctg | 1020 |
| tacatcttta gcaaccctt catgaggcct gtgcagacta ctcaagagga ggacggctgt | 1080 |
| tcatgccggt tcccagagga ggaggaaggc ggctgcgaac tgcgcgtgaa attcagccgc | 1140 |
| agcgcagatg ctccagccta caagcagggg cagaaccagc tctacaacga actcaatctt | 1200 |
| ggtcggagag aggagtacga cgtgctggac aagcggagag acgggacccc agaaatgggc | 1260 |
| gggaagccgc gcagaaagaa tccccaagag ggcctgtaca cgagctcca aaaggataag | 1320 |
| atggcagaag cctatagcga gattggtatg aaagggaac gcagaagagg caaaggccac | 1380 |
| gacggactgt accagggact cagcaccgcc accaaggaca cctatgacgc tcttcacatg | 1440 |
| caggccctgc cgcctcgg | 1458 |

<210> SEQ ID NO 87
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 87

| | |
|---|---|
| atggctctgc ccgtgaccgc actcctcctg ccactggctc tgctgcttca cgccgctcgc | 60 |
| ccacaagtcc agcttcaaga tcagggcct ggtctggtga agccatctga gactctgtcc | 120 |
| ctcacttgca ccgtgagcgg agtgtccctc ccagactacg gagtgagctg gattagacag | 180 |
| cctcccggaa agggactgga gtggatcgga gtgatttggg gtagcgaaac cacttactat | 240 |
| tcatcttccc tgaagtcacg ggtcaccatt tcaaggata actcaaagaa tcaagtgagc | 300 |
| ctcaagctct catcagtcac cgccgctgac accgccgtgt attactgtgc caagcattac | 360 |
| tactatggag ggtcctacgc catggactac tggggccagg gaactctggt cactgtgtca | 420 |
| tctggtggag gaggtagcgg aggaggcggg agcggtggag gtggctccga aatcgtgatg | 480 |
| acccagagcc ctgcaaccct gtcccttct cccggggaac gggctaccct ttcttgtcgg | 540 |
| gcatcacaag atatctcaaa atacctcaat tggtatcaac agaagccggg acaggcccct | 600 |
| aggcttctta tctaccacac ctctcgcctg catagcggga ttcccgcacg ctttagcggg | 660 |
| tctgaagcg ggaccgacta cactctgacc atctcatctc tccagcccga ggacttcgcc | 720 |
| gtctacttct gccagcaggg taacaccctg ccgtacacct tcggccaggg caccaagctt | 780 |

```
gagatcaaaa ccactactcc cgctccaagg ccacccaccc ctgccccgac catcgcctct      840
cagccgcttt ccctgcgtcc ggaggcatgt agacccgcag ctggtggggc cgtgcatacc      900
cggggtcttg acttcgcctg cgatatctac atttgggccc ctctggctgg tacttgcggg      960
gtcctgctgc tttcactcgt gatcactctt tactgtaagc gcggtcggaa gaagctgctg     1020
tacatcttta agcaacccct catgaggcct gtgcagacta ctcaagagga ggacggctgt     1080
tcatgccggt tcccagagga ggaggaaggc ggctgcgaac tgcgcgtgaa attcagccgc     1140
agcgcagatg ctccagccta caagcagggg cagaaccagc tctacaacga actcaatctt     1200
ggtcggagag aggagtacga cgtgctggac aagcggagag acgggacccc agaaatgggc     1260
gggaagccgc gcagaaagaa tccccaagag ggcctgtaca cgagctcca aaaggataag      1320 atggcagaag cctatagcga gattggtatg aaagggaac gcagaagagg caaaggccac      1380
gacggactgt accagggact cagcaccgcc accaaggaca cctatgacgc tcttcacatg     1440
caggccctgc cgcctcgg                                                   1458
```

<210> SEQ ID NO 88
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 88

```
atggctctgc ccgtgaccgc actcctcctg ccactggctc tgctgcttca cgccgctcgc       60
ccacaagtcc agcttcaaga tcagggcct ggtctggtga agccatctga gactctgtcc       120
ctcacttgca ccgtgagcgg agtgtccctc ccagactacg gagtgagctg gattagacag      180
cctcccggaa agggactgga gtggatcgga gtgatttggg gtagcgaaac cacttactat     240
caatcttccc tgaagtcacg ggtcaccatt tcaaaggata actcaaagaa tcaagtgagc     300
ctcaagctct catcagtcac cgccgctgac accgccgtgt attactgtgc caagcattac     360
tactatggag ggtcctacgc catggactac tggggccagg gaactctggt cactgtgtca     420
tctggtggag gaggtagcgg aggaggcggg agcggtggag gtggctccga aatcgtgatg     480
acccagagcc ctgcaaccct gtcccttct cccggggaac gggctaccct ttcttgtcgg      540
gcatcacaag atatctcaaa atacctcaat tggtatcaac agaagccggg acaggcccct     600
aggcttctta tctaccacac ctctcgcctg catagcggga ttcccgcacg ctttagcggg     660
tctggaagcg ggaccgacta cactctgacc atctcatctc tccagcccga ggacttcgcc     720
gtctacttct gccagcaggg taacaccctg ccgtacacct cggccaggg caccaagctt     780 gagatcaaaa ccactactcc cgctccaagg ccacccaccc ctgccccgac catcgcctct    840
cagccgcttt ccctgcgtcc ggaggcatgt agacccgcag ctggtggggc cgtgcatacc    900
cggggtcttg acttcgcctg cgatatctac atttgggccc ctctggctgg tacttgcggg    960
gtcctgctgc tttcactcgt gatcactctt tactgtaagc gcggtcggaa gaagctgctg   1020
tacatcttta agcaacccct catgaggcct gtgcagacta ctcaagagga ggacggctgt   1080
tcatgccggt tcccagagga ggaggaaggc ggctgcgaac tgcgcgtgaa attcagccgc   1140
agcgcagatg ctccagccta caagcagggg cagaaccagc tctacaacga actcaatctt   1200
ggtcggagag aggagtacga cgtgctggac aagcggagag acgggacccc agaaatgggc   1260
```

```
gggaagccgc gcagaaagaa tccccaagag ggcctgtaca acgagctcca aaaggataag    1320
atggcagaag cctatagcga gattggtatg aaagggggaac gcagaagagg caaaggccac   1380
gacggactgt accagggact cagcaccgcc accaaggaca cctatgacgc tcttcacatg    1440
caggccctgc cgcctcgg                                                  1458

<210> SEQ ID NO 89
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 89
atggccctcc ctgtcaccgc cctgctgctt ccgctggctc ttctgctcca cgccgctcgg     60
cccgaaattg tgatgaccca gtcacccgcc actcttagcc tttcacccgg tgagcgcgca    120
accctgtctt gcagagcctc ccaagacatc tcaaaatacc ttaattggta tcaacagaag    180
cccggacagg ctcctcgcct tctgatctac acaccagcc ggctccattc tggaatccct    240
gccaggttca gcgtagcgg atctgggacc gactacaccc tcactatcag ctcactgcag    300
ccagaggact cgctgtctca tttctgtcag caagggaaca ccctgcccta cacctttgga    360
cagggcacca agctcgagat aaaggtgga ggtggcagcg aggaggtgg gtccggcggt     420 ggaggaagcg gcggaggcgg gagccaggtc aactccaag aaagcggacc gggtcttgtg    480
aagccatcag aaactctttc actgacttgt actgtgagcg gagtgtctct ccccgattac    540
ggggtgtctt ggatcagaca gccaccgggg aagggtctgg aatggattgg agtgatttgg    600
ggctctgaga ctacttacta ctcttcatcc ctcaagtcac gcgtcaccat ctcaaaggac    660
aactctaaga tcaggtgtc actgaaactg tcatctgtga ccgcagccga caccgccgtg    720
tactattgcg ctaagcatta ctattatggc gggagctacg caatggatta ctggggacag    780
ggtactctgg tcaccgtgtc cagcaccact accccagcac cgaggccacc caccccggct    840
cctaccatcg cctcccagcc tctgtccctg cgtccgagg catgtagacc cgcagctggt    900
ggggccgtgc atacccgggg tcttgacttc gcctgcgata tctacatttg gccccctctg    960
gctggtactt gcggggtcct gctgctttca ctcgtgatca ctcttactg taagcgcggt   1020 cggaagaagc tgctgtacat ctttaagcaa cccttcatga ggcctgtgca gactactcaa   1080
gaggaggacg gctgttcatg ccggttccca gaggaggagg aaggcggctg cgaactgcgc   1140
gtgaaattca gccgcagcgc agatgctcca gcctacaagc aggggcagaa ccagctctac   1200
aacgaactca atcttggtcg gagagaggag tacgacgtgc tggacaagcg gagaggacgg   1260
gacccagaaa tgggcgggaa gccgcgcaga aagaatcccc aagagggcct gtacaacgag   1320
ctccaaaagg ataagatggc agaagcctat agcgagattg gtatgaaagg gaacgcaga   1380 agaggcaaag gccacgacgg actgtaccag ggactcagca ccgccaccaa ggacacctat   1440
gacgctcttc acatgcaggc cctgccgcct cgg                                1473

<210> SEQ ID NO 90
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 90

```
atggccctcc ctgtcaccgc cctgctgctt ccgctggctc ttctgctcca cgccgctcgg      60
cccgaaattg tgatgaccca gtcacccgcc actcttagcc tttcacccgg tgagcgcgca     120
accctgtctt gcagagcctc ccaagacatc tcaaaatacc ttaattggta tcaacagaag     180
cccggacagg ctcctcgcct tctgatctac acaccagcc ggctccattc tggaatccct     240
gccaggttca gcgtagcgg atctgggacc gactacaccc tcactatcag ctcactgcag     300
ccagaggact cgctgtcta tttctgtcag caagggaaca ccctgcccta cacctttgga     360
cagggcacca agctcgagat taaaggtgga ggtggcagcg gaggaggtgg gtccggcggt     420
ggaggaagcg gaggcggagg gagccaggtc caactccaag aaagcggacc gggtcttgtg     480
aagccatcag aaactctttc actgacttgt actgtgagcg gagtgtctct ccccgattac     540
ggggtgtctt ggatcagaca gccaccgggg aagggtctgg aatggattgg agtgatttgg     600
ggctctgaga ctacttacta ccaatcatcc ctcaagtcac gcgtcaccat ctcaaaggac     660
aactctaaga tcaggtgtc actgaaactg tcatctgtga ccgcagccga caccgccgtg     720
tactattgcg ctaagcatta ctattatggc gggagctacg caatggatta ctggggacag     780
ggtactctgg tcaccgtgtc cagcaccact accccagcac cgaggccacc caccccggct     840
cctaccatcg cctcccagcc tctgtccctg cgtccggagg catgtagacc cgcagctggt     900
ggggccgtgc atacccgggg tcttgacttc gcctgcgata tctacatttg gccccctctg     960
gctggtactt gcggggtcct gctgctttca ctcgtgatca ctctttactg taagcgcggt    1020
cggaagaagc tgctgtacat ctttaagcaa cccttcatga ggcctgtgca gactactcaa    1080
gaggaggacg gctgttcatg ccggttccca gaggaggagg aaggcggctg cgaactgcgc    1140
gtgaaattca gccgcagcgc agatgctcca gcctacaagc aggggcagaa ccagctctac    1200
aacgaactca atcttggtcg agagaggag tacgacgtgc tggacaagcg agaggacgg    1260
gacccagaaa tgggcgggaa gccgcgcaga aagaatcccc aagagggcct gtacaacgag    1320
ctccaaaagg ataagatggc agaagcctat agcgagattg gtatgaaagg gaacgcaga    1380
agaggcaaag ccacgacgg actgtaccag ggactcagca ccgccaccaa ggacacctat    1440
gacgctcttc acatgcaggc cctgccgcct cgg                                1473
```

<210> SEQ ID NO 91
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 91

```
atggctctgc ccgtgaccgc actcctcctg ccactggctc tgctgcttca cgccgctcgc      60
ccacaagtcc agcttcaaga atcagggcct ggtctggtga agccatctga gactctgtcc     120
ctcacttgca ccgtgagcgg agtgtccctc ccagactacg gagtgagctg gattagacag     180
cctcccggaa agggactgga gtggatcgga gtgatttggg gtagcgaaac cacttactat     240
tcatcttccc tgaagtcacg ggtcaccatt tcaaaggata actcaaagaa tcaagtgagc     300
ctcaagctct catcagtcac cgccgctgac accgccgtgt attactgtgc caagcattac     360
tactatggag ggtcctacgc catggactac tggggccagg gaactctggt cactgtgtca     420
```

| | |
|---|---|
| tctggtggag gaggtagcgg aggaggcggg agcggtggag gtggctccgg aggtggcgga | 480 |
| agcgaaatcg tgatgaccca gagccctgca accctgtccc tttctcccgg ggaacgggct | 540 |
| acccttcctt gtcgggcatc acaagatatc tcaaaatacc tcaattggta tcaacagaag | 600 |
| ccgggacagg cccctaggct tcttatctac cacacctctc gcctgcatag cgggattccc | 660 |
| gcacgcttta gcgggtctgg aagcgggacc gactacactc tgaccatctc atctctccag | 720 |
| cccgaggact tcgccgtcta cttctgccag cagggtaaca ccctgccgta caccttcggc | 780 |
| cagggcacca agcttgagat caaaaccact actcccgctc caaggccacc caccccctgcc | 840 |
| ccgaccatcg cctctcagcc gctttccctg cgtccggagg catgtagacc cgcagctggt | 900 |
| ggggccgtgc ataccegggg tcttgacttc gcctgcgata tctacattg ggcccctctg | 960 |
| gctggtactt gcggggtcct gctgctttca ctcgtgatca ctctttactg taagcgcggt | 1020 |
| cggaagaagc tgctgtacat ctttaagcaa cccttcatga ggcctgtgca gactactcaa | 1080 |
| gaggaggacg gctgttcatg ccggttccca gaggaggagg aaggcggctg cgaactgcgc | 1140 |
| gtgaaattca gccgcagcgc agatgctcca gcctacaagc aggggcagaa ccagctctac | 1200 |
| aacgaactca atcttggtcg gagagaggag tacgacgtgc tggacaagcg gagaggacgg | 1260 |
| gacccagaaa tgggcgggaa gccgcgcaga aagaatcccc aagagggcct gtacaacgag | 1320 |
| ctccaaaagg ataagatggc agaagcctat agcgagattg gtatgaaagg gaacgcaga | 1380 |
| agaggcaaag gccacgacgg actgtaccag ggactcagca ccgccaccaa ggacacctat | 1440 |
| gacgctcttc acatgcaggc cctgccgcct cgg | 1473 |

<210> SEQ ID NO 92
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 92

| | |
|---|---|
| atggctctgc ccgtgaccgc actcctcctg ccactggctc tgctgcttca cgccgctcgc | 60 |
| ccacaagtcc agcttcaaga atcagggcct ggtctggtga agccatctga gactctgtcc | 120 |
| ctcacttgca ccgtgagcgg agtgtccctc ccagactacg gagtgagctg gattagacag | 180 |
| cctcccggaa agggactgga gtggatcgga gtgatttggg gtagcgaaac cacttactat | 240 |
| caatcttccc tgaagtcacg ggtcaccatt tcaaaggata actcaaagaa tcaagtgagc | 300 |
| ctcaagctct catcagtcac cgccgctgac accgccgtgt attactgtgc caagcattac | 360 |
| tactatggag gtcctacgc catggactac tggggccagg gaactctggt cactgtgtca | 420 |
| tctggtggag gaggtagcgg aggaggcggg agcggtggag gtggctccgg aggcggtggg | 480 |
| tcagaaatcg tgatgaccca gagccctgca accctgtccc tttctcccgg ggaacgggct | 540 |
| acccttcctt gtcgggcatc acaagatatc tcaaaatacc tcaattggta tcaacagaag | 600 |
| ccgggacagg cccctaggct tcttatctac cacacctctc gcctgcatag cgggattccc | 660 |
| gcacgcttta gcgggtctgg aagcgggacc gactacactc tgaccatctc atctctccag | 720 |
| cccgaggact tcgccgtcta cttctgccag cagggtaaca ccctgccgta caccttcggc | 780 |
| cagggcacca agcttgagat caaaaccact actcccgctc caaggccacc caccccctgcc | 840 |
| ccgaccatcg cctctcagcc gctttccctg cgtccggagg catgtagacc cgcagctggt | 900 |
| ggggccgtgc ataccegggg tcttgacttc gcctgcgata tctacattg ggcccctctg | 960 |

```
gctggtactt gcggggtcct gctgctttca ctcgtgatca ctctttactg taagcgcggt    1020
cggaagaagc tgctgtacat ctttaagcaa cccttcatga ggcctgtgca gactactcaa    1080
gaggaggacg gctgttcatg ccggttccca gaggaggagg aaggcggctg cgaactgcgc    1140
gtgaaattca gccgcagcgc agatgctcca gcctacaagc aggggcagaa ccagctctac    1200
aacgaactca atcttggtcg gagagaggag tacgacgtgc tggacaagcg gagaggacgg    1260
gacccagaaa tgggcgggaa gccgcgcaga aagaatcccc aagagggcct gtacaacgag    1320
ctccaaaagg ataagatggc agaagcctat agcgagattg gtatgaaagg ggaacgcaga    1380
agaggcaaag gccacgacgg actgtaccag ggactcagca ccgccaccaa ggacacctat    1440
gacgctcttc acatgcaggc cctgccgcct cgg                                 1473
```

<210> SEQ ID NO 93
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

```
atggccctcc ctgtcaccgc cctgctgctt ccgctggctc ttctgctcca cgccgctcgg      60
cccgaaattg tgatgaccca gtcacccgcc actcttagcc tttcacccgg tgagcgcgca     120
accctgtctt gcagagcctc ccaagacatc tcaaaatacc ttaattggta tcaacagaag     180
cccggacagg ctcctcgcct tctgatctac cacaccagcc ggctccattc tggaatccct     240
gccaggttca gcgtagcgg atctgggacc gactacaccc tcactatcag ctcactgcag     300
ccagaggact cgctgtctta tttctgtcag caagggaaca ccctgcccta cacctttgga     360
cagggcacca agctcgagat taaaggtgga ggtggcagcg gaggaggtgg gtccggcggt     420
ggaggaagcg gaggcggtgg gagccaggtc caactccaag aaagcggacc gggtcttgtg     480
aagccatcag aaactctttc actgacttgt actgtgagcg gagtgtctct ccccgattac     540
ggggtgtctt ggatcagaca gccaccgggg aagggtctgg aatggattgg agtgatttgg     600
ggctctgaga ctacttacta caactcatcc ctcaagtcac gcgtcaccat ctcaaaggac     660
aactctaaga tcaggtgtc actgaaactg tcatctgtga ccgcagccga caccgccgtg     720
tactattgcg ctaagcatta ctattatggc gggagctacg caatggatta ctggggacag     780
ggtactctgg tcaccgtgtc cagcaccact accccagcac cgaggccacc caccccggct     840
cctaccatcg cctcccagcc tctgtccctg cgtccggagg catgtagacc cgcagctggt     900
ggggccgtgc ataccggggg tcttgacttc gcctgcgata tctacatttg gccccctctg     960
gctggtactt gcggggtcct gctgctttca ctcgtgatca ctctttactg taagcgcggt    1020
cggaagaagc tgctgtacat ctttaagcaa cccttcatga ggcctgtgca gactactcaa    1080
gaggaggacg gctgttcatg ccggttccca gaggaggagg aaggcggctg cgaactgcgc    1140
gtgaaattca gccgcagcgc agatgctcca gcctacaagc aggggcagaa ccagctctac    1200
aacgaactca atcttggtcg gagagaggag tacgacgtgc tggacaagcg gagaggacgg    1260
gacccagaaa tgggcgggaa gccgcgcaga aagaatcccc aagagggcct gtacaacgag    1320
ctccaaaagg ataagatggc agaagcctat agcgagattg gtatgaaagg ggaacgcaga    1380
agaggcaaag gccacgacgg actgtaccag ggactcagca ccgccaccaa ggacacctat    1440
```

```
gacgctcttc acatgcaggc cctgccgcct cgg                           1473
```

<210> SEQ ID NO 94
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 94

```
atggccctcc ctgtcaccgc cctgctgctt ccgctggctc ttctgctcca cgccgctcgg     60
cccgaaattg tgatgaccca gtcacccgcc actcttagcc tttcacccgg tgagcgcgca    120
accctgtctt gcagagcctc ccaagacatc tcaaaatacc ttaattggta tcaacagaag    180
cccggacagg ctcctcgcct tctgatctac cacaccagcc ggctccattc tggaatccct    240
gccaggttca gcggtagcgg atctgggacc gactacaccc tcactatcag ctcactgcag    300
ccagaggact tcgctgtcta tttctgtcag caagggaaca ccctgcccta cacctttgga    360
cagggcacca agctcgagat taaaggtgga ggtggcagcg gaggaggtgg gtccggcggt    420
ggaggaagcg gaggcggtgg gagccaggtc caactccaag aaagcggacc gggtcttgtg    480
aagccatcag aaactctttc actgacttgt actgtgagcg gagtgtctct ccccgattac    540
ggggtgtctt ggatcagaca gccaccgggg aagggtctgg aatggattgg agtgatttgg    600
ggctctgaga ctacttacta caactcatcc ctcaagtcac gcgtcaccat ctcaaaggac    660
aactctaaga tcaggtgtc actgaaactg tcatctgtga ccgcagccga caccgccgtg    720
tactattgcg ctaagcatta ctattatggc gggagctacg caatggatta ctggggacag    780
ggtactctgg tcaccgtgtc cagcaccact accccagcac cgaggccacc caccccggct    840
cctaccatcg cctcccagcc tctgtccctg cgtccggagg catgtagacc cgcagctggt    900
ggggccgtgc atacccgggg tcttgacttc gcctgcgata tctacatttg gcccctctg    960
gctggtactt gcggggtcct gctgctttca ctcgtgatca ctctttactg taagcgcggt   1020
cggaagaagc tgctgtacat ctttaagcaa cccttcatga ggcctgtgca gactactcaa   1080
gaggaggacg gctgttcatg ccggttccca gaggaggagg aaggcggctg cgaactgcgc   1140
gtgaaattca gccgcagcgc agatgctcca gcctacaagc aggggcagaa ccagctctac   1200
aacgaactca atcttggtcg gagagaggag tacgacgtgc tggacaagcg agaggacgg   1260
gacccagaaa tgggcgggaa gccgcgcaga aagaatcccc aagagggcct gtacaacgag   1320
ctccaaaagg ataagatggc agaagcctat agcgagattg gtatgaaagg ggaacgcaga   1380
agaggcaaag gccacgacgg actgtaccag ggactcagca ccgccaccaa ggacacctat   1440
gacgctcttc acatgcaggc cctgccgcct cgg                                 1473
```

<210> SEQ ID NO 95
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 95

```
atggctctgc ccgtgaccgc actcctcctg ccactggctc tgctgcttca cgccgctcgc     60
ccacaagtcc agcttcaaga atcagggcct ggtctggtga agccatctga gactctgtcc    120
```

```
ctcacttgca ccgtgagcgg agtgtccctc ccagactacg gagtgagctg gattagacag      180
cctcccggaa agggactgga gtggatcgga gtgatttggg gtagcgaaac cacttactat      240
aactcttccc tgaagtcacg ggtcaccatt tcaaaggata actcaaagaa tcaagtgagc      300
ctcaagctct catcagtcac cgccgctgac accgccgtgt attactgtgc caagcattac      360
tactatggag ggtcctacgc catggactac tggggccagg gaactctggt cactgtgtca      420
tctggtggag gaggtagcgg aggaggcggg agcggtggag gtggctccgg aggtggcgga      480
agcgaaatcg tgatgaccca gagccctgca accctgtccc tttctcccgg ggaacgggct      540 acctttctt gtcgggcatc acaagatatc tcaaaatacc tcaattggta tcaacagaag      600
ccgggacagg cccctaggct tcttatctac cacacctctc gcctgcatag cgggattccc      660
gcacgcttta gcgggtctgg aagcgggacc gactacactc tgaccatctc atctctccag      720
cccgaggact cgccgtctca cttctgccag cagggtaaca ccctgccgta caccttcggc      780
cagggcacca agcttgagat caaaaccact actcccgctc caaggccacc caccccgtgcc      840 ccgaccatcg cctctcagcc gctttccctg cgtccggagg catgtagacc cgcagctggt      900
ggggccgtgc atacccgggg tcttgacttc gcctgcgata tctacatttg gcccctctg      960 gctggtactt gcggggtcct gctgctttca ctcgtgatca ctctttactg taagcgcggt     1020
cggaagaagc tgctgtacat ctttaagcaa cccttcatga ggcctgtgca gactactcaa     1080
gaggaggacg gctgttcatg ccggttccca gaggaggagg aaggcggctg cgaactgcgc     1140
gtgaaattca gccgcagcgc agatgctcca gcctacaagc aggggcagaa ccagctctac     1200
aacgaactca atcttggtcg gagagaggag tacgacgtgc tggacaagcg gagaggacgg     1260
gacccagaaa tgggcgggaa gccgcgcaga aagaatcccc aagagggcct gtacaacgag     1320
ctccaaaagg ataagatggc agaagcctat agcgagattg gtatgaaagg ggaacgcaga     1380
agaggcaaag gccacgacgg actgtaccag ggactcagca ccgccaccaa ggacacctat     1440
gacgctcttc acatgcaggc cctgccgcct cgg                                  1473
```

<210> SEQ ID NO 96
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 96

```
atggccctcc ctgtcaccgc cctgctgctt ccgctggctc ttctgctcca cgccgctcgg       60
cccgaaattg tgatgaccca gtcacccgcc actcttagcc tttcacccgg tgagcgcgca      120
accctgtctt gcagagcctc ccaagacatc tcaaaatacc ttaattggta tcaacagaag      180
cccggacagg ctcctcgcct tctgatctac cacaccagcc ggctccattc tggaatccct      240
gccaggttca gcggtagcgg atctgggacc gactacaccc tcactatcag ctcactgcag      300
ccagaggact cgctgtctca tttctgtcag caaggaaca ccctgcccta caccttcgga       360
cagggcacca agctcgagat aaaggtgga ggtggcagcg gaggaggtgg gtccggcggt       420
ggaggaagcc aggtccaact ccaagaaagc ggaccgggtc ttgtgaagcc atcagaaact      480
ctttcactga cttgtactgt gagcggagtg tctctccccg attacggggt gtcttggatc      540
agacagccac cggggaaggg tctggaatgg attggagtga tttggggctc tgagactact      600
```

```
tactacaact catccctcaa gtcacgcgtc accatctcaa aggacaactc taagaatcag    660
gtgtcactga aactgtcatc tgtgaccgca gccgacaccg ccgtgtacta ttgcgctaag    720
cattactatt atggcgggag ctacgcaatg gattactggg acagggtac tctggtcacc     780 gtgtccagca ccactacccc agcaccgagg ccacccaccc cggctcctac catcgcctcc    840
cagcctctgt ccctgcgtcc ggaggcatgt agacccgcag ctggtggggc cgtgcatacc    900
cggggtcttg acttcgcctg cgatatctac atttgggccc ctctggctgg tacttgcggg    960
gtcctgctgc tttcactcgt gatcactctt tactgtaagc gcggtcggaa gaagctgctg   1020
tacatcttta gcaaccctt catgaggcct gtgcagacta ctcaagagga ggacggctgt    1080
tcatgccggt tcccagagga ggaggaaggc ggctgcgaac tgcgcgtgaa attcagccgc   1140
agcgcagatg ctccagccta caagcagggg cagaaccagc tctacaacga actcaatctt   1200
ggtcggagag aggagtacga cgtgctggac aagcggagag acgggacccc agaaatgggc   1260
gggaagccgc gcagaaagaa tccccaagag ggcctgtaca acgagctcca aaaggataag   1320
atggcagaag cctatagcga gattggtatg aaagggaac gcagaagagg caaaggccac    1380
gacggactgt accagggact cagcaccgcc accaaggaca cctatgacgc tcttcacatg   1440
caggccctgc cgcctcgg                                                   1458

<210> SEQ ID NO 97
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97
atggccctgc ccgtcaccgc tctgctgctg ccccttgctc tgcttcttca tgcagcaagg     60
ccggacatcc agatgaccca aaccacctca tccctctctg cctctcttgg agacagggtg    120
accatttctt gtcgcgccag ccaggacatc agcaagtatc tgaactggta tcagcagaag   180
ccggacggaa ccgtgaagct cctgatctac catacctctc gcctgcatag cggcgtgccc   240
tcacgcttct ctggaagcgg atcaggaacc gattattctc tcactatttc aaatcttgag   300
caggaagata ttgccaccta tttctgccag cagggtaata ccctgcccta caccttcgga   360
ggagggacca agctcgaaat caccggtgga ggaggcagcg gcggtggagg gtctggtgga   420
ggtggttctg aggtgaagct gcaagaatca ggccctggac ttgtggcccc ttcacagtcc   480
ctgagcgtga cttgcaccgt gtccggagtc tccctgcccg actacggagt gtcatggatc   540
agacaacctc cacggaaagg actgaatgg ctcggtgtca tctggggtag cgaaactact    600
tactacaatt cagccctcaa aagcaggctg actattatca aggacaacag caagtcccaa   660
gtctttctta agatgaactc actccagact gacgacaccg caatctacta ttgtgctaag   720
cactactact acgaggatc ctacgctatg gattactggg acaaggtac ttccgtcact     780 gtctcttcac accatcatca ccatcaccat cac                                   813

<210> SEQ ID NO 98
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 98

Met Ala Leu Pro Val Thr Ala Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
    115                 120                 125

Gly Gly Gly Gly Ser Gly Gly Gly Ser Gly Gly Gly Ser Glu
130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
    195                 200                 205

Arg Leu Thr Ile Ile Lys Asp Asn Ser Lys Ser Gln Val Phe Leu Lys
210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser His His His His His His His
            260                 265                 270

<210> SEQ ID NO 99
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99
atggccttac cagtgaccgc cttgctcctg ccgctggcct tgctgctcca cgccgccagg      60
ccggacatcc agatgacaca gactacatcc tccctgtctg cctctctggg agacagagtc    120
accatcagtt gcagggcaag tcaggacatt agtaaatatt taaattggta tcagcagaaa    180
ccagatggaa ctgttaaact cctgatctac catacatcaa gattacactc aggagtccca    240
tcaaggttca gtggcagtgg gtctggaaca gattattctc tcaccattag caacctggag    300
caagaagata ttgccactta cttttgccaa cagggtaata cgcttccgta cacgttcgga    360
ggggggacca agctggagat cacaggtggc ggtggctcgg gcggtggtgg gtcgggtggc    420

```
ggcggatctg aggtgaaact gcaggagtca ggacctggcc tggtggcgcc ctcacagagc    480
ctgtccgtca catgcactgt ctcaggggtc tcattacccg actatggtgt aagctggatt    540
cgccagcctc cacgaaaggg tctggagtgg ctgggagtaa tatggggtag tgaaaccaca    600
tactataatt cagctctcaa atccagactg accatcatca aggacaactc caagagccaa    660
gttttcttaa aaatgaacag tctgcaaact gatgacacag ccatttacta ctgtgccaaa    720
cattattact acggtggtag ctatgctatg gactactggg gccaaggaac ctcagtcacc    780
gtctcctcaa ccacgacgcc agcgccgcga ccaccaacac cggcgcccac catcgcgtcg    840
cagcccctgt ccctgcgccc agaggcgtgc cggccagcgg cggggggcgc agtgcacacg    900
agggggctgg acttcgcctg tgatatctac atctgggcgc ccttggccgg gacttgtggg    960
gtccttctcc tgtcactggt tatcacccct tactgcaaac ggggcagaaa gaaactcctg   1020
tatatattca acaaccatt tatgagacca gtacaaacta ctcaagagga gatggctgt    1080 agctgccgat ttccagaaga agaagaagga ggatgtgaac tgagagtgaa gttcagcagg   1140
agcgcagacg cccccgcgta caagcagggc cagaaccagc tctataacga gctcaatcta   1200
ggacgaagag aggagtacga tgttttggac aagagacgtg gccgggaccc tgagatgggg   1260
ggaaagccga gaaggaagaa ccctcaggaa ggcctgtaca atgaactgca gaaagataag   1320
atggcggagg cctacagtga gattgggatg aaaggcgagc gccggagggg caaggggcac   1380
gatggccttt accagggtct cagtacagcc accaaggaca cctacgacgc ccttcacatg   1440 caggcccttgc cccctcgc                                                1458

<210> SEQ ID NO 100
<211> LENGTH: 1184
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 100
cgtgaggctc cggtgcccgt cagtgggcag agcgcacatc gcccacagtc cccgagaagt     60
tggggggagg ggtcggcaat tgaaccggtg cctagagaag gtggcgcggg gtaaactggg    120
aaagtgatgt cgtgtactgg ctccgccttt ttcccgaggg tgggggagaa ccgtatataa    180
gtgcagtagt cgccgtgaac gttcttttc gcaacgggtt tgccgccaga acacaggtaa    240
gtgccgtgtg tggttcccgc gggcctggcc tctttacggg ttatggccct tgcgtgcctt    300
gaattacttc cacctggctg cagtacgtga ttcttgatcc cgagcttcgg gttggaagtg    360
ggtgggagag ttcgaggcct tgcgcttaag gagcccttc gcctcgtgct tgagttgagg    420
cctggcctgg gcgctggggc cgccgcgtgc gaatctggtg gcaccttcgc gcctgtctcg    480
ctgctttcga taagtctcta gccatttaaa attttttgatg acctgctgcg acgctttttt    540
tctggcaaga tagtcttgta aatgcgggcc aagatctgca cactggtatt tcggttttttg    600 gggccgcggg cggcgacggg gcccgtgcgt cccagcgcac atgttcggcg aggcggggcc    660
tgcgagcgcg gccaccgaga atcggacggg ggtagtctca agctggccgg cctgctctgg    720
tgcctggcct cgcgccgccg tgtatcgccc cgccctgggc ggcaaggctg gccgggtcgg    780
caccagttgc gtgagcggaa agatggccgc ttccgggccc tgctgcaggg agctcaaaat    840
ggaggacgcg gcgctcggga gagcgggcgg gtgagtcacc cacacaaagg aaaagggcct    900
```

```
ttccgtcctc agccgtcgct tcatgtgact ccacggagta ccgggcgccg tccaggcacc    960
tcgattagtt ctcgagcttt tggagtacgt cgtctttagg ttgggggag gggttttatg   1020 cgatggagtt tccccacact gagtgggtgg agactgaagt taggccagct tggcacttga   1080
tgtaattctc cttggaattt gccctttttg agtttggatc ttggttcatt ctcaagcctc   1140
agacagtggt tcaaagtttt tttcttccat ttcaggtgtc gtga                   1184
```

<210> SEQ ID NO 101
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 101

```
agagtgaagt tcagcaggag cgcagacgcc cccgcgtaca agcagggcca gaaccagctc     60
tataacgagc tcaatctagg acgaagagag gagtacgatg ttttggacaa gagacgtggc    120
cgggaccctg agatggggggg aaagccgaga aggaagaacc ctcaggaagg cctgtacaat    180
gaactgcaga aagataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgc                              336
```

<210> SEQ ID NO 102
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 102

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175
```

```
Pro Pro Val Leu Asp Ser Asp Gly Ser Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
225                 230

<210> SEQ ID NO 103
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 103
gagagcaagt acggccctcc ctgcccccct tgccctgccc ccgagttcct gggcggaccc      60
agcgtgttcc tgttcccccc caagcccaag gacaccctga tgatcagccg gacccccgag     120
gtgacctgtg tggtggtgga cgtgtcccag gaggaccccg aggtccagtt caactggtac     180
gtggacggcg tggaggtgca caacgccaag accaagcccc gggaggagca gttcaatagc     240
acctaccggg tggtgtccgt gctgaccgtg ctgcaccagg actggctgaa cggcaaggaa     300
tacaagtgta aggtgtccaa caagggcctg cccagcagca tcgagaaaac catcagcaag     360
gccaagggcc agcctcggga gccccaggtg tacaccctgc cccctagcca agaggagatg     420
accaagaacc aggtgtccct gacctgcctg gtgaagggct tctacccag cgacatcgcc     480 gtggagtggg agagcaacgg ccagcccgag aacaactaca agaccacccc ccctgtgctg     540
gacagcgacg gcagcttctt cctgtacagc cggctgaccg tggacaagag ccggtggcag     600
gagggcaacg tctttagctg ctccgtgatg cacgaggccc tgcacaacca ctacacccag     660
aagagcctga gcctgtccct gggcaagatg                                      690

<210> SEQ ID NO 104
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 104
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa                                     150

<210> SEQ ID NO 105
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(40)
<223> OTHER INFORMATION: /note="This sequence may encompass 1-10
``` repeating "Gly Gly Gly Ser" repeating units"

<400> SEQUENCE: 105

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 106
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Gly Gly Gly Gly Ser Gly Gly Gly Gly Ser Gly Gly Gly Gly Ser Gly
1               5                   10                  15

Gly Gly Gly Ser
            20

<210> SEQ ID NO 107
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Gly Gly Gly Gly Ser Gly Gly Gly Ser Gly Gly Gly Gly Ser
1               5                   10                  15

<210> SEQ ID NO 108
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Gly Gly Gly Ser
1

<210> SEQ ID NO 109
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(5000)
<223> OTHER INFORMATION: /note="This sequence may encompass 50-5000
      nucleotides"

<400> SEQUENCE: 109
aaaaaaaaaa aaaaaaaaaa aaaaaaaaaa aaaaaaaaaa aaaaaaaaaa aaaaaaaaaa     60

```
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
aaaaaaaaaa aaaaaaaaaa aaaaaaaaaa aaaaaaaaaa aaaaaaaaaa aaaaaaaaaa    240
aaaaaaaaaa aaaaaaaaaa aaaaaaaaaa aaaaaaaaaa aaaaaaaaaa aaaaaaaaaa    300
aaaaaaaaaa aaaaaaaaaa aaaaaaaaaa aaaaaaaaaa aaaaaaaaaa aaaaaaaaaa    360
aaaaaaaaaa aaaaaaaaaa aaaaaaaaaa aaaaaaaaaa aaaaaaaaaa aaaaaaaaaa    420
aaaaaaaaaa aaaaaaaaaa aaaaaaaaaa aaaaaaaaaa aaaaaaaaaa aaaaaaaaaa    480
aaaaaaaaaa aaaaaaaaaa aaaaaaaaaa aaaaaaaaaa aaaaaaaaaa aaaaaaaaaa    540
aaaaaaaaaa aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaaa aaaaaaaaaa aaaaaaaaaa    660
aaaaaaaaaa aaaaaaaaaa aaaaaaaaaa aaaaaaaaaa aaaaaaaaaa aaaaaaaaaa    720
aaaaaaaaaa aaaaaaaaaa aaaaaaaaaa aaaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
```

```
aaaaaaaaaa aaaaaaaaaa aaaaaaaaaa aaaaaaaaaa aaaaaaaaaa aaaaaaaaaa    2460
aaaaaaaaaa aaaaaaaaaa aaaaaaaaaa aaaaaaaaaa aaaaaaaaaa aaaaaaaaaa    2520
aaaaaaaaaa aaaaaaaaaa aaaaaaaaaa aaaaaaaaaa aaaaaaaaaa aaaaaaaaaa    2580
aaaaaaaaaa aaaaaaaaaa aaaaaaaaaa aaaaaaaaaa aaaaaaaaaa aaaaaaaaaa    2640
aaaaaaaaaa aaaaaaaaaa aaaaaaaaaa aaaaaaaaaa aaaaaaaaaa aaaaaaaaaa    2700
aaaaaaaaaa aaaaaaaaaa aaaaaaaaaa aaaaaaaaaa aaaaaaaaaa aaaaaaaaaa    2760
aaaaaaaaaa aaaaaaaaaa aaaaaaaaaa aaaaaaaaaa aaaaaaaaaa aaaaaaaaaa    2820
aaaaaaaaaa aaaaaaaaaa aaaaaaaaaa aaaaaaaaaa aaaaaaaaaa aaaaaaaaaa    2880
aaaaaaaaaa aaaaaaaaaa aaaaaaaaaa aaaaaaaaaa aaaaaaaaaa aaaaaaaaaa    2940
aaaaaaaaaa aaaaaaaaaa aaaaaaaaaa aaaaaaaaaa aaaaaaaaaa aaaaaaaaaa    3000
aaaaaaaaaa aaaaaaaaaa aaaaaaaaaa aaaaaaaaaa aaaaaaaaaa aaaaaaaaaa    3060
aaaaaaaaaa aaaaaaaaaa aaaaaaaaaa aaaaaaaaaa aaaaaaaaaa aaaaaaaaaa    3120
aaaaaaaaaa aaaaaaaaaa aaaaaaaaaa aaaaaaaaaa aaaaaaaaaa aaaaaaaaaa    3180
aaaaaaaaaa aaaaaaaaaa aaaaaaaaaa aaaaaaaaaa aaaaaaaaaa aaaaaaaaaa    3240
aaaaaaaaaa aaaaaaaaaa aaaaaaaaaa aaaaaaaaaa aaaaaaaaaa aaaaaaaaaa    3300
aaaaaaaaaa aaaaaaaaaa aaaaaaaaaa aaaaaaaaaa aaaaaaaaaa aaaaaaaaaa    3360
aaaaaaaaaa aaaaaaaaaa aaaaaaaaaa aaaaaaaaaa aaaaaaaaaa aaaaaaaaaa    3420
aaaaaaaaaa aaaaaaaaaa aaaaaaaaaa aaaaaaaaaa aaaaaaaaaa aaaaaaaaaa    3480
aaaaaaaaaa aaaaaaaaaa aaaaaaaaaa aaaaaaaaaa aaaaaaaaaa aaaaaaaaaa    3540
aaaaaaaaaa aaaaaaaaaa aaaaaaaaaa aaaaaaaaaa aaaaaaaaaa aaaaaaaaaa    3600
aaaaaaaaaa aaaaaaaaaa aaaaaaaaaa aaaaaaaaaa aaaaaaaaaa aaaaaaaaaa    3660
aaaaaaaaaa aaaaaaaaaa aaaaaaaaaa aaaaaaaaaa aaaaaaaaaa aaaaaaaaaa    3720
aaaaaaaaaa aaaaaaaaaa aaaaaaaaaa aaaaaaaaaa aaaaaaaaaa aaaaaaaaaa    3780
aaaaaaaaaa aaaaaaaaaa aaaaaaaaaa aaaaaaaaaa aaaaaaaaaa aaaaaaaaaa    3840
aaaaaaaaaa aaaaaaaaaa aaaaaaaaaa aaaaaaaaaa aaaaaaaaaa aaaaaaaaaa    3900
aaaaaaaaaa aaaaaaaaaa aaaaaaaaaa aaaaaaaaaa aaaaaaaaaa aaaaaaaaaa    3960
aaaaaaaaaa aaaaaaaaaa aaaaaaaaaa aaaaaaaaaa aaaaaaaaaa aaaaaaaaaa    4020
aaaaaaaaaa aaaaaaaaaa aaaaaaaaaa aaaaaaaaaa aaaaaaaaaa aaaaaaaaaa    4080
aaaaaaaaaa aaaaaaaaaa aaaaaaaaaa aaaaaaaaaa aaaaaaaaaa aaaaaaaaaa    4140
aaaaaaaaaa aaaaaaaaaa aaaaaaaaaa aaaaaaaaaa aaaaaaaaaa aaaaaaaaaa    4200
aaaaaaaaaa aaaaaaaaaa aaaaaaaaaa aaaaaaaaaa aaaaaaaaaa aaaaaaaaaa    4260
aaaaaaaaaa aaaaaaaaaa aaaaaaaaaa aaaaaaaaaa aaaaaaaaaa aaaaaaaaaa    4320
aaaaaaaaaa aaaaaaaaaa aaaaaaaaaa aaaaaaaaaa aaaaaaaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaaaaaa aaaaaaaaaa aaaaaaaaaa aaaaaaaaaa aaaaaaaaaa aaaaaaaaaa    4560
aaaaaaaaaa aaaaaaaaaa aaaaaaaaaa aaaaaaaaaa aaaaaaaaaa aaaaaaaaaa    4620
aaaaaaaaaa aaaaaaaaaa aaaaaaaaaa aaaaaaaaaa aaaaaaaaaa aaaaaaaaaa    4680
aaaaaaaaaa aaaaaaaaaa aaaaaaaaaa aaaaaaaaaa aaaaaaaaaa aaaaaaaaaa    4740
aaaaaaaaaa aaaaaaaaaa aaaaaaaaaa aaaaaaaaaa aaaaaaaaaa aaaaaaaaaa    4800
```

```
aaaaaaaaaa aaaaaaaaaa aaaaaaaaaa aaaaaaaaaa aaaaaaaaaa aaaaaaaaaa    4860
aaaaaaaaaa aaaaaaaaaa aaaaaaaaaa aaaaaaaaaa aaaaaaaaaa aaaaaaaaaa    4920
aaaaaaaaaa aaaaaaaaaa aaaaaaaaaa aaaaaaaaaa aaaaaaaaaa aaaaaaaaaa    4980
aaaaaaaaaa aaaaaaaaaa                                                5000

<210> SEQ ID NO 110
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 110
tttttttttt tttttttttt tttttttttt tttttttttt tttttttttt tttttttttt      60
tttttttttt tttttttttt tttttttttt tttttttttt                           100

<210> SEQ ID NO 111
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(5000)
<223> OTHER INFORMATION: /note="This sequence may encompass 50-5000
      nucleotides"

<400> SEQUENCE: 111
tttttttttt tttttttttt tttttttttt tttttttttt tttttttttt tttttttttt      60
tttttttttt tttttttttt tttttttttt tttttttttt tttttttttt tttttttttt     120
tttttttttt tttttttttt tttttttttt tttttttttt tttttttttt tttttttttt     180
tttttttttt tttttttttt tttttttttt tttttttttt tttttttttt tttttttttt     240
tttttttttt tttttttttt tttttttttt tttttttttt tttttttttt tttttttttt     300
tttttttttt tttttttttt tttttttttt tttttttttt tttttttttt tttttttttt     360
tttttttttt tttttttttt tttttttttt tttttttttt tttttttttt tttttttttt     420
tttttttttt tttttttttt tttttttttt tttttttttt tttttttttt tttttttttt     480
tttttttttt tttttttttt tttttttttt tttttttttt tttttttttt tttttttttt     540
tttttttttt tttttttttt tttttttttt tttttttttt tttttttttt tttttttttt     600
tttttttttt tttttttttt tttttttttt tttttttttt tttttttttt tttttttttt     660
tttttttttt tttttttttt tttttttttt tttttttttt tttttttttt tttttttttt     720
tttttttttt tttttttttt tttttttttt tttttttttt tttttttttt tttttttttt     780
tttttttttt tttttttttt tttttttttt tttttttttt tttttttttt tttttttttt     840
tttttttttt tttttttttt tttttttttt tttttttttt tttttttttt tttttttttt     900
tttttttttt tttttttttt tttttttttt tttttttttt tttttttttt tttttttttt     960
tttttttttt tttttttttt tttttttttt tttttttttt tttttttttt tttttttttt    1020
tttttttttt tttttttttt tttttttttt tttttttttt tttttttttt tttttttttt    1080
tttttttttt tttttttttt tttttttttt tttttttttt tttttttttt tttttttttt    1140
```

-continued

| | | | | | | |
|---|---|---|---|---|---|---|
| tttttttttt | tttttttttt | tttttttttt | tttttttttt | tttttttttt | tttttttttt | 1200 |
| tttttttttt | tttttttttt | tttttttttt | tttttttttt | tttttttttt | tttttttttt | 1260 |
| tttttttttt | tttttttttt | tttttttttt | tttttttttt | tttttttttt | tttttttttt | 1320 |
| tttttttttt | tttttttttt | tttttttttt | tttttttttt | tttttttttt | tttttttttt | 1380 |
| tttttttttt | tttttttttt | tttttttttt | tttttttttt | tttttttttt | tttttttttt | 1440 |
| tttttttttt | tttttttttt | tttttttttt | tttttttttt | tttttttttt | tttttttttt | 1500 |
| tttttttttt | tttttttttt | tttttttttt | tttttttttt | tttttttttt | tttttttttt | 1560 |
| tttttttttt | tttttttttt | tttttttttt | tttttttttt | tttttttttt | tttttttttt | 1620 |
| tttttttttt | tttttttttt | tttttttttt | tttttttttt | tttttttttt | tttttttttt | 1680 |
| tttttttttt | tttttttttt | tttttttttt | tttttttttt | tttttttttt | tttttttttt | 1740 |
| tttttttttt | tttttttttt | tttttttttt | tttttttttt | tttttttttt | tttttttttt | 1800 |
| tttttttttt | tttttttttt | tttttttttt | tttttttttt | tttttttttt | tttttttttt | 1860 |
| tttttttttt | tttttttttt | tttttttttt | tttttttttt | tttttttttt | tttttttttt | 1920 |
| tttttttttt | tttttttttt | tttttttttt | tttttttttt | tttttttttt | tttttttttt | 1980 |
| tttttttttt | tttttttttt | tttttttttt | tttttttttt | tttttttttt | tttttttttt | 2040 |
| tttttttttt | tttttttttt | tttttttttt | tttttttttt | tttttttttt | tttttttttt | 2100 |
| tttttttttt | tttttttttt | tttttttttt | tttttttttt | tttttttttt | tttttttttt | 2160 |
| tttttttttt | tttttttttt | tttttttttt | tttttttttt | tttttttttt | tttttttttt | 2220 |
| tttttttttt | tttttttttt | tttttttttt | tttttttttt | tttttttttt | tttttttttt | 2280 |
| tttttttttt | tttttttttt | tttttttttt | tttttttttt | tttttttttt | tttttttttt | 2340 |
| tttttttttt | tttttttttt | tttttttttt | tttttttttt | tttttttttt | tttttttttt | 2400 |
| tttttttttt | tttttttttt | tttttttttt | tttttttttt | tttttttttt | tttttttttt | 2460 |
| tttttttttt | tttttttttt | tttttttttt | tttttttttt | tttttttttt | tttttttttt | 2520 |
| tttttttttt | tttttttttt | tttttttttt | tttttttttt | tttttttttt | tttttttttt | 2580 |
| tttttttttt | tttttttttt | tttttttttt | tttttttttt | tttttttttt | tttttttttt | 2640 |
| tttttttttt | tttttttttt | tttttttttt | tttttttttt | tttttttttt | tttttttttt | 2700 |
| tttttttttt | tttttttttt | tttttttttt | tttttttttt | tttttttttt | tttttttttt | 2760 |
| tttttttttt | tttttttttt | tttttttttt | tttttttttt | tttttttttt | tttttttttt | 2820 |
| tttttttttt | tttttttttt | tttttttttt | tttttttttt | tttttttttt | tttttttttt | 2880 |
| tttttttttt | tttttttttt | tttttttttt | tttttttttt | tttttttttt | tttttttttt | 2940 |
| tttttttttt | tttttttttt | tttttttttt | tttttttttt | tttttttttt | tttttttttt | 3000 |
| tttttttttt | tttttttttt | tttttttttt | tttttttttt | tttttttttt | tttttttttt | 3060 |
| tttttttttt | tttttttttt | tttttttttt | tttttttttt | tttttttttt | tttttttttt | 3120 |
| tttttttttt | tttttttttt | tttttttttt | tttttttttt | tttttttttt | tttttttttt | 3180 |
| tttttttttt | tttttttttt | tttttttttt | tttttttttt | tttttttttt | tttttttttt | 3240 |
| tttttttttt | tttttttttt | tttttttttt | tttttttttt | tttttttttt | tttttttttt | 3300 |
| tttttttttt | tttttttttt | tttttttttt | tttttttttt | tttttttttt | tttttttttt | 3360 |
| tttttttttt | tttttttttt | tttttttttt | tttttttttt | tttttttttt | tttttttttt | 3420 |
| tttttttttt | tttttttttt | tttttttttt | tttttttttt | tttttttttt | tttttttttt | 3480 |

| | |
|---|---:|
| tttttttttt tttttttttt tttttttttt tttttttttt tttttttttt tttttttttt | 3540 |
| tttttttttt tttttttttt tttttttttt tttttttttt tttttttttt tttttttttt | 3600 |
| tttttttttt tttttttttt tttttttttt tttttttttt tttttttttt tttttttttt | 3660 |
| tttttttttt tttttttttt tttttttttt tttttttttt tttttttttt tttttttttt | 3720 |
| tttttttttt tttttttttt tttttttttt tttttttttt tttttttttt tttttttttt | 3780 |
| tttttttttt tttttttttt tttttttttt tttttttttt tttttttttt tttttttttt | 3840 |
| tttttttttt tttttttttt tttttttttt tttttttttt tttttttttt tttttttttt | 3900 |
| tttttttttt tttttttttt tttttttttt tttttttttt tttttttttt tttttttttt | 3960 |
| tttttttttt tttttttttt tttttttttt tttttttttt tttttttttt tttttttttt | 4020 |
| tttttttttt tttttttttt tttttttttt tttttttttt tttttttttt tttttttttt | 4080 |
| tttttttttt tttttttttt tttttttttt tttttttttt tttttttttt tttttttttt | 4140 |
| tttttttttt tttttttttt tttttttttt tttttttttt tttttttttt tttttttttt | 4200 |
| tttttttttt tttttttttt tttttttttt tttttttttt tttttttttt tttttttttt | 4260 |
| tttttttttt tttttttttt tttttttttt tttttttttt tttttttttt tttttttttt | 4320 |
| tttttttttt tttttttttt tttttttttt tttttttttt tttttttttt tttttttttt | 4380 |
| tttttttttt tttttttttt tttttttttt tttttttttt tttttttttt tttttttttt | 4440 |
| tttttttttt tttttttttt tttttttttt tttttttttt tttttttttt tttttttttt | 4500 |
| tttttttttt tttttttttt tttttttttt tttttttttt tttttttttt tttttttttt | 4560 |
| tttttttttt tttttttttt tttttttttt tttttttttt tttttttttt tttttttttt | 4620 |
| tttttttttt tttttttttt tttttttttt tttttttttt tttttttttt tttttttttt | 4680 |
| tttttttttt tttttttttt tttttttttt tttttttttt tttttttttt tttttttttt | 4740 |
| tttttttttt tttttttttt tttttttttt tttttttttt tttttttttt tttttttttt | 4800 |
| tttttttttt tttttttttt tttttttttt tttttttttt tttttttttt tttttttttt | 4860 |
| tttttttttt tttttttttt tttttttttt tttttttttt tttttttttt tttttttttt | 4920 |
| tttttttttt tttttttttt tttttttttt tttttttttt tttttttttt tttttttttt | 4980 |
| tttttttttt tttttttttt | 5000 |

```
<210> SEQ ID NO 112
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(5000)
<223> OTHER INFORMATION: /note="This sequence may encompass 100-5000
      nucleotides"
```

<400> SEQUENCE: 112

| | |
|---|---:|
| aaaaaaaaaa aaaaaaaaaa aaaaaaaaaa aaaaaaaaaa aaaaaaaaaa aaaaaaaaaa | 60 |
| aaaaaaaaaa aaaaaaaaaa aaaaaaaaaa aaaaaaaaaa aaaaaaaaaa aaaaaaaaaa | 120 |
| aaaaaaaaaa aaaaaaaaaa aaaaaaaaaa aaaaaaaaaa aaaaaaaaaa aaaaaaaaaa | 180 |
| aaaaaaaaaa aaaaaaaaaa aaaaaaaaaa aaaaaaaaaa aaaaaaaaaa aaaaaaaaaa | 240 |
| aaaaaaaaaa aaaaaaaaaa aaaaaaaaaa aaaaaaaaaa aaaaaaaaaa aaaaaaaaaa | 300 |

```
aaaaaaaaaa aaaaaaaaaa aaaaaaaaaa aaaaaaaaaa aaaaaaaaaa aaaaaaaaaa      360
aaaaaaaaaa aaaaaaaaaa aaaaaaaaaa aaaaaaaaaa aaaaaaaaaa aaaaaaaaaa      420
aaaaaaaaaa aaaaaaaaaa aaaaaaaaaa aaaaaaaaaa aaaaaaaaaa aaaaaaaaaa      480
aaaaaaaaaa aaaaaaaaaa aaaaaaaaaa aaaaaaaaaa aaaaaaaaaa aaaaaaaaaa      540
aaaaaaaaaa aaaaaaaaaa aaaaaaaaaa aaaaaaaaaa aaaaaaaaaa aaaaaaaaaa      600
aaaaaaaaaa aaaaaaaaaa aaaaaaaaaa aaaaaaaaaa aaaaaaaaaa aaaaaaaaaa      660
aaaaaaaaaa aaaaaaaaaa aaaaaaaaaa aaaaaaaaaa aaaaaaaaaa aaaaaaaaaa      720
aaaaaaaaaa aaaaaaaaaa aaaaaaaaaa aaaaaaaaaa aaaaaaaaaa aaaaaaaaaa      780
aaaaaaaaaa aaaaaaaaaa aaaaaaaaaa aaaaaaaaaa aaaaaaaaaa aaaaaaaaaa      840
aaaaaaaaaa aaaaaaaaaa aaaaaaaaaa aaaaaaaaaa aaaaaaaaaa aaaaaaaaaa      900
aaaaaaaaaa aaaaaaaaaa aaaaaaaaaa aaaaaaaaaa aaaaaaaaaa aaaaaaaaaa      960
aaaaaaaaaa aaaaaaaaaa aaaaaaaaaa aaaaaaaaaa aaaaaaaaaa aaaaaaaaaa     1020
aaaaaaaaaa aaaaaaaaaa aaaaaaaaaa aaaaaaaaaa aaaaaaaaaa aaaaaaaaaa     1080
aaaaaaaaaa aaaaaaaaaa aaaaaaaaaa aaaaaaaaaa aaaaaaaaaa aaaaaaaaaa     1140
aaaaaaaaaa aaaaaaaaaa aaaaaaaaaa aaaaaaaaaa aaaaaaaaaa aaaaaaaaaa     1200
aaaaaaaaaa aaaaaaaaaa aaaaaaaaaa aaaaaaaaaa aaaaaaaaaa aaaaaaaaaa     1260
aaaaaaaaaa aaaaaaaaaa aaaaaaaaaa aaaaaaaaaa aaaaaaaaaa aaaaaaaaaa     1320
aaaaaaaaaa aaaaaaaaaa aaaaaaaaaa aaaaaaaaaa aaaaaaaaaa aaaaaaaaaa     1380
aaaaaaaaaa aaaaaaaaaa aaaaaaaaaa aaaaaaaaaa aaaaaaaaaa aaaaaaaaaa     1440
aaaaaaaaaa aaaaaaaaaa aaaaaaaaaa aaaaaaaaaa aaaaaaaaaa aaaaaaaaaa     1500
aaaaaaaaaa aaaaaaaaaa aaaaaaaaaa aaaaaaaaaa aaaaaaaaaa aaaaaaaaaa     1560
aaaaaaaaaa aaaaaaaaaa aaaaaaaaaa aaaaaaaaaa aaaaaaaaaa aaaaaaaaaa     1620
aaaaaaaaaa aaaaaaaaaa aaaaaaaaaa aaaaaaaaaa aaaaaaaaaa aaaaaaaaaa     1680
aaaaaaaaaa aaaaaaaaaa aaaaaaaaaa aaaaaaaaaa aaaaaaaaaa aaaaaaaaaa     1740
aaaaaaaaaa aaaaaaaaaa aaaaaaaaaa aaaaaaaaaa aaaaaaaaaa aaaaaaaaaa     1800
aaaaaaaaaa aaaaaaaaaa aaaaaaaaaa aaaaaaaaaa aaaaaaaaaa aaaaaaaaaa     1860
aaaaaaaaaa aaaaaaaaaa aaaaaaaaaa aaaaaaaaaa aaaaaaaaaa aaaaaaaaaa     1920
aaaaaaaaaa aaaaaaaaaa aaaaaaaaaa aaaaaaaaaa aaaaaaaaaa aaaaaaaaaa     1980
aaaaaaaaaa aaaaaaaaaa aaaaaaaaaa aaaaaaaaaa aaaaaaaaaa aaaaaaaaaa     2040
aaaaaaaaaa aaaaaaaaaa aaaaaaaaaa aaaaaaaaaa aaaaaaaaaa aaaaaaaaaa     2100
aaaaaaaaaa aaaaaaaaaa aaaaaaaaaa aaaaaaaaaa aaaaaaaaaa aaaaaaaaaa     2160
aaaaaaaaaa aaaaaaaaaa aaaaaaaaaa aaaaaaaaaa aaaaaaaaaa aaaaaaaaaa     2220
aaaaaaaaaa aaaaaaaaaa aaaaaaaaaa aaaaaaaaaa aaaaaaaaaa aaaaaaaaaa     2280
aaaaaaaaaa aaaaaaaaaa aaaaaaaaaa aaaaaaaaaa aaaaaaaaaa aaaaaaaaaa     2340
aaaaaaaaaa aaaaaaaaaa aaaaaaaaaa aaaaaaaaaa aaaaaaaaaa aaaaaaaaaa     2400
aaaaaaaaaa aaaaaaaaaa aaaaaaaaaa aaaaaaaaaa aaaaaaaaaa aaaaaaaaaa     2460
aaaaaaaaaa aaaaaaaaaa aaaaaaaaaa aaaaaaaaaa aaaaaaaaaa aaaaaaaaaa     2520
aaaaaaaaaa aaaaaaaaaa aaaaaaaaaa aaaaaaaaaa aaaaaaaaaa aaaaaaaaaa     2580
aaaaaaaaaa aaaaaaaaaa aaaaaaaaaa aaaaaaaaaa aaaaaaaaaa aaaaaaaaaa     2640
aaaaaaaaaa aaaaaaaaaa aaaaaaaaaa aaaaaaaaaa aaaaaaaaaa aaaaaaaaaa     2700
```

```
aaaaaaaaaa aaaaaaaaaa aaaaaaaaaa aaaaaaaaaa aaaaaaaaaa aaaaaaaaaa    2760
aaaaaaaaaa aaaaaaaaaa aaaaaaaaaa aaaaaaaaaa aaaaaaaaaa aaaaaaaaaa    2820
aaaaaaaaaa aaaaaaaaaa aaaaaaaaaa aaaaaaaaaa aaaaaaaaaa aaaaaaaaaa    2880
aaaaaaaaaa aaaaaaaaaa aaaaaaaaaa aaaaaaaaaa aaaaaaaaaa aaaaaaaaaa    2940
aaaaaaaaaa aaaaaaaaaa aaaaaaaaaa aaaaaaaaaa aaaaaaaaaa aaaaaaaaaa    3000
aaaaaaaaaa aaaaaaaaaa aaaaaaaaaa aaaaaaaaaa aaaaaaaaaa aaaaaaaaaa    3060
aaaaaaaaaa aaaaaaaaaa aaaaaaaaaa aaaaaaaaaa aaaaaaaaaa aaaaaaaaaa    3120
aaaaaaaaaa aaaaaaaaaa aaaaaaaaaa aaaaaaaaaa aaaaaaaaaa aaaaaaaaaa    3180
aaaaaaaaaa aaaaaaaaaa aaaaaaaaaa aaaaaaaaaa aaaaaaaaaa aaaaaaaaaa    3240
aaaaaaaaaa aaaaaaaaaa aaaaaaaaaa aaaaaaaaaa aaaaaaaaaa aaaaaaaaaa    3300
aaaaaaaaaa aaaaaaaaaa aaaaaaaaaa aaaaaaaaaa aaaaaaaaaa aaaaaaaaaa    3360
aaaaaaaaaa aaaaaaaaaa aaaaaaaaaa aaaaaaaaaa aaaaaaaaaa aaaaaaaaaa    3420
aaaaaaaaaa aaaaaaaaaa aaaaaaaaaa aaaaaaaaaa aaaaaaaaaa aaaaaaaaaa    3480
aaaaaaaaaa aaaaaaaaaa aaaaaaaaaa aaaaaaaaaa aaaaaaaaaa aaaaaaaaaa    3540
aaaaaaaaaa aaaaaaaaaa aaaaaaaaaa aaaaaaaaaa aaaaaaaaaa aaaaaaaaaa    3600
aaaaaaaaaa aaaaaaaaaa aaaaaaaaaa aaaaaaaaaa aaaaaaaaaa aaaaaaaaaa    3660
aaaaaaaaaa aaaaaaaaaa aaaaaaaaaa aaaaaaaaaa aaaaaaaaaa aaaaaaaaaa    3720
aaaaaaaaaa aaaaaaaaaa aaaaaaaaaa aaaaaaaaaa aaaaaaaaaa aaaaaaaaaa    3780
aaaaaaaaaa aaaaaaaaaa aaaaaaaaaa aaaaaaaaaa aaaaaaaaaa aaaaaaaaaa    3840
aaaaaaaaaa aaaaaaaaaa aaaaaaaaaa aaaaaaaaaa aaaaaaaaaa aaaaaaaaaa    3900
aaaaaaaaaa aaaaaaaaaa aaaaaaaaaa aaaaaaaaaa aaaaaaaaaa aaaaaaaaaa    3960
aaaaaaaaaa aaaaaaaaaa aaaaaaaaaa aaaaaaaaaa aaaaaaaaaa aaaaaaaaaa    4020
aaaaaaaaaa aaaaaaaaaa aaaaaaaaaa aaaaaaaaaa aaaaaaaaaa aaaaaaaaaa    4080
aaaaaaaaaa aaaaaaaaaa aaaaaaaaaa aaaaaaaaaa aaaaaaaaaa aaaaaaaaaa    4140
aaaaaaaaaa aaaaaaaaaa aaaaaaaaaa aaaaaaaaaa aaaaaaaaaa aaaaaaaaaa    4200
aaaaaaaaaa aaaaaaaaaa aaaaaaaaaa aaaaaaaaaa aaaaaaaaaa aaaaaaaaaa    4260
aaaaaaaaaa aaaaaaaaaa aaaaaaaaaa aaaaaaaaaa aaaaaaaaaa aaaaaaaaaa    4320
aaaaaaaaaa aaaaaaaaaa aaaaaaaaaa aaaaaaaaaa aaaaaaaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaaaaaa aaaaaaaaaa aaaaaaaaaa aaaaaaaaaa aaaaaaaaaa aaaaaaaaaa    4560
aaaaaaaaaa aaaaaaaaaa aaaaaaaaaa aaaaaaaaaa aaaaaaaaaa aaaaaaaaaa    4620
aaaaaaaaaa aaaaaaaaaa aaaaaaaaaa aaaaaaaaaa aaaaaaaaaa aaaaaaaaaa    4680
aaaaaaaaaa aaaaaaaaaa aaaaaaaaaa aaaaaaaaaa aaaaaaaaaa aaaaaaaaaa    4740
aaaaaaaaaa aaaaaaaaaa aaaaaaaaaa aaaaaaaaaa aaaaaaaaaa aaaaaaaaaa    4800
aaaaaaaaaa aaaaaaaaaa aaaaaaaaaa aaaaaaaaaa aaaaaaaaaa aaaaaaaaaa    4860
aaaaaaaaaa aaaaaaaaaa aaaaaaaaaa aaaaaaaaaa aaaaaaaaaa aaaaaaaaaa    4920
aaaaaaaaaa aaaaaaaaaa aaaaaaaaaa aaaaaaaaaa aaaaaaaaaa aaaaaaaaaa    4980
aaaaaaaaaa aaaaaaaaaa                                                5000
```

```
<210> SEQ ID NO 113
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(400)
<223> OTHER INFORMATION: /note="This sequence may encompass 100-400
      nucleotides"

<400> SEQUENCE: 113
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
aaaaaaaaaa aaaaaaaaaa aaaaaaaaaa aaaaaaaaaa aaaaaaaaaa aaaaaaaaaa    240
aaaaaaaaaa aaaaaaaaaa aaaaaaaaaa aaaaaaaaaa aaaaaaaaaa aaaaaaaaaa    300
aaaaaaaaaa aaaaaaaaaa aaaaaaaaaa aaaaaaaaaa aaaaaaaaaa aaaaaaaaaa    360
aaaaaaaaaa aaaaaaaaaa aaaaaaaaaa aaaaaaaaaa                          400

<210> SEQ ID NO 114
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 115
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115
```

-continued

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
            115                 120

<210> SEQ ID NO 116
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
            115                 120

<210> SEQ ID NO 117
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile

```
                35                  40                  45
Tyr His Thr Ser Arg Leu His Ser Gly Ile Pro Ala Arg Phe Ser Gly
            50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys
            100                 105
```

<210> SEQ ID NO 118
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(2000)
<223> OTHER INFORMATION: /note="This sequence may encompass 50-2000 nucleotides"

<400> SEQUENCE: 118

```
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa aaaaaaaaaa aaaaaaaaaa aaaaaaaaaa aaaaaaaaaa     540
aaaaaaaaaa aaaaaaaaaa aaaaaaaaaa aaaaaaaaaa aaaaaaaaaa aaaaaaaaaa     600
aaaaaaaaaa aaaaaaaaaa aaaaaaaaaa aaaaaaaaaa aaaaaaaaaa aaaaaaaaaa     660
aaaaaaaaaa aaaaaaaaaa aaaaaaaaaa aaaaaaaaaa aaaaaaaaaa aaaaaaaaaa     720
aaaaaaaaaa aaaaaaaaaa aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa aaaaaaaaaa    1020
aaaaaaaaaa aaaaaaaaaa aaaaaaaaaa aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaaaaa aaaaaaaaaa aaaaaaaaaa aaaaaaaaaa    1200
aaaaaaaaaa aaaaaaaaaa aaaaaaaaaa aaaaaaaaaa aaaaaaaaaa aaaaaaaaaa    1260
aaaaaaaaaa aaaaaaaaaa aaaaaaaaaa aaaaaaaaaa aaaaaaaaaa aaaaaaaaaa    1320
aaaaaaaaaa aaaaaaaaaa aaaaaaaaaa aaaaaaaaaa aaaaaaaaaa aaaaaaaaaa    1380
aaaaaaaaaa aaaaaaaaaa aaaaaaaaaa aaaaaaaaaa aaaaaaaaaa aaaaaaaaaa    1440
```

```
aaaaaaaaaa aaaaaaaaaa aaaaaaaaaa aaaaaaaaaa aaaaaaaaaa aaaaaaaaaa    1500
aaaaaaaaaa aaaaaaaaaa aaaaaaaaaa aaaaaaaaaa aaaaaaaaaa aaaaaaaaaa    1560
aaaaaaaaaa aaaaaaaaaa aaaaaaaaaa aaaaaaaaaa aaaaaaaaaa aaaaaaaaaa    1620
aaaaaaaaaa aaaaaaaaaa aaaaaaaaaa aaaaaaaaaa aaaaaaaaaa aaaaaaaaaa    1680
aaaaaaaaaa aaaaaaaaaa aaaaaaaaaa aaaaaaaaaa aaaaaaaaaa aaaaaaaaaa    1740
aaaaaaaaaa aaaaaaaaaa aaaaaaaaaa aaaaaaaaaa aaaaaaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaaaaaaa aaaaaaaaaa aaaaaaaaaa aaaaaaaaaa    1920
aaaaaaaaaa aaaaaaaaaa aaaaaaaaaa aaaaaaaaaa aaaaaaaaaa aaaaaaaaaa    1980
aaaaaaaaaa aaaaaaaaaa                                                2000

<210> SEQ ID NO 119
<211> LENGTH: 373
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255
```

Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285

Arg Arg Glu Glu Tyr Asp Val Leu Asp Lys Arg Gly Arg Asp Pro
290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
    370

<210> SEQ ID NO 120
<211> LENGTH: 1182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 120
atggccctcc ctgtcactgc cctgcttctc cccctcgcac tcctgctcca cgccgctaga       60
ccacccggat ggtttctgga ctctccggat cgcccgtgga atcccccaac cttctcaccg      120
gcactcttgg ttgtgactga gggcgataat gcgaccttca cgtgctcgtt ctccaacacc      180
tccgaatcat tcgtgctgaa ctggtaccgc atgagcccgt caaaccagac cgacaagctc      240
gccgcgtttc cggaagatcg gtcgcaaccg ggacaggatt gtcggttccg cgtgactcaa      300
ctgccgaatg gcagagactt ccacatgagc gtggtccgcg ctaggcgaaa cgactccggg      360
acctacctgt gcggagccat ctcgctggcg cctaaggccc aaatcaaaga gagcttgagg      420
gccgaactga gagtgaccga gcgcagagct gaggtgccaa ctgcacatcc atccccatcg      480
cctcggcctg cggggcagtt tcagaccctg gtcacgacca ctccggcgcc cgcgcccacc      540
actccggccc caactatcgc gagccagccc ctgtcgctga ggccggaagc atgccgccct      600
gccgccggag gtgctgtgca tacccgggga ttggacttcg catgcgacat ctacatttgg      660
gctcctctcg ccggaacttg tggcgtgctc cttctgtccc tggtcatcac cctgtactgc      720
aagcggggtc ggaaaaagct tctgtacatt ttcaagcagc ccttcatgag gcccgtgcaa      780
accacccagg aggaggacgg ttgctcctgc cggttccccg aagaggaaga aggaggttgc      840
gagctgcgcg tgaagttctc ccggagcgcc gacgcccccg cctataagca gggccagaac      900
cagctgtaca cgaactgaa cctgggacgg cgggaagagt acgatgtgct ggacaagcgg      960
cgcggccggg accccgaaat gggcgggaag cctagaagaa agaaccctca ggaaggcctg     1020
tataacgagc tgcagaagga caagatggcc gaggcctact ccgaaattgg gatgaaggga     1080
gagcggcgga ggggaaaggg gcacgacggc ctgtaccaag gactgtccac cgccaccaag     1140
gacacatacg atgccctgca catgcaggcc cttccccctc gc                        1182

<210> SEQ ID NO 121

```
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
                20                  25                  30

Trp Asn Pro Pro Thr Phe Ser Pro Ala Leu Leu Val Val Thr Glu Gly
            35                  40                  45

Asp Asn Ala Thr Phe Thr Cys Ser Phe Ser Asn Thr Ser Glu Ser Phe
        50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
                100                 105                 110

Arg Ala Arg Arg Asn Asp Ser Gly Thr Tyr Leu Cys Gly Ala Ile Ser
            115                 120                 125

Leu Ala Pro Lys Ala Gln Ile Lys Glu Ser Leu Arg Ala Glu Leu Arg
        130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Thr Pro Ala
                165                 170                 175

Pro Arg Pro Pro Thr Pro Ala Pro Thr Ile Ala Ser Gln Pro Leu Ser
                180                 185                 190

Leu Arg Pro Glu Ala Cys Arg Pro Ala Ala Gly Gly Ala Val His Thr
            195                 200                 205

Arg Gly Leu Asp Phe Ala Cys Asp Ile Tyr Ile Trp Ala Pro Leu Ala
        210                 215                 220

Gly Thr Cys Gly Val Leu Leu Leu Ser Leu Val Ile Thr Leu Tyr Cys
225                 230                 235                 240

Lys Arg Gly Arg Lys Lys Leu Leu Tyr Ile Phe Lys Gln Pro Phe Met
                245                 250                 255

Arg Pro Val Gln Thr Thr Gln Glu Glu Asp Gly Cys Ser Cys Arg Phe
                260                 265                 270

Pro Glu Glu Glu Glu Gly Gly Cys Glu Leu Arg Val Lys Phe Ser Arg
            275                 280                 285

Ser Ala Asp Ala Pro Ala Tyr Lys Gln Gly Gln Asn Gln Leu Tyr Asn
        290                 295                 300

Glu Leu Asn Leu Gly Arg Arg Glu Glu Tyr Asp Val Leu Asp Lys Arg
305                 310                 315                 320

Arg Gly Arg Asp Pro Glu Met Gly Gly Lys Pro Arg Arg Lys Asn Pro
                325                 330                 335

Gln Glu Gly Leu Tyr Asn Glu Leu Gln Lys Asp Lys Met Ala Glu Ala
                340                 345                 350

Tyr Ser Glu Ile Gly Met Lys Gly Glu Arg Arg Arg Gly Lys Gly His
            355                 360                 365
```

```
Asp Gly Leu Tyr Gln Gly Leu Ser Thr Ala Thr Lys Asp Thr Tyr Asp
    370                 375                 380

Ala Leu His Met Gln Ala Leu Pro Pro Arg
385                 390

<210> SEQ ID NO 122
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Asp Val Pro Asp Tyr Ala Ser Leu Gly Gly Pro Ser Ser Pro Lys Lys
1               5                   10                  15

Lys Arg Lys Val Ser Arg Gly Val Gln Val Glu Thr Ile Ser Pro Gly
                20                  25                  30

Asp Gly Arg Thr Phe Pro Lys Arg Gly Gln Thr Cys Val Val His Tyr
            35                  40                  45

Thr Gly Met Leu Glu Asp Gly Lys Lys Phe Asp Ser Ser Arg Asp Arg
        50                  55                  60

Asn Lys Pro Phe Lys Phe Met Leu Gly Lys Gln Glu Val Ile Arg Gly
65                  70                  75                  80

Trp Glu Glu Gly Val Ala Gln Met Ser Val Gly Gln Arg Ala Lys Leu
                85                  90                  95

Thr Ile Ser Pro Asp Tyr Ala Tyr Gly Ala Thr Gly His Pro Gly Ile
            100                 105                 110

Ile Pro Pro His Ala Thr Leu Val Phe Asp Val Glu Leu Leu Lys Leu
        115                 120                 125

Glu Thr Ser Tyr
    130

<210> SEQ ID NO 123
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Val Gln Val Glu Thr Ile Ser Pro Gly Asp Gly Arg Thr Phe Pro Lys
1               5                   10                  15

Arg Gly Gln Thr Cys Val Val His Tyr Thr Gly Met Leu Glu Asp Gly
                20                  25                  30

Lys Lys Phe Asp Ser Ser Arg Asp Arg Asn Lys Pro Phe Lys Phe Met
            35                  40                  45

Leu Gly Lys Gln Glu Val Ile Arg Gly Trp Glu Glu Gly Val Ala Gln
        50                  55                  60

Met Ser Val Gly Gln Arg Ala Lys Leu Thr Ile Ser Pro Asp Tyr Ala
65                  70                  75                  80

Tyr Gly Ala Thr Gly His Pro Gly Ile Ile Pro Pro His Ala Thr Leu
                85                  90                  95

Val Phe Asp Val Glu Leu Leu Lys Leu Glu Thr Ser
            100                 105
```

```
<210> SEQ ID NO 124
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys
                85                  90

<210> SEQ ID NO 125
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95

<210> SEQ ID NO 126
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45
```

```
Ser Phe Asn Gln Ala Tyr Gly Arg Asp Leu Met Glu Ala Gln Glu Trp
 50                  55                  60

Cys Arg Lys Tyr Met Lys Ser Gly Asn Val Lys Asp Leu Thr Gln Ala
 65                  70                  75                  80

Trp Asp Leu Tyr Tyr His Val Phe Arg Arg Ile Ser Lys Thr Ser
                 85                  90                  95

<210> SEQ ID NO 127
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Ile Leu Trp His Glu Met Trp His Glu Gly Leu Glu Glu Ala Ser Arg
 1               5                  10                  15

Leu Tyr Phe Gly Glu Arg Asn Val Lys Gly Met Phe Glu Val Leu Glu
                 20                  25                  30

Pro Leu His Ala Met Met Glu Arg Gly Pro Gln Thr Leu Lys Glu Thr
             35                  40                  45

Ser Phe Asn Gln Ala Tyr Gly Arg Asp Leu Met Glu Ala Gln Glu Trp
 50                  55                  60

Cys Arg Lys Tyr Met Lys Ser Gly Asn Val Lys Asp Leu Leu Gln Ala
 65                  70                  75                  80

Trp Asp Leu Tyr Tyr His Val Phe Arg Arg Ile Ser Lys Thr Ser
                 85                  90                  95

<210> SEQ ID NO 128
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (78)..(78)
<223> OTHER INFORMATION: Any amino acid

<400> SEQUENCE: 128

Ile Leu Trp His Glu Met Trp His Glu Gly Leu Xaa Glu Ala Ser Arg
 1               5                  10                  15

Leu Tyr Phe Gly Glu Arg Asn Val Lys Gly Met Phe Glu Val Leu Glu
                 20                  25                  30

Pro Leu His Ala Met Met Glu Arg Gly Pro Gln Thr Leu Lys Glu Thr
             35                  40                  45

Ser Phe Asn Gln Ala Tyr Gly Arg Asp Leu Met Glu Ala Gln Glu Trp
 50                  55                  60

Cys Arg Lys Tyr Met Lys Ser Gly Asn Val Lys Asp Leu Xaa Gln Ala
 65                  70                  75                  80

Trp Asp Leu Tyr Tyr His Val Phe Arg Arg Ile Ser Lys Thr Ser
                 85                  90                  95
```

```
<210> SEQ ID NO 129
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95

<210> SEQ ID NO 130
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95

<210> SEQ ID NO 131
<211> LENGTH: 1132
<212> TYPE: PRT
<213> ORGANISM: Homo sapiens

<400> SEQUENCE: 131

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60
```

```
Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Leu Arg Arg Val
            130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
            275                 280                 285

Leu Ser Gly Thr Arg His Ser His Pro Ser Val Gly Arg Gln His His
            290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
            370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
            435                 440                 445

Val Gln Leu Leu Arg Gln His Ser Ser Pro Trp Gln Val Tyr Gly Phe
            450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
```

```
                    485                 490                 495
Leu Gly Lys His Ala Lys Leu Ser Leu Gln Glu Leu Thr Trp Lys Met
                500                 505                 510
Ser Val Arg Gly Cys Ala Trp Leu Arg Arg Ser Pro Gly Val Gly Cys
                515                 520                 525
Val Pro Ala Ala Glu His Arg Leu Arg Glu Glu Ile Leu Ala Lys Phe
530                 535                 540
Leu His Trp Leu Met Ser Val Tyr Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
                580                 585                 590
Leu Lys Arg Val Gln Leu Arg Glu Leu Ser Ala Glu Val Arg Gln
                595                 600                 605
His Arg Glu Ala Arg Pro Ala Leu Leu Thr Ser Arg Leu Arg Phe Ile
                610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
                660                 665                 670
Pro Gly Leu Leu Gly Ala Ser Val Leu Gly Leu Asp Asp Ile His Arg
                675                 680                 685
Ala Trp Arg Thr Phe Val Leu Arg Val Arg Ala Gln Asp Pro Pro
690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
                740                 745                 750
Gly His Val Arg Lys Ala Phe Lys Ser His Val Ser Thr Leu Thr Asp
                755                 760                 765
Leu Gln Pro Tyr Met Arg Gln Phe Val Ala His Leu Gln Glu Thr Ser
                770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
                820                 825                 830
Gln Gly Ser Ile Leu Ser Thr Leu Leu Cys Ser Leu Cys Tyr Gly Asp
                835                 840                 845
Met Glu Asn Lys Leu Phe Ala Gly Ile Arg Arg Asp Gly Leu Leu Leu
850                 855                 860
Arg Leu Val Asp Asp Phe Leu Leu Val Thr Pro His Leu Thr His Ala
865                 870                 875                 880
Lys Thr Phe Leu Arg Thr Leu Val Arg Gly Val Pro Glu Tyr Gly Cys
                885                 890                 895
Val Val Asn Leu Arg Lys Thr Val Val Asn Phe Pro Val Glu Asp Glu
                900                 905                 910
```

```
Ala Leu Gly Gly Thr Ala Phe Val Gln Met Pro Ala His Gly Leu Phe
         915                 920                 925

Pro Trp Cys Gly Leu Leu Leu Asp Thr Arg Thr Leu Glu Val Gln Ser
     930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Lys Leu Phe Gly
             965                 970                 975

Val Leu Arg Leu Lys Cys His Ser Leu Phe Leu Asp Leu Gln Val Asn
             980                 985                 990

Ser Leu Gln Thr Val Cys Thr Asn Ile Tyr Lys Ile Leu Leu Leu Gln
         995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 132
<211> LENGTH: 4027
<212> TYPE: DNA
<213> ORGANISM: Homo sapiens

<400> SEQUENCE: 132
caggcagcgt ggtcctgctg cgcacgtggg aagccctggc cccggccacc cccgcgatgc     60
cgcgcgctcc ccgctgccga gccgtgcgct ccctgctgcg cagccactac gcgcaggtgc    120
tgccgctggc cacgttcgtg cggcgcctgg ggccccaggg ctggcggctg gtgcagcgcg    180
gggacccggc ggctttccgc gcgctggtgg cccagtgcct ggtgtgcgtg ccctgggacg    240
cacggccgcc cccgccgcc cctccttcc gccaggtgtc ctgcctgaag gagctggtgg      300
cccgagtgct gcagaggctg tgcgagcgcg gcgcgaagaa cgtgctggcc ttcggcttcg    360
cgctgctgga cggggcccgc ggggccccc ccgaggcctt caccaccagc gtgcgcagct     420
acctgcccaa cacggtgacc gacgcactgc ggggagcgg ggcgtggggg ctgctgttgc     480
gccgcgtggg cgacgacgtg ctggttcacc tgctggcacg ctgcgcgctc tttgtgctgg    540
tggctcccag ctgcgcctac caggtgtgcg ggccgccgct gtaccagctc ggcgctgcca    600
ctcaggcccg gccccgcca cacgctagtg accccgaag gcgtctggga tgcgaacggg      660
cctggaacca tagcgtcagg gaggccgggg tcccctggg cctgccagcc ccgggtgcga     720
ggaggcgcgg gggcagtgcc agccgaagtc tgccgttgcc caagaggccc aggcgtggcg    780
```

```
ctgcccctga gccggagcgg acgcccgttg ggcagggggtc ctgggcccac ccgggcagga      840
cgcgtggacc gagtgaccgt ggtttctgtg tggtgtcacc tgccagaccc gccgaagaag      900
ccacctcttt ggagggtgcg ctctctggca cgcgccactc ccacccatcc gtgggccgcc      960
agcaccacgc gggccccca  tccacatcgc ggccaccacg tccctgggac acgccttgtc     1020
ccccggtgta cgccgagacc aagcacttcc tctactcctc aggcgacaag gagcagctgc     1080
ggccctcctt cctactcagc tctctgaggc ccagcctgac tggcgctcgg aggctcgtgg     1140
agaccatctt tctgggttcc aggccctgga tgccagggac tccccgcagg ttgccccgcc     1200
tgccccagcg ctactggcaa atgcggcccc tgtttctgga gctgcttggg aaccacgcgc     1260
agtgccccta cggggtgctc ctcaagacgc actgcccgct gcgagctgcg gtcaccccag     1320
cagccggtgt ctgtgcccgg gagaagcccc agggctctgt ggcggccccc gaggaggagg     1380
acacagaccc ccgtcgcctg gtgcagctgc tccgccagca cagcagcccc tggcaggtgt     1440
acggcttcgt gcgggcctgc ctgcgccggc tggtgccccc aggcctctgg ggctccaggc     1500
acaacgaacg ccgcttcctc aggaacacca agaagttcat ctccctgggg aagcatgcca     1560
agctctcgct gcaggagctg acgtggaaga tgagcgtgcg gggctgcgct tggctgcgca     1620
ggagcccagg ggttggctgt gttccggccg cagagcaccg tctgcgtgag gagatcctgg     1680
ccaagttcct gcactggctg atgagtgtgt acgtcgtcga gctgctcagg tctttctttt     1740
atgtcacgga gaccacgttt caaaagaaca ggctcttttt ctaccggaag agtgtctgga     1800
gcaagttgca aagcattgga atcagacagc acttgaagag ggtgcagctg cgggagctgt     1860
cggaagcaga ggtcaggcag catcgggaag ccaggcccgc cctgctgacg tccagactcc     1920
gcttcatccc caagcctgac gggctgcggc cgattgtgaa catggactac gtcgtgggag     1980
ccagaacgtt ccgcagagaa aagagggccg agcgtctcac ctcgagggtg aaggcactgt     2040
tcagcgtgct caactacgag cgggcgcggc gccccggcct cctgggcgcc tctgtgctgg     2100
gcctggacga tatccacagg gcctggcgca ccttcgtgct gcgtgtgcgg gcccaggacc     2160
cgccgcctga gctgtacttt gtcaaggtgg atgtgacggg cgcgtacgac accatccccc     2220
aggacaggct cacggaggtc atcgccagca tcatcaaacc ccagaacacg tactgcgtgc     2280
gtcggtatgc cgtggtccag aaggccgccc atgggcacgt ccgcaaggcc ttcaagagcc     2340
acgtctctac cttgacagac ctccagccgt acatgcgaca gttcgtggct cacctgcagg     2400
agaccagccc gctgagggat gccgtcgtca tcgagcagag ctcctcccng aatgaggcca     2460
gcagtggcct cttcgacgtc ttcctacgct tcatgtgcca ccacgccgtg cgcatcaggg     2520
gcaagtccta cgtccagtgc caggggatcc gcagggctc  catcctctcc acgctgctct     2580
gcagcctgtg ctacgcgac  atggagaaca agctgtttgc ggggattcgg cgggacgggc     2640
tgctcctgcg tttggtggat gatttcttgt tggtgacacc tcacctcacc cacgcgaaaa     2700
ccttcctcag accctggtc  cgaggtgtcc ctgagtatgg ctgcgtggtg aacttgcgga     2760
agacagtggt gaacttccct gtagaagacg aggccctggg tggcacggct tttgttcaga     2820
tgccggccca cggcctattc ccctggtgcg gcctgctgct ggataccggg acctggaggg     2880
tgcagagcga ctactccagc tatgcccgga cctccatcag agccagtctc accttcaacc     2940
gcggcttcaa ggctgggagg aacatgcgtc gcaaactctt ggggtcttg  cggctgaagt     3000 gtcacagcct gtttctggat ttgcaggtga acagcctcca gacggtgtgc accaacatct     3060
acaagatcct cctgctgcag gcgtacaggt ttcacgcatg tgtgctgcag ctcccatttc     3120
```

-continued

```
atcagcaagt tggaagaac cccacatttt tcctgcgcgt catctctgac acggcctccc   3180
tctgctactc catcctgaaa gccaagaacg cagggatgtc gctggggcc aagggcgccg    3240
ccggccctct gccctccgag gccgtgcagt ggctgtgcca ccaagcattc ctgctcaagc   3300
tgactcgaca ccgtgtcacc tacgtgccac tcctggggtc actcaggaca gcccagacgc   3360
agctgagtcg gaagctcccg gggacgacgc tgactgccct ggaggccgca gccaacccgg   3420
cactgccctc agacttcaag accatcctgg actgatggcc acccgcccac agccaggccg   3480
agagcagaca ccagcagccc tgtcacgccg ggctctacgt cccagggagg gagggcggc    3540
ccacacccag gcccgcaccg ctgggagtct gaggcctgag tgagtgtttg gccgaggcct   3600
gcatgtccgg ctgaaggctg agtgtccggc tgaggcctga gcgagtgtcc agccaagggc   3660
tgagtgtcca gcacacctgc cgtcttcact tccccacagg ctggcgctcg gctccacccc   3720
agggccagct tttcctcacc aggagcccgg cttccactcc ccacatagga atagtccatc   3780
cccagattcg ccattgttca cccctcgccc tgccctcctt tgccttccac ccccaccatc   3840
caggtggaga ccctgagaag gaccctggga gctctgggaa tttggagtga ccaaaggtgt   3900
gccctgtaca caggcgagga ccctgcacct ggatgggggt ccctgtgggt caaattgggg   3960
ggaggtgctg tgggagtaaa atactgaata tatgagtttt tcagttttga aaaaaaaaa   4020
aaaaaaa                                                             4027
```

TREATMENT OF CANCER USING ANTI-CD19 CHIMERIC ANTIGEN RECEPTOR

This application claims priority to U.S. Ser. No. 61/976,396 filed Apr. 7, 2014, U.S. Ser. No. 62/007,309 filed Jun. 3, 2014, U.S. Ser. No. 62/036,493 filed Aug. 12, 2014, U.S. Ser. No. 62/076,238 filed Nov. 6, 2014, U.S. Ser. No. 62/087,888 filed Dec. 5, 2014, and U.S. Ser. No. 62/097,278 filed Dec. 29, 2014, the contents of which are incorporated herein by reference in their entireties. International Application Number PCT/US15/24671, filed Apr. 7, 2015, is also incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 6, 2015, is named N2067-7051US_S-L.txt and is 249,332 bytes in size.

FIELD OF THE INVENTION

The present invention relates generally to the use of T cells engineered to express a Chimeric Antigen Receptor (CAR), e.g., in combination with another agent such as, e.g., a kinase inhibitor and/or a cytokine, to treat a disease associated with expression of the Cluster of Differentiation 19 protein (CD19).

BACKGROUND OF THE INVENTION

Many patients with B cell malignancies are incurable with standard therapy. In addition, traditional treatment options often have serious side effects. Attempts have been made in cancer immunotherapy, however, several obstacles render this a very difficult goal to achieve clinical effectiveness. Although hundreds of so-called tumor antigens have been identified, these are generally derived from self and thus are poorly immunogenic. Furthermore, tumors use several mechanisms to render themselves hostile to the initiation and propagation of immune attack.

Recent developments using chimeric antigen receptor (CAR) modified autologous T cell (CART) therapy, which relies on redirecting T cells to a suitable cell-surface molecule on cancer cells such as B cell malignancies, show promising results in harnessing the power of the immune system to treat B cell malignancies and other cancers (see, e.g., Sadelain et al., Cancer Discovery 3:388-398 (2013)). The clinical results of the murine derived CART19 (i.e., "CTL019") have shown promise in establishing complete remissions in patients suffering with CLL as well as in childhood ALL (see, e.g., Kalos et al., Sci Transl Med 3:95ra73 (2011), Porter et al., NEJM 365:725-733 (2011), Grupp et al., NEJM 368:1509-1518 (2013)). Besides the ability for the chimeric antigen receptor on the genetically modified T cells to recognize and destroy the targeted cells, a successful therapeutic T cell therapy needs to have the ability to proliferate and persist over time, and to further monitor for leukemic cell escapees. The variable quality of T cells whether it's a result of anergy, suppression or exhaustion will have effects on CAR-transformed T cells' performance but for which skilled practitioners have limited control over at this time. To be effective, CAR transformed patient T cells need to persist and maintain the ability to proliferate in response to the CAR's antigen. It has been shown that ALL patient T cells perform can do this with CART19 comprising a murine scFv (see, e.g., Grupp et al., NEJM 368:1509-1518 (2013)).

SUMMARY OF THE INVENTION

The disclosure features, at least in part, compositions and methods of treating disorders such as cancer (e.g., hematological cancers or other B-cell malignancies) using immune effector cells (e.g., T cells or NK cells) that express a Chimeric Antigen Receptor (CAR) molecule (e.g., a CAR that binds to a B-cell antigen, e.g., Cluster of Differentiation 19 protein (CD19) (e.g., OMIM Acc. No. 107265, Swiss Prot. Acc No. P15391). The compositions include, and the methods include administering, immune effector cells (e.g., T cells or NK cells) expressing a B cell targeting CAR, in combination with a kinase inhibitor (e.g., one or more of a CDK4/6 inhibitor, a BTK inhibitor, an mTOR inhibitor, a MNK inhibitor, a dual PI3K/mTOR inhibitor, or a combination thereof). In some embodiments, the combination maintains, or has better clinical effectiveness, as compared to either therapy alone. The invention further pertains to the use of engineered cells, e.g., immune effector cells (e.g., T cells or NK cells), to express a CAR molecule that binds to a B-cell antigen, e.g., CD19, in combination with a kinase inhibitor (e.g., a kinase inhibitor chosen from one or more of a cyclin dependent kinase 4 (CDK4) inhibitor, a Bruton's tyrosine kinase (BTK) inhibitor, an mTOR inhibitor, a mitogen activated protein kinase interacting kinase (MNK) inhibitor, a dual phosphatidylinositol 3-kinase (PI3K)/mTOR inhibitor, or a combination thereof) to treat a disorder associated with expression of a B-cell antigen, e.g., CD19 (e.g., a cancer, e.g., a hematological cancer).

Accordingly, in one aspect, the invention pertains to a method of treating a subject, e.g., a mammal, having a disease associated with expression of a B-cell antigen, e.g., CD19. The method comprises administering to the mammal an effective amount of a cell e.g., an immune effector cell (e.g., a T cell or NK cell) that expresses a CAR molecule that binds the B-cell antigen, in combination with a kinase inhibitor, e.g., a kinase inhibitor described herein. In one embodiment, the CAR molecule binds to CD19, e.g., a CAR molecule that binds CD19 described herein. In other embodiments, the CAR molecule binds to one or more of CD20, CD22 or ROR1.

In one embodiment, the disease associated with expression of a B-cell antigen (e.g., expression of one or more of CD19, CD20, CD22 or ROR1), is selected from a proliferative disease such as a cancer, a malignancy, or a precancerous condition such as a myelodysplasia, a myelodysplastic syndrome or a preleukemia, or is a non-cancer related indication associated with expression of the B-cell antigen, e.g., one or more of CD19, CD20, CD22 or ROR1. In one embodiment, the disease is a solid or liquid tumor. In one embodiment, the cancer is pancreatic cancer. In one embodiment, the disease is a hematologic cancer. In one embodiment, the hematological cancer is leukemia. In one embodiment, the cancer is selected from the group consisting of one or more acute leukemias including but not limited to B-cell acute lymphoid leukemia (BALL), T-cell acute lymphoid leukemia (TALL), small lymphocytic leukemia (SLL), acute lymphoid leukemia (ALL); one or more chronic leukemias including but not limited to chronic myelogenous leukemia (CML), chronic lymphocytic leukemia (CLL). Additional hematological cancers or hematologic conditions include, but are not limited to, mantle cell lymphoma (MCL), B cell prolymphocytic leukemia, blastic plasmacytoid dendritic cell neoplasm, Burkitt's lymphoma, diffuse large B cell lymphoma (DLBCL), follicular lymphoma, hairy cell leukemia, small cell- or a large cell-follicular lymphoma, malignant lymphoproliferative conditions, MALT lymphoma, Marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, and Waldenstrom macroglobulinemia. In certain embodiments, the disease associated with B-cell antigen (e.g., e.g., one or more of CD19, CD20, CD22 or ROR1) expression is a "preleukemia" which is a diverse collection of hematological conditions united by ineffective production (or dysplasia) of myeloid blood cells. In some embodiments, the disease associated with B-cell antigen (e.g., one or more of CD19, CD20, CD22 or ROR1) expression includes, but is not limited to atypical and/or non-classical cancers, malignancies, precancerous conditions or proliferative diseases expressing the B-cell antigen (e.g., one or more of CD19, CD20, CD22 or ROR1). Any combination of the diseases associated with B-cell antigen (e.g., one or more of CD19, CD20, CD22 or ROR1) expression described herein can be treated with the methods and compositions described herein.

In one embodiment, the disease associated with expression of the B-cell antigen (e.g., one or more of CD19, CD20, CD22 or ROR1) is a lymphoma, e.g., MCL, Hodgkin lymphoma, or DLBCL. In one embodiment, the disease associated with expression of the B-cell antigen (e.g., one or more of CD19, CD20, CD22 or ROR1) is leukemia, e.g., SLL, CLL and/or ALL. In one embodiment, the disease associated with expression of the B-cell antigen is multiple myeloma (e.g., a multiple myeloma that is CD19-negative, e.g., having a vast majority (99.95%) of the neoplastic plasma cells with a CD19-negative phenotype, e.g., as detected by both flow cytometry and RT-PCR.

In one embodiment, the kinase inhibitor is a CDK4 inhibitor, e.g., a CDK4 inhibitor described herein, e.g., a CD4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo [3,4-d] pyrimidine. The MNK inhibitor can be, e.g., a MNK1a, MNK1b, MNK2a and/or MNK2b inhibitor. In one embodiment, the inhibitor can be a dual PI3K/mTOR inhibitor, e.g., PF-04695102.

In one embodiment, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066); 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); XL281 (BMS908662); and ribociclib.

In one embodiment, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In one embodiment, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In a preferred embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In one embodiment, the kinase inhibitor is a BTK inhibitor, e.g., ibrutinib (PCI-32765), and the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle cycle, or daily for 28 day cycle. In one embodiment, 1, 2, 3, 4, 5, 6, 7, 8, 9, 10, 11, 12 or more cycles of ibrutinib are administered.

In one embodiment, the kinase inhibitor is an mTOR inhibitor selected from temsirolimus; ridaforolimus (1R,2R,4S)-4-[(2R)-2 [(1R,9S,12S,15R,16E,18R,19R,21R, 23S,24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669; everolimus (RAD001); rapamycin (AY22989); semapimod; (5-{2,4-bis[(3S)-3-methylmorpholin-4-yl]pyrido[2,3-d]pyrimidin-7-yl}-2-methoxyphenyl) methanol (AZD8055); 2-amino-8-[trans-4-(2-hydroxyethoxy)cyclohexyl]-6-(6-methoxy-3-pyridinyl)-4-methylpyrido[2,3-d]pyrimidin-7(8H)-one (PF04691502); and N$^2$-[1,4-dioxo-4-[[4-(4-oxo-8-phenyl-4H-1-benzopyran-2-yl) morpholinium-4-yl]methoxy]butyl]-L-arginylglycyl-L-α-aspartylL-serine-, inner salt (SF1126); and XL765.

In one embodiment, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is an MNK inhibitor selected from CGP052088; 4-amino-3-(p-fluorophenylamino)-pyrazolo [3,4-d] pyrimidine (CGP57380); cercosporamide; ETC-1780445-2; and 4-amino-5-(4-fluoroanilino)-pyrazolo [3,4-d] pyrimidine.

In one embodiment, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl] phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

In one embodiment, the cell expresses a CAR molecule comprising an anti-CD19 binding domain (e.g., a murine or humanized antibody or antibody fragment that specifically binds to CD19), a transmembrane domain, and an intracellular signaling domain (e.g., an intracellular signaling domain comprising a costimulatory domain and/or a primary signaling domain). In one embodiment, the CAR comprises an antibody or antibody fragment which includes an anti-CD19 binding domain described herein (e.g., a murine or humanized antibody or antibody fragment that specifically binds to CD19 as described herein), a transmembrane domain described herein, and an intracellular signaling domain described herein (e.g., an intracellular signaling domain comprising a costimulatory domain and/or a primary signaling domain described herein).

In one embodiment, the CAR molecule is capable of binding CD19 (e.g., wild-type or mutant human CD19). In one embodiment, the CAR molecule comprises an anti-CD19 binding domain comprising one or more (e.g., all three) light chain complementary determining region 1 (LC CDR1), light chain complementary determining region 2 (LC CDR2), and light chain complementary determining region 3 (LC CDR3) of an anti-CD19 binding domain described herein, and one or more (e.g., all three) heavy chain complementary determining region 1 (HC CDR1), heavy chain complementary determining region 2 (HC CDR2), and heavy chain complementary determining region 3 (HC CDR3) of an anti-CD19 binding domain described herein, e.g., an anti-CD19 binding domain comprising one or more, e.g., all three, LC CDRs and one or more, e.g., all three, HC CDRs. In one embodiment, the anti-CD19 binding domain comprises one or more (e.g., all three) heavy chain complementary determining region 1 (HC CDR1), heavy chain complementary determining region 2 (HC CDR2), and heavy chain complementary determining region 3 (HC CDR3) of an anti-CD19 binding domain described herein, e.g., the anti-CD19 binding domain has two variable heavy chain regions, each comprising a HC CDR1, a HC CDR2 and a HC CDR3 described herein. In one embodiment, the anti-CD19 binding domain comprises a murine light chain variable region described herein (e.g., in Table 7) and/or a murine heavy chain variable region described herein (e.g., in Table 7). In one embodiment, the anti-CD19 binding domain is a scFv comprising a murine light chain and a murine heavy chain of an amino acid sequence of Table 7. In an embodiment, the anti-CD19 binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 7, or a sequence with 95-99% identity with an amino acid sequence of Table 7; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in Table 7, or a sequence with 95-99% identity to an amino acid sequence of Table 7. In one embodiment, the anti-CD19 binding domain comprises a sequence of SEQ ID NO:59, or a sequence with 95-99% identify thereof. In one embodiment, the anti-CD19 binding domain is a scFv, and a light chain variable region comprising an amino acid sequence described herein, e.g., in Table 7, is attached to a heavy chain variable region comprising an amino acid sequence described herein, e.g., in Table 7, via a linker, e.g., a linker described herein. In one embodiment, the anti-CD19 binding domain includes a (Gly$_4$-Ser)n linker, wherein n is 1, 2, 3, 4, 5, or 6, preferably 3 or 4 (SEQ ID NO: 53). The light chain variable region and heavy chain variable region of a scFv can be, e.g., in any of the following orientations: light chain variable region-linker-heavy chain variable region or heavy chain variable region-linker-light chain variable region.

In one embodiment, the CAR molecule comprises a humanized anti-CD19 binding domain that includes one or more (e.g., all three) light chain complementary determining region 1 (LC CDR1), light chain complementary determining region 2 (LC CDR2), and light chain complementary determining region 3 (LC CDR3) of a humanized anti-CD19 binding domain described herein, and one or more (e.g., all three) heavy chain complementary determining region 1 (HC CDR1), heavy chain complementary determining region 2 (HC CDR2), and heavy chain complementary determining region 3 (HC CDR3) of a humanized anti-CD19 binding domain described herein, e.g., a humanized anti-CD19 binding domain comprising one or more, e.g., all three, LC CDRs and one or more, e.g., all three, HC CDRs. In one embodiment, the humanized anti-CD19 binding domain comprises at least HC CDR2. In one embodiment, the humanized anti-CD19 binding domain comprises one or more (e.g., all three) heavy chain complementary determining region 1 (HC CDR1), heavy chain complementary determining region 2 (HC CDR2), and heavy chain complementary determining region 3 (HC CDR3) of a humanized anti-CD19 binding domain described herein, e.g., the humanized anti-CD19 binding domain has two variable heavy chain regions, each comprising a HC CDR1, a HC CDR2 and a HC CDR3 described herein. In one embodiment, the humanized anti-CD19 binding domain comprises at least HC CDR2. In one embodiment, the light chain variable region comprises one, two, three or all four framework regions of VK3_L25 germline sequence. In one embodiment, the light chain variable region has a modification (e.g., substitution, e.g., a substitution of one or more amino acid found in the corresponding position in the murine light chain variable region of SEQ ID NO: 58, e.g., a substitution at one or more of positions 71 and 87). In one embodiment, the heavy chain variable region comprises one, two, three or all four framework regions of VH4_4-59 germline sequence. In one embodiment, the heavy chain variable region has a modification (e.g., substitution, e.g., a substitution of one or more amino acid found in the corresponding position in the murine heavy chain variable region of SEQ ID NO: 58, e.g., a substitution at one or more of positions 71, 73 and 78). In one embodiment, the humanized anti-CD19 binding domain comprises a light chain variable region described herein (e.g., in Table 3) and/or a heavy chain variable region described herein (e.g., in Table 3). In one embodiment, the humanized anti-CD19 binding domain is a scFv comprising a light chain and a heavy chain of an amino acid sequence of Table 3. In an embodiment, the humanized anti-CD19 binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 3, or a sequence with 95-99% identity with an amino acid sequence of Table 3; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in Table 3, or a sequence with 95-99% identity to an amino acid sequence of Table 3. In one embodiment, the humanized anti-CD19 binding domain comprises a sequence selected from a group consisting of SEQ ID NO:1, SEQ ID NO:2, SEQ ID NO:3, SEQ ID NO: 4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12, or a sequence with 95-99% identify thereof. In one embodiment, the humanized anti-CD19 binding domain is a scFv, and a light chain variable region comprising an amino acid sequence described herein, e.g., in Table 3, is attached to a heavy chain variable region comprising an amino acid sequence described herein, e.g., in Table 3, via a linker, e.g., a linker described herein. In one embodiment, the humanized anti-CD19 binding domain includes a $(Gly_4\text{-Ser})n$ linker, wherein n is 1, 2, 3, 4, 5, or 6, preferably 3 or 4 (SEQ ID NO: 53). The light chain variable region and heavy chain variable region of a scFv can be, e.g., in any of the following orientations: light chain variable region-linker-heavy chain variable region or heavy chain variable region-linker-light chain variable region.

In one embodiment, the CAR molecule comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO: 15. In one embodiment, the transmembrane domain comprises an amino acid sequence having at least one, two or three modifications (e.g., substitutions) but not more than 20, 10 or 5 modifications (e.g., substitutions) of an amino acid sequence of SEQ ID NO: 15, or a sequence with 95-99% identity to an amino acid sequence of SEQ ID NO: 15.

In one embodiment, the anti-CD19 binding domain is connected to the transmembrane domain by a hinge region, e.g., a hinge region described herein. In one embodiment, the encoded hinge region comprises SEQ ID NO:14 or SEQ ID NO:45, or a sequence with 95-99% identity thereof.

In one embodiment, the CAR molecule further comprises a sequence encoding a costimulatory domain, e.g., a costimulatory domain described herein. In one embodiment, the costimulatory domain comprises a functional signaling domain of a protein selected from the group consisting of OX40, CD2, CD27, CD28, CD5, ICAM-1, LFA-1 (CD11a/CD18) and 4-1BB (CD137). In one embodiment, the costimulatory domain comprises a sequence of SEQ ID NO: 16. In one embodiment, the costimulatory domain comprises a sequence of SEQ ID NO:51. In one embodiment, the costimulatory domain comprises an amino acid sequence having at least one, two or three modifications (e.g., substitutions) but not more than 20, 10 or 5 modifications (e.g., substitutions) of an amino acid sequence of SEQ ID NO: 16 or SEQ ID NO:51, or a sequence with 95-99% identity to an amino acid sequence of SEQ ID NO: 16 or SEQ ID NO:51.

In one embodiment, the CAR molecule further comprises a sequence encoding an intracellular signaling domain, e.g., an intracellular signaling domain described herein. In one embodiment, the intracellular signaling domain comprises a functional signaling domain of 4-1BB and/or a functional signaling domain of CD3 zeta. In one embodiment, the intracellular signaling domain comprises the sequence of SEQ ID NO: 16 and/or the sequence of SEQ ID NO:17. In one embodiment, the intracellular signaling domain comprises the sequence of SEQ ID NO:16 and/or the sequence of SEQ ID NO:43. In one embodiment, the intracellular signaling domain comprises a functional signaling domain of CD27 and/or a functional signaling domain of CD3 zeta. In one embodiment, the intracellular signaling domain comprises the sequence of SEQ ID NO: 51 and/or the sequence of SEQ ID NO:17. In one embodiment, the intracellular signaling domain comprises the sequence of SEQ ID NO:51 and/or the sequence of SEQ ID NO:43. In one embodiment, the intracellular signaling domain comprises an amino acid sequence having at least one, two or three modifications (e.g., substitutions) but not more than 20, 10 or 5 modifications (e.g., substitutions) of an amino acid sequence of SEQ ID NO:16 or SEQ ID NO:51 and/or an amino acid sequence of SEQ ID NO:17 or SEQ ID NO:43, or a sequence with 95-99% identity to an amino acid sequence of SEQ ID NO:16 or SEQ ID NO:51 and/or an amino acid sequence of SEQ ID NO:17 or SEQ ID NO:43. In one embodiment, the intracellular signaling domain comprises the sequence of SEQ ID NO:16 or SEQ ID NO:51 and the sequence of SEQ ID NO: 17 or SEQ ID NO:43, wherein the sequences comprising the intracellular signaling domain are expressed in the same frame and as a single polypeptide chain.

In one embodiment, the CAR molecule further comprises a leader sequence, e.g., a leader sequence described herein. In one embodiment, the leader sequence comprises an amino acid sequence of SEQ ID NO: 13, or a sequence with 95-99% identity to an amino acid sequence of SEQ ID NO:13.

In one embodiment, the CAR molecule comprises a leader sequence, e.g., a leader sequence described herein, e.g., a leader sequence of SEQ ID NO: 13, or having 95-99% identity thereof; an anti-CD19 binding domain described herein, e.g., an anti-CD19 binding domain comprising a LC CDR1, a LC CDR2, a LC CDR3, a HC CDR1, a HC CDR2 and a HC CDR3 described herein, e.g., a murine anti-CD19 binding domain described in Table 7, a humanized anti-CD19 binding domain described in Table 3, or a sequence with 95-99% identify thereof; a hinge region, e.g., a hinge region described herein, e.g., a hinge region of SEQ ID NO:14 or having 95-99% identity thereof; a transmembrane domain, e.g., a transmembrane domain described herein, e.g., a transmembrane domain having a sequence of SEQ ID NO:15 or a sequence having 95-99% identity thereof; an intracellular signaling domain, e.g., an intracellular signaling domain described herein (e.g., an intracellular signaling domain comprising a costimulatory domain and/or a primary signaling domain). In one embodiment, the intracellular signaling domain comprises a costimulatory domain, e.g., a costimulatory domain described herein, e.g., a 4-1BB costimulatory domain having a sequence of SEQ ID NO:16 or SEQ ID NO:51, or having 95-99% identity thereof, and/or a primary signaling domain, e.g., a primary signaling domain described herein, e.g., a CD3 zeta stimulatory domain having a sequence of SEQ ID NO:17 or SEQ ID NO:43, or having 95-99% identity thereof.

In one embodiment, the CAR molecule comprises (e.g., consists of) an amino acid sequence of SEQ ID NO:58, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41 or SEQ ID NO:42, or an amino acid sequence having at least one, two, three, four, five, 10, 15, 20 or 30 modifications (e.g., substitutions) but not more than 60, 50 or 40 modifications (e.g., substitutions) of an amino acid sequence of SEQ ID NO:58, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41 or SEQ ID NO:42, or an amino acid sequence having 85%, 90%, 95%, 96%, 97%, 98% or 99% identity to an amino acid sequence of SEQ ID NO:58, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41 or SEQ ID NO:42.

In one embodiment, the cell expressing the CAR molecule comprises a vector that includes a nucleic acid sequence encoding the CAR molecule. In one embodiment, the vector is selected from the group consisting of a DNA, a RNA, a plasmid, a lentivirus vector, adenoviral vector, or a retrovirus vector. In one embodiment, the vector is a lentivirus vector. In one embodiment, the vector further comprises a promoter. In one embodiment, the promoter is an EF-1 promoter. In one embodiment, the EF-1 promoter comprises a sequence of SEQ ID NO: 100. In one embodiment, the vector is an in vitro transcribed vector, e.g., a vector that transcribes RNA of a nucleic acid molecule described herein. In one embodiment, the nucleic acid sequence in the in vitro vector further comprises a poly(A) tail, e.g., a poly A tail described herein, e.g., comprising about 150 adenosine bases (SEQ ID NO:104). In one embodiment, the nucleic acid sequence in the in vitro vector further comprises a 3'UTR, e.g., a 3' UTR described herein, e.g., comprising at least one repeat of a 3'UTR derived from human beta-globulin. In one embodiment, the nucleic acid sequence in the in vitro vector further comprises promoter, e.g., a T2A promoter.

In certain embodiments of the compositions and methods disclosed herein, the cell expressing the CAR molecule (also referred to herein as a "CAR-expressing cell") is a cell or population of cells as described herein, e.g., a human immune effector cell or population of cells (e.g., a human T cell or a human NK cell, e.g., a human T cell described herein or a human NK cell described herein). In one embodiment, the human T cell is a CD8+ T cell. In one embodiment, the cell is an autologous T cell. In one embodiment, the cell is an allogeneic T cell. In one embodiment, the cell is a T cell and the T cell is diaglycerol kinase (DGK) deficient. In one embodiment, the cell is a T cell and the T cell is Ikaros deficient. In one embodiment, the cell is a T cell and the T cell is both DGK and Ikaros deficient. It shall be understood that the compositions and methods disclosed herein reciting the term "cell" encompass compositions and methods comprising one or more cells, e.g., a population of cells.

In another embodiment, the cell expressing the CAR molecule, e.g., as described herein, can further express another agent, e.g., an agent which enhances the activity of a CAR-expressing cell.

In one embodiment, the method further includes administering a cell expressing the CAR molecule, as described herein, optionally in combination with a kinase inhibitor, e.g., a BTK inhibitor such as ibrutinib, in combination with an agent which enhances the activity of a CAR-expressing cell. In certain embodiments, the agent is a cytokine, e.g., IL-7, IL-15, IL-21, or a combination thereof. In one embodiment, the method includes administering IL-7 to the subject. The cytokine can be delivered in combination with, e.g., simultaneously or shortly after, administration of the CAR-expressing cell. Alternatively, the cytokine can be delivered after a prolonged period of time after administration of the CAR-expressing cell, e.g., after assessment of the subject's response to the CAR-expressing cell.

In other embodiments, the agent which enhances the activity of a CAR-expressing cell can be an agent which inhibits an immune inhibitory molecule. Examples of immune inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta. In one embodiment, the agent which inhibits an immune inhibitory molecule comprises a first polypeptide, e.g., an immune inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 or TGFR beta, or a fragment of any of these (e.g., at least a portion of the extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In one embodiment, lymphocyte infusion, for example allogeneic lymphocyte infusion, is used in the treatment of the cancer, wherein the lymphocyte infusion comprises at least one CAR-expressing cell that binds to a B-cell antigen (e.g., CD19) (also referred to herein as CD19 CAR-expressing cell), as described herein. In one embodiment, autologous lymphocyte infusion is used in the treatment of the cancer, wherein the autologous lymphocyte infusion comprises at least one CD19-expressing cell.

In one embodiment, the CD19 CAR expressing cell, e.g., T cell, is administered to a subject that has received a previous stem cell transplantation, e.g., autologous stem cell transplantation.

In one embodiment, the CD19 CAR expressing cell, e.g., T cell, is administered to a subject that has received a previous dose of melphalan.

In one embodiment, the cell expressing the CAR molecule, e.g., a CAR molecule described herein, is administered in combination with an agent that ameliorates one or more side effect associated with administration of a cell expressing a CAR molecule, e.g., an agent described herein.

In one embodiment, the kinase inhibitor, is administered in combination with an agent that ameliorates one or more side effect associated with administration of the kinase inhibitor, e.g., an agent described herein.

In one embodiment, the cell expressing the CAR molecule, e.g., a CAR molecule described herein, and the kinase inhibitor are administered in combination with an additional agent that treats the disease associated with CD19, e.g., an additional agent described herein.

In one embodiment, the cells expressing a CAR molecule, e.g., a CAR molecule described herein, are administered at a dose and/or dosing schedule described herein.

In one embodiment, the CAR molecule is introduced into T cells, e.g., using in vitro transcription, and the subject (e.g., human) receives an initial administration of cells comprising a CAR molecule, and one or more subsequent administrations of cells comprising a CAR molecule, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of cells comprising a CAR molecule are administered to the subject (e.g., human) per week, e.g., 2, 3, or 4 administrations of cells comprising a CAR molecule are administered per week. In one embodiment, the subject (e.g., human subject) receives more than one administration of cells comprising a CAR molecule per week (e.g., 2, 3 or 4 administrations per week) (also referred to herein as a cycle), followed by a week of no administration of cells comprising a CAR molecule, and then one or more additional administration of cells comprising a CAR molecule (e.g., more than one administration of the cells comprising a CAR molecule per week) is administered to the subject. In another embodiment, the subject (e.g., human subject) receives more than one cycle of cells comprising a CAR molecule, and the time between each cycle is less than 10, 9, 8, 7, 6, 5, 4, or 3 days. In one embodiment, the cells comprising a CAR molecule are administered every other day for 3 administrations per week. In one embodiment, the cells comprising a CAR molecule are administered for at least two, three, four, five, six, seven, eight or more weeks.

In one embodiment, the combination of the kinase inhibitor and the cells expressing a CAR molecule, e.g., a CAR molecule described herein, are administered as a first line treatment for the disease, e.g., the cancer, e.g., the cancer described herein. In another embodiment, the combination of the kinase inhibitor and the cells expressing a CAR molecule, e.g., a CAR molecule described herein, are administered as a second, third, fourth line treatment for the disease, e.g., the cancer, e.g., the cancer described herein.

In one embodiment, a cell (e.g., a population of cells) described herein is administered to the subject.

In one embodiment, the method includes administering a population of cells, a plurality of which comprise a CAR molecule described herein. In some embodiments, the population of CAR-expressing cells comprises a mixture of cells expressing different CARs. For example, in one embodiment, the population of CAR-expressing cells can include a first cell expressing a CAR having an anti-CD19 binding domain described herein, and a second cell expressing a CAR having a different anti-CD19 binding domain, e.g., an anti-CD19 binding domain described herein that differs from the anti-CD19 binding domain in the CAR expressed by the first cell. As another example, the population of CAR-expressing cells can include a first cell expressing a CAR that includes an anti-CD19 binding domain, e.g., as described herein, and a second cell expressing a CAR that includes an antigen binding domain to a target other than CD19 (e.g., CD123 or mesothelin). In one embodiment, the population of CAR-expressing cells includes, e.g., a first cell expressing a CAR that includes a primary intracellular signaling domain, and a second cell expressing a CAR that includes a secondary signaling domain.

In one embodiment, the method includes administering a population of cells wherein at least one cell in the population expresses a CAR having an anti-CD19 domain described herein, and an agent which enhances the activity of a CAR-expressing cell, e.g., a second cell expressing the agent which enhances the activity of a CAR-expressing cell. For example, in one embodiment, the agent can be an agent which inhibits an immune inhibitory molecule. Examples of immune inhibitory molecules include PD1, PD-L1, CTLA-4, TIM3, CEACAM (e.g., CEACAM-1, CEACAM-3 and/or CEACAM-5), LAG3, VISTA, BTLA, TIGIT, LAIR1, CD160, 2B4 and TGFR beta. In one embodiment, the agent which inhibits an immune inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 or TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In another aspect, the invention pertains to a cell expressing a CAR molecule described herein for use as a medicament in combination with a kinase inhibitor, e.g., a kinase inhibitor described herein (e.g., a BTK inhibitor such as ibrutinib). In another aspect, the invention pertains to a kinase inhibitor described herein (e.g., a BTK inhibitor such as ibrutinib) for use as a medicament in combination with a cell expressing a CAR molecule described herein.

In another aspect, the invention pertains to a cell expressing a CAR molecule described herein for use in combination with a kinase inhibitor, e.g., a kinase inhibitor described herein (e.g., a BTK inhibitor such as ibrutinib), in the treatment of a disease expressing the B-cell antigen (e.g., CD19). In another aspect, the invention pertains to a kinase inhibitor described herein (e.g., a BTK inhibitor such as ibrutinib), for use in combination with a cell expressing a CAR molecule described herein, in the treatment of a disease expressing the B-cell antigen (e.g., CD19). The disease may be, e.g., a cancer such as a hematologic cancer. The cancer may be, e.g., a lymphoma, CLL, MCL, ALL, DLBCL, multiple myeloma, or another cancer described herein.

In another aspect, the invention pertains to a cell expressing a CAR molecule described herein for use as a medicament in combination with a cytokine, e.g., IL-7, IL-15 and/or IL-21 as described herein. In another aspect, the invention pertains to a cytokine described herein for use as a medicament in combination with a cell expressing a CAR molecule described herein.

In another aspect, the invention pertains to a cell expressing a CAR molecule described herein for use in combination with a cytokine, e.g., IL-7, IL-15 and/or IL-21 as described herein, in the treatment of a disease expressing CD19. In another aspect, the invention pertains to a cytokine described herein for use in combination with a cell expressing a CAR molecule described herein, in the treatment of a disease expressing CD19.

In another aspect, the invention pertains to a method of treating a mammal having Hodgkin lymphoma, comprising administering to the mammal an effective amount of the cell (e.g., cells) expressing a CAR molecule, e.g., a CAR molecule described herein.

In one embodiment, the cell expressing a CAR molecule, e.g., a CAR molecule described herein, is administered in combination with an agent that increases the efficacy of a cell expressing a CAR molecule, e.g., an agent described herein.

In one embodiment, the cell expressing a CAR molecule, e.g., a CAR molecule described herein, is administered in combination with an agent that ameliorates one or more side effect associated with administration of a cell expressing a CAR molecule, e.g., an agent described herein.

In one embodiment, the cell expressing a CAR molecule, e.g., a CAR molecule described herein, is administered in combination with an agent that treats Hodgkin lymphoma, e.g., an agent described herein.

In one embodiment, the cell expressing a CAR molecule, e.g., a CAR molecule described herein, is administered in combination with a low, immune enhancing dose of an mTOR inhibitor, e.g., an mTOR inhibitor described herein. While not wishing to be bound by theory, it is believed that treatment with a low, immune enhancing, dose (e.g., a dose that is insufficient to completely suppress the immune system but sufficient to improve immune function) is accompanied by a decrease in PD-1 positive T cells or an increase in PD-1 negative cells. PD-1 positive T cells, but not PD-1 negative T cells, can be exhausted by engagement with cells which express a PD-1 ligand, e.g., PD-L1 or PD-L2.

In an embodiment this approach can be used to optimize the performance of a CAR cell described herein in the subject. While not wishing to be bound by theory, it is believed that, in an embodiment, the performance of endogenous, non-modified immune effector cells, e.g., T cells, is improved. While not wishing to be bound by theory, it is believed that, in an embodiment, the performance of a CD19 CAR expressing cell is improved. In other embodiments, cells, e.g., T cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In an embodiment, administration of a low, immune enhancing, dose of an mTOR inhibitor, e.g., an allosteric inhibitor, e.g., RAD001, or a catalytic inhibitor, is initiated prior to administration of an CAR expressing cell described herein, e.g., T cells. In an embodiment, the mTOR inhibitor is RAD001 or rapamycin. In an embodiment, the CAR cells are administered after a sufficient time, or sufficient dosing, of an mTOR inhibitor, such that the level of PD1 negative immune effector cells, e.g., T cells, or the ratio of PD1 negative immune effector cells, e.g., T cells/PD1 positive immune effector cells, e.g., T cells, has been, at least transiently, increased.

In an embodiment, the cell, e.g., an immune effector cell (e.g., a T cell or NK cell), to be engineered to express a CAR, is harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In embodiments, any of the methods described herein further comprise performing lymphodepletion on a subject, e.g., prior to administering the one or more cells that express a CAR molecule described herein, e.g., a CAR molecule that binds CD19. The lymphodepletion can comprise, e.g., administering one or more of melphalan, cytoxan, cyclophosphamide, and fludarabine.

In some embodiments, the CAR-expressing cell that is administered comprises a regulatable CAR (RCAR), e.g., an RCAR as described herein. The RCAR may comprise, e.g., an intracellular signaling member comprising an intracellular signaling domain and a first switch domain, an antigen binding member comprising an antigen binding domain that binds CD19 and a second switch domain; and a transmembrane domain. The method may further comprise administering a dimerization molecule, e.g., in an amount sufficient to cause dimerization of the first switch and second switch domains.

In some embodiments, the CAR-expressing cell and the kinase inhibitor are administered simultaneously or substantially simultaneously, e.g., as a first line of therapy. In some embodiments, the method comprises administering a combination of the BTK inhibitor (e.g., ibrutinib) and the CAR-expressing cell (e.g., a CAR19-expressing cell) to the subject, as a first line therapy.

In other embodiments, the CAR-expressing cell and the kinase inhibitor are administered sequentially. For example, the kinase inhibitor is administered before the CAR-expressing cell, or the CAR-expressing cell is administered before the kinase inhibitor.

In some embodiments, the disease associated with expression of CD19 is a hematological cancer (e.g., a hematological cancer described herein such as CLL, MCL, or ALL) and the subject is, or is identified as, a partial responder, non-responder, or relapser to one or more therapies for the hematological cancer, e.g., to a BTK inhibitor such as ibrutinib. In some embodiments, the subject has, or is identified as having, a BTK mutation. The mutation may be, e.g., a point mutation, an insertion, or a deletion. The mutation may be, e.g., a mutation at the binding site for the BTK inhibitor, e.g., at or near the ATP-binding pocket. The mutation may confer a decreased response (e.g., resistance) to the BTK inhibitor.

In some embodiments of any of the methods disclosed herein, the method comprises administering the BTK inhibitor (e.g., ibrutinib) to the subject, reducing the amount (e.g., ceasing administration) of the BTK inhibitor, and subsequently administering the CAR-expressing cell (e.g., a CAR19-expressing cell) to the subject.

In some embodiments, the method comprises administering the BTK inhibitor (e.g., ibrutinib) to the subject and subsequently administering a combination of the BTK inhibitor and the CAR-expressing cell (e.g., a CAR19-expressing cell) to the subject.

In some embodiments, the method comprises administering the BTK inhibitor (e.g., ibrutinib) to the subject, reducing the amount (e.g., ceasing or discontinuing administration) of the BTK inhibitor, and subsequently administering a combination of the CAR-expressing cell (e.g., a CAR19-expressing cell) and a second BTK inhibitor (e.g., a BTK inhibitor other than the first BTK inhibitor, e.g., other than ibrutinib) to the subject. In some embodiments, the second BTK inhibitor is chosen from one or more of GDC-0834, RN-486, CGI-560, CGI-1764, HM-71224, CC-292, ONO-4059, CNX-774, or LFM-A13, or a combination thereof.

In some embodiments, the disease associated with expression of the B-cell antigen (e.g., CD19) is a hematological cancer (e.g., a hematological cancer described herein, e.g., CLL, MCL, or ALL), and the method delays or decreases resistance to the kinase inhibitor (e.g., a BTK inhibitor such as ibrutinib), the the CAR-expressing cell (e.g., a CAR19-expressing cell) to the subject, or both. In some embodiments, the disease associated with expression of CD19 is a hematological cancer (e.g., a hematological cancer described herein, e.g., CLL, MCL, or ALL), and wherein the method prolongs remission or delays relapse of the hematological cancer. For example, remission can be prolonged, relapse can be delayed, resistance can be delayed, or resistance can be decreased, compared to the expected course of disease when treated with a monotherapy of the kinase inhibitor or the CAR-expressing cell.

Exemplary treatment regimens that can be used in any of the aforesaid methods include one or more of the following:

In one embodiment, the kinase inhibitor and the CAR-expressing cell (e.g., the CAR19-expressing cell) are administered to the subject, e.g., mammal, as a first line of therapy.

In another embodiment, the CAR-expressing cell (e.g., the CAR19-expressing cell) is administered to the subject, e.g., mammal, after administration of the kinase inhibitor.

In other embodiments, the CAR-expressing cell (e.g., the CAR19-expressing cell) is administered after ceasing administration of the kinase inhibitor.

In other embodiments, administration of the kinase inhibitor is begun prior to administration of the CAR19-expressing cell, and the CAR19-expressing cell is administered in combination with continued administration of the kinase inhibitor.

In one embodiment, a subject is administered a kinase inhibitor (e.g., a BTK inhibitor such as ibrutinib), e.g., as a first line therapy. After a predetermined time interval, (e.g., 1 or 2 months but also 2 weeks, 3 weeks, 1 month, 1.5 months, 2 months, 3 months, 4 months, 6 months, 9 months, 12 months, 15 months, or 18 months), a CAR-expressing cell (e.g., a CAR19-expressing cell) is administered to the subject alone, or in combination with the kinase inhibitor. In some embodiments, the subject's response to the treatment is assessed at predetermined time intervals, e.g., before or during treatment with the kinase inhibitor and/or CAR-expressing cell. If the assessment shows that the subject is a complete responder, the CAR-expressing cell (e.g., a CAR19-expressing cell) is not administered. If the assessment shows that the subject is a partial responder, or has stable disease in response, to the kinase inhibitor, the CAR-expressing cell (e.g., a CAR19-expressing cell) is administered in combination with the kinase inhibitor e.g., as described herein. If the assessment shows that the subject is a non-responder or relapser, the CAR-expressing cell (e.g., a CAR19-expressing cell) is administered in combination with the kinase inhibitor or a second kinase inhibitor, e.g., a second kinase inhibitor as described herein.

In other embodiments, the subject, e.g., mammal, is, or is identified as being, a complete or partial responder to the BTK inhibitor (e.g., ibrutinib), or a complete or partial responder to the CAR19-expressing cell.

In some embodiments, when a subject is (or is identified as being) a complete responder to the kinase inhibitor (e.g., a BTK inhibitor such as ibrutinib), the subject is not administered a CAR-expressing cell (e.g., a CAR19-expressing cell) during the period of complete response. In other embodiments, when a subject is (or is identified as being) a complete responder (e.g., a complete responder to ibrutinib) to the kinase inhibitor, the subject is administered a CAR-expressing cell (e.g., a CAR19-expressing cell) during the period of complete response. In an embodiment, after the CAR-expressing cell (e.g., a CAR19-expressing cell), the subject experiences a prolonged response or delayed relapse (e.g., compared to the expected course of disease when treated without the CAR therapy).

In some embodiments, when a subject is (or is identified as being) a partial responder to the kinase inhibitor (e.g., a BTK inhibitor such as ibrutinib), the subject is not administered a CAR-expressing cell (e.g., a CAR19-expressing cell) during the period of partial response. In other embodiments, when a subject is (or is identified as being) a partial responder to the kinase inhibitor, the subject is administered a CAR-expressing cell (e.g., a CAR19-expressing cell) (alone or in combination with the BTK inhibitor) during the period of partial response. In an embodiment, after the CAR therapy, the subject experiences a complete response and/or prolonged response or delayed relapse (e.g., compared to the expected course of disease when treated without CAR therapy).

In some embodiments, when a subject has (or is identified as having) stable disease after treatment with the kinase inhibitor (e.g., a BTK inhibitor such as ibrutinib), the subject is not administered a CAR therapy during the period of stable disease. In other embodiments, when a subject has (or is identified as having) stable disease after treatment with the kinase inhibitor, the subject is administered a CAR therapy during the period of stable disease. In an embodiment, after the CAR therapy, the subject experiences a partial response, a complete response and/or prolonged response or delayed relapse (e.g., compared to the expected course of disease when treated without CAR therapy).

In some embodiments, when a subject has (or is identified as having) progressive disease after treatment with the kinase inhibitor (e.g., a BTK inhibitor such as ibrutinib), the subject is not administered a CAR-expressing cell (e.g., a CAR19-expressing cell) during the period of progressive disease. In other embodiments, when a subject has (or is identified as having) progressive disease after treatment with the kinase inhibitor, the subject is administered a CAR-expressing cell (e.g., a CAR19-expressing cell) during the period of progressive disease. In an embodiment, after the CAR therapy, the subject experiences stable disease, a partial response, a complete response and/or prolonged response or delayed relapse (e.g., compared to the expected course of disease when treated without CAR therapy).

In other embodiments, the CAR-expressing cell is administered in combination a second kinase inhibitor, wherein the second kinase inhibitor is other than ibrutinib, when the mammal is, or is identified as being, a non-responder or relapser to ibrutinib. The second kinase inhibitor can be chosen from one or more of GDC-0834, RN-486, CGI-560, CGI-1764, HM-71224, CC-292, ONO-4059, CNX-774, or LFM-A13, or a combination thereof.

In other embodiments, the subject, e.g., the mammal, is (or is identified as being) a partial responder to the kinase inhibitor, and the subject is administered the CAR-expressing cell (e.g., the CAR19-expressing cell), alone or in combination with the BTK inhibitor, during the period of partial response.

In other embodiments, the subject, e.g., the mammal, is (or has identified as being) a non-responder having progressive or stable disease after treatment with ibrutinib, and the subject is administered the CAR-expressing cell (e.g., the CAR19-expressing cell), alone or in combination with a second BTK inhibitor, during the period of progressive or stable disease, wherein the second kinase inhibitor is other than ibrutinib.

In another aspect, provided herein is a method of treating a subject, e.g., a mammal, having a disease associated with expression of the B-cell antigen (e.g., CD19). The method comprises administering to the subject an effective amount of a kinase inhibitor as described herein (e.g., a BTK kinase inhibitor described herein, e.g., ibrutinib) and a CAR-expressing cell (e.g., a CAR19-expressing cell) in combination (e.g. simultaneously (or substantially simultaneously), or sequentially).

In some embodiments, the kinase inhibitor and the CAR-expressing cell (e.g., a CAR19 cell) are administered, in combination, e.g., as a first line of therapy, In some embodiments, the kinase inhibitor is administered initially, e.g., a monotherapy or first line of therapy; after reducing the amount (e.g., ceasing or discontinuing administration) of the kinase inhibitor, administering the CAR-expressing cell (e.g., a CAR19-expressing cell) to the subject.

In other embodiments, the kinase inhibitor is administered initially, e.g., a monotherapy or first line of therapy; and subsequently administering a combination of the kinase inhibitor and the CAR-expressing cell (e.g., a CAR19-expressing cell) to the subject.

In other embodiments, the kinase inhibitor is administered initially, e.g., a monotherapy or first line of therapy; after reducing the amount (e.g., ceasing or discontinuing administration) of the kinase inhibitor, administering a combination of a second kinase inhibitor and the CAR-expressing cell (e.g., a CAR19-expressing cell) to the subject.

In some embodiments, the subject's response to the treatment is assessed at predetermined time intervals, e.g., before or during treatment with the kinase inhibitor and/or CAR-expressing cell. If the assessment shows that the subject is a complete responder, the CAR-expressing cell (e.g., a CAR19-expressing cell) is not administered. If the assessment shows that the subject is a partial responder, or has stable disease in response, to the kinase inhibitor, the CAR-expressing cell (e.g., a CAR19-expressing cell) is administered in combination with the kinase inhibitor e.g., as described herein. If the assessment shows that the subject is a non-responder or relapser, the CAR-expressing cell (e.g., a CAR19-expressing cell) is administered in combination with the kinase inhibitor or a second kinase inhibitor, e.g., a second kinase inhibitor as described herein.

In some embodiments, the disease associated with expression of a B-cell antigen (e.g., CD19) is a hematological cancer, leukemia, lymphoma, MCL, CLL, ALL, Hodgkin lymphoma, or multiple myeloma.

In some embodiments, the kinase inhibitor is a BTK inhibitor chosen from ibrutinib, GDC-0834, RN-486, CGI-560, CGI-1764, HM-71224, CC-292, ONO-4059, CNX-774, or LFM-A13; a CDK4 inhibitor chosen from palbociclib, aloisine A, flavopiridol, 2-(2-chlorophenyl)-5,7-dihydroxy-8-[(3S,4R)-3-hydroxy-1-methyl-4-piperidinyl]-4-chromenone; crizotinib (PF-02341066, P276-00, RAF265, indisulam, roscovitine, dinaciclib, BMS 387032, MLN8054, AG-024322, AT7519, AZD5438, BMS908662; or ribociclib; a mTOR inhibitor chosen from rapamycin, a rapamycin analog such as everolimus, temsirolimus, ridaforolimus, semapimod, AZD8055, PF04691502, SF1126, XL765, or OSI-027; or a MNK inhibitor is chosen from: CGP052088, CGP57380, cercosporamide, or ETC-1780445-2, or 4-amino-5-(4-fluoroanilino)-pyrazolo [3,4-d] pyrimidine.

In some aspects, the invention features a method of treating or providing an anti-tumor immunity in a subject, e.g., mammal, having Hodgkin lymphoma. The method comprises administering to the subject an effective amount of a cell that expresses a CAR molecule that binds CD19, alone or in combination with a second therapy.

In another aspect, the invention features a method of treating, or providing anti-tumor immunity to a subject, e.g., a mammal, having a multiple myeloma (e.g., a CD19-positive multiple myeloma, or a CD19-negative myeloma). In one embodiment, the multiple myeloma is CD19-negative, e.g., has a vast majority (99.95%) of the neoplastic plasma cells with a CD19-negative phenotype, e.g., as detected by both flow cytometry and RT-PCR. The method comprises administering to the subject an effective amount of a cell that expresses a CAR molecule that binds CD19, alone or in combination with a second therapy (e.g., a standard of care therapy for multiple myeloma). The method may further comprise administering a kinase inhibitor as described herein.

In embodiments of the methods related to Hodgkin lymphoma or multiple myeloma, the CAR molecule is a humanized CAR molecule, e.g., as described herein. In embodiments, the CAR molecule is a CAR molecule as described herein. For instance, in embodiments the CAR molecule comprises an anti-CD19 binding domain that comprises a one or more of (e.g., 2, 3, 4, 5, or all of) LC CDR1 of SEQ ID NO: 5, a LC CDR2 of SEQ ID NO: 26, and a LC CDR3 of SEQ ID NO: 27; a HC CDR1 of SEQ ID NO: 19, a LC CDR2 of any of SEQ ID NOS: 20-23, and a HC CDR3 of SEQ ID NO: 24.

In some embodiments of the methods related to Hodgkin lymphoma or multiple myeloma, the CAR molecule (e.g., CART19 or CTL019) is administered as a monotherapy. In some embodiments, the method further comprises administering a kinase inhibitor, e.g., a BTK inhibitor (such as ibrutinib), a CDK4 inhibitor, an mTOR inhibitor, or a MNK inhibitor.

In some embodiments of the methods related to multiple myeloma, the CAR molecule (e.g., CART19 or CTL019) is administered in combination a standard of care therapy for multiple myeloma, e.g., with myeloablative chemotherapy and/or autologous stem cell transplant rescue (e.g., after melphalan administration (e.g., high dose melphalan)).

In another aspect, the invention features a composition comprising a cell that expresses a CAR molecule that binds a B cell antigen (e.g., one or more of CD19, CD20. CD22 or ROR1), and one or more kinase inhibitors, wherein the kinase inhibitor is chosen from a Bruton's tyrosine kinase (BTK) inhibitor, a cyclin dependent kinase 4 (CDK4) inhibitor, an mTOR inhibitor, or a mitogen activated protein kinase interacting kinase (MNK) inhibitor. The CAR-expressing cell and the one or more kinase inhibitors can be present in a single dose form, or as two or more dose forms.

In embodiments, the compositions disclosed herein are for use as a medicament.

In embodiments, the compositions disclosed herein are use in the treatment of a disease associated with expression of a B-cell antigen (e.g., CD19).

Methods and Compositions for Producing CAR-Expressing Cells

The present disclosure also provides, in certain aspects, a method of making a population of immune effector cells (e.g., T cells or NK cells) that can be engineered to express a CAR (e.g., a CAR described herein), the method comprising: providing a population of immune effector cells; and contacting the immune effector cells with a kinase inhibitor (e.g., a BTK inhibitor such as ibrutinib) under conditions sufficient to inhibit a target of the kinase inhibitor (e.g., BTK and/or ITK). The method can further comprise contacting, e.g., transducing, the immune effector cells with a nucleic acid encoding a CAR molecule.

In some aspects, the disclosure provides a method of making a CAR-expressing cell (e.g., a CAR-expressing immune effector cell or population of cells), comprising: contacting the cell or population of cells with a kinase inhibitor, e.g., a BTK inhibitor such as ibrutinib; and introducing (e.g., transducing) a nucleic acid encoding a CAR molecule into the cell or population of cells under conditions such that the CAR molecule is expressed.

In certain embodiments of the methods of producing CAR-expressing cells, the CAR molecule encoded by the nucleic acid is a CAR molecule that binds CD19. In embodiments, the method further comprises culturing the cell or cells under conditions that allow the cell or at least a sub-population of the cells to express the CAR molecule. In embodiments, the cell is a T cell or NK cell, or the population of cells includes T cells, NK cells, or both. In embodiments, the method comprises contacting the cell or cells with the kinase inhibitor (e.g., for 10-20, 20-30, 30-40, 40-60, or 60-120 minutes) and subsequently removing most or all of the kinase inhibitor from the cell or cells. In embodiments, the kinase inhibitor is added after the cell or cells are harvested or before the cell or cells are stimulated. In embodiments, the kinase inhibitor is a BTK inhibitor, a CDK4 inhibitor, an mTOR inhibitor, or a MNK inhibitor. In embodiments, the kinase inhibitor is ibrutinib. In embodiments, the population of cells also comprises cancer cells, e.g., leukemia or lymphoma cells. The cancer cells may be, e.g., CLL, MCL, or ALL cells. In embodiments, the kinase inhibitor inhibits a target (e.g., BTK) in the cancer cells, e.g., reduces its activity by at least 10%, 20%, 30%, 40%, 50%, 60%, 70%, 80%, 90%, 95%, or 99%. In embodiments, the kinase inhibitor inhibits a target (e.g., ITK) in the immune effector cells, e.g., reduces its activity by at least 10%, 20%, 30%, 40%, 50%, 60%, 70%, 80%, 90%, 95%, or 99%.

In some aspects, the present disclosure also provides a reaction mixture comprising a kinase inhibitor (e.g., a BTK inhibitor) and a CAR molecule or a nucleic acid encoding a CAR molecule. In some embodiments, the reaction mixture further comprises a population of immune effector cells.

In some embodiments, one or more of the immune effector cells expresses the CAR molecule or comprises the nucleic acid encoding the CAR molecule. In some embodiments, the kinase inhibitor is chosen from a BTK inhibitor, a CDK4 inhibitor, an mTOR inhibitor, or a MNK inhibitor. In some embodiments, the BTK inhibitor is chosen from: ibrutinib, GDC-0834, RN-486, CGI-560, CGI-1764, HM-71224, CC-292, ONO-4059, CNX-774, or LFM-A13. In embodiments, the reaction mixture comprises cancer cells, e.g., haematological cancer cells. The cancer cells may be, e.g., cells that were harvested from the subject when the immune effector cells were harvested from the subject.

In certain aspects, the present disclosure also provides a reaction mixture comprising a population of immune effector cells, and a CAR molecule or a nucleic acid encoding a CAR molecule, wherein the immune effector cells comprise covalently inactivated ITK. In embodiments, at least 10%, 20%, 30%, 40%, 50%, 60%, 70%, 80%, 90%, 95%, or 99% of ITK is covalently inactivated. In some embodiments, the reaction mixture further comprises cancer cells. In embodiments, the cancer cells comprise covalently inactivated BTK. In embodiments, at least 10%, 20%, 30%, 40%, 50%, 60%, 70%, 80%, 90%, 95%, or 99% of BTK is covalently inactivated. In embodiments, the BTK or ITK forms a covalent bond at or near its ATP binding domain to a small molecule such as ibrutinib. In embodiments, the BTK forms a covalent bond at or near its cysteine-481 to a small molecule such as ibrutinib.

In embodiments, a reaction mixture as described herein further comprises a buffer or other reagent, e.g., a PBS containing solution. In embodiments, the reaction mixture further comprises an agent that activates and/or expands to cells of the population, e.g., an agent that stimulates a CD3/TCR complex associated signal and/or a ligand that stimulates a costimulatory molecule on the surface of the cells. In embodiments, the agent is a bead conjugated with anti-CD3 antibody, or a fragment thereof, and/or anti-CD28 antibody, or a fragment thereof. In embodiments, the reaction mixture further comprises one or more factors for proliferation and/or viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells. In embodiments, the reaction mixture further comprises IL-15 and/or IL-7. In embodiments, a plurality of the cells of the population in the reaction mixture comprise a nucleic acid molecule, e.g., a nucleic acid molecule described herein, that comprises a CAR encoding sequence, e.g., a CD19 CAR encoding sequence, e.g., as described herein. In embodiments, a plurality of the cells of the population in the reaction mixture comprise a vector comprising a nucleic acid sequence encoding a CAR, e.g., a CAR described herein, e.g., a CD19 CAR described herein. In embodiments, the vector is a vector described herein, e.g., a vector selected from the group consisting of a DNA, a RNA, a plasmid, a lentivirus vector, adenoviral vector, or a retrovirus vector. In embodiments, the reaction mixture further comprises a cryoprotectant or stabilizer such as, e.g., a saccharide, an oligosaccharide, a polysaccharide and a polyol (e.g., trehalose, mannitol, sorbitol, lactose, sucrose, glucose and dextran), salts and crown ethers. In one embodiment, the cryoprotectant is dextran.

In some embodiments, the method of making disclosed herein further comprises contacting the population of immune effector cells with a nucleic acid encoding a telomerase subunit, e.g., hTERT. The the nucleic acid encoding the telomerase subunit can be DNA.

In some embodiments, the method of making disclosed herein further comprises culturing the population of immune effector cells in serum comprising 2% hAB serum.

Headings, sub-headings or numbered or lettered elements, e.g., (a), (b), (i) etc, are presented merely for ease of reading. The use of headings or numbered or lettered elements in this document does not require the steps or elements be performed in alphabetical order or that the steps or elements are necessarily discrete from one another.

All publications, patent applications, patents, and other references mentioned herein are incorporated by reference in their entirety.

BRIEF DESCRIPTION OF THE DRAWINGS

FIGS. 10A-1, 10A-2, 10A-3, 10A-4, and 10B shows the proliferation of CART19 cells stimulated with MCL cell lines, while in the presence or absence of ibrutinib. FIGS. 10A-1, 10A-2, 10A-3, and 10A-4 is a series of histograms showing the proliferation of CART19 cells stimulated with tumor cell lines MOLM14, JEKO-1, and RL, in the presence or absence of increasing concentrations of ibrutinib (10 nM, 100 nM, and 1000 nM). Cells were stained by CFSE and analyzed by flow cytometry to determine the percentage of proliferating cells, designated by the bar in each histogram. FIG. 10B is a quantification of representative histograms in FIGS. 10A-1, 10A-2, 10A-3, and 10A-4.

FIGS. 11A-1, 11A-2, 11A-3, 11A-4, 11A-5, 11A-6, and 11B shows CD107a degranulation of CART19 cells stimulated with MCL cell lines in the presence or absence of ibrutinib. FIGS. 11A-1, 11A-2, 11A-3, 11A-4, 11A-5, and 11A-6 is a series of flow cytometry profiles showing CD107a degranulation of CART19 cells stimulated with tumor cell lines (MOLM14, JEKO-1, and RL) in the presence or absence of increasing concentrations of ibrutinib (10 nM, 100 nM, and 1000 nM). CD107a expression is measured in the y-axis. FIG. 11B is the quantification of the results from FIGS. 11A-1, 11A-2, 11A-3, 11A-4, 11A-5, and 11A-6.

FIGS. 12-1, 12-1, 12-3, 12-4, 12-5, and 12-6 is a series of flow cytometry profiles showing intra-cytoplasmatic IL-2 production by CART19 cells stimulated with tumor cell lines (MOLM14, JEKO-1, and RL) in the presence or absence of increasing concentrations of ibrutinib (10 nM, 100 nM, and 1000 nM). The y-axis represents IL-2 expression.

FIGS. 13-1, 13-2, 13-3, 13-4, 13-5, and 13-6 is a series of flow cytometry profiles showing intra-cytoplasmatic TNF-α production by CART19 cells stimulated with tumor cell lines (MOLM14, JEKO-1, and RL) in the presence or absence of increasing concentrations of ibrutinib (10 nM, 100 nM, and 1000 nM). The y-axis represents TNF-α expression.

FIGS. 14-1, 14-2, 14-3, 14-4, 14-5, and 14-6 is a series of flow cytometry profiles showing intra-cytoplasmatic IFN-g production by CART19 cells stimulated with tumor cell lines (MOLM14, JEKO-1, and RL) in the presence or absence of increasing concentrations of ibrutinib (10 nM, 100 nM, and 1000 nM). The y-axis represents IFN-g expression.

FIGS. 15-1, 15-2, 15-3, 15-4, 15-5, 15-6, 15-7, 15-8, 15-9, and 15-10 are a series of graphs showing cytokine secretion from CART19 cells stimulated with tumor cell lines (MOLM14, JEKO-1, and RL) in the presence or absence of increasing concentrations of ibrutinib (10 nM, 100 nM, and 1000 nM).

FIGS. 19A and 19B are graphic representations of CART19 dose finding in the JEKO-1 MCL mouse model. Tumor size is monitored by bioluminescence imaging (BLI) over time (FIG. 19A) and overall survival was also monitored over time (FIG. 19B).

FIGS. 22A, 22B, 22C, 22D, and 22E is a graphic representation of the effect of ibrutinib treatment on CD3/CD28-stimulated T cell proliferation. Increasing concentrations of ibrutinib was assessed: untreated (FIG. 22A); 0.1 µM ibrutinib (FIG. 22B); 0.5 µM ibrutinib (FIG. 22C), 1 µM ibrutinib (FIG. 22D), and 5 µM ibrutinib (FIG. 22E).

FIG. 25A shows the Nalm/6 cells detected in peripheral blood during each treatment regimen. FIG. 25B shows a Kaplan-Meier survival curve comparing the survival of mice receiving CART19 with or without ibrutinib dosing.

FIGS. 26A, 26B, 26C, 26D, 26E, and 26F are graphic representations that showing the efficiency of CAR19 transduction in CLL patient cells at the indicated timepoints during ibrutinib treatment. Cells were not transduced (FIGS. 26A, 26B, and 26C), or were transduced with CAR19 (FIGS. 26D, 26E, and 26F). Cells stained with GAM express CAR19 and are present in the boxes in each profile.

FIGS. 27-1, 27-2, and 27-3 are a series of graphic representations depicting the proliferation rate of untransduced cells compared to cells that were transduced with CAR19 at the indicated timepoints during ibrutinib treatment from a panel of patients.

FIGS. 29A, 29B, and 29C are graphic representations demonstrating that ibrutinib treatment in three CLL patients reduces CD200 expression on tumor cells over time in CLL. Each profile contains an overlay of CD200 expression histograms from cells isolated at the indicated timepoints: baseline (screen); cycle 2, day 1; and cycle 12, day 1.

FIGS. 30A, 30B, and 30C are graphic representations demonstrating that ibrutinib treatment in CLL patients decreases the frequency of PD1+ T cells over time. Cells from the patient were isolated at the indicated timepoints: baseline (FIG. 30A); cycle 2, day 1 (FIG. 30B); and cycle 12, day 1 (FIG. 30C).

FIG. 33 (left panel) is at 1× magnification and FIG. 33 (right panel) is at 20× magnification.

FIGS. 35A, 35B, 35C, and 35D show flow cytometry analysis of PD1 and CAR19 expression on T cells. FIGS. 35A and 35B are representative flow cytometry profiles demonstrating the distribution of PD-1 and CAR19 expression on CD4+ T cells from subjects that are complete responders (CR) or non-responders (NR) to CART therapy. FIG. 35C is a graph showing the percent of PD1 cells in the CD4+ T cell population from groups of subjects with different responses to CART therapy. FIG. 35D is a graph showing the percent of PD1 cells in the CD8+ T cell population from groups of subjects with different responses to CART therapy.

In FIG. 40A, the increase above baseline in influenza geometric mean titers to each of the 3 influenza vaccine strains (H1N1 A/California/07/2009, H3N2 A/Victoria/210/2009, B/Brisbane/60/2008) relative to the increase in the placebo cohort 4 weeks after vaccination is shown for each of the RAD001 dosing cohorts in the intention to treat population. The bold black line indicates the 1.2 fold increase in titers relative to placebo that is required to be met for 2 out of 3 influenza vaccine strains to meet the primary endpoint of the study. The star "*" indicates that the increase in GMT titer relative to placebo exceeds 1 with posterior probability of at least 80%. FIG. 40B is a graph of the same data as in FIG. 40A for the subset of subjects with baseline influenza titers <=1:40.

FIG. 44A shows there was a significant decrease (−37.1-−28.5%) in PD-1-positive CD4 T cells at week 12 in cohorts receiving RAD001 at dose levels 0.5 mg/Day (n=25), 5 mg/Week (n=29) and 20 mg/Week (n=30) as compared to the placebo cohort (n=25) with p=0.002 (0.02), p=0.003 (q=0.03), and p=0.01 (q=0.05) respectively. FIG. 44B shows there was a significant decrease (−43.3-−38.5%) in PD-1-positive CD8 T cells at week 12 in cohorts receiving RAD001 (n=109) at dose levels 0.5 mg/Day (n=25), 5 mg/Week (n=29) and 20 mg/Week (n=30) as compared to the placebo cohort (n=25) with p=0.01 (0.05), p=0.007 (q=0.04), and p=0.01 (q=0.05) respectively. FIG. 44C shows was a significant increase (3.0-4.9%) in PD-1-negative CD4 T cells at week 12 in cohorts receiving RAD001 (n=109) at dose levels 0.5 mg/Day (n=25), 5 mg/Week (n=29) and 20 mg/Week (n=30) as compared to the placebo cohort (n=25) with p=0.0007 (0.02), p=0.03 (q=0.07), and p=0.03 (q=0.08) respectively.

FIG. 45A shows a significant decrease of 30.2% in PD-1+CD4 T cells at week 6 in the pooled RAD cohort (n=84) compared to placebo cohort (n=25) with p=0.03 (q=0.13). The decrease in PD-1-positive CD4 T cells at week 12 in the pooled RAD as compared to the placebo cohort is 32.7% with p=0.05 (q=0.19). FIG. 45B shows a significant decrease of 37.4% in PD-1-positive CD8 T cells at week 6 in the pooled RAD001 cohort (n=84) compared to placebo cohort (n=25) with p=0.008 (q=0.07). The decrease in PD-1-positive CD8 T cells at week 12 in the pooled RAD001 as compared to the placebo cohort is 41.4% with p=0.066 (q=0.21). FIGS. 45A and 45B represent the data in FIGS. 44A, 44B, and 44C but with the different RAD001 dosage groups of FIGS. 44A, 44B, and 44C pooled into the single RAD001-treated group in FIGS. 45A and 45B.

FIG. 47A depicts P70 S6 kinase inhibition with higher doses of weekly and daily RAD001; FIG. 47B depicts P70 S6 kinase inhibition with lower doses of weekly RAD001.

FIG. 52F is a set of histological images showing localization of MCL cells to various organs in mice.

FIG. 53F is a set of graphs showing the percentage of untranduced or CAR-19 transduced T cells that express or produce various biomolecules (e.g., cytokines).

FIG. 54B is a set of graphs showing CD107a surface expression (a measure of degranulation), IL-2 production, and TNF-alpha production by CART19 cells with various concentrations with ibrutinib.

FIGS. 54D-1 and 54D-2 is a set of graphs showing the expression or production of various cytokines and biomarkers as indicators of the Th1 or Th2 state of CART19 cells when combined with different concentrations of ibrutinib.

DETAILED DESCRIPTION

Definitions

Figure 1A:
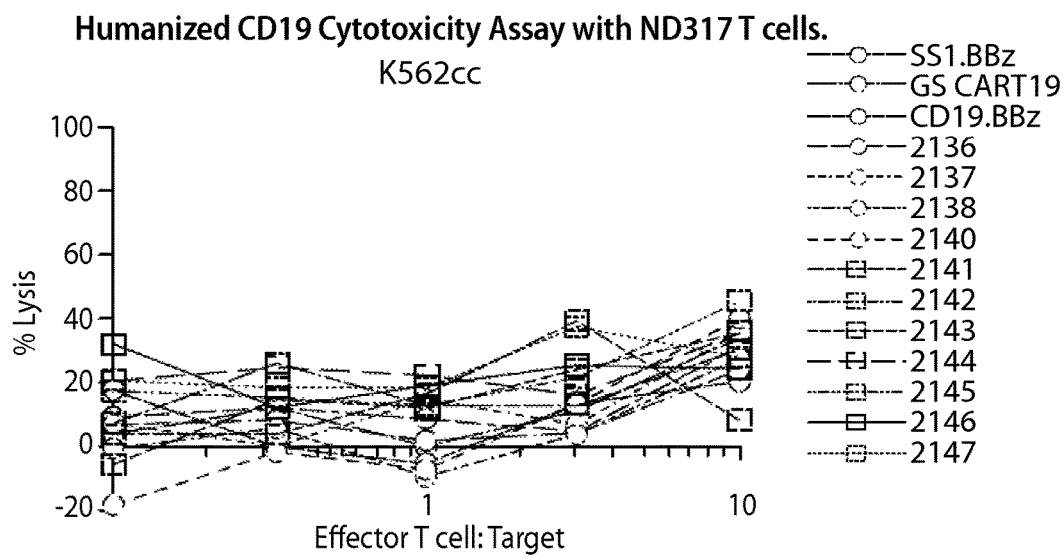
FIGS. 1A, 1B and 1C are graphic representations of cytotoxicity as assayed in ND317 (normal donor) T cell transduced with mouse anti-CD19 CAR or the humanized anti-CD19 CARs of the invention and cultured with either control K562 cells that do not express CD19 (K562cc) as shown in FIG. 1A, K562 cells transformed with CD19 (K562.CD19) as shown in FIG. 1B or malignant B cells isolated from a CLL patient (Pt 14 B cell isolate) as shown in FIG. 1C.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "Chimeric Antigen Receptor" or alternatively a "CAR" refers to a set of polypeptides, typically two in the simplest embodiments, which when in an immune effector cell, provides the cell with specificity for a target cell, typically a cancer cell, and with intracellular signal generation. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined below. In some aspects, the set of polypeptides are contiguous with each other, e.g., are in the same polypeptide chain (e.g., comprise a chimeric fusion protein). In some embodiments, the set of polypeptides are not contiguous with each other, e.g., are in different polypeptide chains. In some embodiments, the set of polypeptides include a dimerization switch that, upon the presence of a dimerization molecule, can couple the polypeptides to one another, e.g., can couple an antigen binding domain to an intracellular signaling domain. In one aspect, the stimulatory molecule is the zeta chain associated with the T cell receptor complex. In one aspect, the cytoplasmic signaling domain further comprises one or more functional signaling domains derived from at least one costimulatory molecule as defined below. In one aspect, the costimulatory molecule is chosen from the costimulatory molecules described herein, e.g., 4-1BB (i.e., CD137), CD27 and/or CD28. In one aspect, the CAR comprises a chimeric fusion protein comprising an extracellular antigen binding domain, a transmembrane domain and an intracellular signaling domain comprising a functional signaling domain derived from a stimulatory molecule. In one aspect, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule. In one aspect, the CAR comprises a chimeric fusion protein comprising an extracellular antigen binding domain, a transmembrane domain and an intracellular signaling domain comprising two functional signaling domains derived from one or more costimulatory molecule(s) and a functional signaling domain derived from a stimulatory molecule. In one aspect, the CAR comprises a chimeric fusion protein comprising an extracellular antigen binding domain, a transmembrane domain and an intracellular signaling domain comprising at least two functional signaling domains derived from one or more costimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen binding domain, wherein the leader sequence is optionally cleaved from the antigen binding domain (e.g., a scFv) during cellular processing and localization of the CAR to the cellular membrane.

The term "signaling domain" refers to the functional portion of a protein which acts by transmitting information within the cell to regulate cellular activity via defined signaling pathways by generating second messengers or functioning as effectors by responding to such messengers.

As used herein, the term "CD19" refers to the Cluster of Differentiation 19 protein, which is an antigenic determinant detectable on leukemia precursor cells. The human and murine amino acid and nucleic acid sequences can be found in a public database, such as GenBank, UniProt and Swiss-Prot. For example, the amino acid sequence of human CD19 can be found as UniProt/Swiss-Prot Accession No. P15391 and the nucleotide sequence encoding of the human CD19 can be found at Accession No. NM_001178098. As used herein, "CD19" includes proteins comprising mutations, e.g., point mutations, fragments, insertions, deletions and splice variants of full length wild-type CD19. CD19 is expressed on most B lineage cancers, including, e.g., acute lymphoblastic leukaemia, chronic lymphocyte leukaemia and non-Hodgkin lymphoma. Other cells with express CD19 are provided below in the definition of "disease associated with expression of CD19." It is also an early marker of B cell progenitors. See, e.g., Nicholson et al. Mol. Immun. 34 (16-17): 1157-1165 (1997). In one aspect the antigen-binding portion of the CART recognizes and binds an antigen within the extracellular domain of the CD19 protein. In one aspect, the CD19 protein is expressed on a cancer cell.

As used herein, the term "CD20" refers to an antigenic determinant known to be detectable on B cells. Human CD20 is also called membrane-spanning 4-domains, subfamily A, member 1 (MS4A1). The human and murine amino acid and nucleic acid sequences can be found in a public database, such as GenBank, UniProt and Swiss-Prot. For example, the amino acid sequence of human CD20 can be found at Accession Nos. NP_690605.1 and NP_068769.2, and the nucleotide sequence encoding transcript variants 1 and 3 of the human CD20 can be found at Accession No. NM_152866.2 and NM_021950.3, respectively. In one aspect the antigen-binding portion of the CAR recognizes and binds an antigen within the extracellular domain of the CD20 protein. In one aspect, the CD20 protein is expressed on a cancer cell.

As used herein, the term "CD22," refers to an antigenic determinant known to be detectable on leukemia precursor cells. The human and murine amino acid and nucleic acid sequences can be found in a public database, such as GenBank, UniProt and Swiss-Prot. For example, the amino acid sequences of isoforms 1-5 human CD22 can be found at Accession Nos. NP 001762.2, NP 001172028.1, NP 001172029.1, NP 001172030.1, and NP 001265346.1, respectively, and the nucleotide sequence encoding variants 1-5 of the human CD22 can be found at Accession No. NM 001771.3, NM 001185099.1, NM 001185100.1, NM 001185101.1, and NM 001278417.1, respectively. In one aspect the antigen-binding portion of the CAR recognizes and binds an antigen within the extracellular domain of the CD22 protein. In one aspect, the CD22 protein is expressed on a cancer cell.

As used herein, the term "ROR1" refers to an antigenic determinant known to be detectable on leukemia precursor cells. The human and murine amino acid and nucleic acid sequences can be found in a public database, such as GenBank, UniProt and Swiss-Prot. For example, the amino acid sequences of isoforms 1 and 2 precursors of human ROR1 can be found at Accession Nos. NP_005003.2 and NP_001077061.1, respectively, and the mRNA sequences encoding them can be found at Accession Nos. NM_005012.3 and NM_001083592.1, respectively. In one aspect the antigen-binding portion of the CAR recognizes and binds an antigen within the extracellular domain of the ROR1 protein. In one aspect, the ROR1 protein is expressed on a cancer cell.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an antibody, that retains the ability to specifically interact with (e.g., by binding, steric hinderance, stabilizing/destabilizing, spatial distribution) an epitope of an antigen. Examples of antibody fragments include, but are not limited to, Fab, Fab', F(ab')$_2$, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3)(see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The portion of the CAR of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv. The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme), or a combination thereof.

As used herein, the term "binding domain" or "antibody molecule" refers to a protein, e.g., an immunoglobulin chain or fragment thereof, comprising at least one immunoglobulin variable domain sequence. The term "binding domain" or "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The portion of the CAR of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody, or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place. The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival.

The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically The term "xenogeneic" refers to a graft derived from an animal of a different species.

The term "cancer" refers to a disease characterized by the uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

The phrase "disease associated with expression of CD19" includes, but is not limited to, a disease associated with expression of CD19 or condition associated with cells which express, or at any time expressed, CD19 including, e.g., proliferative diseases such as a cancer or malignancy or a precancerous condition such as a myelodysplasia, a myelodysplastic syndrome or a preleukemia; or a noncancer related indication associated with cells which express CD19. For the avoidance of doubt, a disease associated with expression of CD19 may include a condition associated with cells which do not presently express CD19, e.g., because CD19 expression has been downregulated, e.g., due to treatment with a molecule targeting CD19, e.g., a CD19 CAR, but which at one time expressed CD19. In one aspect, a cancer associated with expression of CD19 is a hematological cancer. In one aspect, the hematolical cancer is a leukemia or a lymphoma. In one aspect, a cancer associated with expression of CD19 includes cancers and malignancies including, but not limited to, e.g., one or more acute leukemias including but not limited to, e.g., B-cell acute Lymphoid Leukemia (BALL), T-cell acute Lymphoid Leukemia (TALL), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of CD19 comprise, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma (MCL), Marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further diseases associated with expression of CD19 expression include, but not limited to, e.g., atypical and/or non-classical cancers, malignancies, precancerous conditions or proliferative diseases associated with expression of CD19. Non-cancer related indications associated with expression of CD19 include, but are not limited to, e.g., autoimmune disease, (e.g., lupus), inflammatory disorders (allergy and asthma) and transplantation. In some embodiments, the tumor antigen-expressing cells express, or at any time expressed, mRNA encoding the tumor antigen. In an embodiment, the tumor antigen-expressing cells produce the tumor antigen protein (e.g., wild-type or mutant), and the tumor antigen protein may be present at normal levels or reduced levels. In an embodiment, the tumor antigen-expressing cells produced detectable levels of a tumor antigen protein at one point, and subsequently produced substantially no detectable tumor antigen protein.

The phrase "disease associated with expression of a B-cell antigen" includes, but is not limited to, a disease associated with expression of one or more of CD19, CD20, CD22 or ROR1, or a condition associated with cells which express, or at any time expressed, one or more of CD19, CD20, CD22 or ROR1, including, e.g., proliferative diseases such as a cancer or malignancy or a precancerous condition such as a myelodysplasia, a myelodysplastic syndrome or a preleukemia; or a noncancer related indication associated with cells which express one or more of CD19, CD20, CD22 or ROR1. For the avoidance of doubt, a disease associated with expression of the B-cell antigen may include a condition associated with cells which do not presently express the B-cell antigen, e.g., because the antigen expression has been downregulated, e.g., due to treatment with a molecule targeting the B-cell antigen, e.g., a B-cell targeting CAR, but which at one time expressed the antigen. The phrase "disease associated with expression of a B-cell antigen" includes a disease associated with expression of CD19, as described herein.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested using the functional assays described herein.

The term "stimulation," refers to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules.

The term "stimulatory molecule," refers to a molecule expressed by an immune cell (e.g., T cell, NK cell, B cell) that provides the cytoplasmic signaling sequence(s) that regulate activation of the immune cell in a stimulatory way for at least some aspect of the immune cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing cytoplasmic signaling sequence that is of particular use in the invention includes, but is not limited to, those derived from CD3 zeta, common FcR gamma (FCER1G), Fc gamma RIIa, FcR beta (Fc Epsilon Rib), CD3 gamma, CD3 delta, CD3 epsilon, CD79a, CD79b, DAP10, and DAP12. In a specific CAR of the invention, the intracellular signaling domain in any one or more CARS of the invention comprises an intracellular signaling sequence, e.g., a primary signaling sequence of CD3-zeta. In a specific CAR of the invention, the primary signaling sequence of CD3-zeta is the sequence provided as SEQ ID NO: 17, or the equivalent residues from a non-human species, e.g., mouse, rodent, monkey, ape and the like. In a specific CAR of the invention, the primary signaling sequence of CD3-zeta is the sequence as provided in SEQ ID NO: 43, or the equivalent residues from a non-human species, e.g., mouse, rodent, monkey, ape and the like.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular signaling domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12.

The term "zeta" or alternatively "zeta chain", "CD3-zeta" or "TCR-zeta" is defined as the protein provided as GenB an Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain, or functional derivatives thereof, that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO:17. In one aspect, the "zeta stimulatory domain" or a "CD3-zeta stimulatory domain" is the sequence provided as SEQ ID NO:43.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are contribute to an efficient immune response. Costimulatory molecules include, but are not limited to an MHC class I molecule, BTLA and a Toll ligand receptor, as well as OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, ICAM-1, lymphocyte function-associated antigen-1 (LFA-1), CD2, CDS, CD7, CD287, LIGHT, NKG2C, NKG2D, SLAMF7, NKp80, NKp30, NKp44, NKp46, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment or derivative thereof.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank accno. AAA62478.2, or the equivalent residues from a non-human species, e.g., mouse, rodent, monkey, ape and the like. In one aspect, the "4-1BB costimulatory domain" is the sequence provided as SEQ ID NO:16 or the equivalent residues from a non-human species, e.g., mouse, rodent, monkey, ape and the like.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloic-derived phagocytes.

"Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" are used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The term "flexible polypeptide linker" or "linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)$_n$, where n is a positive integer equal to or greater than 1. For example, n=1, n=2, n=3. n=4, n=5 and n=6, n=7, n=8, n=9 and n=10 (SEQ ID NO:105). In one embodiment, the flexible polypeptide linkers include, but are not limited to, (Gly$_4$ Ser)$_4$ (SEQ ID NO:106) or (Gly$_4$ Ser)$_3$ (SEQ ID NO:107). In another embodiment, the linkers include multiple repeats of (Gly$_2$Ser), (GlySer) or (Gly$_3$Ser) (SEQ ID NO:108). Also included within the scope of the invention are linkers described in WO2012/138475, incorporated herein by reference).

As used herein, a 5' cap (also termed an RNA cap, an RNA 7-methylguanosine cap or an RNA m$^7$G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000 (SEQ ID NO: 109), preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin lymphoma, Hodgkin lymphoma, leukemias, uterine cancer, cervical cancer, bladder cancer, kidney cancer and adenocarcinomas such as breast cancer, prostate cancer, ovarian cancer, pancreatic cancer, and the like.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, or a ligand, which recognizes and binds with a binding partner (e.g., a stimulatory tumor antigen) protein present in a sample, but which antibody or ligand does not substantially recognize or bind other molecules in the sample.

"Regulatable chimeric antigen receptor (RCAR)," as that term is used herein, refers to a set of polypeptides, typically two in the simplest embodiments, which when in a RCARX cell, provides the RCARX cell with specificity for a target cell, typically a cancer cell, and with regulatable intracellular signal generation or proliferation, which can optimize an immune effector property of the RCARX cell. An RCARX cell relies at least in part, on an antigen binding domain to provide specificity to a target cell that comprises the antigen bound by the antigen binding domain. In an embodiment, an RCAR includes a dimerization switch that, upon the presence of a dimerization molecule, can couple an intracellular signaling domain to the antigen binding domain.

"Membrane anchor" or "membrane tethering domain", as that term is used herein, refers to a polypeptide or moiety, e.g., a myristoyl group, sufficient to anchor an extracellular or intracellular domain to the plasma membrane.

"Switch domain," as that term is used herein, e.g., when referring to an RCAR, refers to an entity, typically a polypeptide-based entity, that, in the presence of a dimerization molecule, associates with another switch domain. The association results in a functional coupling of a first entity linked to, e.g., fused to, a first switch domain, and a second entity linked to, e.g., fused to, a second switch domain. A first and second switch domain are collectively referred to as a dimerization switch. In embodiments, the first and second switch domains are the same as one another, e.g., they are polypeptides having the same primary amino acid sequence, and are referred to collectively as a homodimerization switch. In embodiments, the first and second switch domains are different from one another, e.g., they are polypeptides having different primary amino acid sequences, and are referred to collectively as a heterodimerization switch. In embodiments, the switch is intracellular. In embodiments, the switch is extracellular. In embodiments, the switch domain is a polypeptide-based entity, e.g., FKBP or FRB-based, and the dimerization molecule is small molecule, e.g., a rapalogue. In embodiments, the switch domain is a polypeptide-based entity, e.g., an scFv that binds a myc peptide, and the dimerization molecule is a polypeptide, a fragment thereof, or a multimer of a polypeptide, e.g., a myc ligand or multimers of a myc ligand that bind to one or more myc scFvs. In embodiments, the switch domain is a polypeptide-based entity, e.g., myc receptor, and the dimerization molecule is an antibody or fragments thereof, e.g., myc antibody.

"Dimerization molecule," as that term is used herein, e.g., when referring to an RCAR, refers to a molecule that promotes the association of a first switch domain with a second switch domain. In embodiments, the dimerization molecule does not naturally occur in the subject, or does not occur in concentrations that would result in significant dimerization. In embodiments, the dimerization molecule is a small molecule, e.g., rapamycin or a rapalogue, e.g, RAD001.

The term "bioequivalent" refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay, or measurement of phosphorylated S6 levels by western blot. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells as does the reference dose or reference amount of a reference compound.

The term "low, immune enhancing, dose" when used in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In an embodiment, the low, immune enhancing, dose of mTOR inhibitor results in an increase in the number of naive T cells. In an embodiment, the low, immune enhancing, dose of mTOR inhibitor results in one or more of the following:

an increase in the expression of one or more of the following markers: $CD62L^{high}$, $CD127^{high}$, $CD27^+$, and BCL2, e.g., on memory T cells, e.g., memory T cell precursors;

a decrease in the expression of KLRG1, e.g., on memory T cells, e.g., memory T cell precursors; and an increase in the number of memory T cell precursors, e.g., cells with any one or combination of the following characteristics: increased $CD62L^{high}$, increased $CD127^{high}$, increased $CD27^+$, decreased KLRG1, and increased BCL2; wherein any of the changes described above occurs, e.g., at least transiently, e.g., as compared to a non-treated subject.

"Refractory" as used herein refers to a disease, e.g., cancer, that does not respond to a treatment. In embodiments, a refractory cancer can be resistant to a treatment before or at the beginning of the treatment. In other embodiments, the refractory cancer can become refractory during a treatment.

A "complete responder" as used herein refers to a subject having a disease, e.g., a cancer, who exhibits a complete response, e.g., a complete remission, to a treatment. A complete response may be identified, e.g., using the Cheson criteria as described herein.

A "partial responder" as used herein refers to a subject having a disease, e.g., a cancer, who exhibits a partial response, e.g., a partial remission, to a treatment. A partial response may be identified, e.g., using the Cheson criteria.

A "non-responder" as used herein refers to a subject having a disease, e.g., a cancer, who does not exhibit a response to a treatment, e.g., the patient has stable disease or progressive disease. A non-responder may be identified, e.g., using the Cheson criteria as described herein.

The term "relapse" as used herein refers to reappearance of a disease (e.g., cancer) after an initial period of responsiveness (e.g., complete response or partial response). The initial period of responsiveness may involve the level of cancer cells falling below a certain threshold, e.g., below 20%, 1%, 10%, 5%, 4%, 3%, 2%, or 1%. The reappearance may involve the level of cancer cells rising above a certain threshold, e.g., above 20%, 1%, 10%, 5%, 4%, 3%, 2%, or 1%. Relapse may be identified, e.g., using the Cheson criteria as described herein.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

Description

Provided herein are compositions of matter and methods of use for the treatment of a disease such as cancer (e.g., hematological cancers or other B cell malignancies) using immune effector cells (e.g., T cells or NK cells) that express a chimeric antigen receptor (CAR) (e.g., a CAR that targets a B-cell marker, such as CD19). The methods include, inter alia, administering immune effector cells (e.g., T cells or NK cells) expressing a B cell targeting CAR described herein in combination with another agent such as a kinase inhibitor, e.g., a kinase inhibitor described herein.

The present invention provides, at least in part, experiments supporting the high efficacy of a combination of a CAR therapy (e.g., a B-cell targeting CAR therapy) and a kinase inhibitor, e.g., a BTK inhibitor such as ibrutinib. The combination of a kinase inhibitor, e.g., a BTK inhibitor such as ibrutinib, with a CAR therapy can increase efficacy of the combination therapy relative to a monotherapy of the kinase inhibitor, or a dose of CAR-expressing cells, or both. These beneficial effects can, for example, allow for a lower dose of the kinase inhibitor or the CAR-expressing cells, or both, while maintaining efficacy. The results herein are applicable to a wide range of cancers, e.g., hematological cancers and other B cell malignancies. For example, ibrutinib inhibits BTK, which is elevated in most lymphomas. An immune effector cell (e.g., T cell or NK cell) that expresses CAR19 targets cancers with CD19 surface expression, which is expressed in most B cell malignancies. Alternatively or in combination with CAR19, any other B-cell targeting CAR (e.g., a CAR targeting one or more of: CD20, CD22, or ROR1) can be used in the combination therapies described herein. Therefore, the combination of a CAR therapy (e.g., one or more of a CD19 CAR, CD20 CAR, CD22 CAR or ROR1 CAR therapy) with a BTK inhibitor (e.g., ibrutinib) is suitable for treating a wide range of cancers involving overproliferation of B cells, including lymphomas (e.g., Hodgkin lymphoma), MCL, CLL, DLBCL, and multiple myeloma.

According to the present invention, ibrutinib can reduce tumor masses and mobilize neoplastic B cells in the peripheral blood (see e.g., Example 8 herein). Without wishing to be bound by theory, certain lymphomas, such as MCL, are characterized by masses of cancerous cells in proliferation centers in lymph nodes. CAR-expressing immune effector cells sometimes have difficulty penetrating these densely packed masses. Thus, a BTK inhibitor, such as ibrutinib, can reduce tumor masses and mobilize neoplastic B cells in the peripheral blood, making the lymphoma cells more vulnerable to the CAR-expressing cells.

Alternatively or in combination, BTK inhibitors, such as ibrutinib, can also affect the CAR-expressing cells. The present invention demonstrates that ibrutinib treatment increases the level of circulating CART19 cells (see e.g., data shown in Example 8). Without wishing to be bound by theory, the increase in the level of circulating CART19 cells may be a result of, for example, increased proliferation, alteration of T cell phenotype, or other factors. For example, ibrutinib can inhibit ITK, a kinase with homology to BTK. ITK is expressed in T cells, and its inhibition may alter the T cell phenotype. Treatment with a kinase inhibitor, such as ibrutinib, can alter the T cell phenotype from a Th2 phenotype to a Th1 phenotype, and thus increase the T cell proliferative capacity. Pre-treatment, or co-administration, to a subject, of a BTK inhibitor may increase the T cell proliferative capacity in the subject, thus increasing the level of circulating CAR-expressing cells. In addition, a subject pre-treated with a BTK inhibitor, e.g., ibrutinib, can have a T cell population with a higher proliferative capacity in their apheresis for CAR manufacturing.

In one aspect, the invention provides a number of chimeric antigen receptors (CAR) comprising an antibody or antibody fragment engineered for specific binding to a B-cell antigen (e.g., chosen from one or more of CD19, CD20, CD22 or ROR1 protein). In one aspect, the invention provides a cell (e.g., T cell) engineered to express a CAR, wherein the CAR T cell ("CART") exhibits an anticancer property. In one aspect a cell is transformed with the CAR and the CAR is expressed on the cell surface. In some embodiments, the cell (e.g., T cell) is transduced with a viral vector encoding a CAR. In some embodiments, the viral vector is a retroviral vector. In some embodiments, the viral vector is a lentiviral vector. In some such embodiments, the cell may stably express the CAR. In another embodiment, the cell (e.g., T cell) is transfected with a nucleic acid, e.g., mRNA, cDNA, DNA, encoding a CAR. In some such embodiments, the cell may transiently express the CAR.

In one aspect, the anti-CD19 protein binding portion of the CAR is a scFv antibody fragment. In one aspect such antibody fragments are functional in that they retain the equivalent binding affinity, e.g., they bind the same antigen with comparable affinity, as the IgG antibody from which it is derived. In one aspect such antibody fragments are functional in that they provide a biological response that can include, but is not limited to, activation of an immune response, inhibition of signal-transduction origination from its target antigen, inhibition of kinase activity, and the like, as will be understood by a skilled artisan. In one aspect, the anti-CD19 antigen binding domain of the CAR is a scFv antibody fragment that is humanized compared to the murine sequence of the scFv from which it is derived. In one aspect, the parental murine scFv sequence is the CAR19 construct provided in PCT publication WO2012/079000 (incorporated herein by reference) and provided herein as SEQ ID NO:59. In one embodiment, the anti-CD19 binding domain is a scFv described in WO2012/079000 and provided in SEQ ID NO:59.

In some aspects, the antibodies of the invention are incorporated into a chimeric antigen receptor (CAR). In one aspect, the CAR comprises the polypeptide sequence provided as SEQ ID NO: 12 in PCT publication WO2012/079000, and provided herein as SEQ ID NO: 58, wherein the scFv domain is substituted by one or more sequences selected from SEQ ID NOS: 1-12. In one aspect, the scFv domains of SEQ ID NOS:1-12 are humanized variants of the scFv domain of SEQ ID NO:59, which is an scFv fragment of murine origin that specifically binds to human CD19. Humanization of this mouse scFv may be desired for the clinical setting, where the mouse-specific residues may induce a human-anti-mouse antigen (HAMA) response in patients who receive CART19 treatment, e.g., treatment with T cells transduced with the CAR19 construct.

In one aspect, the anti-CD19 binding domain, e.g., humanized scFv, portion of a CAR of the invention is encoded by a transgene whose sequence has been codon optimized for expression in a mammalian cell. In one aspect, entire CAR construct of the invention is encoded by a transgene whose entire sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148.

In one aspect, the humanized CAR19 comprises the scFv portion provided in SEQ ID NO:1. In one aspect, the humanized CAR19 comprises the scFv portion provided in SEQ ID NO:2. In one aspect, the humanized CAR19 comprises the scFv portion provided in SEQ ID NO:3. In one aspect, the humanized CAR19 comprises the scFv portion provided in SEQ ID NO:4. In one aspect, the humanized CAR19 comprises the scFv portion provided in SEQ ID NO:5. In one aspect, the humanized CAR19 comprises the scFv portion provided in SEQ ID NO:6. In one aspect, the humanized CAR19 comprises the scFv portion provided in SEQ ID NO:7. In one aspect, the humanized CAR19 comprises the scFv portion provided in SEQ ID NO:8. In one aspect, the humanized CAR19 comprises the scFv portion provided in SEQ ID NO:9. In one aspect, the humanized CAR19 comprises the scFv portion provided in SEQ ID NO:10. In one aspect, the humanized CAR19 comprises the scFv portion provided in SEQ ID NO:11. In one aspect, the humanized CAR19 comprises the scFv portion provided in SEQ ID NO:12.

In one aspect, the CARs of the invention combine an antigen binding domain of a specific antibody with an intracellular signaling molecule. For example, in some aspects, the intracellular signaling molecule includes, but is not limited to, CD3-zeta chain, 4-1BB and CD28 signaling modules and combinations thereof. In one aspect, the CD19 CAR comprises a CAR selected from the sequence provided in one or more of SEQ ID NOS: 31-42. In one aspect, the CD19 CAR comprises the sequence provided in SEQ ID NO:31. In one aspect, the CD19 CAR comprises the sequence provided in SEQ ID NO:32. In one aspect, the CD19 CAR comprises the sequence provided in SEQ ID NO:33. In one aspect, the CD19 CAR comprises the sequence provided in SEQ ID NO:34. In one aspect, the CD19 CAR comprises the sequence provided in SEQ ID NO:35. In one aspect, the CD19 CAR comprises the sequence provided in SEQ ID NO:36. In one aspect, the CD19 CAR comprises the sequence provided in SEQ ID NO:37. In one aspect, the CD19 CAR comprises the sequence provided in SEQ ID NO:38. In one aspect, the CD19 CAR comprises the sequence provided in SEQ ID NO:39. In one aspect, the CD19 CAR comprises the sequence provided in SEQ ID NO:40. In one aspect, the CD19 CAR comprises the sequence provided in SEQ ID NO:41. In one aspect, the CD19 CAR comprises the sequence provided in SEQ ID NO:42.

Furthermore, the present invention provides CD19 CAR compositions and their use in medicaments or methods for treating, among other diseases, cancer or any malignancy or autoimmune diseases involving cells or tissues which express CD19.

In one aspect, the CAR of the invention can be used to eradicate CD19-expressing normal cells, thereby applicable for use as a cellular conditioning therapy prior to cell transplantation. In one aspect, the CD19-expressing normal cell is a CD19-expressing normal stem cell and the cell transplantation is a stem cell transplantation.

In one aspect, the invention provides a cell (e.g., T cell) engineered to express a chimeric antigen receptor (CAR), wherein the CAR-expressing cell, e.g., CAR T cell ("CART"), exhibits an anticancer property. A preferred antigen is CD19. In one aspect, the antigen binding domain of the CAR comprises a partially humanized anti-CD19 antibody fragment. In one aspect, the antigen binding domain of the CAR comprises a partially humanized anti-CD19 antibody fragment comprising a scFv. Accordingly, the invention provides a CD19-CAR that comprises a humanized anti-CD19 binding domain and is engineered into an immune effector cell, e.g., a T cell or an NK cell, and methods of their use for adoptive therapy.

In one aspect, the CD19-CAR comprises at least one intracellular domain selected from the group of a CD137 (4-1BB) signaling domain, a CD28 signaling domain, a CD3zeta signal domain, and any combination thereof. In one aspect, the CD19-CAR comprises at least one intracellular signaling domain is from one or more co-stimulatory molecule(s) other than a CD137 (4-1BB) or CD28.

Chimeric Antigen Receptor (CAR)

The present invention encompasses a recombinant DNA construct comprising sequences encoding a CAR, wherein the CAR comprises an antibody or antibody fragment that binds specifically to a B-cell antigen (e.g., CD19, e.g., human CD19), wherein the sequence of the antibody fragment is contiguous with and in the same reading frame as a nucleic acid sequence encoding an intracellular signaling domain. The intracellular signaling domain can comprise a costimulatory signaling domain and/or a primary signaling domain, e.g., a zeta chain. The costimulatory signaling domain refers to a portion of the CAR comprising at least a portion of the intracellular domain of a costimulatory molecule. In one embodiment, the antigen binding domain is a murine antibody or antibody fragment described herein. In one embodiment, the antigen binding domain is a humanized antibody or antibody fragment.

In specific aspects, a CAR construct of the invention comprises a scFv domain selected from the group consisting of SEQ ID NOS:1-12 or an scFV domain of SEQ ID NO:59, wherein the scFv may be preceded by an optional leader sequence such as provided in SEQ ID NO: 13, and followed by an optional hinge sequence such as provided in SEQ ID NO:14 or SEQ ID NO:45 or SEQ ID NO:47 or SEQ ID NO:49, a transmembrane region such as provided in SEQ ID NO:15, an intracellular signalling domain that includes SEQ ID NO:16 or SEQ ID NO:51 and a CD3 zeta sequence that includes SEQ ID NO:17 or SEQ ID NO:43, wherein the domains are contiguous with and in the same reading frame to form a single fusion protein. Also included in the invention is a nucleotide sequence that encodes the polypeptide of each of the scFv fragments selected from the group consisting of SEQ IS NO:1, SEQ ID NO:2, SEQ ID NO:3, SEQ ID NO:4, SEQ ID NO:5, SEQ IS NO:6, SEQ ID NO:7, SEQ ID NO:8, SEQ ID NO:9, SEQ ID NO:10, SEQ ID NO:11, SEQ ID NO:12 and SEQ ID NO:59. Also included in the invention is a nucleotide sequence that encodes the polypeptide of each of the scFv fragments selected from the group consisting of SEQ IS NO:1, SEQ ID NO:2, SEQ ID NO:3, SEQ ID NO:4, SEQ ID NO:5, SEQ IS NO:6, SEQ ID NO:7, SEQ ID NO:8, SEQ ID NO:9, SEQ ID NO:10, SEQ ID NO:11, SEQ ID NO:12 and SEQ ID NO:59, and each of the domains of SEQ ID NOS: 13-17, plus the encoded CD19CAR fusion protein of the invention. In one aspect an exemplary CD19CAR constructs comprise an optional leader sequence, an extracellular antigen binding domain, a hinge, a transmembrane domain, and an intracellular stimulatory domain. In one aspect an exemplary CD19CAR construct comprises an optional leader sequence, an extracellular antigen binding domain, a hinge, a transmembrane domain, an intracellular costimulatory domain and an intracellular stimulatory domain. Specific CD19 CAR constructs containing humanized scFv domains of the invention are provided as SEQ ID NOS: 31-42, or a murine scFv domain as provided as SEQ ID NO:59.

Full-length CAR sequences are also provided herein as SEQ ID NOS: 31-42 and 58, as shown in Table 7 and Table 3.

An exemplary leader sequence is provided as SEQ ID NO: 13. An exemplary hinge/spacer sequence is provided as SEQ ID NO: 14 or SEQ ID NO:45 or SEQ ID NO:47 or SEQ ID NO:49. An exemplary transmembrane domain sequence is provided as SEQ ID NO:15. An exemplary sequence of the intracellular signaling domain of the 4-1BB protein is provided as SEQ ID NO: 16. An exemplary sequence of the intracellular signaling domain of CD27 is provided as SEQ ID NO:51. An exemplary CD3zeta domain sequence is provided as SEQ ID NO: 17 or SEQ ID NO:43.

In one aspect, the present invention encompasses a recombinant nucleic acid construct comprising a nucleic acid molecule encoding a CAR, wherein the nucleic acid molecule comprises the nucleic acid sequence encoding an anti-CD19 binding domain, e.g., described herein, that is contiguous with and in the same reading frame as a nucleic acid sequence encoding an intracellular signaling domain. In one aspect, the anti-CD19 binding domain is selected from one or more of SEQ ID NOS:1-12 and 58. In one aspect, the anti-CD19 binding domain is encoded by a nucleotide residues 64 to 813 of the sequence provided in one or more of SEQ ID NOS:61-72 and 59. In one aspect, the anti-CD19 binding domain is encoded by a nucleotide residues 64 to 813 of SEQ ID NO:61. In one aspect, the anti-CD19 binding domain is encoded by a nucleotide residues 64 to 813 of SEQ ID NO:62. In one aspect, the anti-CD19 binding domain is encoded by a nucleotide residues 64 to 813 of SEQ ID NO:63. In one aspect, the anti-CD19 binding domain is encoded by a nucleotide residues 64 to 813 of SEQ ID NO:64. In one aspect, the anti-CD19 binding domain is encoded by a nucleotide residues 64 to 813 of SEQ ID NO:65. In one aspect, the anti-CD19 binding domain is encoded by a nucleotide residues 64 to 813 of SEQ ID NO:66. In one aspect, the anti-CD19 binding domain is encoded by a nucleotide residues 64 to 813 of SEQ ID NO:67. In one aspect, the anti-CD19 binding domain is encoded by a nucleotide residues 64 to 813 of SEQ ID NO:68. In one aspect, the anti-CD19 binding domain is encoded by a nucleotide residues 64 to 813 of SEQ ID NO:69. In one aspect, the anti-CD19 binding domain is encoded by a nucleotide residues 64 to 813 of SEQ ID NO:70. In one aspect, the anti-CD19 binding domain is encoded by a nucleotide residues 64 to 813 of SEQ ID NO:71. In one aspect, the anti-CD19 binding domain is encoded by a nucleotide residues 64 to 813 of SEQ ID NO:72.

In one aspect, the present invention encompasses a recombinant nucleic acid construct comprising a transgene encoding a CAR, wherein the nucleic acid molecule comprises a nucleic acid sequence encoding an anti-CD19 binding domain selected from one or more of SEQ ID NOS:61-72, wherein the sequence is contiguous with and in the same reading frame as the nucleic acid sequence encoding an intracellular signaling domain. An exemplary intracellular signaling domain that can be used in the CAR includes, but is not limited to, one or more intracellular signaling domains of, e.g., CD3-zeta, CD28, 4-1BB, and the like. In some instances, the CAR can comprise any combination of CD3-zeta, CD28, 4-1BB, and the like. In one aspect the nucleic acid sequence of a CAR construct of the invention is selected from one or more of SEQ ID NOS: 85-96. In one aspect the nucleic acid sequence of a CAR construct is SEQ ID NO:85. In one aspect the nucleic acid sequence of a CAR construct is SEQ ID NO:86. In one aspect the nucleic acid sequence of a CAR construct is SEQ ID NO:87. In one aspect the nucleic acid sequence of a CAR construct is SEQ ID NO:88. In one aspect the nucleic acid sequence of a CAR construct is SEQ ID NO:89. In one aspect the nucleic acid sequence of a CAR construct is SEQ ID NO:90. In one aspect the nucleic acid sequence of a CAR construct is SEQ ID NO:91. In one aspect the nucleic acid sequence of a CAR construct is SEQ ID NO:92. In one aspect the nucleic acid sequence of a CAR construct is SEQ ID NO:93. In one aspect the nucleic acid sequence of a CAR construct is SEQ ID NO:94. In one aspect the nucleic acid sequence of a CAR construct is SEQ ID NO:95. In one aspect the nucleic acid sequence of a CAR construct is SEQ ID NO:96. In one aspect the nucleic acid sequence of a CAR construct is SEQ ID NO:97. In one aspect the nucleic acid sequence of a CAR construct is SEQ ID NO:98. In one aspect the nucleic acid sequence of a CAR construct is SEQ ID NO:99.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the nucleic acid of interest can be produced synthetically, rather than cloned.

The present invention includes retroviral and lentiviral vector constructs expressing a CAR that can be directly transduced into a cell.

The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO:118). RNA so produced can efficiently transfect different kinds of cells. In one embodiment, the template includes sequences for the CAR. In an embodiment, an RNA CAR vector is transduced into a T cell by electroporation.

Antigen Binding Domain

In one aspect, the CAR of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in a CAR of the invention include those associated with viral, bacterial and parasitic infections, autoimmune disease and cancer cells.

In one aspect, the CAR-mediated T-cell response can be directed to an antigen of interest by way of engineering an antigen binding domain that specifically binds a desired antigen into the CAR.

In one aspect, the portion of the CAR comprising the antigen binding domain comprises an antigen binding domain that targets CD19. In one aspect, the antigen binding domain targets human CD19. In one aspect, the antigen binding domain of the CAR has the same or a similar binding specificity as the FMC63 scFv fragment described in Nicholson et al. Mol. Immun. 34 (16-17): 1157-1165 (1997). In one embodiment, the antigen binding domain of the CAR includes the scFv fragment described in Nicholson et al. Mol. Immun. 34 (16-17): 1157-1165 (1997).

The antigen binding domain can be any domain that binds to the antigen including but not limited to a monoclonal antibody, a polyclonal antibody, a recombinant antibody, a murine antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, and the like.

In one embodiment, the CAR molecule comprises an anti-CD19 binding domain comprising one or more (e.g., all three) light chain complementary determining region 1 (LC CDR1), light chain complementary determining region 2 (LC CDR2), and light chain complementary determining region 3 (LC CDR3) of an anti-CD19 binding domain described herein, and one or more (e.g., all three) heavy chain complementary determining region 1 (HC CDR1), heavy chain complementary determining region 2 (HC CDR2), and heavy chain complementary determining region 3 (HC CDR3) of an anti-CD19 binding domain described herein, e.g., an anti-CD19 binding domain comprising one or more, e.g., all three, LC CDRs and one or more, e.g., all three, HC CDRs. In one embodiment, the anti-CD19 binding domain comprises one or more (e.g., all three) heavy chain complementary determining region 1 (HC CDR1), heavy chain complementary determining region 2 (HC CDR2), and heavy chain complementary determining region 3 (HC CDR3) of an anti-CD19 binding domain described herein, e.g., the anti-CD19 binding domain has two variable heavy chain regions, each comprising a HC CDR1, a HC CDR2 and a HC CDR3 described herein. In one embodiment, the anti-CD19 binding domain comprises a murine light chain variable region described herein (e.g., in Table 7) and/or a murine heavy chain variable region described herein (e.g., in Table 7). In one embodiment, the anti-CD19 binding domain is a scFv comprising a murine light chain and a murine heavy chain of an amino acid sequence of Table 7. In an embodiment, the anti-CD19 binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 7, or a sequence with 95-99% identity with an amino acid sequence of Table 7; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in Table 7, or a sequence with 95-99% identity to an amino acid sequence of Table 7. In one embodiment, the anti-CD19 binding domain comprises a sequence of SEQ ID NO:59, or a sequence with 95-99% identify thereof. In one embodiment, the anti-CD19 binding domain is a scFv, and a light chain variable region comprising an amino acid sequence described herein, e.g., in Table 7, is attached to a heavy chain variable region comprising an amino acid sequence described herein, e.g., in Table 7, via a linker, e.g., a linker described herein. In one embodiment, the anti-CD19 binding domain includes a (Gly$_4$-Ser)n linker, wherein n is 1, 2, 3, 4, 5, or 6, preferably 3 or 4 (SEQ ID NO: 53). The light chain variable region and heavy chain variable region of a scFv can be, e.g., in any of the following orientations: light chain variable region-linker-heavy chain variable region or heavy chain variable region-linker-light chain variable region.

In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

Thus, in one aspect, the antigen binding domain comprises a humanized antibody or an antibody fragment. In one embodiment, the humanized anti-CD19 binding domain comprises one or more (e.g., all three) light chain complementary determining region 1 (LC CDR1), light chain complementary determining region 2 (LC CDR2), and light chain complementary determining region 3 (LC CDR3) of a murine or humanized anti-CD19 binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a murine or humanized anti-CD19 binding domain described herein, e.g., a humanized anti-CD19 binding domain comprising one or more, e.g., all three, LC CDRs and one or more, e.g., all three, HC CDRs. In one embodiment, the humanized anti-CD19 binding domain comprises one or more (e.g., all three) heavy chain complementary determining region 1 (HC CDR1), heavy chain complementary determining region 2 (HC CDR2), and heavy chain complementary determining region 3 (HC CDR3) of a murine or humanized anti-CD19 binding domain described herein, e.g., the humanized anti-CD19 binding domain has two variable heavy chain regions, each comprising a HC CDR1, a HC CDR2 and a HC CDR3 described herein. In one embodiment, the humanized anti-CD19 binding domain comprises a humanized light chain variable region described herein (e.g., in Table 3) and/or a humanized heavy chain variable region described herein (e.g., in Table 3). In one embodiment, the humanized anti-CD19 binding domain comprises a humanized heavy chain variable region described herein (e.g., in Table 3), e.g., at least two humanized heavy chain variable regions described herein (e.g., in Table 3). In one embodiment, the anti-CD19 binding domain is a scFv comprising a light chain and a heavy chain of an amino acid sequence of Table 3. In an embodiment, the anti-CD19 binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 3, or a sequence with 95-99% identity with an amino acid sequence of Table 3; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in Table 3, or a sequence with 95-99% identity to an amino acid sequence of Table 3. In one embodiment, the humanized anti-CD19 binding domain comprises a sequence selected from a group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, or a sequence with 95-99% identify thereof. In one embodiment, the nucleic acid sequence encoding the humanized anti-CD19 binding domain comprises a sequence selected from a group consisting of SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:70, SEQ ID NO:71 and SEQ ID NO:72, or a sequence with 95-99% identify thereof. In one embodiment, the humanized anti-CD19 binding domain is a scFv, and a light chain variable region comprising an amino acid sequence described herein, e.g., in Table 3, is attached to a heavy chain variable region comprising an amino acid sequence described herein, e.g., in Table 3, via a linker, e.g., a linker described herein. In one embodiment, the humanized anti-CD19 binding domain includes a $(Gly_4\text{-}Ser)n$ linker, wherein n is 1, 2, 3, 4, 5, or 6, preferably 3 or 4 (SEQ ID NO:53). The light chain variable region and heavy chain variable region of a scFv can be, e.g., in any of the following orientations: light chain variable region-linker-heavy chain variable region or heavy chain variable region-linker-light chain variable region.

In one aspect, the antigen binding domain portion comprises one or more sequence selected from SEQ ID NOS: 1-12. In one aspect the humanized CAR is selected from one or more sequence selected from SEQ ID NOS: 31-42. In some aspects, a non-human antibody is humanized, where specific sequences or regions of the antibody are modified to increase similarity to an antibody naturally produced in a human or fragment thereof.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody or antibody fragment has one or more amino acid residues remaining in it from a source which is nonhuman. These nonhuman amino acid residues are often referred to as "import" residues, which are typically taken from an "import" variable domain. As provided herein, humanized antibodies or antibody fragments comprise one or more CDRs from nonhuman immunoglobulin molecules and framework regions wherein the amino acid residues comprising the framework are derived completely or mostly from human germline. Multiple techniques for humanization of antibodies or antibody fragments are well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized antibodies and antibody fragments, substantially less than an intact human variable domain has been substituted by the corresponding sequence from a nonhuman species. Humanized antibodies are often human antibodies in which some CDR residues and possibly some framework (FR) residues are substituted by residues from analogous sites in rodent antibodies. Humanization of antibodies and antibody fragments can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (see, e.g., Nicholson et al. Mol. Immun. 34 (16-17): 1157-1165 (1997); Carter et al., Proc. Natl. Acad. Sci. USA, 89:4285 (1992); Presta et al., J. Immunol., 151:2623 (1993), the contents of which are incorporated herein by reference herein in their entirety). In some embodiments, the framework region, e.g., all four framework regions, of the heavy chain variable region are derived from a VH4_4-59 germline sequence. In one embodiment, the framework region can comprise, one, two, three, four or five modifications, e.g., substitutions, e.g., from the amino acid at the corresponding murine sequence (e.g., of SEQ ID NO:59). In one embodiment, the framework region, e.g., all four framework regions of the light chain variable region are derived from a VK3_1.25 germline sequence. In one embodiment, the framework region can comprise, one, two, three, four or five modifications, e.g., substitutions, e.g., from the amino acid at the corresponding murine sequence (e.g., of SEQ ID NO:59).

In some aspects, the portion of a CAR composition of the invention that comprises an antibody fragment is humanized with retention of high affinity for the target antigen and other favorable biological properties. According to one aspect of the invention, humanized antibodies and antibody fragments are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences.

Inspection of these displays permits analysis of the likely role of the residues in the functioning of the candidate immunoglobulin sequence, e.g., the analysis of residues that influence the ability of the candidate immunoglobulin to bind the target antigen. In this way, FR residues can be selected and combined from the recipient and import sequences so that the desired antibody or antibody fragment characteristic, such as increased affinity for the target antigen, is achieved. In general, the CDR residues are directly and most substantially involved in influencing antigen binding.

A humanized antibody or antibody fragment may retain a similar antigenic specificity as the original antibody, e.g., in the present invention, the ability to bind human CD19. In some embodiments, a humanized antibody or antibody fragment may have improved affinity and/or specificity of binding to human CD19.

In one aspect, the anti-CD19 binding domain is characterized by particular functional features or properties of an antibody or antibody fragment. For example, in one aspect, the portion of a CAR composition of the invention that comprises an antigen binding domain specifically binds human CD19. In one aspect, the antigen binding domain has the same or a similar binding specificity to human CD19 as the FMC63 scFv described in Nicholson et al. Mol. Immun. 34 (16-17): 1157-1165 (1997). In one aspect, the invention relates to an antigen binding domain comprising an antibody or antibody fragment, wherein the antibody binding domain specifically binds to a CD19 protein or fragment thereof, wherein the antibody or antibody fragment comprises a variable light chain and/or a variable heavy chain that includes an amino acid sequence of SEQ ID NO: 1-12 or SEQ ID NO:59. In one aspect, the antigen binding domain comprises an amino acid sequence of an scFv selected from SEQ ID NOs: 1-12 or SEQ ID NO:59. In certain aspects, the scFv is contiguous with and in the same reading frame as a leader sequence. In one aspect the leader sequence is the polypeptide sequence provided as SEQ ID NO:13.

In one aspect, the anti-CD19 binding domain is a fragment, e.g., a single chain variable fragment (scFv). In one aspect, the anti-CD19 binding domain is a Fv, a Fab, a (Fab')2, or a bi-functional (e.g. bi-specific) hybrid antibody (e.g., Lanzavecchia et al., Eur. J. Immunol. 17, 105 (1987)). In one aspect, the antibodies and fragments thereof of the invention binds a CD19 protein with wild-type or enhanced affinity.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

A scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as (Gly$_4$Ser)n, where n is a positive integer equal to or greater than 1 (SEQ ID NO:18). In one embodiment, the linker can be (Gly$_4$Ser)$_4$ (SEQ ID NO:106) or (Gly$_4$Ser)$_3$ (SEQ ID NO:107). Variation in the linker length may retain or enhance activity, giving rise to superior efficacy in activity studies.

In some embodiments, the amino acid sequence of the antigen binding domain (or other portions or the entire CAR) can be modified, e.g., an amino acid sequence described herein can be modified, e.g., by a conservative substitution. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences, refers to two or more sequences that are the same. Two sequences are "substantially identical" if two sequences have a specified percentage of amino acid residues or nucleotides that are the same (e.g., 60% identity, optionally 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

In one aspect, the present invention contemplates modifications of the starting antibody or fragment (e.g., scFv) amino acid sequence that generate functionally equivalent molecules. For example, the VH or VL of an anti-CD19 binding domain, e.g., scFv, comprised in the CAR can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting VH or VL framework region of the anti-CD19 binding domain, e.g., scFv. The present invention contemplates modifications of the entire CAR construct, e.g., modifications in one or more amino acid sequences of the various domains of the CAR construct in order to generate functionally equivalent molecules. The CAR construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting CAR construct.

Bispecific CARs

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR, e.g., in one embodiment, the transmembrane domain may be from the same protein that the signaling domain, costimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the cell surface of a CAR-expressing cell. In a different aspect the amino acid sequence of the transmembrane domain may be modified or substituted so as to minimize interactions with the binding domains of the native binding partner present in the same CAR-expressing cell.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the CAR has bound to a target. A transmembrane domain of particular use in this invention may include at least the transmembrane region(s) of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge, e.g., an IgG4 hinge, an IgD hinge), a GS linker (e.g., a GS linker described herein), a KIR2DS2 hinge or a CD8a hinge. In one embodiment, the hinge or spacer comprises (e.g., consists of) the amino acid sequence of SEQ ID NO:14. In one aspect, the transmembrane domain comprises (e.g., consists of) a transmembrane domain of SEQ ID NO: 15.

In one aspect, the hinge or spacer comprises an IgG4 hinge. For example, in one embodiment, the hinge or spacer comprises a hinge of the amino acid sequence ESKYGPP-CPPCPAPEFLGGPSVFLFPPKPKDTLMISRTPEVTCV-VVDVSQEDPEVQFNW YVDGVEVHNAKTKPREEQF-NSTYRVVSVLTVLHQDWLNGKEYKCKVSNKGLPSS-IEK TISKAKGQPREPQVYTLPPSQEEMTKNQVSLT-CLVKGFYPSDIAVEWESNGQPENNYK TTPPVLDS-DGSFFLYSRLTVDKSRWQEGNVFSCSVMHEALHN-HYTQKSLSLSLGKM (SEQ ID NO:45). In some embodiments, the hinge or spacer comprises a hinge encoded by a nucleotide sequence of (SEQ ID NO: 46)
GAGAGCAAGTACGGCCCTCCCTGCCCCCCTTGCCCTGCCCCCGAGTTCCT

GGGCGGACCCAGCGTGTTCCTGTTCCCCCCCAAGCCCAAGGACACCCTGA

TGATCAGCCGGACCCCCGAGGTGACCTGTGTGGTGGTGGACGTGTCCCAG

GAGGACCCCGAGGTCCAGTTCAACTGGTACGTGGACGGCGTGGAGGTGCA

CAACGCCAAGACCAAGCCCCGGGAGGAGCAGTTCAATAGCACCTACCGGG

TGGTGTCCGTGCTGACCGTGCTGCACCAGGACTGGCTGAACGGCAAGGAA

TACAAGTGTAAGGTGTCCAACAAGGGCCTGCCCAGCAGCATCGAGAAAAC

CATCAGCAAGGCCAAGGGCCAGCCTCGGGAGCCCCAGGTGTACACCCTGC

CCCCTAGCCAAGAGGAGATGACCAAGAACCAGGTGTCCCTGACCTGCCTG

GTGAAGGGCTTCTACCCCAGCGACATCGCCGTGGAGTGGGAGAGCAACGG

CCAGCCCGAGAACAACTACAAGACCACCCCCCCTGTGCTGGACAGCGACG

GCAGCTTCTTCCTGTACAGCCGGCTGACCGTGGACAAGAGCCGGTGGCAG

GAGGGCAACGTCTTTAGCTGCTCCGTGATGCACGAGGCCCTGCACAACCA

CTACACCCAGAAGAGCCTGAGCCTGTCCCTGGGCAAGATG.

In one aspect, the hinge or spacer comprises an IgD hinge. For example, in one embodiment, the hinge or spacer comprises a hinge of the amino acid sequence RWPESP-KAQASSVPTAQPQAEGSLAKATTAPATTRNTGRG-GEEKKKEKEKEEQEERET KTPECPSHTQPLGVYLLT-PAVQDLWLRDKATFTCFVVGSDLKDAHLTWEVAGK-VPTG GVEEGLLERHSNGSQSQHSRLTL-PRSLWNAGTSVTCTLNHPSLPPQRLMALREPAAQA PVKLSLNLLASSDPPEAASWLLCEVSGFSPPNILLM-WLEDQREVNTSGFAPARPPPQPG STTFWAWSVLRV-PAPPSPQPATYTCVVSHEDSRTLL-NASRSLEVSYVTDH (SEQ ID NO:47). In some embodiments, the hinge or spacer comprises a hinge encoded by a nucleotide sequence of (SEQ ID NO: 48)
AGGTGGCCCGAAAGTCCCAAGGCCCAGGCATCTAGTGTTCCTACTGCACA

GCCCCAGGCAGAAGGCAGCCTAGCCAAAGCTACTACTGCACCTGCCACTA

CGCGCAATACTGGCCGTGGCGGGAGGAGAAGAAAAAGGAGAAAGAGAAA

GAAGAACAGGAAGAGAGGGAGACCAAGACCCCTGAATGTCCATCCCATAC

CCAGCCGCTGGGCGTCTATCTCTTGACTCCCGCAGTACAGGACTTGTGGC

TTAGAGATAAGGCCACCTTTACATGTTTCGTCGTGGGCTCTGACCTGAAG

GATGCCCATTTGACTTGGGAGGTTGCCGGAAAGGTACCCACAGGGGGGGT

TGAGGAAGGGTTGCTGGAGCGCCATTCCAATGGCTCTCAGAGCCAGCACT

CAAGACTCACCCTTCCGAGATCCCTGTGGAACGCCGGGACCTCTGTCACA

TGTACTCTAAATCATCCTAGCCTGCCCCCACAGCGTCTGATGGCCCTTAG

AGAGCCAGCCGCCCAGGCACCAGTTAAGCTTAGCCTGAATCTGCTCGCCA

GTAGTGATCCCCCAGAGGCCGCCAGCTGGCTCTTATGCGAAGTGTCCGGC

TTTAGCCCGCCCAACATCTTGCTCATGTGGCTGGAGGACCAGCGAGAAGT

GAACACCAGCGGCTTCGCTCCAGCCCGGCCCCCACCCCAGCCGGGTTCTA

CCACATTCTGGGCCTGGAGTGTCTTAAGGGTCCCAGCACCACCTAGCCCC

CAGCCAGCCACATACACCTGTGTTGTGTCCCATGAAGATAGCAGGACCCT

GCTAAATGCTTCTAGGAGTCTGGAGGTTTCCTACGTGACTGACCATT.

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic region of the CAR. A glycine-serine doublet provides a particularly suitable linker. For example, in one aspect, the linker comprises the amino acid sequence of GGGGSGGGGS (SEQ ID NO:49). In some embodiments, the linker is encoded by a nucleotide sequence of GGTG-GCGGAGGTTCTGGAGGTGGAGGTTCC (SEQ ID NO:50).

In one aspect, the hinge or spacer comprises a KIR2DS2 hinge.

Cytoplasmic Domain

The cytoplasmic domain or region of the CAR includes an intracellular signaling domain. An intracellular signaling domain is generally responsible for activation of at least one of the normal effector functions of the immune cell in which the CAR has been introduced. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of CD3 zeta, common FcR gamma (FCER1G), Fc gamma RIIa, FcR beta (Fc Epsilon Rib), CD3 gamma, CD3 delta, CD3 epsilon, CD79a, CD79b, DAP10, and DAP12. In one embodiment, a CAR of the invention comprises an intracellular signaling domain, e.g., a primary signaling domain of CD3-zeta.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

Further examples of molecules containing a primary intracellular signaling domain that are of particular use in the invention include those of DAP10, DAP12, and CD32.

The intracellular signalling domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), NKG2D, CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and CD19a.

The intracellular signaling sequences within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB. In one aspect, the signaling domain of 4-1BB is a signaling domain of SEQ ID NO: 16. In one aspect, the signaling domain of CD3-zeta is a signaling domain of SEQ ID NO: 17.

In one aspect, the intracellular signaling domain is designed to comprise the signaling domain of CD3-zeta and the signaling domain of CD27. In one aspect, the signaling domain of CD27 comprises an amino acid sequence of (SEQ ID NO: 51)
QRRKYRSNKGESPVEPAEPCRYSCPREEEGSTIPIQEDYRKPEPACSP.

In one aspect, the signalling domain of CD27 is encoded by a nucleic acid sequence of (SEQ ID NO: 52)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC.

In one aspect, the CAR-expressing cell described herein can further comprise a second CAR, e.g., a second CAR that includes a different antigen binding domain, e.g., to the same target (CD19) or a different target (e.g., CD123 or mesothelin). In one embodiment, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a VHH.

In another aspect, the CAR-expressing cell described herein can further express another agent, e.g., an agent which enhances the activity of a CAR-expressing cell. For example, in one embodiment, the agent can be an agent which inhibits an inhibitory molecule. Inhibitory molecules, e.g., PD1, can, in some embodiments, decrease the ability of a CAR-expressing cell to mount an immune effector response. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 or TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In one embodiment, the agent comprises the extracellular domain (ECD) of an inhibitory molecule, e.g., Programmed Death 1 (PD1), can be fused to a transmembrane domain and intracellular signaling domains such as 41BB and CD3 zeta (also referred to herein as a PD1 CAR). In one embodiment, the PD1 CAR, when used in combinations with a CD19 CAR described herein, improves the persistence of the T cell. In one embodiment, the CAR is a PD1 CAR comprising the extracellular domain of PD1 indicated as underlined in SEQ ID NO: 121. In one embodiment, the PD1 CAR comprises the amino acid sequence of SEQ ID NO:121.

(SEQ ID NO: 121)
Malpvtalllplalllhaarppqwfldspdrpwnpptfspallvvteqdn atftcsfsntsesfvlnwyrmspsnqtdklaafpedrsqpgqdcrfrvtq lpngrdfhmsvvrarrndsqtylcqaislapkaqikeslraelrvterra evptahpspsprpagqfqtlvtttpaprpptpaptiasqplslrpeacrp aaggavhtrgldfacdiyiwaplagtcgvlllslvitlyckrgrkkllyi fkqpfmrpvqttqeedgcscrfpeeeeggcelrvkfsrsadapaykqgqn qlynelnlgrreeydvldkrrgrdpemggkprrknpqeglynelqkdkma eayseigmkgerrrgkghdglyqglstatkdtydalhmqalppr.

In one embodiment, the PD1 CAR comprises the amino acid sequence provided below (SEQ ID NO:119).

(SEQ ID NO: 119)
pqwfldspdrpwnpptfspallvvteqdnatftcsfsntsesfvlnwyrm spsnqtdklaafpedrsqpgqdcrfrvtqlpngrdfhmsvvrarrndsqt ylcqaislapkaqikeslraelrvterraevptahpspsprpagqfqtlv tttpaprpptpaptiasqplslrpeacrpaaggavhtrgldfacdiyiwa plagtcgvlllslvitlyckrgrkkllyifkqpfmrpvqttqeedgcscr fpeeeeggcelrvkfsrsadapaykqgqnqlynelnlgrreeydvldkrr grdpemggkprrknpqeglynelqkdkmaeayseigmkgerrrgkghdgl yqglstatkdtydalhmqalppr.

In one embodiment, the agent comprises a nucleic acid sequence encoding the PD1 CAR, e.g., the PD1 CAR described herein. In one embodiment, the nucleic acid sequence for the PD1 CAR is shown below, with the PD1 ECD underlined below in SEQ ID NO: 120

(SEQ ID NO: 120)
atggccctccctgtcactgccctgcttctcccctcgcactcctgctcca cgccgctagaccacccggatggtttctggactctccggatcgcccgtgga atccccaaccttctcaccggcactcttggttgtgactgagggcgataat gcgaccttcacgtgctcgttctccaacacctccgaatcattcgtgctgaa ctggtaccgcatgagcccgtcaaaccagaccgacaagctcgccgcgtttc cggaagatcggtcgcaaccgggacaggattgtcggttccgcgtgactcaa ctgccgaatggcagagacttccacatgagcgtggtccgcgctaggcgaaa cgactccgggacctacctgtgcggagccatctcgctggcgcctaaggccc aaatcaaagagagcttgagggccgaactgagagtgaccgagcgcagagct gaggtgccaactgcacatccatccccatcgcctcggcctgcggggcagtt tcagaccctggtcacgaccactccggcgccgcgccaccgactccggccc caactatcgcgagccagcccctgtcgctgaggccggaagcatgccgccct gccgccggaggtgctgtgcatacccggggattggacttcgcatgcgacat ctacatttgggctcctctcgccggaacttgtggcgtgctccttctgtccc tggtcatcaccctgtactgcaagcggggtcggaaaaagcttctgtacatt ttcaagcagcccttcatgaggcccgtgcaaaccacccaggaggaggacgg ttgctcctgccggttccccgaagaggaagaaggaggttgcgagctgcgcg tgaagttctcccggagcgccgacgccccgcctataagcagggccagaac cagctgtacaacgaactgaacctgggacggcgggaagagtacgatgtgct ggacaagcggcgcggccggcgggacccgaaatgggcgggaagcctagaagaa

```
-continued
agaaccctcaggaaggcctgtataacgagctgcagaaggacaagatggcc gaggcctactccgaaattgggatgaagggagagcggcggaggggaaaggg gcacgacggcctgtaccaaggactgtccaccgccaccaaggacacatacg atgccctgcacatgcaggcccttcccctcgc.
```

In another aspect, the present invention provides a population of CAR-expressing cells, e.g., CART cells. In some embodiments, the population of CAR-expressing cells comprises a mixture of cells expressing different CARs. For example, in one embodiment, the population of CAR-expressing cells can include a first cell expressing a CAR having an anti-CD19 binding domain described herein, and a second cell expressing a CAR having a different anti-CD19 binding domain, e.g., an anti-CD19 binding domain described herein that differs from the anti-CD19 binding domain in the CAR expressed by the first cell. As another example, the population of CAR-expressing cells can include a first cell expressing a CAR that includes an anti-CD19 binding domain, e.g., as described herein, and a second cell expressing a CAR that includes an antigen binding domain to a target other than CD19 (e.g., CD123). In one embodiment, the population of CAR-expressing cells includes, e.g., a first cell expressing a CAR that includes a primary intracellular signaling domain, and a second cell expressing a CAR that includes a secondary signaling domain.

In another aspect, the present invention provides a population of cells wherein at least one cell in the population expresses a CAR having an anti-CD19 binding domain described herein, and a second cell expressing another agent, e.g., an agent which enhances the activity of a CAR-expressing cell. For example, in one embodiment, the agent can be an agent which inhibits an inhibitory molecule. Inhibitory molecules, e.g., can, in some embodiments, decrease the ability of a CAR-expressing cell to mount an immune effector response. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 or TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 or TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

Regulatable Chimeric Antigen Receptors

In some embodiments, a regulatable CAR (RCAR) where the CAR activity can be controlled is desirable to optimize the safety and efficacy of a CAR therapy. There are many ways CAR activities can be regulated. For example, inducible apoptosis using, e.g., a caspase fused to a dimerization domain (see, e.g., Di Stasa et al., N Engl. J. Med. 2011 Nov. 3; 365(18):1673-1683), can be used as a safety switch in the CAR therapy of the instant invention. In one embodiment, the cells (e.g., T cells or NK cells) expressing a CAR of the present invention further comprise an inducible apoptosis switch, wherein a human caspase (e.g., caspase 9) or a modified version is fused to a modification of the human FKB protein that allows conditional dimerization. In the presence of a small molecule, such as a rapalog (e.g., AP 1903, AP20187), the inducible caspase (e.g., caspase 9) is activated and leads to the rapid apoptosis and death of the cells (e.g., T cells or NK cells) expressing a CAR of the present invention. Examples of a caspase-based inducible apoptosis switch (or one or more aspects of such a switch) have been described in, e.g., US2004040047; US20110286980; US20140255360; WO1997031899; WO2014151960; WO2014164348; WO2014197638; WO2014197638; all of which are incorporated by reference herein.

In an aspect, a RCAR comprises a set of polypeptides, typically two in the simplest embodiments, in which the components of a standard CAR described herein, e.g., an antigen binding domain and an intracellular signaling domain, are partitioned on separate polypeptides or members. In some embodiments, the set of polypeptides include a dimerization switch that, upon the presence of a dimerization molecule, can couple the polypeptides to one another, e.g., can couple an antigen binding domain to an intracellular signaling domain. In one embodiment, the CARs of the present invention utilizes a dimerization switch as those described in, e.g., WO2014127261, which is incorporated by reference herein.

In an aspect, an RCAR comprises two polypeptides or members: 1) an intracellular signaling member comprising an intracellular signaling domain, e.g., a primary intracellular signaling domain described herein, and a first switch domain; 2) an antigen binding member comprising an antigen binding domain, e.g., that targets CD19, as described herein and a second switch domain. Optionally, the RCAR comprises a transmembrane domain described herein. In an embodiment, a transmembrane domain can be disposed on the intracellular signaling member, on the antigen binding member, or on both. (Unless otherwise indicated, when members or elements of an RCAR are described herein, the order can be as provided, but other orders are included as well. In other words, in an embodiment, the order is as set out in the text, but in other embodiments, the order can be different. E.g., the order of elements on one side of a transmembrane region can be different from the example, e.g., the placement of a switch domain relative to a intracellular signaling domain can be different, e.g., reversed).

In an embodiment, the first and second switch domains can form an intracellular or an extracellular dimerization switch. In an embodiment, the dimerization switch can be a homodimerization switch, e.g., where the first and second switch domain are the same, or a heterodimerization switch, e.g., where the first and second switch domain are different from one another.

In embodiments, an RCAR can comprise a "multi switch." A multi switch can comprise heterodimerization switch domains or homodimerization switch domains. A multi switch comprises a plurality of, e.g., 2, 3, 4, 5, 6, 7, 8, 9, or 10, switch domains, independently, on a first member, e.g., an antigen binding member, and a second member, e.g., an intracellular signaling member. In an embodiment, the first member can comprise a plurality of first switch domains, e.g., FKBP-based switch domains, and the second member can comprise a plurality of second switch domains, e.g., FRB-based switch domains. In an embodiment, the first member can comprise a first and a second switch domain, e.g., a FKBP-based switch domain and a FRB-based switch domain, and the second member can comprise a first and a second switch domain, e.g., a FKBP-based switch domain and a FRB-based switch domain.

In an embodiment, the intracellular signaling member comprises one or more intracellular signaling domains, e.g., a primary intracellular signaling domain and one or more costimulatory signaling domains.

In an embodiment, the antigen binding member may comprise one or more intracellular signaling domains, e.g., one or more costimulatory signaling domains. In an embodiment, the antigen binding member comprises a plurality, e.g., 2 or 3 costimulatory signaling domains described herein, e.g., selected from 41BB, CD28, CD27, ICOS, and OX40, and in embodiments, no primary intracellular signaling domain. In an embodiment, the antigen binding member comprises the following costimulatory signaling domains, from the extracellular to intracellular direction: 41BB-CD27; 41BB-CD27; CD27-41BB; 41BB-CD28; CD28-41BB; OX40-CD28; CD28-OX40; CD28-41BB; or 41BB-CD28. In such embodiments, the intracellular binding member comprises a CD3zeta domain. In one such embodiment the RCAR comprises (1) an antigen binding member comprising, an antigen binding domain, a transmembrane domain, and two costimulatory domains and a first switch domain; and (2) an intracellular signaling domain comprising a transmembrane domain or membrane tethering domain and at least one primary intracellular signaling domain, and a second switch domain.

An embodiment provides RCARs wherein the antigen binding member is not tethered to the surface of the CAR cell. This allows a cell having an intracellular signaling member to be conveniently paired with one or more antigen binding domains, without transforming the cell with a sequence that encodes the antigen binding member. In such embodiments, the RCAR comprises: 1) an intracellular signaling member comprising: a first switch domain, a transmembrane domain, an intracellular signaling domain, e.g., a primary intracellular signaling domain, and a first switch domain; and 2) an antigen binding member comprising: an antigen binding domain, and a second switch domain, wherein the antigen binding member does not comprise a transmembrane domain or membrane tethering domain, and, optionally, does not comprise an intracellular signaling domain. In some embodiments, the RCAR may further comprise 3) a second antigen binding member comprising: a second antigen binding domain, e.g., a second antigen binding domain that binds a different antigen than is bound by the antigen binding domain; and a second switch domain.

Also provided herein are RCARs wherein the antigen binding member comprises bispecific activation and targeting capacity. In this embodiment, the antigen binding member can comprise a plurality, e.g., 2, 3, 4, or 5 antigen binding domains, e.g., scFvs, wherein each antigen binding domain binds to a target antigen, e.g. different antigens or the same antigen, e.g., the same or different epitopes on the same antigen. In an embodiment, the plurality of antigen binding domains are in tandem, and optionally, a linker or hinge region is disposed between each of the antigen binding domains. Suitable linkers and hinge regions are described herein.

An embodiment provides RCARs having a configuration that allows switching of proliferation. In this embodiment, the RCAR comprises: 1) an intracellular signaling member comprising: optionally, a transmembrane domain or membrane tethering domain; one or more co-stimulatory signaling domain, e.g., selected from 41BB, CD28, CD27, ICOS, and OX40, and a switch domain; and 2) an antigen binding member comprising: an antigen binding domain, a transmembrane domain, and a primary intracellular signaling domain, e.g., a CD3zeta domain, wherein the antigen binding member does not comprise a switch domain, or does not comprise a switch domain that dimerizes with a switch domain on the intracellular signaling member. In an embodiment, the antigen binding member does not comprise a co-stimulatory signaling domain. In an embodiment, the intracellular signaling member comprises a switch domain from a homodimerization switch. In an embodiment, the intracellular signaling member comprises a first switch domain of a heterodimerization switch and the RCAR comprises a second intracellular signaling member which comprises a second switch domain of the heterodimerization switch. In such embodiments, the second intracellular signaling member comprises the same intracellular signaling domains as the intracellular signaling member. In an embodiment, the dimerization switch is intracellular. In an embodiment, the dimerization switch is extracellular.

In any of the RCAR configurations described here, the first and second switch domains comprise a FKBP-FRB based switch as described herein.

Also provided herein are cells comprising an RCAR described herein. Any cell that is engineered to express a RCAR can be used as a RCARX cell. In an embodiment the RCARX cell is a T cell, and is referred to as a RCART cell. In an embodiment the RCARX cell is an NK cell, and is referred to as a RCARN cell.

Also provided herein are nucleic acids and vectors comprising RCAR encoding sequences. Sequence encoding various elements of an RCAR can be disposed on the same nucleic acid molecule, e.g., the same plasmid or vector, e.g., viral vector, e.g., lentiviral vector. In an embodiment, (i) sequence encoding an antigen binding member and (ii) sequence encoding an intracellular signaling member, can be present on the same nucleic acid, e.g., vector. Production of the corresponding proteins can be achieved, e.g., by the use of separate promoters, or by the use of a bicistronic transcription product (which can result in the production of two proteins by cleavage of a single translation product or by the translation of two separate protein products). In an embodiment, a sequence encoding a cleavable peptide, e.g., a P2A or F2A sequence, is disposed between (i) and (ii). In an embodiment, a sequence encoding an IRES, e.g., an EMCV or EV71 IRES, is disposed between (i) and (ii). In these embodiments, (i) and (ii) are transcribed as a single RNA. In an embodiment, a first promoter is operably linked to (i) and a second promoter is operably linked to (ii), such that (i) and (ii) are transcribed as separate mRNAs.

Alternatively, the sequence encoding various elements of an RCAR can be disposed on the different nucleic acid molecules, e.g., different plasmids or vectors, e.g., viral vector, e.g., lentiviral vector. E.g., the (i) sequence encoding an antigen binding member can be present on a first nucleic acid, e.g., a first vector, and the (ii) sequence encoding an intracellular signaling member can be present on the second nucleic acid, e.g., the second vector.

Dimerization Switches

Dimerization switches can be non-covalent or covalent. In a non-covalent dimerization switch, the dimerization molecule promotes a non-covalent interaction between the switch domains. In a covalent dimerization switch, the dimerization molecule promotes a covalent interaction between the switch domains.

In an embodiment, the RCAR comprises a FKBP/FRAP, or FKBP/FRB-based dimerization switch. FKBP12 (FKBP, or FK506 binding protein) is an abundant cytoplasmic protein that serves as the initial intracellular target for the natural product immunosuppressive drug, rapamycin. Rapamycin binds to FKBP and to the large PI3K homolog FRAP (RAFT, mTOR). FRB is a 93 amino acid portion of FRAP, that is sufficient for binding the FKBP-rapamycin complex (Chen, J., Zheng, X. F., Brown, E. J. & Schreiber, S. L. (1995) *Identification of an 11-kDa FKBP12-rapamycin-binding domain within the 289-kDa FKBP12-rapamycin-associated protein and characterization of a critical serine residue.* Proc Natl Acad Sci USA 92: 4947-51.)

In embodiments, an FKBP/FRAP, e.g., an FKBP/FRB, based switch can use a dimerization molecule, e.g., rapamycin or a rapamycin analog.

The amino acid sequence of FKBP is as follows:

```
                                          (SEQ ID NO: 122)
D V P D Y A S L G G P S S P K K K R K V S R G V Q

V E T I S P G D G R T F P K R G Q T C V V H Y T G

M L E D G K K F D S S R D R N K P F K F M L G K Q

E V I R G W E E G V A Q M S V G Q R A K L T I S P

D Y A Y G A T G H P G I I P P H A T L V F D V E L

L K L E T S Y
```

In embodiments, an FKBP switch domain can comprise a fragment of FKBP having the ability to bind with FRB, or a fragment or analog thereof, in the presence of rapamycin or a rapalog, e.g., the underlined portion of SEQ ID NO: 122, which is:

```
                                          (SEQ ID NO: 123)
V Q V E T I S P G D G R T F P K R G Q T C V V H Y

T G M L E D G K K F D S S R D R N K P F K F M L G

K Q E V I R G W E E G V A Q M S V G Q R A K L T I

S P D Y A Y G A T G H P G I I P P H A T L V F D V

E L L K L E T S
```

The amino acid sequence of FRB is as follows:

```
                                          (SEQ ID NO: 124)
ILWHEMWHEG LEEASRLYFG ERNVKGMFEV LEPLHAMMER

GPQTLKETSF NQAYGRDLME AQEWCRKYMK SGNVKDLTQA

WDLYYHVFRR ISK
```

"FKBP/FRAP, e.g., an FKBP/FRB, based switch" as that term is used herein, refers to a dimerization switch comprising: a first switch domain, which comprises an FKBP fragment or analog thereof having the ability to bind with FRB, or a fragment or analog thereof, in the presence of rapamycin or a rapalog, e.g., RAD001, and has at least 70, 75, 80, 85, 90, 95, 96, 97, 98, or 99% identity with, or differs by no more than 30, 25, 20, 15, 10, 5, 4, 3, 2, or 1 amino acid residues from, the FKBP sequence of SEQ ID NO: 122 or 123; and a second switch domain, which comprises an FRB fragment or analog thereof having the ability to bind with FRB, or a fragment or analog thereof, in the presence of rapamycin or a rapalog, and has at least 70, 75, 80, 85, 90, 95, 96, 97, 98, or 99% identity with, or differs by no more than 30, 25, 20, 15, 10, 5, 4, 3, 2, or 1 amino acid residues from, the FRB sequence of SEQ ID NO: 124. In an embodiment, a RCAR described herein comprises one switch domain comprises amino acid residues disclosed in SEQ ID NO: 122 (or SEQ ID NO: 123), and one switch domain comprises amino acid residues disclosed in SEQ ID NO: 124.

In embodiments, the FKBP/FRB dimerization switch comprises a modified FRB switch domain that exhibits altered, e.g., enhanced, complex formation between an FRB-based switch domain, e.g., the modified FRB switch domain, a FKBP-based switch domain, and the dimerization molecule, e.g., rapamycin or a rapalogue, e.g., RAD001. In an embodiment, the modified FRB switch domain comprises one or more mutations, e.g., 2, 3, 4, 5, 6, 7, 8, 9, 10 or more, selected from mutations at amino acid position(s) L2031, E2032, 52035, R2036, F2039, G2040, T2098, W2101, D2102, Y2105, and F2108, where the wild-type amino acid is mutated to any other naturally-occurring amino acid. In an embodiment, a mutant FRB comprises a mutation at E2032, where E2032 is mutated to phenylalanine (E2032F), methionine (E2032M), arginine (E2032R), valine (E2032V), tyrosine (E2032Y), isoleucine (E20321), e.g., SEQ ID NO: 125, or leucine (E2032L), e.g., SEQ ID NO: 126. In an embodiment, a mutant FRB comprises a mutation at T2098, where T2098 is mutated to phenylalanine (T2098F) or leucine (T2098L), e.g., SEQ ID NO: 127. In an embodiment, a mutant FRB comprises a mutation at E2032 and at T2098, where E2032 is mutated to any amino acid, and where T2098 is mutated to any amino acid, e.g., SEQ ID NO: 128. In an embodiment, a mutant FRB comprises an E20321 and a T2098L mutation, e.g., SEQ ID NO: 129. In an embodiment, a mutant FRB comprises an E2032L and a T2098L mutation, e.g., SEQ ID NO: 130.

TABLE 13

Exemplary mutant FRB having increased affinity for a dimerization molecule.

| FRB mutant | Amino Acid Sequence | SEQ ID NO: |
|---|---|---|
| E2032I mutant | ILWHEMWHEGLIEASRLYFGERNVKGMFEVLEPLHAMMERGPQTLKETSFNQAYGRDLMEAQEWCRKYMKSGNVKDLTQAWDLYYHVFRRISKTS | 125 |

TABLE 13-continued

Exemplary mutant FRB having increased affinity for a dimerization molecule.

| FRB mutant | Amino Acid Sequence | SEQ ID NO: |
|---|---|---|
| E2032L mutant | ILWHEMWHEGLLEASRLYFGERNVKGMFEVLEPLHAMMERGPQTLKETSFNQAYGR DLMEAQEWCRKYMKSGNVKDLTQAWDLYYHVFRRISKTS | 126 |
| T2098L mutant | ILWHEMWHEGLEEASRLYFGERNVKGMFEVLEPLHAMMERGPQTLKETSFNQAYGR DLMEAQEWCRKYMKSGNVKDLLQAWDLYYHVFRRISKTS | 127 |
| E2032, T2098 mutant | ILWHEMWHEGLXEASRLYFGERNVKGMFEVLEPLHAMMERGPQTLKETSFNQAYGR DLMEAQEWCRKYMKSGNVKDLXQAWDLYYHVFRRISKTS | 128 |
| E2032I, T2098L mutant | ILWHEMWHEGLIEASRLYFGERNVKGMFEVLEPLHAMMERGPQTLKETSFNQAYGR DLMEAQEWCRKYMKSGNVKDLLQAWDLYYHVFRRISKTS | 129 |
| E2032L, T2098L mutant | ILWHEMWHEGLLEASRLYFGERNVKGMFEVLEPLHAMMERGPQTLKETSFNQAYGR DLMEAQEWCRKYMKSGNVKDLLQAWDLYYHVFRRISKTS | 130 |

Other suitable dimerization switches include a GyrB-GyrB based dimerization switch, a Gibberellin-based dimerization switch, a tag/binder dimerization switch, and a halo-tag/snap-tag dimerization switch. Following the guidance provided herein, such switches and relevant dimerization molecules will be apparent to one of ordinary skill.

Dimerization Molecule

Association between the switch domains is promoted by the dimerization molecule. In the presence of dimerization molecule interaction or association between switch domains allows for signal transduction between a polypeptide associated with, e.g., fused to, a first switch domain, and a polypeptide associated with, e.g., fused to, a second switch domain. In the presence of non-limiting levels of dimerization molecule signal transduction is increased by 1.1, 1.2, 1.3, 1.4, 1.5, 1.6, 1.7, 1.8, 1.9, 2, 5, 10, 50, 100 fold, e.g., as measured in a system described herein.

Rapamycin and rapamycin analogs (sometimes referred to as rapalogues), e.g., RAD001, can be used as dimerization molecules in a FKBP/FRB-based dimerization switch described herein. In an embodiment the dimerization molecule can be selected from rapamycin (sirolimus), RAD001 (everolimus), zotarolimus, temsirolimus, AP-23573 (ridaforolimus), biolimus and AP21967. Additional rapamycin analogs suitable for use with FKBP/FRB-based dimerization switches are further described in the section entitled "Combination Therapies", or in the subsection entitled "Exemplary mTOR inhibitors".

Split CAR

In some embodiments, the CAR-expressing cell uses a split CAR. The split CAR approach is described in more detail in publications WO2014/055442 and WO2014/055657. Briefly, a split CAR system comprises a cell expressing a first CAR having a first antigen binding domain and a costimulatory domain (e.g., 41BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens.

RNA Transfection

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO:118). RNA so produced can efficiently transfect different kinds of cells. In one aspect, the template includes sequences for the CAR.

In one aspect the anti-CD19 CAR is encoded by a messenger RNA (mRNA). In one aspect, the mRNA encoding the anti-CD19 CAR is introduced into an immune effector cell, e.g., a T cell or a NK cell, for production of a CAR-expressing cell, e.g., a CART cell or a CAR NK cell.

In one embodiment, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR of the present invention. For example, the template for the RNA CAR comprises an extracellular region comprising a single chain variable domain of an anti-tumor antibody; a hinge region, a transmembrane domain (e.g., a transmembrane domain of CD8a); and a cytoplasmic region that includes an intracellular signaling domain, e.g., comprising the signaling domain of CD3-zeta and the signaling domain of 4-1BB.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (SEQ ID NO: 110) (size can be 50-5000 T (SEQ ID NO: 111)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines (SEQ ID NO: 112).

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides (SEQ ID NO: 113) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Non-Viral Delivery Methods

In some aspects, non-viral methods can be used to deliver a nucleic acid encoding a CAR described herein into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

Exemplary methods of nucleic acid delivery using a transposon include a Sleeping Beauty transposon system (SBTS) and a piggyBac (PB) transposon system. See, e.g., Aronovich et al. Hum. Mol. Genet. 20.R1 (2011):R14-20; Singh et al. Cancer Res. 15 (2008):2961-2971; Huang et al. Mol. Ther. 16 (2008):580-589; Grabundzija et al. Mol. Ther. 18 (2010):1200-1209; Kebriaei et al. Blood. 122.21 (2013): 166; Williams. Molecular Therapy 16.9 (2008):1515-16; Bell et al. Nat. Protoc. 2.12 (2007):3153-65; and Ding et al. Cell. 122.3 (2005):473-83, all of which are incorporated herein by reference.

The SBTS includes two components: 1) a transposon containing a transgene and 2) a source of transposase enzyme. The transposase can transpose the transposon from a carrier plasmid (or other donor DNA) to a target DNA, such as a host cell chromosome/genome. For example, the transposase binds to the carrier plasmid/donor DNA, cuts the transposon (including transgene(s)) out of the plasmid, and inserts it into the genome of the host cell. See, e.g., Aronovich et al. supra.

Exemplary transposons include a pT2-based transposon. See, e.g., Grabundzija et al. Nucleic Acids Res. 41.3 (2013): 1829-47; and Singh et al. Cancer Res. 68.8 (2008): 2961-2971, all of which are incorporated herein by reference. Exemplary transposases include a Tc1/mariner-type transposase, e.g., the SB10 transposase or the SB11 transposase (a hyperactive transposase which can be expressed, e.g., from a cytomegalovirus promoter). See, e.g., Aronovich et al.; Kebriaei et al.; and Grabundzija et al., all of which are incorporated herein by reference.

Use of the SBTS permits efficient integration and expression of a transgene, e.g., a nucleic acid encoding a CAR described herein. Provided herein are methods of generating a cell, e.g., T cell or NK cell, that stably expresses a CAR described herein, e.g., using a transposon system such as SBTS.

In accordance with methods described herein, in some embodiments, one or more nucleic acids, e.g., plasmids, containing the SBTS components are delivered to a cell (e.g., T or NK cell). For example, the nucleic acid(s) are delivered by standard methods of nucleic acid (e.g., plasmid DNA) delivery, e.g., methods described herein, e.g., electroporation, transfection, or lipofection. In some embodiments, the nucleic acid contains a transposon comprising a transgene, e.g., a nucleic acid encoding a CAR described herein. In some embodiments, the nucleic acid contains a transposon comprising a transgene (e.g., a nucleic acid encoding a CAR described herein) as well as a nucleic acid sequence encoding a transposase enzyme. In other embodiments, a system with two nucleic acids is provided, e.g., a dual-plasmid system, e.g., where a first plasmid contains a transposon comprising a transgene, and a second plasmid contains a nucleic acid sequence encoding a transposase enzyme. For example, the first and the second nucleic acids are co-delivered into a host cell.

In some embodiments, cells, e.g., T or NK cells, are generated that express a CAR described herein by using a combination of gene insertion using the SBTS and genetic editing using a nuclease (e.g., Zinc finger nucleases (ZFNs), Transcription Activator-Like Effector Nucleases (TALENs), the CRISPR/Cas system, or engineered meganuclease re-engineered homing endonucleases).

In some embodiments, use of a non-viral method of delivery permits reprogramming of cells, e.g., T or NK cells, and direct infusion of the cells into a subject. Advantages of non-viral vectors include but are not limited to the ease and relatively low cost of producing sufficient amounts required to meet a patient population, stability during storage, and lack of immunogenicity.

Nucleic Acid Constructs Encoding a CAR

The present invention also provides nucleic acid molecules encoding one or more CAR constructs described herein. In one aspect, the nucleic acid molecule is provided as a messenger RNA transcript. In one aspect, the nucleic acid molecule is provided as a DNA construct.

Accordingly, in one aspect, the invention pertains to an isolated nucleic acid molecule encoding a chimeric antigen receptor (CAR), wherein the CAR comprises a anti-CD19 binding domain (e.g., a humanized anti-CD19 binding domain), a transmembrane domain, and an intracellular signaling domain comprising a stimulatory domain, e.g., a costimulatory signaling domain and/or a primary signaling domain, e.g., zeta chain. In one embodiment, the anti-CD19 binding domain is an anti-CD19 binding domain described herein, e.g., an anti-CD19 binding domain which comprises a sequence selected from a group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:59, or a sequence with 95-99% identify thereof. In one embodiment, the transmembrane domain is transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO: 15, or a sequence with 95-99% identity thereof. In one embodiment, the anti-CD19 binding domain is connected to the transmembrane domain by a hinge region, e.g., a hinge described herein. In one embodiment, the hinge region comprises SEQ ID NO:14 or SEQ ID NO:45 or SEQ ID NO:47 or SEQ ID NO:49, or a sequence with 95-99% identity thereof. In one embodiment, the isolated nucleic acid molecule further comprises a sequence encoding a costimulatory domain. In one embodiment, the costimulatory domain is a functional signaling domain of a protein selected from the group consisting of OX40, CD27, CD28, CDS, ICAM-1, LFA-1 (CD11a/CD18), ICOS (CD278), and 4-1BB (CD137). In one embodiment, the costimulatory domain comprises a sequence of SEQ ID NO:16, or a sequence with 95-99% identity thereof. In one embodiment, the intracellular signaling domain comprises a functional signaling domain of 4-1BB and a functional signaling domain of CD3 zeta. In one embodiment, the intracellular signaling domain comprises the sequence of SEQ ID NO: 16 or SEQ ID NO:51, or a sequence with 95-99% identity thereof, and the sequence of SEQ ID NO: 17 or SEQ ID NO:43, or a sequence with 95-99% identity thereof, wherein the sequences comprising the intracellular signaling domain are expressed in the same frame and as a single polypeptide chain.

In another aspect, the invention pertains to an isolated nucleic acid molecule encoding a CAR construct comprising a leader sequence of SEQ ID NO: 13, a scFv domain having a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:59, (or a sequence with 95-99% identify thereof), a hinge region of SEQ ID NO:14 or SEQ ID NO:45 or SEQ ID NO:47 or SEQ ID NO:49 (or a sequence with 95-99% identity thereof), a transmembrane domain having a sequence of SEQ ID NO: 15 (or a sequence with 95-99% identity thereof), a 4-1BB costimulatory domain having a sequence of SEQ ID NO:16 or a CD27 costimulatory domain having a sequence of SEQ ID NO:51 (or a sequence with 95-99% identity thereof), and a CD3 zeta stimulatory domain having a sequence of SEQ ID NO:17 or SEQ ID NO:43 (or a sequence with 95-99% identity thereof).

In another aspect, the invention pertains to an isolated polypeptide molecule encoded by the nucleic acid molecule. In one embodiment, the isolated polypeptide molecule comprises a sequence selected from the group consisting of SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:59 or a sequence with 95-99% identify thereof.

In another aspect, the invention pertains to a nucleic acid molecule encoding a chimeric antigen receptor (CAR) molecule that comprises an anti-CD19 binding domain, a transmembrane domain, and an intracellular signaling domain comprising a stimulatory domain, and wherein said anti-CD19 binding domain comprises a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:59, or a sequence with 95-99% identify thereof.

In one embodiment, the encoded CAR molecule further comprises a sequence encoding a costimulatory domain. In one embodiment, the costimulatory domain is a functional signaling domain of a protein selected from the group consisting of OX40, CD27, CD28, CDS, ICAM-1, LFA-1 (CD11a/CD18) and 4-1BB (CD137). In one embodiment, the costimulatory domain comprises a sequence of SEQ ID NO:16. In one embodiment, the transmembrane domain is a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO:15. In one embodiment, the intracellular signaling domain comprises a functional signaling domain of 4-1BB and a functional signaling domain of zeta. In one embodiment, the intracellular signaling domain comprises the sequence of SEQ ID NO: 16 and the sequence of SEQ ID NO: 17, wherein the sequences comprising the intracellular signaling domain are expressed in the same frame and as a single polypeptide chain. In one embodiment, the anti-CD19 binding domain is connected to the transmembrane domain by a hinge region. In one embodiment, the hinge region comprises SEQ ID NO:14. In one embodiment, the hinge region comprises SEQ ID NO:45 or SEQ ID NO:47 or SEQ ID NO:49.

In another aspect, the invention pertains to an encoded CAR molecule comprising a leader sequence of SEQ ID NO: 13, a scFv domain having a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:59, or a sequence with 95-99% identify thereof, a hinge region of SEQ ID NO:14 or SEQ ID NO:45 or SEQ ID NO:47 or SEQ ID NO:49, a transmembrane domain having a sequence of SEQ ID NO: 15, a 4-1BB costimulatory domain having a sequence of SEQ ID NO:16 or a CD27 costimulatory domain having a sequence of SEQ ID NO:51, and a CD3 zeta stimulatory domain having a sequence of SEQ ID NO:17 or SEQ ID NO:43. In one embodiment, the encoded CAR molecule comprises a sequence selected from a group consisting of SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, and SEQ ID NO:59, or a sequence with 95-99% identify thereof.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, e.g., a gammaretroviral vector. A gammaretroviral vector may include, e.g., a promoter, a packaging signal (w), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, crisper, CAS9, and zinc finger nucleases. See below June et al. 2009 *Nature Reviews Immunology* 9.10: 704-716, is incorporated herein by reference.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription. Exemplary promoters include the CMV IE gene, EF-1a, ubiquitin C, or phosphoglycerokinase (PGK) promoters.

An example of a promoter that is capable of expressing a CAR transgene in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009). In one aspect, the EF1a promoter comprises the sequence provided as SEQ ID NO:100.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1α promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection (e.g., ampicillin resistance gene and/or zeocin marker).

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A preferred method for the introduction of a polynucleotide into a host cell is calcium phosphate transfection Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots)

or by assays described herein to identify agents falling within the scope of the invention.

The present invention further provides a vector comprising a CAR encoding nucleic acid molecule. In one aspect, a CAR vector can be directly transduced into a cell, e.g., a T cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian T cells. In one aspect, the mammalian T cell is a human T cell.

Sources of Cells

Prior to expansion and genetic modification or other modification, a source of cells, e.g., T cells or natural killer (NK) cells, can be obtained from a subject. The term "subject" is intended to include living organisms in which an immune response can be elicited (e.g., mammals). Examples of subjects include humans, monkeys, chimpanzees, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In certain aspects of the present disclosure, immune effector cells, e.g., T cells, can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations.

Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In one aspect, T cells are isolated from peripheral blood lymphocytes by lysing the red blood cells and depleting the monocytes, for example, by centrifugation through a PERCOLL™ gradient or by counterflow centrifugal elutriation.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-CD25 antibody, or fragment thereof, or a CD25-binding ligand, IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Miltenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL. In one embodiment, e.g., for T regulatory cells, e.g., CD25+ depletion, greater than 500 million cells/ml is used. In a further aspect, a concentration of cells of 600, 700, 800, or 900 million cells/ml is used.

In one embodiment, the population of immune effector cells to be depleted includes about $6 \times 10^9$ CD25+ T cells. In other aspects, the population of immune effector cells to be depleted include about $1 \times 10^9$ to $1 \times 10^{10}$ CD25+ T cell, and any integer value in between. In one embodiment, the resulting population T regulatory depleted cells has $2 \times 10^9$ T regulatory cells, e.g., CD25+ cells, or less (e.g., $1 \times 10^9$, $5 \times 10^8$, $1 \times 10^8$, $5 \times 10^7$, $1 \times 10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a CAR-expressing cell product can reduce the risk of subject relapse. For example, methods of depleting $T_{REG}$ cells are known in the art. Methods of decreasing $T_{REG}$ cells include, but are not limited to, cyclophosphamide, anti-GITR antibody (an anti-GITR antibody described herein), CD25-depletion, and combinations thereof.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

In an embodiment, a subject is pre-treated with one or more therapies that reduce $T_{REG}$ cells prior to collection of cells for CAR-expressing cell product manufacturing, thereby reducing the risk of subject relapse to CAR-expressing cell treatment. In an embodiment, methods of decreasing $T_{REG}$ cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the CAR-expressing cell product.

In an embodiment, a subject is pre-treated with cyclophosphamide prior to collection of cells for CAR-expressing cell product manufacturing, thereby reducing the risk of subject relapse to CAR-expressing cell treatment. In an embodiment, a subject is pre-treated with an anti-GITR antibody prior to collection of cells for CAR-expressing cell product manufacturing, thereby reducing the risk of subject relapse to CAR-expressing cell treatment.

In one embodiment, the population of cells to be removed are neither the regulatory T cells or tumor cells, but cells that otherwise negatively affect the expansion and/or function of CART cells, e.g. cells expressing CD14, CD11b, CD33, CD15, or other markers expressed by potentially immune suppressive cells. In one embodiment, such cells are envisioned to be removed concurrently with regulatory T cells and/or tumor cells, or following said depletion, or in another order.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include B7-H1, B7-1, CD160, P1H, 2B4, PD1, TIM3, CEACAM (e.g., CEACAM-1, CEACAM-3 and/or CEACAM-5), LAG3, TIGIT, CTLA-4, BTLA and LAIR1. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

Methods described herein can include a positive selection step. For example, T cells can isolated by incubation with anti-CD3/anti-CD28 (e.g., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours, e.g., 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points.

In one embodiment, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 10 billion cells/ml, 9 billion/ml, 8 billion/ml, 7 billion/ml, 6 billion/ml, or 5 billion/ml is used. In one aspect, a concentration of 1 billion cells/ml is used. In yet one aspect, a concentration of cells from 75, 80, 85, 90, 95, or 100 million cells/ml is used. In further aspects, concentrations of 125 or 150 million cells/ml can be used.

Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is $5\times10^6$/ml. In other aspects, the concentration used can be from about $1 \times 10^5$/ml to $1 \times 10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in immune effector cell therapy for any number of diseases or conditions that would benefit from immune effector cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAM-PATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, the immune effector cells expressing a CAR molecule, e.g., a CAR molecule described herein, are obtained from a subject that has received a low, immune enhancing dose of an mTOR inhibitor. In an embodiment, the population of immune effector cells, e.g., T cells, to be engineered to express a CAR, are harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In other embodiments, population of immune effector cells, e.g., T cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In one embodiment, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

Allogeneic CAR

In embodiments described herein, the immune effector cell can be an allogeneic immune effector cell, e.g., T cell or NK cell. For example, the cell can be an allogeneic T cell, e.g., an allogeneic T cell lacking expression of a functional T cell receptor (TCR) and/or human leukocyte antigen (HLA), e.g., HLA class I and/or HLA class II.

A T cell lacking a functional TCR can be, e.g., engineered such that it does not express any functional TCR on its surface, engineered such that it does not express one or more subunits that comprise a functional TCR or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

A T cell described herein can be, e.g., engineered such that it does not express a functional HLA on its surface. For example, a T cell described herein, can be engineered such that cell surface expression HLA, e.g., HLA class 1 and/or HLA class II, is downregulated.

In some embodiments, the T cell can lack a functional TCR and a functional HLA, e.g., HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not express or expresses at low levels an inhibitory molecule, e.g. by any method described herein. For example, the cell can be a cell that does not express or expresses at low levels an inhibitory molecule, e.g., that can decrease the ability of a CAR-expressing cell to mount an immune effector response. Examples of inhibitory molecules include PD1, PD-L1, CTLA4, TIM3, CEACAM (e.g., CEACAM-1, CEACAM-3 and/or CEACAM-5), LAGS, VISTA, BTLA, TIGIT, LAIR1, CD160, 2B4 and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

siRNA and shRNA to Inhibit TCR or HLA

In some embodiments, TCR expression and/or HLA expression can be inhibited using siRNA or shRNA that targets a nucleic acid encoding a TCR and/or HLA in a T cell.

Expression of siRNA and shRNAs in T cells can be achieved using any conventional expression system, e.g., such as a lentiviral expression system.

Exemplary shRNAs that downregulate expression of components of the TCR are described, e.g., in US Publication No.: 2012/0321667. Exemplary siRNA and shRNA that downregulate expression of HLA class I and/or HLA class II genes are described, e.g., in U.S. publication No.: US 2007/0036773.

CRISPR to Inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene.

Naturally-occurring CRISPR/Cas systems are found in approximately 40% of sequenced eubacteria genomes and 90% of sequenced archaea. Grissa et al. (2007) *BMC Bioinformatics* 8: 172. This system is a type of prokaryotic immune system that confers resistance to foreign genetic elements such as plasmids and phages and provides a form of acquired immunity. Barrangou et al. (2007) *Science* 315: 1709-1712; Marragini et al. (2008) *Science* 322: 1843-1845.

The CRISPR/Cas system has been modified for use in gene editing (silencing, enhancing or changing specific genes) in eukaryotes such as mice or primates. Wiedenheft et al. (2012) *Nature* 482: 331-8. This is accomplished by introducing into the eukaryotic cell a plasmid containing a specifically designed CRISPR and one or more appropriate Cas.

The CRISPR sequence, sometimes called a CRISPR locus, comprises alternating repeats and spacers. In a naturally-occurring CRISPR, the spacers usually comprise sequences foreign to the bacterium such as a plasmid or phage sequence; in the TCR and/or HLA CRISPR/Cas system, the spacers are derived from the TCR or HLA gene sequence.

RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. (2010) *Science* 327: 167-170; Makarova et al. (2006) *Biology Direct* 1: 7. The spacers thus serve as templates for RNA molecules, analogously to siRNAs. Pennisi (2013) *Science* 341: 833-836.

As these naturally occur in many different types of bacteria, the exact arrangements of the CRISPR and structure, function and number of Cas genes and their product differ somewhat from species to species. Haft et al. (2005) *PLoS Comput. Biol.* 1: e60; Kunin et al. (2007) *Genome Biol.* 8: R61; Mojica et al. (2005) *J. Mol. Evol.* 60: 174-182; Bolotin et al. (2005) *Microbiol.* 151: 2551-2561; Pourcel et al. (2005) *Microbiol.* 151: 653-663; and Stern et al. (2010) *Trends. Genet.* 28: 335-340. For example, the Cse (Cas subtype, *E. coli*) proteins (e.g., CasA) form a functional complex, Cascade, that processes CRISPR RNA transcripts into spacer-repeat units that Cascade retains. Brouns et al. (2008) *Science* 321: 960-964. In other prokaryotes, Cas6 processes the CRISPR transcript. The CRISPR-based phage inactivation in *E. coli* requires Cascade and Cas3, but not Cas1 or Cas2. The Cmr (Cas RAMP module) proteins in *Pyrococcus furiosus* and other prokaryotes form a functional complex with small CRISPR RNAs that recognizes and cleaves complementary target RNAs. A simpler CRISPR system relies on the protein Cas9, which is a nuclease with two active cutting sites, one for each strand of the double helix. Combining Cas9 and modified CRISPR locus RNA can be used in a system for gene editing. Pennisi (2013) *Science* 341: 833-836.

The CRISPR/Cas system can thus be used to edit a TCR and/or HLA gene (adding or deleting a basepair), or introducing a premature stop which thus decreases expression of a TCR and/or HLA. The CRISPR/Cas system can alternatively be used like RNA interference, turning off TCR and/or HLA gene in a reversible fashion. In a mammalian cell, for example, the RNA can guide the Cas protein to a TCR and/or HLA promoter, sterically blocking RNA polymerases.

Artificial CRISPR/Cas systems can be generated which inhibit TCR and/or HLA, using technology known in the art, e.g., that described in U.S. Publication No. 20140068797, and Cong (2013) Science 339: 819-823. Other artificial CRISPR/Cas systems that are known in the art may also be generated which inhibit TCR and/or HLA, e.g., that described in Tsai (2014) Nature Biotechnol., 32:6 569-576, U.S. Pat. Nos. 8,871,445; 8,865,406; 8,795,965; 8,771,945; and 8,697,359.

TALEN to Inhibit TCR and/or HLA

"TALEN" or "TALEN to HLA and/or TCR" or "TALEN to inhibit HLA and/or TCR" refers to a transcription activator-like effector nuclease, an artificial nuclease which can be used to edit the HLA and/or TCR gene.

TALENs are produced artificially by fusing a TAL effector DNA binding domain to a DNA cleavage domain. Transcription activator-like effects (TALEs) can be engineered to bind any desired DNA sequence, including a portion of the HLA or TCR gene. By combining an engineered TALE with a DNA cleavage domain, a restriction enzyme can be produced which is specific to any desired DNA sequence, including a HLA or TCR sequence. These can then be introduced into a cell, wherein they can be used for genome editing. Boch (2011) Nature Biotech. 29: 135-6; and Boch et al. (2009) Science 326: 1509-12; Moscou et al. (2009) Science 326: 3501.

TALEs are proteins secreted by Xanthomonas bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence.

To produce a TALEN, a TALE protein is fused to a nuclease (N), which is a wild-type or mutated FokI endonuclease. Several mutations to FokI have been made for its use in TALENs; these, for example, improve cleavage specificity or activity. Cermak et al. (2011) Nucl. Acids Res. 39: e82; Miller et al. (2011) Nature Biotech. 29: 143-8; Hockemeyer et al. (2011) Nature Biotech. 29: 731-734; Wood et al. (2011) Science 333: 307; Doyon et al. (2010) Nature Methods 8: 74-79; Szczepek et al. (2007) Nature Biotech. 25: 786-793; and Guo et al. (2010) J. Mol. Biol. 200: 96.

The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) Nature Biotech. 29: 143-8.

A HLA or TCR TALEN can be used inside a cell to produce a double-stranded break (DSB). A mutation can be introduced at the break site if the repair mechanisms improperly repair the break via non-homologous end joining. For example, improper repair may introduce a frame shift mutation. Alternatively, foreign DNA can be introduced into the cell along with the TALEN; depending on the sequences of the foreign DNA and chromosomal sequence, this process can be used to correct a defect in the HLA or TCR gene or introduce such a defect into a wt HLA or TCR gene, thus decreasing expression of HLA or TCR.

TALENs specific to sequences in HLA or TCR can be constructed using any method known in the art, including various schemes using modular components. Zhang et al. (2011) Nature Biotech. 29: 149-53; Geibler et al. (2011) PLoS ONE 6: e19509.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene.

Like a TALEN, a ZFN comprises a FokI nuclease domain (or derivative thereof) fused to a DNA-binding domain. In the case of a ZFN, the DNA-binding domain comprises one or more zinc fingers. Carroll et al. (2011) Genetics Society of America 188: 773-782; and Kim et al. (1996) Proc. Natl. Acad. Sci. USA 93: 1156-1160.

A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells.

Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart. Bitinaite et al. (1998) Proc. Natl. Acad. Sci. USA 95: 10570-5.

Also like a TALEN, a ZFN can create a double-stranded break in the DNA, which can create a frame-shift mutation if improperly repaired, leading to a decrease in the expression and amount of HLA and/or TCR in a cell. ZFNs can also be used with homologous recombination to mutate in the HLA or TCR gene.

ZFNs specific to sequences in HLA AND/OR TCR can be constructed using any method known in the art. See, e.g., Provasi (2011) Nature Med. 18: 807-815; Torikai (2013) Blood 122: 1341-1349; Cathomen et al. (2008) Mol. Ther. 16: 1200-7; and Guo et al. (2010) J. Mol. Biol. 400: 96; U.S. Patent Publication 2011/0158957; and U.S. Patent Publication 2012/0060230.

Telomerase Expression

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in an embodiment, an immune effector cell, e.g., a T cell, ectopically expresses a telomerase subunit, e.g., the catalytic subunit of telomerase, e.g., TERT, e.g., hTERT. In some aspects, this disclosure provides a method of producing a CAR-expressing cell, comprising contacting a cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CAR.

In one aspect, the disclosure features a method of making a population of immune effector cells (e.g., T cells or NK cells). In an embodiment, the method comprises: providing a population of immune effector cells (e.g., T cells or NK cells), contacting the population of immune effector cells with a nucleic acid encoding a CAR; and contacting the population of immune effector cells with a nucleic acid encoding a telomerase subunit, e.g., hTERT, under conditions that allow for CAR and telomerase expression.

In an embodiment, the nucleic acid encoding the telomerase subunit is DNA. In an embodiment, the nucleic acid encoding the telomerase subunit comprises a promoter capable of driving expression of the telomerase subunit.

In an embodiment, hTERT has the amino acid sequence of GenBank Protein ID AAC51724.1 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795) as follows:

```
                                                (SEQ ID NO: 131)
MPRAPRCRAVRSLLRSHYREVLPLATFVRRLGPQGWRLVQRGDPAAFRAL

VAQCLVCVPWDARPPPAAPSFRQVSCLKELVARVLQRLCERGAKNVLAFG

FALLDGARGGPPEAFTTSVRSYLPNTVTDALRGSGAWGLLLRRVGDDVLV

HLLARCALFVLVAPSCAYQVCGPPLYQLGAATQARPPPHASGPRRRLGCE

RAWNHSVREAGVPLGLPAPGARRRGGSASRSLPLPKRPRRGAAPEPERTP

VGQGSWAHPGRTRGPSDRGFCVVSPARPAEEATSLEGALSGTRHSHPSVG

RQHHAGPPSTSRPPRPWDTPCPPVYAETKHFLYSSGDKEQLRPSFLLSSL

RPSLTGARRLVETIFLGSRPWMPGTPRRLPRLPQRYWQMRPLFLELLGNH

AQCPYGVLLKTHCPLRAAVTPAAGVCAREKPQGSVAAPEEEDTDPRRLVQ

LLRQHSSPWQVYGFVRACLRRLVPPGLWGSRHNERRFLRNTKKFISLGKH

AKLSLQELTWKMSVRGCAWLRRSPGVGCVPAAEHRLREEILAKFLHWLMS

-continued
VYVVELLRSFFYVTETTFQKNRLFFYRKSVWSKLQSIGIRQHLKRVQLRE

LSEAEVRQHREARPALLTSRLRFIPKPDGLRPIVNMDYVVGARTFRREKR

AERLTSRVKALFSVLNYERARRPGLLGASVLGLDDIHRAWRTFVLRVRAQ

DPPPELYFVKVDVTGAYDTIPQDRLTEVIASIIKPQNTYCVRRYAVVQKA

AHGHVRKAFKSHVSTLTDLQPYMRQFVAHLQETSPLRDAVVIEQSSSLNE

ASSGLFDVFLRFMCHHAVRIRGKSYVQCQGIPQGSILSTLLCSLCYGDME

NKLFAGIRRDGLLLRLVDDFLLVTPHLTHAKTFLRTLVRGVPEYGCVVNL

RKTVVNFPVEDEALGGTAFVQMPAHGLFPWCGLLLDTRTLEVQSDYSSYA

RTSIRASLTFNRGFKAGRNMRRKLFGVLRLKCHSLFLDLQVNSLQTVCTN

IYKILLLQAYRFHACVLQLPFHQQVWKNPTFFLRVISDTASLCYSILKAK

NAGMSLGAKGAAGPLPSEAVQWLCHQAFLLKLTRHRVTYVPLLGSLRTAQ

TQLSRKLPGTTLTALEAAANPALPSDFKTILD
```

In an embodiment, the hTERT has a sequence at least 80%, 85%, 90%, 95%, 96^, 97%, 98%, or 99% identical to the sequence of SEQ ID NO: 131. In an embodiment, the hTERT has a sequence of SEQ ID NO: 131. In an embodiment, the hTERT comprises a deletion (e.g., of no more than 5, 10, 15, 20, or 30 amino acids) at the N-terminus, the C-terminus, or both. In an embodiment, the hTERT comprises a transgenic amino acid sequence (e.g., of no more than 5, 10, 15, 20, or 30 amino acids) at the N-terminus, the C-terminus, or both.

In an embodiment, the hTERT is encoded by the nucleic acid sequence of GenBank Accession No. AF018167 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795):

```
                                                                  (SEQ ID NO: 132)
   1 caggcagcgt ggtcctgctg cgcacgtggg aagccctggc ccggccacc ccgcgatgc 61 cgcgcgctcc ccgctgccga gccgtgcgct ccctgctgcg cagccactac cgcgaggtgc 121 tgccgctggc cacgttcgtg cggcgcctgg gccccaggg ctggcggctg gtgcagcgcg 181 gggaccccggc ggctttccgc gcgctggtgg cccagtgcct ggtgtgcgtg ccctgggacg 241 cacgccgcc ccccgccgcc ccctccttcc gccaggtgtc ctgcctgaag gagctggtgg 301 cccgagtgct gcagaggctg tgcgagcgcg gcgcgaagaa cgtgctggcc ttcggcttcg 361 cgctgctgga cggggcccgc gggggccccc ccgaggcctt caccaccagc gtgcgcagct 421 acctgcccaa cacggtgacc gacgcactgc gggggagcgg ggcgtggggg ctgctgttgc 481 gccgcgtggg cgacgacgtg ctggttcacc tgctggcacg ctgcgcgctc tttgtgctgg 541 tggctcccag ctgcgcctac caggtgtgcg ggccgccgct gtaccagctc ggcgctgcca 601 ctcaggcccg gccccgcca cacgctagtg gaccccgaag gcgtctggga tgcgaacggg 661 cctggaacca tagcgtcagg gaggccgggg tcccctggg cctgccagcc ccgggtgcga 721 ggaggcgcgg gggcagtgcc agccgaagtc tgccgttgcc caagaggccc aggcgtggcg 781 ctgcccctga gccggagcgg acgcccgttg ggcagggtc ctgggcccac ccgggcagga 841 cgcgtggacc gagtgaccgt ggtttctgtg tggtgtcacc tgccagaccc gccgaagaag 901 ccacctcttt ggagggtgcg ctctctggca cgcgccactc ccacccatcc gtgggccgcc 961 agcaccacgc gggcccccca tccacatcgc ggccaccacg tcctgggac acgccttgtc 1021 ccccggtgta cgccgagacc aagcacttcc tctactcctc aggcgacaag gagcagctgc
```

-continued

```
1081 ggccctcctt cctactcagc tctctgaggc ccagcctgac tggcgctcgg aggctcgtgg 1141 agaccatctt tctgggttcc aggccctgga tgccagggac tccccgcagg ttgccccgcc 1201 tgccccagcg ctactggcaa atgcggcccc tgtttctgga gctgcttggg aaccacgcgc 1261 agtgcccta cggggtgctc ctcaagacgc actgcccgct gcgagctgcg gtcaccccag 1321 cagccggtgt ctgtgcccgg agaagcccc agggctctgt ggcggccccc gaggaggagg 1381 acacagaccc ccgtcgcctg gtgcagctgc tccgccagca cagcagcccc tggcaggtgt 1441 acggcttcgt gcgggcctgc ctgcgccggc tggtgccccc aggcctctgg ggctccaggc 1501 acaacgaacg ccgcttcctc aggaacacca agaagttcat ctccctgggg aagcatgcca 1561 agctctcgct gcaggagctg acgtggaaga tgagcgtgcg gggctgcgct tggctgcgca 1621 ggagcccagg ggttggctgt gttccggccg cagagcaccg tctgcgtgag gagatcctgg 1681 ccaagttcct gcactggctg atgagtgtgt acgtcgtcga gctgctcagg tctttctttt 1741 atgtcacgga gaccacgttt caaaagaaca ggctcttttt ctaccggaag agtgtctgga 1801 gcaagttgca aagcattgga atcagacagc acttgaagag ggtgcagctg cgggagctgt 1861 cggaagcaga ggtcaggcag catcgggaag ccaggcccgc cctgctgacg tccagactcc 1921 gcttcatccc caagcctgac gggctgcggc cgattgtgaa catggactac gtcgtgggag 1981 ccagaacgtt ccgcagagaa aagagggccg agcgtctcac ctcgagggtg aaggcactgt 2041 tcagcgtgct caactacgag cgggcgcggc gccccggcct cctgggcgcc tctgtgctgg 2101 gcctggacga tatccacagg gcctggcgca ccttcgtgct gcgtgtgcgg gcccaggacc 2161 cgccgcctga gctgtacttt gtcaaggtgg atgtgacggg cgcgtacgac accatccccc 2221 aggacaggct cacggaggtc atcgccagca tcatcaaacc ccagaacacg tactgcgtgc 2281 gtcggtatgc cgtggtccag aaggccgccc atgggcacgt ccgcaaggcc ttcaagagcc 2341 acgtctctac cttgacagac ctccagccgt acatgcgaca gttcgtggct cacctgcagg 2401 agaccagccc gctgagggat gccgtcgtca tcgagcagag ctcctccctg aatgaggcca 2461 gcagtggcct cttcgacgtc ttcctacgct tcatgtgcca ccacgccgtg cgcatcaggg 2521 gcaagtccta cgtccagtgc caggggatcc cgcagggctc catcctctcc acgctgctct 2581 gcagcctgtg ctacggcgac atggagaaca agctgtttgc ggggattcgg cgggacgggc 2641 tgctcctgcg tttggtggat gatttcttgt tggtgacacc tcacctcacc cacgcgaaaa 2701 ccttcctcag gaccctggtc cgaggtgtcc ctgagtatgg ctgcgtggtg aacttgcgga 2761 agacagtggt gaacttccct gtagaagacg aggccctggg tggcacggct tttgttcaga 2821 tgccggccca cggcctattc ccctggtgcg gcctgctgct ggataccccgg accctggagg 2881 tgcagagcga ctactccagc tatgcccgga cctccatcag agccagtctc accttcaacc 2941 gcggcttcaa ggctgggagg aacatgcgtc gcaaactctt tggggtcttg cggctgaagt 3001 gtcacagcct gtttctggat ttgcaggtga acagcctcca gacggtgtgc accaacatct 3061 acaagatcct cctgctgcag gcgtacaggt ttcacgcatg tgtgctgcag ctcccatttc 3121 atcagcaagt ttggaagaac ccacattttt tcctgcgcgt catctctgac acggcctccc 3181 tctgctactc catcctgaaa gccaagaacg cagggatgtc gctggggggcc aagggcgccg 3241 ccggccctct gccctccgag gccgtgcagt ggctgtgcca ccaagcattc ctgctcaagc 3301 tgactcgaca ccgtgtcacc tacgtgccac tcctggggtc actcaggaca gcccagacgc 3361 agctgagtcg gaagctcccg gggacgacgc tgactgccct ggaggccgca gccaacccgg 3421 cactgccctc agacttcaag accatcctgg actgatggcc acccgcccac agccaggccg 3481 agagcagaca ccagcagccc tgtcacgccg ggctctacgt cccagggagg gaggggcggc
```

```
-continued
3541 ccacacccag gcccgcaccg ctgggagtct gaggcctgag tgagtgtttg gccgaggcct 3601 gcatgtccgg ctgaaggctg agtgtccggc tgaggcctga gcgagtgtcc agccaagggc 3661 tgagtgtcca gcacacctgc cgtcttcact tccccacagg ctggcgctcg gctccacccc 3721 agggccagct tttcctcacc aggagcccgg cttccactcc ccacatagga atagtccatc 3781 cccagattcg ccattgttca cccctcgccc tgccctcctt tgccttccac ccccaccatc 3841 caggtggaga ccctgagaag gaccctggga gctctgggaa tttggagtga ccaaaggtgt 3901 gccctgtaca caggcgagga ccctgcacct ggatgggggt ccctgtgggt caaattgggg 3961 ggaggtgctg tgggagtaaa atactgaata tatgagtttt tcagttttga aaaaaaaaaa 4021 aaaaaaa
```

In an embodiment, the hTERT is encoded by a nucleic acid having a sequence at least 80%, 85%, 90%, 95%, 96, 97%, 98%, or 99% identical to the sequence of SEQ ID NO: 132. In an embodiment, the hTERT is encoded by a nucleic acid of SEQ ID NO: 132.

Activation and Expansion of Immune Effector Cells (e.g., T Cells)

Immune effector cells such as T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells can comprise: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

Generally, a population of immune effector cells e.g., T regulatory cell depleted cells, may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect, more anti-CD28 antibody is bound to the particles than anti-CD3 antibody, i.e., the ratio of CD3:CD28 is less than one. In certain aspects, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle: cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 10 billion cells/ml, 9 billion/ml, 8 billion/ml, 7 billion/ml, 6 billion/ml, 5 billion/ml, or 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one embodiment, cells transduced with a nucleic acid encoding a CAR, e.g., a CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of 8 days or less, e.g., 7, 6 or 5 days. In one embodiment, the cells, e.g., a CD19 CAR cell described herein, are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells, e.g., a CD19 CAR cell described herein, expanded for 5 days show at least a one, two, three or four fold increase in cells doublings upon antigen stimulation as compared to the same cells expanded in culture for 9 days under the same culture conditions. In one embodiment, the cells, e.g., the cells expressing a CD19 CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells, e.g., a CD19 CAR cell described herein, expanded for 5 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions.

Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence of IL-15 and/or IL-7 (e.g., IL-15 and IL-7).

In embodiments, methods described herein, e.g., CAR-expressing cell manufacturing methods, comprise removing T regulatory cells, e.g., CD25+ T cells, from a cell population, e.g., using an anti-CD25 antibody, or fragment thereof, or a CD25-binding ligand, IL-2. Methods of removing T regulatory cells, e.g., CD25+ T cells, from a cell population are described herein. In embodiments, the methods, e.g., manufacturing methods, further comprise contacting a cell population (e.g., a cell population in which T regulatory cells, such as CD25+ T cells, have been depleted; or a cell population that has previously contacted an anti-CD25 antibody, fragment thereof, or CD25-binding ligand) with IL-15 and/or IL-7. For example, the cell population (e.g., that has previously contacted an anti-CD25 antibody, fragment thereof, or CD25-binding ligand) is expanded in the presence of IL-15 and/or IL-7.

In some embodiments a CAR-expressing cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15, during the manufacturing of the CAR-expressing cell, e.g., ex vivo. In embodiments, a CAR-expressing cell described herein is contacted with a composition comprising a IL-15 polypeptide during the manufacturing of the CAR-expressing cell, e.g., ex vivo. In embodiments, a CAR-expressing cell described herein is contacted with a composition comprising a combination of both a IL-15 polypeptide and a IL-15 Ra polypeptide during the manufacturing of the CAR-expressing cell, e.g., ex vivo. In embodiments, a CAR-expressing cell described herein is contacted with a composition comprising hetIL-15 during the manufacturing of the CAR-expressing cell, e.g., ex vivo.

In one embodiment the CAR-expressing cell described herein is contacted with a composition comprising hetIL-15 during ex vivo expansion. In an embodiment, the CAR-expressing cell described herein is contacted with a composition comprising an IL-15 polypeptide during ex vivo expansion. In an embodiment, the CAR-expressing cell described herein is contacted with a composition comprising both an IL-15 polypeptide and an IL-15Ra polypeptide during ex vivo expansion. In one embodiment the contacting results in the survival and proliferation of a lymphocyte subpopulation, e.g., CD8+ T cells.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In other embodiments, the method of making disclosed herein further comprises contacting the population of immune effector cells with a nucleic acid encoding a telomerase subunit, e.g., hTERT. The the nucleic acid encoding the telomerase subunit can be DNA.

In some embodiments, a kinase inhibitor (e.g., a BTK inhibitor such as ibrutinib) is added during the CAR cell manufacturing process. According to the non-limiting theory herein, the kinase inhibitor can improve the quality of the population of cells produced. For instance, CAR-expressing cells are often produced from a cancer patient's own plasma apheresis sample, which can contain cancer cells, and the kinase inhibitor can alter signalling in those cancer cells (e.g., a BTK-expressing cancer such as CLL or MCL), e.g., reducing their proliferation or increasing levels of apoptosis. As another example, the kinase inhibitor may alter signalling in the CAR-expressing cells (or immune effector cells before they express CAR), e.g., by inhibiting ITK in T cells. The kinase inhibitor may shift the balance of T cells from TH2 cells towards TH1 cells.

The kinase inhibitor (e.g., a BTK inhibitor such as ibrutinib) can be added to the reaction mixture in a level sufficient to inhibit its target, e.g., BTK. In some embodiments, the kinase inhibitor (e.g., a BTK inhibitor such as ibrutinib) is added at a concentration of about 0.1-0.2, 0.2-0.5, 0.5-1, 1-2, 2-5, or 5-10 μM. In some embodiments, the kinase inhibitor is a covalent inhibitor (such as ibrutinib) and a short pulse is sufficient to irreversibly inactivate the target while avoiding nonspecific toxicity. Consequently, the kinase inhibitor may be added for, e.g., 10-20, 20-30, 30-40, 40-60, or 60-120 minutes. The kinase inhibitor may also be added for longer periods of time, for instance if the kinase inhibitor has a noncovalent mode of action. Thus, the kinase inhibitor may be added for, e.g., 2-4, 4-6, 6-8, 8-12, 12-18, or 18-24 hours, or for 1-2, 2-3, 3-4, 4-6, 6-8, 8-10 days, or for the entire length of time the cells are being cultured. The kinase inhibitor may be added at various points during the manufacturing process, for example, after harvesting the cells, before stimulating with beads, after stimulating with beads, before transduction, after transduction, or before administration of the cells to the patient. In some embodiments, the kinase inhibitor (e.g., a BTK inhibitor such as ibrutinib) is added after harvesting the cells or before stimulating, e.g., with beads. Before and after, in this context, can refer to, e.g., about 1, 5, 15, 30, 45, or 60 minutes before or after, or 1, 2, 3, 4, 5, or 6 hours before or after.

Once a CD19 CAR is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a CD19 CAR are described in further detail below Western blot analysis of CAR expression in primary T cells can be used to detect the presence of monomers and dimers. See, e.g., Milone et al., Molecular Therapy 17(8): 1453-1464 (2009). Very briefly, T cells (1:1 mixture of CD4$^+$ and CD8$^+$ T cells) expressing the CARs are expanded in vitro for more than 10 days followed by lysis and SDS-PAGE under reducing conditions. CARs containing the full length TCR-ζ cytoplasmic domain and the endogenous TCR-ζ chain are detected by western blotting using an antibody to the TCR-ζ chain. The same T cell subsets are used for SDS-PAGE analysis under non-reducing conditions to permit evaluation of covalent dimer formation.

In vitro expansion of CAR$^+$ T cells following antigen stimulation can be measured by flow cytometry. For example, a mixture of CD4$^+$ and CD8$^+$ T cells are stimulated with αCD3/αCD28 beads followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the CD4$^+$ and/or CD8$^+$ T cell subsets by flow cytometry. See, e.g., Milone et al., Molecular Therapy 17(8): 1453-1464 (2009). Alternatively, a mixture of CD4$^+$ and CD8$^+$ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures are re-stimulated with either CD19$^+$ K562 cells (K562-CD19), wild-type K562 cells (K562 wild type) or K562 cells expressing hCD32 and 4-1BBL in the presence of anti-CD3 and anti-CD28 antibody (K562-BBL-3/28) following washing. Exogenous IL-2 is added to the cultures every other day at 100 IU/ml. GFP$^+$ T cells are enumerated by flow cytometry using bead-based counting. See, e.g., Milone et al., Molecular Therapy 17(8): 1453-1464 (2009).

Sustained CAR$^+$ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer particle counter, a Nexcelom Cellometer Vision or Millipore Scepter, following stimulation with αCD3/αCD28 coated magnetic beads on day 0, and transduction with the indicated CAR on day 1.

Animal models can also be used to measure a CART activity. For example, xenograft model using human CD19-specific CAR$^+$ T cells to treat a primary human pre-B ALL in immunodeficient mice can be used. See, e.g., Milone et al., Molecular Therapy 17(8): 1453-1464 (2009). Very briefly, after establishment of ALL, mice are randomized as to treatment groups. Different numbers of αCD19-ζ and αCD19-BB-ζ engineered T cells are coinjected at a 1:1 ratio into NOD-SCID-γ$^{-/-}$ mice bearing B-ALL. The number of copies of αCD19-ζ and αCD19-BB-ζ vector in spleen DNA from mice is evaluated at various times following T cell injection. Animals are assessed for leukemia at weekly intervals. Peripheral blood CD19$^+$ B-ALL blast cell counts are measured in mice that are injected with αCD19-ζ CAR$^+$ T cells or mock-transduced T cells. Survival curves for the groups are compared using the log-rank test. In addition, absolute peripheral blood CD4$^+$ and CD8$^+$ T cell counts 4 weeks following T cell injection in NOD-SCID-γ$^{-/-}$ mice can also be analyzed. Mice are injected with leukemic cells and 3 weeks later are injected with T cells engineered to express CAR by a bicistronic lentiviral vector that encodes the CAR linked to eGFP. T cells are normalized to 45-50% input GFP$^+$ T cells by mixing with mock-transduced cells prior to injection, and confirmed by flow cytometry. Animals are assessed for leukemia at 1-week intervals. Survival curves for the CAR$^+$ T cell groups are compared using the log-rank test.

Dose dependent CAR treatment response can be evaluated. See, e.g., Milone et al., Molecular Therapy 17(8): 1453-1464 (2009). For example, peripheral blood is obtained 35-70 days after establishing leukemia in mice injected on day 21 with CAR T cells, an equivalent number of mock-transduced T cells, or no T cells. Mice from each group are randomly bled for determination of peripheral blood CD19$^+$ ALL blast counts and then killed on days 35 and 49. The remaining animals are evaluated on days 57 and 70.

Assessment of cell proliferation and cytokine production has been previously described, e.g., at Milone et al., Molecular Therapy 17(8): 1453-1464 (2009). Briefly, assessment of CAR-mediated proliferation is performed in microtiter plates by mixing washed T cells with K562 cells expressing CD19 (K19) or CD32 and CD137 (KT32-BBL) for a final T-cell:K562 ratio of 2:1. K562 cells are irradiated with gamma-radiation prior to use. Anti-CD3 (clone OKT3) and anti-CD28 (clone 9.3) monoclonal antibodies are added to cultures with KT32-BBL cells to serve as a positive control for stimulating T-cell proliferation since these signals support long-term CD8$^+$ T cell expansion ex vivo. T cells are enumerated in cultures using CountBright™ fluorescent beads (Invitrogen, Carlsbad, Calif.) and flow cytometry as described by the manufacturer. CAR$^+$ T cells are identified by GFP expression using T cells that are engineered with eGFP-2A linked CAR-expressing lentiviral vectors. For CAR+ T cells not expressing GFP, the CAR+ T cells are detected with biotinylated recombinant CD19 protein and a secondary avidin-PE conjugate. CD4+ and CD8$^+$ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences, San Diego, Calif.) according the manufacturer's instructions. Fluorescence is assessed using a FACScalibur flow cytometer, and data is analyzed according to the manufacturer's instructions.

Cytotoxicity can be assessed by a standard $^{51}$Cr-release assay. See, e.g., Milone et al., Molecular Therapy 17(8): 1453-1464 (2009). Briefly, target cells (K562 lines and primary pro-B-ALL cells) are loaded with $^{51}$Cr (as NaCrO$_4$, New England Nuclear, Boston, Mass.) at 37° C. for 2 hours with frequent agitation, washed twice in complete RPMI and plated into microtiter plates. Effector T cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released 51Cr is then measured using a gamma particle counter (Packard Instrument Co., Waltham, Mass.). Each condition is performed in at least triplicate, and the percentage of lysis is calculated using the formula: % Lysis=(ER−SR)/(TR−SR), where ER represents the average 51Cr released for each experimental condition.

Imaging technologies can be used to evaluate specific trafficking and proliferation of CARs in tumor-bearing animal models. Such assays have been described, for example, in Barrett et al., Human Gene Therapy 22:1575-1586 (2011).

Briefly, NOD/SCID/γc$^{-/-}$ (NSG) mice are injected IV with Nalm-6 cells followed 7 days later with T cells 4 hour after electroporation with the CAR constructs. The T cells are stably transfected with a lentiviral construct to express firefly luciferase, and mice are imaged for bioluminescence. Alternatively, therapeutic efficacy and specificity of a single injection of CAR$^+$ T cells in Nalm-6 xenograft model can be measured as the following: NSG mice are injected with Nalm-6 transduced to stably express firefly luciferase, followed by a single tail-vein injection of T cells electroporated with CD19 CAR 7 days later. Animals are imaged at various time points post injection. For example, photon-density heat maps of firefly luciferasepositive leukemia in representative mice at day 5 (2 days before treatment) and day 8 (24 hr post CAR$^+$ PBLs) can be generated.

Other assays, including those described in the Example section herein as well as those that are known in the art can also be used to evaluate the CD19 CAR constructs of the invention.

Kinase Inhibitor

In one embodiment, the kinase inhibitor is a CDK4 inhibitor, e.g., a CDK4 inhibitor described herein, e.g., a CDK4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo [3,4-d] pyrimidine. The MNK inhibitor can be, e.g., a MNK1a, MNK1b, MNK2a and/or MNK2b inhibitor.

In one embodiment, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In one embodiment, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

An exemplary CDK4/6 inhibitor is LEE011 (also called ribociclib), the structure of which is shown below.

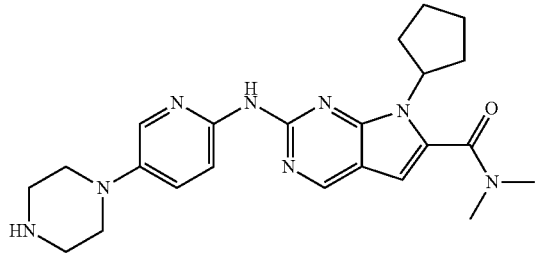 [SMILES: CN(C)C(=O)c1cc2cnc(Nc3ccc(N4CCNCC4)cn3)nc2n1C1CCCC1]

Without being bound by theory, it is believed that administration of a CAR-expressing cell described herein with a CDK4/6 inhibitor (e.g., LEE011 or other CDK4/6 inhibitor described herein) can achieve higher responsiveness, e.g., with higher remission rates and/or lower relapse rates, e.g., compared to a CDK4/6 inhibitor alone.

While not wishing to be bound by theory, in some embodiments the CDK4/6 inhibitor acts to reduce cyclin D1 activity in cancer cells, e.g., MCL cells. Some cancer cells are characterized by elevated cyclin D1 levels due to a translocation. CDK4 complexes with cyclin D to promote cell cycle progression. Accordingly, in some embodiments, administration of the CK4/6 inhibitor reduces cancer cell proliferation. See, e.g., Marzec et al., "Mantle cell lymphoma cells express predominantly cyclin D1a isoform and are highly sensitive to selective inhibition of CDK4 kinase activity." Blood. 2006 Sep. 1; 108(5):1744-50. Epub 2006 May 11.

In one embodiment, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In an embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In one embodiment, the kinase inhibitor is a BTK inhibitor, e.g., ibrutinib (PCI-32765), and the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle cycle, or daily for 28 day cycle. In one embodiment, 1, 2, 3, 4, 5, 6, 7, 8, 9, 10, 11, 12 or more cycles of ibrutinib are administered.

In embodiments, the BTK inhibitor (e.g., ibrutinib) is administered to a subject that has CLL, mantle cell lymphoma (MCL), or small lymphocytic lymphoma (SLL). For example, the subject to whom the BTK inhibitor is administered has a deletion in the short arm of chromosome 17 (del(17p), e.g., in a leukemic cell). In other examples, the subject to whom the BTK inhibitor is administered does not have a del(17p). In embodiments, the subject to whom the BTK inhibitor is administered has relapsed CLL or SLL, e.g., the subject has previously been administered a cancer therapy (e.g., previously been administered one, two, three, or four prior cancer therapies). In embodiments, the subject to whom the BTK inhibitor is administered has refractory CLL or SLL. In other embodiments, the subject to whom the BTK inhibitor is administered has follicular lymphoma, e.g., relapse or refractory follicular lymphoma.

The structure of ibrutinib (1-[(3R)-3-[4-Amino-3-(4-phenoxyphenyl)-1H-pyrazolo[3,4-d]pyrimidin-1-yl]piperidin-1-yl]prop-2-en-1-one) is shown below.

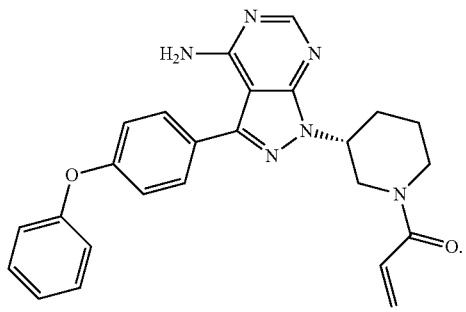 [SMILES: C=CC(=O)N1CCC[C@@H](n2nc(-c3ccc(Oc4ccccc4)cc3)c3c(N)ncnc32)C1]

Concentrations of ibrutinib exceeding approximately 400 nM are not clinically relevant. In the study by Advani et al (J Clin Oncol 2012; 31:88), the mean peak serum concentration of ibrutinib was about 130 ng/ml, which is equivalent to 295 nM (based on the molecular weight of ibrutinib of 440.5). Therefore, data showing the effect of ibrutinib on T cells at a concentration of 1 uM significantly exceeds the clinically relevant concentration in vivo.

In one embodiment, the kinase inhibitor is an mTOR inhibitor selected from temsirolimus; ridaforolimus (1R,2R,4S)-4-[(2R)-2 [(1R,9S,12S,15R,16E,18R,19R,21R, 23S, 24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl) methanol (AZD8055); 2-amino-8-[trans-4-(2-hydroxyethoxy)cyclohexyl]-6-(6-methoxy-3-pyridinyl)-4-methylpyrido[2,3-d]pyrimidin-7(8H)-one (PF04691502); and N$^2$-[1,4-dioxo-4-[[4-(4-oxo-8-phenyl-4H-1-benzopyran-2-yl) morpholinium-4-yl]methoxy]butyl]-L-arginylglycyl-L-α-aspartylL-serine-, inner salt (SF1126); and XL765.

In one embodiment, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is an MNK inhibitor selected from CGP052088; 4-amino-3-(p-fluorophenylamino)-pyrazolo [3,4-d] pyrimidine (CGP57380); cercosporamide; ETC-1780445-2; and 4-amino-5-(4-fluoroanilino)-pyrazolo [3,4-d] pyrimidine.

In embodiments, a CAR-expressing cell described herein, optionally in combination with a kinase inhibitor, e.g., a BTK inhibitor such as ibrutinib, is administered to a subject in combination with a phosphoinositide 3-kinase (PI3K) inhibitor (e.g., a PI3K inhibitor described herein, e.g., idelalisib or duvelisib) and/or rituximab. In embodiments, a CAR-expressing cell described herein is administered to a subject in combination with idelalisib and rituximab. In embodiments, a CAR-expressing cell described herein is administered to a subject in combination with duvelisib and rituximab. Idelalisib (also called GS-1101 or CAL-101; Gilead) is a small molecule that blocks the delta isoform of PI3K. The structure of idelalisib (5-Fluoro-3-phenyl-2-[(1S)-1-(7H-purin-6-ylamino)propyl]-4(3H)-quinazolinone) is shown below.

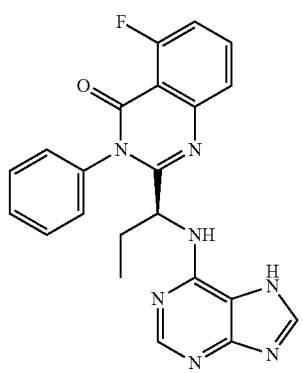 [SMILES: CC[C@H](Nc1ncnc2nc[nH]c12)c1nc2cccc(F)c2c(=O)n1-c1ccccc1]

Duvelisib is a small molecule that blocks PI3K-δ,γ. The structure of duvelisib (8-Chloro-2-phenyl-3-[(1S)-1-(9H-purin-6-ylamino)ethyl]-1(2H)-isoquinolinone) is shown below.

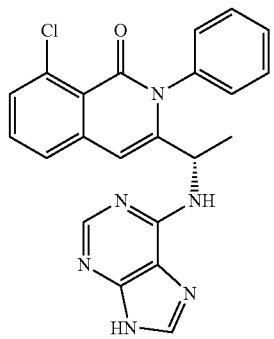 [SMILES: C[C@H](Nc1ncnc2[nH]cnc12)c1cc2cccc(Cl)c2c(=O)n1-c1ccccc1]

In embodiments, the subject has CLL. In embodiments, the subject has relapsed CLL, e.g., the subject has previously been administered a cancer therapy (e.g., previously been administered an anti-CD20 antibody or previously been administered ibrutinib). For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region (IgV$_H$) gene. In other embodiments, the subject does not comprise a leukemic cell comprising a mutation in the immunoglobulin heavy-chain variable-region (IgV$_H$) gene. In embodiments, the subject has a deletion in the long arm of chromosome 11 (del(11q)). In other embodiments, the subject does not have a del(11q). In embodiments, idelalisib is administered at a dosage of about 100-400 mg (e.g., 100-125, 125-150, 150-175, 175-200, 200-225, 225-250, 250-275, 275-300, 325-350, 350-375, or 375-400 mg), e.g., BID. In embodiments, duvelisib is administered at a dosage of about 15-100 mg (e.g., about 15-25, 25-50, 50-75, or 75-100 mg), e.g., twice a day. In embodiments, rituximab is administered at a dosage of about 350-550 mg/m² (e.g., 350-375, 375-400, 400-425, 425-450, 450-475, or 475-500 mg/m²), e.g., intravenously.

In one embodiment, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

In embodiments, a CAR-expressing cell described herein, optionally in combination with a kinase inhibitor, e.g., a BTK inhibitor such as ibrutinib, is administered to a subject in combination with an anaplastic lymphoma kinase (ALK) inhibitor. Exemplary ALK kinase inhibitors include but are not limited to crizotinib (Pfizer), ceritinib (Novartis), alectinib (Chugai), brigatinib (also called AP26113; Ariad), entrectinib (Ignyta), PF-06463922 (Pfizer), TSR-011 (Tesaro) (see, e.g., Clinical Trial Identifier No. NCT02048488), CEP-37440 (Teva), and X-396 (Xcovery). In some embodiments, the subject has a solid cancer, e.g., a solid cancer described herein, e.g., lung cancer.

The chemical name of crizotinib is 3-[(1R)-1-(2,6-dichloro-3-fluorophenyl)ethoxy]-5-(1-piperidin-4-ylpyrazol-4-yl)pyridin-2-amine. The chemical name of ceritinib is 5-Chloro-N²-[2-isopropoxy-5-methyl-4-(4-piperidinyl)phenyl]-N⁴-[2-(isopropylsulfonyl)phenyl]-2,4-pyrimidinediamine. The chemical name of alectinib is 9-ethyl-6,6-dimethyl-8-(4-morpholinopiperidin-1-yl)-11-oxo-6,11-dihydro-5H-benzo[b]carbazole-3-carbonitrile. The chemical name of brigatinib is 5-Chloro-N²-{4-[4-(dimethylamino)-1-piperidinyl]-2-methoxyphenyl}-N⁴-[2-(dimethylphosphoryl)phenyl]-2,4-pyrimidinediamine. The chemical name of entrectinib is N-(5-(3,5-difluorobenzyl)-1H-indazol-3-yl)-4-(4-methylpiperazin-1-yl)-2-((tetrahydro-2H-pyran-4-yl)amino)benzamide. The chemical name of PF-06463922 is (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile. The chemical structure of CEP-37440 is (S)-2-((5-chloro-2-((6-(4-(2-hydroxyethyl)piperazin-1-yl)-1-methoxy-6,7,8,9-tetrahydro-5H-benzo[7]annulen-2-yl)amino)pyrimidin-4-yl)amino)-N-methylbenzamide. The chemical name of X-396 is (R)-6-amino-5-(1-(2,6-dichloro-3-fluorophenyl)ethoxy)-N-(4-(4-methylpiperazine-1-carbonyl)phenyl)pyridazine-3-carboxamide.

In embodiments, a CAR-expressing cell described herein, optionally in combination with a kinase inhibitor, e.g., a BTK inhibitor such as ibrutinib, is administered to a subject in combination with an indoleamine 2,3-dioxygenase (IDO) inhibitor. IDO is an enzyme that catalyzes the degradation of the amino acid, L-tryptophan, to kynurenine. Many cancers overexpress IDO, e.g., prostatic, colorectal, pancreatic, cervical, gastric, ovarian, head, and lung cancer. pDCs, macrophages, and dendritic cells (DCs) can express IDO. Without being bound by theory, it is thought that a decrease in L-tryptophan (e.g., catalyzed by IDO) results in an immunosuppressive milieu by inducing T-cell anergy and apoptosis. Thus, without being bound by theory, it is thought that an IDO inhibitor can enhance the efficacy of a CAR-expressing cell described herein, e.g., by decreasing the suppression or death of a CAR-expressing immune cell. In embodiments, the subject has a solid tumor, e.g., a solid tumor described herein, e.g., prostatic, colorectal, pancreatic, cervical, gastric, ovarian, head, or lung cancer. Exemplary inhibitors of IDO include but are not limited to 1-methyl-tryptophan, indoximod (NewLink Genetics) (see, e.g., Clinical Trial Identifier Nos. NCT01191216; NCT01792050), and INCB024360 (Incyte Corp.) (see, e.g., Clinical Trial Identifier Nos. NCT01604889; NCT01685255)

In embodiments, a CAR-expressing cell described herein, optionally in combination with a kinase inhibitor, e.g., a BTK inhibitor such as ibrutinib, is administered to a subject in combination with a modulator of myeloid-derived suppressor cells (MDSCs). MDSCs accumulate in the periphery and at the tumor site of many solid tumors. These cells suppress T cell responses, thereby hindering the efficacy of CAR-expressing cell therapy. Without being bound by theory, it is thought that administration of a MDSC modulator enhances the efficacy of a CAR-expressing cell described herein. In an embodiment, the subject has a solid tumor, e.g., a solid tumor described herein, e.g., glioblastoma. Exemplary modulators of MDSCs include but are not limited to MCS110 and BLZ945. MCS110 is a monoclonal antibody (mAb) against macrophage colony-stimulating factor (M-CSF). See, e.g., Clinical Trial Identifier No. NCT00757757. BLZ945 is a small molecule inhibitor of colony stimulating factor 1 receptor (CSF1R). See, e.g., Pyonteck et al. Nat. Med. 19 (2013):1264-72. The structure of BLZ945 is shown below.

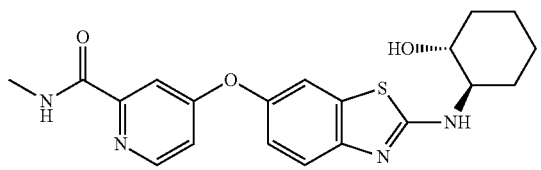 [SMILES: CNC(=O)c1cc(Oc2ccc3nc(N[C@@H]4CCCC[C@H]4O)sc3c2)ccn1]

In some embodiments, a CAR-expressing cell described herein, optionally in combination with a kinase inhibitor, e.g., a BTK inhibitor such as ibrutinib, is administered to a subject in combination with a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15 (Admune Therapeutics, LLC). hetIL-15 is a heterodimeric non-covalent complex of IL-15 and IL-15Ra. hetIL-15 is described in, e.g., U.S. Pat. No. 8,124,084, U.S. 2012/0177598, U.S. 2009/0082299, U.S. 2012/0141413, and U.S. 2011/0081311, incorporated herein by reference. In embodiments, het-IL-15 is administered subcutaneously. In embodiments, the subject has a cancer, e.g., solid cancer, e.g., melanoma or colon cancer. In embodiments, the subject has a metastatic cancer.

Therapeutic Application
CD19 Associated Diseases and/or Disorders

In one aspect, the invention provides methods for treating a disease associated with CD19 expression. In one aspect, the invention provides methods for treating a disease wherein part of the tumor is negative for CD19 and part of the tumor is positive for CD19. For example, the CAR of the invention is useful for treating subjects that have undergone treatment for a disease associated with elevated expression of CD19, wherein the subject that has undergone treatment for elevated levels of CD19 exhibits a disease associated with elevated levels of CD19.

The therapies described herein can be used to treat, e.g., subjects who respond to a kinase inhibitor such as ibrutinib (e.g., partial response or complete response) or subjects who do not (e.g., non-responders or relapsers). Without wishing to be bound by theory, a number of patients undergoing treatment with kinase inhibitors (e.g., BTK inhibitors such as ibrutinib) may show a reduced response to the treatment (e.g., are partial or non-responders to the treatment, or relapse during treatment). According, administration of the CAR-therapies disclosed herein, in combination with the kinase inhibitors can result in beneficial effects.

Exemplary therapeutic regimens for these subjects are described below.

In some cases, when the subject is a non-responder or relapser to a kinase inhibitor (e.g. a BTK inhibitor such as ibrutinib), the kinase inhibitor is withdrawn and CAR therapy is administered. In other cases, when the subjects does not respond to a kinase inhibitor (e.g. a BTK inhibitor such as ibrutinib), the kinase inhibitor therapy is continued and CAR therapy is added to the regimen. This use is supported, e.g., by experiments in Example 8 herein which indicate that CAR therapy is effective as a monotherapy in ibrutinib-resistant cells. Without wishing to be bound by theory, continuing kinase inhibitor therapy can improve the efficacy of the CAR therapy, e.g., by increasing the number of CAR-expressing cells in the bloodstream (see Example 8 herein).

Without being bound by theory, a subject who is a non-responder or relapser to a kinase inhibitor (e.g., a BTK inhibitor such as ibrutinib) can be non-responsive for at least two reasons: the subjects may have a mutation in the drug target (e.g., BTK, e.g., a C481S mutation) that prevents target inhibition, or can have alterations in other pathways that can drive proliferation even when the target is adequately inhibited (e.g., a mutation in PLCγ, such as an activating mutation in PLCγ resulting in constitutive BTK-independent cell signaling). The treatment can be altered depending on the reason for non-responsiveness. For instance, in the first situation (in some embodiments), if the subjects has (or is identified as having) a mutation that prevents the kinase inhibitor from inhibiting its target, a second kinase inhibitor (e.g., directed against the same target) can be substituted for (or administered in combination with) the kinase inhibitor. More specifically, in some embodiments where the patient has (or is identified as having) a mutation that prevents ibrutinib from inhibiting BTK, a second BTK inhibitor, e.g., a BTK inhibitor described herein such as GDC-0834, RN-486, CGI-560, CGI-1764, HM-71224, CC-292, ONO-4059, CNX-774, or LFM-A13) can be substituted for ibrutinib. Without wishing to be bound by theory, the second kinase inhibitor may act on a region of the target that is not disrupted by the mutation, and therefore the subject is sensitive to the second kinase inhibitor. In other embodiments, the original kinase inhibitor (e.g. a BTK inhibitor such as ibrutinib) is maintained. According to the non-limiting theory here, the original kinase inhibitor may have useful activity on the CAR-expressing cells, e.g., promoting a TH1 phenotype, promoting proliferation, or otherwise increasing levels or activity of the cells.

As noted above, in some cases a subject is non-responsive because the subject has an alteration (e.g., a mutation) in another pathway that can drive proliferation even when the target is adequately inhibited. Accordingly, if the subject has (or is identified has having) an alteration in a pathway that makes the kinase inhibitor's activity ineffectual, the kinase inhibitor therapy can be maintained. Without wishing to be bound by theory, the kinase inhibitor (e.g., a BTK inhibitor such as ibrutinib) activity can promote useful biological changes in the cancer cells even if the kinase inhibitor alone is not sufficient to slow proliferation. For instance, the kinase inhibitor can be sufficient to mobilize cancer cells out of the lymph nodes, making them more vulnerable to the CAR therapy.

Turning now to subjects who respond to a kinase inhibitor (e.g., a BTK inhibitor such as ibrutinib), various therapeutic regimens are now described. In some embodiments, when a subject is (or is identified as being) a complete responder to the kinase inhibitor, the subject is not administered a CAR therapy during the period of complete response. In other embodiments, when a subject is (or is identified as being) a complete responder to the kinase inhibitor, the subject is administered a CAR therapy during the period of complete response. In an embodiment, after the CAR therapy, the subject experiences a prolonged response or delayed relapse (e.g., compared to the expected course of disease when treated without CAR therapy). For instance, MCL treated with ibrutinib monotherapy has a median duration of response of about 17.5 months.

In some embodiments, when a subject is (or is identified as being) a partial responder to the kinase inhibitor (e.g., a BTK inhibitor such as ibrutinib), the subject is not administered a CAR therapy during the period of partial response. In other embodiments, when a subject is (or is identified as being) a partial responder to the kinase inhibitor, the subject is administered a CAR therapy during the period of partial response. In an embodiment, after the CAR therapy, the subject experiences a complete response and/or prolonged response or delayed relapse (e.g., compared to the expected course of disease when treated without CAR therapy).

In some embodiments, when a subject has (or is identified as having) stable disease after the beginning of treatment with the kinase inhibitor (e.g., a BTK inhibitor such as ibrutinib), the subject is not administered a CAR therapy during the period of stable disease. In other embodiments, when a subject has (or is identified as having) stable disease after the beginning of treatment with the kinase inhibitor, the subject is administered a CAR therapy during the period of stable disease. In an embodiment, after the CAR therapy, the subject experiences a partial response, a complete response and/or prolonged response or delayed relapse (e.g., compared to the expected course of disease when treated without CAR therapy).

In some embodiments, when a subject has (or is identified as having) progressive disease after the beginning of treatment with the kinase inhibitor (e.g., a BTK inhibitor such as ibrutinib), the subject is not administered a CAR therapy during the period of progressive disease. In other embodiments, when a subject has (or is identified as having) progressive disease after the beginning of treatment with the kinase inhibitor, the subject is administered a CAR therapy during the period of progressive disease. In an embodiment, after the CAR therapy, the subject experiences stable disease, a partial response, a complete response and/or prolonged response or delayed relapse (e.g., compared to the expected course of disease when treated without CAR therapy).

Thus, one or more disease assessment steps can be performed before or during treatment, to determine which course of treatment is suitable for a given patient. For instance, a subject can be administered a kinase inhibitor (e.g., a BTK inhibitor such as ibrutinib) as a first line therapy. Then, after a period of time (e.g., 1 or 2 months but also 2 weeks, 3 weeks, 1 month, 1.5 months, 2 months, 3 months, 4 months, 6 months, 9 months, 12 months, 15 months, or 18 months) the patient's response can be assessed. If the assessment shows that the subject is a complete responder, in some embodiments CAR therapy is not administered, e.g., as described above. If the assessment shows that the subject is a partial responder or has stable disease, in some embodiments CAR therapy is administered in combination with the kinase inhibitor e.g., as described above. If the assessment shows that the subject is a nonresponder or relapser, in some embodiments CAR therapy is administered in combination with the kinase inhibitor or a second kinase inhibitor, e.g., as described above. In some embodiments, the kinase inhibitor controls the disease while a CAR-expressing cell is being manufactured, e.g., while the patient's own T cells are being engineered to express a CAR and/or other factors.

Clinical standards for classifying a patient's responder status or relapser status are known in the art. As an example, for malignant lymphoma, standardized response criteria are described in Cheson et al, J Clin Oncol 17:1244 (1999) and Cheson et al., "Revised Response Criteria for Malignant Lymphoma", J Clin Oncol 25:579-586 (2007) (both of which are incorporated by reference herein in their entireties). Accordingly, in some embodiments, a subject is considered a complete responder, partial responder, having stable disease, a non-responder, or a relapser according to Cheson criteria or modified Cheson criteria. Criteria for classifying other hematological malignancies are known in the art.

According to the criteria in Table 2 of Cheson 2007, a complete responder has disappearance of all evidence of disease; a partial responder has regression of measurable disease and no new sites; a patient with stable disease has a failure to attain CR/PR or PD; and a patient with relapsed disease or progressive disease has any new lesion or increase by greater than or equal to 50% of previously involved sites from nadir. The assessment can involve a determination of whether the disease is FDG-avid, PET positive or negative, whether nodules are present e.g., palpable in the liver or spleen, and whether bone marrow is cleared or shows involvement.

The CAR therapy and the kinase inhibitor (e.g., a BTK inhibitor such as ibrutinib) can be administered, e.g., simultaneously or sequentially. In some embodiments, the CAR therapy is begun at substantially the same time as kinase inhibitor therapy begins. In some embodiments, the CAR therapy is begun before the kinase inhibitor therapy begins. In some embodiments, the CAR therapy is begun after the kinase inhibitor therapy begins. For instance, the CAR therapy can be begun, e.g., at least 1, 2, 3, or 4 weeks, or 1, 2, 3, 4, 6, 9, 12, 15, 18, or 24 months after the kinase inhibitor therapy begins. In some embodiments, the CAR therapy is begun while a patient has physiologically relevant levels of the kinase inhibitor in their body.

When administered in combination, the CAR therapy and the kinase inhibitor (e.g., a BTK inhibitor such as ibrutinib), or both, can be administered in an amount or dose that is higher, lower or the same than the amount or dosage of each agent used individually, e.g., as a monotherapy. In certain embodiments, the administered amount or dosage of the CAR therapy, the kinase inhibitor, or both, is lower (e.g., at least 20%, at least 30%, at least 40%, or at least 50%) than the amount or dosage of each agent used individually, e.g., as a monotherapy. In other embodiments, the amount or dosage of the CAR therapy, the kinase inhibitor, or both, that results in a desired effect (e.g., treatment of cancer) is lower (e.g., at least 20%, at least 30%, at least 40%, or at least 50% lower) than the amount or dosage of each agent used individually, e.g., as a monotherapy, required to achieve the same therapeutic effect.

When administered in combination, the CAR therapy and the kinase inhibitor (e.g., a BTK inhibitor such as ibrutinib), or both, can be administered with a duration that is longer, shorter, or the same than the duration of each agent used individually, e.g., as a monotherapy. In certain embodiments, the duration of administration of the CAR therapy, the kinase inhibitor, or both, is shorter (e.g., at least 20%, at least 30%, at least 40%, or at least 50%) than the duration of each agent used individually, e.g., as a monotherapy. In other embodiments, the duration of administration of the CAR therapy, the kinase inhibitor, or both, that results in a desired effect (e.g., treatment of cancer) is shorter (e.g., at least 20%, at least 30%, at least 40%, or at least 50% shorter) than the duration of each agent used individually, e.g., as a monotherapy, required to achieve the same therapeutic effect. In some embodiment, the patient is administered an abbreviated course of the kinase inhibitor (e.g., a BTK inhibitor such as ibrutinib). For instance, the abbreviated course of the kinase inhibitor may last about 0-2, 2-4, 4-6, 6-8, 8-10, 10-12, 12-15, 15-18, 18-21, or 21-24 months total or may last about 0-2, 2-4, 4-6, 6-8, 8-10, 10-12, 12-15, 15-18, 18-21, or 21-24 months after administration of the CAR therapy. In embodiments, the abbreviated course of the kinase inhibitor ends before relapse. In embodiments, the kinase inhibitor is administered at normal (e.g., monotherapy) levels during the abbreviated course.

In embodiments, a single dose of CAR-expressing cells comprises about $5 \times 10^8$ CD19 CART cells. A dose of CAR-expressing cells may also comprise about $5 \times 10^6$, $1 \times 10^7$, $2 \times 10^7$, $5 \times 10^7$, $1 \times 10^8$, $2 \times 10^8$, $5 \times 10^8$, $1 \times 10^9$, $2 \times 10^9$, or $5 \times 10^9$ cells, e.g., CD19 CAR cells, e.g., CD19 CART cells.

In one aspect, the invention pertains to a vector comprising CD19 CAR operably linked to promoter for expression in mammalian cells, e.g., T cells. In one aspect, the invention provides a recombinant cell, e.g., a T cell, expressing the CD19 CAR for use in treating CD19-expressing tumors, wherein the recombinant T cell expressing the CD19 CAR is termed a CD19 CART. In one aspect, the CD19 CART described herein, is capable of contacting a tumor cell with at least one CD19 CAR expressed on its surface such that the CART targets the tumor cell and growth of the tumor is inhibited.

In one aspect, the invention pertains to a method of inhibiting growth of a CD19-expressing tumor cell, comprising contacting the tumor cell with a CD19 CAR expressing cell, e.g., a CD19 CART cell, described herein such that the CART is activated in response to the antigen and targets the cancer cell, wherein the growth of the tumor is inhibited. The CD19 CAR-expressing cell, e.g., T cell, is administered in combination with a kinase inhibitor, e.g., a kinase inhibitor described herein.

Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. In one embodiment, the CAR-expressing cell is administered at a dose and/or dosing schedule described herein, and the kinase inhibitor or agent that enhances the activity of the CAR-expressing cell is administered at a dose and/or dosing schedule described herein.

The invention includes a type of cellular therapy where T cells are genetically modified to express a chimeric antigen receptor (CAR) and the CAR T cell is infused to a recipient in need thereof. The infused cell is able to kill tumor cells in the recipient. Unlike antibody therapies, CAR-modified T cells are able to replicate in vivo resulting in long-term persistence that can lead to sustained tumor control. In various aspects, the T cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the patient.

The invention also includes a type of cellular therapy where T cells are modified, e.g., by in vitro transcribed RNA, to transiently express a chimeric antigen receptor (CAR) and the CAR T cell is infused to a recipient in need thereof. The infused cell is able to kill tumor cells in the recipient. Thus, in various aspects, the T cells administered to the patient, is present for less than one month, e.g., three weeks, two weeks, one week, after administration of the T cell to the patient.

Without wishing to be bound by any particular theory, the anti-tumor immunity response elicited by the CAR-modified T cells may be an active or a passive immune response, or alternatively may be due to a direct vs indirect immune response. In one aspect, the CAR transduced T cells exhibit specific proinflammatory cytokine secretion and potent cytolytic activity in response to human cancer cells expressing the CD19, resist soluble CD19 inhibition, mediate bystander killing and mediate regression of an established human tumor. For example, antigen-less tumor cells within a heterogeneous field of CD19-expressing tumor may be susceptible to indirect destruction by CD19-redirected T cells that has previously reacted against adjacent antigen-positive cancer cells.

In one aspect, the fully-human CAR-modified T cells of the invention may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient. In addition to using a cell-based vaccine in terms of ex vivo immunization, also included in the methods described herein are compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-expressing cells described herein are used in the treatment of diseases, disorders and conditions associated with expression of CD19. In certain aspects, the cells are used in the treatment of patients at risk for developing diseases, disorders and conditions associated with expression of CD19. Thus, the present invention provides methods for the treatment or prevention of diseases, disorders and conditions associated with expression of CD19 comprising administering to a subject in need thereof, a therapeutically effective amount of the CAR-expressing cells described herein, in combination with a kinase inhibitor, e.g., a kinase inhibitor described herein.

The present invention also provides methods for inhibiting the proliferation or reducing a CD19-expressing cell population, the methods comprising contacting a population of cells comprising a CD19-expressing cell with an anti-CD19 CAR-expressing cell described herein that binds to the CD19-expressing cell, and contacting the population of CD19-expressing cells with a kinase inhibitor, e.g., a kinase inhibitor described herein. In a specific aspect, the present invention provides methods for inhibiting the proliferation or reducing the population of cancer cells expressing CD19, the methods comprising contacting the CD19-expressing cancer cell population with an anti-CD19 CAR-expressing cell described herein that binds to the CD19-expressing cell, and contacting the CD19-expressing cell with a kinase inhibitor, e.g., a kinase inhibitor described herein. In one aspect, the present invention provides methods for inhibiting the proliferation or reducing the population of cancer cells expressing CD19, the methods comprising contacting the CD19-expressing cancer cell population with an anti-CD19 CAR-expressing cell described herein that binds to the CD19-expressing cell and contacting the CD19-expressing cell with a kinase inhibitor, e.g., a kinase inhibitor described herein. In certain aspects, the combination of the anti-CD19 CAR-expressing cell described herein and the kinase inhibitor, e.g., a kinase inhibitor described herein, reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for a hematological cancer or another cancer associated with CD19-expressing cells relative to a negative control. In one aspect, the subject is a human.

The present invention also provides methods for preventing, treating and/or managing a disease associated with CD19-expressing cells (e.g., a hematologic cancer or atypical cancer expressing CD19), the methods comprising administering to a subject in need an anti-CD19 CAR-expressing cell that binds to the CD19-expressing cell and administering a kinase inhibitor, e.g., a kinase inhibitor described herein. In one aspect, the subject is a human. Non-limiting examples of disorders associated with CD19-expressing cells include autoimmune disorders (such as lupus), inflammatory disorders (such as allergies and asthma) and cancers (such as hematological cancers or atypical cancers expressing CD19).

The present invention also provides methods for preventing, treating and/or managing a disease associated with CD19-expressing cells, the methods comprising administering to a subject in need an anti-CD19 CART cell of the invention that binds to the CD19-expressing cell. In one aspect, the subject is a human.

The present invention provides methods for preventing relapse of cancer associated with CD19-expressing cells, the methods comprising administering to a subject in need thereof an anti-CD19 expressing cell (such as an anti-CD19 CART cell) of the invention that binds to the CD19-expressing cell. In one aspect, the methods comprise administering to the subject in need thereof an effective amount of an anti-CD19 expressing cell (such as an anti-CD19 CART cell) described herein that binds to the CD19-expressing cell in combination with an effective amount of another therapy.

In one aspect, the invention pertains to a method of treating cancer in a subject. The method comprises administering to the subject a cell (e.g., an immune effector cell) expressing a B-cell targeting CAR, e.g., a T cell or NK cell, described herein, in combination with a kinase inhibitor, e.g., a kinase inhibitor described herein, such that the cancer is treated in the subject. An example of a cancer that is treatable by the methods described herein is a cancer associated with expression of the B-cell antigen, e.g., CD19. In one embodiment, the disease is a solid or liquid tumor. In one embodiment, the disease is a hematologic cancer. In one embodiment, the hematologic cancer is leukemia. In one embodiment, the hematologic cancer is a mature B cell neoplasm, e.g., according to WHO classification. In one embodiment, the hematologic cancer is a CD19+B-lymphocyte-derived malignancy. In one embodiment, the cancer is selected from the group consisting of one or more acute leukemias including but not limited to B-cell acute lymphoid leukemia (BALL), T-cell acute lymphoid leukemia (TALL), small lymphocytic leukemia (SLL), acute lymphoid leukemia (ALL); one or more chronic leukemias including but not limited to chronic myelogenous leukemia (CML), chronic lymphocytic leukemia (CLL); additional hematologic cancers or hematologic conditions including, but not limited to mantle cell lymphoma (MCL), B cell prolymphocytic leukemia, blastic plasmacytoid dendritic cell neoplasm, Burkitt's lymphoma, diffuse large B cell lymphoma (DLBCL) (e.g., T-cell/histiocyte rich large B-cell lymphoma, primary DLCBL of the CNS, primary cutaneous DLBCL leg type, or EBV+DLBCL of the elderly), DLBCL associated with chronic inflammation, follicular lymphoma, pediatric follicular lymphoma, hairy cell leukemia, small cell- or a large cell-follicular lymphoma, malignant lymphoproliferative conditions, MALT lymphoma (extranodal marginal zone lymphoma of mucosa-associated lymphoid tissue), Marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, Waldenstrom macroglobulinemia, splenic marginal zone lymphoma, splenic lymphoma/leukemia (e.g., unclassifiable), splenic diffuse red pulp small B-cell lymphoma, hairy cell leukemia-variant, lymphoplasmacytic lymphoma, a heavy chain disease (e.g., alpha heavy chain disease, gamma heavy chain disease, or mu heavy chain disease), plasma cell myeloma, solitary plasmocytoma of bone, extraosseous plasmocytoma, nodal marginal zone lymphoma, pediatric nodal marginal zone lymphoma, primary cutaneous follicle center lymphoma, lymphomatoid granulomatosis, primary mediastinal (theymic) large B-cell lymphoma, intravascular large B-cell lymphoma, ALK+ large B-cell lymphoma, large B-cell lymphoma arising in HHV8-associated multicenric Castleman disease, primary effusion lymphoma, B-cell lymphoma, unclassifiable (e.g., with features intermediate between DLBCL and Burkitt lymphoma or intermediate between DLBCL and classical Hodgkin lymphoma), and "preleukemia" which are a diverse collection of hematological conditions united by ineffective production (or dysplasia) of myeloid blood cells, and to disease associated with B-cell antigen- (e.g., CD19-) expression include, but not limited to atypical and/or non-classical cancers, malignancies, precancerous conditions or proliferative diseases expressing B-cell antigen (e.g., CD19); and any combination thereof.

In some embodiments, the cancer is Hodgkin lymphoma, and the patient is treated with CAR expressing cells, e.g., as a monotherapy, or in combination with one or more additional therapeutics. In embodiments, the Hodgkin lymphoma is stage I, II, III, or IV. The additional therapeutic may comprise, e.g., a kinase inhibitor such as a BTK inhibitor like ibrutinib. The additional therapeutic may comprise a treatment for Hodgkin lymphoma. The additional therapeutic may comprise, e.g., radiation therapy, MOPP (Mustargen, Oncovin, Prednisone, and Procarbazine), ABVD (Adriamycin, bleomycin, vinblastine, and dacarbazine), Stanford V (a regimen with chemotherapy and radiation treatment), or BEACOPP (Bleomycin, Etoposide, Adriamycin, Cyclophosphamide, Oncovin, Procarbazine, Prednisone). In some embodiments, the subject has previously been treated with, or is resistant to, or is refractory to, one or more of radiation therapy, MOPP, Stanford V, or BEACOPP.

Non-cancer related indications associated with expression of B-cell antigen, e.g., one or more of CD19, CD20, CD22 or ROR1, include, but are not limited to, e.g., autoimmune disease, (e.g., lupus), inflammatory disorders (allergy and asthma) and transplantation.

In some embodiments, a cancer that can be treated with the combination described herein is multiple myeloma. Multiple myeloma is a cancer of the blood, characterized by accumulation of a plasma cell clone in the bone marrow. Current therapies for multiple myeloma include, but are not limited to, treatment with lenalidomide, which is an analog of thalidomide. Lenalidomide has activities which include anti-tumor activity, angiogenesis inhibition, and immunomodulation. In some embodiments, a CD19 CAR, e.g., as described herein, may be used to target myeloma cells. In some embodiments, the combination described herein can be used with one or more additional therapies, e.g., lenalidomide treatment.

The CAR-expressing cells described herein may be administered either alone, or as a pharmaceutical composition in combination with diluents and/or with other components such as IL-2 or other cytokines or cell populations.

In embodiments, a lymphodepleting chemotherapy is administered to the subject prior to, concurrently with, or after administration (e.g., infusion) of CAR cells, e.g., CAR-expressing cells described herein. In an example, the lymphodepleting chemotherapy is administered to the subject prior to administration of CAR cells. For example, the lymphodepleting chemotherapy ends 1-4 days (e.g., 1, 2, 3, or 4 days) prior to CAR cell infusion. In embodiments, multiple doses of CAR cells are administered, e.g., as described herein. For example, a single dose comprises about $5 \times 10^8$ CAR cells. In embodiments, a lymphodepleting chemotherapy is administered to the subject prior to, concurrently with, or after administration (e.g., infusion) of a CAR-expressing cell described herein.

Hematologic Cancer

Hematological cancer conditions are the types of cancer such as leukemia, lymphoma and malignant lymphoproliferative conditions that affect blood, bone marrow and the lymphatic system.

Leukemia can be classified as acute leukemia and chronic leukemia. Acute leukemia can be further classified as acute myelogenous leukemia (AML) and acute lymphoid leukemia (ALL). Chronic leukemia includes chronic myelogenous leukemia (CML) and chronic lymphoid leukemia (CLL). Other related conditions include myelodysplastic syndromes (MDS, formerly known as "preleukemia") which are a diverse collection of hematological conditions united by ineffective production (or dysplasia) of myeloid blood cells and risk of transformation to AML.

Lymphoma is a group of blood cell tumors that develop from lymphocytes. Exemplary lymphomas include non-Hodgkin lymphoma and Hodgkin lymphoma.

Combination Therapies

The combination of a CAR-expressing cell described herein (e.g., and a kinase inhibitor described herein) may be used in combination with other known agents and therapies.

A CAR-expressing cell described herein, the kinase inhibitor and/or the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

The CAR therapy and/or other therapeutic agents, procedures or modalities can be administered during periods of active disorder, or during a period of remission or less active disease. The CAR therapy can be administered before another treatment, concurrently with the treatment, post-treatment, or during remission of the disorder.

When administered in combination, the CAR therapy and one or more additional agent (e.g., kinase inhibitor and/or a third agent), or all, can be administered in an amount or dose that is higher, lower or the same than the amount or dosage of each agent used individually, e.g., as a monotherapy. In certain embodiments, the administered amount or dosage of the CAR therapy, the additional agent (e.g., kinase inhibitor and/or third agent), or all, is lower (e.g., at least 20%, at least 30%, at least 40%, or at least 50%) than the amount or dosage of each agent used individually, e.g., as a monotherapy. In other embodiments, the amount or dosage of the CAR therapy, the additional agent (e.g., kinase inhibitor and/or third agent), or all, that results in a desired effect (e.g., treatment of cancer) is lower (e.g., at least 20%, at least 30%, at least 40%, or at least 50% lower) than the amount or dosage of each agent used individually, e.g., as a monotherapy, required to achieve the same therapeutic effect.

In further aspects, the combination of the CAR-expressing cell described herein (e.g., and the kinase inhibitor) may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. peptide vaccine, such as that described in Izumoto et al. 2008 J Neurosurg 108:963-971.

In one embodiment, the combination of a CAR-expressing cell described herein (e.g., and a kinase inhibitor described herein) can be used in combination with another chemotherapeutic agent. Exemplary chemotherapeutic agents include an anthracycline (e.g., doxorubicin (e.g., liposomal doxorubicin)); a vinca alkaloid (e.g., vinblastine, vincristine, vindesine, vinorelbine); an alkylating agent (e.g., cyclophosphamide, decarbazine, melphalan, ifosfamide, temozolomide); an immune cell antibody (e.g., alemtuzamab, gemtuzumab, rituximab, ofatumumab, tositumomab, brentuximab); an antimetabolite (including, e.g., folic acid antagonists, pyrimidine analogs, purine analogs and adenosine deaminase inhibitors (e.g., fludarabine)); a TNFR glucocorticoid induced TNFR related protein (GITR) agonist; a proteasome inhibitor (e.g., aclacinomycin A, gliotoxin or bortezomib); an immunomodulator such as thalidomide or a thalidomide derivative (e.g., lenalidomide).

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustine®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

In embodiments, a CAR-expressing cell described herein, optionally in combination with a kinase inhibitor e.g., a BTK inhibitor such as ibrutinib, is administered to a subject in combination with fludarabine, cyclophosphamide, and/or rituximab. In embodiments, a CAR-expressing cell described herein is administered to a subject in combination with fludarabine, cyclophosphamide, and rituximab (FCR). In embodiments, the subject has CLL. For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region (IgV$_H$) gene. In other embodiments, the subject does not comprise a leukemic cell comprising a mutation in the immunoglobulin heavy-chain variable-region (IgV$_H$) gene. In embodiments, the fludarabine is administered at a dosage of about 10-50 mg/m$^2$ (e.g., about 10-15, 15-20, 20-25, 25-30, 30-35, 35-40, 40-45, or 45-50 mg/m$^2$), e.g., intravenously. In embodiments, the cyclophosphamide is administered at a dosage of about 200-300 mg/m$^2$ (e.g., about 200-225, 225-250, 250-275, or 275-300 mg/m$^2$), e.g., intravenously. In embodiments, the rituximab is administered at a dosage of about 400-600 mg/m$^2$ (e.g., 400-450, 450-500, 500-550, or 550-600 mg/m$^2$), e.g., intravenously.

In embodiments, a CAR-expressing cell described herein, optionally in combination with a kinase inhibitor e.g., a BTK inhibitor such as ibrutinib, is administered to a subject in combination with bendamustine and rituximab. In embodiments, the subject has CLL. For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region (IgV$_H$) gene. In other embodiments, the subject does not comprise a leukemic cell comprising a mutation in the immunoglobulin heavy-chain variable-region (IgV$_H$) gene. In embodiments, the bendamustine is administered at a dosage of about 70-110 mg/m$^2$ (e.g., 70-80, 80-90, 90-100, or 100-110 mg/m$^2$), e.g., intravenously. In embodiments, the rituximab is administered at a dosage of about 400-600 mg/m$^2$ (e.g., 400-450, 450-500, 500-550, or 550-600 mg/m$^2$), e.g., intravenously.

In embodiments, a CAR-expressing cell described herein, optionally in combination with a kinase inhibitor e.g., a BTK inhibitor such as ibrutinib, is administered to a subject in combination with rituximab, cyclophosphamide, doxorubicine, vincristine, and/or a corticosteroid (e.g., prednisone). In embodiments, a CAR-expressing cell described herein is administered to a subject in combination with rituximab, cyclophosphamide, doxorubicine, vincristine, and prednisone (R-CHOP). In embodiments, the subject has diffuse large B-cell lymphoma (DLBCL). In embodiments, the subject has nonbulky limited-stage DLBCL (e.g., comprises a tumor having a size/diameter of less than 7 cm). In embodiments, the subject is treated with radiation in combination with the R-CHOP. For example, the subject is administered R-CHOP (e.g., 1-6 cycles, e.g., 1, 2, 3, 4, 5, or 6 cycles of R-CHOP), followed by radiation. In some cases, the subject is administered R-CHOP (e.g., 1-6 cycles, e.g., 1, 2, 3, 4, 5, or 6 cycles of R-CHOP) following radiation.

In embodiments, a CAR-expressing cell described herein, optionally in combination with a kinase inhibitor e.g., a BTK inhibitor such as ibrutinib, is administered to a subject in combination with etoposide, prednisone, vincristine, cyclophosphamide, doxorubicin, and/or rituximab. In embodiments, a CAR-expressing cell described herein is administered to a subject in combination with etoposide, prednisone, vincristine, cyclophosphamide, doxorubicin, and rituximab (EPOCH-R). In embodiments, a CAR-expressing cell described herein is administered to a subject in combination with dose-adjusted EPOCH-R (DA-EPOCH-R). In embodiments, the subject has a B cell lymphoma, e.g., a Myc-rearranged aggressive B cell lymphoma.

In embodiments, a CAR-expressing cell described herein, optionally in combination with a kinase inhibitor e.g., a BTK inhibitor such as ibrutinib, is administered to a subject in combination with rituximab and/or lenalidomide. Lenalidomide ((RS)-3-(4-Amino-1-oxo 1,3-dihydro-2H-isoindol-2-yl)piperidine-2,6-dione) is an immunomodulator. In embodiments, a CAR-expressing cell described herein is administered to a subject in combination with rituximab and lenalidomide. In embodiments, the subject has follicular lymphoma (FL) or mantle cell lymphoma (MCL). In embodiments, the subject has FL and has not previously been treated with a cancer therapy. In embodiments, lenalidomide is administered at a dosage of about 10-20 mg (e.g., 10-15 or 15-20 mg), e.g., daily. In embodiments, rituximab is administered at a dosage of about 350-550 mg/m$^2$ (e.g., 350-375, 375-400, 400-425, 425-450, 450-475, or 475-500 mg/m$^2$), e.g., intravenously.

Exemplary immunomodulators include, e.g., afutuzumab (available from Roche®); pegfilgrastim (Neulasta®); lenalidomide (CC-5013, Revlimid®); thalidomide (Thalomid®), pomelidomide, actimid (CC4047); and IRX-2 (mixture of human cytokines including interleukin 1, interleukin 2, and interferon γ, CAS 951209-71-5, available from IRX Therapeutics).

Exemplary anthracyclines include, e.g., doxorubicin (Adriamycin® and Rubex®); bleomycin (Lenoxane®);

daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include bortezomib (Velcade®); carfilzomib (PX-171-007, (S)-4-Methyl-N-((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In embodiments, a CAR-expressing cell described herein, optionally in combination with a kinase inhibitor e.g., a BTK inhibitor such as ibrutinib, is administered to a subject in combination with brentuximab. Brentuximab is an antibody-drug conjugate of anti-CD30 antibody and monomethyl auristatin E. In embodiments, the subject has Hodgkin lymphoma (HL), e.g., relapsed or refractory HL. In embodiments, the subject comprises CD30+HL. In embodiments, the subject has undergone an autologous stem cell transplant (ASCT). In embodiments, the subject has not undergone an ASCT. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In embodiments, a CAR-expressing cell described herein, optionally in combination with a kinase inhibitor e.g., a BTK inhibitor such as ibrutinib, is administered to a subject in combination with brentuximab and dacarbazine or in combination with brentuximab and bendamustine. Dacarbazine is an alkylating agent with a chemical name of 5-(3,3-Dimethyl-1-triazenyl)imidazole-4-carboxamide. Bendamustine is an alkylating agent with a chemical name of 4-[5-[Bis(2-chloroethyl)amino]-1-methylbenzimidazol-2-yl]butanoic acid. In embodiments, the subject has Hodgkin lymphoma (HL). In embodiments, the subject has not previously been treated with a cancer therapy. In embodiments, the subject is at least 60 years of age, e.g., 60, 65, 70, 75, 80, 85, or older. In embodiments, dacarbazine is administered at a dosage of about 300-450 mg/m$^2$ (e.g., about 300-325, 325-350, 350-375, 375-400, 400-425, or 425-450 mg/m$^2$), e.g., intravenously. In embodiments, bendamustine is administered at a dosage of about 75-125 mg/m$^2$ (e.g., 75-100 or 100-125 mg/m$^2$, e.g., about 90 mg/m$^2$), e.g., intravenously. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In some embodiments, a CAR-expressing cell described herein is administered to a subject in combination with a CD20 inhibitor, e.g., an anti-CD20 antibody (e.g., an anti-CD20 mono- or bispecific antibody) or a fragment thereof. Exemplary anti-CD20 antibodies include but are not limited to rituximab, ofatumumab, ocrelizumab, veltuzumab, obinutuzumab, TRU-015 (Trubion Pharmaceuticals), ocaratuzumab, and Pro131921 (Genentech). See, e.g., Lim et al. Haematologica. 95.1 (2010):135-43.

In some embodiments, the anti-CD20 antibody comprises rituximab. Rituximab is a chimeric mouse/human monoclonal antibody IgG1 kappa that binds to CD20 and causes cytolysis of a CD20 expressing cell, e.g., as described in www.accessdata.fda.gov/drugsatfda_docs/label/2010/103705s5311lbl.pdf. In embodiments, a CAR-expressing cell described herein is administered to a subject in combination with rituximab. In embodiments, the subject has CLL or SLL.

In some embodiments, rituximab is administered intravenously, e.g., as an intravenous infusion. For example, each infusion provides about 500-2000 mg (e.g., about 500-550, 550-600, 600-650, 650-700, 700-750, 750-800, 800-850, 850-900, 900-950, 950-1000, 1000-1100, 1100-1200, 1200-1300, 1300-1400, 1400-1500, 1500-1600, 1600-1700, 1700-1800, 1800-1900, or 1900-2000 mg) of rituximab. In some embodiments, rituximab is administered at a dose of 150 mg/m$^2$ to 750 mg/m$^2$, e.g., about 150-175 mg/m$^2$, 175-200 mg/m$^2$, 200-225 mg/m$^2$, 225-250 mg/m$^2$, 250-300 mg/m$^2$, 300-325 mg/m$^2$, 325-350 mg/m$^2$, 350-375 mg/m$^2$, 375-400 mg/m$^2$, 400-425 mg/m$^2$, 425-450 mg/m$^2$, 450-475 mg/m$^2$, 475-500 mg/m$^2$, 500-525 mg/m$^2$, 525-550 mg/m$^2$, 550-575 mg/m$^2$, 575-600 mg/m$^2$, 600-625 mg/m$^2$, 625-650 mg/m$^2$, 650-675 mg/m$^2$, or 675-700 mg/m$^2$, where m$^2$ indicates the body surface area of the subject. In some embodiments, rituximab is administered at a dosing interval of at least 4 days, e.g., 4, 7, 14, 21, 28, 35 days, or more. For example, rituximab is administered at a dosing interval of at least 0.5 weeks, e.g., 0.5, 1, 2, 3, 4, 5, 6, 7, 8 weeks, or more. In some embodiments, rituximab is administered at a dose and dosing interval described herein for a period of time, e.g., at least 2 weeks, e.g., at least 2, 3, 4, 5, 6, 7, 8, 9, 10, 11, 12, 13, 14, 15, 16, 17, 18, 19, 20 weeks, or greater. For example, rituximab is administered at a dose and dosing interval described herein for a total of at least 4 doses per treatment cycle (e.g., at least 4, 5, 6, 7, 8, 9, 10, 11, 12, 13, 14, 15, 16, or more doses per treatment cycle).

In some embodiments, the anti-CD20 antibody comprises ofatumumab. Ofatumumab is an anti-CD20 IgG1κ human monoclonal antibody with a molecular weight of approximately 149 kDa. For example, ofatumumab is generated using transgenic mouse and hybridoma technology and is expressed and purified from a recombinant murine cell line (NS0). See, e.g., www.accessdata.fda.gov/drugsatfda_docs/label/2009/125326lbl.pdf; and Clinical Trial Identifier number NCT01363128, NCT01515176, NCT01626352, and NCT01397591. In embodiments, a CAR-expressing cell described herein is administered to a subject in combination with ofatumumab. In embodiments, the subject has CLL or SLL.

In some embodiments, ofatumumab is administered as an intravenous infusion. For example, each infusion provides about 150-3000 mg (e.g., about 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1200, 1200-1400, 1400-1600, 1600-1800, 1800-2000, 2000-2200, 2200-2400, 2400-2600, 2600-2800, or 2800-3000 mg) of ofatumumab. In embodiments, ofatumumab is administered at a starting dosage of about 300 mg, followed by 2000 mg, e.g., for about 11 doses, e.g., for 24 weeks. In some embodiments, ofatumumab is administered at a dosing interval of at least 4 days, e.g., 4, 7, 14, 21, 28, 35 days, or more. For example, ofatumumab is administered at a dosing interval of at least 1 week, e.g., 1, 2, 3, 4, 5, 6, 7, 8, 9, 10, 11, 12, 24, 26, 28, 20, 22, 24, 26, 28, 30 weeks, or more. In some embodiments, ofatumumab is administered at a dose and dosing interval described herein for a period of time, e.g., at least 1 week, e.g., 1, 2, 3, 4, 5, 6, 7, 8, 9, 10, 11, 12, 13, 14, 15, 16, 17, 18, 19, 20, 22, 24, 26, 28, 30, 40, 50, 60 weeks or greater, or 1, 2, 3, 4, 5, 6, 7, 8, 9, 10, 11, 12 months or greater, or 1, 2, 3, 4, 5 years or greater. For example, ofatumumab is administered at a dose and dosing interval described herein for a total of at least 2 doses per treatment cycle (e.g., at least 2, 3, 4, 5, 6, 7, 8, 9, 10, 11, 12, 13, 14, 15, 16, 18, 20, or more doses per treatment cycle).

In some cases, the anti-CD20 antibody comprises ocrelizumab. Ocrelizumab is a humanized anti-CD20 monoclonal antibody, e.g., as described in Clinical Trials Identifier Nos. NCT00077870, NCT01412333, NCT00779220, NCT00673920, NCT01194570, and Kappos et al. Lancet. 19.378 (2011):1779-87.

In some cases, the anti-CD20 antibody comprises veltuzumab. Veltuzumab is a humanized monoclonal antibody against CD20. See, e.g., Clinical Trial Identifier No. NCT00547066, NCT00546793, NCT01101581, and Goldenberg et al. Leuk Lymphoma. 51(5)(2010):747-55.

In some cases, the anti-CD20 antibody comprises GA101. GA101 (also called obinutuzumab or RO5072759) is a humanized and glyco-engineered anti-CD20 monoclonal antibody. See, e.g., Robak. Curr. Opin. Investig. Drugs. 10.6 (2009):588-96; Clinical Trial Identifier Numbers: NCT01995669, NCT01889797, NCT02229422, and NCT01414205; and www.accessdata.fda.gov/drugsatfda_docs/label/2013/125486s000lbl.pdf.

In some cases, the anti-CD20 antibody comprises AME-133v. AME-133v (also called LY2469298 or ocaratuzumab) is a humanized IgG1 monoclonal antibody against CD20 with increased affinity for the FcγRIIIa receptor and an enhanced antibody dependent cellular cytotoxicity (ADCC) activity compared with rituximab. See, e.g., Robak et al. BioDrugs 25.1 (2011):13-25; and Forero-Torres et al. Clin Cancer Res. 18.5 (2012):1395-403.

In some cases, the anti-CD20 antibody comprises PRO131921. PRO131921 is a humanized anti-CD20 monoclonal antibody engineered to have better binding to FcγRIIIa and enhanced ADCC compared with rituximab. See, e.g., Robak et al. BioDrugs 25.1 (2011):13-25; and Casulo et al. Clin Immunol. 154.1 (2014):37-46; and Clinical Trial Identifier No. NCT00452127.

In some cases, the anti-CD20 antibody comprises TRU-015. TRU-015 is an anti-CD20 fusion protein derived from domains of an antibody against CD20. TRU-015 is smaller than monoclonal antibodies, but retains Fc-mediated effector functions. See, e.g., Robak et al. BioDrugs 25.1 (2011):13-25. TRU-015 contains an anti-CD20 single-chain variable fragment (scFv) linked to human IgG1 hinge, CH2, and CH3 domains but lacks CH1 and CL domains.

In some embodiments, an anti-CD20 antibody described herein is conjugated or otherwise bound to a therapeutic agent, e.g., a chemotherapeutic agent (e.g., cytoxan, fludarabine, histone deacetylase inhibitor, demethylating agent, peptide vaccine, anti-tumor antibiotic, tyrosine kinase inhibitor, alkylating agent, anti-microtubule or anti-mitotic agent), anti-allergic agent, anti-nausea agent (or anti-emetic), pain reliever, or cytoprotective agent described herein.

In embodiments, a CAR-expressing cell described herein is administered to a subject in combination with a B-cell lymphoma 2 (BCL-2) inhibitor (e.g., venetoclax, also called ABT-199 or GDC-0199;) and/or rituximab. In embodiments, a CAR-expressing cell described herein is administered to a subject in combination with venetoclax and rituximab. Venetoclax is a small molecule that inhibits the anti-apoptotic protein, BCL-2. The structure of venetoclax (4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) is shown below.

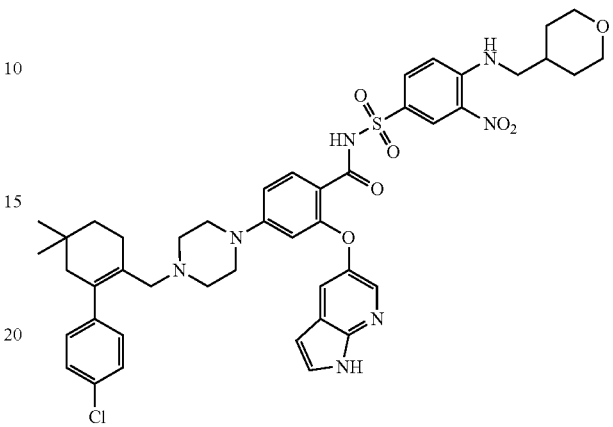

In embodiments, the subject has CLL. In embodiments, the subject has relapsed CLL, e.g., the subject has previously been administered a cancer therapy. In embodiments, venetoclax is administered at a dosage of about 15-600 mg (e.g., 15-20, 20-50, 50-75, 75-100, 100-200, 200-300, 300-400, 400-500, or 500-600 mg), e.g., daily. In embodiments, rituximab is administered at a dosage of about 350-550 mg/m2 (e.g., 350-375, 375-400, 400-425, 425-450, 450-475, or 475-500 mg/m2), e.g., intravenously, e.g., monthly.

In an embodiment, cells expressing a CAR described herein, optionally in combination with a kinase inhibitor, e.g., a BTK inhibitor such as ibrutinib, are administered to a subject in combination with a molecule that decreases the Treg cell population. Methods that decrease the number of (e.g., deplete) Treg cells are known in the art and include, e.g., CD25 depletion, cyclophosphamide administration, modulating GITR function. Without wishing to be bound by theory, it is believed that reducing the number of Treg cells in a subject prior to apheresis or prior to administration of a CAR-expressing cell described herein reduces the number of unwanted immune cells (e.g., Tregs) in the tumor microenvironment and reduces the subject's risk of relapse. In one embodiment, cells expressing a CAR described herein, optionally in combination with a kinase inhibitor, e.g., a BTK inhibitor such as ibrutinib, are administered to a subject in combination with a molecule targeting GITR and/or modulating GITR functions, such as a GITR agonist and/or a GITR antibody that depletes regulatory T cells (Tregs). In embodiments, cells expressing a CAR described herein, optionally in combination with a kinase inhibitor, e.g., a BTK inhibitor such as ibrutinib, are administered to a subject in combination with cyclophosphamide. In one embodiment, the GITR binding molecules and/or molecules modulating GITR functions (e.g., GITR agonist and/or Treg depleting GITR antibodies) are administered prior to administration of the CAR-expressing cell. For example, in one embodiment, the GITR agonist can be administered prior to apheresis of the cells. In embodiments, cyclophosphamide is administered to the subject prior to administration (e.g., infusion or re-infusion) of the CAR-expressing cell or prior to apheresis of the cells. In embodiments, cyclophosphamide and an anti-GITR antibody are administered to the subject prior to administration (e.g., infusion or re-infusion) of the CAR-expressing cell or prior to apheresis of the cells. In one embodiment, the subject has cancer (e.g., a solid cancer or a hematological cancer such as ALL or CLL). In an embodiment, the subject has CLL. In embodiments, the subject has ALL. In embodiments, the subject has a solid cancer, e.g., a solid cancer described herein.

Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the combination of a CAR expressing cell described herein and a kinase inhibitor described herein is administered to a subject in combination with a GITR agonist, e.g., a GITR agonist described herein. In one embodiment, the GITR agonist is administered prior to the CAR-expressing cell. For example, in one embodiment, the GITR agonist can be administered prior to apheresis of the cells. In one embodiment, the subject has CLL.

Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present invention may be administered to a patient in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAMPATH. In one aspect, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In one embodiment, the subject can be administered an agent which reduces or ameliorates a side effect associated with the administration of a CAR-expressing cell. Side effects associated with the administration of a CAR-expressing cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. Accordingly, the methods described herein can comprise administering a CAR-expressing cell described herein to a subject and further administering an agent to manage elevated levels of a soluble factor resulting from treatment with a CAR-expressing cell. In one embodiment, the soluble factor elevated in the subject is one or more of IFN-γ, TNFα, IL-2 receptor and IL-6. Therefore, an agent administered to treat this side effect can be an agent that neutralizes one or more of these soluble factors. Examples of such agents include, but are not limited to a steroid (e.g., corticosteroid), an inhibitor of TNFα, and an inhibitor of IL-6. An example of a TNFα inhibitor is an anti-TNFα antibody molecule such as, infliximab, adalimumab, certolizumab pegol, and golimumab. Another example of a TNFα inhibitor is a fusion protein such as entanercept. Small molecule inhibitor of TNFα include, but are not limited to, xanthine derivatives (e.g. pentoxifylline) and bupropion. An example of an IL-6 inhibitor is an anti-IL-6 antibody molecule or anti-IL-6 receptor antibody molecule such as tocilizumab (toc), sarilumab, elsilimomab, CNTO 328, ALD518/BMS-945429, CNTO 136, CPSI-2364, CDP6038, VX30, ARGX-109, FE301, and FM101. In one embodiment, the anti-IL-6 receptor antibody molecule is tocilizumab. An example of an IL-1R based inhibitor is anakinra.

In one embodiment, the subject can be administered an agent which enhances the activity of a CAR-expressing cell. For example, in one embodiment, the agent can be an agent which inhibits an inhibitory molecule. Inhibitory molecules, e.g., Programmed Death 1 (PD1), can, in some embodiments, decrease the ability of a CAR-expressing cell to mount an immune effector response. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), can be used to inhibit expression of an inhibitory molecule in the CAR-expressing cell. In an embodiment the inhibitor is an shRNA. In an embodiment, the inhibitory molecule is inhibited within a CAR-expressing cell. In these embodiments, a dsRNA molecule that inhibits expression of the inhibitory molecule is linked to the nucleic acid that encodes a component, e.g., all of the components, of the CAR. In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206).). In an embodiment, the agent is an antibody or antibody fragment that binds to TIM3. In an embodiment, the agent is an antibody or antibody fragment that binds to LAG3. In an embodiment, the agent is an antibody or antibody fragment that binds to CEACAM (e.g., CEACAM-1, CEACAM-3 and/or CEACAM-5).

PD1 is an inhibitory member of the CD28 family of receptors that also includes CD28, CTLA-4, ICOS, and BTLA. PD1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et al. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005

Cancer Immunol. Immunother 54:307-314; Konishi et al. 2004 Clin Cancer Res 10:5094). Immune suppression can be reversed by inhibiting the local interaction of PD1 with PD-L1. Antibodies, antibody fragments, and other inhibitors of PD1, PD-L1 and PD-L2 are known and may be used in combination with a CD19 CAR described herein. For example, nivolumab (also referred to as BMS-936558 or MDX1106; Bristol-Myers Squibb) is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. Pidilizumab (CT-011; Cure Tech) is a humanized IgG1k monoclonal antibody that binds to PD1. Pidilizumab and other humanized anti-PD1 monoclonal antibodies are disclosed in WO2009/101611. Pembrolizumab (formerly known as lambrolizumab, and also referred to as Keytruda, MK03475; Merck) is a humanized IgG4 monoclonal antibody that binds to PD1. Pembrolizumab and other humanized anti-PD1 antibodies are disclosed in U.S. Pat. No. 8,354,509 and WO2009/114335. MEDI4736 (Medimmune) is a human monoclonal antibody that binds to PDL1, and inhibits interaction of the ligand with PD1. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.570 (heavy and light chain variable regions are shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD1 and B7-H1. Other anti-PD1 antibodies include AMP 514 (Amplimmune), among others, e.g., anti-PD1 antibodies disclosed in U.S. Pat. No. 8,609,089, US 2010028330, and/or US 20120114649.

TIM3 (T cell immunoglobulin-3) also negatively regulates T cell function, particularly in IFN-g-secreting CD4+T helper 1 and CD8+T cytotoxic 1 cells, and plays a critical role in T cell exhaustion. Inhibition of the interaction between TIM3 and its ligands, e.g., galectin-9 (Gal9), phosphotidylserine (PS), and HMGB1, can increase immune response. Antibodies, antibody fragments, and other inhibitors of TIM3 and its ligands are available in the art and may be used combination with a CD19 CAR described herein. For example, antibodies, antibody fragments, small molecules, or peptide inhibitors that target TIM3 binds to the IgV domain of TIM3 to inhibit interaction with its ligands. Antibodies and peptides that inhibit TIM3 are disclosed in WO2013/006490 and US20100247521. Other anti-TIM3 antibodies include humanized versions of RMT3-23 (disclosed in Ngiow et al., 2011, Cancer Res, 71:3540-3551), and clone 8B.2C12 (disclosed in Monney et al., 2002, Nature, 415:536-541). Bi-specific antibodies that inhibit TIM3 and PD-1 are disclosed in US20130156774.

In other embodiments, the agent which enhances the activity of a CAR-expressing cell is a CEACAM inhibitor (e.g., CEACAM-1, CEACAM-3, and/or CEACAM-5 inhibitor). In one embodiment, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. *PLoS One.* 2010 Sep. 2; 5(9). pii: e12529 (DOI:10:1371/journal.pone.0021146), or crossreacts with CEACAM-1 and CEACAM-5 as described in, e.g., WO 2013/054331 and US 2014/0271618.

Without wishing to be bound by theory, carcinoembryonic antigen cell adhesion molecules (CEACAM), such as CEACAM-1 and CEACAM-5, are believed to mediate, at least in part, inhibition of an anti-tumor immune response (see e.g., Markel et al. *J Immunol.* 2002 Mar. 15; 168(6): 2803-10; Markel et al. *J Immunol.* 2006 Nov. 1; 177(9): 6062-71; Markel et al. *Immunology.* 2009 February; 126(2): 186-200; Markel et al. Cancer *Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529). For example, CEACAM-1 has been described as a heterophilic ligand for TIM-3 and as playing a role in TIM-3-mediated T cell tolerance and exhaustion (see e.g., WO 2014/022332; Huang, et al. (2014) *Nature* doi:10.1038/nature13848). In embodiments, co-blockade of CEACAM-1 and TIM-3 has been shown to enhance an anti-tumor immune response in xenograft colorectal cancer models (see e.g., WO 2014/022332; Huang, et al. (2014), supra). In other embodiments, co-blockade of CEACAM-1 and PD-1 reduce T cell tolerance as described, e.g., in WO 2014/059251. Thus, CEACAM inhibitors can be used with the other immunomodulators described herein (e.g., anti-PD-1 and/or anti-TIM-3 inhibitors) to enhance an immune response against a cancer, e.g., a melanoma, a lung cancer (e.g., NSCLC), a bladder cancer, a colon cancer an ovarian cancer, and other cancers as described herein.

LAG3 (lymphocyte activation gene-3 or CD223) is a cell surface molecule expressed on activated T cells and B cells that has been shown to play a role in CD8+ T cell exhaustion. Antibodies, antibody fragments, and other inhibitors of LAG3 and its ligands are available in the art and may be used combination with a CD19 CAR described herein. For example, BMS-986016 (Bristol-Myers Squib) is a monoclonal antibody that targets LAG3. IMP701 (Immutep) is an antagonist LAG3 antibody and. IMP731 (Immutep and GlaxoSmithKline) is a depleting LAG3 antibody. Other LAG3 inhibitors include IMP321 (Immutep), which is a recombinant fusion protein of a soluble portion of LAG3 and Ig that binds to MHC class II molecules and activates antigen presenting cells (APC). Other antibodies are disclosed, e.g., in WO2010/019570.

In some embodiments, the CAR therapy and kinase inhibitor are administered in combination with a toll like receptor (TLR) agonist. The TLR agonist can be a TLR9 agonist. In some embodiments, the TLR agonist is an oligodeoxynucleotide, e.g., a CG-enriched oligodeoxynucleotide, e.g., an unmethylated CG-enriched oligodeoxynucleotide. See, e.g., Sagiv-Barfi et al., "Ibrutinib enhances the antitumor immune response induced by intratumoral injection of a TLR9 ligand in syngeneic mouse lymphoma model." Blood. 2015 Feb. 6. pii: blood-2014-08-593137, which is incorporated herein by reference in its entirety. In some embodiments, the TLR agonist is administered in combination with a CAR-expressing NK cell. Without being bound by theory, the TLR agonist may promote activation of NK cells such as CAR-expressing NK cells. In some embodiments, the TLR agonist is administered by injection, e.g., intratumoral injection.

In some embodiments, the agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an antracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the CAR. In another embodiment, the fusion protein is expressed by a cell, e.g., a T cell that does not express an anti-CD19 CAR.

In one embodiment, the agent which enhances activity of a CAR-expressing cell described herein is miR-17-92.

In one embodiment, the agent which enhances activity of a CAR-described herein is a cytokine. Cytokines have important functions related to T cell expansion, differentiation, survival, and homeostatis. Cytokines that can be administered to the subject receiving a CAR-expressing cell described herein include: IL-2, IL-4, IL-7, IL-9, IL-15, IL-18, and IL-21, or a combination thereof. In preferred embodiments, the cytokine administered is IL-7, IL-15, or IL-21, or a combination thereof. The cytokine can be administered once a day or more than once a day, e.g., twice a day, three times a day, or four times a day. The cytokine can be administered for more than one day, e.g. the cytokine is administered for 2 days, 3 days, 4 days, 5 days, 6 days, 1 week, 2 weeks, 3 weeks, or 4 weeks. For example, the cytokine is administered once a day for 7 days.

In embodiments, the cytokine is administered in combination with CAR-expressing cells. The cytokine can be administered simultaneously or concurrently with the CAR-expressing cells, e.g., administered on the same day. The cytokine may be prepared in the same pharmaceutical composition as the CAR-expressing cells, or may be prepared in a separate pharmaceutical composition. Alternatively, the cytokine can be administered shortly after administration of the CAR-expressing T cells, e.g., 1 day, 2 days, 3 days, 4 days, 5 days, 6 days, or 7 days after administration of the CAR-expressing cells. In embodiments where the cytokine is administered in a dosing regimen that occurs over more than one day, the first day of the cytokine dosing regimen can be on the same day as administration with the CAR-expressing cells, or the first day of the cytokine dosing regimen can be 1 day, 2 days, 3 days, 4 days, 5 days, 6 days, or 7 days after administration of the CAR-expressing T cells. In one embodiment, on the first day, the CAR-expressing cells are administered to the subject, and on the second day, a cytokine is administered once a day for the next 7 days. In a preferred embodiment, the cytokine to be administered in combination with the CAR-expressing cells is IL-7, IL-15, and/or IL-21.

In other embodiments, the cytokine is administered a sufficient period of time after administration of the CAR-expressing cells, e.g., at least 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells. In one embodiment, the cytokine is administered after assessment of the subject's response to the CAR-expressing cells. For example, the subject is administered CAR-expressing cells according to the dosage and regimens described herein. The response of the subject to CART therapy is assessed at 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells, using any of the methods described herein, including inhibition of tumor growth, reduction of circulating tumor cells, or tumor regression. Subjects that do not exhibit a sufficient response to CART therapy can be administered a cytokine. Administration of the cytokine to the subject that has sub-optimal response to the CART therapy improves CART efficacy and/or anti-tumor activity. In a preferred embodiment, the cytokine administered after administration of CAR-expressing cells is IL-7.

Combination with a Low Dose of an mTOR Inhibitor

In one embodiment, the cells expressing a CAR molecule, e.g., a CAR molecule described herein, are administered in combination with a low, immune enhancing dose of an mTOR inhibitor.

In an embodiment, a dose of an mTOR inhibitor is associated with, or provides, mTOR inhibition of at least 5 but no more than 90%, at least 10 but no more than 90%, at least 15, but no more than 90%, at least 20 but no more than 90%, at least 30 but no more than 90%, at least 40 but no more than 90%, at least 50 but no more than 90%, at least 60 but no more than 90%, or at least 70 but no more than 90%.

In an embodiment, a dose of an mTOR inhibitor is associated with, or provides, mTOR inhibition of at least 5 but no more than 80%, at least 10 but no more than 80%, at least 15, but no more than 80%, at least 20 but no more than 80%, at least 30 but no more than 80%, at least 40 but no more than 80%, at least 50 but no more than 80%, or at least 60 but no more than 80%.

In an embodiment, a dose of an mTOR inhibitor is associated with, or provides, mTOR inhibition of at least 5 but no more than 70%, at least 10 but no more than 70%, at least 15, but no more than 70%, at least 20 but no more than 70%, at least 30 but no more than 70%, at least 40 but no more than 70%, or at least 50 but no more than 70%.

In an embodiment, a dose of an mTOR inhibitor is associated with, or provides, mTOR inhibition of at least 5 but no more than 60%, at least 10 but no more than 60%, at least 15, but no more than 60%, at least 20 but no more than 60%, at least 30 but no more than 60%, or at least 40 but no more than 60%.

In an embodiment, a dose of an mTOR inhibitor is associated with, or provides, mTOR inhibition of at least 5 but no more than 50%, at least 10 but no more than 50%, at least 15, but no more than 50%, at least 20 but no more than 50%, at least 30 but no more than 50%, or at least 40 but no more than 50%.

In an embodiment, a dose of an mTOR inhibitor is associated with, or provides, mTOR inhibition of at least 5 but no more than 40%, at least 10 but no more than 40%, at least 15, but no more than 40%, at least 20 but no more than 40%, at least 30 but no more than 40%, or at least 35 but no more than 40%.

In an embodiment, a dose of an mTOR inhibitor is associated with, or provides, mTOR inhibition of at least 5 but no more than 30%, at least 10 but no more than 30%, at least 15, but no more than 30%, at least 20 but no more than 30%, or at least 25 but no more than 30%.

In an embodiment, a dose of an mTOR inhibitor is associated with, or provides, mTOR inhibition of at least 1, 2, 3, 4 or 5 but no more than 20%, at least 1, 2, 3, 4 or 5 but no more than 30%, at least 1, 2, 3, 4 or 5, but no more than 35, at least 1, 2, 3, 4 or 5 but no more than 40%, or at least 1, 2, 3, 4 or 5 but no more than 45%.

In an embodiment, a dose of an mTOR inhibitor is associated with, or provides, mTOR inhibition of at least 1, 2, 3, 4 or 5 but no more than 90%.

As is discussed herein, the extent of mTOR inhibition can be expressed as the extent of P70 S6 kinase inhibition, e.g., the extent of mTOR inhibition can be determined by the level of decrease in P70 S6 kinase activity, e.g., by the decrease in phosphorylation of a P70 S6 kinase substrate. The level of mTOR inhibition can be evaluated by a method described herein, e.g. by the Boulay assay, or measurement of phosphorylated S6 levels by western blot.

Exemplary mTOR Inhibitors

As used herein, the term "mTOR inhibitor" refers to a compound or ligand, or a pharmaceutically acceptable salt thereof, which inhibits the mTOR kinase in a cell. In an embodiment an mTOR inhibitor is an allosteric inhibitor. In an embodiment an mTOR inhibitor is a catalytic inhibitor.

Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity.

Rapamycin is a known macrolide antibiotic produced by *Streptomyces hygroscopicus* having the structure shown in Formula A.

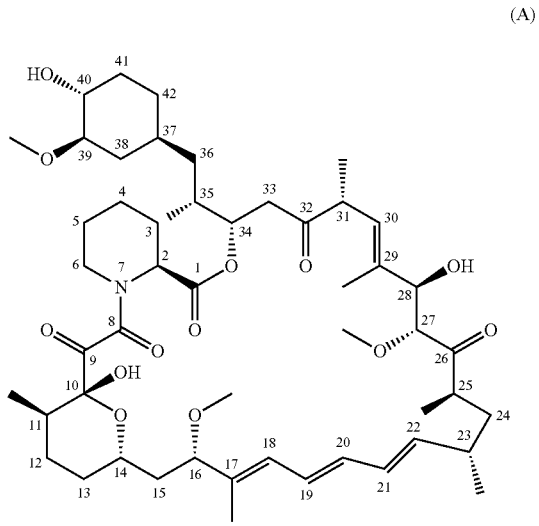 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

(A)

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. There are various numbering schemes proposed for rapamycin. To avoid confusion, when specific rapamycin analogs are named herein, the names are given with reference to rapamycin using the numbering scheme of formula A.

Rapamycin analogs useful in the invention are, for example, 0-substituted analogs in which the hydroxyl group on the cyclohexyl ring of rapamycin is replaced by $OR_1$ in which $R_1$ is hydroxyalkyl, hydroxyalkoxyalkyl, acylaminoalkyl, or aminoalkyl; e.g. RAD001, also known as, everolimus as described in U.S. Pat. No. 5,665,772 and WO94/09010 the contents of which are incorporated by reference. Other suitable rapamycin analogs include those substituted at the 26- or 28-position. The rapamycin analog may be an epimer of an analog mentioned above, particularly an epimer of an analog substituted in position 40, 28 or 26, and may optionally be further hydrogenated, e.g. as described in U.S. Pat. No. 6,015,815, WO95/14023 and WO99/15530 the contents of which are incorporated by reference, e.g. ABT578 also known as zotarolimus or a rapamycin analog described in U.S. Pat. No. 7,091,213, WO98/02441 and WO01/14387 the contents of which are incorporated by reference, e.g. AP23573 also known as ridaforolimus.

Examples of rapamycin analogs suitable for use in the present invention from U.S. Pat. No. 5,665,772 include, but are not limited to, 40-O-benzyl-rapamycin, 40-O-(4'-hydroxymethyl)benzyl-rapamycin, 40-O-[4'-(1,2-dihydroxyethyl)]benzyl-rapamycin, 40-O-allyl-rapamycin, 40-O-[3'-(2,2-dimethyl-1,3-dioxolan-4(S)-yl)-prop-2'-en-1'-yl]-rapamycin, (2'E,4'S)-40-O-(4',5'-dihydroxypent-2'-en-1'-yl)-rapamycin, 40-O-(2-hydroxy)ethoxycarbonylmethyl-rapamycin, 40-O-(2-hydroxy)ethyl-rapamycin, 40-O-(3-hydroxy)propyl-rapamycin, 40-O-(6-hydroxy)hexyl-rapamycin, 40-O-[2-(2-hydroxy)ethoxy]ethyl-rapamycin, 40-O-[(3S)-2,2-dimethyldioxolan-3-yl]methyl-rapamycin, 40-O-[(2S)-2,3-dihydroxyprop-1-yl]-rapamycin, 40-O-(2-acetoxy)ethyl-rapamycin, 40-O-(2-nicotinoyloxy)ethyl-rapamycin, 40-O-[2-(N-morpholino)acetoxy]ethyl-rapamycin, 40-O-(2-N-imidazolylacetoxy)ethyl-rapamycin, 40-O-[2-(N-methyl-N'-piperazinyl)acetoxy]ethyl-rapamycin, 39-O-desmethyl-39,40-O,O-ethylene-rapamycin, (26R)-26-dihydro-40-O-(2-hydroxy)ethyl-rapamycin, 40-O-(2-aminoethyl)-rapamycin, 40-O-(2-acetaminoethyl)-rapamycin, 40-O-(2-nicotinamidoethyl)-rapamycin, 40-O-(2-(N-methyl-imidazo-2'-ylcarbethoxamido)ethyl)-rapamycin, 40-O-(2-ethoxycarbonylaminoethyl)-rapamycin, 40-O-(2-tolylsulfonamidoethyl)-rapamycin and 40-O-[2-(4',5'-dicarboethoxy-1',2',3'-triazol-1'-yl)-ethyl]-rapamycin.

Other rapamycin analogs useful in the present invention are analogs where the hydroxyl group on the cyclohexyl ring of rapamycin and/or the hydroxy group at the 28 position is replaced with an hydroxyester group are known, for example, rapamycin analogs found in U.S. RE44,768, e.g. temsirolimus.

Other rapamycin analogs useful in the preset invention include those wherein the methoxy group at the 16 position is replaced with another substituent, preferably (optionally hydroxy-substituted) alkynyloxy, benzyl, orthomethoxybenzyl or chlorobenzyl and/or wherein the mexthoxy group at the 39 position is deleted together with the 39 carbon so that the cyclohexyl ring of rapamycin becomes a cyclopentyl ring lacking the 39 position methyoxy group; e.g. as described in WO95/16691 and WO96/41807 the contents of which are incorporated by reference. The analogs can be further modified such that the hydroxy at the 40-position of rapamycin is alkylated and/or the 32-carbonyl is reduced.

Rapamycin analogs from WO95/16691 include, but are not limited to, 16-demthoxy-16-(pent-2-ynyl)oxy-rapamycin, 16-demthoxy-16-(but-2-ynyl)oxy-rapamycin, 16-demthoxy-16-(propargyl)oxy-rapamycin, 16-demethoxy-16-(4-hydroxy-but-2-ynyl)oxy-rapamycin, 16-demthoxy-16-benzyloxy-40-O-(2-hydroxyethyl)-rapamycin, 16-demthoxy-16-benzyloxy-rapamycin, 16-demethoxy-16-ortho-methoxybenzyl-rapamycin, 16-demethoxy-40-O-(2-methoxyethyl)-16-pent-2-ynyl)oxy-rapamycin, 39-demethoxy-40-desoxy-39-formyl-42-nor-rapamycin, 39-demethoxy-40-desoxy-39-hydroxymethyl-42-nor-rapamycin, 39-demethoxy-40-desoxy-39-carboxy-42-nor-rapamycin, 39-demethoxy-40-desoxy-39-(4-methylpiperazin-1-yl)carbonyl-42-nor-rapamycin, 39-demethoxy-40-desoxy-39-(morpholin-4-yl)carbonyl-42-nor-rapamycin, 39-demethoxy-40-desoxy-39-[N-methyl, N-(2-pyridin-2-yl-ethyl)]carbamoyl-42-nor-rapamycin and 39-demethoxy-40-desoxy-39-(p-toluenesulfonylhydrazonomethyl)-42-nor-rapamycin.

Rapamycin analogs from WO96/41807 include, but are not limited to, 32-deoxo-rapamycin, 16-O-pent-2-ynyl-32-deoxo-rapamycin, 16-O-pent-2-ynyl-32-deoxo-40-O-(2-hydroxy-ethyl)-rapamycin, 16-O-pent-2-ynyl-32-(S)-dihydro-40-O-(2-hydroxyethyl)-rapamycin, 32(S)-dihydro-40-O-(2-methoxy)ethyl-rapamycin and 32(S)-dihydro-40-O-(2-hydroxyethyl)-rapamycin.

Another suitable rapamycin analog is umirolimus as described in US2005/0101624 the contents of which are incorporated by reference.

RAD001, otherwise known as everolimus (Afinitor®), has the chemical name (1R,9S,12S,15R,16E,18R,19R,21R,23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29,35-hexamethyl-11,36-dioxa-4-aza-tricyclo[30.3.1.04,9]hexatriaconta-16,24,26,28-tetraene-2,3,10,14,20-pentaone Further examples of allosteric mTOR inhibitors include sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/MK-8669). Other examples of allosteric mTor inhibitors include zotarolimus (ABT578) and umirolimus.

Alternatively or additionally, catalytic, ATP-competitive mTOR inhibitors have been found to target the mTOR kinase domain directly and target both mTORC1 and mTORC2. These are also more effective inhibitors of mTORC1 than such allosteric mTOR inhibitors as rapamycin, because they modulate rapamycin-resistant mTORC1 outputs such as 4EBP1-T37/46 phosphorylation and cap-dependent translation.

Catalytic inhibitors include: BEZ235 or 2-methyl-2-[4-(3-methyl-2-oxo-8-quinolin-3-yl-2,3-dihydro-imidazo[4,5-c]quinolin-1-yl)-phenyl]-propionitrile, or the monotosylate salt form. the synthesis of BEZ235 is described in WO2006/122806; CCG168 (otherwise known as AZD-8055, Chresta, C. M., et al., Cancer Res, 2010, 70(1), 288-298) which has the chemical name {5-[2,4-bis-((S)-3-methyl-morpholin-4-yl)-pyrido[2,3d]pyrimidin-7-yl]-2-methoxy-phenyl}-methanol; 3-[2,4-bis[(3S)-3-methylmorpholin-4-yl]pyrido[2,3-d]pyrimidin-7-yl]-N-methylbenzamide (WO09104019); 3-(2-aminobenzo[d]oxazol-5-yl)-1-isopropyl-1H-pyrazolo[3,4-d]pyrimidin-4-amine (WO10051043 and WO2013023184); A N-(3-(N-(3-((3,5-dimethoxyphenyl)amino)quinoxaline-2-yl)sulfamoyl)phenyl)-3-methoxy-4-methylbenzamide (WO07044729 and WO12006552); PKI-587 (Venkatesan, A. M., J. Med. Chem., 2010, 53, 2636-2645) which has the chemical name 1-[4-[4-(dimethylamino)piperidine-1-carbonyl]phenyl]-3-[4-(4,6-dimorpholino-1,3,5-triazin-2-yl)phenyl]urea; GSK-2126458 (ACS Med. Chem. Lett., 2010, 1, 39-43) which has the chemical name 2,4-difluoro-N-{2-methoxy-5-[4-(4-pyridazinyl)-6-quinolinyl]-3-pyridinyl}benzenesulfonamide; 5-(9-isopropyl-8-methyl-2-morpholino-9H-purin-6-yl)pyrimidin-2-amine (WO10114484); (E)-N-(8-(6-amino-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide (WO12007926).

Further examples of catalytic mTOR inhibitors include 8-(6-methoxy-pyridin-3-yl)-3-methyl-1-(4-piperazin-1-yl-3-trifluoromethyl-phenyl)-1,3-dihydro-imidazo[4,5-c]quinolin-2-one (WO2006/122806) and Ku-0063794 (Garcia-Martinez J M, et al., Biochem J., 2009, 421(1), 29-42. Ku-0063794 is a specific inhibitor of the mammalian target of rapamycin (mTOR).) WYE-354 is another example of a catalytic mTor inhibitor (Yu K, et al. (2009). Biochemical, Cellular, and In vivo Activity of Novel ATP-Competitive and Selective Inhibitors of the Mammalian Target of Rapamycin. Cancer Res. 69(15): 6232-6240).

mTOR inhibitors useful according to the present invention also include prodrugs, derivatives, pharmaceutically acceptable salts, or analogs thereof of any of the foregoing.

mTOR inhibitors, such as RAD001, may be formulated for delivery based on well-established methods in the art based on the particular dosages described herein. In particular, U.S. Pat. No. 6,004,973 (incorporated herein by reference) provides examples of formulations useable with the mTOR inhibitors described herein.

Evaluation of mTOR Inhibition mTOR phosphorylates the kinase P70 S6, thereby activating P70 S6 kinase and allowing it to phosphorylate its substrate. The extent of mTOR inhibition can be expressed as the extent of P70 S6 kinase inhibition, e.g., the extent of mTOR inhibition can be determined by the level of decrease in P70 S6 kinase activity, e.g., by the decrease in phosphorylation of a P70 S6 kinase substrate. One can determine the level of mTOR inhibition, by measuring P70 S6 kinase activity (the ability of P70 S6 kinase to phsophorylate a substrate), in the absence of inhibitor, e.g., prior to administration of inhibitor, and in the presences of inhibitor, or after the administration of inhibitor. The level of inhibition of P70 S6 kinase gives the level of mTOR inhibition. Thus, if P70 S6 kinase is inhibited by 40%, mTOR activity, as measured by P70 S6 kinase activity, is inhibited by 40%. The extent or level of inhibition referred to herein is the average level of inhibition over the dosage interval. By way of example, if the inhibitor is given once per week, the level of inhibition is given by the average level of inhibition over that interval, namely a week.

Boulay et al., Cancer Res, 2004, 64:252-61, hereby incorporated by reference, teaches an assay that can be used to assess the level of mTOR inhibition (referred to herein as the Boulay assay). In an embodiment, the assay relies on the measurement of P70 S6 kinase activity from biological samples before and after administration of an mTOR inhibitor, e.g., RAD001. Samples can be taken at preselected times after treatment with an mTOR inhibitor, e.g., 24, 48, and 72 hours after treatment. Biological samples, e.g., from skin or peripheral blood mononuclear cells (PBMCs) can be used. Total protein extracts are prepared from the samples. P70 S6 kinase is isolated from the protein extracts by immunoprecipitation using an antibody that specifically recognizes the P70 S6 kinase. Activity of the isolated P70 S6 kinase can be measured in an in vitro kinase assay. The isolated kinase can be incubated with 40S ribosomal subunit substrates (which is an endogenous substrate of P70 S6 kinase) and gamma-$^{32}$P under conditions that allow phosphorylation of the substrate. Then the reaction mixture can be resolved on an SDS-PAGE gel, and $^{32}$P signal analyzed using a PhosphorImager. A $^{32}$P signal corresponding to the size of the 40S ribosomal subunit indicates phosphorylated substrate and the activity of P70 S6 kinase. Increases and decreases in kinase activity can be calculated by quantifying the area and intensity of the $^{32}$P signal of the phosphorylated substrate (e.g., using ImageQuant, Molecular Dynamics), assigning arbitrary unit values to the quantified signal, and comparing the values from after administration with values from before administration or with a reference value. For example, percent inhibition of kinase activity can be calculated with the following formula: 1−(value obtained after administration/value obtained before administration)×100. As described above, the extent or level of inhibition referred to herein is the average level of inhibition over the dosage interval.

Methods for the evaluation of kinase activity, e.g., P70 S6 kinase activity, are also provided in U.S. Pat. No. 7,727,950, hereby incorporated by reference.

The level of mTOR inhibition can also be evaluated by a change in the ration of PD1 negative to PD1 positive T cells. T cells from peripheral blood can be identified as PD1 negative or positive by art-known methods.

Low-Dose mTOR Inhibitors

Methods described herein use low, immune enhancing, dose mTOR inhibitors, doses of mTOR inhibitors, e.g., allosteric mTOR inhibitors, including rapalogs such as RAD001. In contrast, levels of inhibitor that fully or near fully inhibit the mTOR pathway are immunosuppressive and are used, e.g., to prevent organ transplant rejection. In addition, high doses of rapalogs that fully inhibit mTOR also inhibit tumor cell growth and are used to treat a variety of cancers (See, e.g., Antineoplastic effects of mammalian target of rapamycine inhibitors. Salvadori M. World J Transplant. 2012 Oct. 24; 2(5):74-83; Current and Future Treatment Strategies for Patients with Advanced Hepatocellular Carcinoma: Role of mTOR Inhibition. Finn R S. Liver Cancer. 2012 November; 1(3-4):247-256; Emerging Signaling Pathways in Hepatocellular Carcinoma. Moeini A, Cornellà H, Villanueva A. Liver Cancer. 2012 September; 1(2):83-93; Targeted cancer therapy—Are the days of systemic chemotherapy numbered? Joo W D, Visintin I, Mor G. Maturitas. 2013 Sep. 20.; Role of natural and adaptive immunity in renal cell carcinoma response to VEGFR-TKIs and mTOR inhibitor. Santoni M, Berardi R, Amantini C, Burattini L, Santini D, Santoni G, Cascinu S. Int J Cancer. 2013 Oct. 2).

The present invention is based, at least in part, on the surprising finding that doses of mTOR inhibitors well below those used in current clinical settings had a superior effect in increasing an immune response in a subject and increasing the ratio of PD-1 negative T cells/PD-1 positive T cells. It was surprising that low doses of mTOR inhibitors, producing only partial inhibition of mTOR activity, were able to effectively improve immune responses in human human subjects and increase the ratio of PD-1 negative T cells/PD-1 positive T cells.

Alternatively, or in addition, without wishing to be bound by any theory, it is believed that low, a low, immune enhancing, dose of an mTOR inhibitor can increase naive T cell numbers, e.g., at least transiently, e.g., as compared to a non-treated subject. Alternatively or additionally, again while not wishing to be bound by theory, it is believed that treatment with an mTOR inhibitor after a sufficient amount of time or sufficient dosing results in one or more of the following:

an increase in the expression of one or more of the following markers: $CD62L^{high}$, $CD127^{high}$, $CD27^+$, and BCL2, e.g., on memory T cells, e.g., memory T cell precursors;

a decrease in the expression of KLRG1, e.g., on memory T cells, e.g., memory T cell precursors; and an increase in the number of memory T cell precursors, e.g., cells with any one or combination of the following characteristics: increased $CD62L^{high}$, increased $CD127^{high}$, increased $CD27^+$, decreased KLRG1, and increased BCL2; and wherein any of the changes described above occurs, e.g., at least transiently, e.g., as compared to a non-treated subject (Araki, K et al. (2009) Nature 460:108-112). Memory T cell precursors are memory T cells that are early in the differentiation program. For example, memory T cells have one or more of the following characteristics: increased $CD62L^{high}$, increased $CD127^{high}$, increased $CD27^+$, decreased KLRG1, and/or increased BCL2.

In an embodiment, the invention relates to a composition, or dosage form, of an mTOR inhibitor, e.g., an allosteric mTOR inhibitor, e.g., a rapalog, rapamycin, or RAD001, or a catalytic mTOR inhibitor, which, when administered on a selected dosing regimen, e.g., once daily or once weekly, is associated with: a level of mTOR inhibition that is not associated with complete, or significant immune suppression, but is associated with enhancement of the immune response.

An mTOR inhibitor, e.g., an allosteric mTOR inhibitor, e.g., a rapalog, rapamycin, or RAD001, or a catalytic mTOR inhibitor, can be provided in a sustained release formulation. Any of the compositions or unit dosage forms described herein can be provided in a sustained release formulation. In some embodiments, a sustained release formulation will have lower bioavailability than an immediate release formulation. E.g., in embodiments, to attain a similar therapeutic effect of an immediate release formulation a sustained release formulation will have from about 2 to about 5, about 2.5 to about 3.5, or about 3 times the amount of inhibitor provided in the immediate release formulation.

In an embodiment, immediate release forms, e.g., of RAD001, typically used for one administration per week, having 0.1 to 20, 0.5 to 10, 2.5 to 7.5, 3 to 6, or about 5, mgs per unit dosage form, are provided. For once per week administrations, these immediate release formulations correspond to sustained release forms, having, respectively, 0.3 to 60, 1.5 to 30, 7.5 to 22.5, 9 to 18, or about 15 mgs of an mTOR inhibitor, e.g., an allosteric mTOR inhibitor, e.g., rapamycin or RAD001. In embodiments both forms are administered on a once/week basis.

In an embodiment, immediate release forms, e.g., of RAD001, typically used for one administration per day, having having 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs per unit dosage form, are provided. For once per day administrations, these immediate release forms correspond to sustained release forms, having, respectively, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of an mTOR inhibitor, e.g., an allosteric mTOR inhibitor, e.g., rapamycin or RAD001. For once per week administrations, these immediate release forms correspond to sustained release forms, having, respectively, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of an mTOR inhibitor, e.g., an allosteric mTOR inhibitor, e.g., rapamycin or RAD001.

In an embodiment, immediate release forms, e.g., of RAD001, typically used for one administration per day, having having 0.01 to 1.0 mgs per unit dosage form, are provided. For once per day administrations, these immediate release forms correspond to sustained release forms, having, respectively, 0.03 to 3 mgs of an mTOR inhibitor, e.g., an allosteric mTOR inhibitor, e.g., rapamycin or RAD001. For once per week administrations, these immediate release forms correspond to sustained release forms, having, respectively, 0.2 to 20 mgs of an mTOR inhibitor, e.g., an allosteric mTOR inhibitor, e.g., rapamycin or RAD001.

In an embodiment, immediate release forms, e.g., of RAD001, typically used for one administration per week, having having 0.5 to 5.0 mgs per unit dosage form, are provided. For once per week administrations, these immediate release forms correspond to sustained release forms, having, respectively, 1.5 to 15 mgs of an mTOR inhibitor, e.g., an allosteric mTOR inhibitor, e.g., rapamycin or RAD001.

As described above, one target of the mTOR pathway is the P70 S6 kinase. Thus, doses of mTOR inhibitors which are useful in the methods and compositions described herein are those which are sufficient to achieve no greater than 80% inhibition of P70 S6 kinase activity relative to the activity of the P70 S6 kinase in the absence of an mTOR inhibitor, e.g., as measured by an assay described herein, e.g., the Boulay assay. In a further aspect, the invention provides an amount of an mTOR inhibitor sufficient to achieve no greater than 38% inhibition of P70 S6 kinase activity relative to P70 S6 kinase activity in the absence of an mTOR inhibitor.

In one aspect the dose of mTOR inhibitor useful in the methods and compositions of the invention is sufficient to achieve, e.g., when administered to a human subject, 90+/−5% (i.e., 85-95%), 89+/−5%, 88+/−5%, 87+/−5%, 86+/−5%, 85+/−5%, 84+/−5%, 83+/−5%, 82+/−5%, 81+/−5%, 80+/−5%, 79+/−5%, 78+/−5%, 77+/−5%, 76+/−5%, 75+/−5%, 74+/−5%, 73+/−5%, 72+/−5%, 71+/−5%, 70+/−5%, 69+/−5%, 68+/−5%, 67+/−5%, 66+/−5%, 65+/−5%, 64+/−5%, 63+/−5%, 62+/−5%, 61+/−5%, 60+/−5%, 59+/−5%, 58+/−5%, 57+/−5%, 56+/−5%, 55+/−5%, 54+/−5%, 54+/−5%, 53+/−5%, 52+/−5%, 51+/−5%, 50+/−5%, 49+/−5%, 48+/−5%, 47+/−5%, 46+/−5%, 45+/−5%, 44+/−5%, 43+/−5%, 42+/−5%, 41+/−5%, 40+/−5%, 39+/−5%, 38+/−5%, 37+/−5%, 36+/−5%, 35+/−5%, 34+/−5%, 33+/−5%, 32+/−5%, 31+/−5%, 30+/−5%, 29+/−5%, 28+/−5%, 27+/−5%, 26+/−5%, 25+/−5%, 24+/−5%, 23+/−5%, 22+/−5%, 21+/−5%, 20+/−5%, 19+/−5%, 18+/−5%, 17+/−5%, 16+/−5%, 15+/−5%, 14+/−5%, 13+/−5%, 12+/−5%, 11+/−5%, or 10+/−5%, inhibition of P70 S6 kinase activity, e.g., as measured by an assay described herein, e.g., the Boulay assay.

P70 S6 kinase activity in a subject may be measured using methods known in the art, such as, for example, according to the methods described in U.S. Pat. No. 7,727,950, by immunoblot analysis of phosphoP70 S6K levels and/or phosphoP70 S6 levels or by in vitro kinase activity assays.

As used herein, the term "about" in reference to a dose of mTOR inhibitor refers to up to a +/−10% variability in the amount of mTOR inhibitor, but can include no variability around the stated dose.

In some embodiments, the invention provides methods comprising administering to a subject an mTOR inhibitor, e.g., an allosteric inhibitor, e.g., RAD001, at a dosage within a target trough level. In some embodiments, the trough level is significantly lower than trough levels associated with dosing regimens used in organ transplant and cancer patients. In an embodiment mTOR inhibitor, e.g., RAD001, or rapamycin, is administered to result in a trough level that is less than ½, ¼, 1/10, or 1/20 of the trough level that results in immunosuppression or an anticancer effect. In an embodiment mTOR inhibitor, e.g., RAD001, or rapamycin, is administered to result in a trough level that is less than ½, ¼, 1/10, or 1/20 of the trough level provided on the FDA approved packaging insert for use in immunosuppression or an anticancer indications.

In an embodiment a method disclosed herein comprises administering to a subject an mTOR inhibitor, e.g., an allosteric inhibitor, e.g., RAD001, at a dosage that provides a target trough level of 0.1 to 10 ng/ml, 0.1 to 5 ng/ml, 0.1 to 3 ng/ml, 0.1 to 2 ng/ml, or 0.1 to 1 ng/ml.

In an embodiment a method disclosed herein comprises administering to a subject an mTOR inhibitor, e.g., an allosteric inhibitor, e.g., RAD001, at a dosage that provides a target trough level of 0.2 to 10 ng/ml, 0.2 to 5 ng/ml, 0.2 to 3 ng/ml, 0.2 to 2 ng/ml, or 0.2 to 1 ng/ml.

In an embodiment a method disclosed herein comprises administering to a subject an mTOR inhibitor, e.g. an, allosteric inhibitor, e.g., RAD001, at a dosage that provides a target trough level of 0.3 to 10 ng/ml, 0.3 to 5 ng/ml, 0.3 to 3 ng/ml, 0.3 to 2 ng/ml, or 0.3 to 1 ng/ml.

In an embodiment a method disclosed herein comprises administering to a subject an mTOR inhibitor, e.g., an allosteric inhibitor, e.g., RAD001, at a dosage that provides a target trough level of 0.4 to 10 ng/ml, 0.4 to 5 ng/ml, 0.4 to 3 ng/ml, 0.4 to 2 ng/ml, or 0.4 to 1 ng/ml.

In an embodiment a method disclosed herein comprises administering to a subject an mTOR inhibitor, e.g., an allosteric inhibitor, e.g., RAD001, at a dosage that provides a target trough level of 0.5 to 10 ng/ml, 0.5 to 5 ng/ml, 0.5 to 3 ng/ml, 0.5 to 2 ng/ml, or 0.5 to 1 ng/ml.

In an embodiment a method disclosed herein comprises administering to a subject an mTOR inhibitor, e.g., an allosteric inhibitor, e.g., RAD001, at a dosage that provides a target trough level of 1 to 10 ng/ml, 1 to 5 ng/ml, 1 to 3 ng/ml, or 1 to 2 ng/ml.

As used herein, the term "trough level" refers to the concentration of a drug in plasma just before the next dose, or the minimum drug concentration between two doses.

In some embodiments, a target trough level of RAD001 is in a range of between about 0.1 and 4.9 ng/ml. In an embodiment, the target trough level is below 3 ng/ml, e.g., is between 0.3 or less and 3 ng/ml. In an embodiment, the target trough level is below 3 ng/ml, e.g., is between 0.3 or less and 1 ng/ml.

In a further aspect, the invention can utilize an mTOR inhibitor other than RAD001 in an amount that is associated with a target trough level that is bioequivalent to the specified target trough level for RAD001. In an embodiment, the target trough level for an mTOR inhibitor other than RAD001, is a level that gives the same level of mTOR inhibition (e.g., as measured by a method described herein, e.g., the inhibition of P70 S6 kinase) as does a trough level of RAD001 described herein.

Pharmaceutical Compositions: mTOR Inhibitors

In one aspect, the present invention relates to pharmaceutical compositions comprising an mTOR inhibitor, e.g., an mTOR inhibitor as described herein, formulated for use in combination with CAR cells described herein.

In some embodiments, the mTOR inhibitor is formulated for administration in combination with an additional, e.g., as described herein.

In general, compounds of the invention will be administered in therapeutically effective amounts as described above via any of the usual and acceptable modes known in the art, either singly or in combination with one or more therapeutic agents.

The pharmaceutical formulations may be prepared using conventional dissolution and mixing procedures. For example, the bulk drug substance (e.g., an mTOR inhibitor or stabilized form of the compound (e.g., complex with a cyclodextrin derivative or other known complexation agent) is dissolved in a suitable solvent in the presence of one or more of the excipients described herein. The mTOR inhibitor is typically formulated into pharmaceutical dosage forms to provide an easily controllable dosage of the drug and to give the patient an elegant and easily handleable product.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Where an mTOR inhibitor is administered in combination with (either simultaneously with or separately from) another agent as described herein, in one aspect, both components can be administered by the same route (e.g., parenterally). Alternatively, another agent may be administered by a different route relative to the mTOR inhibitor. For example, an mTOR inhibitor may be administered orally and the other agent may be administered parenterally.

Sustained Release mTOR inhibitors, e.g., allosteric mTOR inhibitors or catalytic mTOR inhibitors, disclosed herein can be provided as pharmaceutical formulations in form of oral solid dosage forms comprising an mTOR inhibitor disclosed herein, e.g., rapamycin or RAD001, which satisfy product stability requirements and/or have favorable pharmacokinetic properties over the immediate release (IR) tablets, such as reduced average plasma peak concentrations, reduced inter- and intra-patient variability in the extent of drug absorption and in the plasma peak concentration, reduced $C_{max}/C_{min}$ ratio and/or reduced food effects. Provided pharmaceutical formulations may allow for more precise dose adjustment and/or reduce frequency of adverse events thus providing safer treatments for patients with an mTOR inhibitor disclosed herein, e.g., rapamycin or RAD001.

In some embodiments, the present disclosure provides stable extended release formulations of an mTOR inhibitor disclosed herein, e.g., rapamycin or RAD001, which are multi-particulate systems and may have functional layers and coatings.

The term "extended release, multi-particulate formulation as used herein refers to a formulation which enables release of an mTOR inhibitor disclosed herein, e.g., rapamycin or RAD001, over an extended period of time e.g. over at least 1, 2, 3, 4, 5 or 6 hours. The extended release formulation may contain matrices and coatings made of special excipients, e.g., as described herein, which are formulated in a manner as to make the active ingredient available over an extended period of time following ingestion.

The term "extended release" can be interchangeably used with the terms "sustained release" (SR) or "prolonged release". The term "extended release" relates to a pharmaceutical formulation that does not release active drug substance immediately after oral dosing but over an extended in accordance with the definition in the pharmacopoeias Ph. Eur. (7$^{th}$ edition) mongraph for tablets and capsules and USP general chapter <1151> for pharmaceutical dosage forms. The term "Immediate Release" (IR) as used herein refers to a pharmaceutical formulation which releases 85% of the active drug substance within less than 60 minutes in accordance with the definition of "Guidance for Industry: "Dissolution Testing of Immediate Release Solid Oral Dosage Forms" (FDA CDER, 1997). In some embodiments, the term "immediate release" means release of everolismus from tablets within the time of 30 minutes, e.g., as measured in the dissolution assay described herein.

Stable extended release formulations of an mTOR inhibitor disclosed herein, e.g., rapamycin or RAD001, can be characterized by an in-vitro release profile using assays known in the art, such as a dissolution assay as described herein: a dissolution vessel filled with 900 mL phosphate buffer pH 6.8 containing sodium dodecyl sulfate 0.2% at 37° C. and the dissolution is performed using a paddle method at 75 rpm according to USP by according to USP testing monograph 711, and Ph. Eur. testing monograph 2.9.3. respectively.

In some embodiments, stable extended release formulations of an mTOR inhibitor disclosed herein, e.g., rapamycin or RAD001, release the mTOR inhibitor in the in-vitro release assay according to following release specifications:

0.5 h: <45%, or <40, e.g., <30%
1 h: 20-80%, e.g., 30-60%
2 h: >50%, or >70%, e.g., >75%
3 h: >60%, or >65%, e.g., >85%, e.g., >90%.

In some embodiments, stable extended release formulations of an mTOR inhibitor disclosed herein, e.g., rapamycin or RAD001, release 50% of the mTOR inhibitor not earlier than 45, 60, 75, 90, 105 min or 120 min in the in-vitro dissolution assay.

Biopolymer Delivery Methods

In some embodiments, one or more CAR-expressing cells as disclosed herein, optionally in combination with a kinase inhibitor, e.g., a BTK inhibitor such as ibrutinib, can be administered or delivered to the subject via a biopolymer scaffold, e.g., a biopolymer implant. Biopolymer scaffolds can support or enhance the delivery, expansion, and/or dispersion of the CAR-expressing cells described herein. A biopolymer scaffold comprises a biocompatible (e.g., does not substantially induce an inflammatory or immune response) and/or a biodegradable polymer that can be naturally occurring or synthetic.

Examples of suitable biopolymers include, but are not limited to, agar, agarose, alginate, alginate/calcium phosphate cement (CPC), beta-galactosidase (β-GAL), (1,2,3,4, 6-pentaacetyl a-D-galactose), cellulose, chitin, chitosan, collagen, elastin, gelatin, hyaluronic acid collagen, hydroxyapatite, poly(3-hydroxybutyrate-co-3-hydroxyhexanoate) (PHBHHx), poly(lactide), poly(caprolactone) (PCL), poly(lactide-co-glycolide) (PLG), polyethylene oxide (PEO), poly(lactic-co-glycolic acid) (PLGA), polypropylene oxide (PPO), polyvinyl alcohol) (PVA), silk, soy protein, and soy protein isolate, alone or in combination with any other polymer composition, in any concentration and in any ratio. The biopolymer can be augmented or modified with adhesion- or migration-promoting molecules, e.g., collagen-mimetic peptides that bind to the collagen receptor of lymphocytes, and/or stimulatory molecules to enhance the delivery, expansion, or function, e.g., anti-cancer activity, of the cells to be delivered. The biopolymer scaffold can be an injectable, e.g., a gel or a semi-solid, or a solid composition.

In some embodiments, CAR-expressing cells described herein are seeded onto the biopolymer scaffold prior to delivery to the subject. In embodiments, the biopolymer scaffold further comprises one or more additional therapeutic agents described herein (e.g., another CAR-expressing cell, an antibody, or a small molecule) or agents that enhance the activity of a CAR-expressing cell, e.g., incorporated or conjugated to the biopolymers of the scaffold. In embodiments, the biopolymer scaffold is injected, e.g., intratumorally, or surgically implanted at the tumor or within a proximity of the tumor sufficient to mediate an anti-tumor effect. Additional examples of biopolymer compositions and methods for their delivery are described in Stephan et al., Nature Biotechnology, 2015, 33:97-101; and WO2014/110591.

Pharmaceutical Compositions and Treatments

Pharmaceutical compositions of the present invention may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection. In one aspect, the T cell compositions of the present invention are administered by i.v. injection. The compositions of T cells may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., T cells. These T cell isolates may be expanded by methods known in the art and treated such that one or more CAR constructs of the invention may be introduced, thereby creating a CAR T cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded CAR T cells of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In one embodiment, the CAR is introduced into T cells, e.g., using in vitro transcription, and the subject (e.g., human) receives an initial administration of CAR T cells of the invention, and one or more subsequent administrations of the CAR T cells of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR T cells of the invention are administered to the subject (e.g., human) per week, e.g., 2, 3, or 4 administrations of the CAR T cells of the invention are administered per week. In one embodiment, the subject (e.g., human subject) receives more than one administration of the CAR T cells per week (e.g., 2, 3 or 4 administrations per week) (also referred to herein as a cycle), followed by a week of no CAR T cells administrations, and then one or more additional administration of the CAR T cells (e.g., more than one administration of the CAR T cells per week) is administered to the subject. In another embodiment, the subject (e.g., human subject) receives more than one cycle of CAR T cells, and the time between each cycle is less than 10, 9, 8, 7, 6, 5, 4, or 3 days. In one embodiment, the CAR T cells are administered every other day for 3 administrations per week. In one embodiment, the CAR T cells of the invention are administered for at least two, three, four, five, six, seven, eight or more weeks.

In one aspect, CAR-expressing cells are generated using lentiviral viral vectors, such as lentivirus. Cells, e.g., CARTs generated that way will have stable CAR expression.

In one aspect, CAR-expressing cells, e.g., CARTs, are generated using a viral vector such as a gammaretroviral vector, e.g., a gammaretroviral vector described herein. CARTs generated using these vectors can have stable CAR expression.

In one aspect, CARTs transiently express CAR vectors for 4, 5, 6, 7, 8, 9, 10, 11, 12, 13, 14, 15 days after transduction. Transient expression of CARs can be effected by RNA CAR vector delivery. In one aspect, the CAR RNA is transduced into the T cell by electroporation.

A potential issue that can arise in patients being treated using transiently expressing CAR T cells (particularly with murine scFv bearing CARTs) is anaphylaxis after multiple treatments.

Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-CAR antibody response during the course of transient CAR therapy (such as those generated by RNA transductions), CART infusion breaks should not last more than ten to fourteen days.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: Humanization of Murine Anti-CD19 Antibody

A CD19 antibody molecule can be, e.g., an antibody molecule (e.g., a humanized anti-CD19 antibody molecule) described in WO2014/153270, which is incorporated herein by reference in its entirety. Humanization of murine CD19 antibody is desired for the clinical setting, where the mouse-specific residues may induce a human-anti-mouse antigen (HAMA) response in patients who receive CART19 treatment, i.e., treatment with T cells transduced with the CAR19 construct. VH and VL sequences of hybridoma derived murine CD19 antibody were extracted from published literature (Nicholson et al, 1997, supra). Humanization was accomplished by grafting CDR regions from murine CD19 antibody onto human germline acceptor frameworks VH4_4-59 and VK3_L25 (vBASE database). In addition to the CDR regions, five framework residues, i.e. VH #71, #73, #78 and VL #71 #87, thought to support the structural integrity of the CDR regions were retained from the murine sequence. Further, the human J elements JH4 and JK2 were used for the heavy and light chain, respectively. The resulting amino acid sequences of the humanized antibody were designated FMC63_VL_hz and FMC63_VH_hz1, respectively, and are shown below in Table 1. The residue numbering follows Kabat (Kabat E. A. et al, 1991, supra). For CDR definitions, both Kabat as well as Chothia et al, 1987 supra) were used. Residues coming from mouse CD19 are shown in bold/italic. Positions #60/61/62 boxed indicate potential post-translational modification (PTM) site in CDR H2, also termed HCDR2.

TABLE 1

Amino acid sequences of humanized CD19 variable domains (SEQ ID NOS: 114-117, respectively, in order of appearance).

| | | | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Chothia CDR | | | | | | | | | | | | | | | | | | | | | | | | | | | | | | | | | | CDR H1 | | | | | | | | | | | |
| Kabat CDR | | | | | | | | | | | | | | | | | | | | | | | | | | | | | | | CDR H1 | | | | | | | | | | | | | |
| Kabat # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35a | 35b | 36 | 37 | 38 | 39 | 40 | 41 | 42 | 43 | 44 | 45 | 46 |
| FMC63_VH_hz1 | Q | V | Q | L | Q | E | S | G | P | G | L | V | K | P | S | E | T | L | S | L | T | C | T | V | S | G | V | S | *L* | *P* | *D* | *Y* | *G* | *V* | S | | | W | I | R | Q | P | P | G | K | G | L | E |
| FMC63_VH_hz2 | Q | V | Q | L | Q | E | S | G | P | G | L | V | K | P | S | E | T | L | S | L | T | C | T | V | S | G | V | S | *L* | *P* | *D* | *Y* | *G* | *V* | S | | | W | I | R | Q | P | P | G | K | G | L | E |
| FMC63_VH_hz3 | Q | V | Q | L | Q | E | S | G | P | G | L | V | K | P | S | E | T | L | S | L | T | C | T | V | S | G | V | S | *L* | *P* | *D* | *Y* | *G* | *V* | S | | | W | I | R | Q | P | P | G | K | G | L | E |

| | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|
| Chothia CDR | | | | | | | | CDR H2 | | | | | | | | | | | | | | | | | | | | | | | | | | | | | | |
| Kabat CDR | | | | | CDR H2 | | | | | | | | | | | | | | | | | | | | | | | | | | | | | | | | | |
| Kabat # | 47 | 48 | 49 | 50 | 51 | 52 | 52a | 52b | 52c | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82a | 82b | 82c | 83 | 84 |
| FMC63_VH_hz1 | W | I | G | V | I | *W* | | | | *G* | S | *E* | *T* | *T* | *Y* | *Y* | *N* | S | *S* | L | K | S | R | V | T | I | S | *K* | *D* | *N* | S | K | N | Q | *V* | S | L | K | L | S | S | V | T | A |
| FMC63_VH_hz2 | W | I | G | V | I | *W* | | | | *G* | S | *E* | *T* | *T* | *Y* | *Y* | *S* | S | *S* | L | K | S | R | V | T | I | S | *K* | *D* | *N* | S | K | N | Q | *V* | S | L | K | L | S | S | V | T | A |
| FMC63_VH_hz3 | W | I | G | V | I | *W* | | | | *G* | S | *E* | *T* | *T* | *Y* | *Y* | *Q* | S | *S* | L | K | S | R | V | T | I | S | *K* | *D* | *N* | S | K | N | Q | *V* | S | L | K | L | S | S | V | T | A |

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| Chothia CDR | | | | | | | | | CDR H3 | | | | | | | | | | | | | | | | | | | | | |
| Kabat CDR | | | | | | | | | CDR H3 | | | | | | | | | | | | | | | | | | | | | |
| Kabat # | 85 | 86 | 87 | 88 | 89 | 90 | 91 | 92 | 93 | 94 | 95 | 96 | 97 | 98 | 99 | 100 | 100a | 100b | 100c | 100d | * | * | * | * | 101 | 102 | 103 | 104 | 105 | 106 | 107 | 108 | 109 | 110 | 111 | 112 | 113 |
| FMC63_VH_hz1 | A | D | T | A | V | Y | Y | Y | C | A | K | *H* | *Y* | *Y* | *Y* | *G* | *G* | *S* | *Y* | *A* | *M* | | | | D | Y | W | G | Q | G | T | L | V | T | V | S | S |
| FMC63_VH_hz2 | A | D | T | A | V | Y | Y | Y | C | A | K | *H* | *Y* | *Y* | *Y* | *G* | *G* | *S* | *Y* | *A* | *M* | | | | D | Y | W | G | Q | G | T | L | V | T | V | S | S |
| FMC63_VH_hz3 | A | D | T | A | V | Y | Y | Y | C | A | K | *H* | *Y* | *Y* | *Y* | *G* | *G* | *S* | *Y* | *A* | *M* | | | | D | Y | W | G | Q | G | T | L | V | T | V | S | S |

| | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| Chothia CDR | | | | | | | | | | | | | | | | | | | | | | | | | CDR L1 | | | | | | | | | | | | | | | | |
| Kabat CDR | | | | | | | | | | | | | | | | | | | | | | | | CDR L1 | | | | | | | | | | | | | | | | | |
| Kabat # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 27e | 27f | 28 | 29 | 30 | 31 | 32 | 33 | 34 | 35 |
| RMC63 VL hz | E | I | V | M | T | Q | S | P | A | T | L | S | L | S | P | G | E | R | A | T | L | S | C | R | A | S | Q | | | | | | | D | I | S | *K* | *Y* | L | *N* | W |

| | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| Chothia CDR | | | | | | | CDR L2 | | | | | | | | | | | | | | | | | | | | | | | | | |
| Kabat CDR | | | | | | | CDR L2 | | | | | | | | | | | | | | | | | | | | | | | | | |
| Kabat # | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 |
| RMC63 VL hz | Y | Q | Q | K | P | G | Q | A | P | R | L | L | I | Y | *H* | *T* | *S* | *R* | *L* | *H* | *S* | G | I | P | A | R | F | S | G | S | G | S |

| | | | | | | | | | | | | | | | | | | | | |
|---|---|---|---|---|---|---|---|---|---|---|---|---|---|---|---|---|---|---|---|---|
| Chothia CDR | | | | | | | | | CDR L3 | | | | | | | | | | | |
| Kabat CDR | | | | | | | | | CDR L3 | | | | | | | | | | | | |
| Kabat # | 68 | 69 | 70 | 71 | 72 | 73 | 74 | 75 | 76 | 77 | 78 | 79 | 80 | 81 | 82 | 83 | 84 | 85 | 86 | 87 |
| RMC63 VL hz | G | T | D | *Y* | T | L | T | I | S | S | L | Q | P | E | D | F | A | V | Y | F |

| | | | | | | | | | | | | | | | | | | | | |
|---|---|---|---|---|---|---|---|---|---|---|---|---|---|---|---|---|---|---|---|---|
| Kabat # | 88 | 89 | 90 | 91 | 92 | 93 | 94 | 95 | 95a | 95b | 95c | 95d | 95e | 95f | 96 | 97 | 98 | 99 | 100 | 101 | 102 | 103 | 104 | 105 | 106 | 107 |
| RMC63 VL hz | C | Q | Q | *G* | *N* | *T* | L | P | | | | | | | Y | T | F | G | Q | G | T | K | L | E | I | K |

These humanized CD19 IgGs were used to generate soluble scFvs to test for expression and scFvs for the full CART CD19 constructs (See Examples below). Of interest was that during humanization, position 62 in the CDRH2 region prefers to be a serine residue rather than the alanine present in the murine CDRH2. The murine sequence lacks a post-translational modification (PTM), and has asparagine-serine-alanine at positions 60/61/62, respectively in CDRH2. This generates potential PTM motifs (indicated as the boxed cite in CDRH2) during the course of humanization. Whether the PTM site generated during humanization process was actually a "true" PTM site or merely a theoretical one was tested. It was hypothesized that the amino acid motif asparagine followed by serine (NS) may be susceptible to post-translational deamidation but not something that was readily apparent. It was also hypothesized that asparagine followed by any amino acid except proline and then followed by serine (N×S, x≠P) may be susceptible to post-translational N-glycosylation. To test this hypothesis, two IgG variants, were generated in which the asparagine at position 60 (known to be a glycosylation site) was mutated to serine, or glutamine and designated FMC63_VH_hz2 (N60S) and FMC63_VH_hz2 (N60Q), respectively. These constructs were generated in order to eliminate the potential post-translational modification site (PTM) and test for retained activity (See Example 2 below).

Cloning:

DNA sequences coding for mouse and humanized VL and VH domains were obtained, and the codons for the constructs were optimized for expression in cells from *Homo sapiens*.

Sequences coding for VL and VH domain were subcloned from the cloning vectors into expression vectors suitable for secretion in mammalian cells. The heavy and light chains were cloned into individual expression vectors to allow co-transfection. Elements of the expression vector include a promoter (Cytomegalovirus (CMV) enhancer-promoter), a signal sequence to facilitate secretion, a polyadenylation signal and transcription terminator (Bovine Growth Hormone (BGH) gene), an element allowing episomal replication and replication in prokaryotes (e.g. SV40 origin and ColE1 or others known in the art) and elements to allow selection (ampicillin resistance gene and zeocin marker).

Expression:

Chimera and humanized IgG candidates were expressed in HEK293F mammalian cells at 1 ml scale. Cleared supernatants were used for FACS binding studies. More precisely, HEK293F cells were diluted to 5E5 cells/ml in FreeStyle medium supplemented with Pen/Strep and 1 ml transferred into 24 round bottom deep well plate. 0.5 μg of light and 0.5 μg of heavy chain mammalian expression plasmids were diluted in the same medium together with 4 μl of FuGENE HD (Roche REF 04709705001). After 15 min RT incubation, DNA/Fugene mix was added drop-wise to the cells and placed in a 5% $CO_2$ incubator at 250 rpm, 37° C. for five days. Supernatant were then separated from the cells by centrifugation. To measure IgG content, aliquots of 200 μL were placed in the wells of 96-well microtiter plates. All samples and standards were measured in duplicate using Protein A Dip and read biosensors (Fortebio Cat No 18-5010). The plate was placed in an Octet instrument (ForteBio) and allowed to equilibrate to 27° C. in the thermostated chamber. Data were processed automatically using the Octet User Software version 3.0 and concentration determined by comparing to an IgG standard curve.

Binding Analysis by FACS:

Humanized and chimera antibodies were evaluated with a flow cytometry binding assay using cell line 300.19-hsCD19FL. This cell line was generated by transfecting the mouse preB cell line 300.19 with a vector (hCD19 FL/pEF4-myc-His A) encoding the full length human CD19 encoding sequence and natural promoter as well as a Zeocin resistance gene. In brief, 300.19 cells were electroporated with the linearized plasmid and then cells expressing high levels of hsCD19 were identified using an APC-conjugated anti-human CD19 Ab (clone HIB19 from BD 555415) and subsequently sorted using a FACS Aria flow cytometer. The sorted hsCD19+ cells were cultured and confirmed to stably express high levels of hsCD19.

The binding assay could be performed directly with the serum free culture media containing the expressed IgG. All evaluated IgGs were normalized to the same concentration (85 nM), before to be diluted by a 3 fold serial dilution down to 1.4 pM. Then, in a 96-well plate, aliquots of $5\times10^5$ cells/well were incubated for 30 min at 4° C. with diluted IgGs. Cells were washed twice with FACS buffer (0.5% BSA in PBS) before addition of the detection antibody, an APC conjugated goat anti-hu IgG, Fc fragment specific (Dianova #109-136-098), diluted 1:1000 in FACS buffer. Cells were incubated a further 30 min at 4° C., then washed twice in FACS buffer and assayed using FACS Calibur (BD Bioscience). Binding curves plotting (median of fluorescence intensity versus IgG concentration) and $EC_{50}$ determination were performed with GraphPad Prism™ 3.0 software with nonlinear regression analysis, sigmoidal dose response (variable slope).

The FACS analyses show that apparent binding for all evaluated IgGs can vary widely, with some constructs exhibiting a 5 to 10 fold shift in EC50 as an IgG versus a scFv. Based on $EC_{50}$ values, lead candidates are chosen that have a binding affinity within a factor of 2 or better compared to the chimeric reference.

Example 2: Characterization of Anti-CD19 Soluble scFv Fragments Derived from Humanized CD19 IgG Antibodies Soluble scFv fragments were generated from the humanized CD19 IgGs described in Example 1 using standard molecule biology techniques. These soluble scFvs were used in characterization studies to examine the stability, cell surface expression, and binding properties of the scFvs. Additionally, experiments were also conducted to investigate the impact of the potential PTM introduced during the humanization process.

scFv Expression and Purification

For transfection of each scFv construct, around 3e8 293F cells were transfected with 100 μg of plasmid using PEI as the transfection reagent at the ratio of 3:1 (PEI:DNA). The cells were grown in 100 ml EXPi293 Expression media (Invitrogen) in a shaker flask at 37° C., 125 rpm, 8% $CO_2$. The culture was harvested after six days and used for protein purification.

293F cells were harvested by spinning down at 3500 g for 20 minutes. The supernatant was collected and filtered through VacuCap90 PF Filter Unit (w/0.8/0.2 μm Super Membrane, PALL). Around 400 μl 400 ul of Ni-NTA agarose beads (Qiagen) were added to the supernatant. The mixture was rotated and incubated for 4 hrs at 4° C. It was loaded onto a purification column and washed with washing buffer with 20 mM Histidine. The protein was eluted with 500 μl elution buffer with 300 mM Histidine. The samples were dialyzed against PBS buffer at 4 C overnight. Protein samples were quantified using nanodrop 2000c.

scFv Conformation and Colloidal Stability Analysis

Thermostability of the scFv was determined by DSF: mix 10-20 μl of protein sample with the dye Sypro Orange (Invitrogen Cat#S6650) of a final dilution at 1:1000, in a total volume of 25 μl in PBS, run BioRad CFX1000 (25 C for 2 min, then increment 0.5° C. for 30 second, 25 to 95° C.).

For analytical SEC experiment, around 15-20 μg of scFv protein sample in 20 μl PBS was injected onto TSKgel Super SW2000 at 0.3 ml/min flow rate on n Agilent 1100 series.

EC50 by FACS Binding

Mouse cell line 300. CD19 were grown in RPMI 1640 with 0.5 mg/ml Zeocin. Around 5e5 cells/per well were transferred to the BD Falcon 96 well plate. The cells were spin down at 900 rpm (Sorval Legend XT centrifuge) for 3 minutes. The supernatant were removed. Anti-CD19 scFv protein samples were diluted in DPBS with 5% FBS. The samples were added into the wells, mixed well with the cells and incubated for 1 hour. The cells were washed twice in the DPBS with 5% FBS. The cells were incubated with antipoly His PE (R&D) for 1 hour, washed twice before FACS analysis (LSRII from BD Biosciences).

Kinetic Analysis by Proteon

Kinetics were determined using Bio-Rad Proteon. Immobilization was performed using standard amine coupling on a GLC sensor chip. The scFv samples were diluted to 0.03 mg/mL in acetate pH 4.5 and applied to the chip at a flow rate of 30 μL/min for 300 seconds. The CD19 ligand was then serial diluted in PBS-Tween and injected at a flow rate of 50 μL/min for 120 seconds with a dissociation time of 480 seconds. The chip surface was regenerated with glycine pH 2.5. Data was fitted using a 1:1 Langmuir model.

Surface Expression of CART19 Constructs and Staining by FACS

HEK293F suspension cells transiently transfected with different anti-hCD19 CARTs were harvested 2 days after the transfection. Around 1e6 cells were placed into each well of a V-shape 96 well plate (Greiner Bio-One, Germany) and washed three times with 0.2 ml FACS buffer (1×PBS containing 4% bovine serum albumin (BSA) (BSA fraction V, Roche Diagnostics, Indianapolis, Ind.). Cells were resuspended in 0.2 ml of the FCAS buffer with either 0.2 μg of biotinylated protein L (GenScript, Piscataway, N.J.) or 100 nM of hCD19(AA 1-291)-hIgG1 Fc (Generated in NIBRI) and incubated at 4° C. for 30 minutes. Cells were then washed with 0.2 ml of FACS buffer three times, and incubated with 1 μl Streptavidin Alexa Fluor 488 (Life Technologies, Grand Island, N.Y.) in 0.2 ml of FACS buffer for samples with protein L, or 2 μl of PE anti-human Fcτ (Jackson ImmunoResearch Laboratories, West Grove, Pa.) in 0.2 ml of FACS buffer for samples with hCD19-hIgG1 Fc for 30 minutes at 4° C. in the dark. After washing with 0.2 ml of FACS buffer three times, cells were analyzed on a LSRII (BD Biosciences, San Jose, Calif.) machine using the FACSDiva software (BD Biosciences, San Jose, Calif.). Immunofluorescence staining was analyzed as the relative log fluorescence of live cells, and the percentage of the Alexa Fluor 488 positive or PE positive cells were measured.

Analysis of Potential PMTs Generated During the Humanization Process

Of interest was that during humanization, position 62 in the CDRH2 region prefers to be a serine residue rather than the alanine present in the murine CDRH2 as described in Example 1. Whether the PTM site generated during humanization process was actually a "true" PTM site or merely a theoretical one was tested. Two IgG variants were generated in which the asparagine at position 60 (known to be a glycosylation site) was mutated to serine, or glutamine and designated FMC63_VH_hz2 (N60S) and FMC63_VH_hz2 (N60Q), respectively. These constructs were generated in order to eliminate the potential post-translational modification site (PTM) and test for retained activity.

Results

Anti-CD19 humanized scFvs and mouse scFv were expressed in 293F cells and purified through His tag. The expression and yield of all humanized scFvs was much higher than the original mouse scFv (data not shown).

To confirm identity and assess integrity, the scFV constructs are analyzed with or without incubation with N-glycanase F (PNGaseF) followed by both high-performance liquid chromatography mass spectrometry (HPLC-MS) (See FIG. 3) and SDS-PAGE (data not shown). PNGaseF is an enzyme specific for the removal of N-linked glycan structures from the consensus sequence N-X-S/T/C where X is any amino acid except proline. Briefly, the samples are diluted in water to 0.1 μg/μL and either left untreated or incubated with PNGaseF at a 1:2 (w/w) PNGaseF: scFV ratio for 3 hours at 37° C.

SDS-PAGE analysis is performed using a NuPAGE 4-12% Bis-Tris gel from Novex. Approximately 2 μg scFV are loaded into each lane and the electrophoresis is conducted at 200 V constant for 40 minutes. Following electrophoresis, the gel is stained using PhastGel Blue R 250 stain (Amersham Pharmacia) and destained with 10% acetic acid, 30% methanol.

HPLC-MS analysis is performed on the Water's Acquity UPLC system coupled to a Xevo-Tof mass spectrometer. Approximately 1 μg of each sample is loaded onto a R ⅒ 2.1×100 mm 10 μm POROS column (Applied Biosciences) set to 60° C. at a flow rate of 0.5 mL/min. Mobile phases are composed of 0.1% formic acid (A) and 0.1% formic acid, 75% isopropanol, 25% acetonitrile (B). Protein is eluted from the column with a reverse phase gradient from 25%-90% B in 12 minutes. The acquisition is performed using electrospray positive scan at the m/z range of 600-4000 Da with a source cone voltage ramp 20-50V. The resulting spectra are deconvoluted using MaxEnt1.

Figure 3:
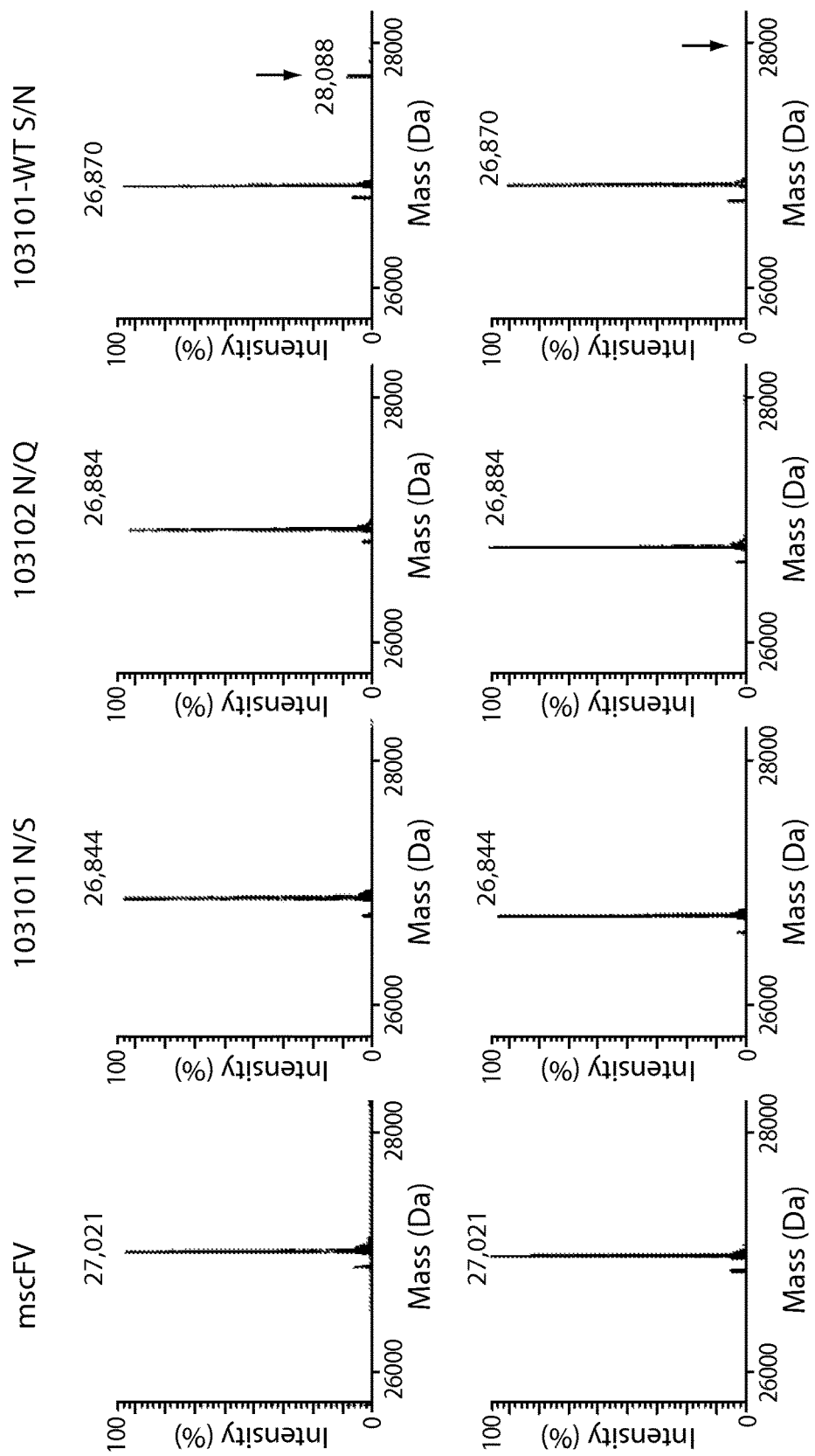
FIG. 3 is a graphic representation of the deconvoluted HPLC mass spectra for scFvs of the invention, where the top row depicts untreated scFv and the bottom row depicts the cognate deglycosylated scFv.

The glycosylation site was introduced during the process of humanization. The non-PTM variants (VH: N60S or N60Q) were without this additional form. The construct was the only one with a consensus site of N-linked glycosylation in HC CDR2. From the SDS-PAGE analysis, the untreated samples migrated as single bands consistent with the approximate molecular weights of the sequences for all constructs except 103101-WT (S/N) for which doublet is observed. This construct is the only one with a consensus site of N-linked glycosylation in H-CDR2. When treated with PNGaseF, the higher molecular weight band of the doublet is no longer present suggesting partial occupancy of the site. Similarly, the observed molecular weights from the deconvoluted mass spectra are consistent with those predicted from the amino acid sequences. However, while the other constructs demonstrated a single primary molecular species, 103101-WT (S/N) also had a population 1217 Daltons higher than that predicted from the sequence which is no longer present after treatment with PNGaseF. This is consistent with the presence of a single predominant N-linked glycoform, likely oligomannose 5 based upon mass. The presence of the glycosylated form was confirmed by the MS analysis as shown in FIG. 3.

Figure 4:
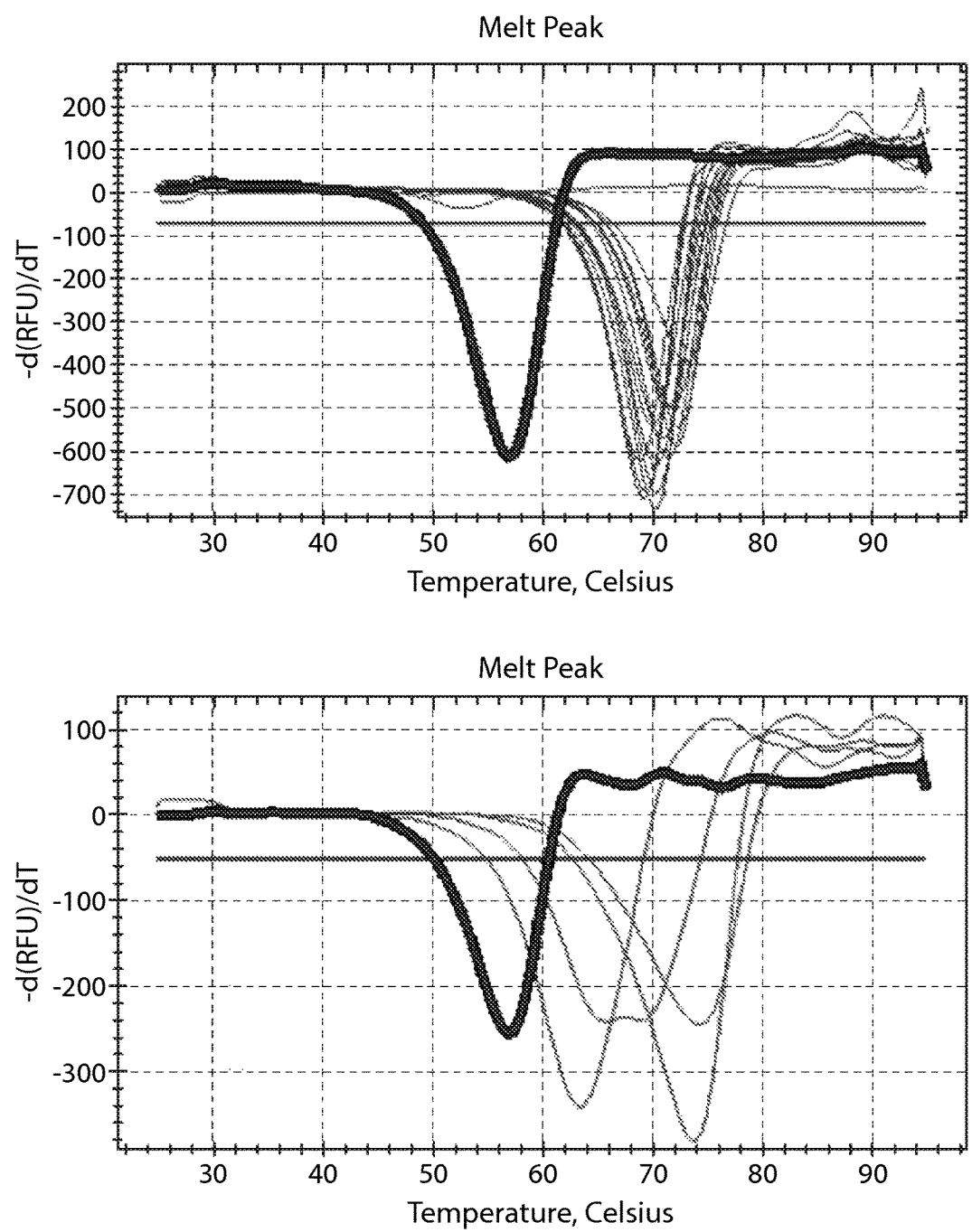
FIG. 4 is a graphic representation of the conformation stability as measured by Differential Scanning Fluorimetry. The Tm of mouse scFv was 57° C. (thick line). All humanized scFv variants show higher Tm at around 70° C. as compared to the parental mouse scFv. The residues introduced by humanization have improved the Tm by more than 10° C.

The conformation stability was measured by Differential Scanning Fluorimetry (DSF). As shown in FIG. 4, the Tm of mouse scFv was 57° C., while the human variants showed higher Tm at around 70° C. The Tm for all the humanized scFv is much better than the murine scFv, clearly showing that all the humanized scFv are more stable than the murine scFv. This stability will likely translate to the CART19 construct, likely leading to improved therapeutic properties.

The activity of the purified scFv was measure by binding to hCD19 expression cells as well as by binding to hCD19 antigen using SPR based detection method. Mouse cell line 300 was used to determine the binding of scFvs. The $EC_{50}$ of mouse scFv for hCD19 was around 06-1.6 nM. The humanized variants showed $EC_{50}$ of the same range in the low or sub nM $EC_{50}$s range.

Example 3: CD19 CAR Constructs

ScFv to be used in the final CAR construct were derived from the humanized IgG described in Example 1. The order in which the VL and VH domains appear in the scFv was varied (i.e., VL-VH, or VH-VL orientation), and where either three or four copies of the "G4S" (SEQ ID NO:18) subunit, in which each subunit comprises the sequence GGGGS (SEQ ID NO:18) (e.g., (G4S)$_3$ (SEQ ID NO:107) or (G4S)$_4$ (SEQ ID NO:106)), connect the variable domains to create the entirety of the scFv domain, as shown in Table 2.

TABLE 2

Humanized CD19 scFv constructs showing VH and VL orientation and linker length ("3G4S" is disclosed as SEQ ID NO: 107 and "4G4S" is disclosed as SEQ ID NO: 106).

| construct ID | Length aa | annotation | Vh change |
|---|---|---|---|
| mscFvCTL019 | 486 | VL-VH, 3G4S | |
| 104879 | 491 | VL-VH, 4G4S | N/S |
| 104880 | 491 | VL-VH, 4G4S | N/Q |
| 104881 | 491 | VH-VL, 4G4S | N/S |
| 104882 | 491 | VH-VL, 4G4S | N/Q |
| 104875 | 486 | VL-VH, 3G4S | N/S |
| 104876 | 486 | VL-VH, 3G4S | N/Q |
| 104877 | 486 | VH-VL, 3G4S | N/S |
| 104878 | 486 | VH-VL, 3G4S | N/Q |
| 105974 | 491 | VL-VH, 4G4S | S/N |
| 105975 | 491 | VH-VL, 4G4S | S/N |
| 105976 | 486 | VL-VH, 3G4S | S/N |
| 105977 | 486 | VH-VL, 3G4S | S/N |

The sequences of the humanized scFv fragments (SEQ ID NOS: 1-12) are provided below in Table 3. Full CAR constructs were generated using SEQ ID NOs: 1-12 with additional sequences, SEQ ID NOs: 13-17, shown below, to generate full CAR constructs with SEQ ID NOs: 31-42.

leader (amino acid sequence)
(SEQ ID NO: 13)
MALPVTALLLPLALLLHAARP leader (nucleic acid sequence)
(SEQ ID NO: 54)
ATGGCCCTGCCTGTGACAGCCCTGCTGCTGCCTCTGGCTCTGCTGCTGCA

TGCCGCTAGACCC

CD8 hinge (amino acid sequence)
(SEQ ID NO: 14)
TTTPAPRPPTPAPTIASQPLSLRPEACRPAAGGAVHTRGLDFACD CD8 hinge (nucleic acid sequence)
(SEQ ID NO: 55)
ACCACGACGCCAGCGCCGCGACCACCAACACCGGCGCCCACCATCGCGTC

GCAGCCCCTGTCCCTGCGCCCAGAGGCGTGCCGGCCAGCGGCGGGGGGCG

CAGTGCACACGAGGGGGCTGGACTTCGCCTGTGAT

CD8 transmembrane (amino acid sequence)
(SEQ ID NO: 15)
IYIWAPLAGTCGVLLLSLVITLYC transmembrane (nucleic acid sequence)
(SEQ ID NO: 56)
ATCTACATCTGGGCGCCCTTGGCCGGGACTTGTGGGGTCCTTCTCCTGTC

ACTGGTTATCACCCTTTACTGC 4-1BB Intracellular domain (amino acid sequence)
(SEQ ID NO: 16)
KRGRKKLLYIFKQPFMRPVQTTQEEDGCSCRFPEEEEGGCEL 4-1BB Intracellular domain (nucleic acid sequence)
(SEQ ID NO: 60)
AAACGGGGCAGAAAGAAACTCCTGTATATATTCAAACAACCATTTATGAG

ACCAGTACAAACTACTCAAGAGGAAGATGGCTGTAGCTGCCGATTTCCAG

AAGAAGAAGAAGGAGGATGTGAACTG

CD3 zeta domain (amino acid sequence)
(SEQ ID NO: 17)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

CD3 zeta (nucleic acid sequence)
(SEQ ID NO: 101)
AGAGTGAAGTTCAGCAGGAGCGCAGACGCCCCCGCGTACAAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC

CD3 zeta domain (amino acid sequence; NCBI Reference Sequence NM_000734.3)
(SEQ ID NO: 43)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

CD3 zeta (nucleic acid sequence; NCBI Reference Sequence NM_000734.3);
(SEQ ID NO: 44)
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC

-continued

IgG4 Hinge (amino acid sequence)
(SEQ ID NO: 102)
ESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGKM

IgG4 Hinge (nucleotide sequence)
(SEQ ID NO: 103)
GAGAGCAAGTACGGCCCTCCCTGCCCCCCTTGCCCTGCCCCCGAGTTCCT

GGGCGGACCCAGCGTGTTCCTGTTCCCCCCCAAGCCCAAGGACACCCTGA

TGATCAGCCGGACCCCCGAGGTGACCTGTGTGGTGGTGGACGTGTCCCAG

GAGGACCCCGAGGTCCAGTTCAACTGGTACGTGGACGGCGTGGAGGTGCA

CAACGCCAAGACCAAGCCCCGGGAGGAGCAGTTCAATAGCACCTACCGGG

TGGTGTCCGTGCTGACCGTGCTGCACCAGGACTGGCTGAACGGCAAGGAA

TACAAGTGTAAGGTGTCCAACAAGGGCCTGCCCAGCAGCATCGAGAAAAC

CATCAGCAAGGCCAAGGGCCAGCCTCGGGAGCCCCAGGTGTACACCCTGC

CCCCTAGCCAAGAGGAGATGACCAAGAACCAGGTGTCCCTGACCTGCCTG

GTGAAGGGCTTCTACCCCAGCGACATCGCCGTGGAGTGGGAGAGCAACGG

CCAGCCCGAGAACAACTACAAGACCACCCCCCCTGTGCTGGACAGCGACG

GCAGCTTCTTCCTGTACAGCCGGCTGACCGTGGACAAGAGCCGGTGGCAG

GAGGGCAACGTCTTTAGCTGCTCCGTGATGCACGAGGCCCTGCACAACCA

CTACACCCAGAAGAGCCTGAGCCTGTCCCTGGGCAAGATG

These clones all contained a Q/K residue change in the signal domain of the co-stimulatory domain derived from 4-1BB.

TABLE 3

Humanized CD19 CAR Constructs

| Name | SEQ ID | Sequence |
|---|---|---|
| CAR 1 | | |
| CAR1 scFv domain | 1 | EIVMTQSPATLSLSPGERATLSCRASQDISKYLNWYQQKPGQAPRLLIYHT SRLHSGIPARFSGSGSGTDYTLTISSLQPEDFAVYFCQQGNTLPYTFGQGT KLEIKGGGGSGGGGSGGGGSQVQLQESGPGLVKPSETLSLTCTVSGVSLPD YGVSWIRQPPGKGLEWIGVIWGSETTYYSSSLKSRVTISKDNSKNQVSLKL SSVTAADTAVYYCAKHYYYGGSYAMDYWGQGTLVTVSS |
| 103101 CAR1 Soluble scFv-nt | 61 | atggcctccctgtcaccgccctgctgcttccgctggctcttctgctccacgccgc tcggcccgaaattgtgatgacccagtcacccgccactcttagcctttcaccggtg agcgcgcaaccctgtcttgcagagcctcccaagacatctcaaataccttaattgg tatcaacagaagcccggacaggctcctcgccttctgatctaccacaccagccggct ccattctggaatccctgccaggttcagcggtagcggatctgggaccgactacaccc tcactatcagctcactgcagccagaggacttcgctgtctatttctgtcagcaaggg aacaccctgccctacaccttggacagggcaccaagctcgagattaaaggtggagg tggcagcggaggaggtgggtccggcggtggaggaagccaggtccaactccaagaaa gcggacccgggtcttgtgaagccatcagaaactctttcactgacttgtactgtgagc ggagtgtctctccccgattacggggtgtcttggatcagacagccaccggggaaggg tctggaatggattggagtgatttggggctctgagactacttactactcttcatccc tcaagtcacgcgtcaccatctcaaaggacaactctaagaatcaggtgtcactgaaa ctgtcatctgtgaccgcagccgacaccgccgtgtactattgcgctaagcattacta ttatggcgggagctacgcaatggattactggggacagggtactctggtcaccgtgt ccagccaccaccatcatcaccatcat |
| 103101 CAR1 Soluble scFv-aa | 73 | MALPVTALLLPLALLLHAARPeivmtqspatlslspgeratlscrasqdiskylnw yqqkpgqaprlliyhtsrlhsgiparfsgsgsgtdytltisslqpedfavyfcqqg ntlpytfgqgtkleikggggsggggsggggsqvqlqesgpglvkpsetlsltctvs gvslpdygvswirqppgkglewigviwgsettyysssksrvtiskdnsknqvslk lssvtaadtavyycakhyyyggsyamdywgqgtlvtvsshhhhhhhh |
| 104875 CAR 1-Full-nt | 85 | atggcctccctgtcaccgccctgctgcttccgctggctcttctgctccacgccgc tcggcccgaaattgtgatgacccagtcacccgccactcttagcctttcaccggtg agcgcgcaaccctgtcttgcagagcctcccaagacatctcaaataccttaattgg tatcaacagaagcccggacaggctcctcgccttctgatctaccacaccagccggct ccattctggaatccctgccaggttcagcggtagcggatctgggaccgactacaccc tcactatcagctcactgcagccagaggacttcgctgtctatttctgtcagcaaggg aacaccctgccctacaccttggacagggcaccaagctcgagattaaaggtggagg tggcagcggaggaggtgggtccggcggtggaggaagccaggtccaactccaagaaa gcggacccgggtcttgtgaagccatcagaaactctttcactgacttgtactgtgagc ggagtgtctctccccgattacggggtgtcttggatcagacagccaccggggaaggg tctggaatggattggagtgatttggggctctgagactacttactactcttcatccc tcaagtcacgcgtcaccatctcaaaggacaactctaagaatcaggtgtcactgaaa ctgtcatctgtgaccgcagccgacaccgccgtgtactattgcgctaagcattacta ttatggcgggagctacgcaatggattactggggacagggtactctggtcaccgtgt ccagcaccactacccagcaccgaggccacccaccccggctcctaccatcgcctcc cagcctctgtccctgcgtccggaggcatgtagacccgcagctggtggggccgtgca tacccggggtcttgacttcgcctgcgatatctacatttgggcccctctggctggta cttgcgggtcctgctgctttcactcgtgatcactcttactgtaagcgcggtcgg aagaagctgctgtacatctttaagcaaccccttcatgaggcctgtgcagactactca |

TABLE 3-continued

Humanized CD19 CAR Constructs

| Name | SEQ ID | Sequence |
|---|---|---|
| | | agaggaggacggctgttcatgccggttcccagaggaggaggaaggcggctgcgaac<br>tgcgcgtgaaattcagccgcagcgcagatgctccagcctacaagcaggggcagaac<br>cagctctacaacgaactcaatcttggtcggagagaggagtacgacgtgctggacaa<br>gcggagaggacgggacccagaaatgggcggaagccgcgcagaaagaatccccaag<br>agggcctgtacaacgagctccaaaaggataagatggcagaagcctatagcgagatt<br>ggtatgaaggggaacgcagaagaggcaaaggccacgacggactgtaccagggact<br>cagcaccgccaccaaggacacctatgacgctcttcacatgcaggccctgccgcctc<br>gg |
| 104875<br>CAR 1-<br>Full-aa | 31 | MALPVTALLLPLALLLHAARPeivmtqspatlslspgeratlscrasqdiskylnw<br>yqqkpgqaprlliyhtsrlhsgiparfsgsgsgtdytltisslqpedfavyfcqqg<br>ntlpytfgqgtkleikgggsggggsggggsqvqlqesgpglvkpsetlsltctvs<br>gvslpdygvswirqppgkglewigviwgsettyysslksrvtiskdnsknqvslk<br>lssvtaadtavyyckakhyyyggsyamdywgqgtlvtvssttpaprpptpaptias<br>qplslrpeacrpaaggavhtrgldfacdiyiwaplagtcgvlllslvitlyckrgr<br>kkllyifkqpfmrpvqttqeedgcscrfpeeeeggcelrvkfsrsadapaykqgqn<br>qlynelnlgrreeydvldkrrgrdpemggkprrknpqeglynelqkdkmaeaysei<br>gmkgerrrgkghdglyqglstatkdtydalhmqalppr |

CAR 2

| CAR2 scFv domain | 2 | eivmtqspatlslspgeratlscrasqdiskylnwyqqkpgqaprlliyhtsrlhs<br>giparfsgsgsgtdytltisslqpedfavyfcqqgntlpytfgqgtkleikgggs<br>ggggsggggsqvqlqesgpglvkpsetlsltctvsgvslpdygvswirqppgkgle<br>wigviwgsettyyqsslksrvtiskdnsknqvslklssvtaadtavyyckahyyyg<br>gsyamdywgqgtlvtvss |
| 103102<br>CAR2-<br>Soluble<br>scFv-nt | 62 | atggccctccctgtcaccgccctgctgcttccgctggctcttctgctccacgccgc<br>tcggcccgaaattgtgatgacccagtcacccgccactcttagcctttcacccggtg<br>agcgcgcaaccctgtcttgcagagcctcccaagacatctcaaaatacccttaattgg<br>tatcaacagaagcccggacaggctcctcgccttctgatctaccacaccagccggct<br>ccattctggaatcccctgccaggttcagcggtagcggatctgggaccgactacaccc<br>tcactatcagctcactgcagccagaggacttcgctgtctatttctgtcagcaaggg<br>aacaccctgccctacacctttggacagggcaccaagctcgagattaaaggtggagg<br>tggcagcggaggaggtgggtccggcggtggaggaagccaggtccaactccaagaaa<br>gcggaccgggtcttgtgaagccatcagaaactctttcactgacttgtactgtgagc<br>ggagtgtctctcccgattacggggtgtcttggatcagacagccaccggggaaggg<br>tctggaatggattggagtgatttggggctctgagactacttactaccaatcatccc<br>tcaagtcacgcgtcaccatctcaaaggacaactctaagaatcaggtgtcactgaaa<br>ctgtcatctgtgaccgcagccgacaccgccgtgtactattgcgctaagcattacta<br>ttatggcgggagctacgcaatggattactggggacagggtactctggtcaccgtgt<br>ccagccaccaccatcatcaccatcaccat |
| 103102<br>CAR2-<br>Soluble<br>scFv-aa | 74 | MALPVTALLLPLALLLHAARPeivmtqspatlslspgeratlscrasqdiskylnw<br>yqqkpgqaprlliyhtsrlhsgiparfsgsgsgtdytltisslqpedfavyfcqqg<br>ntlpytfgqgtkleikgggsggggsggggsqvqlqesgpglvkpsetlsltctvs<br>gvslpdygvswirqppgkglewigviwgsettyyqsslksrvtiskdnsknqvslk<br>lssvtaadtavyyckahyyyggsyamdywgqgtlvtvsshhhhhhhh |
| 104876<br>CAR 2-<br>Full-nt | 86 | atggccctccctgtcaccgccctgctgcttccgctggctcttctgctccacgccgc<br>tcggcccgaaattgtgatgacccagtcacccgccactcttagcctttcacccggtg<br>agcgcgcaaccctgtcttgcagagcctcccaagacatctcaaaatacccttaattgg<br>tatcaacagaagcccggacaggctcctcgccttctgatctaccacaccagccggct<br>ccattctggaatcccctgccaggttcagcggtagcggatctgggaccgactacaccc<br>tcactatcagctcactgcagccagaggacttcgctgtctatttctgtcagcaaggg<br>aacaccctgccctacacctttggacagggcaccaagctcgagattaaaggtggagg<br>tggcagcggaggaggtgggtccggcggtggaggaagccaggtccaactccaagaaa<br>gcggaccgggtcttgtgaagccatcagaaactctttcactgacttgtactgtgagc<br>ggagtgtctctcccgattacggggtgtcttggatcagacagccaccggggaaggg<br>tctggaatggattggagtgatttggggctctgagactacttactaccaatcatccc<br>tcaagtcacgcgtcaccatctcaaaggacaactctaagaatcaggtgtcactgaaa<br>ctgtcatctgtgaccgcagccgacaccgccgtgtactattgcgctaagcattacta<br>ttatggcgggagctacgcaatggattactggggacagggtactctggtcaccgtgt<br>ccagcaccactaccccagcaccgaggccacccaccccggctcctaccatcgcctcc<br>cagcctctgtccctgcgtccggaggcatgtagacccgcagctggtggggccgtgca<br>tacccggggtcttgacttcgcctgcgatatctacatttgggcccctctggctggta<br>cttgcgggtcctgctgctttcactcgtgatcactcttttactgtaagcgcggtcgg<br>aagaagctgctgtacatctttaagcaacccttcatgaggcctgtgcagactactca<br>agaggaggacggctgttcatgccggttcccagaggaggaggaaggcggctgcgaac<br>tgcgcgtgaaattcagccgcagcgcagatgctccagcctacaagcaggggcagaac<br>cagctctacaacgaactcaatcttggtcggagagaggagtacgacgtgctggacaa<br>gcggagaggacgggacccagaaatgggcggaagccgcgcagaaagaatccccaag<br>agggcctgtacaacgagctccaaaaggataagatggcagaagcctatagcgagatt |

TABLE 3-continued

Humanized CD19 CAR Constructs

| Name | SEQ ID | Sequence |
|---|---|---|
| | | ggtatgaaaggggaacgcagaagaggcaaaggccacgacggactgtaccagggact<br>cagcaccgccaccaaggacacctatgacgctcttcacatgcaggccctgccgcctc<br>gg |
| 104876<br>CAR 2-<br>Full-aa | 32 | MALPVTALLLPLALLLHAARPeivmtqspatlslspgeratlscrasqdiskylnw<br>yqqkpgqaprlliyhtsrlhsgiparfsgsgsgtdytltisslqpedfavyfcqqg<br>ntlpytfgqgtkleikggggsggggsggggsqvqlqesgpglvkpsetlsltctvs<br>gvslpdygvswirqppgkglewigviwgsettyyqsslksrvtiskdnsknqvslk<br>lssvtaadtavyycakhyyyggsyamdywgqgtlvtvssttttpaprpptpaptias<br>qplslrpeacrpaaggavhtrgldfacdiyiwaplagtcgvlllslvitlyckrgr<br>kkllyifkqpfmrpvqttqeedgcscrfpeeeeggcelrvkfsrsadapaykqgqn<br>qlynelnlgrreeydvldkrrgrdpemggkprrknpqeglynelqkdkmaeaysei<br>gmkgerrrgkghdglyqglstatkdtydalhmqalppr |

CAR 3

| CAR3 scFv<br>domain | 3 | qvqlqesgpglvkpsetlsltctvsgvslpdygvswirqppgkglewigviwgset<br>tyyssslksrvtiskdnsknqvslklssvtaadtavyycakhyyyggsyamdywgq<br>gtlvtvssggggsggggsggggseivmtqspatlslspgeratlscrasqdiskyl<br>nwyqqkpgqaprlliyhtsrlhsgiparfsgsgsgtdytltisslqpedfavyfcq<br>qgntlpytfgqgtkleik |
| 103104<br>CAR 3-<br>Soluble<br>scFv-nt | 63 | atggctctgcccgtgaccgcactcctcctgccactggctctgctgcttcacgccgc<br>tcgcccacaagtccagcttcaagaatcagggcctggtctggtgaagccatctgaga<br>ctctgtccctcacttgcaccgtgagcggagtgtccctcccagactacggagtgagc<br>tggattagacagcctcccggaaagggactggagtggatcggagtgatttggggtag<br>cgaaaccacttactattcatcttccctgaagtcacgggtcaccatttcaaaggata<br>actcaaagaatcaagtgagcctcaagctctcatcagtcaccgccgctgacaccgcc<br>gtgtattactgtgccaagcattactactatggagggtcctacgccatggactactg<br>gggccagggaactctggtcactgtgtcatctggtggaggaggtagcggaggaggcg<br>ggagcggtggaggtggctccgaaatcgtgatgacccagagccctgcaaccctgtcc<br>ctttctcccggggaacgggctacccttcttgtcgggcatcacaagatatctcaaa<br>atacctcaattggtatcaacagaagccgggacaggcccctaggcttcttatctacc<br>acacctctcgcctgcatagcgggattcccgcacgctttagcgggtctggaagcggg<br>accgactacactctgaccatctcatctctccagcccgaggacttcgccgtctactt<br>ctgccagcagggtaacacccctgccgtacaccttcggccagggcaccaagcttgaga<br>tcaaacatcaccaccatcatcaccatcac |
| 103104<br>CAR 3-<br>Soluble<br>scFv-aa | 75 | MALPVTALLLPLALLLHAARPqvqlqesgpglvkpsetlsltctvsgvslpdygvs<br>wirqppgkglewigviwgsettyyssslksrvtiskdnsknqvslklssvtaadta<br>vyycakhyyyggsyamdywgqgtlvtvssggggsggggsggggseivmtqspatls<br>lspgeratlscrasqdiskylnwyqqkpgqaprlliyhtsrlhsgiparfsgsgsg<br>tdytltisslqpedfavyfcqqgntlpytfgqgtkleikhhhhhhhh |
| 104877<br>CAR 3-<br>Full-nt | 87 | atggctctgcccgtgaccgcactcctcctgccactggctctgctgcttcacgccgc<br>tcgcccacaagtccagcttcaagaatcagggcctggtctggtgaagccatctgaga<br>ctctgtccctcacttgcaccgtgagcggagtgtccctcccagactacggagtgagc<br>tggattagacagcctcccggaaagggactggagtggatcggagtgatttggggtag<br>cgaaaccacttactattcatcttccctgaagtcacgggtcaccatttcaaaggata<br>actcaaagaatcaagtgagcctcaagctctcatcagtcaccgccgctgacaccgcc<br>gtgtattactgtgccaagcattactactatggagggtcctacgccatggactactg<br>gggccagggaactctggtcactgtgtcatctggtggaggaggtagcggaggaggcg<br>ggagcggtggaggtggctccgaaatcgtgatgacccagagccctgcaaccctgtcc<br>ctttctcccggggaacgggctacccttcttgtcgggcatcacaagatatctcaaa<br>atacctcaattggtatcaacagaagccgggacaggcccctaggcttcttatctacc<br>acacctctcgcctgcatagcgggattcccgcacgctttagcgggtctggaagcggg<br>accgactacactctgaccatctcatctctccagcccgaggacttcgccgtctactt<br>ctgccagcagggtaacacccctgccgtacaccttcggccagggcaccaagcttgaga<br>tcaaaaccactactcccgctccaaggcaccacccctgcccgaccatcgcctct<br>cagccgctttccctgcgtccggaggcatgtagaccccgcagctggtggggccgtgca<br>tacccggggtcttgacttcgcctgcgatatctacatttgggcccctctggctggta<br>cttgcgggtcctgctgctttcactcgtgatcactctttactgtaagcgcggtcgg<br>aagaagctgctgtacatctttaagcaacccttcatgaggcctgtgcagactactca<br>agaggaggacggctgttcatgccggttcccagaggaggaggaaggcggctgcgaac<br>tgcgcgtgaaattcagccgcagcgcagatgctccagcctacaagcaggggcagaac<br>cagctctacaacgaactcaatcttggtcggagagaggagtacgacgtgctggacaa<br>gcggagaggacgggacccagaaatgggcgggaagccgcgcagaagaatccccaag<br>agggcctgtacaacgagctccaaaaggataagatggcagaagcctatagcgagatt<br>ggtatgaaaggggaacgcagaagaggcaaaggccacgacggactgtaccagggact<br>cagcaccgccaccaaggacacctatgacgctcttcacatgcaggccctgccgcctc<br>gg |
| 104877<br>CAR 3-<br>Full-aa | 33 | MALPVTALLLPLALLLHAARPqvqlqesgpglvkpsetlsltctvsgvslpdygvs<br>wirqppgkglewigviwgsettyyssslksrvtiskdnsknqvslklssvtaadta<br>vyycakhyyyggsyamdywgqgtlvtvssggggsggggsggggseivmtqspatls |

TABLE 3-continued

Humanized CD19 CAR Constructs

| Name | SEQ ID | Sequence |
|---|---|---|
| | | lspgeratlscrasqdiskylnwyqqkpgqaprlliyhtsrlhsgiparfsgsgsg<br>tdytltisslqpedfavyfcqqgntlpytfgqgtkleiktttpaprpptpaptias<br>qplslrpeacrpaaggavhtrgldfacdiyiwaplagtcgvlllslvitlyckrgr<br>kkllyifkqpfmrpvqttqeedgcscrfpeeeeggcelrvkfsrsadapaykgqgqn<br>qlynelnlgrreeydvldkrrgrdpemggkprrknpqeglynelqkdkmaeaysei<br>gmkgerrrgkghdglyqglstatkdtydalhmqalppr |

CAR 4

| Name | SEQ ID | Sequence |
|---|---|---|
| CAR4 scFv domain | 4 | qvqlqesgpglvkpsetlsltctvsgvslpdygvswirqppgkglewigviwgset<br>tyyqsslksrvtiskdnsknqvslklssvtaadtavyycakhyyyggsyamdywgq<br>gtlvtvssggggsggggsggggseivmtqspatlslspgeratlscrasqdiskyl<br>nwyqqkpgqaprlliyhtsrlhsgiparfsgsgsgtdytltisslqpedfavyfcq<br>qgntlpytfgqgtkleik |
| 103106 CAR4-Soluble scFv-nt | 64 | atggctctgccgtgaccgcactcctcctgccactggctctgctgcttcacgccgc<br>tcgcccacaagtccagcttcaagaatcagggcctggtctggtgaagccatctgaga<br>ctctgtccctcacttgcaccgtgagcggagtgtccctcccagactacggagtgagc<br>tggattagacagcctcccggaaagggactggagtggatcggagtgatttggggtag<br>cgaaaccacttactatcaatcttccctgaagtcacgggtcaccattttcaaaggata<br>actcaaagaatcaagtgagcctcaagctctcatcagtcaccgccgctgacaccgcc<br>gtgtattactgtgccaagcattactactatggaggtcctacgccatggactactg<br>gggccagggaactctggtcactgtgtcatctggtggaggaggtagcggaggaggcg<br>ggagcggtggaggtggctccgaaatcgtgatgacccagagcctgcaaccctgtcc<br>ctttctcccggggaacgggctacccttcttgtcgggcatcacaagatatctcaaa<br>atacctcaattggtatcaacagaagccgggacaggcccctaggcttcttatctacc<br>acacctctcgcctgcatagcgggattcccgcacgctttagcgggtctggaagcggg<br>accgactacactctgaccatctcatctctccagcccgaggacttcgccgtctactt<br>ctgccagcagggtaaacacctgccgtacaccttcggccagggcaccaagcttgaga<br>tcaaacatcaccaccatcatcaccatcac |
| 103106 CAR4-Soluble scFv-aa | 76 | MALPVTALLLPLALLLHAARPqvqlqesgpglvkpsetlsltctvsgvslpdygvs<br>wirqppgkglewigviwgsettyyqsslksrvtiskdnsknqvslklssvtaadta<br>vyycakhyyyggsyamdywgqgtlvtvssggggsggggsggggseivmtqspatls<br>lspgeratlscrasqdiskylnwyqqkpgqaprlliyhtsrlhsgiparfsgsgsg<br>tdytltisslqpedfavyfcqqgntlpytfgqgtkleikhhhhhhhh |
| 104878 CAR 4-Full-nt | 88 | atggctctgccgtgaccgcactcctcctgccactggctctgctgcttcacgccgc<br>tcgcccacaagtccagcttcaagaatcagggcctggtctggtgaagccatctgaga<br>ctctgtccctcacttgcaccgtgagcggagtgtccctcccagactacggagtgagc<br>tggattagacagcctcccggaaagggactggagtggatcggagtgatttggggtag<br>cgaaaccacttactatcaatcttccctgaagtcacgggtcaccattttcaaaggata<br>actcaaagaatcaagtgagcctcaagctctcatcagtcaccgccgctgacaccgcc<br>gtgtattactgtgccaagcattactactatggaggtcctacgccatggactactg<br>gggccagggaactctggtcactgtgtcatctggtggaggaggtagcggaggaggcg<br>ggagcggtggaggtggctccgaaatcgtgatgacccagagcctgcaaccctgtcc<br>ctttctcccggggaacgggctacccttcttgtcgggcatcacaagatatctcaaa<br>atacctcaattggtatcaacagaagccgggacaggcccctaggcttcttatctacc<br>acacctctcgcctgcatagcgggattcccgcacgctttagcgggtctggaagcggg<br>accgactacactctgaccatctcatctctccagcccgaggacttcgccgtctactt<br>ctgccagcagggtaaacacctgccgtacaccttcggccagggcaccaagcttgaga<br>tcaaaccactactcccgctccaaggccacccaccccctgccccgaccatcgcctct<br>cagccgctttccctgcgtccggaggcatgtagacccgcagctggtggggccgtgca<br>tacccgggtcttgacttcgcctgcgatatctacatttgggccctctgcgtggta<br>cttgcggggtcctgctgctttcactcgtgatcactcttttactgtaagcgcggtcgg<br>aagaagctgctgtacatctttaagcaacccttcatgaggcctgtgcagactactca<br>agaggaggacggctgttcatgccggttcccagaggaggaggaaggcggctgcgaac<br>tgcgcgtgaaattcagccgcagcgcagatgctccagcctacaagcagggcagaac<br>cagctctacaacgaactcaatcttggtcggagagaggagtacgacgtgctggacaa<br>gcggagaggacgggacccagaaatgggcgggaagccgcgcagaaagaatccccaag<br>agggcctgtacaacgagctccaaaaggataagatggcagaagcctatagcgagatt<br>ggtatgaaaggggaacgcagaagaggcaaaggccacgacggactgtaccagggact<br>cagcaccgccaccaaggacacctatgacgctcttcacatgcaggccctgccgcctc<br>gg |
| 104878 CAR 4-Full-aa | 34 | MALPVTALLLPLALLLHAARPqvqlqesgpglvkpsetlsltctvsgvslpdygvs<br>wirqppgkglewigviwgsettyyqsslksrvtiskdnsknqvslklssvtaadta<br>vyycakhyyyggsyamdywgqgtlvtvssggggsggggsggggseivmtqspatls<br>lspgeratlscrasqdiskylnwyqqkpgqaprlliyhtsrlhsgiparfsgsgsg<br>tdytltisslqpedfavyfcqqgntlpytfgqgtkleiktttpaprpptpaptias<br>qplslrpeacrpaaggavhtrgldfacdiyiwaplagtcgvlllslvitlyckrgr<br>kkllyifkqpfmrpvqttqeedgcscrfpeeeeggcelrvkfsrsadapaykqgqn<br>qlynelnlgrreeydvldkrrgrdpemggkprrknpqeglynelqkdkmaeaysei<br>gmkgerrrgkghdglyqglstatkdtydalhmqalppr |

TABLE 3-continued

Humanized CD19 CAR Constructs

| Name | SEQ ID | Sequence |
|---|---|---|
| CAR 5 | | |
| CAR5 scFv domain | 5 | eivmtqspatlslspgeratlscrasqdiskylnwyqqkpgqaprlliyhtsrlhs giparfsgsgsgtdytltisslqpedfavyfcqqgntlpytfgqgtkleikggggs ggggsggggsggggsqvqlqesgpglvkpsetlsltctvsgvslpdygvswirqpp gkglewigviwgsettyyssslksrvtiskdnsknqvslklssvtaadtavyycak hyyyggsyamdywgqgtlvtvss |
| 99789 CAR5- Soluble scFv-nt | 65 | atggcccctcccagtgaccgctctgctgctgcctctcgcacttcttctccatgccgc tcggcctgagatcgtcatgacccaaagcccccgctaccctgtccctgtcacccggcg agagggcaacccctttcatgcagggccagccaggacatttctaagtacctcaactgg tatcagcagaagccagggcaggctcctcgcctgctgatctaccacaccagccgcct ccacagcggtatccccgccagattttccgggagcgggtctggaaccgactacaccc tcaccatctcttctctgcagcccgaggattcgccgtctatttctgccagcagggg aatactctgccgtacaccttcggtcaaggtaccaagctggaaatcaagggaggcgg aggatcaggcggtggcgaagcggaggaggtggctccggaggggaggttcccaag tgcagcttcaagaatcaggaccggacttgtgaagccatcagaaaccctctccctg acttgtaccgtgtccggtgtgagcctcccgactacggagtctcttggattcgcca gcctccggggaagggtcttgaatggattggggtgatttgggatcagagactactt actactcttcatcacttaagtcacgggtcaccatcagcaaagataatagcaagaac caagtgtcacttaagctgtcatctgtgaccgccgctgacaccgccgtgtactattg tgccaaacattactattacggagggtcttatgctatggactactggggacagggga ccctggtgactgtctctagccatcaccatcaccaccatcac |
| 99789 CAR5- Soluble scFv-aa | 77 | MALPVTALLLPLALLLHAARPeivmtqspatlslspgeratlscrasqdiskylnw yqqkpgqaprlliyhtsrlhsgiparfsgsgsgtdytltisslqpedfavyfcqqg ntlpytfgqgtkleikggggsggggsggggsggggsqvqlqesgpglvkpsetlsl tctvsgvslpdygvswirqppgkglewigviwgsettyyssslksrvtiskdnskn qvslklssvtaadtavyycakhyyyggsyamdywgqgtlvtvsshhhhhhhh |
| 104879 CAR 5- Full-nt | 89 | atggcccctccctgtcaccgccctgctgcttccgctggctcttctgctccacgccgc tcggcccgaaattgtgatgacccagtcacccgccactcttagcctttcacccggtg agcgcgcaaccctgtcttgcagagcctcccaagacatctcaaatacctttaattgg tatcaacagaagcccggacaggctcctcgccttctgatctaccacaccagccggct ccattctggaatcctgccaggttcagcggtagcggatctgggaccgactacaccc tcactatcagctcactgcagccagaggacttcgctgtctatttctgtcagcaaggg aacaccctgccctacacctttggacagggcaccaagctcgagattaaaggtggagg tggcagcggaggaggtgggtccggcggtggaggaagcggcggaggcgggagccagg tccaactccaagaaagcggaccgggtcttgtgaagccatcagaaactctttcactg acttgtactgtgagcggagtgtctctccccgattacggggtgtcttggatcagaca gccaccggggaagggtctggaatggattggagtgatttgggctctgagactactt actactcttcatccctaagtcacgcgtcaccatctcaaaggacaactctaagaat caggtgtcactgaaactgtcatctgtgaccgcagccgacaccgccgtgtactattg cgctaagcattactattatggcgggagctacgcaatggattactggggacagggta cctctggtcaccgtgtccagcaccactaccccagcaccgaggccacccaccccggct cctaccatcgcctcccagcctctgtccctgcgtccggaggcatgtagacccgcagc tggtggggccgtgcatacccgggtcttgacttcgcctgcgatatctacatttggg cccctctggctggtacttgcggggtcctgctgctttcactcgtgatcactctttac tgtaagcgcggtcggaagaagctgctgtacatcttaagcaaccctttcatgaggcc tgtgcagactactcaagaggaggacggctgttcatgccggtccccagaggaggagg aaggcggctgcgaactgcgcgtgaaattcagccgcagcgcagatgctccagcctac aagcaggggcagaaccagctctacaacgaactcaatcttggtcggagagaggagta cgacgtgctggacaagcggagagacgggacccagaaatgggcgggaagccgcgca gaaagaatccccaagggcctgtacaacgagctccaaaaggataagatggcagaa gcctatagcgagattggtatgaaagggaacgcagaagaggcaaaggccacgacgg actgtaccagggactcagcaccgccaccaaggacacctatgacgctcttcacatgc aggccctgccgcctcgg |
| 104879 CAR 5- Full-aa | 35 | MALPVTALLLPLALLLHAARPeivmtqspatlslspgeratlscrasqdiskylnw yqqkpgqaprlliyhtsrlhsgiparfsgsgsgtdytltisslqpedfavyfcqqg ntlpytfgqgtkleikggggsggggsggggsggggsqvqlqesgpglvkpsetlsl tctvsgvslpdygvswirqppgkglewigviwgsettyyssslksrvtiskdnskn qvslklssvtaadtavyycakhyyyggsyamdywgqgtlvtvsstttpaprpptpa ptiasqplslrpeacrpaaggavhtrgldfacdiyiwaplagtcgvlllslvitly ckrgrkkllyifkqpfmrpvqttqeedgcscrfpeeeeggcelrvkfsrsadapay kqgqnqlynelnlgrreeydvldkrrgrdpemggkprrknpqeglynelqkdkmae ayseigmkgerrrgkghdglyqglstatkdtydalhmqalppr |
| CAR 6 | | |
| CAR6 scFv domain | 6 | eivmtqspatlslspgeratlscrasqdiskylnwyqqkpgqaprlliyhtsrlhs giparfsgsgsgtdytltisslqpedfavyfcqqgntlpytfgqgtkleikggggs ggggsggggsggggsqvqlqesgpglvkpsetlsltctvsgvslpdygvswirqpp gkglewigviwgsettyyqsslksrvtiskdnsknqvslklssvtaadtavyycak hyyyggsyamdywgqgtlvtvss |

TABLE 3-continued

Humanized CD19 CAR Constructs

| Name | SEQ ID | Sequence |
|---|---|---|
| 99790 CAR6- Soluble scFv-nt | 66 | atggccctcccagtgaccgctctgctgctgcctctcgcacttcttctccatgccgc tcggcctgagatcgtcatgacccaaagccccgctaccctgtccctgtcacccggcg agagggcaacccttccatgcagggccagccaggacatttctaagtacctcaactgg tatcagcagaagccagggcaggctcctcgcctgctgatctaccacaccagccggcct ccacagcggtatccccgccagattttccgggagcgggtctggaaccgactacaccc tcaccatctcttctctgcagcccgaggattcgccgtctatttctgccagcagggg aatactctgccgtacaccttcggtcaaggtaccaagctggaaatcaagggaggcgg aggatcaggcggtggcgaagcggaggaggtggctccggaggaggaggttcccaag tgcagcttcaagaatcaggacccggacttgtgaagccatcagaaaccctctccctg acttgtaccgtgtccggtgtgagcctccccgactacggagtctcttggattcgcca gcctccggggaagggtcttgaatggattgggtgatttgggatcagagactactt actaccagtcatcacttaagtcacgggtcaccatcagcaaagataatagcaagaac caagtgtcacttaagctgtcatctgtgaccgccgctgacaccgccgtgtactattg tgccaaacattactattacggagggtcttatgctatggactactggggacagggga cctggtgactgtctctagccatcaccatcaccaccatcatcac |
| 99790 CAR6- Soluble scFv-aa | 78 | MALPVTALLLPLALLLHAARPeivmtqspatlslspgeratlscrasqdiskylnw yqqkpgqaprlliyhtsrlhsgiparfsgsgsgtdytltisslqpedfavyfcqqg ntlpytfgqgtkleikgggggsgggsgggsgggsqvqlqesgpglvkpsetlsl tctvsgvslpdygvswirqppgkglewigviwgsettyyqsslksrvtiskdnskn qvslklssvtaadtavyycakhyyyggsyamdywgqgtlvtvsshhhhhhhh |
| 104880 CAR6- Full-nt | 90 | atggccctccctgtcaccgccctgctgcttccgctggctcttctgctccacgccgc tcggcccgaaattgtgatgacccagtcacccgccactcttagcctttcacccggtg agcgcgcaacctgtcttgcagagcctcccaagacatctcaaaatacctcaattgg tatcaacagaagcccggacaggtcctcgccttctgatctaccacaccagccggct ccattctggaatccctgccaggttcagcggtagcggatctgggaccgactacaccc tcactatcagctcactgcagccagaggacttcgctgtctatttctgtcagcaaggg aacaccctgccctacacctttggacagggcaccaaagctcgagattaaaggtggagg tggcagcggaggaggtgggtccggcggtggaggaagcggaggcggagggagccagg tccaactccaagaaagcggacccgggtcttgtgaagccatcagaaactctttcactg acttgtactgtgagcggagtgtctctcccgattacggggtgtcttggatcagaca gccaccggggaagggtctggaatggattggagtgatttgggctctgagactactt actaccaatcatccctcaagtcacgcgtcaccatctcaaaggacaactctaagaat caggtgtcactgaaactgtcatctgtgaccgcagccgacaccgccgtgtactattg cgctaagcattactattatggcgggagctacgcaatggattactggggacagggta ctctggtcaccgtgtccagcaccactacccgcaccgaggccacccacccatctcct cctaccatcgcctcccagcctctgtccctgcgtccggaggcatgtagacccgcagc tggtggggccgtgcatacccgggtcttgacttcgcctgcgatatctacatttggg ccctctggctggtacttgcggggtcctgctgctttcactcgtgatcactctttac tgtaagcgcggtcggaagaagctgctgtacatcttaagcaacccttcatgaggcc tgtgcagactactcaagaggaggacggctgttcatgccggttcccagaggaggagg aaggcggctgcgaactgcgcgtgaaattcagccgcagcgcagatgctccagcctac aagcaggggcagaaccagctctacaacgaactcaatcttggtcggagagaggagta cgacgtgctggacaagcggagaggacgggacccagaaatgggcggaagccgcgca gaaagaatccccaagagggcctgtacaacgagctccaaaaggataagatggcagaa gcctatagcgagattggtatgaaaggggaacgcagaagaggcaaaggccacgacgg actgtaccagggactcagcaccgccaccaaggacacctatgacgctcttcacatgc aggccctgccgcctcgg |
| 104880 CAR6- Full-aa | 36 | MALPVTALLLPLALLLHAARPeivmtqspatlslspgeratlscrasqdiskylnw yqqkpgqaprlliyhtsrlhsgiparfsgsgsgtdytltisslqpedfavyfcqqg ntlpytfgqgtkleikgggggsgggsgggsgggsqvqlqesgpglvkpsetlsl tctvsgvslpdygvswirqppgkglewigviwgsettyyqsslksrvtiskdnskn qvslklssvtaadtavyycakhyyyggsyamdywgqgtlvtvssttttpaprpptpa ptiasqplslrpeacrpaaggavhtrgldfacdiyiwaplagtcgvlllslvitly ckrgrkkllyifkqpfmrpvqttgeedgcscrfpeeeeggcelrvkfsrsadapay kqgqnqlynelnlgrreeydvldkrrgrdpemggkprrknpqeglynelqkdkmae ayseigmkgerrrgkghdglyqglstatkdtydalhmqalppr |

CAR 7

| CAR7 scFv domain | 7 | qvqlqesgpglvkpsetsltctvsgvslpdygvswirqppgkglewigviwgset tyysslksrvtiskdnsknqvslklssvtaadtavyycakhyyyggsyamdywgq gtlvtvssggggsggggsggggsggggseivmtqspatlslspgeratlscrasqd iskylnwyqqkpgqaprlliyhtsrlhsgiparfsgsgsgtdytltisslqpedfa vyfcqqgntlpytfgqgtkleik |
| 100796 CAR7- Soluble scFv-nt | 67 | atggcactgcctgtcactgccctcctgctgcctctggcctccttctgcatgccgc caggccccaagtccagctgcaagagtcaggacccggacttggtgaagcgtctgaga ctctctcactgacttgtaccgtcagcggcgtgtccctccccgactacggagtgtca tggatccgccaacctcccgggaagggcttgaatggattggtgtcatctggggttc tgaaaccacctactactcatcttccctgaagtccagggtgaccatcagcaaggata attccaagaaccaggtcagccttaagctgtcatctgtgaccgctgctgacaccgcc gtgtattactgcgccaagcactactattacggaggaagctacgctatggactattg |

TABLE 3-continued

Humanized CD19 CAR Constructs

| Name | SEQ ID | Sequence |
|---|---|---|
| | | gggacagggcactctcgtgactgtgagcagcggcggtggagggtctggaggtggag gatccggtggtggtgggtcaggcggaggagggagcgagattgtgatgactcagtca ccagccacccttctctttcacccggcgagagagcaaccctgagctgtagagccag ccaggacatttctaagtacctcaactggtatcagcaaaaaccggggcaggcccctc gcctcctgatctaccatacctcacgccttcactctggtatcccgctcggtttagc ggatcaggatctggtaccgactacactctgaccatttccagcctgcagccagaaga tttcgcagtgtatttctgccagcagggcaatacccttccttacaccttcggtcagg gaaccaagctcgaaatcaagcaccatcaccatcatcaccat |
| 100796 CAR7-Soluble scFv-aa | 79 | MALPVTALLLPLALLLHAARPqvqlqesgpglvkpsetlsltctvsgvslpdygvs wirqppgkglewigviwgsettyyssslksrvtiskdnsknqvslklssvtaadta vyycakhyyyggsyamdywgqgtlvtvssggggsggggsggggsggggseivmtqs patlslspgeratlscrasqdiskylnwyqqkpgqaprlliyhtsrlhsgiparfs gsgsgtdytltisslqpedfavyfcqqgntlpytfgqgtkleikhhhhhhhh |
| 104881 CAR 7 Full-nt | 91 | atggctctgccgtgaccgcactcctcctgccactggctctgctgcttcacgccgc tcgcccacaagtccagcttcaagaatcagggcctggtctggtgaagccatctgaga ctctgtccctcacttgcaccgtgagcggagtgtccctcccagactacggagtgagc tggattagacagcctcccggaaagggactggagtggatcggagtgatttggggtag cgaaaccacttactattcatctttccctgaagtcacgggtcaccatttcaaaggata actcaaagaatcaagtgagcctcaagctctcatcagtcaccgccgctgacaccgcc gtgtattactgtgccaagcattactactatggaggtcctacgccatggactactg gggccagggaactctggtcactgtgtcatctggtggaggaggtagcggaggaggcg ggagcggtggaggtggctccggaggtggcgaagcgaaatcgtgatgacccagagc cctgcaacctgtcccttctcccggggaacgggctaccctttcttgtcgggcatc acaagatatctcaaaatacctcaattggtatcaacagaagccgggacaggcccta ggcttctatctaccacacctctcgcctgcatagcgggattcccgcacgctttagc gggtctggaagcgggaccgactacactctgaccatctcatctctccagcccgagga cttcgccgtctacttctgccagcagggtaaccctgccgtacaccttcggccagg gcaccaagcttgagatcaaaaccactactcccgctccaaggccaccaccccctgcc ccgaccatcgcctctcagccgctttccctgcgtccggaggcatgtagaccccgcagc tggtggggccgtgcatacccggggtcttgacttcgcctgcgatatctacatttggg cccctctggctggtacttgcgggtcctgctgctttcactcgtgatcactctttac tgtaagcgcggtcggaagaagctgctgtacatcttttaagcaacccttcatgaggcc tgtgcagactactcaagaggaggacggctgttcatgccggttcccagaggaggag aaggcggctgcgaactgcgcgtgaaattcagccgcagcgcagatgctccagcctac aagcagggcagaaccagctctacaacgaactcaatcttggtcggagagaggagta cgacgtgctggacaagcggagaggacgggacccagaaatgggcgggaagccgcgca gaaagaatccccaagagggcctgtacaacgagctccaaaggataagatggcagaa gcctatagcgagattggtatgaaaggggaacgcagaagaggcaaaggccacgacgg actgtaccagggactcagcaccgccaccaaggacacctatgacgctcttcacatgc aggccctgccgcctcgg |
| 104881 CAR 7 Full-aa | 37 | MALPVTALLLPLALLLHAARPqvqlqesgpglvkpsetlsltctvsgvslpdygvs wirqppgkglewigviwgsettyyssslksrvtiskdnsknqvslklssvtaadta vyycakhyyyggsyamdywgqgtlvtvssggggsggggsggggsggggseivmtqs patlslspgeratlscrasqdiskylnwyqqkpgqaprlliyhtsrlhsgiparfs gsgsgtdytltisslqpedfavyfcqqgntlpytfgqgtkleiktttpaprppptpa ptiasqplslrpeacrpaaggavhtrgldfacdiyiwaplagtcgvlllslvitly ckrgrkkllyifkqpfmrpvqttqeedgcscrfpeeeeggcelrvkfsrsadapay kqgqnqlynelnlgrreeydvldkrrgrdpemggkprrknpqeglynelqkdkmae ayseigmkgerrrgkghdglyqglstatkdtydalhmqalppr |

CAR 8

| CAR8 scFv domain | 8 | qvqlqesgpglvkpsetlsltctvsgvslpdygvswirqppgkglewigviwgset tyyqsslksrvtiskdnsknqvslklssvtaadtavyycakhyyyggsyamdywgq gtlvtvssggggsggggsggggsggggseivmtqspatlslspgeratlscrasqd iskylnwyqqkpgqaprlliyhtsrlhsgiparfsgsgsgtdytltisslqpedfa vyfcqqgntlpytfgqgtkleik |
| 100798 CAR8-Soluble scFv-nt | 68 | atggcactgcctgtcactgccctcctgctgcctctggccctccttctgcatgccgc caggcccaagtccagctgcaagatcaggacccgactggtgaagccgtctgaga ctctctcactgacttgtaccgtcagcggcgtgtccctcccgactacggagtgtca tggatccgccaacctcccggaaagggcttgaatggattggtgtcatctggggttc tgaaaccacctactaccagtcttccctgaagtccagggtgaccatcagcaaggata attccaagaaccaggtcagccttaagctgtcatctgtgaccgctgctgacaccgcc gtgtattactgcgccaagcactactattacggaggaagctacgctatggactattg gggacagggcactctcgtgactgtgagcagcggcggtggagggtctggaggtggag gatccggtggtggtgggtcaggcggaggagggagcgagattgtgatgactcagtca ccagccacccttctctttcacccggcgagagagcaaccctgagctgtagagccag ccaggacatttctaagtacctcaactggtatcagcaaaaaccggggcaggcccctc gcctcctgatctaccatacctcacgccttcactctggtatcccgctcggtttagc ggatcaggatctggtaccgactacactctgaccatttccagcctgcagccagaaga tttcgcagtgtatttctgccagcagggcaatacccttccttacaccttcggtcagg gaaccaagctcgaaatcaagcaccatcaccatcatcatcaccac |

TABLE 3-continued

Humanized CD19 CAR Constructs

| Name | SEQ ID | Sequence |
|---|---|---|
| 100798 CAR8-Soluble scFv-aa | 80 | MALPVTALLLPLALLLHAARPqvqlqesgpglvkpsetlsltctvsgvslpdygvs wirqppgkglewigviwgsettyyqsslksrvtiskdnsknqvslklssvtaadta vyycakhyyyggsyamdywgqgtlvtvssggggsggggsggggsggggseivmtqs patlslspgeratlscrasqdiskylnwyqqkpgqaprlliyhtsrlhsgiparfs gsgsgtdytltisslqpedfavyfcqqgntlpytfgqgtkleikhhhhhhhh |
| 104882 CAR 8-Full-nt | 92 | atggctctgcccgtgaccgcactcctcctgccactggctctgctgcttcacgccgc tcgcccacaagtccagcttcaagaatcagggcctggtctggtgaagccatctgaga ctctgtccctcacttgcaccgtgagcggagtgtccctcccagactacggagtgagc tggattagacagcctcccggaaagggactggagtggatcggagtgatttggggtag cgaaaccacttactatcaatcttccctgaagtcacgggtcaccatttcaaaggata actcaaagaatcaagtgagcctcaagctctcatcagtcaccgccgctgacaccgcc gtgtattactgtgccaagcattactactatggagggtcctacgccatggactactg gggccagggaactctggtcactgtgtcatctggtggaggaggtagcggaggaggcg ggagcggtggaggtggctccggaggcggtgggtcagaaatcgtgatgacccagagc cctgcaaccctgtcccttctctccggggaacgggctacccttcttgtcgggcatc acaagatatctcaaaatacctcaattggtatcaacagaagccgggacaggcccctg gcttcttatctaccacacctctcgcctgcatagcgggattcccgcacgctttagc gggtctggaagcgggaccgactacactctgaccatctcatctctccagcccgagga cttcgccgtctacttctgccagcagggtaacacctgccgtacaccttcggccagg gcaccaagcttgagatcaaaaccactactcccgctccaaggccacccacccctgcc ccgaccatcgcctctcagccgctttccctgcgtccggaggcatgtagacccgcagc tggtgggccgtgcatacccgggtcttgacttcgcctgcgatatctacatttggg cccctctggctggtacttgcggggtcctgctgctttcactcgtgatcactctttac tgtaagcgcggtcggaagaagctgctgtacatcttaagcaaccctcatgaggcc tgtgcagactactcaagaggaggacggctgttcatgccggttcccagaggaggagg aaggcggctgcgaactgcgcgtgaaattcagccgcagcgcagatgctccagcctac aagcaggggcagaaccagctctacaacgaactcaatcttggtcggagagaggagta cgacgtgctggacaagcggaggacgggacccagaaatggcgggaagccgcgca gaaagaatccccaagagggcctgtacaacgagctccaaaaggataagatggcagaa gcctatagcgagattggtatgaaggggaacgcagaagaggcaaaggccacgacgg actgtaccagggactcagcaccgccaccaaggacacctatgacgctcttcacatgc aggccctgccgcctcgg |
| 104882 CAR 8-Full-aa | 38 | MALPVTALLLPLALLLHAARPqvqlqesgpglvkpsetlsltctvsgvslpdygvs wirqppgkglewigviwgsettyyqsslksrvtiskdnsknqvslklssvtaadta vyycakhyyyggsyamdywgqgtlvtvssggggsggggsggggsggggseivmtqs patlslspgeratlscrasqdiskylnwyqqkpgqaprlliyhtsrlhsgiparfs gsgsgtdytltisslqpedfavyfcqqgntlpytfgqgtkleiktttpaprpptpa ptiasqplslrpeacrpaaggavhtrgldfacdiyiwaplagtcgvllllslvitly ckrgrkkllyifkqpfmrpvqttgeedgcscrfpeeeeggcelrvkfsrsadapay kqgqnqlynelnlgrreeydvldkrrgrdpemggkprrknpqeglynelqkdkmae ayseigmkgerrrgkghdglyqglstatkdtydalhmqalppr |

CAR 9

| CAR9 scFv domain | 9 | eivmtqspatlslspgeratlscrasqdiskylnwyqqkpgqaprlliyhtsrlhs giparfsgsgsgtdytltisslqpedfavyfcqqgntlpytfgqgtkleikggggs ggggsggggsggggsqvqlqesgpglvkpsetlsltctvsgvslpdygvswirqpp gkglewigviwgsettyynsslksrvtiskdnsknqvslklssvtaadtavyycak hyyyggsyamdywgqgtlvtvss |
| 99789 CAR9-Soluble scFv-nt | 69 | atggcctcccagtgaccgctctgctgctgcctctcgcacttcttctccatgccgc tcggcctgagatcgtcatgacccaaagccccgctaccctgtccctgtcacccggcg agagggcaaccctttcatgcagggccagccaggacatttctaagtacctcaactgg tatcagcagaagccagggcaggctcctcgcctgctgatctaccacaccagccgcct ccacagcggtatcccgccagattttccgggagcgggtctgaaccgactacaccc tcaccatctcttctctgcagcccgaggatttcgccgtctatttctgccagcaggg aatactctgccgtacaccttcggtcaaggtaccaagctggaaatcaagggaggcgg aggatcaggcggtggcggaagcggaggaggtggctccggaggaggaggttcccaag tgcagcttcaagaatcaggaccggacttgtgaagccatcagaaaccctctccctg acttgtaccgtcgtggtgtgagcctccccgactacggagtctcttggattcgcca gcctccggaagggtcttgaatggattggggtgatttggggatcagagactactt actacaattcatcacttaagtcacgggtcaccatcagcaaagataatagcaagaac caagtgtcacttaagctgtcatctgtgaccgccgctgacaccgccgtgtactattg tgccaaacattactattacggagggtcttatgctatggactactggggacagggga ccctggtgactgtctctagccatcaccatcaccaccatcatcac |
| 99789 CAR9-Soluble scFv-aa | 81 | MALPVTALLLPLALLLHAARPeivmtqspatlslspgeratlscrasqdiskylnw yqqkpgqaprlliyhtsrlhsgiparfsgsgsgtdytltisslqpedfavyfcqqg ntlpytfgqgtkleikggggsggggsggggsggggsqvqlqesgpglvkpsetlsl tctvsgvslpdygvswirqppgkglewigviwgsettyynsslksrvtiskdnskn qvslklssvtaadtavyycakhyyyggsyamdywgqgtlvtvsshhhhhhhh |

TABLE 3-continued

Humanized CD19 CAR Constructs

| Name | SEQ ID | Sequence |
|---|---|---|
| 105974 CAR 9- Full-nt | 93 | atggccctccctgtcaccgccctgctgcttccgctggctcttctgctccacgccgc tcggcccgaaattgtgatgacccagtcacccgccactcttagcctttcaccggtg agcgcgcaaccctgtcttgcagagcctcccaagacatctcaaaatacctta attgg tatcaacagaagcccggacaggctcctcgccttctgatctaccacaccagccggct ccattctggaatccctgccaggttcagcggtagcggatctgggaccgactacaccc tcactatcagctcactgcagccagaggacttcgctgtctatttctgtcagcaaggg aacacccctgccctacacctttggacagggcaccaagctcgagattaaaggtggagg tggcagcggaggaggtgggtccggcggtggaggaagcggaggcggtgggagccagg tccaactccaagaaagcggacccgggtcttgtgaagccatcagaaactctttcactg acttgtactgtgagcggagtgtctctccccgattacggggtgtcttggatcagaca gccaccggggaagggtctggaatggattggagtgatttggggctctgagactactt actacaactcatccctcaagtcacgcgtcaccatctcaaaggacaactctaagaat caggtgtcactgaaactgtcatctgtgaccgcagccgacaccgccgtgtactattg cgctaagcattactattatggcgggagctacgcaatggattactgggg acagggta ctctggtcaccgtgtccagcaccactacccc agcaccgaggccacccaccccggct cctaccatcgcctcccagcctctgtcc ctgcgtccggaggcatgtagaccgcagc tggtggggccgtgcatacccggggtcttgacttcgcctgcgatatctacatttggg cccctctggctggtacttgcggggtcctgctgctttcactcgtgatcactctttac tgtaagcgcggtcggaagaagctgctgtacatctttaagcaacccttcatgaggcc tgtgcagactactcaagaggaggacggctgttcatgccggttcccagaggaggagg aaggcggctgcgaactgcgcgtgaaattcagccgcagcgcagatgctccagcctac aagcaggggcagaaccagctctacaacgaactcaatcttggtcggagagaggagta cgacgtgctggacaagcggagaggacgggacccagaaatgggcgggaagccgcgca gaaagaatccccaagagggcctgtacaacgagctccaaaaggataagatggcagaa gcctatagcgagattggtatgaaggggaacgcagaagaggcaaaggccacgacgg actgtaccagggactcagcaccgccaccaaggacacctatgacgctcttcacatgc aggccctgccgcctcgg |
| 105974 CAR 9- Full-aa | 39 | MALPVTALLLPLALLLHAARPeivmtqspatlslspgeratlscrasqdiskylnw yqqkpgqaprlliyhtsrlhsgiparfsgsgsgtdytltisslqpedfavyfcqqg ntlpytfgqgtkleikggggsggggsggggsggggsqvqlqesgpglvkpsetlsl tctvsgvslpdygvswirqppgkglewigviwgsettyynsslksrvtiskdnskn qvslklssvtaadtavyycakhyyyggsyamdywgqgtlvtvssttttpaprpptpa ptiasqplslrpeacrpaaggavhtrgldfacdiyiwaplagtcgvlllslvitly ckrgrkllyifkqpfmrpvqttqeedgcscrfpeeeeggcelrvkfsrsadapay kqgqnqlynelnlgrreeydvldkrrgrdpemggkprrknpqeglynelqkdkmae ayseigmkgerrrgkghdglyqglstatkdtydalhmqalppr |

CAR10

| CAR10 scFv domain | 10 | qvqlqesgpglvkpsetlsltctvsgvslpdygvswirqppgkglewigviwgset tyynsslksrvtiskdnsknqvslklssvtaadtavyycakhyyyggsyamdywgq gtlvtvssggggsggggsggggsggggseivmtqspatlslspgeratlscrasqd iskylnwyqqkpgqaprlliyhtsrlhsgiparfsgsgsgtdytltisslqpedfa vyfcqqgntlpytfgqgtkleik |
| 100796 CAR10- Soluble scFv-nt | 70 | atggcactgcctgtcactgccctcctgctgcctctggccctccttctgcatgccgc caggccccaagtccagctgcaagagtcaggacccggactggtgaagccgtctgaga ctctctcactgacttgtaccgtcagcggcgtgtccctccccgactacggatgtgtca tggatccgccaacctcccgggaaaggcttgaatggattggtgtcacttggggttc tgaaaccacctactacaactctttccctgaagtccagggtgaccatcagcaaggata attccaagaaccaggtcagccttaagctgtcatctgtgaccgctgctgacaccgcc gtgtattactgcgccaagcactactattacggaggaagctacgctatggactattg gggacagggcactctcgtgactgtgagcagcggcggtggaggtctggaggtggag gatccggtggtggtgggtcaggcggaggagggagcgagattgtgatgactcagtca ccagccacccttctctttcaccggcgagagagcaacctgagctgtagagccag ccaggacatttctaagtacctcaactggtatcagcaaaaccggggcaggccctc gcctcctgatctaccatacctcacgccttcactctggtatcccgctcggtttagc ggatcaggatctggtaccgactacactctgaccatttccagcctgcagccagaaga tttcgcagtgtatttctgccagcagggcaatacccttccttacaccttcggtcagg gaaccaagctcgaaatcaagcaccatcaccatcatcaccat |
| 100796 CAR10- Soluble scFv-aa | 82 | MALPVTALLLPLALLLHAARPqvqlqesgpglvkpsetlsltctvsgvslpdygvs wirqppgkglewigviwgsettyynsslksrvtiskdnsknqvslklssvtaadta vyycakhyyyggsyamdywgqgtlvtvssggggsggggsggggsggggseivmtqs patlslspgeratlscrasqdiskylnwyqqkpgqaprlliyhtsrlhsgiparfs gsgsgtdytltisslqpedfavyfcqqgntlpytfgqgtkleikhhhhhhhh |
| 105975 CAR 10 Full-nt | 94 | atggccctccctgtcaccgccctgctgcttccgctggctcttctgctccacgccgc tcggcccgaaattgtgatgacccagtcacccgccactcttagcctttcaccggtg agcgcgcaaccctgtcttgcagagcctcccaagacatctcaaaatacctta attgg tatcaacagaagcccggacaggctcctcgccttctgatctaccacaccagccggct ccattctggaatccctgccaggttcagcggtagcggatctgggaccgactacaccc tcactatcagctcactgcagccagaggacttcgctgtctatttctgtcagcaaggg aacacccctgccctacacctttggacagggcaccaagctcgagattaaaggtggagg |

TABLE 3-continued

Humanized CD19 CAR Constructs

| Name | SEQ ID | Sequence |
|---|---|---|
| | | tggcagcggaggaggtgggtccggcggtggaggaagcggaggcggtgggagccagg |
| | | tccaactccaagaaagcggaccgggtcttgtgaagccatcagaaactctttcactg |
| | | acttgtactgtgagcggagtgtctctccccgattacggggtgtcttggatcagaca |
| | | gccaccggggaagggtctggaatggattggagtgatttggggtctgagactactt |
| | | actacaactcatccctcaagtcacgcgtcaccatctcaaaggacaactctaagaat |
| | | caggtgtcactgaaactgtcatctgtgaccgcagccgacaccgccgtgtactattg |
| | | cgctaagcattactattatggcgggagctacgcaatggattactgggacagggta |
| | | ctctggtcaccgtgtccagcaccactaccccagcaccgaggccaccccaccccggct |
| | | cctaccatcgcctcccagcctctgtccctgcgtccggaggcatgtagacccgcagc |
| | | tggtggggccgtgcatacccgggtcttgacttcgcctgcgatatctacatttggg |
| | | cccctctggctggtacttgcggggtcctgctgctttcactcgtgatcactctttac |
| | | tgtaagcgcggtcggaagaagctgctgtacatctttaagcaaccttcatgaggcc |
| | | tgtgcagactactcaagaggaggacggctgttcatgccggttcccagaggaggagg |
| | | aaggcggctgcgaactgcgcgtgaaattcagccgcagccagatgctccagcctac |
| | | aagcaggggcagaaccagctctacaacgaactcaatcttggtcggagagaggagta |
| | | cgacgtgctggacaagcggagaggacgggacccagaaatggcggggaagccgcgca |
| | | gaaagaatccccaagagggcctgtacaacgagctccaaaaggataagatggcagaa |
| | | gcctatagcgagattggtatgaaagggaacgcagaagaggcaaaggccacgacgg |
| | | actgtaccagggactcagcaccgccaccaaggacacctatgacgctcttcacatgc |
| | | aggccctgccgcctcgg |
| 105975 CAR 10 Full-aa | 40 | MALPVTALLLPLALLLHAARPEIVMTQSPATLSLSPGERATLSCRASQDISKYLNW YQQKPGQAPRLLIYHTSRLHSGIPARFSGSGSGTDYTLTISSLQPEDFAVYFCQQG NTLPYTFGQGTKLEIKGGGGSGGGGSGGGGSGGGGSQVQLQESGPGLVKPSETLSL TCTVSGVSLPDYGVSWIRQPPGKGLEWIGVIWGSETTYYNSSLKSRVTISKDNSKN QVSLKLSSVTAADTAVYYCAKHYYYGGSYAMDYWGQGTLVTVSSTTTPAPRPPTPA PTIASQPLSLRPEACRPAAGGAVHTRGLDFACDIYIWAPLAGTCGVLLLSLVITLY CKRGRKKLLYIFKQPFMRPVQTTQEEDGCSCRFPEEEEGGCELRVKFSRSADAPAY KQGQNQLYNELNLGRREEYDVLDKRRGRDPEMGGKPRRKNPQEGLYNELQKDKMAE AYSEIGMKGERRRGKGHDGLYQGLSTATKDTYDALHMQALPPR |

CAR11

| CAR11 scFv domain | 11 | eivmtqspatlslspgeratlscrasqdiskylnwyqqkpgqaprlliyhtsrlhs giparfsgsgsgtdytltisslqpedfavyfcqqgntlpytfgqgtkleikggggs ggggsggggsqvqlqesgpglvkpsetsltctvsgvslpdygvswirqppgkgle wigviwgsettyynsslksrvtiskdnsknqvslklssvtaadtavyycakhyyyg gsyamdywgqgtlvtvss |
| 103101 CAR11- Soluble scFv-nt | 71 | Atggcccctcctgtcaccgccctgctgcttccgctggctcttctgctccacgccgc tcggcccgaaattgtgatgacccagtcacccgccactcttagcctttcacccgtg agcgcgcaacccctgtcttgcagagcctcccaagacatctcaaaatacctaattgg tatcaacagaagcccggacaggctcctcgccttctgatctaccacaccagccggct ccattctggaatccctgccaggttcagcggtagcggatctgggaccgactacaccc tcactatcagctcactgcagccagaggacttcgctgtctatttctgtcagcaaggg aacacccctgccctacacctttggacagggcaccaagctcgagattaaaggtggagg tggcagcggaggaggtgggtccggcggtggaggaagccaggtccaactccaagaaa gcggaccgggtcttgtgaagccatcagaaactctttcactgacttgtactgtgagc ggagtgtctctccccgattacggggtgtcttggatcagacagccaccggggaaggg tctggaatggattggagtgatttggggtctgagactactacaattcatccc tcaagtcacgcgtcaccatctcaaaggacaactctaagaatcaggtgtcactgaaa ctgtcatctgtgaccgcagccgacaccgccgtgtactattgcgctaagcattacta ttatggcgggagctacgcaatggattactgggacagggtactctggtcaccgtgt ccagccaccaccatcatcaccatcaccat |
| 103101 CAR11- Soluble scFv-aa | 83 | MALPVTALLLPLALLLHAARPeivmtqspatlslspgeratlscrasqdiskylnw yqqkpgqaprlliyhtsrlhsgiparfsgsgsgtdytltisslqpedfavyfcqqg ntlpytfgqgtkleikggggsggggsggggsqvqlqesgpglvkpsetsltctvs gvslpdygvswirqppgkglewigviwgsettyynsslksrvtiskdnsknqvslk lssvtaadtavyycakhyyyggsyamdywgqgtlvtvsshhhhhhhh |
| 105976 CAR 11 Full-nt | 95 | atggctctgccccgtgaccgcactcctcctgccactggctctgctgcttcacgccgc tcgcccacaagtccagcttcaagaatcaggggcctggtctggtgaagccatctgaga ctctgtccctcacttgcaccgtgagcggagtgtccctcccagactacggagtgagc tggattagacagcctcccggaaagggactggagtggatcggagtgatttggggtag cgaaaccacttactataactcttccctgaagtcacgggtcaccatttcaaaggata actcaaagaatcaagtgagcctcaagctctcatcagtcaccgccgctgacaccgcc gtgtattactgtgccaagcattactactatggaggtcctacgccatggactactg gggccagggaactctggtcactgtgtcatctggtggaggtagcggaggaggcg gagcggtggaggtggctccggaggtggcgaagcgaaatcgtgatgacccagagc cctgcaacccctgtcccttttctcccggggaacgggctacccctttcttgtcgggcatc acaagatatctcaaaatacctcaattggtatcaacagaagcccggacaggcccctta ggcttctatctaccacacctctcgcctgcatagcgggattccgcacgctttagc gggtctggaagcgggaccgactacactctgaccatctcatctctcagcccgagga cttcgccgtctacttctgccagcagggtaacaccctgccgtacaccttcggccagg |

TABLE 3-continued

Humanized CD19 CAR Constructs

| Name | SEQ ID | Sequence |
|---|---|---|
| | | gcaccaagcttgagatcaaaaccactactcccgctccaaggccacccacccctgcc<br>ccgaccatcgcctctcagccgctttccctgcgtccggaggcatgtagacccgcagc<br>tggtggggccgtgcatacccggggtcttgacttcgcctgcgatatctacatttggg<br>cccctctggctggtacttgcggggtcctgctgctttcactcgtgatcactctttac<br>tgtaagcgcggtcggaagaagctgctgtacatctttaagcaacccttcatgaggcc<br>tgtgcagactactcaagaggaggacggctgttcatgccggttcccagaggaggagg<br>aaggcggctgcgaactgcgcgtgaaattcagccgcagcgcagatgctccagcctac<br>aagcaggggcagaaccagctctacaacgaactcaatcttggtcggagagaggagta<br>cgacgtgctggacaagcggagaggacgggacccagaaatgggcgggaagccgcgca<br>gaaagaatccccaagagggcctgtacaacgagctccaaaaggataagatggcagaa<br>gcctatagcgagattggtatgaaaggggaacgcagaagaggcaaaggccacgacgg<br>actgtaccagggactcagcaccgccaccaaggacacctatgacgctcttcacatgc<br>aggccctgccgcctcgg |
| 105976<br>CAR 11<br>Full-aa | 41 | MALPVTALLLPLALLLHAARPQVQLQESGPGLVKPSETLSLTCTVSGVSLPDYGVS<br>WIRQPPGKGLEWIGVIWGSETTYYNSSLKSRVTISKDNSKNQVSLKLSSVTAADTA<br>VYYCAKHYYYGGSYAMDYWGQGTLVTVSSGGGGSGGGGSGGGGSGGGGSFIVMTQS<br>PATLSLSPGERATLSCRASQDISKYLNWYQQKPGQAPRLLIYHTSRLHSGIPARFS<br>GSGSGTDYTLTISSLQPEDFAVYFCQQGNTLPYTFGQGTKLEIKTTTPAPRPPTPA<br>PTIASQPLSLRPEACRPAAGGAVHTRGLDFACDIYIWAPLAGTCGVLLLSLVITLY<br>CKRGRKKLLYIFKQPFMRPVQTTQEEDGCSCRFPEEEEGGCELRVKFSRSADAPAY<br>KQGQNQLYNELNLGRREEYDVLDKRRGRDPEMGGKPRRKNPQEGLYNELQKDKMAE<br>AYSEIGMKGERRRGKGHDGLYQGLSTATKDTYDALHMQALPPR |

CAR12

| CAR12<br>scFv<br>domain | 12 | qvqlqesgpglvkpsetlsltctvsgvslpdygvswirqppgkglewigviwgset<br>tyynsslksrvtiskdnsknqvslklssvtaadtavyycakhyyyggsyamdywgq<br>gtlvtvssggggsggggsggggseivmtqspatlslspgeratlscrasqdiskyl<br>nwyqqkpgqaprlliyhtsrlhsgiparfsgsgsgtdytltisslqpedfavyfcq<br>qgntlpytfgqgtkleik |
| 103104<br>CAR12-<br>Soluble<br>scFv-nt | 72 | atggctctgccgtgaccgcactcctcctgccactggctctgctgcttcacgccgc<br>tcgccacaagtccagcttcaagaatcagggcctggtctggtgaagccatctgaga<br>ctctgtccctcacttgcaccgtgagcggagtgtccctcccagactacggagtgagc<br>tggattagacagcctcccggaaagggactggagtggatcggagtgatttggggtag<br>cgaaaccacttactataactctccctgaagtcacgggtcaccattttcaaaggata<br>actcaaagaatcaagtgagcctcaagctctcatcagtcaccgccgctgacaccgcc<br>gtgtattactgtgccaagcattactactatggagggtcctacgccatggactactg<br>gggccagggaactctggtcactgtgtcatctggtggaggaggtagcggaggaggcg<br>ggagcggtggaggtggctccgaaatcgtgatgacccagagccctgcaaccctgtcc<br>ctttctcccggggaacgggctaccctttcttgtcgggcatcacaagatatctcaaa<br>atacctcaattggtatcaacagaagccgggacaggcccctaggcttcttatctacc<br>acacctctcgcctgcatagcgggattcccgcacgctttagcgggtctggaagcggg<br>accgactacactctgaccatctcatctctccagcccgaggacttcgccgtctactt<br>ctgccagcagggtaaccccttgccgtacaccttcggccagggcaccaagcttgaga<br>tcaaacatcaccaccatcatcaccatcac |
| 103104<br>CAR12-<br>Soluble<br>scFv-aa | 84 | MALPVTALLLPLALLLHAARPqvqlqesgpglvkpsetlsltctvsgvslpdygvs<br>wirqppgkglewigviwgsettyynsslksrvtiskdnsknqvslklssvtaadta<br>vyycakhyyyggsyamdywgqgtlvtvssggggsggggsggggseivmtqspatls<br>lspgeratlscrasqdiskylnwyqqkpgqaprlliyhtsrlhsgiparfsgsgsg<br>tdytltisslqpedfavyfcqqgntlpytfgqgtkleikhhhhhhhh |
| 105977<br>CAR 12-<br>Full-nt | 96 | atggcctcccctgtcaccgcctgctgcttccgctggctcttctgctccacgccgc<br>tcgcccgaaattgtgatgacccagtcaccgccactcttagcctttcacccggtg<br>agcgcgcaaccctgtcttgcagagcctcccaagacatctcaaaatacctaattgg<br>tatcaacagaagcccggacaggcctcgcctctgatctaccacaccagccgct<br>ccattctggaatccctgccaggttcagcggtagcggatctggaccgactacaccc<br>tcactatcagctcactgcagccagaggacttcgctgtctatttctgtcagcaaggg<br>aacacccctgccctacacctttggacagggcaccaagctcgagattaaaggtggagg<br>tggcagcggaggaggtgggtccggcggtggaggaagccaggtccaactccaagaaa<br>gcggacccgggtcttgtgaagccatcagaaactcttcactgacttgtactgtgagc<br>ggagtgtctctcccgattacggggtgtcttggatcagacagccaccggggaaggg<br>tctggaatggattggagtgatttggggctctgagactacttactacaactcatccc<br>tcaagtcacgcgtcaccatctcaaaggacaactctaagaatcaggtgtcactgaaa<br>ctgtcatctgtgaccgcagccgacaccgccgtgtactattgcgctaagcattacta<br>ttatggcgggagctacgcaatggattactgggacagggtactctggtcaccgtgt<br>ccagcaccactacccagcaccgaggccacccaccccggctcctaccatcgcctcc<br>cagcctctgtccctgcgtccggaggcatgtagaccgcagctggtggggccgtgca<br>tacccggggtcttgacttcgcctgcgatatctacatttgggcccctctggctggta<br>cttgcggggtcctgctgctttcactcgtgatcactctttactgtaagcgcggtcgg<br>aagaagctgctgtacatctttaagcaacccttcatgaggcctgtgcagactactca<br>agaggaggacggctgttcatgccggttcccagaggaggaggaaggcggctgcgaac<br>tgcgcgtgaaattcagccgcagcgcagatgctccagcctacaagcaggggcagaac |

TABLE 3-continued

Humanized CD19 CAR Constructs

| Name | SEQ ID | Sequence |
|---|---|---|
| | | cagctctacaacgaactcaatcttggtcggagagaggagtacgacgtgctggacaa<br>gcggagaggacgggacccagaaatgggcgggaagccgcgcagaaagaatccccaag<br>agggcctgtacaacgagctccaaaaggataagatggcagaagcctatagcgagatt<br>ggtatgaaggggaacgcagaagaggcaaaggccacgacggactgtaccagggact<br>cagcaccgccaccaaggacacctatgacgctcttcacatgcaggccctgccgcctc<br>gg |
| 105977<br>CAR 12-<br>Full-aa | 42 | MALPVTALLLPLALLLHAARPEIVMTQSPATLSLSPGERATLSCRASQDISKYLNW<br>YQQKPGQAPRLLIYHTSRLHSGIPARFSGSGSGTDYTLTISSLQPEDFAVYFCQQG<br>NTLPYTFGQGTKLEIKGGGGSGGGGSGGGGSQVQLQESGPGLVKPSETLSLTCTVS<br>GVSLPDYGVSWIRQPPGKGLEWIGVIWGSETTYYNSSLKSRVTISKDNSKNQVSLK<br>LSSVTAADTAVYYCAKHYYYGGSYAMDYWGQGTLVTVSSTTTPAPRPPTPAPTIAS<br>QPLSLRPEACRPAAGGAVHTRGLDFACDIYIWAPLAGTCGVLLLSLVITLYCKRGR<br>KKLLYIFKQPFMRPVQTTQEEDGCSCRFPEEEEGGCELRVKFSRSADAPAYKQGQN<br>QLYNELNLGRREEYDVLDKRRGRDPEMGGKPRRKNPQEGLYNELQKDKMAEAYSEI<br>GMKGERRRGKGHDGLYQGLSTATKDTYDALHMQALPPR |

TABLE 7

Murine CD19 CAR Constructs
CTL019

| CTL019 -<br>Soluble<br>scFv-Histag -<br>nt | 97 | atggccctgcccgtcaccgctctgctgctgcccttgctctgcttcttcatgcagc<br>aaggccggacatccagatgacccaaaccacctcatccctctctgcctctcttggag<br>acagggtgaccatttcttgtcgcgccagccaggacatcagcaagtatctgaactgg<br>tatcagcagaagccggacgaaccgtgaagctcctgatctaccatacctctcgcct<br>gcatagcggcgtgccctcacgcttctctggaagcggatcaggaaccgattattctc<br>tcactatttcaaatcttgagcaggaagatattgccacctatttctgccagcagggt<br>aataccctgccctacaccttcggaggagggaccaagctcgaaatcaccggtggagg<br>aggcagcggcggtggagggtctggtggaggtggttctgaggtgaagctgcaagaat<br>caggccctggacttgtggcccttcacagtccctgagcgtgacttgcaccgtgtcc<br>ggagtctcctgcccgactacggagtgtcatggatcagacaacctccacggaaagg<br>actggaatggctcggtgtcatctggggtagcgaaactacttactacaattcagccc<br>tcaaaagcaggctgactattatcaaggacaacagcaagtcccaagtctttcttaag<br>atgaactcactccagactgacgacaccgcaatctactattgtgctaagcactacta<br>ctacggaggatcctacgctatggattactggggacaaggtacttccgtcactgtct<br>cttcacaccatcatcaccatcaccatcac |
| CTL019 -<br>Soluble<br>scFv-Histag -<br>aa | 98 | MALPVTALLLPLALLLHAARPdiqmtqttsslsaslgdrvtiscrasqdiskylnw<br>yqqkpdgtvklliyhtsrlhsgvpsrfsgsgsgtdysltisnleqediatyfcqqg<br>ntlpytfgggtkleitggggsggggsggggsevklqesgpglvapsqslsvtctvs<br>gvslpdygvswirqpprkglewlgviwgsettyynsalksrltiikdnsksqvflk<br>mnslqtddtaiyycakhyyyggsyamdywgqgtsvtvsshhhhhhhh |
| CTL019<br>Full - nt | 99 | atggccttaccagtgaccgccttgctcctgccgctggccttgctgctccacgccgc<br>caggccggacatccagatgacacagactacatcctccctgtctgcctctctggag<br>acagagtcaccatcagttgcagggcaagtcaggacattagtaaatatttaaattgg<br>tatcagcagaaaccagatggaactgttaaaactcctgatctaccatacatcaagatt<br>acactcaggagtcccatcaaggttcagtggcagtgggtctggaacagattattctc<br>tcaccattagcaacctggagcaagaagatattgccacttactttgccaacagggt<br>aatacgcttccgtacacgttcggaggggggaccaagctggagatcacaggtggcgg<br>tggctcgggcggtggtgggtcggtggcggcggatctgaggtgaaactgcaggagt<br>caggacctggcctggtggcgccctcacagagcctgtccgtcacatgcactgtctca<br>gggtctcattacccgactatggtgtaagctggattcgccagcctccacgaaaggg<br>tctggagtggctgggagtaatatggggtagtgaaaccacatactataattcagctc<br>tcaaatccagactgaccatcatcaaggacaactccaagagccaagttttcttaaaa<br>atgaacagtctgcaaactgatgacacagccatttactactgtgccaaacattatta<br>ctacggtggtagctatgctatggactactggggccaaggaacctcagtcaccgtct<br>cctcaaccacgacgccagcgccgcgaccaccaacaccggcgcccaatcgcgtcg<br>cagcccctgtccctgcgcccagaggcgtgccggcagcggcggggggcgcagtgca<br>cacgaggggctggacttcgcctgtgatatctacatctgggcgcccttggccggga<br>cttgtggggtccttctcctgtcactggttatcacccttttactgcaaacggggcaga<br>aagaaactcctgtatatattcaaacaaccatttatgagacgcagtacaaactactca<br>agaggaagatggctgtagctgccgatttccagaagaagaagaaggaggatgtgaac<br>tgagagtgaagttcagcaggagcgcagacgcccccgcgtacaagcagggccagaac<br>cagctctataacgagctcaatctaggacgaagagaggagtacgatgtttggacaa<br>gagacgtggccgggaccctgagatgggggaaagccgagaaggaagaaccccagg<br>aaggcctgtacaatgaactgcagaaagataagatggcggaggcctacagtgagatt<br>gggatgaaggcgagcgccggaggggcaaggggcacgatggcctttaccagggtct<br>cagtacgccaccaaggacacctacgacgcccttcacatgcaggccctgccccctgc<br>gc |

TABLE 7-continued

Murine CD19 CAR Constructs
CTL019

| CTL019 Full - aa | 58 | MALPVTALLLPLALLLHAARPdiqmtqttsslsaslgdrvtiscrasqdiskylnw<br>yqqkpdgtvklliyhtsrlhsgvpsrfsgsgsgtdysltisnleqediatyfcqqg<br>ntlpytfgggtkleitggggsggggsggggsevklqesgpglvapsqslsvtctvs<br>gvslpdygvswirqpprkglewlgviwgsettyynsalksrltiikdnsksqvflk<br>mnslqtddtaiyycakhyyyggsyamdywgqgtsvtvsstttpaprpptpaptias<br>qplslrpeacrpaaggavhtrgldfacdiyiwaplagtcgvlllslvitlyckrgr<br>kkllyifkqpfmrpvqttqeedgcscrfpeeeeggcelrvkfsrsadapaykqgqn<br>qlynelnlgrreeydvldkrrgrdpemggkprrknpqeglynelqkdkmaeaysei<br>gmkgerrrgkghdglyqglstatkdtydalhmqalppr |
| --- | --- | --- |
| CTL019 scFv domain | 59 | diqmtqttsslsaslgdrvtiscrasqdiskylnwyqqkpdgtvklliyhtsrlhs<br>gvpsrfsgsgsgtdysltisnleqediatyfcqqgntlpytfgggtkleitggggs<br>ggggsggggsevklqesgpglvapsqslsvtctvsgvslpdygvswirqpprkgle<br>wlgviwgsettyynsalksrltiikdnsksqvflkmnslqtddtaiyycakhyyyg<br>gsyamdywgqgtsvtvss |

The sequences of humanized CDR sequences of the scFv domains are shown in Table 4 for the heavy chain variable domains and in Table 5 for the light chain variable domains. "ID" stands for the respective SEQ ID NO for each CDR.

TABLE 4

Heavy Chain Variable Domain CDRs (Kabat)

| Candidate | FW | HCDR1 | ID | HCDR2 | ID | HCDR3 | ID |
| --- | --- | --- | --- | --- | --- | --- | --- |
| murine_CART19 | | GVSLPDYGVS | 19 | VIWGSETTYYNSALKS | 20 | HYYYGGSYAMDY | 24 |
| humanized_CART19 a | VH4 | GVSLPDYGVS | 19 | VIWGSETTYYSSSLKS | 21 | HYYYGGSYAMDY | 24 |
| humanized_CART19 b | VH4 | GVSLPDYGVS | 19 | VIWGSETTYYQSSLKS | 22 | HYYYGGSYAMDY | 24 |
| humanized_CART19 c | VH4 | GVSLPDYGVS | 19 | VIWGSETTYYNSSLKS | 23 | HYYYGGSYAMDY | 24 |

TABLE 5

Light Chain Variable Domain CDRs

| Candidate | FW | LCDR1 | ID | LCDR2 | ID | LCDR3 | ID |
| --- | --- | --- | --- | --- | --- | --- | --- |
| murine_CART19 | | RASQDISKYLN | 25 | HTSRLHS | 26 | QQGNTLPYT | 27 |
| humanized_CART19 a | VK3 | RASQDISKYLN | 25 | HTSRLHS | 26 | QQGNTLPYT | 27 |
| humanized_CART19 b | VK3 | RASQDISKYLN | 25 | HTSRLHS | 26 | QQGNTLPYT | 27 |
| humanized_CART19 c | VK3 | RASQDISKYLN | 25 | HTSRLHS | 26 | QQGNTLPYT | 27 |

Table 6 is an identification key correlating the CD19 constructs numerical names to the specific orientation of the light and heavy chains of the scFv, the number of linker units (i.e., (G4S)$_3$ (SEQ ID NO:107) or (G4S)$_4$ (SEQ ID NO:106)), separating the heavy and light chains, and the distinguishing amino acid sequences in the heavy chain CDR2.

TABLE 6

CD19 CAR designations.

| Clone ID/CAR# | Alt. Clone ID | Chain Orien- tation | Linkers | Site of Heavy CDR2 mutation | SEQ ID NO |
| --- | --- | --- | --- | --- | --- |
| 104875 (CAR1) | C2136 | L2H | 3x | YSSSL | 28 |

TABLE 6-continued

CD19 CAR designations.

| Clone ID/CAR# | Alt. Clone ID | Chain Orien- tation | Linkers | Site of Heavy CDR2 mutation | SEQ ID NO |
| --- | --- | --- | --- | --- | --- |
| 104876 (CAR2) | C2137 | L2H | 3x | YQSSL | 29 |
| 104877 (CAR3) | C2138 | H2L | 3x | YSSSL | 28 |
| 104878 (CAR4) | C2139 | H2L | 3x | YQSSL | 29 |
| 104879 (CAR5) | C2140 | L2H | 4x | YSSSL | 28 |
| 104880 (CAR6) | C2141 | L2H | 4x | YQSSL | 29 |
| 104881 (CAR7) | C2142 | H2L | 4x | YSSSL | 28 |

TABLE 6-continued

CD19 CAR designations.

| Clone ID/CAR# | Alt. Clone ID | Chain Orientation | Linkers | Site of Heavy CDR2 mutation | SEQ ID NO |
|---|---|---|---|---|---|
| 104882 (CAR8) | C2143 | H2L | 4x | YQSSL | 29 |
| 105974 (CAR9) | C2144 | L2H | 4x | YNSSL | 30 |
| 105975 (CAR10) | C2145 | H2L | 4x | YNSSL | 30 |
| 105976 (CAR11) | C2146 | L2H | 3x | YNSSL | 30 |
| 105977 (CAR12) | C2147 | H2L | 3x | YNSSL | 30 |
| CTL019 | muCART19 | L2H | 3x | YNSAL | 57 |

The CAR scFv fragments were then cloned into lentiviral vectors to create a full length CAR construct in a single coding frame, and using the EF1 alpha promoter for expression (SEQ ID NO: 100).

EF1 alpha promoter
(SEQ ID NO: 100)
CGTGAGGCTCCGGTGCCCGTCAGTGGGCAGAGCGCACATCGCCCACAGTC

CCCGAGAAGTTGGGGGGAGGGGTCGGCAATTGAACCGGTGCCTAGAGAAG

GTGGCGCGGGGTAAACTGGGAAAGTGATGTCGTGTACTGGCTCCGCCTTT

TTCCCGAGGGTGGGGAGAACCGTATATAAGTGCAGTAGTCGCCGTGAAC

GTTCTTTTTCGCAACGGGTTTGCCGCCAGAACACAGGTAAGTGCCGTGTG

TGGTTCCCGCGGGCCTGGCCTCTTTACGGGTTATGGCCCTTGCGTGCCTT

GAATTACTTCCACCTGGCTGCAGTACGTGATTCTTGATCCCGAGCTTCGG

GTTGGAAGTGGGTGGGAGAGTTCGAGGCCTTGCGCTTAAGGAGCCCCTTC

GCCTCGTGCTTGAGTTGAGGCCTGGCCTGGGCGCTGGGGCCGCCGCGTGC

GAATCTGGTGGCACCTTCGCGCCTGTCTCGCTGCTTTCGATAAGTCTCTA

GCCATTTAAAATTTTTGATGACCTGCTGCGACGCTTTTTTTCTGGCAAGA

TAGTCTTGTAAATGCGGGCCAAGATCTGCACACTGGTATTTCGGTTTTTG

GGGCCGCGGGCGGCGACGGGGCCCGTGCGTCCCAGCGCACATGTTCGGCG

AGGCGGGGCCTGCGAGCGCGGCCACCGAGAATCGGACGGGGGTAGTCTCA

AGCTGGCCGGCCTGCTCTGGTGCCTGGCCTCGCGCCGCCGTGTATCGCCC

CGCCCTGGGCGGCAAGGCTGGCCCGGTCGGCACCAGTTGCGTGAGCGGAA

AGATGGCCGCTTCCCGGCCCTGCTGCAGGGAGCTCAAAATGGAGGACGCG

GCGCTCGGGAGAGCGGGCGGGTGAGTCACCCACACAAAGGAAAAGGGCCT

TTCCGTCCTCAGCCGTCGCTTCATGTGACTCCACGGAGTACCGGGCGCCG

TCCAGGCACCTCGATTAGTTCTCGAGCTTTTGGAGTACGTCGTCTTTAGG

TTGGGGGAGGGGTTTTATGCGATGGAGTTTCCCCACACTGAGTGGGTGG

AGACTGAAGTTAGGCCAGCTTGGCACTTGATGTAATTCTCCTTGGAATTT

GCCCTTTTTGAGTTTGGATCTTGGTTCATTCTCAAGCCTCAGACAGTGGT

TCAAAGTTTTTTTCTTCCATTTCAGGTGTCGTGA.

Analysis of the humanized CAR constructs was conducted as described in Example 4.

Example 4: Analysis of Humanized CD19 Constructs in CART

To evaluate the feasibility of targeting CD19 via a CAR technology, the single chain variable fragments for an anti-CD19 antibody is cloned into a lentiviral CAR expression vector with the CD3zeta chain and the 4-1BB costimulatory molecule in four different configurations and the optimal construct is selected based on the quantity and quality of the effector T cell response of CD19 CAR transduced T cells ("CART19" or "CART19 T cells") in response to CD19+ targets. Effector T cell responses include, but are not limited to, cellular expansion, proliferation, doubling, cytokine production and target cell killing or cytolytic activity (degranulation).

Materials and Methods
Generation of Redirected Humanized CART19 T Cells

The humanized CART19 lentiviral transfer vectors are used to produce the genomic material packaged into the VSVg psuedotyped lentiviral particles. Lentiviral transfer vector DNA is mixed with the three packaging components of VSVg, gag/pol and rev in combination with lipofectamine reagent to transfect them together in to 293T cells. After 24 and 48 hr, the media is collected, filtered and concentrated by ultracentrifugation. The resulting viral preparation is stored at −80 C. The number of transducing units is determined by titration on SupT1 cells. Redirected CART19 T cells are produced by activating fresh naïve T cells by engaging with CD3×28 beads for 24 hrs and then adding the appropriate number of transducing units to obtain the desired percentage of transduced T cells. These modified T cells are allowed to expand until they become rested and come down in size at which point they are cryopreserved for later analysis. The cell numbers and sizes are measured using a coulter multisizer III. Before cryopreserving, percentage of cells transduced (expressing the CART19 on the cell surface) and their relative fluorescence intensity of that expression are determined by flow cytometric analysis on an LSRII. From the histogram plots, the relative expression levels of the CARs can be examined by comparing percentage transduced with their relative fluorescent intensity.

Evaluating Cytolytic Activity, Proliferation Capabilities and Cytokine Secretion of Humanized CART19 Redirected T Cells.

To evaluate the functional abilities of humanized CAR19 T cells to kill, proliferate and secrete cytokines, the cells are thawed and allowed to recover overnight. In addition to the humanized CART19, the murine CART19 was used for comparative purposes while SS1-BBz was used as non-targeting expressed CAR for background CAR/T cell effect. The "control" gold standard (GS) CART19 was used in all assays to compare assay variation. Importantly, the GS CART19 are cells produced in research grade (i.e., not clinical grade) manufacturing conditions and include the addition of IL-2 to the growth culture. This likely impacts the overall viability and functionality of these cells and should not be evaluated as a direct comparison to the research grade production of the other transduced T cell populations. The T cell killing was directed towards K562, a chronic myelogenous leukemia cell line expressing or not expressing CD19 or Pt14, B cells isolated from CLL patients. For this flow based cytotoxicity assay, the target cells are stained with CSFE to quantitate their presence. The target cells were stained for CD19 expression to confirm similar target antigens levels. The cytolytic activities of CAR19 T cells are measured at a titration of effector:target cell ratios of 10:1, 3:1, 1:1, 0.3:1 and 0:1 where effectors were defined as T cells expressing the anti-CD19 chimeric receptor. Assays were initiated by mixing an appropriate number of T cells with a constant number of targets cells. After 16 hrs, total volume of each mixture was removed and each well washed combining appropriately. The T cells were stained for CD2 and all cells stained with live/dead marker 7AAD. After the final wash, the pelleted cells were re-suspended in a specific volume with a predetermined number of counting beads. Cell staining data was collected by LSRII flow cytometry and analyzed with FloJo software using beads to quantitate results.

For measuring cell proliferation and cytokine production of humanized CAR19 T cells, cells are thawed and allowed to recover overnight. In addition to the humanized CART19, the murine CART19 was used for comparative purposes while SS1-BBz was used as a non-targeting expressed CAR for background CAR/T cell effect. The "control" gold standard (GS) CART19 was used in all assays to compare assay variation. The T cells were directed either towards K562, a chronic myelogenous leukemia cell line expressing or not expressing CD19 or Pt14, B cells isolated from CLL patients. In addition, CD3x28 beads were used to evaluate the potential of T cells to respond to the endogenous immunological signals. To analyze proliferation, T cells were stained with CSFE. The proliferation is the dilution of the CSFE stain reflecting the separation of the parental markings now into two daughter cells. The assay tests only an effector:target ratios of 1:1 and 1:0 where effectors were defined as T cells expressing the anti-CD19 chimeric receptor. The assay is done in duplicate and 24 hrs after mixing of the cells, 50% of the media is removed/replaced for cytokine analysis using the Luminex 10-plex panel of human cytokines detection. After 5 days, T cells were stained for CAR expression, phenotyped as either CD4 or CD8 cells and stained for live/dead with 7AAD. After the final wash, the pelleted cells were re-suspended in a specific volume with a predetermined number of BD counting beads. Cell staining data was collected by LSRII flow cytometry and analyzed with FloJo software using beads to quantitate results. Total cell counts were determined by number of cells counted relative to a specific number of beads multiplied by the fraction of beads yet to be counted.

To evaluate the potential for the humanized CART19 cells to function similarly to the currently successful murine CART19, we wanted to assess in vitro their ability to kill targeted cells, to proliferate in response to the targeted antigen and to show signs of persistence. By packaging each of the humanized CART19 lentiviral constructs and titering them on SupT1 cells, we are able to determine the amount of virus to normalize transductions to be around 50%. This allows for more direct comparisons of activity starting with similar average intergration sites per cell.

The therapeutic CAR19 T cells are generated by starting with the blood from a normal apheresed donor whose naïve T cells are obtained by negative selection for T cells, CD4+ and CD8+ lymphocytes. These cells are activated by CD3× 28 beads in 10% RPMI at 37C, 5% $CO_2$ After 24 hrs, the T cells are blasting and the normalized amount of virus is added. The T cells begin to divide into a logarithmic growth pattern which is monitored by measuring the cell counts per ml and cell size. As the T cells begin to rest down, the logarithmic growth wanes and the cell size shrinks. The combination of slowing growth rate and T cell size approaching ~300 fl determines the state for T cells to be cryopreserved or restimulated.

There is a very similar trend of T cells resting down as seen by size. The almost overlapping pattern between the humanized CART cells with the current murine CART19 and UTD population indicates no unusual effect of the humanized CAR19 on the normal T cell expansion following activation. As a control, SS1-BBz is used to define unwanted antigen independent CAR activity. The expansion profile in total cell numbers shows the differences in the actual numbers in the individual expansions are likely due mainly to different starting number of cells. By normalizing starting T cell numbers, a tight cluster is seen for all the CART19 cells. In addition, the unwanted effect of antigen independent CAR activation is detected in the line running lower and away from the group.

The level of surface expression for each of these CAR19 expressing cells was determined. The titered virus normalized for transduction show comparable expression levels correlating with transduction efficiency, percent cells transduced. Some CARs had their titers extrapolated from earlier packagings, and though their percentages transduced are lower, their MFI are also reduced as expected. The results indicate that there is no detectable negative effect of the humanized CAR19 on the cells ability to expand normally when compared to the UTD and murine CAR19 T cells.

The ability of the humanized CART19 cells to selectively discern a cell surface specific epitope expressed on cells and destroy them is analyzed. Wild type K562 cells do not express CD19 but can be transduced to express CD19. Comparing these killing curves, titrating the amount of effector cells shows that those cells expressing CD19 are destroyed. Redirected T cells from the same donor and modified with either humanized CART19 cells or current clinical murine CART19 cells indicate no difference in their ability to kill. The killing curves show that a very similar killing capacity is found among humanized CART19 cells targeting CD19+ CLL cells from patient 14. Interestingly, there is a decrease in overall cytolytic activity, in particularly GS CART19, suggesting these cells may possess specific inhibitory properties. The similar level of CD19 expressed on the targets cells indicates the expression level is not the reason for differences in cell killing.

The necessary property of the humanized CART19 cells to proliferate after seeing target cells is found in all constructs after being stimulated by the control CD3×28 beads and the CD19 expressing targets. Targeting Pt14 CLL cells appear to indicate a slightly greater proliferation rate with scFvs with a light to heavy chain orientation with no bias seen when having a 3× or 4×GGGGS linkage (SEQ ID NOS 107 and 106, respectively). The proliferative results reflect the total number of cells accumulated over the 5 days, indicating that the humanized CART19s, 2146, 2144, 2136, 2141 and 2137 drive a more proliferative signal to the T cells. Impressively, this was detected in the humanized CART19 cells targeting Pt14 CLL cells.

Overall, the humanized CART19 constructs exhibit very similar characteristics to the current murine CART19 in cytolytic activity, proliferative response and cytokine secretion to antigen specific targets. The potential of humanized CART19 cells, (2146, 2144, 2136, 2141 and 2137), to drive a more proliferative signal to the T cells upon target activation would seem to be an extra benefit of these new constructs to potentially enhance therapeutic response.

Results

Using both degranulation and cytokine production assays, it is demonstrated that the engineered CART19 T cells specifically target CD19+ cells.

ND317 cells transduced with humanized CD19CAR constructs (a.k.a. "huCART19") of the invention were analyzed. There was a tight similarity in size of the T cells during their expansions after CD3×28 activation and transduction with the humanized CART19 candidates relative to the murine CART19 and unmodified (UTD) T cells.

Experiments showed little difference in the number of T cells that accumulated during their expansions after CD3×28 activation and transduction with the different humanized CART19 candidates relative to the murine CART19 and unmodified (UTD) T cells.

Cell surface expressions of humanized CART19 are comparable and their expression level very similar to murine CART19. The overlay of histograms plotting the cell surface expression staining pattern of each humanized CART19 transduced T cells and the mean fluorescent intensity (MFI) calculated from these profiles correlates well with the percentage of cells transduced.

Figure 1B:
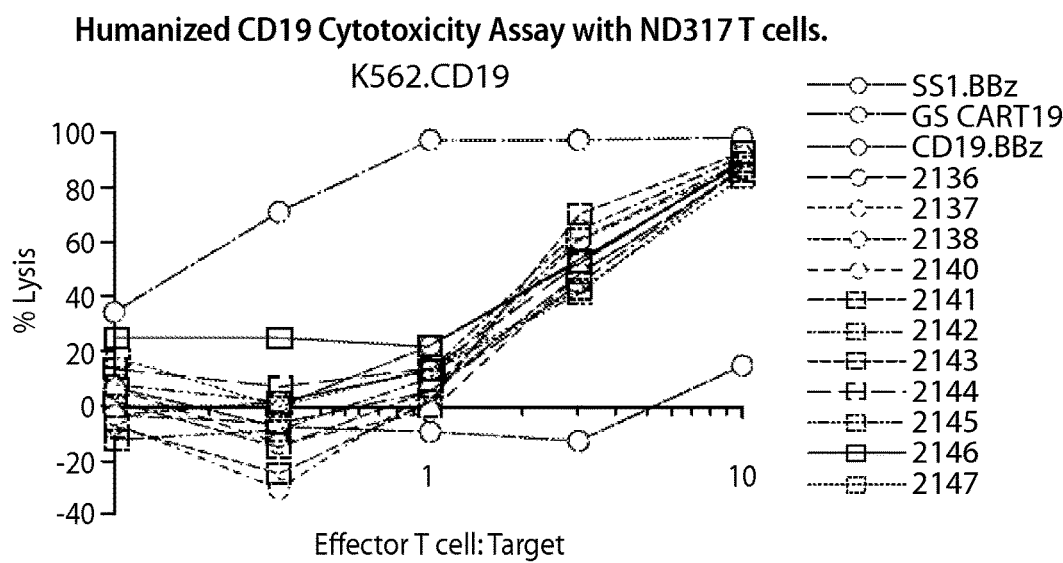
Figure 1C:
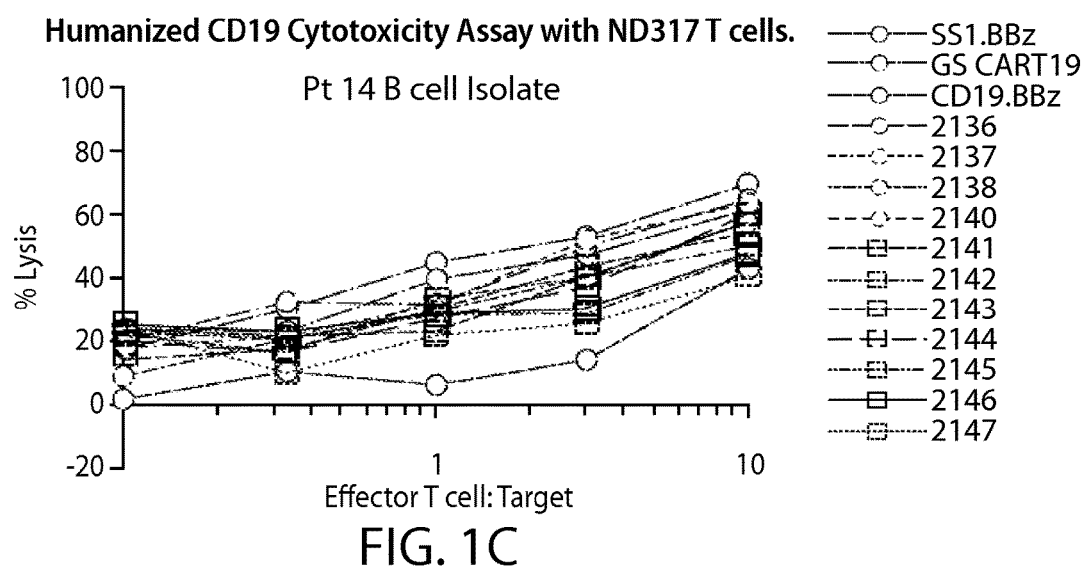

Furthermore the humanized CART19 have similar specific cytotoxic activities in targeting CD19 expressing target cells and comparable to murine CART19. Plots from 16 hr-flow-based killing assays using titrating Effector to Target (E:T) ratios with effector humanized CART19 cells targeting CSFE labeled K562cc (FIG. 1A. non-expressing CD19 controls), K562.CD19 (FIG. 1B, K562 cells transduced to express CD19) or Pt14 (FIG. 1C, B cells from CLL patient). The cytolytic activities of all the humanized CART19 cells are similar and comparable to the murine CART19. The differences in the cytolytic activity between different targets is similar and comparable indicating the murine CART19's activity is preserved in the humanized form of CART19.

Figure 5:
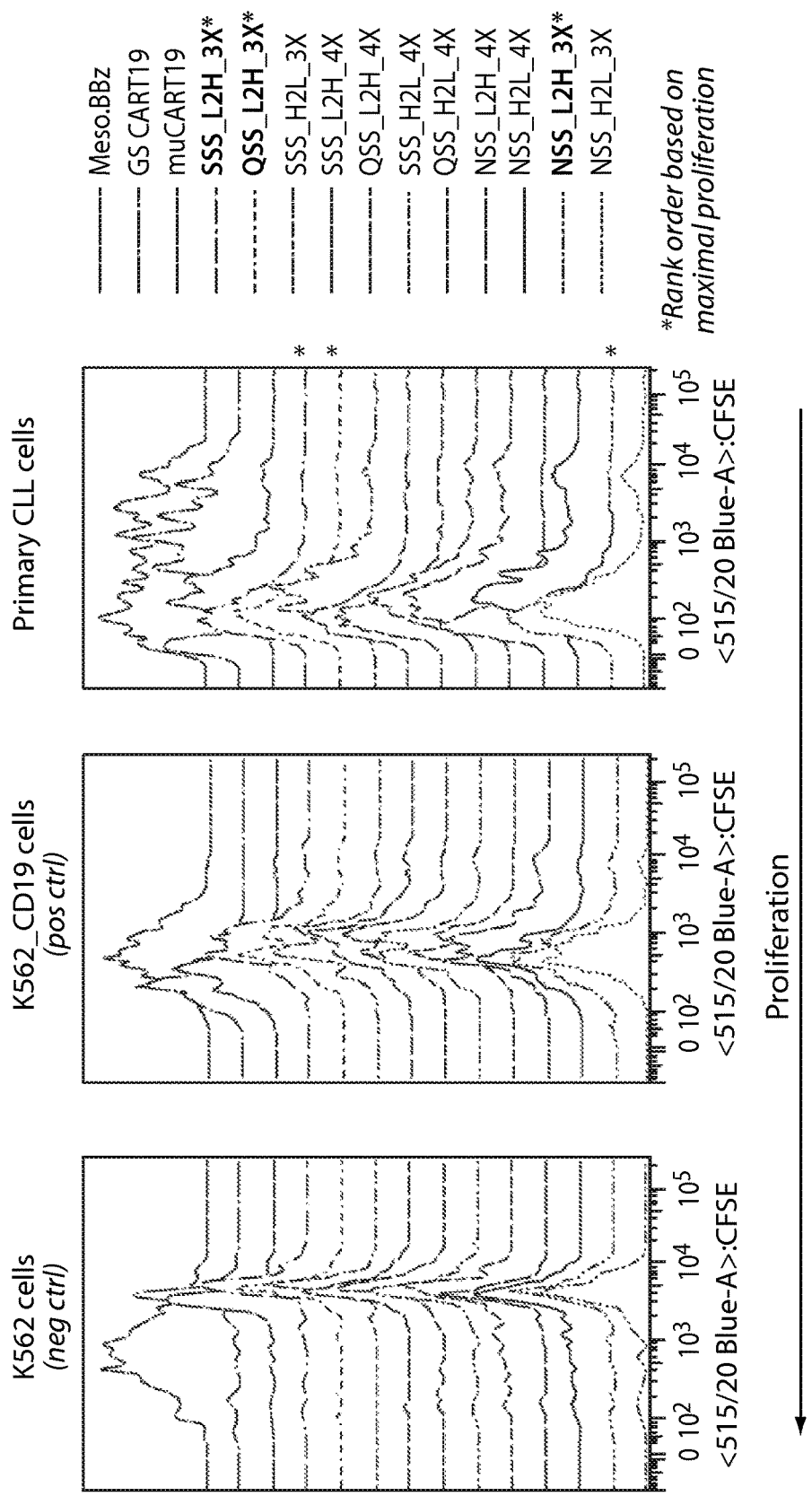
FIG. 5 is a graphic representation of CD19 CAR transduced T cell proliferation, wherein the CART19 cells are directed either towards (a) a chronic myelogenous leukemia ("CML") cell line that is negative for the expression of CD19, and hence used as a negative control; (b) recombinant K562 cells positive for expression of CD19, and hence used as a positive control; or (c) to Pt14 B cells isolated from a CLL patient and which expresses CD19 on the cell surface.
Figure 6A:
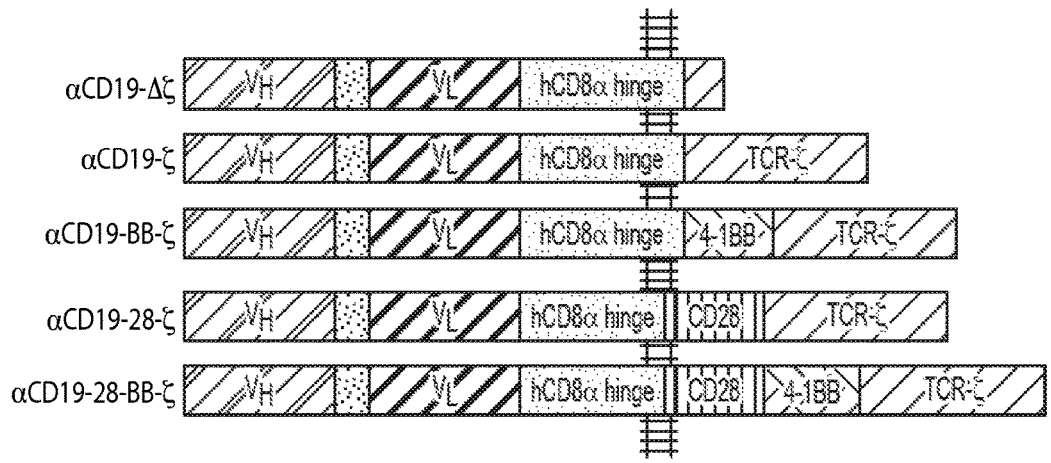
FIGS. 6A and 6B are schematics of representative CARs.
Figure 6B:
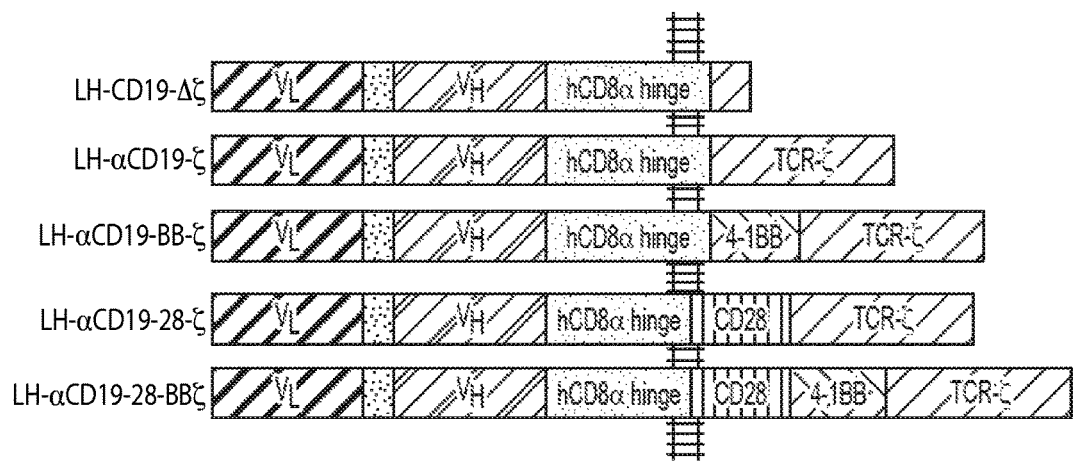

Histogram overlays of CFSE marked humanized CART19 cells 6 days after being mixed with target cells show their proliferative capacity (FIG. 5). The proliferative response delivered from the CAR19 is a necessary response after engagement with and killing of target cells to develop a positive clinical response. The dilution of SS1-BBz CSFE staining, an indicator of dividing daughter cells diluting out the parental cell's stain, is a result of unrested T cells maintaining divisions in a targeting independent mechanism.

Figure 2A:
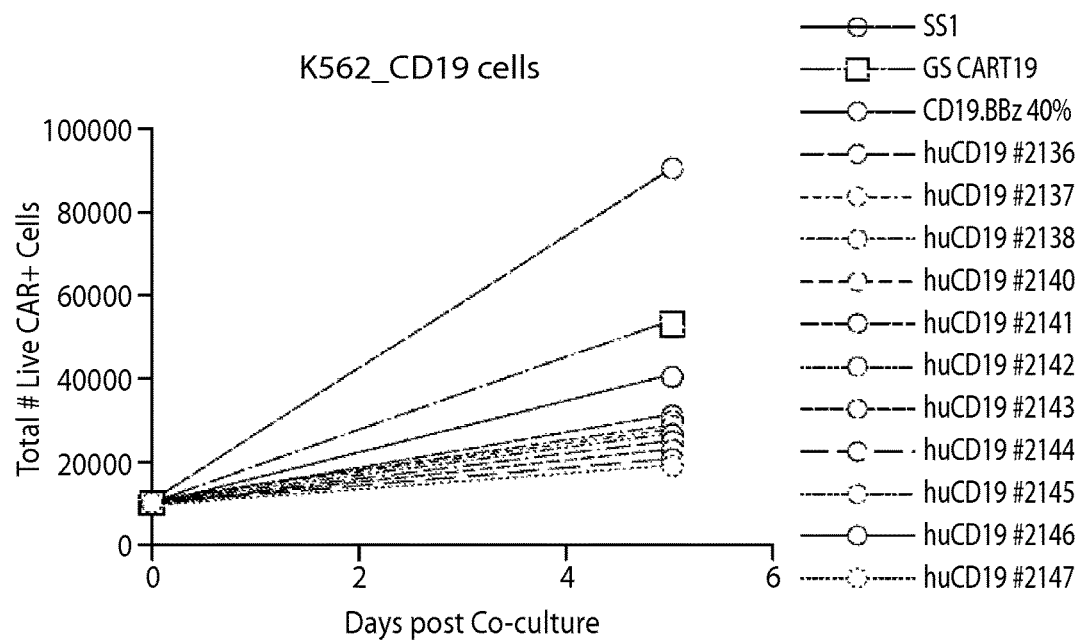
FIGS. 2A and 2B are graphs showing the proliferative response of humanized and mouse anti-CD19 CAR-expressing cells to CD19+ cells, where higher number of viable CAR+ T cells correlates with populations showing maximal CD4+ and CD8+ T cell proliferation to primary CLL cells.
Figure 2B:
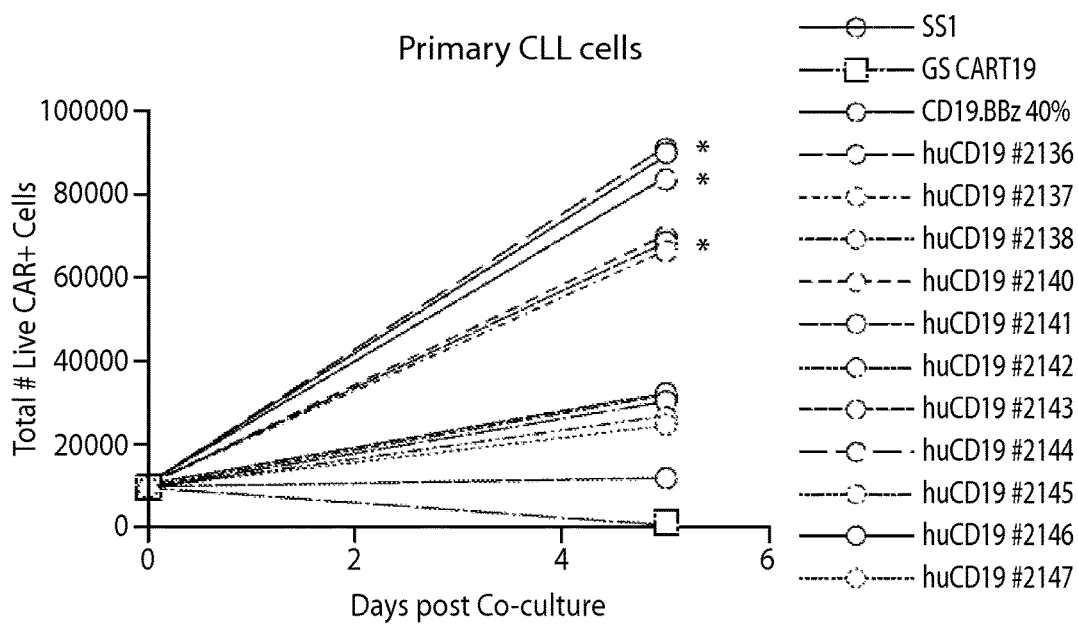

The cell populations overall ability to proliferate is evaluated with CD3×28 beads which mimics the endogenous engagement of the TCR and the co-stimulator CD28. Data indicates each cell population has a comparable proliferation potential. All humanized and murine CART19 cells proliferate strongly and comparably upon engagement with K562 cells expressing CD19. Humanized CART19 cells also responded well to B cells obtained from a CLL patient though some seem to respond slightly less. As shown in FIGS. 2A and 2B, the humanized CART19 cells 2136, 2137, 2140, 2141, 2144 and 2146 can be seen to have a slightly more robust proliferation as evidenced by the greater dilution of CSFE staining. These constructs all have the same variable chain orientation of light to heavy, indicating that this is the orientation of choice. A closer look at the amino acid changes in the heavy CDR2 site (Table 1) reveals that each of the three variations YSSSL, YQSSL and YNSSL (SEQ ID NOS:28, 29 and 30, respectively) are represented in the constructs that appeared to have the more robust proliferations after seeing targets. In addition, these observed constructs have both the G4S linker containing 3 copies of the subunit (3G4S) (SEQ ID NO: 107) and the G4S linker containing 4 copies of the subunit (4G4S) (SEQ ID NO: 106), indicating the linker size did not influence function.

From the proliferative expansions described above, the total cell numbers after 5 days post tumor engagement is determined. The cells show a decline in numbers than were initially seeded, indicating activation is required to maintain survival. An endogenous activation control is analyzed to show that the total cell count at the end of 6 days was similar. Humanized CART19 cells targeting K562 cells expressing CD19 show that the two murine CART19 cells both end up with the higher cell numbers, with 2146 slightly above all the other constructs with similar values. Total cell numbers were also analyzed 6 days after exposure to B cells from Patient 14 (pt14), and interestingly shows that the previously selected out humanized CART19 constructs 2146, 2144, 2136, 2141 and 2137, all of which have the light to heavy chain orientation and represent the three amino acid variations YSSSL, YQSSL and YNSSL (SEQ ID NOS: 28, 29 and 30, respectively), resulted in higher total cell numbers, higher than the murine CART19s. This unexpected differentiation between the various humanized anti-CD19CAR clones may translate to better clinical efficacy of CART cells transduced with these constructs.

Background levels of cytokine produced from humanized CART19 cells after exposure to the control K562 cells not expressing CD19 were analyzed. 24 hr supernatants were analyzed using a luminex 30-plex panel. The potential cytokine profile from stimulation of the endogenous immune system with the CD3×28 beads indicate each of the cell populations have a comparable cytokine profile.

Data also shows that the humanized CART19 and murine CART19 produce similar cytokine profiles at similar levels when responding to the same targets. The cytokine profile was lower but similar when targeting the Pt14 target cells.

Example 5: Humanized CD19 CAR T Cell Treatment in an In Vivo ALL Model

Primary human ALL cells can be grown in immune compromised mice without having to culture them in vitro. These mice can be used to test the efficacy of chimeric antigen receptor (CAR) T cells in a model that represents the patient population that will be found in the clinic. The model used here, HALLX5447, was passaged twice in NOD.Cg-Prkdc$^{scid}$Il2rg$^{tm1/Wjl}$/SzJ (NSG) mice, prior to use in studies testing the efficacy of CAR T cells.

Murine CD19 CAR T cells have previously been shown to target and kill leukemia cells in an NSG mouse model of primary human ALL. The CD19 scFv (single chain Fc variable fragment) has been humanized and the present example compares the ability of T cells expressing a humanized CD19 CAR (CAR 2) to eliminate ALL tumor cells in vivo to that of the murine CD19 CAR T cells. Here, the efficacy of these cells has been directly compared in mice with established primary human ALL, as assayed by peripheral blood FACS analysis of human CD19$^+$ cells. Following an implant of 1.5×10$^6$ primary ALL cells intravenously, a disease burden of 2.5-4% CD19$^+$ human cells in the blood was achieved by 2 weeks post-tumor implantation. This CD19 percentage is of total cells in the blood of the mice. 100% of human cells in the mice prior to treatment with CAR T cells are tumor cells. Percentages above 2% CD19$^+$ human cells in the peripheral blood are considered to be established human ALL disease in this model. The leukemia-bearing mice were treated with the CAR T cells once the leukemia is established in the mice, approximately two to three weeks after tumor implantation. Mice in each group were treated with 5×10$^6$ total human T cells. The transduction efficiencies of the donor human T cells with the CAR expressing lentivirus were between 40-60%. Following treatment with the T cells, mice were bled weekly for analysis of the percentage of CD19$^+$ human cells in the blood as a biomarker for disease progression.

Materials and Methods:

Primary Human ALL Cells:

Primary cells were not cultured in vitro prior to implantation. These cells were harvested from a patient with ALL and then transferred into mice for establishment and expansion. After the tumor cells were expanded in the mice, the bone marrow and splenocytes were harvested and viably frozen in separate batches for re-implantation. The cells were frozen in 90% FBS and 10% DMSO at a minimum concentration of $5\times10^6$ cells per milliliter. For re-implantation, the frozen ALL cells were thawed and then injected intravenously in to NSG mice, in order to generate mice with ALL that will be used to compare the anti-tumor efficacy of the humanized CD19 CAR T cells and the murine CD19 CAR T cells.

Mice:

6 week old NSG (NOD.Cg-Prkdc$^{scid}$ Il2rg$^{tm1/Wjl}$/SzJ) mice were received from the Jackson Laboratory (stock number 005557). Animals were allowed to acclimate to the Novartis NIBRI animal facility for at least 3 days prior to experimentation. Animals were handled in accordance with Novartis ACUC regulations and guidelines.

Tumor Implantation:

In vivo serially passaged primary human ALL cells, model HALLX5447, were thawed in a 37° C. water bath. The cells were then transferred to a 15 ml conical tube and washed twice with cold sterile PBS. The primary ALL cells were then counted and resuspended at a concentration of $15\times10^6$ cells per milliliter of PBS. The cells were placed on ice and immediately (within one hour) implanted in the mice. The ALL cells were injected intravenously via the tail vein in a 100 µl volume, for a total of $1.5\times10^6$ cells per mouse.

CAR T Cell Dosing:

Mice were administered $5\times10^6$ T cells 16 days after tumor implantation. Cells were partially thawed in a 37 degree Celsius water bath and then completely thawed by the addition of 1 ml of cold sterile PBS to the tube containing the cells. The thawed cells were transferred to a 15 ml falcon tube and adjusted to a final volume of 10 mls with PBS. The cells were washed twice at 1000 rpm for 10 minutes each time and then counted on a hemocytometer. T cells were then resuspended at a concentration of $50\times10^6$ cells per ml of cold PBS and kept on ice until the mice were dosed. The mice were injected intravenously via the tail vein with 100 µl of the CAR T cells for a dose of $5\times10^6$ T cells per mouse. Five mice per group were treated either with 100 µl of PBS alone (PBS), untransduced T cells (Mock), murine CD19 CAR T cells (muCTL019), or humanized CD19 CAR T cells (huCTL019). The untransduced T cells, muCTL019 T cells, and huCTL019 T cells were all prepared from the same human donor in parallel.

Animal Monitoring:

The health status of the mice was monitored daily, including twice weekly body weight measurements. The percent change in body weight was calculated as $(BW_{current}-BW_{initial})/(BW_{initial})\times100\%$. Tumor burden was monitored weekly by peripheral blood FACS analysis. Mice were bled weekly via the tail vein into EDTA coated tubes that were kept on ice. 10-20 µl of blood was plated from the tubes into 96 well plates on ice. Red blood cells were lysed with ACK red blood cell lysis buffer (Life Technologies, catalog number A10492-01) and then washed twice with cold PBS. The cells were incubated with an Fc blocking mix of human and mouse Fc block (Miltenyi Biotec, catalog numbers 130-059-901 and 130-092-575) for 30 minutes and then incubated with an anti-human CD19 antibody for 30 minutes. The cells were fixed with a 2% paraformaldehyde solution for 20 minutes, washed and stored in PBS+2% FBS overnight prior to analysis on a BD Canto or Fortessa, followed by further analysis using the FlowJo FACS analysis software. The cells were analyzed to determine the percent of human CD19$^+$ cells in the blood of the human HALLX5447 ALL tumor-bearing NSG mice. CD19 percentages in the blood are reported as the mean±standard error of the mean (SEM).

Percent treatment/control (T/C) values were calculated using the following formula:

% $T/C=100\times\Delta T/\Delta C$ if $\Delta T\geq0$;

% Regression=$100\times\Delta T/T_{initial}$ if $\Delta T<0$;

where T=mean peripheral blood CD19 percentage of the drug-treated group on the final day of the study; $T_{initial}$=peripheral blood CD19 percentage of the drug-treated group on initial day of dosing; $\Delta T$=mean peripheral blood CD19 percentage of the drug-treated group on the final day of the study−mean peripheral blood CD19 percentage of the drug treated group on the initial day of dosing; C=mean peripheral blood CD19 percentage of the control group on the final day of the study; and $\Delta C$=mean peripheral blood CD19 percentage of the control group on the final day of the study−mean peripheral blood CD19 percentage of the control group on the initial day of dosing.

T/C values in the range of 100% to 42% are interpreted to have no or minimal anti-tumor activity; T/C values that are ≤42% and ≥10% are interpreted to have anti-tumor activity or tumor growth inhibition. T/C values ≤10% or regression values ≥−10% are interpreted to be tumor stasis. Regression values <−10% are reported as regression.

Results:

The anti-tumor activity of murine and humanized CD19 CAR T cells were evaluated and directly compared in a primary model of human ALL. Following tumor implantation on day 0, mice were randomized into treatment groups and treated with $5\times10^6$ T cells intravenously on day 16. ALL disease burden and animal health were monitored until animals achieved endpoint. The mice in all the groups were euthanized on day 65 post-tumor implantation when disease burden in the control groups was above 80% human CD19$^+$ cells in the peripheral blood.

Figure 7:
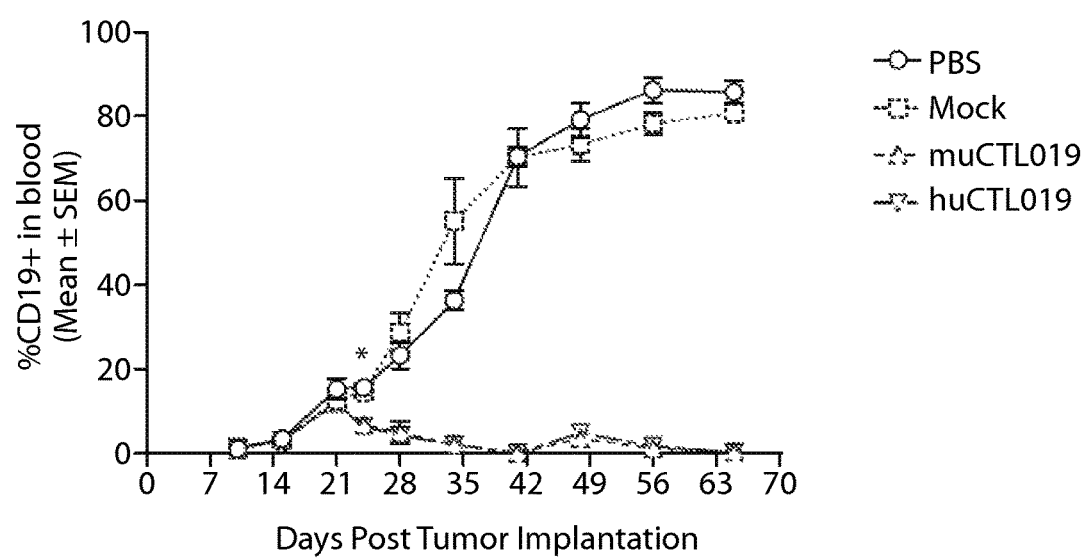
FIG. 7 depicts HALLX5447 primary ALL disease progression in NSG mice after treatment with CD19 transduced CAR T cells. The growth of primary human ALL cells in NSG mice after treatment with CAR T cells specific for CD19 demonstrated control of disease progression. Mean percentage of CD19+ human ALL cells was an indicator of disease burden in the peripheral blood in NSG mice to day 65 post tumor implant. Black circles: mice treated with 100 ul of PBS via the tail vein; red squares: mice treated with mock transduced T cells; blue triangles: mice treated with murine CD19 CAR transduced T cells; and inverted purple triangles: mice treated with humanized CD19 CAR transduced T cells. Significance calculated by ANOVA; * denotes P<0.01.

A clear difference in disease burden was seen between the control groups and the groups treated with either the murine or the humanized CD19 CAR T cells with P<0.01 from day 24 after tumor implantation, and continuing to the end of the study at day 65. The murine and human CD19 CAR T cells demonstrate a similar ability to control human HALLX5447 ALL tumor cell growth in NSG mice. Both groups showed a peak peripheral blood disease level of 12-15% human CD19$^+$ cells at day 21 post HALLX5447 implantation. 42 days after tumor cell implantation, no human CD19$^+$ cells were detectable in the huCTL019 group, while the percentage of human CD19$^+$ cells in the muCTL019 group dropped to about 1%. Both the murine and the humanized CD19 CAR T cells resulted in a comparable ability to control the expansion of primary human ALL cells in this model (P>0.05). The % T/C values for the mock transduced T cell group was 94.40%, demonstrating that the mock transduced T cells had no anti-tumor activity. The percent regression of the muCTL019 group was −89.75% and the huCTL019 group was −90.46%, demonstrating that both of these treatments were able to cause a regression of the HALLX5447 tumor model. The peripheral blood human CD19$^+$ cell percentages as a measure of the disease burden in these mice is shown in FIG. 7. The PBS treatment group, which did not receive any T cells, demonstrated baseline primary ALL tumor growth kinetics in intravenously implanted NSG mice. The Mock treatment group received untransduced T cells that underwent the same in vitro expansion process as the CAR T cells. These cells serve as a T cell control to show the non-specific response of the T cells in this tumor model. Both the PBS and Mock transduced T cell treatment groups demonstrated continuous tumor progression throughout the experiment. Both the murine and the humanized CD19 CAR T cells control the progression of disease within one week of the $5\times10^6$ T cell injections and demonstrate a similar ability to sustain disease control over the course of this 65 day study.

The anti-tumor activity of murine and humanized CD19 CAR transduced T cells was assessed in an efficacy study in NSG mice bearing a primary human ALL model, HALLX5447. This study demonstrated that both the murine and humanized CD19 CAR T cells (muCTL019 and huCTL019) are capable of mounting an anti-tumor response in a primary model of human ALL. In addition, this response, as assayed by peripheral blood disease burden is the same for the muCTL019 and huCTL019 cells. Both the murine and humanized CD19 CAR T cells control primary ALL growth within a week of the mice being dosed with the T cells. Initially after treatment, the disease burden continued to increase before decreasing to virtually undetectable levels. One treatment with either the murine or humanized CAR T cells resulted in a sustained anti-tumor response over the course of the 65 day disease progression in control treated mice. The humanized CD19 CAR T cells demonstrated a similar ability to mount an efficacious anti-CD19 tumor response and control ALL disease burden as was seen with the murine CD19 CAR T cells.

Example 6: CD19 CAR T Cells for Use in Treating Multiple Myeloma

Even with current regimens of chemotherapy, targeted therapies, and autologous stem cell transplant, myeloma is considered an incurable disease. The present example describes treating multiple myeloma (MM) with autologous T cells directed to CD19 with a chimeric antigen receptor (lentivirus/CD19:4-1BB:CD3zeta; also known as "CART19" or CTL019). This example demonstrates that CD19-directed CAR therapies have the potential to establish deep, long-term durable remissions based on targeting the myeloma stem cell and/or tumor cells that express very low (undetectable by most methods) levels of CD19.

In treating a patient with an aggressive secondary plasma cell leukemia, we found that CART19 administered two days after a salvage autologous stem cell transplant resulted in rapid clearance of plasma cell leukemia and a very good partial response in a patient who had progressed through multiple lines of chemotherapy. This patient was transfusion-dependent for months prior to the treatment; at two months after the treatment, she has recovered her blood counts (with normal-range platelet counts and white blood cell counts) and has not required transfusions since she was discharged from the hospital from her treatment.

Because myeloma cells do not naturally express CD19, the finding that CART19 treatment induced a rapid and significant tumor response in this tumor was surprising. Without wishing to be bound by a particular theory, it was reasoned that CART19 could be used to treat myeloma because: (1) while myeloma cells are traditionally thought to be negative for CD19 expression by flow cytometry, there are data indicating that myeloma cells may express very low levels of CD19, such that expression is detectable by RNA but not by flow cytometry or immunohistochemistry; and (2) the concept of targeting the clonotypic B cell, which is thought to be the cancerous stem cell that gives rise to multiple myeloma, and is particularly resistant to chemotherapy. There is a clonal relationship between B cells and myeloma tumor cells, but traditional myeloma therapy is aimed at the malignant plasma cells rather than B cells. CART19 for treating myeloma therefore targets a different cell population than most myeloma therapies.

Figure 8:
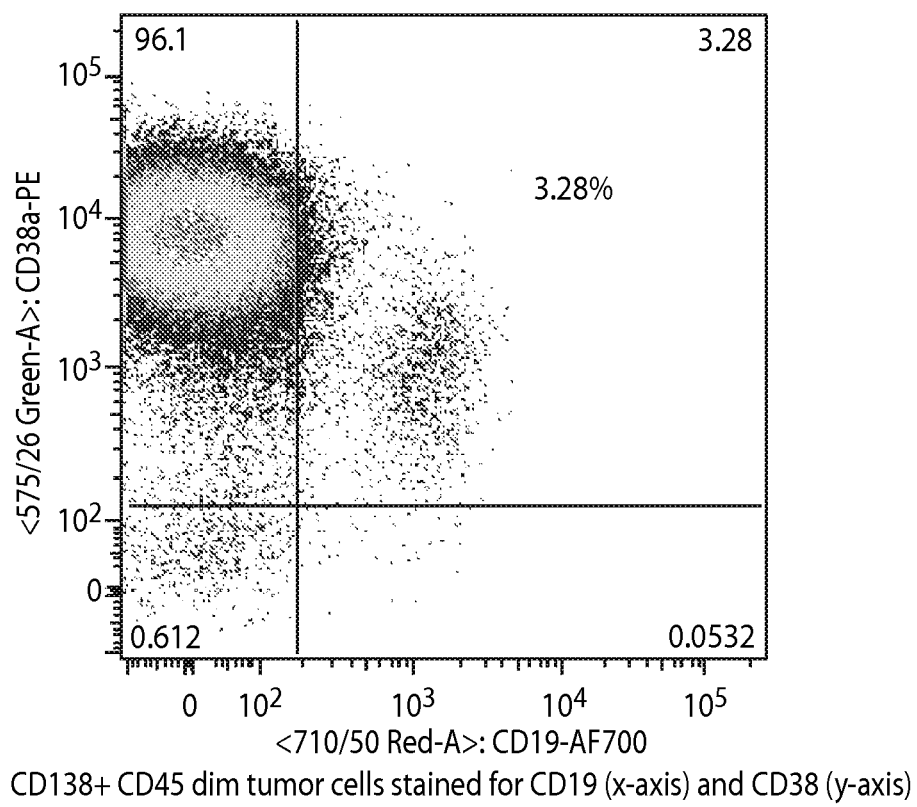
FIG. 8 depicts CD19 expression in a patient's tumor cells. CD138+ CD45$^{dim}$ tumor cells were stained for CD19 (x-axis) and CD38 (y-axis). Approximately 1-2% of the tumor cells expressed the CD19 antigen.

In our single patient experience, the patient had circulating plasma cells, and we were able to test her tumor cells for the expression of CD19. Approximately 1-2% of her tumor cells expressed the CD19 antigen. (FIG. 8). Thus, it was reasoned that CART19 may have a direct effect on a very small population of her tumor cells; a very good partial response, though would not have been predicted based on targeting only the very small population of CD19+ tumor cells.

In this case, CART19 was administered following autologous stem cell transplant rescue after high-dose melphalan. Although this is a standard therapy in myeloma, it is not curative. Furthermore, this patient had previously undergone tandem autologous stem cell transplants and relapsed early (<6 months) after transplant. Without wishing to be bound by a particular theory, use of CART19 cells as described in the present example may have a non-overlapping mechanism in the treatment of myeloma when combined with a salvage autologous stem cell transplant.

A patient with refractory multiple myeloma was treated with CTL019 after myeloablative chemotherapy and ASCT. Remission was maintained despite loss of detectable CTL019 and reconstitution of normal CD19-positive B cells, indicating that this response did not require sustained CTL019 activity. Moreover, this patient's response was realized even though the vast majority (99.95%) of the neoplastic plasma cells were CD19-negative by both flow cytometry and RT-PCR.

The absence of detectable CD19 expression in this patient's dominant neoplastic plasma cell population suggests that the clinically relevant target of CTL019 resided outside this dominant CD19-negative population. Neoplastic plasma cells in multiple myeloma patients exhibit genetic, immunophenotypic, and functional heterogeneity. Particular subpopulations may be required for survival of the clone through anti-myeloma therapy. In the patient reported here, for example, the small CD19-expressing subset of plasma cells might have been relatively melphalan-resistant but sensitive to CTL019. This finding suggests that therapeutically targeting a small subset of the clone can lead to durable clinical benefit when coupled with conventional anti-myeloma therapy.

Alternatively, the clinically relevant target of CTL019 in this patient may have resided outside the neoplastic plasma cell population. For instance, the CTL019 may target a stem cell population that is relatively small but gives rise to neoplastic plasma cells. Multiple myeloma may therefore be a disease of multiple late B-lineage cell types, not just terminally differentiated plasma cells, such that therapies like CTL019 that target B lymphocytes might be useful adjuncts to therapies that directly target plasma cells.

Ten additional multiple myeloma patients will be treated with CART19 in a Phase I trial, at least three patients have been treated to date.

Dose Rationale and Risks/Benefits

We have chosen to use flat dosing via the intravenous route of administration for this protocol. The primary objective of this protocol was to test the safety and feasibility of administering CART-19 cells to patients with multiple myeloma. The primary toxicities that were anticipated are (1) cytokine release when the CARs encounter their surrogate CD 19 antigen on malignant or normal B cells; (2) depletion of normal B cells, similar to rituximab therapy; (3) steroid-responsive skin and gastrointestinal syndromes resembling graft-versus-host disease as has been seen previously when expanded/costimulated autologous T-cells have been coupled with ASCT for MM. A theoretical concern was whether transformation or uncontrolled proliferation of the CART-19 T cells might occur in response to high levels of CD 19. This was less a concern in this application compared to another study of CLL patients, as the burden of clonotypic B-cells in MM is expected to be far lower than the burden of malignant B-cells in the refractory CLL patients treated on that study.

Dose Rationale

With the first 3 patients, we have observed clinical activity at doses ranging from $1.4 \times 10^7$ to $1.1 \times 10^9$ CART-19 cells. This observation demonstrates, at least in the first 3 patients treated, that there is not an obvious dose response relationship. A complete response was observed in patients administered with two log fold difference in dose. Thus, unlike standard drugs that are metabolized, CAR T cells can have a wide dose response range. This is most likely because the CAR T cells are able to proliferate extensively in the patients. We therefore set a dose range of $1-5 \times 10^8$ CART-19 cells for infusion. In this single-patient study offered on a compassionate use basis, the patient was offered up to $5 \times 10^8$ CART19 cells, with no lower dose limit. For the ten patient trial, patients will be offered $1-5 \times 10^7$ CART-19 cells.

General Design

This was single patient-study offered on a compassionate use basis; it was modeled after a Phase I study to determine if the infusion of autologous T cells transduced to express CART-19 is safe. The primary goals of the study were to determine the safety, tolerability and engraftment potential of CART-19 T cells in patients undergoing salvage ASCT after early relapse following first ASCT. The protocol consists of an open label pilot study.

At entry subjects will undergo a bone marrow biopsy and routine laboratory and imaging assessment of their MM. Eligible subjects will undergo steady-state apheresis to obtain large numbers of peripheral blood mononuclear cells (PBMC) for CART-19 manufacturing. The T cells will be purified from the PBMC, transduced with TCK/4-1BB lentiviral vector, expanded in vitro and then frozen for future administration. The number of patients who have inadequate T cell collections, expansion or manufacturing compared to the number of patients who have T cells successfully manufactured will be recorded; feasibility of product manufacturing is not expected to be problematic in this patient population.

Subjects will generally have had adequate peripheral blood stem cells remaining stored from the mobilization/collection performed in preparation for their first ASCT to conduct two additional ASCT. Those who do not will undergo a second mobilization/collection procedure either before or after their steady-state apheresis with a regimen according to the treating physician's preference. Approximately two weeks after the initial leukapheresis, subjects will be admitted to the hospital and receive high-dose melphalan (day −2) followed by infusion of autologous stem cells two days later (day 0), and all subjects will receive infusion of CART-19 cells twelve to fourteen days later (day +12-14). Up to 10 patients will be enrolled.

All subjects will have blood tests to assess safety, and engraftment and persistence of the CART-19 cells at regular intervals through week 4 of the study. At day +42 and day +100, subjects will undergo bone marrow aspirates/biopsies to assess the bone marrow plasma cell burden and trafficking of CART-19 cells to the bone marrow. A formal response assessment will be made at day 100 according to International Myeloma Working Group (IMWG) criteria136, and TTP will be monitored according to routine clinical practice for patients with multiple myeloma. The main efficacy outcome measured in this study will be a comparison of TTP after a patient's initial ASCT to TTP after the ASCT on this study.

As the primary endpoint of this study is safety and feasibility of infusion of CART-19 cells with ASCT, the study will employ an early stopping rule. Briefly, if less than 2 severe, unexpected adverse events occur among the first five subjects treated, the study will then accrue an additional five subjects towards a target enrollment of 10. We will observe treated subjects for 40 days after CART-19 infusion (i.e., through the first official response assessment at day 42) before enrolling a subsequent subject until five subjects have been enrolled and so observed. For treatment of the second group of five patients, no waiting period will be required between subjects.

Following the 6 months of intensive follow-up, subjects will be evaluated at least quarterly for two years with a medical history, physical examination, and blood tests. Following this evaluation, subjects will enter a roll-over study for annual follow-up by phone and questionnaire for up to additional thirteen years to assess for the diagnosis of long-term health problems, such as development of new malignancy.

Primary Study Endpoints

This pilot trial is designed to test the safety and feasibility of the autologous T cells transduced with the CD19 TCK/4-1BB in patients undergoing salvage ASCT for MM following early relapse after first ASCT.

Primary Safety and Feasibility Endpoints Include:

Occurrence of study-related adverse events, defined as NCJ CTC 2: grade 3 signs/symptoms, laboratory toxicities and clinical events that are possibly, likely or definitely related to study treatment at any time from the infusion until week 24. This will include infusional toxicity and any toxicity possibly related to the CART-19 cells including but not limited to:
a. Fevers
b. Rash
c. Neutropenia, thrombocytopenia, anemia, marrow aplasia
d. Hepatic dysfunction
e. Pulmonary infiltrates or other pulmonary toxicity
f. GVHD-like syndromes affecting gastrointestinal tract or skin.

Feasibility to manufacture CART-19 cells from patient apheresis products. The number of manufactured products that do not meet release criteria for vector transduction efficiency, T cell purity, viability, sterility and tumor contamination will be determined.

The depth and duration of response following autologous stem cell transplant with CART19 will be compared to the depth and duration of response that each patient initially achieved following standard autologous stem cell transplant.

Subject Selection and Withdrawal

Inclusion Criteria

Subjects must have undergone a prior ASCT for MM and have progressed within 365 days of stem cell infusion. Subjects who have undergone two prior ASCTs as part of a planned tandem ASCT consolidation regimen are eligible. Progression will be defined according to IMWG criteria for progressive disease or, for patients who attained CR or sCR after initial ASCT, criteria for relapse from CR (Durie et al. Leukemia 2006; 20(9):1467-1473). N.B.: There is no requirement that patients must enroll within 365 days of prior ASCT, and patients may be treated with other agents, including experimental agents, following relapse/progression after prior ASCT before enrollment on this study.

Subjects must have signed written, informed consent.

Subjects must have adequate vital organ function to receive high-dose melphalan as defined by the following criteria, measured within 12 weeks prior to the date of melphalan infusion: a. Serum creatinine ≤2.5 or estimated creatinine clearance ≥30 ml/min and not dialysis-dependent. b. SGOT ≤3× the upper limit of normal and total bilirubin ≤2.0 mg/dl (except for patients in whom hyperbilirubinemia is attributed to Gilbert's syndrome). c. Left ventricular ejection fraction (LVEF) ≥45% or, if LVEF is <45%, a formal evaluation by a cardiologist identifying no clinically significant cardiovascular function impairment. LVEF assessment must have been performed within six weeks of enrollment. d. Adequate pulmonary function with FEV1, FVC, TLC, DLCO (after appropriate adjustment for lung volume and hemoglobin concentration) ≥40% of predicted values. Pulmonary function testing must have been performed within six weeks of enrollment.

Subjects must have an ECOG performance status of 0-2, unless a higher performance status is due solely to bone pain.

Exclusion Criteria Subjects must not:

Have any active and uncontrolled infection.

Have active hepatitis B, hepatitis C, or HIV infection.

Any uncontrolled medical disorder that would preclude participation as outlined.

Treatment Regimen

Therapy for Relapsed/Progressive Multiple Myeloma

Patients may receive, prior to enrollment, therapy for relapsed/progressive multiple myeloma according to the preference of their treating physicians. Therapy may continue upon enrollment.

Patients must stop all therapy for two weeks prior to apheresis and for two weeks prior to high-dose melphalan. If more than two weeks are expected to lapse between apheresis and high-dose melphalan, patients may resume therapy after apheresis at the discretion of their treating physicians.

High-Dose Melphalan (Day −2)

Patients will be admitted to the hospital on day −3 or −2 and will undergo examination by the attending physician and routine laboratory tests, which will include monitoring parameters for tumor lysis syndrome, prior to commencement of the treatment protocol. Blood for MM monitoring laboratory tests (SPEP, quantitative immunoglobulins, and serum free light chain analysis), will be drawn prior to initiation of therapy if such tests had not been drawn within 7 days of admission.

High-dose therapy will consist of melphalan at a dose of 200 mg/m² administered intravenously over approximately 20 minutes on day −2. The dose of melphalan will be reduced to 140 mg/m² for patients >70 years of age or for patients of any age whom, at the discretion of the treating physician, may not tolerate a dose of 200 mg/m² All patients will receive standard anti-emetic prophylaxis, which may include dexamethasone, and standard antibiotic prophylaxis.

Stem-Cell Re-Infusion (Day 0)

Stem cell infusion will take place on day 0, at least 18 hours after the administration of the high-dose melphalan. Stem cells will be infused intravenously over approximately 20-60 minutes following premedication according to standard institutional practice. At least $2\times10^6$ CD34+ progenitors/kg body weight should be infused. In addition, at least $1\times10^6$ CD34+ progenitors/kg body weight should be available as a back-up stem-cell product to be infused in the event of delayed engraftment or late graft failure. G-CSF should be administered SQ beginning on day +5, dosed according to standard institutional practice. Other supportive care measures such as transfusion support will be done in accordance with standard institutional guidelines.

CART19 Cell Infusion (Day +12-14)

A single dose of CART-19 transduced T cells will be given consisting of up to $5\times10^7$ CART-19 cells. The minimal acceptable dose for infusion of cells transduced with the CD19 TCζ4-1BB vector is $1\times10^7$. CART-19 cells will be given as a single dose by rapid i.v. infusion on day +12-14 after stern cell infusion. If patient fails to meet any of the inclusion criteria described herein in the 12-14 day window, the CART-19 infusion may be delayed beyond day +12-14 until the criteria is satisfied.

Maintenance Lenalidomide

Subjects who received and tolerated maintenance lenalidomide after their first ASCT will re-initiate lenalidomide maintenance therapy at approximately day +100, assuming there are no contraindications in the judgment of the treating physician. The starting dose will be 10 mg daily unless prior experience dictates an alternative starting dose for a particular patient. Maintenance therapy will continue until disease progression or intolerance.

Preparation and Administration of Study Drug

The CART-19 T cells are prepared in the CVPF and are not released from the CVPF until FDA approved release criteria for the infused cells (e.g., cell dose, cell purity, sterility, average copy number of vectors/cell, etc.) are met. Upon release, the cells are taken to the bedside for administration.

Cell thawing. The frozen cells will be transported in dry ice to the subject's bedside. The cells will be thawed at the bedside using a water bath maintained at 36° C. to 38° C. The bag will be gently massaged until the cells have just thawed. There should be no frozen clumps left in the container. If the CART-19 cell product appears to have a damaged or the bag to be leaking, or otherwise appears to be compromised, it should not be infused and should be returned to the CVPF as specified below.

Premedication. Side effects following T cell infusions include transient fever, chills, and/or nausea; see Cruz et al. for review (Cytotherapy 2010; 12(6):743-749). It is recommended that the subject be pre-medicated with acetaminophen and diphenhydramine hydrochloride prior to the infusion of CART-19 cells. These medications may be repeated every six hours as needed. A course of non-steroidal anti-inflammatory medication may be prescribed if the patient continues to have fever not relieved by acetaminophen. It is recommended that patients not receive systemic corticosteroids such as hydrocortisone, prednisone, methylprednisolone or dexamethasone at any time, except in the case of a life-threatening emergency, since this may have an adverse effect on T cells.

Febrile reaction. In the unlikely event that the subject develops sepsis or systemic bacteremia following CAR T cell infusion, appropriate cultures and medical management should be initiated. If a contaminated CART-19 T cell product is suspected, the product can be retested for sterility using archived samples that are stored in the CVPF.

Administration. The infusion will take place in an isolated room in Rhoads, using precautions for immunosuppressed patients. The transduced T cells will be administered by rapid intravenous infusion at a flow rate of approximately 10 mL to 20 ml per minute through an 18-gauge latex free Y-type blood set with a 3-way stopcock. The duration of the infusion will be based on the total volume to be infused and the recommended infusion rate. Each infusion bag will have affixed to it a label containing the following: "FOR AUTOLOGOUS USE ONLY." In addition the label will have at least two unique identifiers such as the subject's initials, birth date, and study number. Prior to the infusion, two individuals will independently verify all this information in the presence of the subject and so confirm that the information is correctly matched to the participant.

Emergency medical equipment (i.e., emergency trolley) will be available during the infusion in case the subject has an allergic response, or severe hypotensive crisis, or any other reaction to the infusion. Vital signs (temperature, respiration rate, pulse, and blood pressure) will be taken before and after infusion, then every 15 minutes for at least one hour and until these signs are satisfactory and stable. The subject will be asked not to leave until the physician considers it is safe for him or her to do so.

Packaging

Infusion will be comprised of a single dose of $1$-$5\times10^7$ CA T19-transduced cells, with a minimal acceptable dose of $1\times10^7$ CART-19 cells for infusion. Each bag will contain an aliquot (volume dependent upon dose) of cryomedia containing the following infusible grade reagents (% v/v): 31.25% plasmalyte-A, 31.25% dextrose (5%), 0.45% NaCl, up to 7.5% DMSO, 1% dextran 40, 5% human serum albumin.

Apheresis

A large volume (12-15 liters or 4-6 blood volumes) apheresis procedure is carried out at the apheresis center. PBMC are obtained for CART-19 during this procedure. From a single leukapheresis, the intention is to harvest at least $5\times10^9$ white blood cells to manufacture CART-19 T cells. Baseline blood leukocytes for FDA look-back requirements and for research are also obtained and cryopreserved. The cell product is expected to be ready for release approximately 2-4 weeks later. Flow cytometry lymphocyte subset quantitation, including CD19 and CD20 B cell determination. Baseline assessment is made for human anti-VSV-G and anti-murine antibody (HAMA). If a subject has previously had an adequate apheresis collection banked according to current Good Manufacturing Practices at the Clinical Cell and Vaccine Production Facility these cells may be used as the source of cells for CART-19 manufacturing. Using a banked apheresis product would avert the expense, time, and risk to the subject of undergoing an additional apheresis collection.

Cytoreductive Chemotherapy

The lymphodepleting chemotherapy will be high-dose melphalan as described herein.

CART-19 Infusion

Infusion will begin on day +12-14 after stem-cell reinfusion.

On day +12-14 prior to the first infusion, patients will have a CBC with differential, and assessment of CD3, CD4 and CD8 counts since chemotherapy is given in part to induce lymphopenia.

The first dose will be administered using a single dose. The cells are thawed at the patient's bedside. The thawed cells will be given at as rapid an infusion rate as tolerated such that the duration of the infusion will be approximately 10-15 minutes. In order to facilitate mixing, the cells will be administered simultaneously using a Y-adapter. Subjects will be infused and premedicated as described herein. Subjects' vital signs will be assessed and pulse oximetry done prior to dosing, at the end of the infusion, and every 15 minutes thereafter for 1 hour and until these are stable and satisfactory. A blood sample for determination of a baseline CART-19 level is obtained any time prior to the first infusion and 20 minutes to 4 hours after each infusion (and sent to TCSL).

Patients experiencing toxicities related to high-dose melphalan will have their infusion schedule delayed until these toxicities have resolved. The specific toxicities warranting delay of T cell infusions include: 1) Pulmonary: Requirement for supplemental oxygen to keep saturation greater than 95% or presence of radiographic abnormalities on chest x-ray that are progressive; 2) Cardiac: New cardiac arrhythmia not controlled with medical management 3) Hypotension requiring vasopressor support. 4) Active Infection: Positive blood cultures for bacteria, fungus, or virus within 48-hours of T cell infusion.

Management of Toxicity

Uncontrolled T cell proliferation. Toxicity associated with allogeneic or autologous T cell infusions has been managed with a course of pharmacologic immunosuppression. T body associated toxicity has been reported to respond to systemic corticosteroids. If uncontrolled T cell proliferation occurs (grade 3 or 4 toxicity related to CART-19 cells), subjects may be treated with corticosteroids. Subjects will be treated with pulse methylprednisolone (2 mg/kg i.v. divided q8 hr×2 days), followed by a rapid taper.

In addition, based on the observations of subjects treated on another protocol, there is some concern for macrophage activation syndrome (MAS), though the CD 19+ tumor burden is expected to be much lower in patients with myeloma than in patients with CLL. Treatment and timing of treatment of this toxicity will be at the discretion of the patient's physician and the study investigator. Suggested management might include: if the subject has a fever greater than 101° F. that lasts more than 2 consecutive days and there is no evidence of infection (negative blood cultures, CXR or other source), tocilizumab 4 mg/kg can be considered. The addition of corticosteroids and anti-TNF therapy can be considered at the physician's discretion.

B cell depletion. It is possible that B cell depletion and hypogammaglobulinemia will occur. This is common with anti-CD20 directed therapies. In the event of clinically significant hypogammaglobulinemia (i.e. systemic infections), subjects will be given intravenous immunoglobulin (WIG) by established clinical dosing guidelines to restore normal levels of serum immunoglobulin levels, as has been done with Rituximab.

Primary graft failure. Primary graft failure (i.e., non-engraftment) may be more common after second ASCT compared to first ASCT. Eligibility criteria stipulate that sufficient stem cells must be available for rescue reinfusion at the discretion of the treating physician in the event of primary graft failure.

Results

Three treatment-refractory, advanced multiple myeloma patients have now been treated with CTL019 in this ongoing trial. Results for two of these patients show that both have had substantial anti-tumor effects from the CTL019 therapy based on the primary efficacy assessment at the three-month time-point. The third patient has not yet reached the three-month time point. The results for the two patients are described in more detail below.

Figure 39:
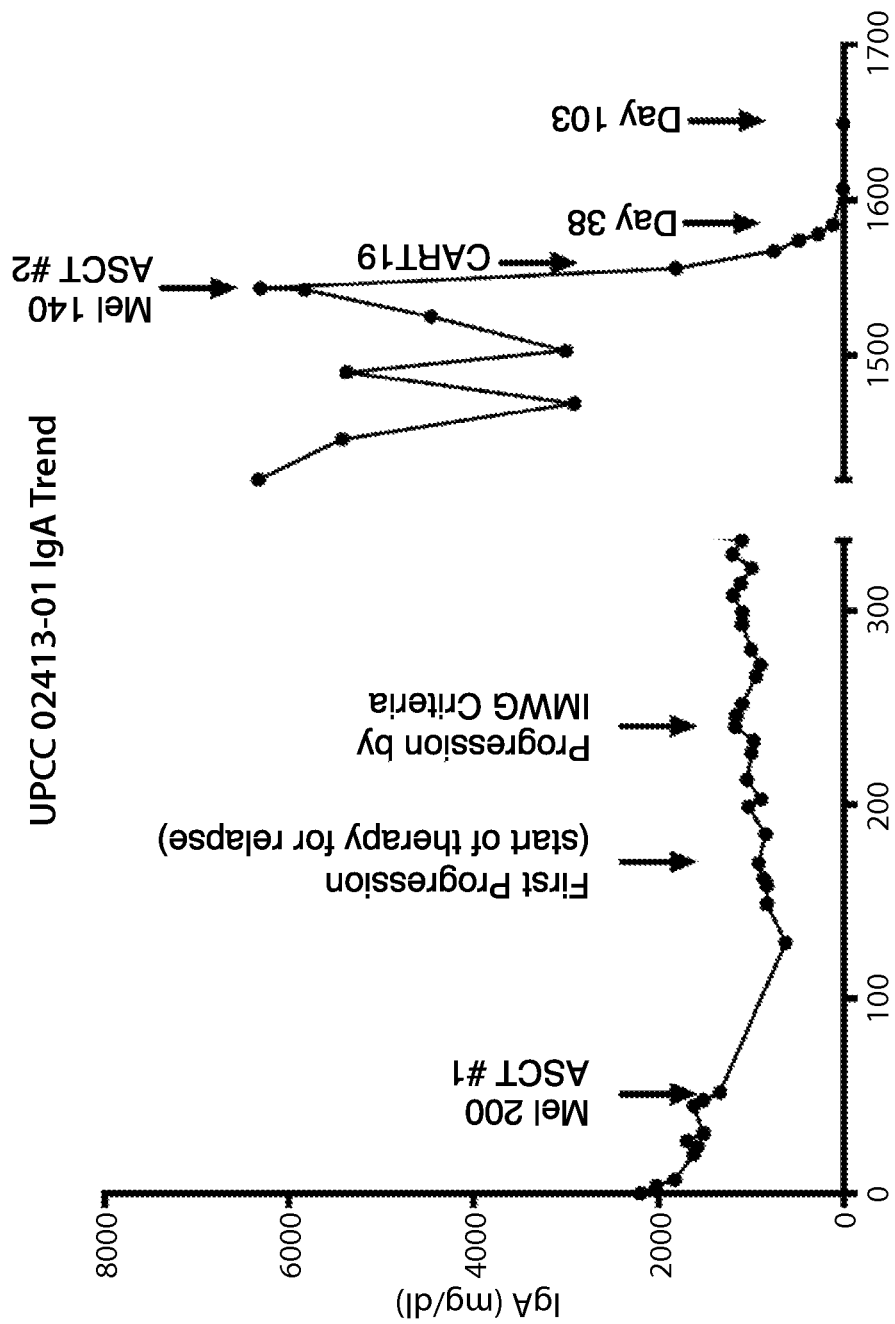
FIG. 39 shows the plasma cell IgA immunophenotyping from a myeloma patient who received CART19, demonstrating the response to CART19 therapy.

The first myeloma patient has completed her +100 day response assessment and she had a very good response to the CART19 therapy. The following tests were performed with the following results:
SPEP/immunofixation: negative
urine immunofixation: faint unmeasurable kappa light chain band on her immunofixation (also present at day 38, so not new)
Otherwise, the patient meet the criteria for stringent complete remission including:
serum free light chain ratio: normal
bone marrow biopsy: negative
IgA immunophenotyping: IgA is below the limit of detection Other than the faint unmeasurable kappa light chain result from urine immunofixation, the patient met all criteria for "stringent complete remission". The summary of the plasma cell immunophenotyping at 3 time points (day −2, day +38, day +103) is shown in FIG. 39, and demonstrates that the patient's IgA is below the limit of detection. The summary shows heavy myeloma burden at day −2 and none detectable at day +38 and +103, which classifies the patient as "MRD negative" by flow analysis. At day +103, the summary shows recovery of normal, polyclonal, CD19+ plasma cells and B cells. The patient had no symptoms of disease or therapy and is functioning like a normal person.

The second patient treated has not yet reached the +100 day time point. However, at this time point, she is doing well but it is too early to determine the effect of the CTL019 infusion.

Example 7: Kinase Inhibitor/CAR19 T-Cell Combined Therapy for Mantle Cell Lymphoma Adoptive T-cell therapy holds considerable promise for the treatment of lymphoid malignancies. Promising clinical responses in small lymphocytic lymphoma/chronic lymphocytic leukemia (SLL/CLL) and acute lymphocytic leukemia (ALL), using adoptive transfer of autologous T cells transduced with chimeric antigen receptors (CAR) against the B-cell specific CD19 antigen (CAR19 T cells/CART19 cells) using CTL109. We have recently reported initial data on 3 patients with chemotherapy-refractive SLL/CLL enrolled in a phase I trial to treat CD19-positive malignancies using CD19-specific CAR (CAR19 T cells/CART19 cells). The approach used involved the genetic modification of patient-derived bulk T cells using a lentivirus to express a CD19-targeting CAR that contains signaling domains derived from CD137 and TcRz. For this study cells were expanded using our anti-CD3 and -CD28 bead expansion methodology, and cells were infused early post lymphodepletion without cytokine support (Kalos M, et al. (2011) Sci Transl Med. 3: 95ra73; and Porter D L, et al. (2011) N Engl J Med. 365: 725-733). These early results were extremely promising: (i) following a single course of treatment 2/3 patients achieved complete remissions and remain disease free now at 15+ months post treatment, while the third patient, who was treated with corticosteroids soon after the T cell infusion demonstrated a strong partial response. (ii) In these patients we were able to recapitulate the elements thought to be required for ultimate efficacy of adoptive T cell therapy-based strategies, namely robust in vivo T cell expansion, disease eradication, T cell contraction, and long-term functional persistence. To date, 10 SLL/CLL patients have been treated with 2 remaining in the complete clinical and molecular remission, 5 experiencing partial remission, and 3 displaying lack of measurable response. In another study, two patients with B cell ALL achieved complete remission with 1 relapsing with leukemic cells lacking CD19 expression.

Mantle cell lymphoma (MCL), both before and after large cell transformation, will also likely to benefit from the CART19-based adoptive therapy, in particular when combined with kinase inhibitors such as those that directly affect MCL cells.

To further analyze the combination of CART19-based adoptive therapy in combination with kinase inhibitors, high throughput screens will be used to evaluate several inhibitors targeting the kinases critical for MCL pathogenesis: CDK4/6, BTK, and mTOR in combination with CART19 cells. The most promising combinations will be evaluated in greater detail, both in vitro and in vivo, in MCL xenotransplant mouse model, which ultimately may guide the development of a clinical protocol to evaluate combination of small molecule kinase inhibitor and the CART cell immunotherapy in MCL patients.

In this study, preclinical studies will be performed to determine potential clinical efficacy of this approach in the various subtypes of MCL and to evaluate the ability to therapeutically target MCL cells using CART19 cells either alone or in will combination with small molecule inhibitors of selected proteins from the kinase family expression and activity of which is critical for survival and growth of MCL cells.

Research Plan

In a pre-clinical setting, the ability to therapeutically target MCL cells, both cultured and primary-type cells, using inhibitors of kinases with documented pathogenic relevance in MCL and CART19 cells will be evaluated. A high throughput MTT assay will be used to determine the effect of these agents to identify potential optimal combinations, dosing and timing of the agent application. The most promising 2-3 combinations will be evaluated in the greater detail in regard to cell function, phosphorylation-based cell signaling, and gene expression first in vitro and later in vivo in the MCL xenotransplant model.

In-Vitro Studies to Characterize the Ability of Kinase Inhibitor/CART-19 Cell Combinations to Effectively Target MCL Cells In this aim, detailed functional, phenotypic, biochemical, and molecular assays listed above to study in-vitro the impact of the small molecule kinase inhibitors on MCL cells as well as to examine interactions between CART19 cells and MCL cells and the impact of the inhibitors on these interactions will be examined.

The benchmarks for accomplishing this aim will be to generate a comprehensive data set to:
i. document that CART19 cells are activated by and lyse the cultured and primary MCL cells;
ii. demonstrate that the selected kinase inhibitors enhance the ability of each other and/or CART19 cells to eliminate MCL cells without negatively impacting CART19 cell function when appropriately applied in regard to the dose and, for some, timing of the inhibitor vs. CART19 cell administration; and
iii. establish a regimen for the schedule and dosing for the BTK inhibitor to be used in the in vivo MCL xenotransplant experiments using the NSG mice.

The goals of this study are, e.g., to evaluate whether identify the optimal therapeutic combinations of small molecule inhibitors targeting kinases critical for MCL pathobiology: CDK4, BTK, and mTOR together with CART19 cells, monitor CART19 activity, and characterize the functional, biochemical, and molecular effects of the therapy on MCL.

These studies should to establish a rational schema for schedule for the timing and dose of BTK treatment kinase inhibitor in conjunction with CART19 therapy to be evaluated in-vivo in aim 2.

In-Vivo Studies to Evaluate the Ability of CART19 Cells to Target Follicular Lymphoma, Alone and in Combination with BTK Inhibitor In this aim, we will test in animal models the ability of the selected inhibitor/CART19 cell combination(s) to affect growth of established and primary MCL cells.

The benchmarks for accomplishing this aim will be to generate a data set to:
 i. demonstrate that the selected inhibitor/CART19 cell combination markedly enhances the survival of animals engrafted with MCL as compared to the controls (single and mock agent treated animals);
 ii. establish a regimen for the schedule and dosing for the selected kinase inhibitor/CART19 combination to be used as the basis for a future clinical trial.

The goals of this study include evaluating the treatment and dose schedule defined in aim 1 for the identified kinase inhibitor/CART19 plus BTK inhibitor combination, and to test whether BTK treatment synergizes with CART19 to target MCL in NSG mice xenotransplanted with MCL cells, both cultured and primary.

The following cell types, compounds, animals and experimental methodologies will be used to accomplish the proposed aims:

MCL Cells:

Four MCL cell lines (Jeko-1, Mino, SP-49, and SP-53) and viably frozen samples from 15 primary MCL (12 typical and 3 blastoid). While the cell lines grow well spontaneously, the primary cells will be cultured alone as well as in the presence of conditioned medium collected from HS5 bone marrow stromal cells to improve their viability.

CART19 Cells:

Primary human T cells engineered to express CAR19 will be generated using lentivirus transduction and using the established protocols ((Kalos M, et al. (2011) Sci Transl Med. 3: 95ra73; and Porter D L, et al. (2011) N Engl J Med. 365: 725-733). Following a single transduction event T cells typically express CAR19 at frequencies exceeding 30%.

Our studies will use CART 19 populations from five SLL/CLL patients (50-100 vials/patient at with $1\times10^7$ cells/vial are already available). CART19 cells will be identified using an anti-CAR19-specific idiotype antibody (STM). CART19 activity will be controlled both in vitro and in vivo in NSG mice in the standardized manner using CD19+ NALM-6, CD19-negative K562, and CD19-transduced K562 cell lines. Although CART19 cell function is not MHC restricted, CART19 cell from at least 5 MCL patients will also be used.

Kinase Inhibitors.

Inhibitors of the following kinases will be tested: CDK4/6 (PD0332991), BTK (PCI-32765), mTORC1 (rapamycin), MNK (4-Amino-5-(4-fluoroanilino)-pyrazolo[3,4-d]pyrimidine (Marzec M, et al. PLoS One 6:e24849); and a novel compound from Eli Lilly (Gupta M, et al. (2012) Blood 119:476-487); mTOR (OSI-027), and dual PI3K/mTOR (PF-04691502).

The compounds will be evaluated first at the pre-determined spectrum of effective doses, including the non-toxic concentrations reached in patients' sera, to assure optimal kinase inhibition.

Animals:

The in-vivo experiments will be performed using NOD-SCID-IL-2Rgc null (NSG) mice which are bred and available from the Stem Cell and Xenograft Core using breeders obtained from Jackson Laboratory (Bar Harbor). Mice will be housed in sterile conditions using HEPAfiltered microisolators and fed with irradiated food and acidified water.

Transplanted mice are treated with antibiotics (neomycin and polymixin) for the duration of the experiment. Six to eight week-old animals, equal mixes of males and females, will be utilized for all studies in accordance with protocols approved by the Institutional Animal Care and Use Committee.

We have used NSG animals in previous T cell adoptive transfer studies specifically to evaluate differential activity of CART19 cells (Witzig T E, et al. (2010) Hematology Am Soc Hematol Educ Program. 2010:265-270, MTT assay). The high throughput MTT assay to evaluate MCL cell growth will be performed first in response to the kinase inhibitors applied either alone or in various combinations. This assay is able to simultaneously determine cell proliferation rate and viability, allowing efficient evaluation of many possible combinations of small molecule inhibitors in the presence or absence of CART19 cells. The key aspects of this analysis will be to characterize the drug effect in regard to potential synergistic, additive, or antagonistic effect. In addition, the effect of the small molecule inhibitors on CART19 cells will be evaluated. While BTK inhibition should be B-cell specific, mTOR and CDK4/6 inhibition will affect CART19 cells. Establishing the proper timing of the drug application to minimize their potential effect on CART19 cells will be one of the aims of these experiments.

To perform the test, MCL cells will be seeded in 96-well plates at $1\times10^4$ cells/well, in triplicates, and exposed to medium or kinase inhibitors in various combinations and various concentrations of CART-19 cells. After 48 and 74 hrs, the relative number of metabolically active cells will be determined by the use of MTT reduction colorimetric assay (Promega).

The significance of difference between the mean values (+/−S.D.) of the controls and different treatment conditions will be evaluated using Student's t-test with the P value of <0.05 considered to be statistically significant.

Cell Proliferation and Apoptosis Assays:

The most promising drug combinations will be next evaluated in the CFSE labeling and terminal dUTP nick-end labeling (tunel) assays to determine both cytostatic and cytotoxic components of MCL cell growth inhibition, respectively. In the former assay, MCL cells will be labeled with CFSE addition of the BTK inhibitor and/or unlabeled CART-19 cells. After 48 hrs, the cultured cells will be the analyzed by FACS for the CFSE labeling pattern of the MCL-type cells. The tunel assay will be done using the ApoAlert DNA Fragmentation Assay Kit from BD Biosciences according to the manufacturer's protocol.

In brief, MCL cells will be cultured with the inhibitors and/or CART19 cells for 48 or 72 hours. After being washed, cells will be stained with labeled anti-CD20 antibody and permeabilized, washed, and incubated in TdT buffer for 1 hour at 37° C. The reaction will be stopped, the cells washed, resuspended, and analyzed by flow cytometry using the CellQuest PRO software.

CART19 Functional Assays:

We will measure effector activity of CART19 cells against MCL cell lines using CD107 degranulation, Intracellular Cytokine Secretion (ICS) assays, proliferationcytolysis assays, and multiplex cytokine detection assays (32). For degranulation and ICS assays, effector (T cells) and Target (tumor cells) will be co-incubated in the presence of anti-CD107 antibody for 4 hours at E:T of 0.2:1 followed by staining for surface (CAR19, CD3, CD8, CD4) and intracellular cytokine markers as per established protocols. Cytolysis of MCL cells will be assessed using flow-cytometry-based cytolysis assays. For proliferation assays, effector cells will be pre-loaded with CFSE (Carboxyfluorescein succinimidyl estercarboxy-fluoroscein-succinil esterase), mixed with target cells at E:T of 0.2:1, co-incubated at 37° C. for 4 days, stained for surface markers (CAR19, CD3, CD8, CD4) and analyzed for dilution of CFSE by flow-cytometry.

Multiplex Cytokine Assays.

We will measure production of cytokines by CART19 cells in response to MCL targets using Luminex-based bead assays as described in (STM32). For these analyses we will employ the Invitrogen 30-plex kit that simultaneously measures IL-1β, IL-1RA, IL-2, IL-2R, IL-4, IL-5, IL-6, IL-7, IL-8, IL-10, IL-12 (p40/p70), IL-13, IL-15, IL-17, TNF-α, IFN-α, IFN-γ, GM-CSF, MIP-1α, MIP-1β, IP-10, MIG, Eotaxin, RANTES, MCP-1, VEGF, G-CSF, EGF, FGF-basic, and HGF in serum, plasma, or tissue culture supernatant.

Multiparametric Flow Cytometry Analysis of CART19T Cells:

We will measure the modulation of surface markers associated with functional activation and suppression on CART19 cells following co-incubation with tumor cells using four color flow cytometry and a custom BD LSR II equipped with 4 lasers (blue (488 nM), violet (405 nM), Green (532 nM), and Red (633 nM) available through the University of Pennsylvania Abramson Cancer Center Flow Cytometry Core. All flow cytometry data will be analyzed using FlowJo software (TreeStar, San Carlos, Calif.). These analyses will be performed essentially as described in (STM42), using a dump channel to exclude dead cells and target cells (CD19+), and a CAR19 idiotype-specific reagent to detect CART19 cells (STM). We will evaluate the following markers on CART19-positive and -negative cells (CD3+/CD8+ and CD3+/CD4+) post co-incubation with tumor cells, on either intact or permeabilized cells as needed. We have established multi-parametric panels for these markers:

activation/effector function: CD25, CD154, CD134, CD137, CD69, CD57, CD28, T-bet
inhibition: CD152 (CTLA4), PD1, LAG3, CD200
suppression (Treg) CD4+/CD25++/CD127-, Fox-P3+

Simultaneously, MCL cells identified by CD19 and CD5 staining, will be examined for expression of the immunosuppressive proteins: CD174 (PD-L1) CD173 (PD-L2) and CD152.

Inhibitor Impact on Cell Signaling:

This part of the study will focus only on the selected compounds; the ones that proved to be the most effective in the functional assays (cell growth, proliferation, and apoptosis) described above. The effect will be studied separately for each drug and for the selected combinations and the studies will be adjusted to the specific compounds. For example, while the mTORC1 and MNK inhibitor combination will evaluate mTORC1 signaling, in particular the eIF-4E phosphorylation, BTK inhibition will focus on the PI3K-AKT and MEK-ERK pathways, and CDK4/6 inhibition on Rb phosphorylation. These studies will be performed by Western blotting using phospho-specific antibodies as described (Marzec M, et al. (2006) Blood. 108:1744-1750; Marzec M, et al. (2008) Blood 111: 2181-2189; Zhang Q, et al. (2011) Proc Natl Acad Sci USA 108: 11977-11982). In brief, the MCL cells will be lysed and the protein extracts will be assayed using the Lowry method (Bio-Rad) and loaded into the polyacrylamide gel. To examine protein phosphorylation, the blotted membranes will incubated with the phosphor-specific antibodies, for example the ones specific for S6rp S235/236, eIF4E S209, 4E-BP1 T37/46, 4E-BP1 T70 (Cell Signaling) to evaluate the mTORC1 and MNK activity and their inhibition. Next, the membranes will be incubated with the appropriate secondary, peroxidase-conjugated antibodies. The blots will be developed using the ECL Plus System from Amersham.

Genome-Scale Gene Expression Analysis:

Inhibition of cell signaling typically leads to changes in gene transcription. To determine the effects of the selected inhibitor, or a few inhibitors on gene transcription in MCL, a genome-scale gene expression analysis will be performed as done as described in Marzec M, et al. (2008) Blood 111: 2181-2189; Zhang Q, et al. (2011) Proc Natl Acad Sci USA 108: 11977-11982. In brief, the cells will be treated in triplicate cultures with the selected inhibitor or its diluent for 0, 4, and 8 hours. The total RNA will be further purified to enrich for mRNA which will be reverse transcribed, labeled and examined by hybridization to the Affimetrix microchip against all known gene exons. The microarray data will be normalized and summarized using RMA as implemented in GeneSpring and MASS algorithm. The resulting pvalues will be corrected for multiple testing using false discovery rate (FDR) by the Benjamini-Hochberg step-up method. Differential expression testing will be accomplished using a variety of tools including SAM and PartekPro. The emerging genes of interest will then be clustered based on expression patterns (GeneSpring or Spotfire), and clusters will be analyzed for functional groups and pathways in KEGG, Ingenuity Pathway Analysis, and Gene Ontology databases using the NIH-David as the search tool. For the genes identified based on the data, the independent expression conformation by the quantitative RTPCR will be performed on a larger pool of samples (at least 20) of various types of MCL (standard vs. blastoid and SOX11-positive vs. SOX11-negative).

Whole-Exome DNA Sequence Analysis:

To better characterize the MCL cases in regard to their pathogenesis and, to the extent possible, response to the proposed here combination therapies, the sequence of exomic DNA will be examined. Whole-exome capture and next generation sequencing of the MCL and normal peripheral blood DNA samples will performed using the NimbleGen Sequence Capture 2.1M Human Exome Array and the HiSeq 2000/1000 Illumina instrument.

Evaluation of the Treatment Effect in the Xenotransplanted Tumors:

The NSG mice will carry the MCL tumors tumors (derived from both MCL cell lines: Jeko and Mino and primary cells implanted as either tissue fragments or, less preferably, cell suspensions). The tumors will be propagated by subcutaneous implantation of the small tumor fragments. The therapy will be initiated once the tumors reach 0.2-0.3 cm in the diameter. The kinase inhibitor(s) will administered by gavage at dose and timing preselected in vitro (for example, we expect to apply BTK inhibitor simultaneously with CART19 cells, given its B-cell specificity and expected lack of any inhibitory effect on CART19 cells). CART-19 cells will be injected into the tail vein of the tumor-bearing mice at a dose of $1 \times 10^7$/animal, the kinase inhibitor(s) will administered by gavage at dose and timing preselected in vitro. a dose we have established to be sufficient to reproducibly eradicate malignant cells and, at the same time, not to induce xeno-graft versus host disease. A large master stock of CART19 cells (lx $10^{10}$) will be generated and frozen to minimize variability associated with effector cell differences. The primary measure from these experiments will be survival, which we will assess using Kaplan/Meier curves. As a secondary measure we will evaluate differential expansion of CART19 cells in animals following T cell infusion. This will be made possible by the fact that the infused T cell product will be composed of CART19-positive and -negative cells at a defined ratio. For these analyses, animals will be bled weekly by tail vein bleed (25 microliters each time), followed by red blood cell lysis and staining for human CD3, CD4, CD8, and CART19. Preferential expansion of CART19 cells (at least a 2-fold increase in the CART19+/CART19-ratio will be evidence for selective MCL-driven CART19 cell expansion. To assess the treatment results, volumes of the implanted subcutaneous tumors will be measured determined as follows, according to the formula: volume=0.4ab2, where a and b designate respectively long and short diameters of the tumor. Tumor volumes differences between the treated and untreated groups of mice will be statistically analyzed using a standard t-test. Mice will be sacrificed at either the end-point of the experiments (>30 days), or if tumors reach >1.2 cm in diameter, or when any evidence of the animal distress noted. Tumor volumes differences between the treated and untreated groups of mice will be statistically analyzed using a standard t-test. The tumors as well as the internal organs will be harvested, processed and analyzed by histology and, for selected tissues, by immuno-histochemistry using the battery of antibodies against B cells (CD20, CD79a, Pax-5, CD10, BCL-6) and T cells (CD2, CD3, CD4, CD5, CD7, CD8, TIA-1), and the proliferation marker Ki-67.

Statistical Analysis:

In the in vitro functional studies, the significance of difference between the mean values (+/−S.D.) of the controls and different treatment conditions will be evaluated using Student's t-test with the P value of <0.05 considered to be statistically significant. Based on our previous experiences, the differences between the experimental mouse groups are expected to be large. Thus, 10 NSG mice will be used for each treatment group, which will ensure at least 90% power at 0.05 type 1 error level with a two-sided two sample/-test, given the ratio between the difference in treatment means and the standard deviation is at least 3, which is expected. Data will be presented as mean±SEM. Comparison among groups will be made using the two sample t-test. A value of p<0.05 is considered to be significant. For tumor-free survival studies, groups of 10 mice will be used for survival comparison, and the disease status (tumor vs. no tumor) and tumor-free time for each mouse will be recorded. The Kaplan-Meier survival curve will be plotted and the log-rank test will be performed to compare the survival curves. The significance level is controlled at 0.05.

Example 8: Ibrutinib/CAR19 T-Cell Combined Therapy for Mantle Cell Lymphoma

The experiments described in this example characterize CART19 activity in combination with ibrutinib treatment for treating mantle cell lymphoma in vitro and in vivo. Ibrutinib is a small molecule inhibitor of BTK often used for treatment of some hematological cancers. The in vitro experiments described herein include assessment of proliferation, cytokine production, CD107a degranulation, and cytotoxicity. Xenoplant mouse models were utilized to investigate the efficacy and optimal dosage of CART19 with ibrutinib treatment in vivo. Although ibrutinib displays considerable activity in MCL, about 30% of patients do not respond, and among the responders, only 21% to about one-third experience complete remission (Wang et al. NEJM 369.6 (2013): 507-16). Achievement of a complete remission is associated with improved progression-free survival. Furthermore, therapy can lead to drug resistance with the duration of median response of 17.5 months. In some settings, mutations in BTK binding sites or immediately downstream have been observed after ibrutinib therapy, highlighting a mechanism of drug resistance that may become increasingly frequent. See, e.g., Woyach et al. NEJM. 370.24 (2014):2286-94. Also, blockade of BTK function leads to inhibition of B cell receptor (BCR) signaling and is not directly cytotoxic. See, e.g., Ponader et al. Blood. 119.5 (2012):1182-89. Lack of cytotoxicity and failure to eradicate malignant clones predispose to clonal evolution under a selection pressure. Also, preliminary findings of increased transformation to aggressive disease in patients treated with ibrutinib for CLL are concerning. See, e.g., Byrd et al. NEJM. 369.1 (2013): 32-42; and Parikh et al. Blood. 123.11 (2014):1647-57.

Infusion of autologous T cells transduced with chimeric antigen receptors (CAR) against the B-cell specific CD19 antigen (CTL019, CART19) leads to dramatic clinical responses in the majority of patients with various B-cell neoplasms, foremost acute lymphoblastic leukemia (ALL). See, e.g., Maude et al. NEJM. 371.16 (2014):1507-17; and Ruella et al. Expert Opin. Biol. Ther. (2015):1-6. The presence of lymph node masses or bulky disease may lead to decreased T cell infiltration and consequent reduced anti-tumor activity. Bulky lymphadenopathy does not appear to impair the response to ibrutinib. Wang et al. NEJM. 369.6 (2013):507-16. Also, ibrutinib has shown particular efficacy in reducing tumor masses and mobilizing neoplastic B cells in the peripheral blood.

Methods

Cell Lines and Primary Samples.

MCL cell lines were obtained from ATCC (Mino, Jeko-1, SP-49) while MCL-RL was generated from a progressive pleural effusion of a MCL patient. For in vitro experiments, cell lines were maintained in culture with RPMI media supplemented with 10% fetal calf serum, penicillin, and streptomycin. For some experiments, MCL-RL and Jeko-1 cells were transduced with click beetle green luciferase/eGFP and then sorted to obtain a >99% positive population. The acute leukemia cell lines MOLM-14, K562 or NALM-6 and the T-ALL cell line JURKAT were used as controls. These cell lines were originally obtained from the ATCC. De-identified primary human MCL bone marrow (BM) and peripheral blood (PB) specimens were obtained from the clinical practices of University of Pennsylvania. For all functional studies, primary cells were thawed at least 12 hours before experiment and rested at 37° C.

Generation of CAR Constructs and CAR T Cells.

The murine anti-CD19 Chimeric antigen receptor (containing a CD8 hinge, 41BB costimulatory domain and CD3 zeta signaling domain) was generated as previously described. See, e.g., Milone et al. Molecular Therapy: the Journal of the American Society of Gene Therapy. 17.8 (2009):1453-64. Production of CAR-expressing T cells was performed as previously described. See, e.g., Gill et al. Blood. 123.15 (2014):2343-54. Normal donor CD4 and CD8 T cells or PB mononuclear cells (PBMC) were obtained from the Human Immunology Core of the University of Pennsylvania. T cells were plated at 1×10⁶/ml, with a CD4:CD8 ratio of 1:1 and expanded in X-vivo 15 media (Lonza, 04-418Q), human serum AB 5% (Gemini, 100-512), penicillin/streptomycin (Gibco, 15070063) and Glutamax (Gibco, 35050061) using anti-CD3/CD28 Dynabeads (Life Technologies, 11161D) added on the day 1 of culture and removed on day 6. T cells were transduced with lentivirus on day 2. T cells were expanded in culture for 8-15 days and harvested when the median cell volume was below 300 fl. T cells were then cryopreserved in FBS 10% DMSO for future experiments. Prior to all experiments, T cells were thawed and rested overnight at 37° C.

Ibrutinib.

Ibrutinib (PCI-32765) was purchased from MedKoo (#202171) or Selleck Biochemicals (#S2680) as a powder or DMSO solution. For in vitro experiments, ibrutinib was diluted to the concentrations of 10, 100 and 1000 nM. For in vivo experiments, ibrutinib powder was dissolved in a 10% HP-beta-cyclodextrin solution (1.6 mg/ml) and administered to mice in the drinking water.

Multiparametric Flow Cytometry Analysis.

Anti-human antibodies were purchased from Biolegend, eBioscience, or Becton Dickinson. Cells were isolated from in vitro culture or from animals, washed once in PBS supplemented with 2% fetal calf serum, and stained for 15 minutes at room temperature. For cell number quantitation, Countbright (Invitrogen) beads were used according to the manufacturer's instructions. In all analyses, the population of interest was gated based on forward vs. side scatter characteristics followed by singlet gating, and live cells were gated using Live Dead Aqua (Invitrogen). Time gating was included for quality control. Surface expression of CAR19 was detected as previously described. See, e.g., Kalos et al. Science Translational Medicine. 3.95 (2011):95ra73. Flow cytometry was performed on a four-laser Fortessa-LSR cytometer (Becton-Dickinson) and analyzed with FlowJo X 10.0.7r2 (Tree Star).

Degranulation Assay.

Degranulation assay was performed as previously described. See, e.g., Kalos et al. Science Translational Medicine. 3.95 (2011):95ra73. T cells were incubated with target cells at a 1:5 ratio in T cell media. Anti-CD107a-PECY7 (Biolegend), anti-CD28 (BD Biosciences), anti-CD49d (BD Biosciences) antibodies and monensin (BD Biosciences) were added to the co-culture. After 4 hours, cells were harvested and stained for CAR expression, CD3, CD8 and Live Dead aqua staining (Invitrogen). Cells were fixed and permeabilized (Invitrogen Fix/Perm buffers) and intracellular staining was then performed to detect multiple cytokines (IFN, TNFa, IL-2, GM-CSF, MIP1b).

Proliferation Assay.

T cells were washed and resuspended at $1\times10^7$/m1 in 100 ul of PBS and stained with 100 ul of CFSE 2.5 uM (Invitrogen) for 5 minutes at 37° C. The reaction was then quenched with cold media, and cells were washed three times. Targets were irradiated at a dose of 100 Gy. T cells were incubated at a 1:1 ratio with irradiated target cells for 120 hours, adding media at 24 hours. Cells were then harvested, stained for CD3, CAR and Live Dead aqua (Invitrogen), and Countbright beads (Invitrogen) were added prior to flow cytometric analysis for absolute quantification.

Cytotoxicity Assays.

Luciferase/eGFP+ NALM-6 or RL cells were used for cytotoxicity assay as previously described. See, e.g., Gill et al. Blood. 123.15 (2014):2343-54. Targets were incubated at the indicated ratios with effector T cells for 4 or 16 hours. Killing was calculated by bioluminescence imaging on a Xenogen IVIS-200 Spectrum camera.

Cytokine Measurements.

Effector and target cells were co-incubated at a 1:1 ratio in T cell media for 24 h. Supernatant was harvested and analyzed by 30-plex Luminex array (Luminex Corp, FLEX-MAP 3D) according to the manufacturer's protocol (Invitrogen). See, e.g., Kalos et al. Science Translational Medicine. 3.95 (2011):95ra73.

In Vivo Experiments.

NOD-SCID-γ chain−/− (NSG) mice originally obtained from Jackson Laboratories were purchased from the Stem Cell and Xenograft Core of the University of Pennsylvania. All experiments were performed on protocols approved by the Institutional Animal Care and Use Committee (IACUC). Schematics of the utilized xenograft models are discussed herein. Cells (MCL cell lines or T cells) were injected in 200 ul of PBS at the indicated concentration into the tail veins of mice. Bioluminescent imaging was performed using a Xenogen IVIS-200 Spectrum camera and analyzed with LivingImage software v. 4.3.1 (Caliper LifeSciencies). Animals were euthanized at the end of the experiment or when they met pre-specified endpoints according to the IACUC protocols.

Immunohistochemistry.

Immuno-histochemical (IHC) staining of formalin fixed paraffin embedded tissues was performed on a Leica Bond-III instrument using the Bond Polymer Refine Detection System. Antibodies against CD3, CD4, CD8, Pax5 and CyclinD1 were used undiluted. Heat-induced epitope retrieval was done for 20 minutes with ER2 solution (Leica Microsystems AR9640). Images were digitally acquired using the Aperio ScanScope™.

Statistical Analysis.

All statistics were performed using GraphPad Prism 6 for windows, version 6.04.

Mantle Cell Lymphoma Cell Lines

Figure 52A:
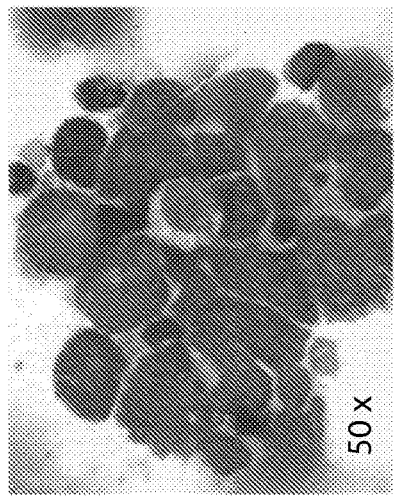
FIG. 52A is an image of a RL cell line.
Figure 52B:
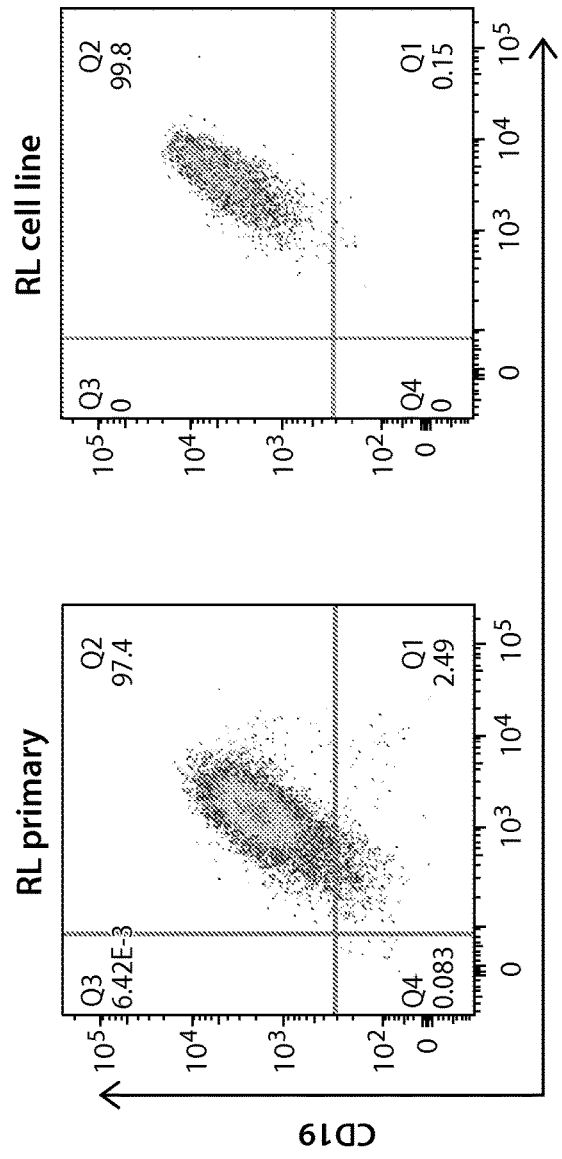
FIG. 52B is a set of flow cytometry scatterplots showing the expression of CD19 and CD5 in RL primary and RL cell lines.
Figure 52C:
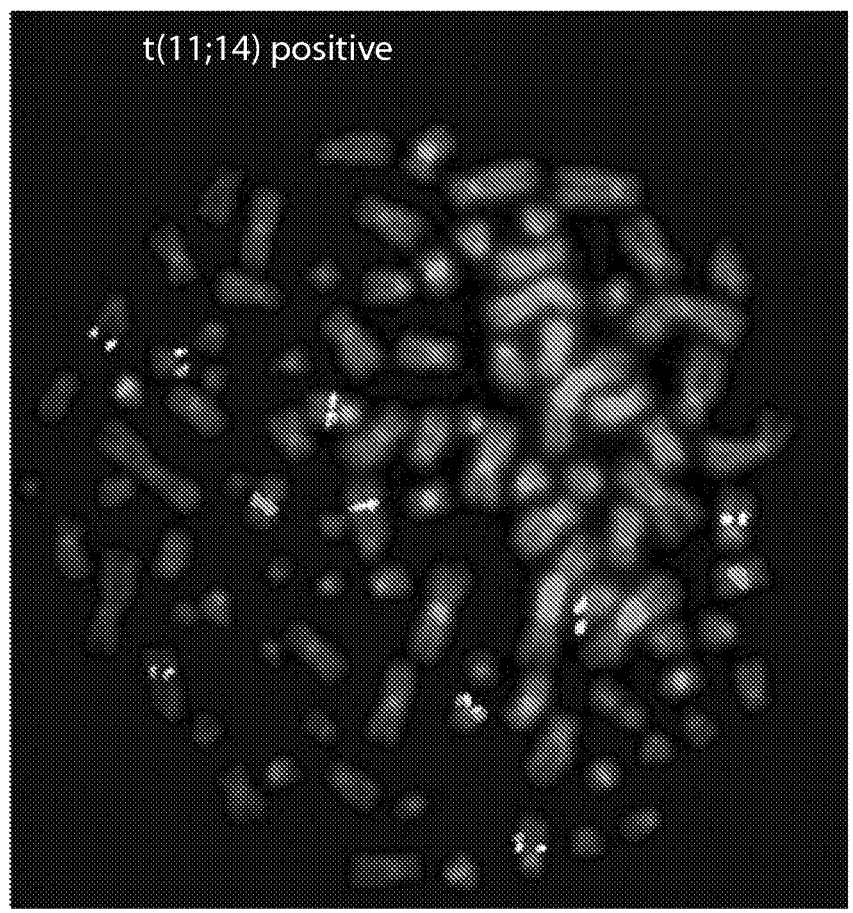
FIG. 52C is an image showing t(11;14) translocation by fluorescence in-situ hybridization (FISH).

Most mantle cell lymphoma (MCL) lines in existence have been immortalized and propagated for many generations in vitro, thus losing their dependence on B cell receptor signaling. Consequently, they are poorly sensitive to ibrutinib. In vitro experiments were performed to determine the sensitivity of MCL cell lines on ibrutinib treatment. These cell lines were also used to assess the efficacy of ibrutinib/CART19 combination treatment in experiments discussed further in this example. MCL cells were harvested from the pleural effusion of a patient with multiply relapsed MCL. Both the original cells ($RL^{primary}$) and a cell line derived from them (RL) had a blastoid morphology, typical MCL immunophenotype and were positive for the classical t(11; 14) translocation by fluorescence in-situ hybridization (FISH) (FIG. 52A, 52B, 52C).

Figure 31A:
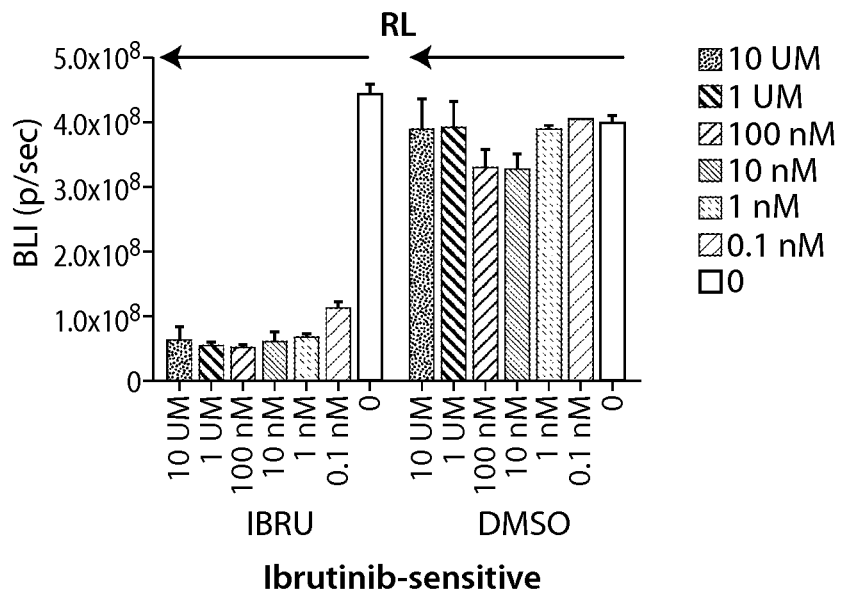
FIGS. 31A and 31B is a graphic representation demonstrating the sensitivity of MCL cell lines RL (FIG. 31A) and JEKO-1 (FIG. 31B) to ibrutinib treatment.
Figure 31B:
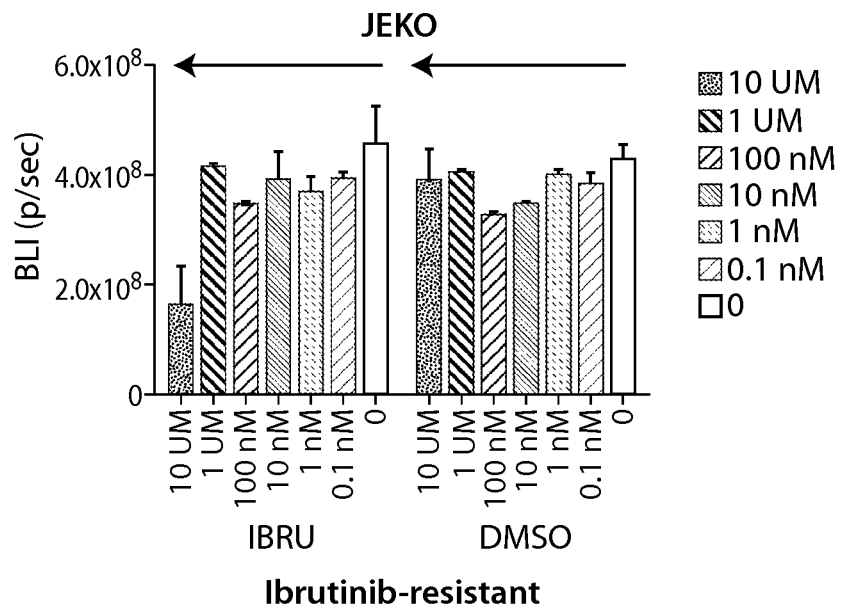

RL and JEKO-1 cells were cultured with different doses of ibrutinib (0.1 nM, 1 nM, 10 nM, 100 nM, 1 μM, and 10 μM) and sensitivity to ibrutinib was determined by measuring the reduction of bioluminescence (BLI). As shown in FIG. 31A, RL cells were sensitive to ibrutinib treatment in a dose-dependent manner. However, JEKO-1 cells were resistant to ibrutinib treatment (no demonstration of reduced bioluminescence as a function of increased ibrutinib dosage).

Figure 52D:
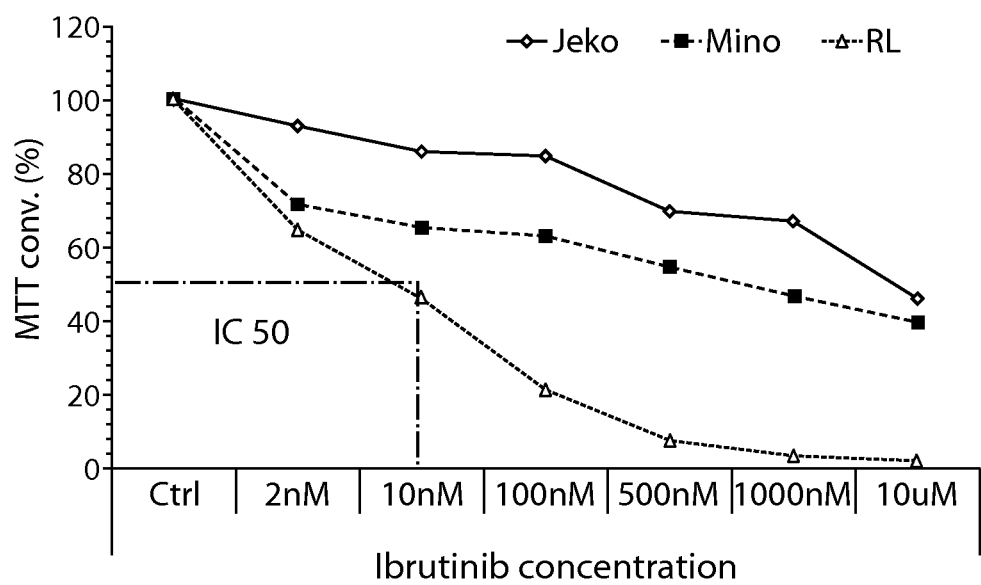
FIG. 52D is a graph showing the IC50 (by percentage MTT conversion) of ibrutinib inhibition in different cell lines.
Figure 52E:
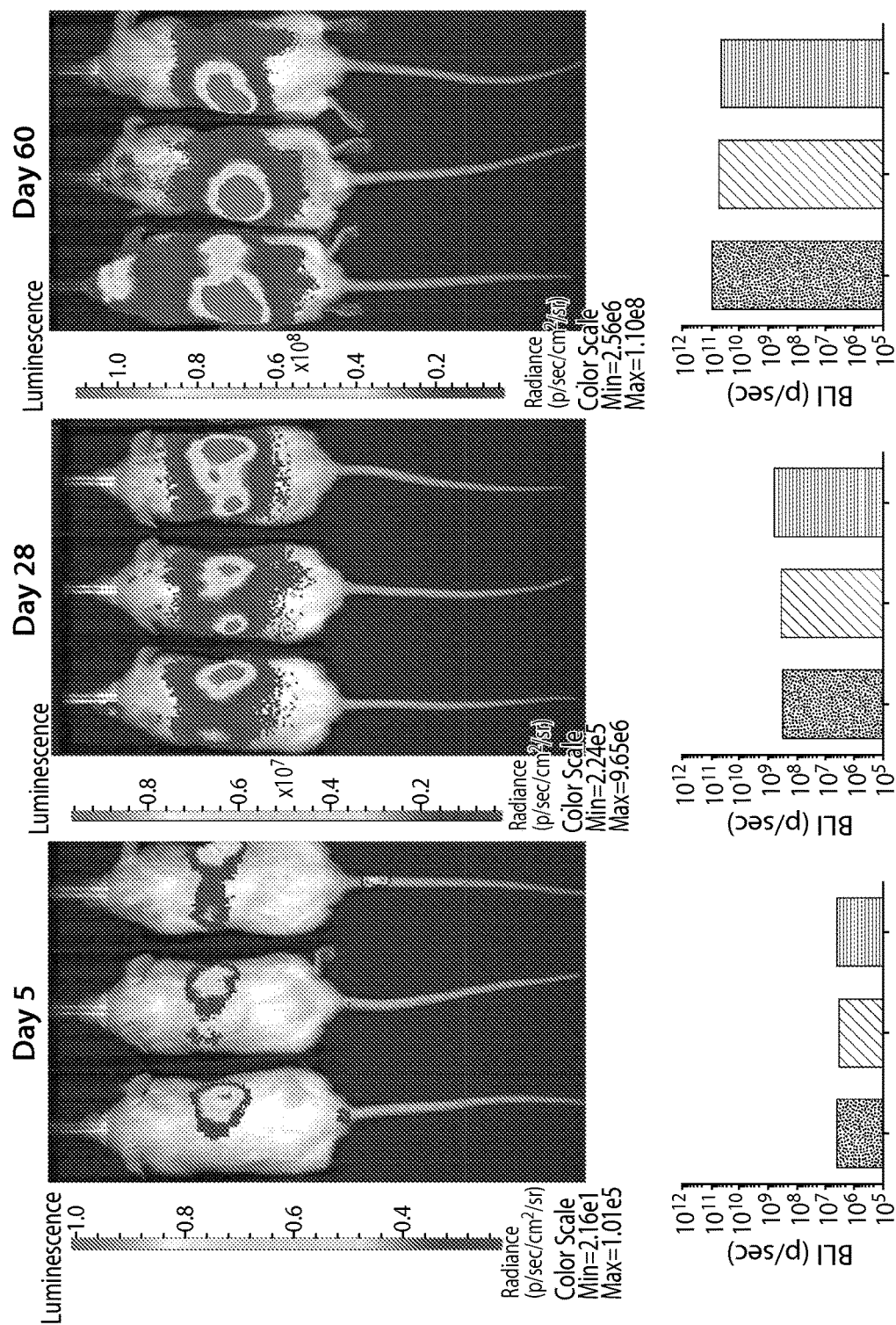
FIG. 52E is a set of images and graphs showing engraftment of RL cells in NOD-SCID-gamma chain knockout (NSG) mice and the resulting tumor burden.
Figure 52G:
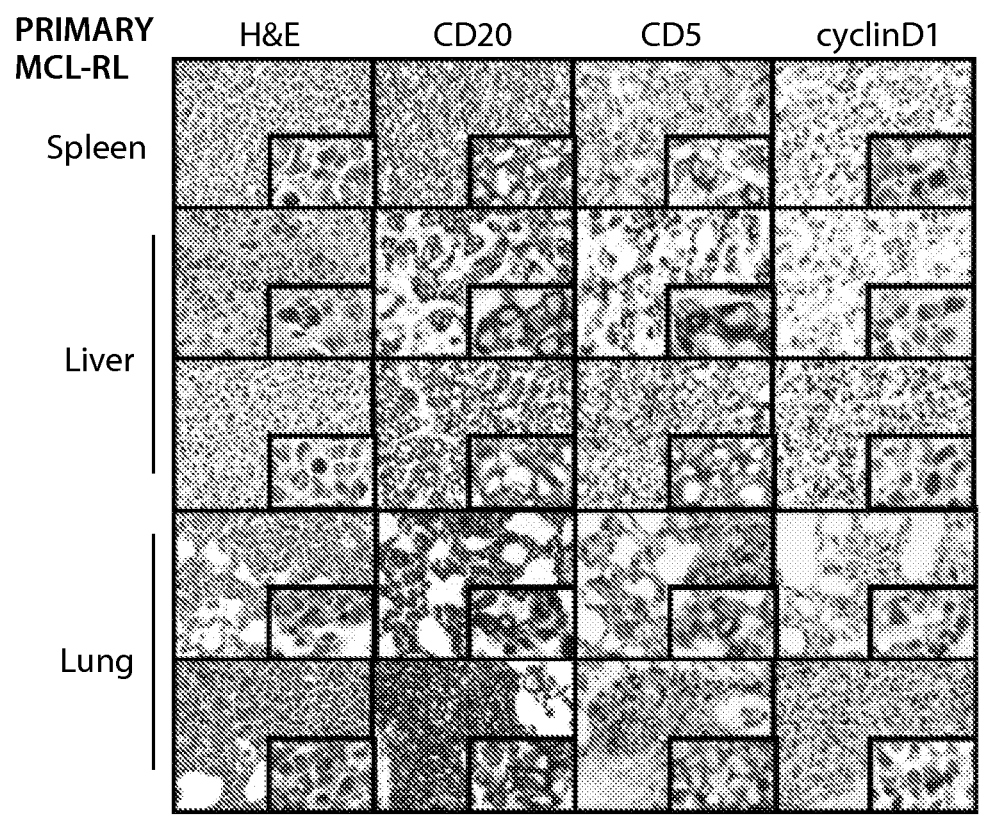
FIG. 52G is a set of histological images of mice that have been injected with MCL-RL cells.

Sensitivity of RL, Jeko-1, and Mino cells to ibrutinib were also assayed using a MTT assay. Exposure of RL to increasing concentrations of ibrutinib in vitro led to a dose-dependent inhibition of proliferation and of downstream mediator phosphorylation, indicating an on-target effect of ibrutinib, with an IC50 of 10 nM. In contrast, the established MCL cell lines Jeko-1 and Mino were relatively resistant to ibrutinib, with IC50 results up to 10 μM (FIG. 52D). To confirm RL as a viable model for in vivo experiments, immunodeficient NOD-SCID-γ chain knockout (NSG) mice were engrafted with $1\times10^6$ luciferase-expressing RL cells (FIG. 52E). Their tumor burden and survival were assessed. After intravenous injection, MCL engrafted in all mice and localized to the spleen and liver, followed by dissemination to bone marrow, blood and lymph nodes (FIG. 52F). Histology of affected spleen and liver is consistent with parenchymal infiltration of MCL. (FIG. 52G).

These results showed that these different cell lines could therefore be used to model both ibrutinib-sensitive and ibrutinib-resistant MCL.

Mantle Cell Lymphoma Cells are Sensitive to Killing by CART19

Most preclinical work showing the efficacy of CART19 has been done using B-ALL cell lines, which are not sensitive to ibrutinib. Furthermore, the best clinical responses to date have been reported in patients with B-ALL, whereas patients with indolent B-cell malignancies have reportedly lower responses.

Figure 53A:
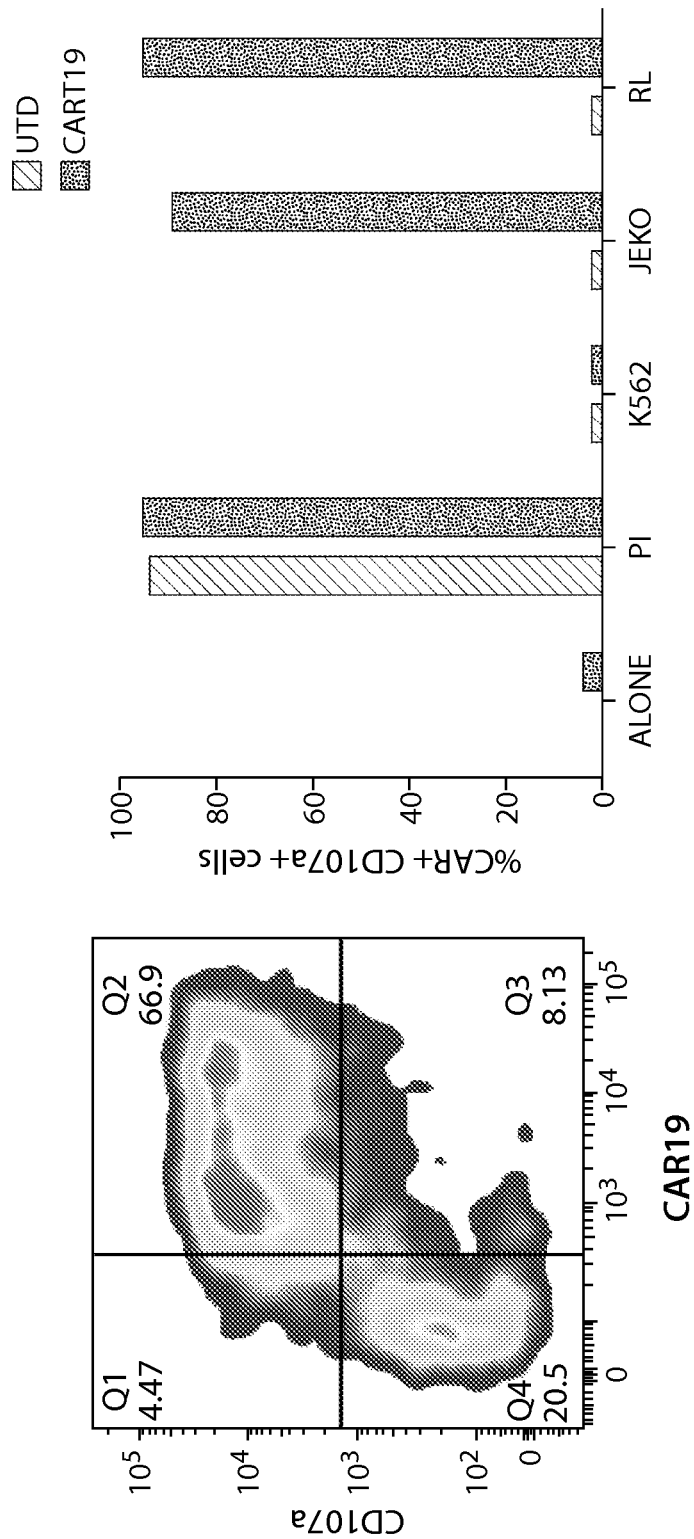
FIG. 53A is a set of graphs showing the number of CD107a+ CART19 cells when exposed to various MCL cell lines.
Figure 53B:
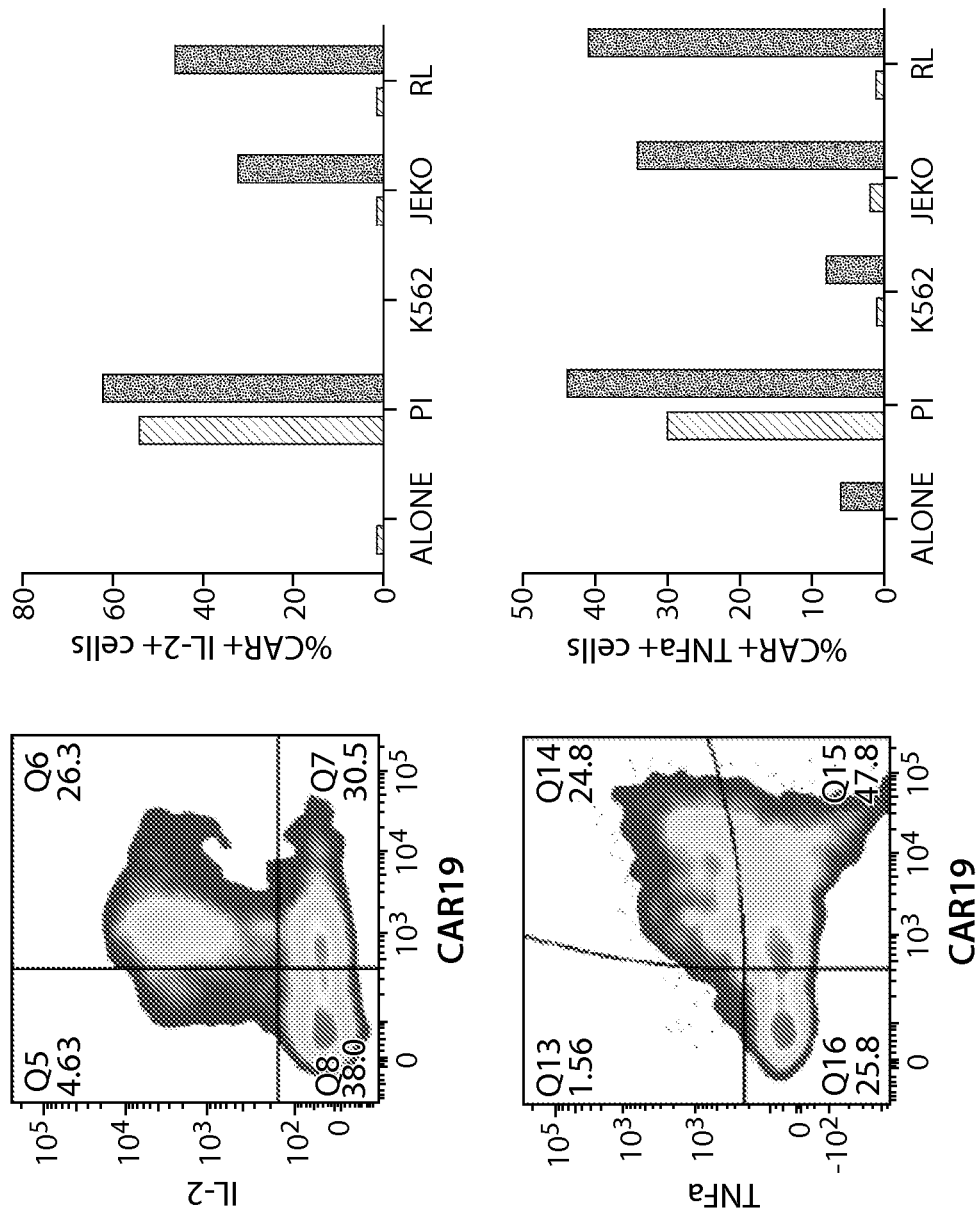
FIG. 53B is a set of graphs showing the amount of IL-2 and TNF-alpha produced by CART19 cells when exposed to various MCL cell lines.
Figure 53C:
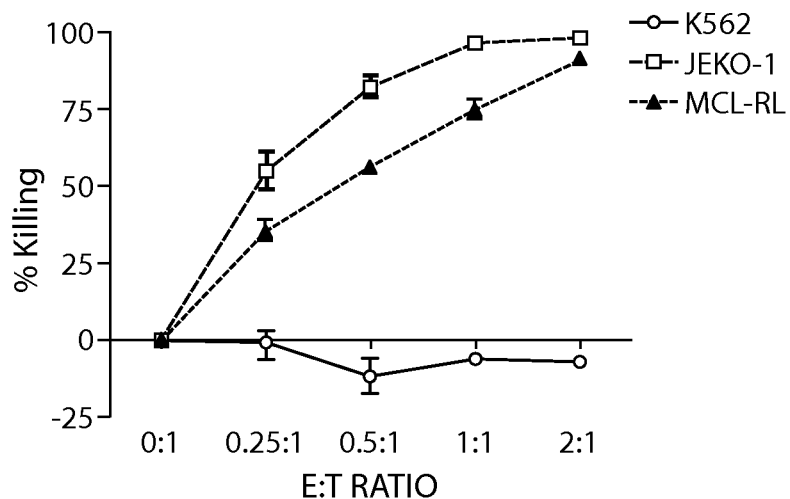
FIG. 53C is a graph showing the percent killing of various MCL cell lines by CART19 cells at various effector:target cell ratios.
Figure 53D:
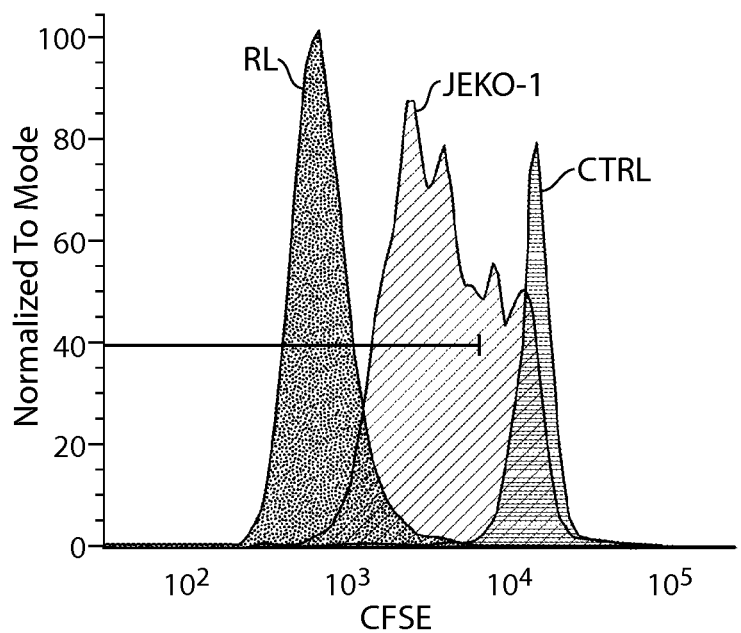
FIG. 53D is a graph showing the amount of carboxyfluorescein succinimidyl ester (CFSE), a measure of proliferation, in CART19 cells exposed to various MCL cell lines.
Figure 53E:
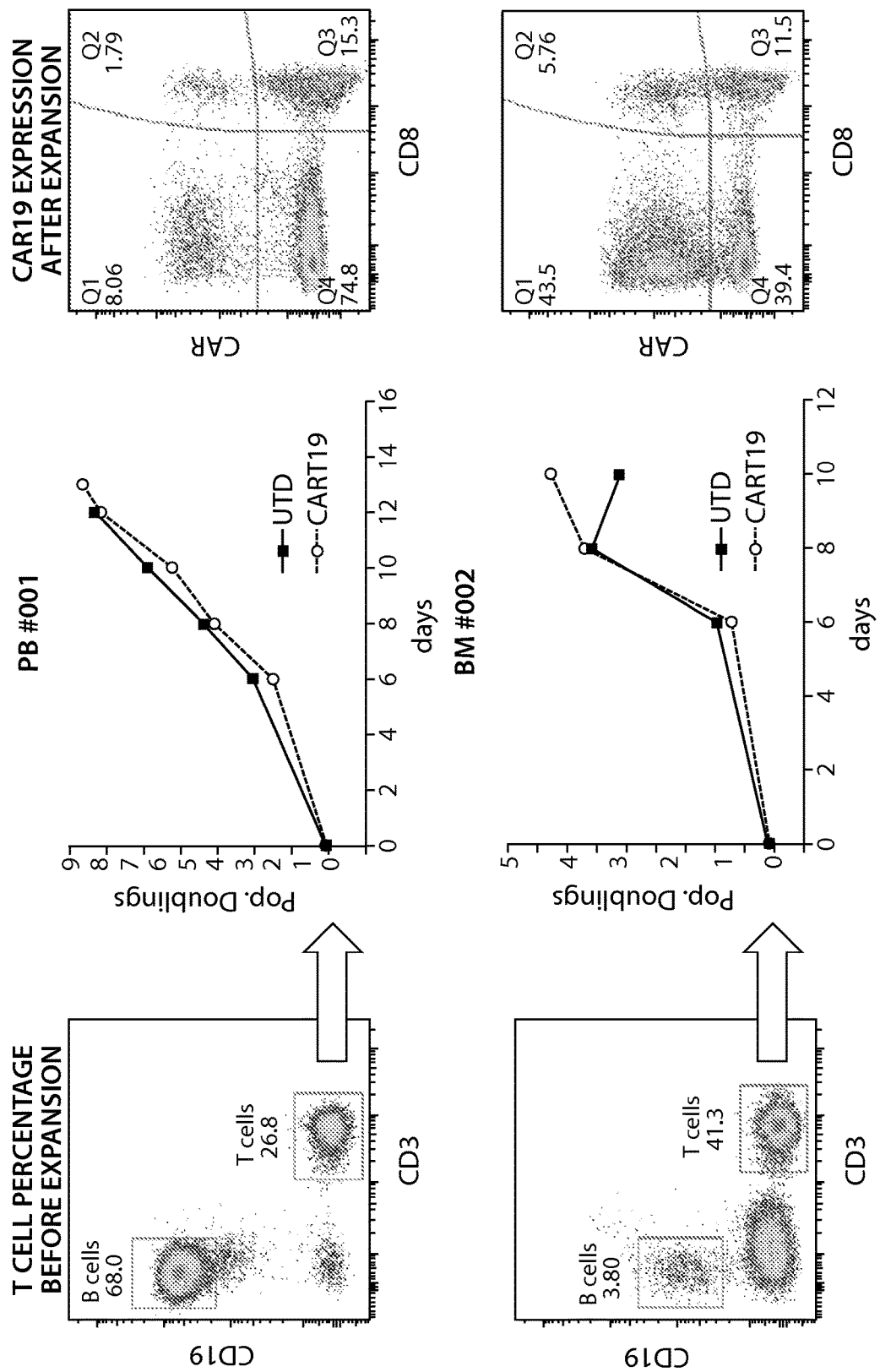
FIG. 53E is a set of graphs showing the percentage of T cells before and after expansion.

To show that MCL is sensitive to killing by CART19 in this model, healthy donor T cells were transduced with an anti-CD19 CAR construct that has been used in clinical trials. See, e.g., Porter, NEJM 2011. A series of in vitro experiments were performed to show that the ibrutinib-sensitive cell line RL and the ibrutinib-resistant cell line Jeko-1 lead to equivalent CART-19 degranulation, cytokine production, killing and proliferation (FIG. 53A, 53B, 53C, 53D). In addition, peripheral blood or bone marrow was obtained from two patients with MCL in leukemic phase, permitting the expansion and transduction of autologous T cells with anti-CD19 CAR. Autologous patient-derived CART19 cells were reactive to MCL whereas the untransduced T cells were unreactive to their respective autologous MCL (FIG. 53E, 53F). These results indicate that MCL are sensitive to the effector functions of CART19.

Assessment of Ibrutinib/CART19 Treatment In Vitro

An effect of ibrutinib on T cells was previously discounted based on short-term activity assays, as described in Honigberg et al. Proc. Natl. Acad. Sci. USA. 107 (2010): 13075-80. Later, an analysis of the effect of ibrutinib on the T cell kinase ITK was reported to support an immunomodulatory role of ibrutinib on CD4 T cells by inhibiting Th2-type polarization. See Dubovsky et al. Blood 122.15 (2013): 2539-49. Cytokine analysis of patients treated with CART19 by several groups indicates that CART19 therapy is associated with both Th1 (IL2, IFNγ, TNF), Th2 (IL-4, IL-5, IL-10) and other cytokines (see, e.g., Kalos et al. Science Translational Medicine 3.95 (2011):95ra73). In this example, the effect of CART19 function was evaluated with ibrutinib at, above, and below the ibrutinib concentrations that would be expected in patients (mean peak concentration in serum 100-150 ng/ml) See Advani et al. J. Clin. Oncol. 2013; 31:88.

Figure 54A:
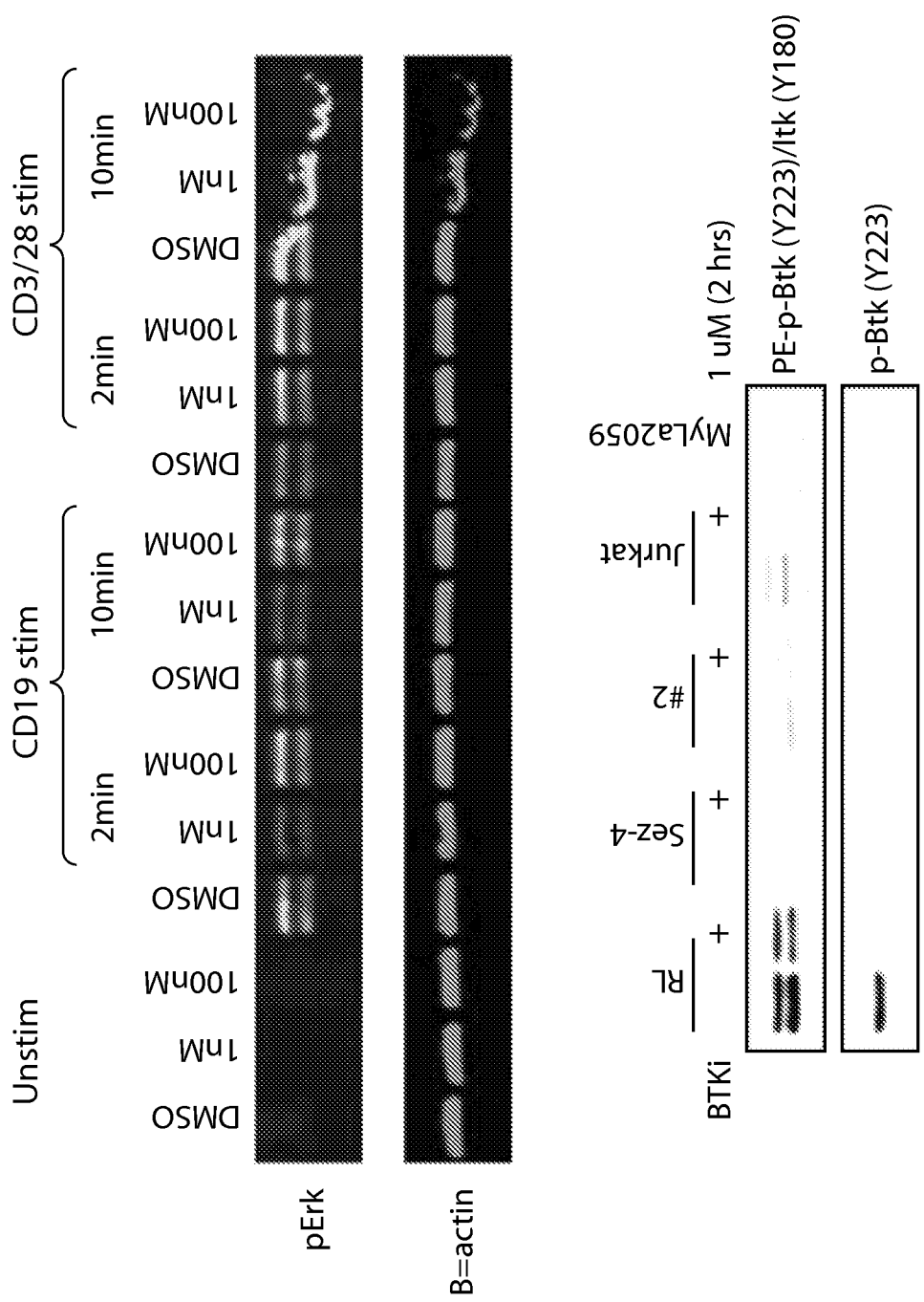
FIG. 54A is a set of images showing the activation of interleukin-2-inducible T-cell kinase (ITK) when CART19 cells were stimulated specifically or non-specifically.

CART19 cells were found to contain ITK. Non-specific stimulation of CART19 cells via the TCR in the presence of ibrutinib led to a reduction in phosphorylated ITK (pITK-$Y_{180}$) as previously reported for CD4+ T cells. See Dubovsky et al. Blood 122.15 (2013):2539-49. In contrast, specific stimulation of CART19 cells via the CAR did not lead to diminished ITK activation (FIG. 54A). This observation indicated that CART19 function would likely not be adversely affected by exposure to ibrutinib.

Figures 1, 10A:
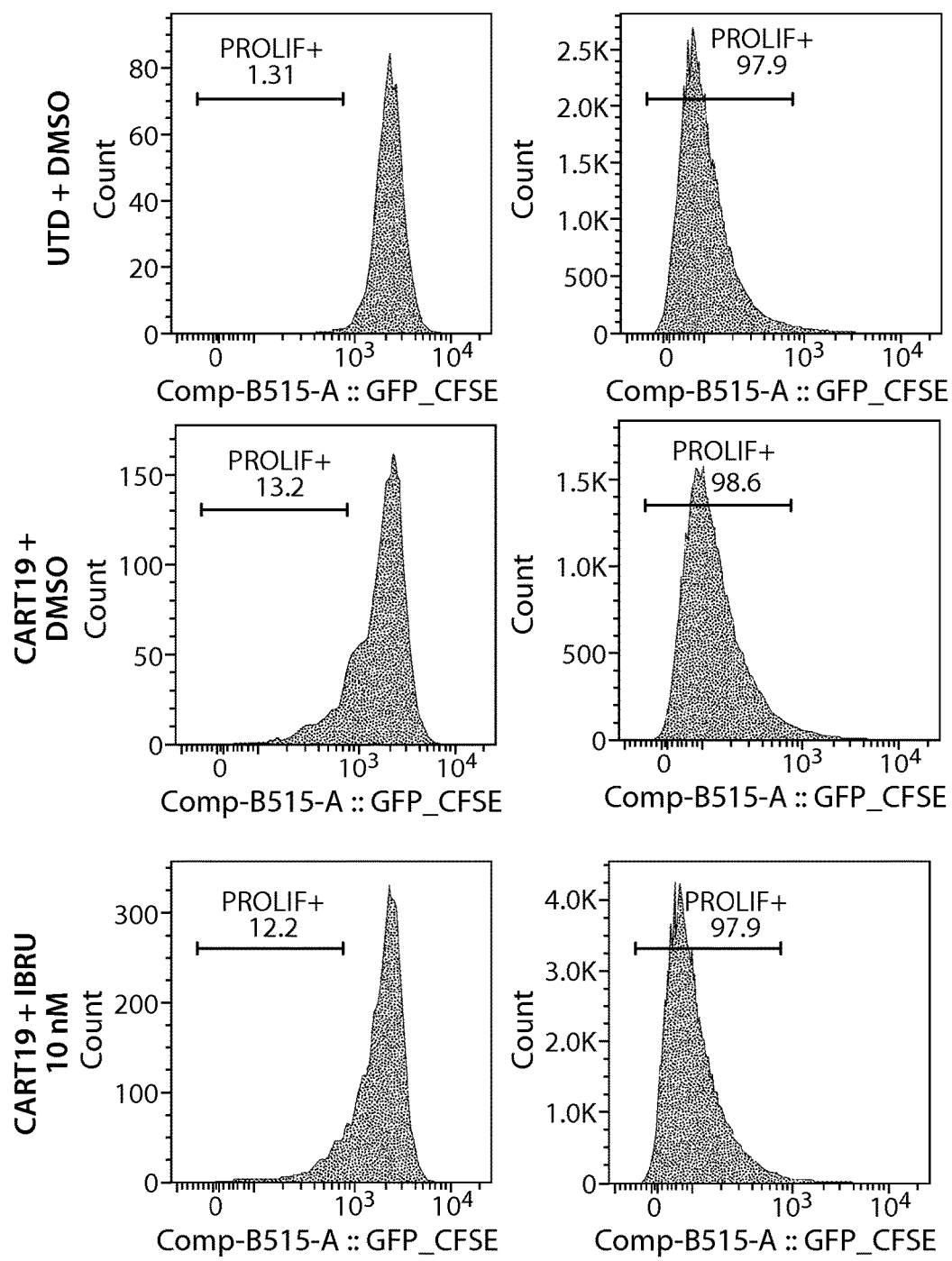
Figure 54C:
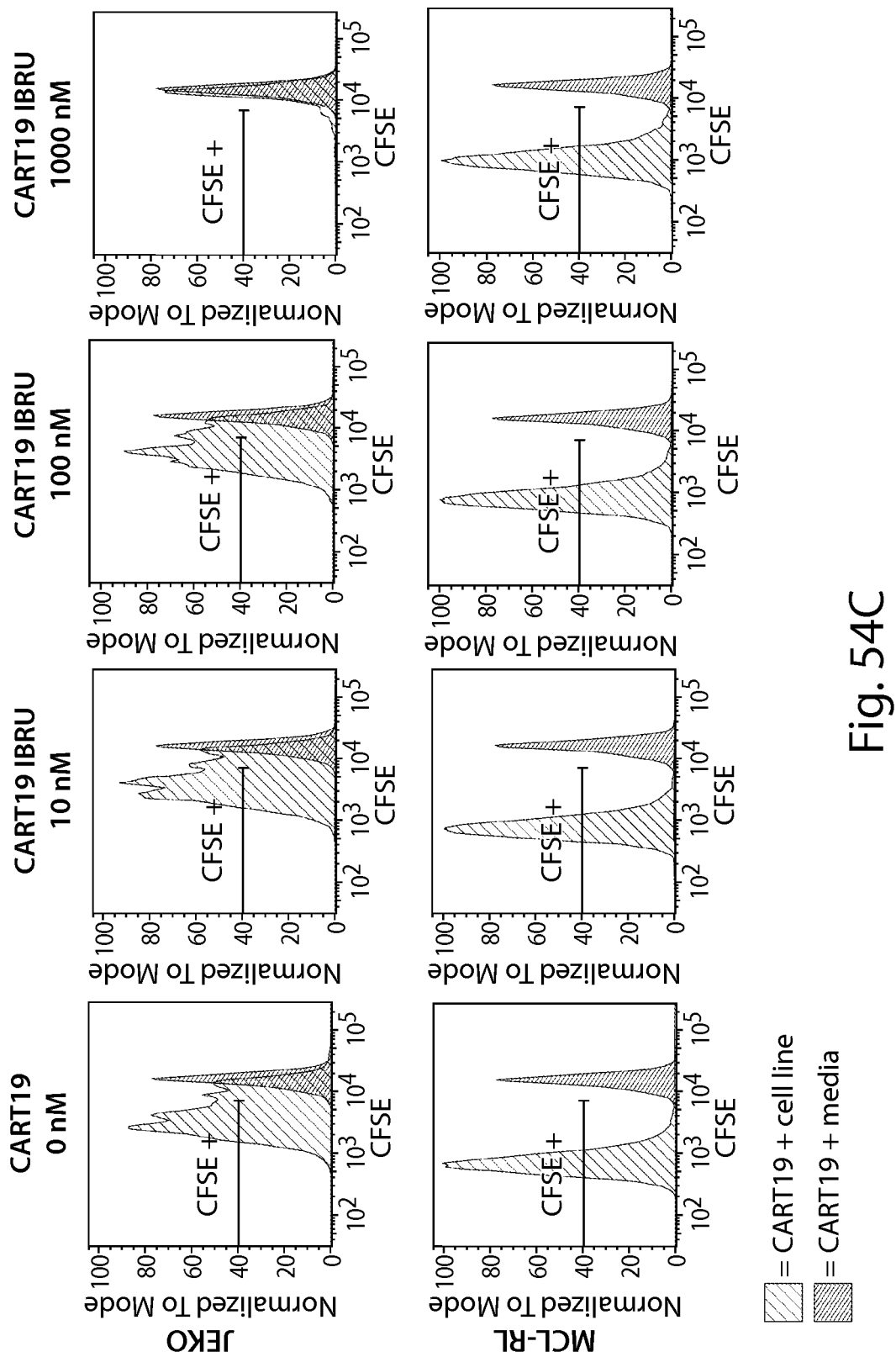
FIG. 54C is a set of histograms showing the amount of CFSE in CART19 cells with various concentrations of ibrutinib and exposed to various MCL cell lines.

In addition, the short- and long-term in vitro function of CART19 cells in the presence of ibrutinib was determined. Ibrutinib at clinically relevant concentrations did not impair CART19 cell proliferation, degranulation or cytokine production; although at supra-physiologic concentrations, there was inhibition of CART19 cell functions, likely representing non-specific toxicity (FIG. 54B, 54C, 10B).

Figure 9A:
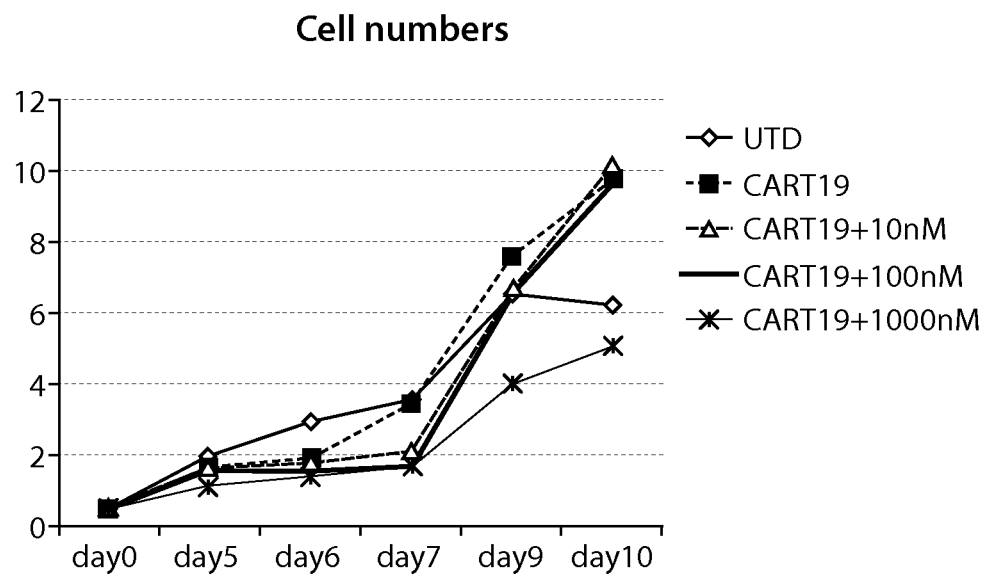
FIGS. 9A and 9B are two graphs showing the cell proliferation and cell size of CART19 cells when treated with increasing concentrations of ibrutinib (10 nM, 100 nM, and 1000 nM).
Figure 9B:
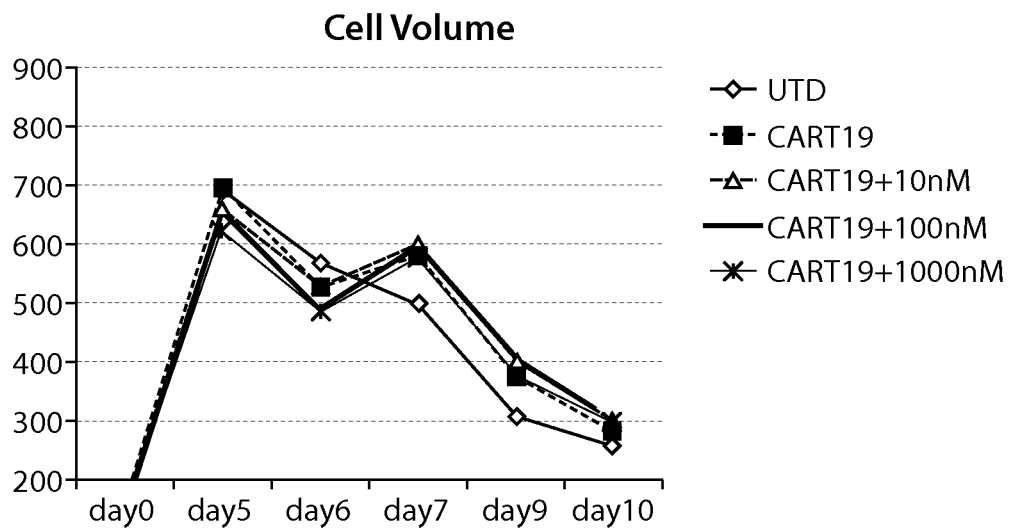

In particular, PBMCs isolated from a normal healthy donor was transduced with a lentiviral anti-CD19 CAR construct as described above. The resulting CAR19-expressing T cells (CART19) were cultured and passaged to determine proliferation and expansion capacity. A 1:1 ratio of CD4:CD8 expressing T cells were cultured culture with or without different concentrations of ibrutinib (10 nM, 100 nM, and 1000 nM ibrutinib). Ibrutinib was added at each cell passage. The number of cells was counted at day 0, day 5, day 6, day 7, day 9, and day 10 (FIG. 9A). Cell volume was also monitored (FIG. 9B).

CFSE-staining and flow cytometry analysis was also used to assess proliferation of the CART19 cells in the presence of ibrutinib after stimulation by tumor cell lines MOLM14, JEKO-1, and RL. MOLM14 is an AML cell line, and JEKO-1 and RL are mantle cell lymphoma cell lines. Specifically, the RL cells are a novel MCL cell line derived from neoplastic B-cells obtained from a pleural effusion of a relapsed MCL patient. CART19 cells and tumor cells were mixed in a 1:1 ratio and proliferation was assessed over 5 days. Percentage of proliferating cells are designated in each histogram in FIGS. 10A-1, 10A-2, 10A-3, and 10A-4. Quantification of proliferation as shown in FIG. 10B shows that high doses of ibrutinib might inhibit CART 19 cell proliferation during co-culture with MCL cell lines.

Degranulation of T cells indicates the activation of cytolytic T cells and the ability to initiate antigen-specific cytotoxicity. CD107a is a functional marker of degranulation of T cells transiently expressed on the cell surface after T cell stimulation. Flow cytometry analysis was used to quantify CD107a-expressing CART19 T cells after stimulation with tumor cell lines MOLM14, JEKO-1, and RL. CD107a-expressing cells were present in Q2 (quadrant 2) of the cell profiles shown in FIGS. 11A-1, 11A-2, 11A-3, 11A-4, 11A-5, and 11A-6. Quantification of the results obtained from the profiles of FIGS. 11A-1, 11A-2, 11A-3, 11A-4, 11A-5, and 11A-6 is shown in FIG. 11B. These results indicate that co-culture of CART19 cells with either MCL-RL or JEKO-1 led to massive CAR-specific CD107a degranulation.

Cytokine production by CART19 T cells in the presence of ibrutinib was also quantified after stimulation by different tumor cell lines. IL-2, TNF-α, and IFN-γ production was assessed by flow cytometry. Cells producing the cytokines are present in quadrant 2 of the profiles shown in FIGS. 12-1, 12-1, 12-3, 12-4, 12-5, and 12-6, FIGS. 13-1, 13-2, 13-3, 13-4, 13-5, and 13-6, and FIGS. 14-1, 14-2, 14-3, 14-4, 14-5, and 14-6. CART19 T cells stimulated by JEKO-1 and RL showed an increase in cytokine expression. Also, increasing concentrations of ibrutinib treatment did not affect the percentage of the CART19 cytokine-producing cells.

Figures 1, 15:
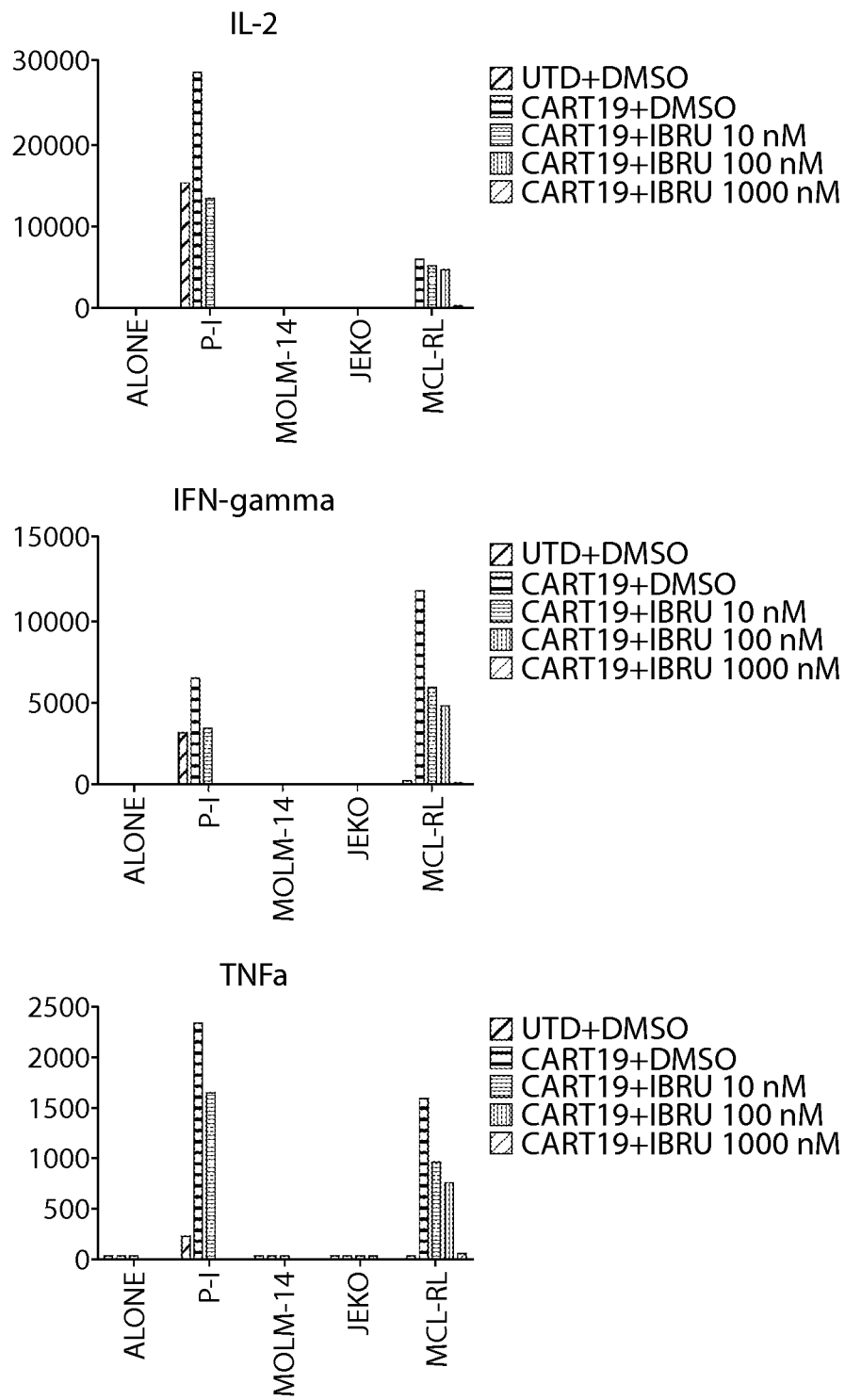
Figures 2, 15:
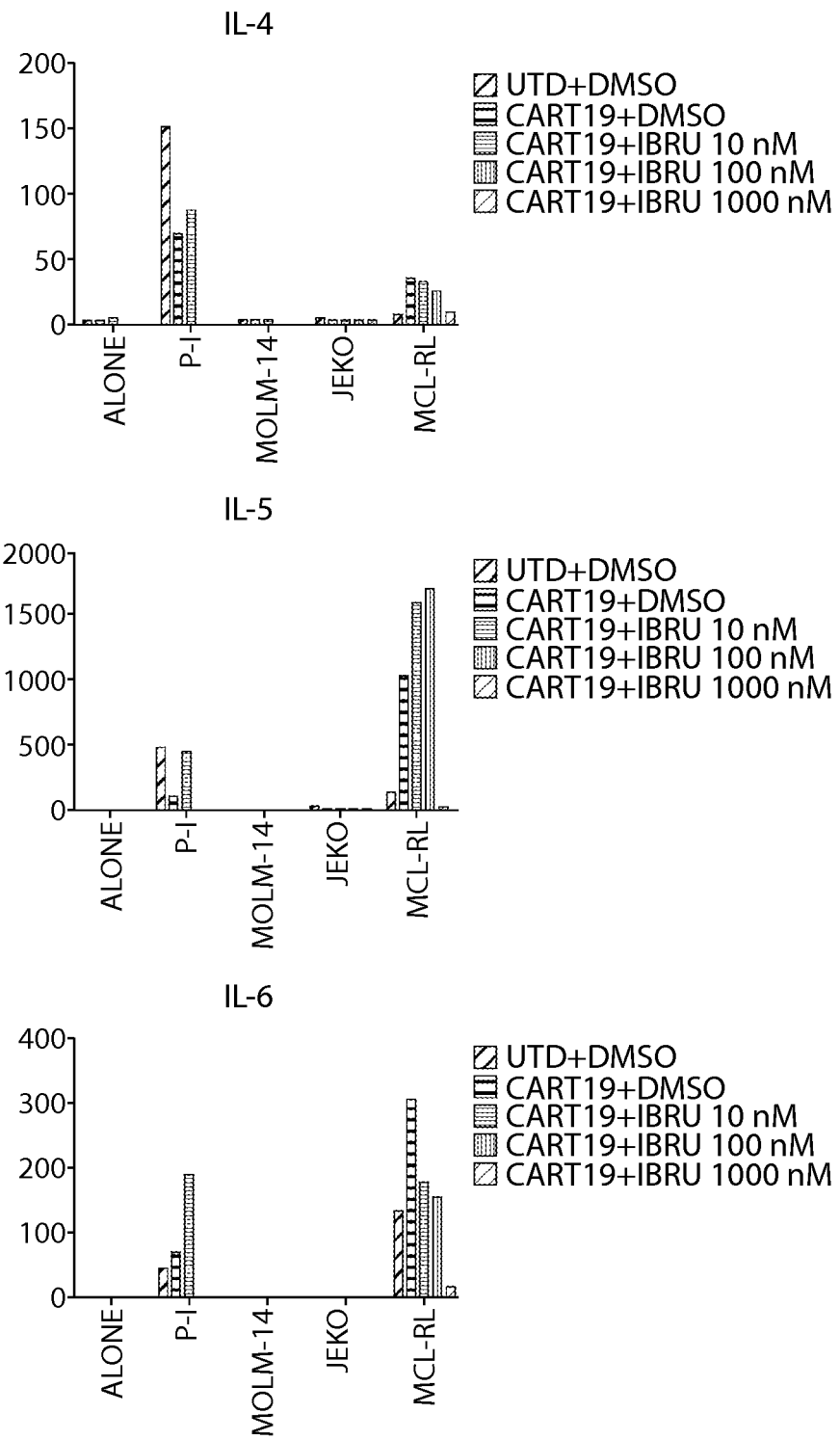
Figures 3, 15:
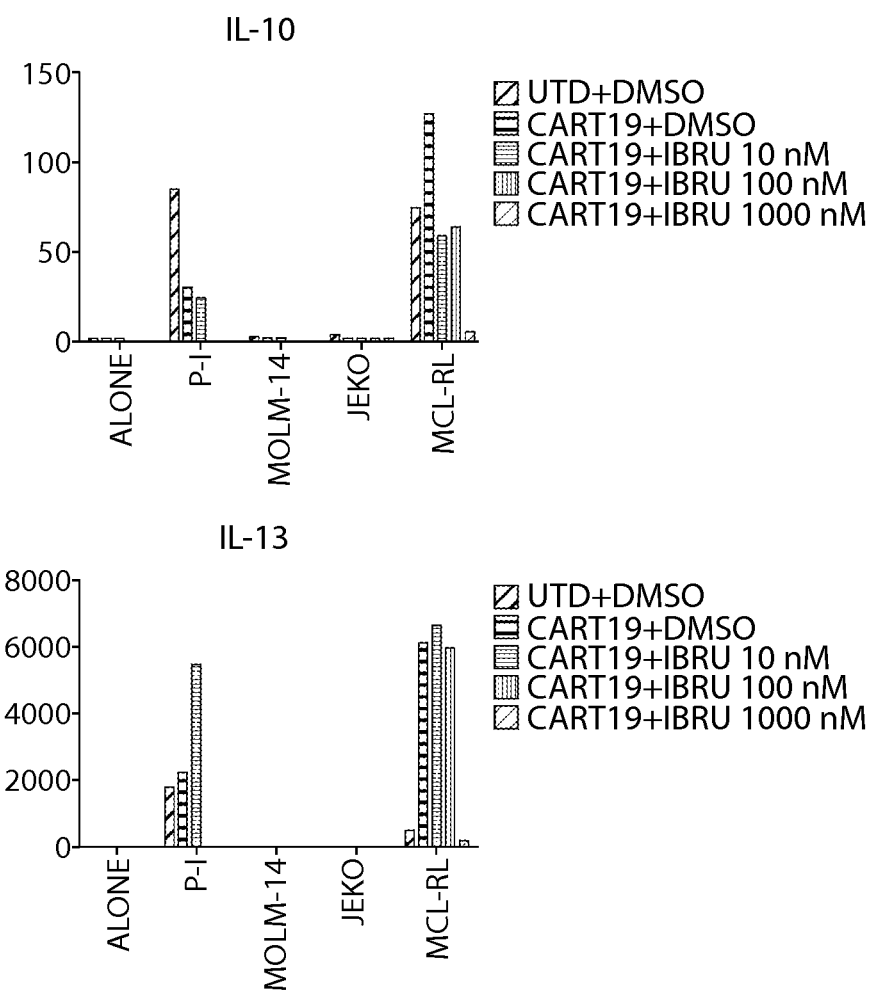
Figures 4, 15:
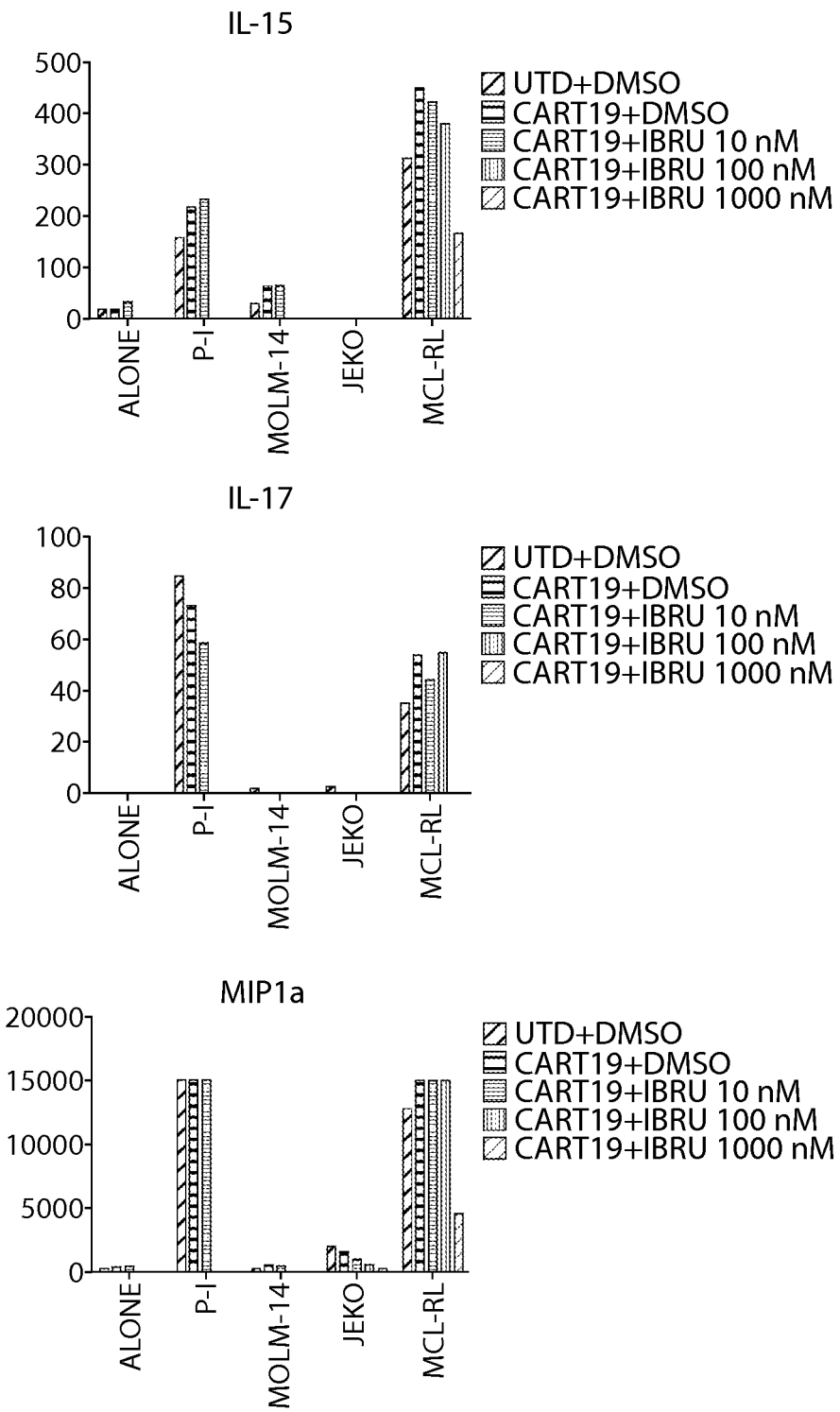
Figures 5, 15:
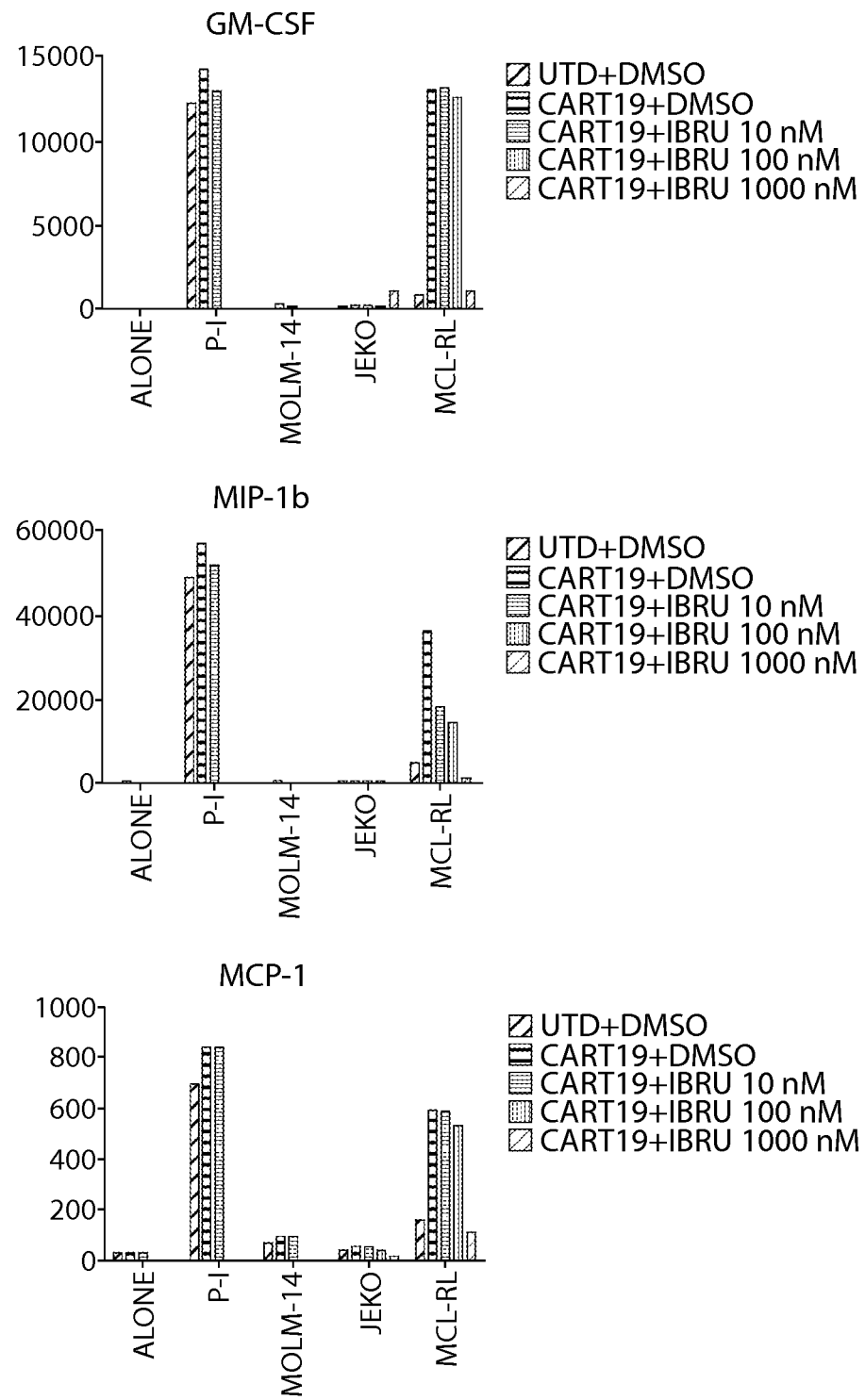
Figures 6, 15:
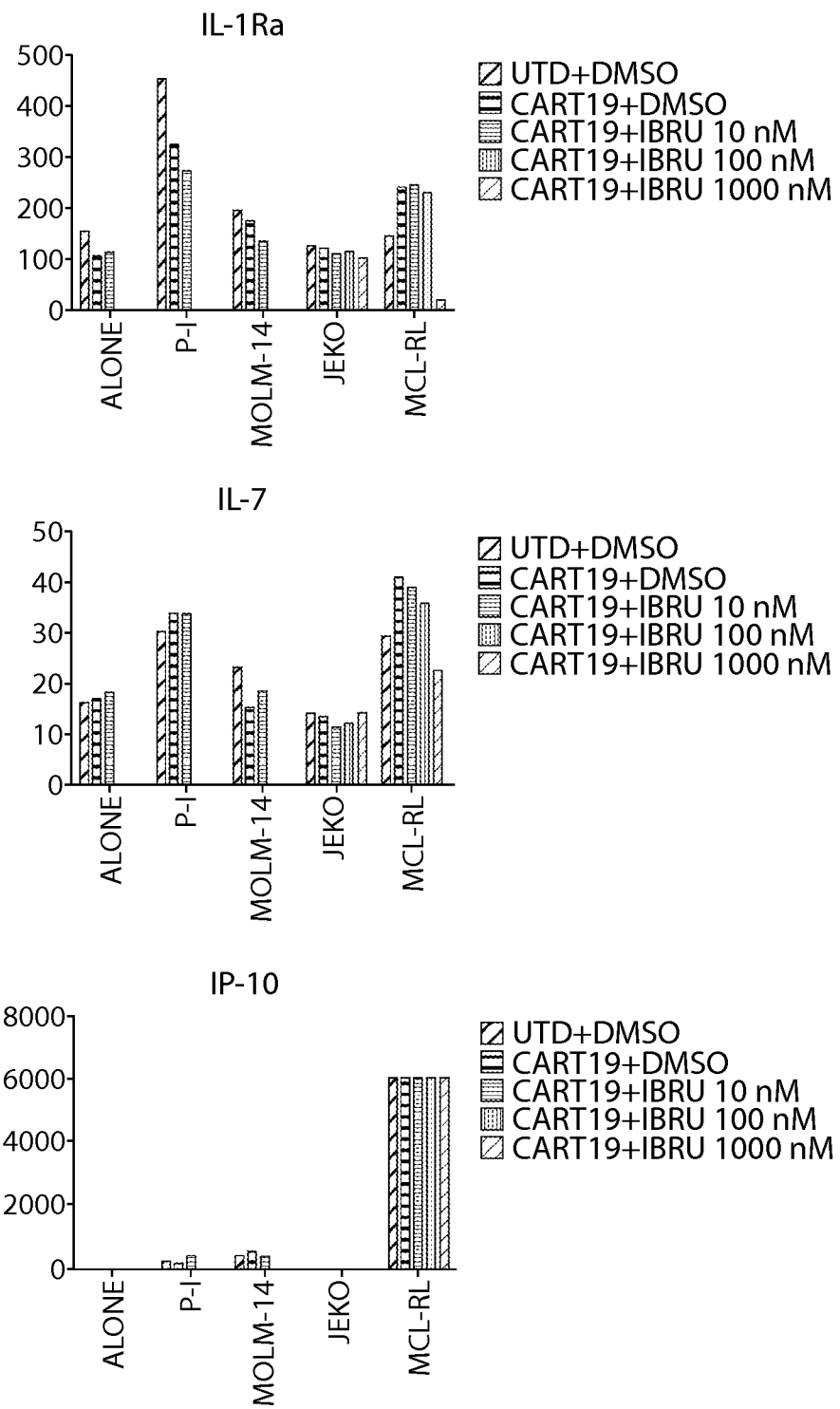
Figures 7, 15:
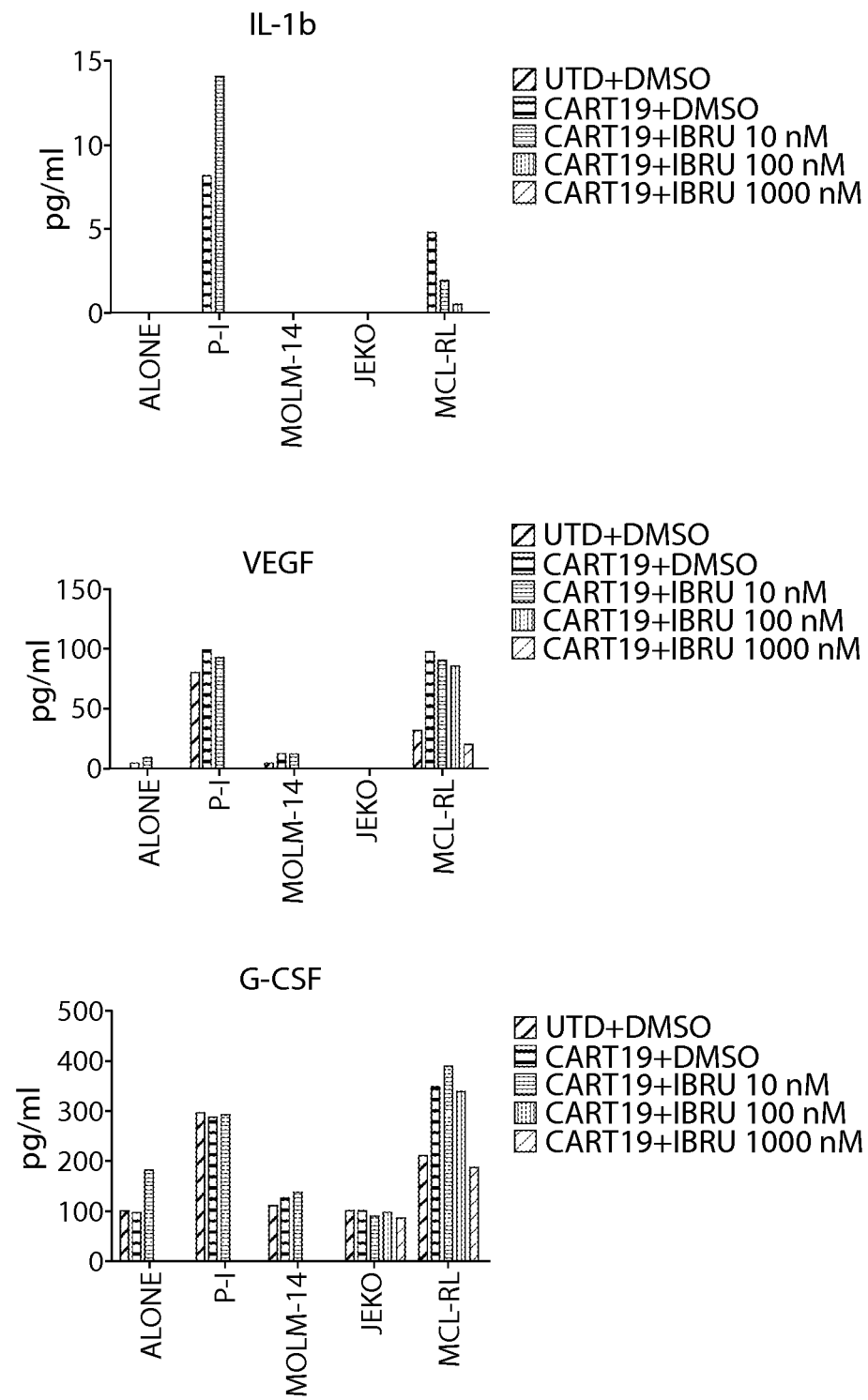
Figures 8, 15:
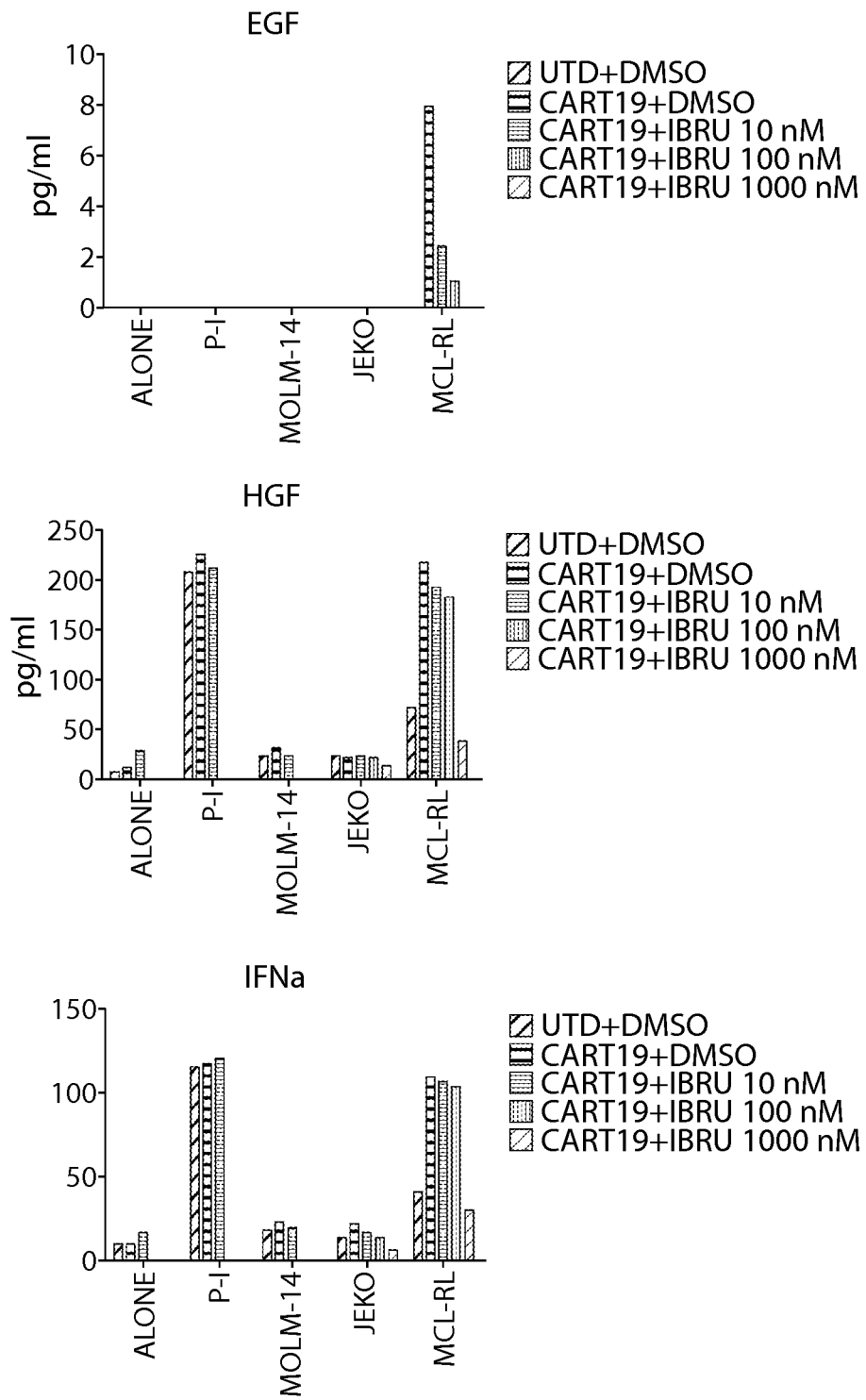
Figures 9, 15:
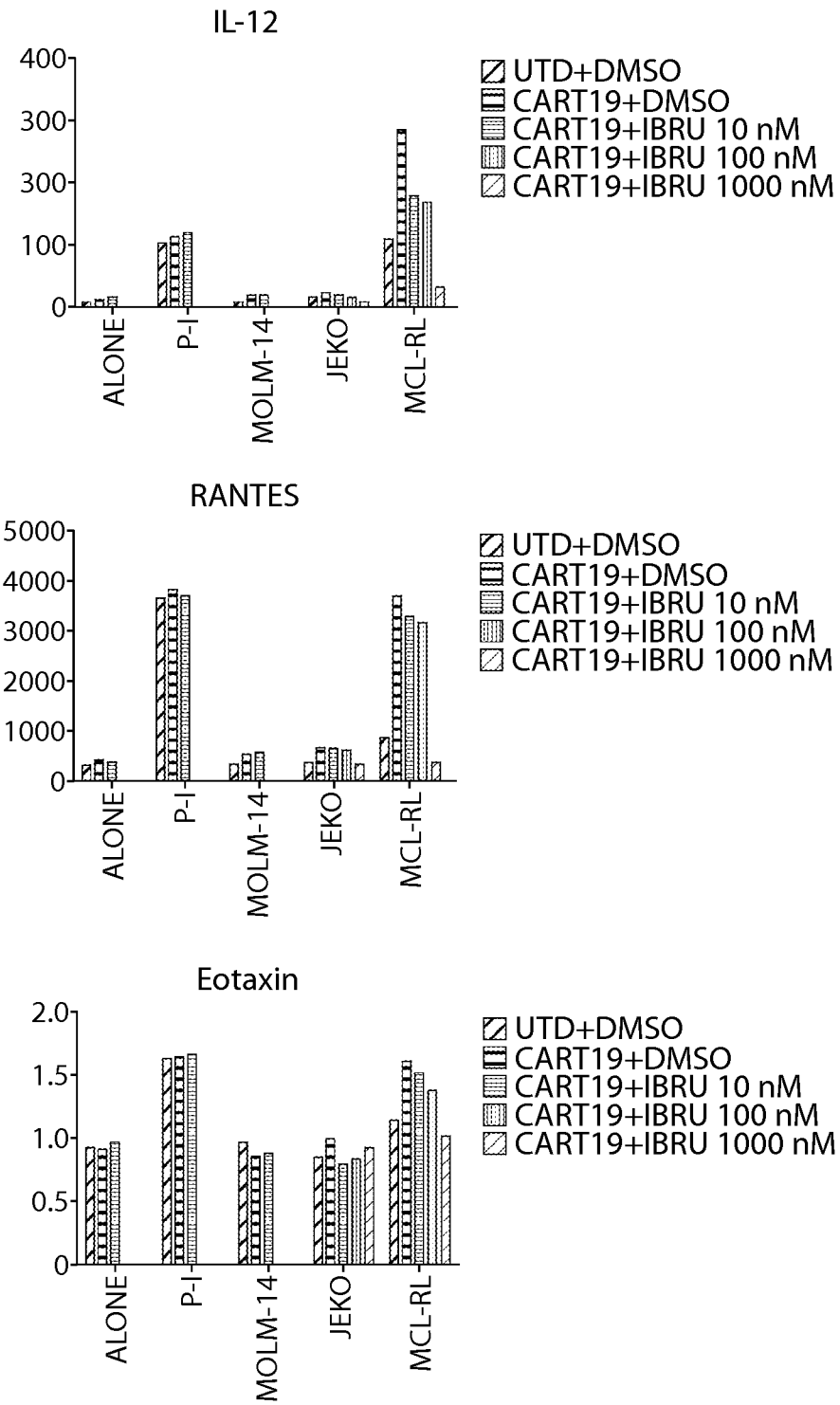
Figure 16A:
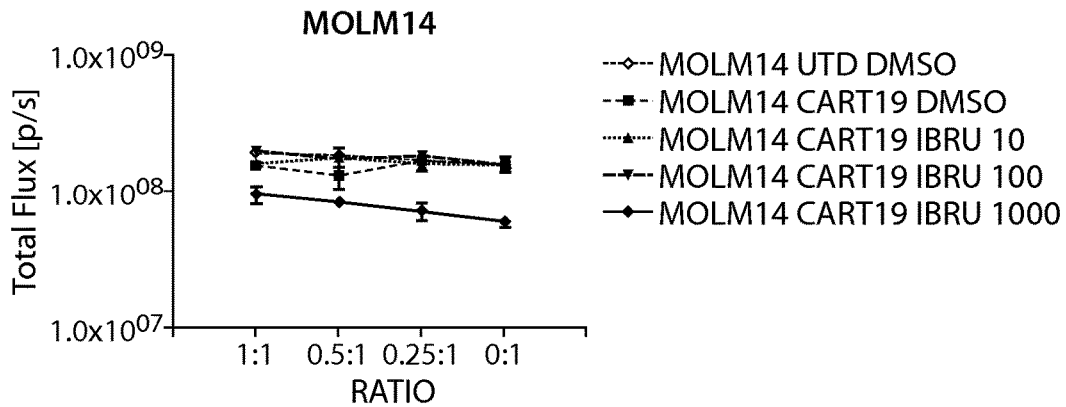
FIGS. 16A, 16B, 16C, 16D, 16E, and 16 F are graphs showing CART19 killing of tumor cells, MOLM14 (FIGS. 16A and 16D), JEKO (FIGS. 16B and 16E), and RL (FIGS. 16C and 16F), alone or in the presence of increasing concentrations of ibrutinib. Untransduced (UTD) or CART19 cells were incubated with tumor cells at varying ratios and the total flux of cells (FIGS. 16A, 16B, and 16C) and percentage of dead cells was assessed (16D, 16E, and 16F).
Figure 16B:
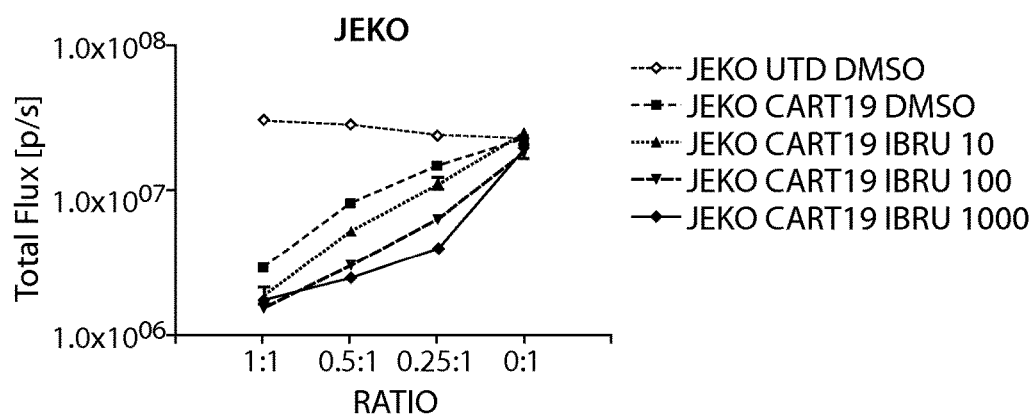
Figure 16C:
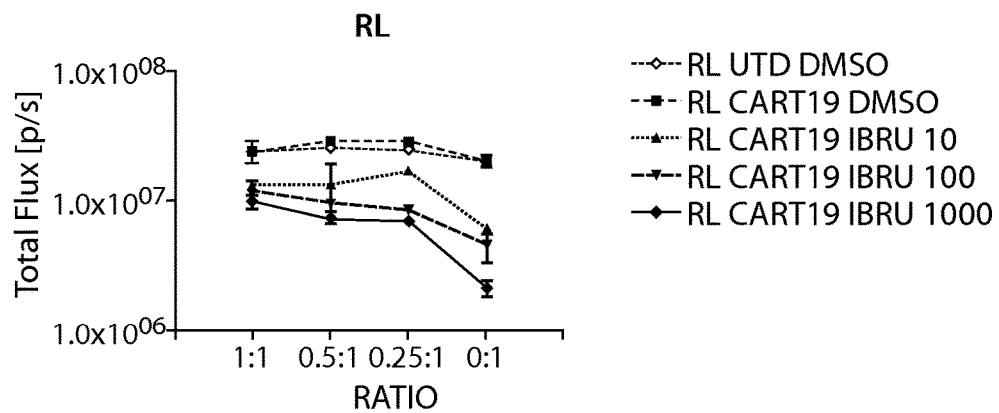
Figure 16D:
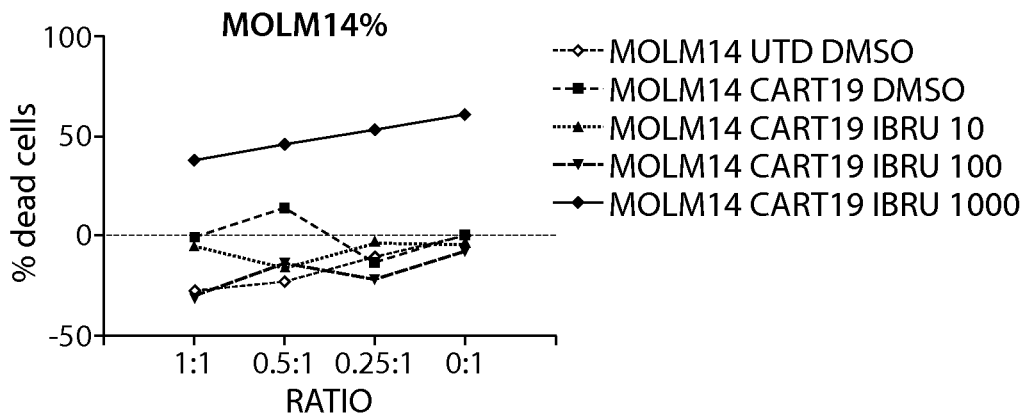
Figure 16E:
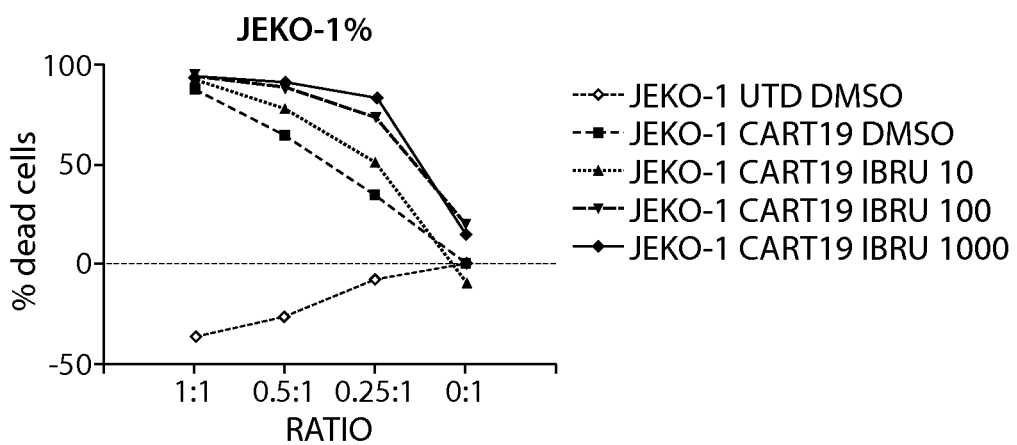
Figure 16F:
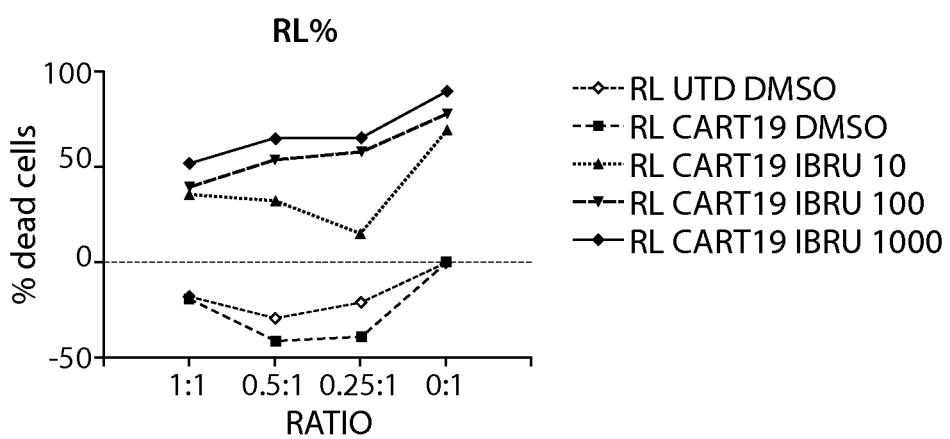

Cytokine secretion from CART19 cells after stimulation by tumor cells and in the presence of varying concentration of ibrutinib was analyzed by 30-plex LUMINEX assay. Cytokines secreted by $T_H1$ cells, such as IL-2, IFN-γ, and TNF-α, was assayed. Cytokines secreted by $T_H2$ cells, including IL-4, IL-5, IL-6, IL-10, IL-13, IL-15, IL-17, MIP1a, GM-CSF, MIP-1b, CP-1, IL-1Ra, IL-7, IP-10, IL-1b, VEGF, G-CSF, EGF, HGF, IFNa, IL-12, RANTES, Eotaxin, IL-2R, MIG, and IL-8, was assayed. As shown in FIG. 15-1 through 15-10, $T_H1$ and $T_H2$ cytokines were secreted by the CART19 T cells.

Figures 2, 10A:
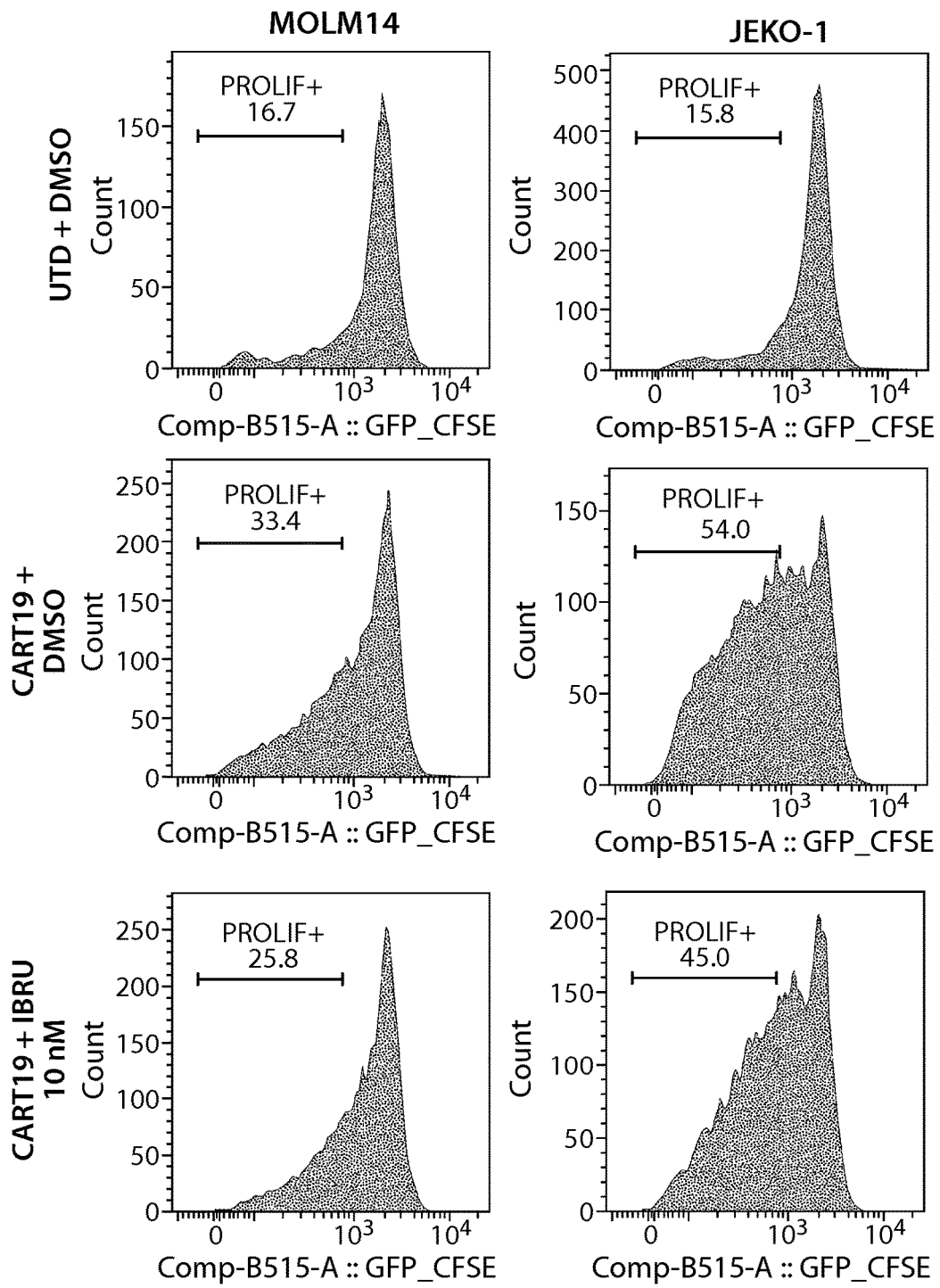
Figures 3, 10A:
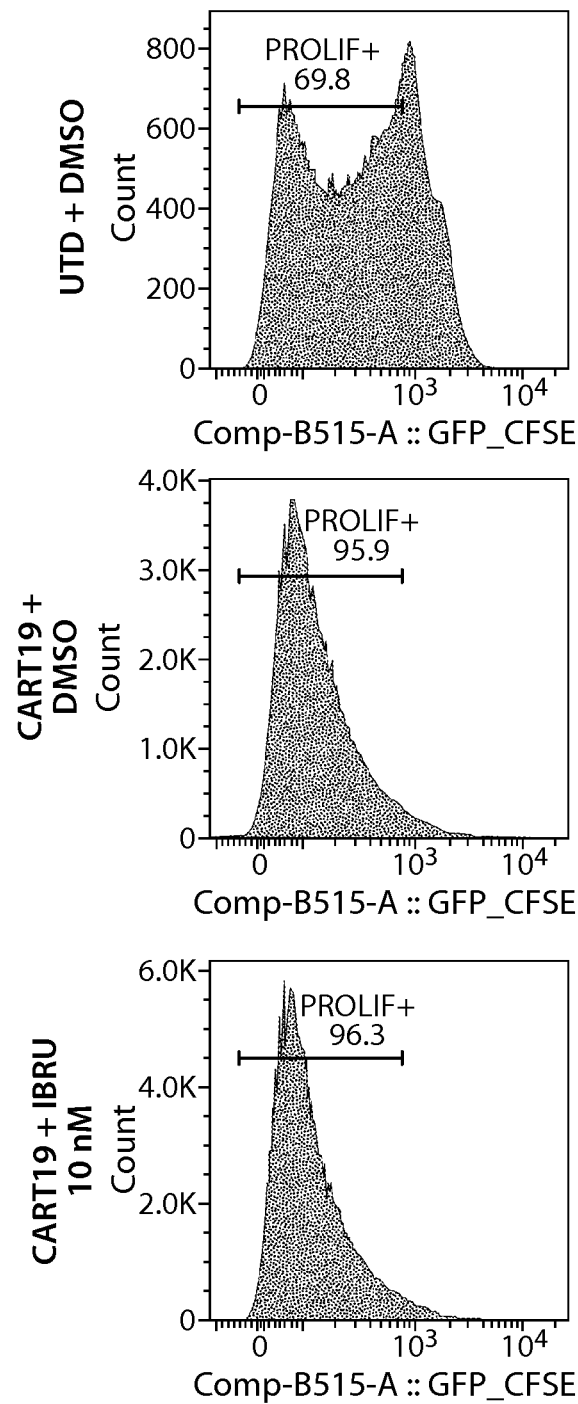
Figures 4, 10A:
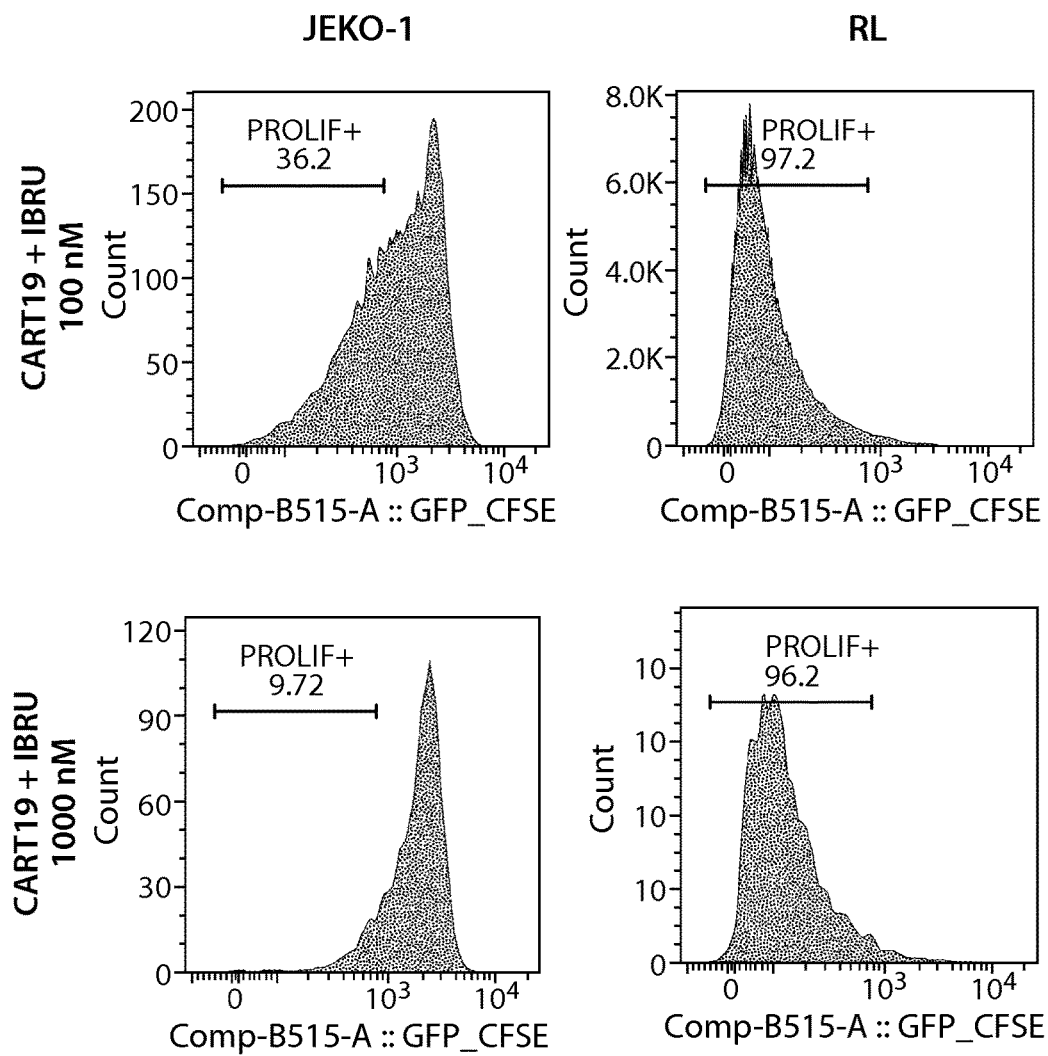
Figure 10B:
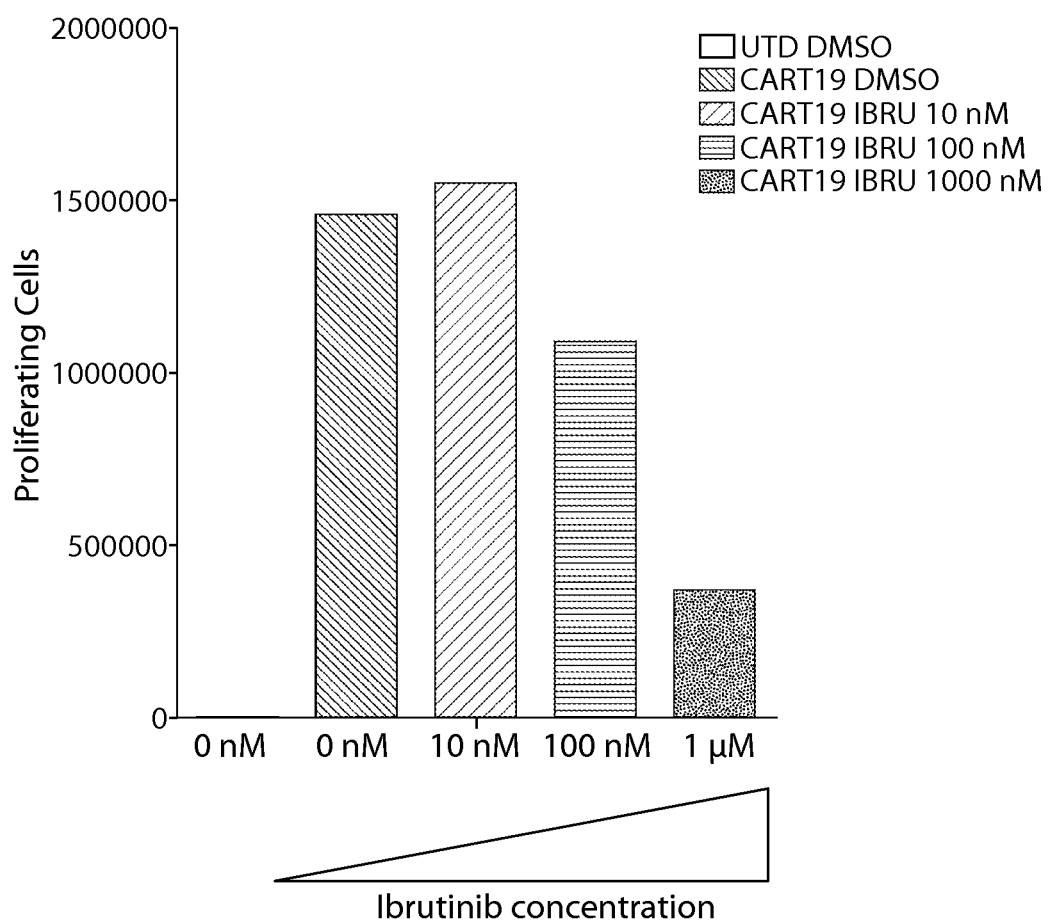
Figures 1, 11A:
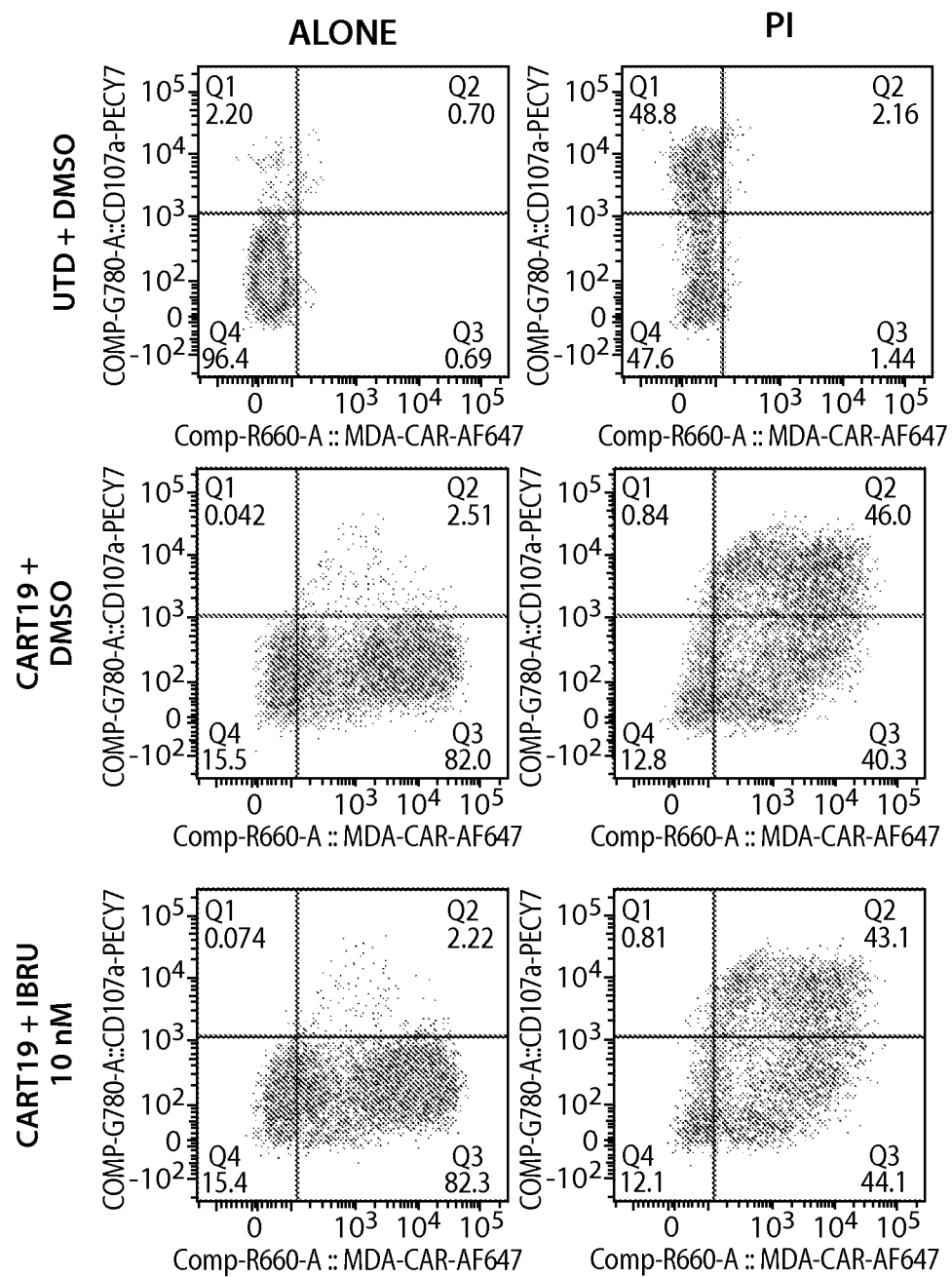
Figures 2, 11A:
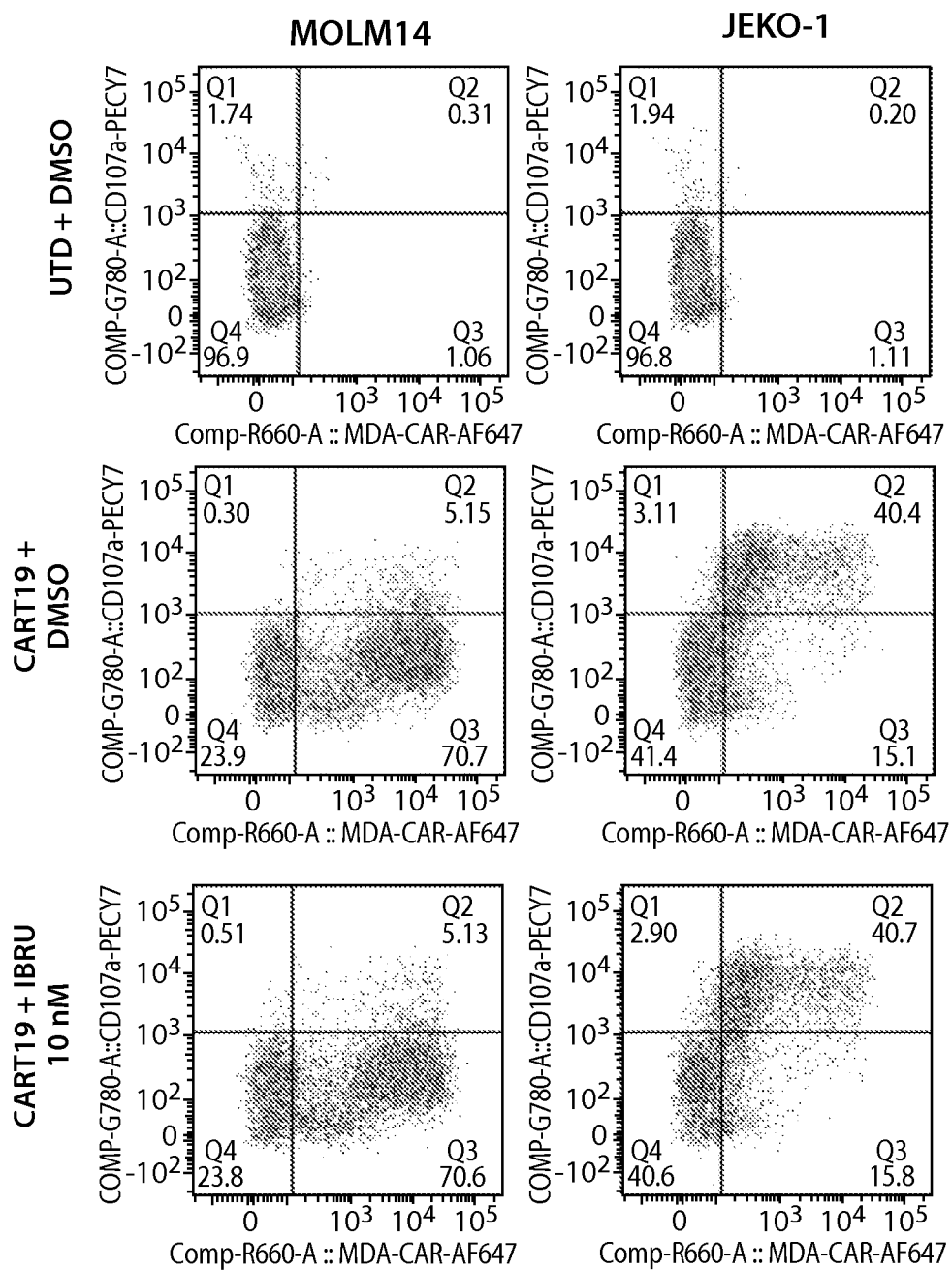
Figures 3, 11A:
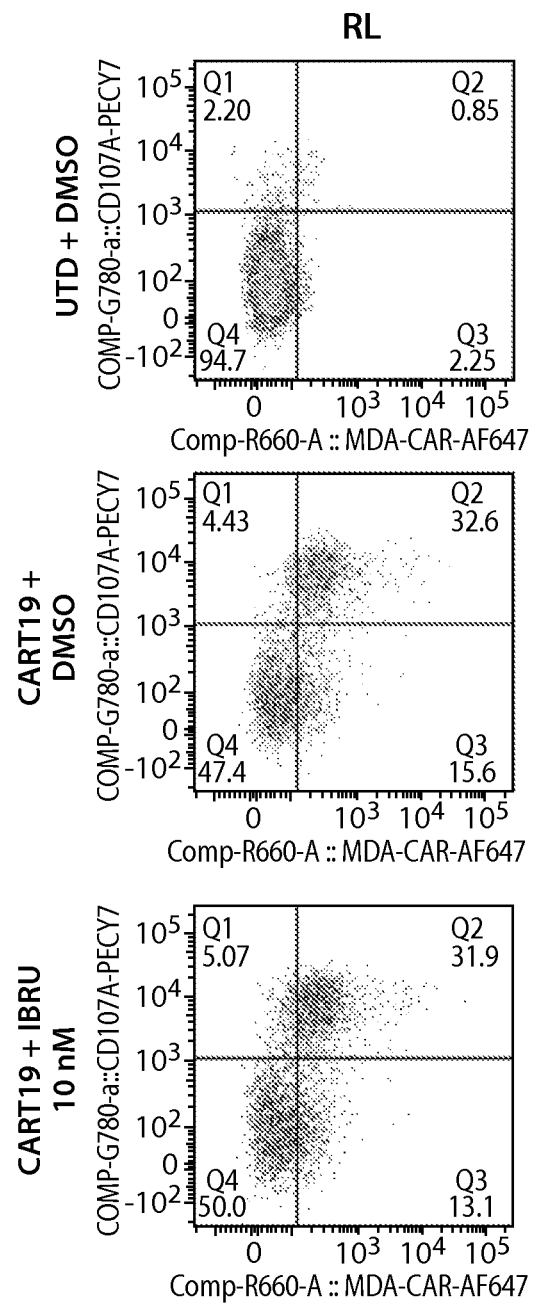
Figures 4, 11A:
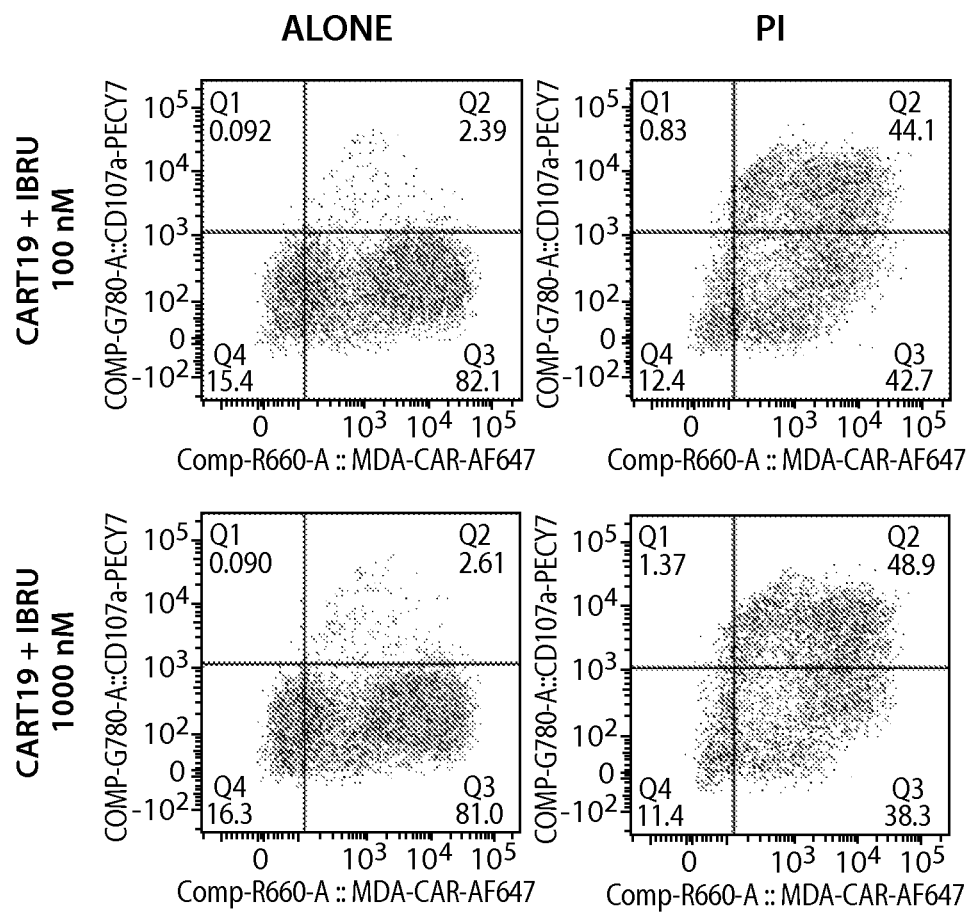
Figures 5, 11A:
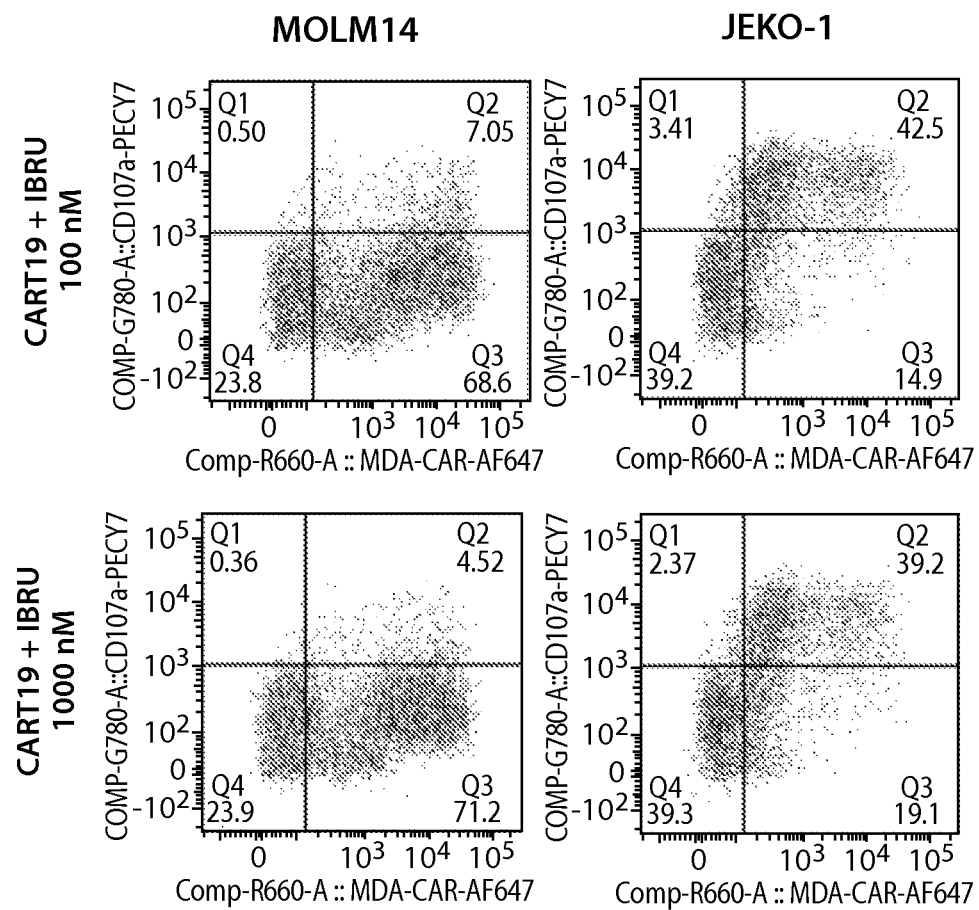
Figures 6, 11A:
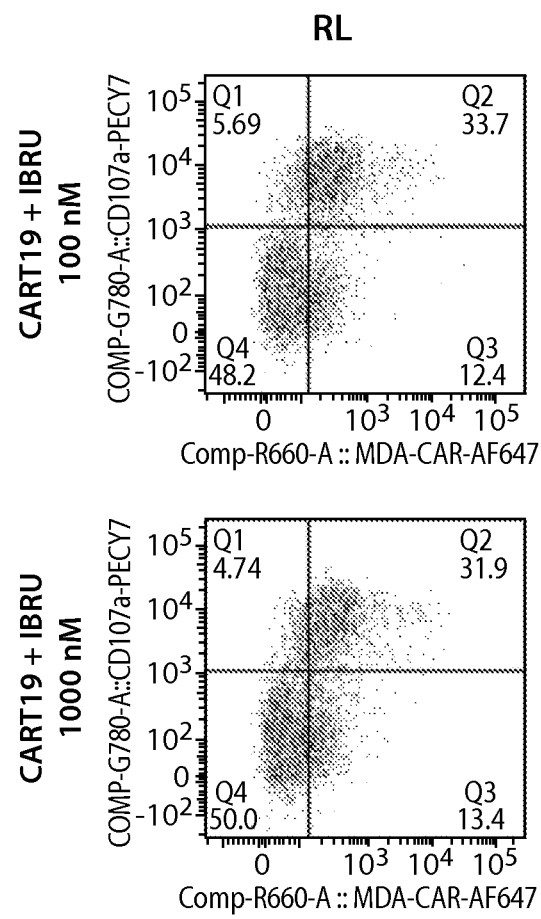
Figure 11B:
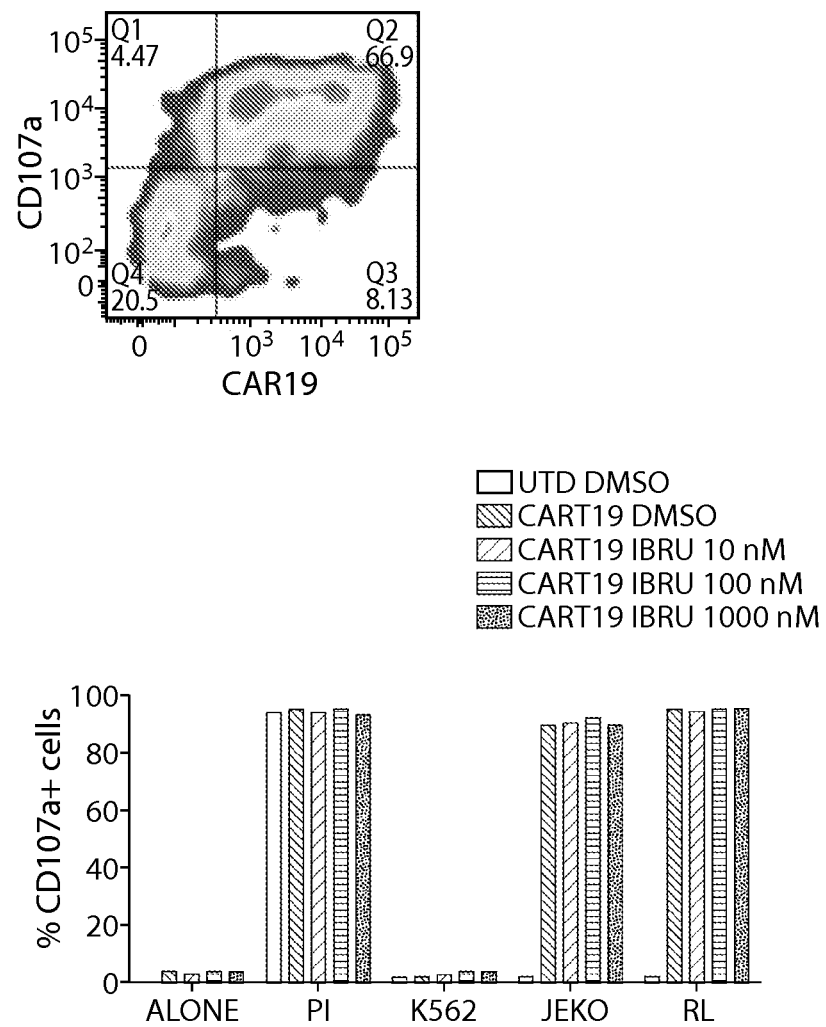
Figures 1, 12:
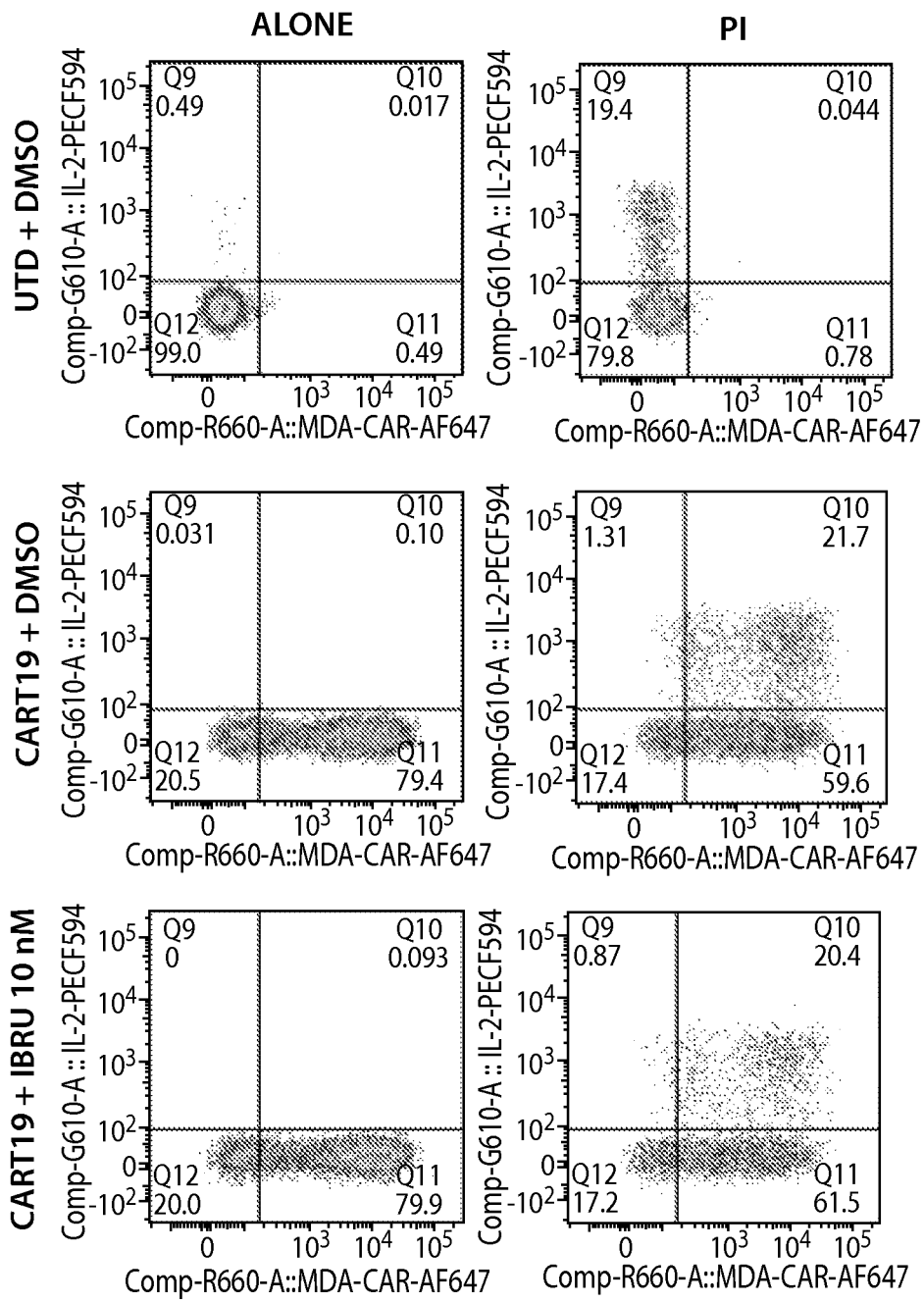
Figures 2, 12:
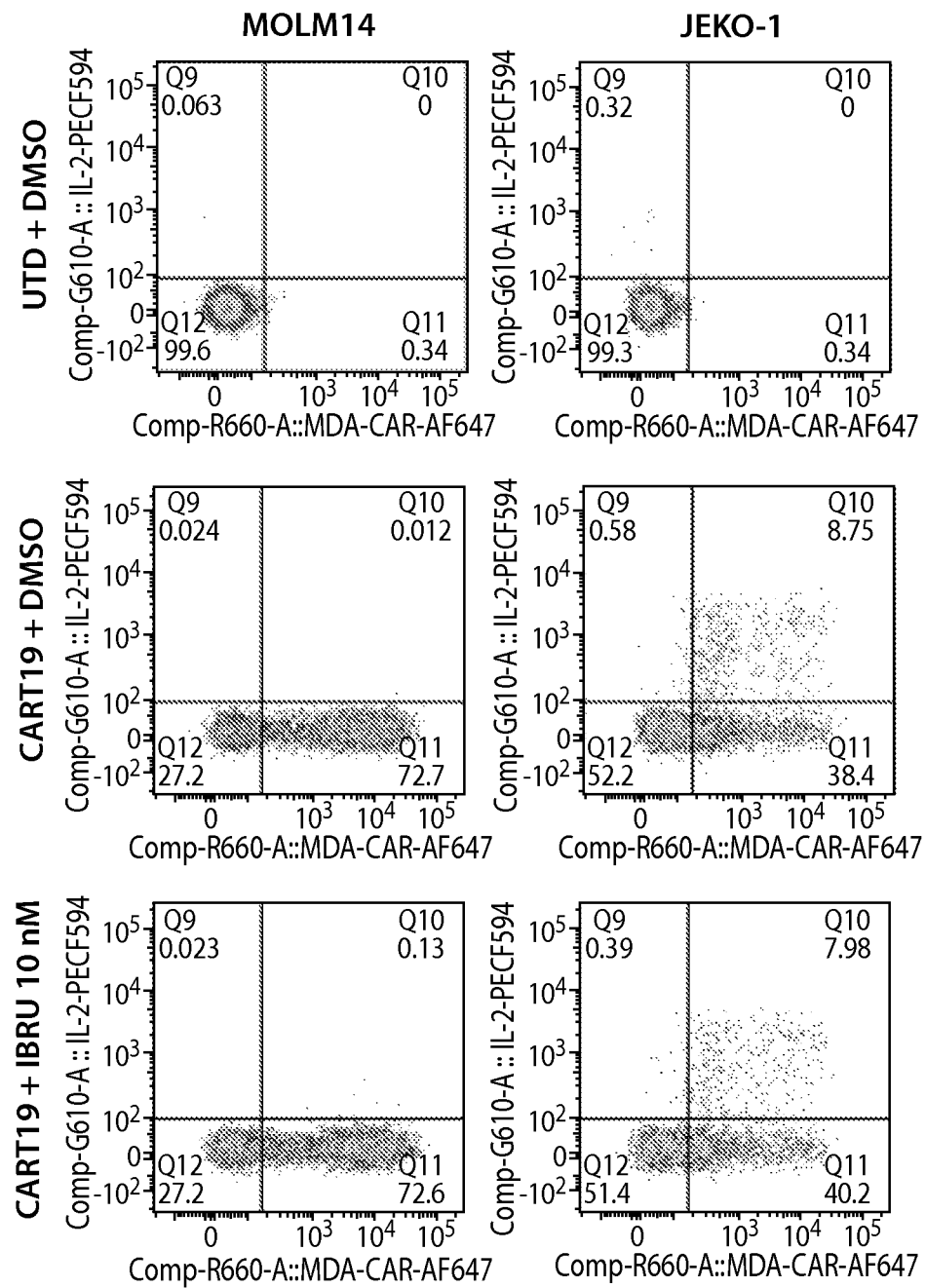
Figures 3, 12:
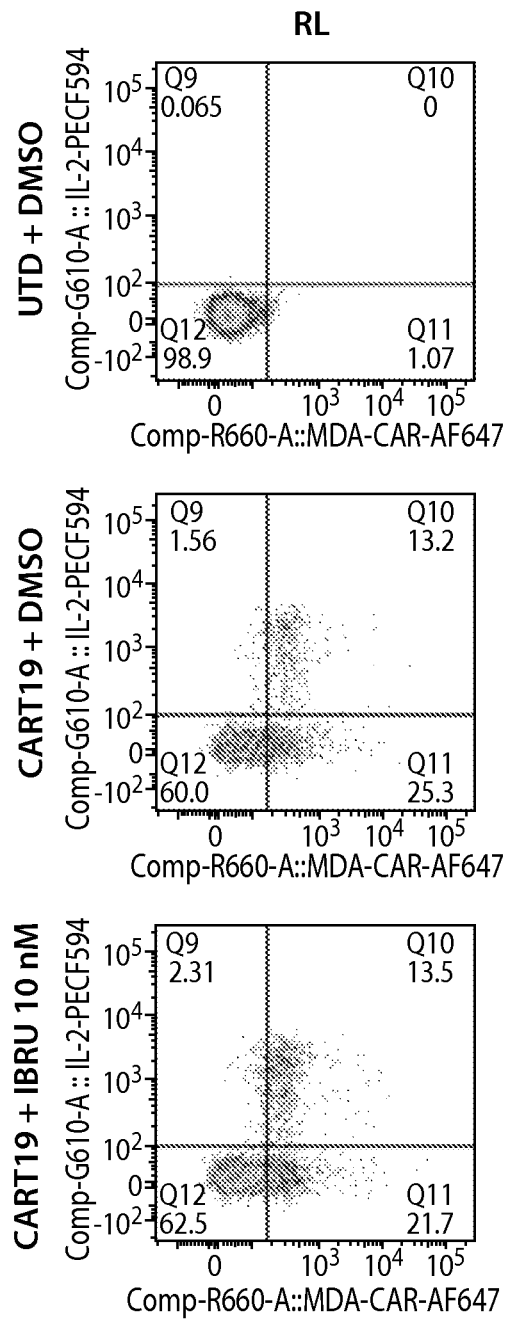
Figures 4, 12:
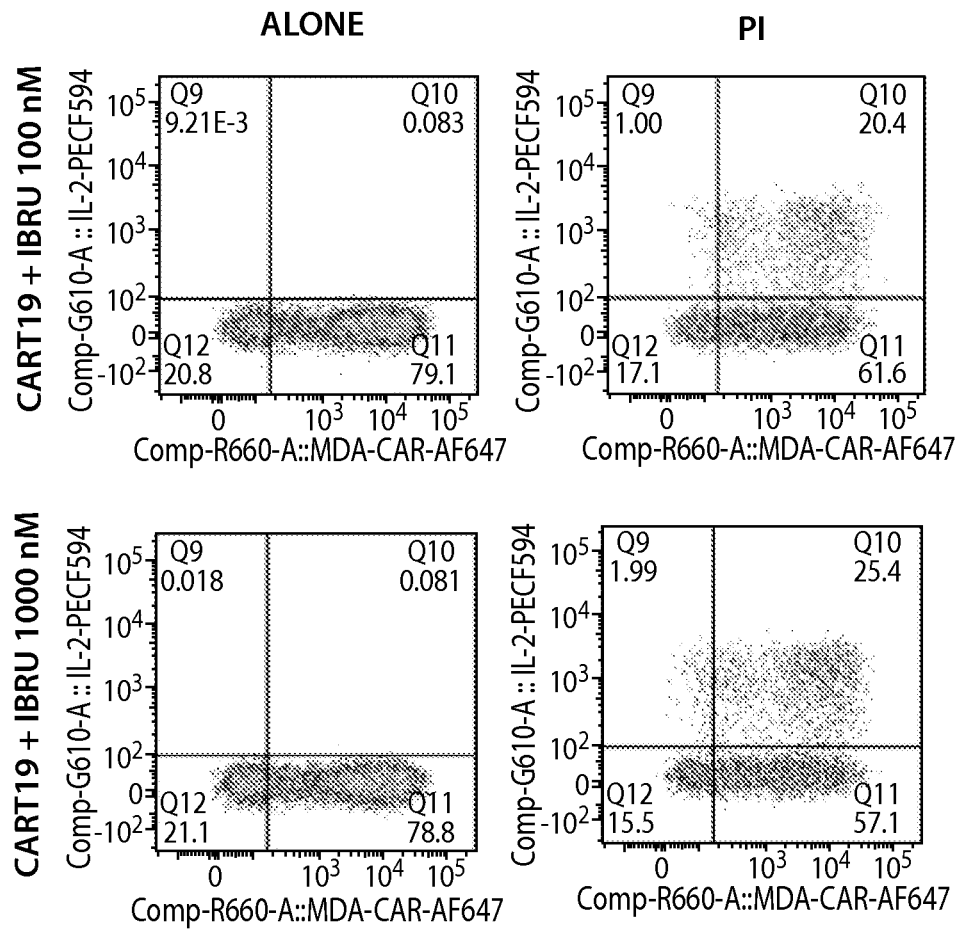
Figures 5, 12:
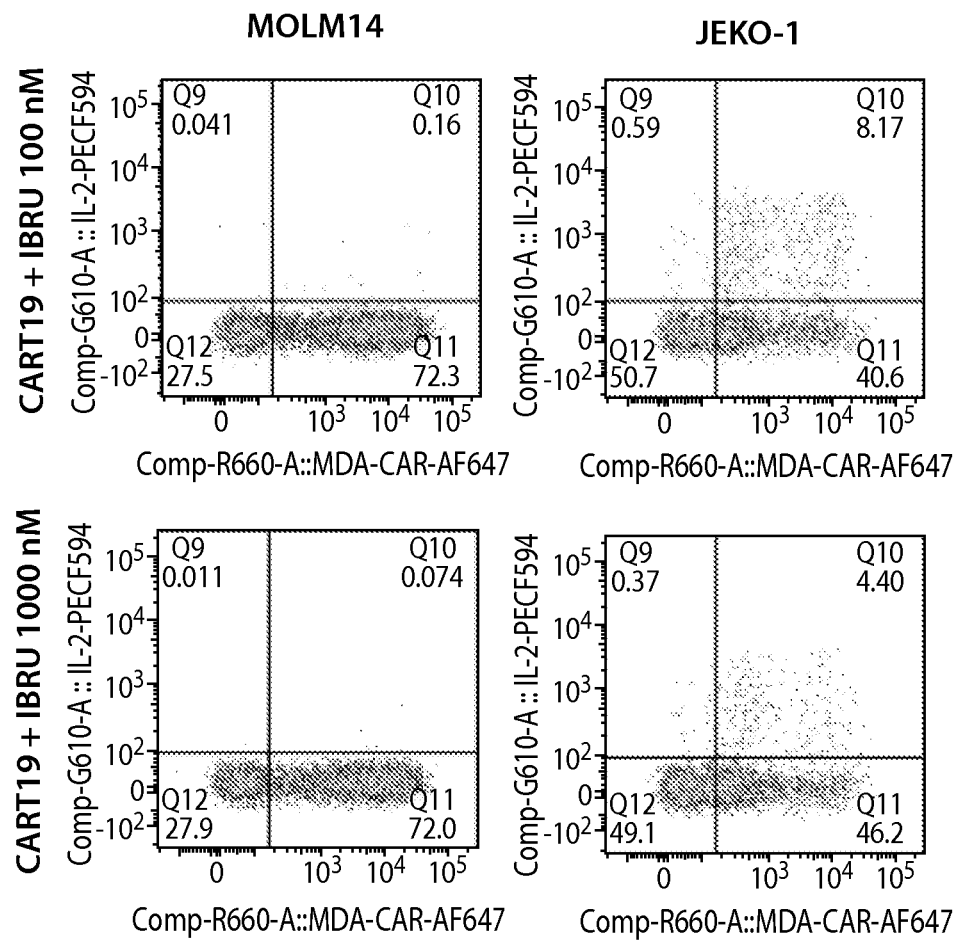
Figures 6, 12:
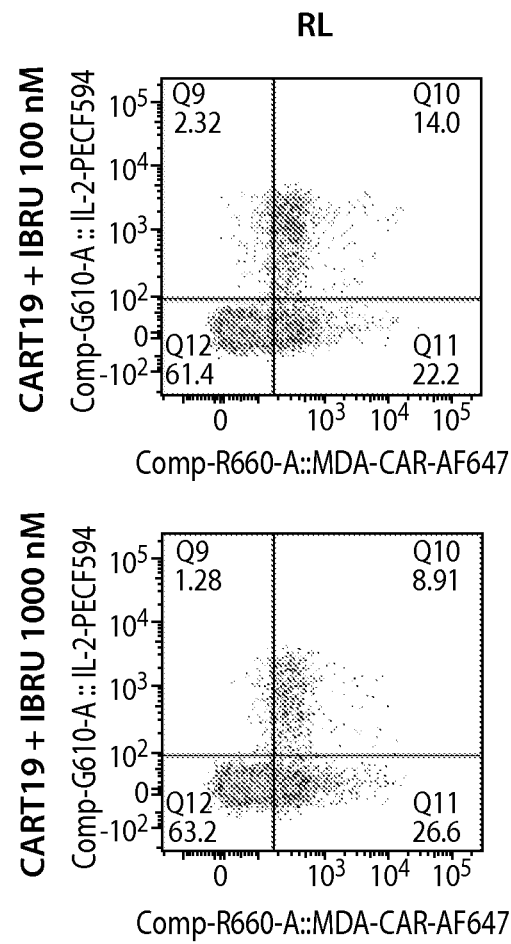
Figures 1, 13:
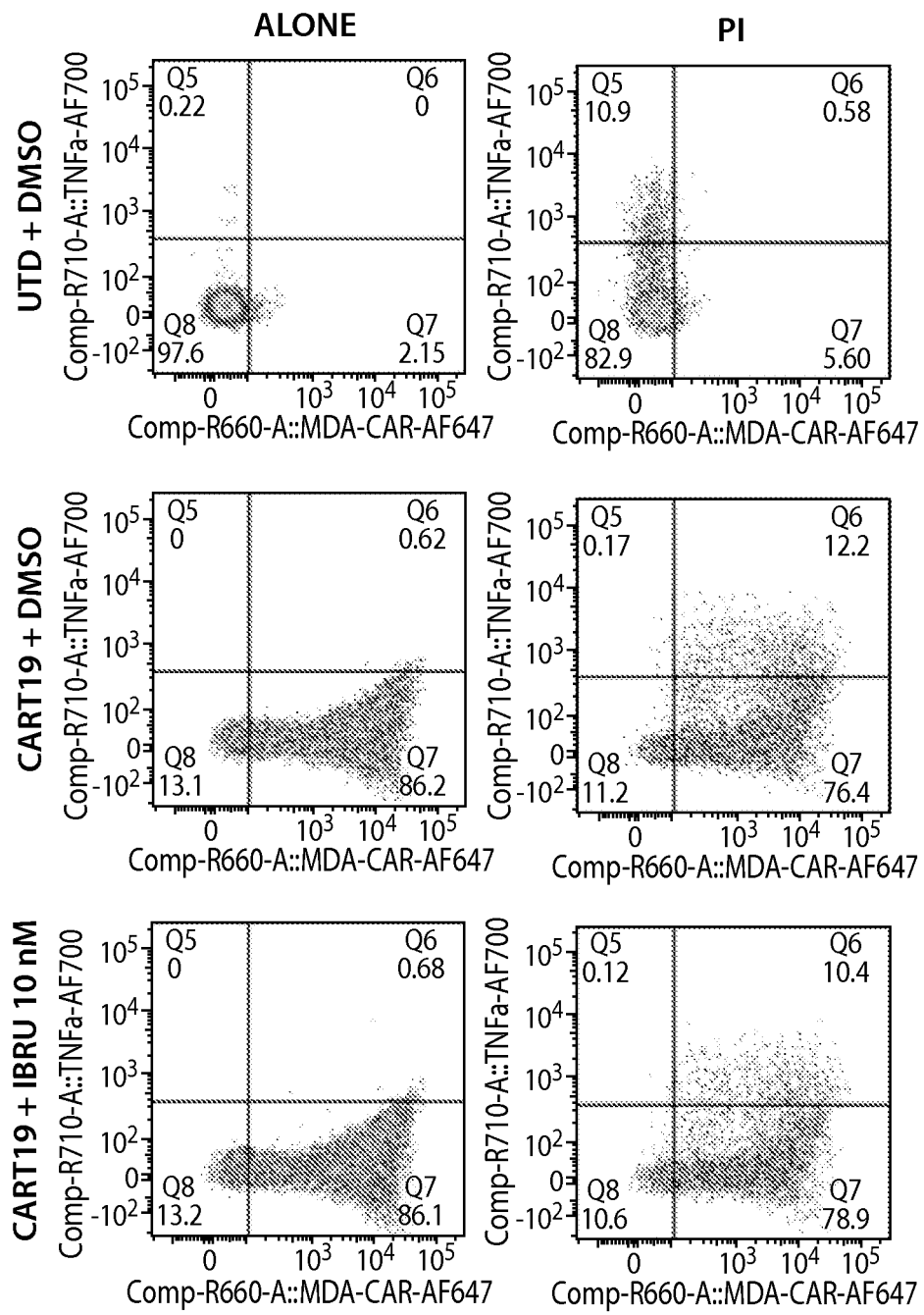
Figures 2, 13:
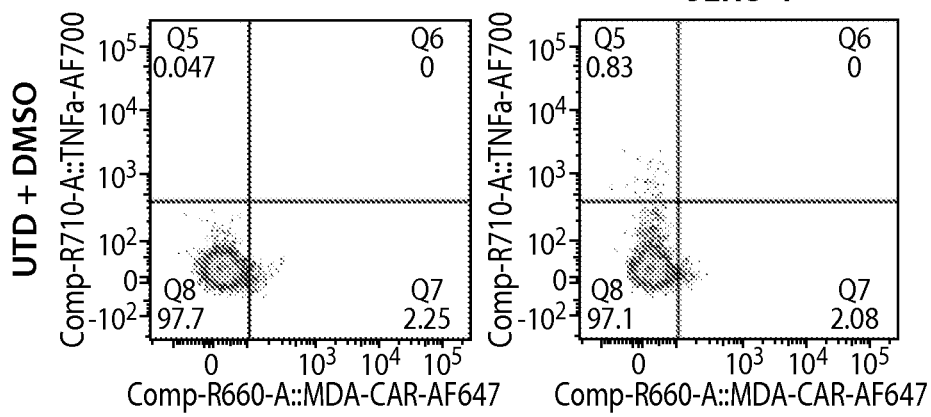
Figures 3, 13:
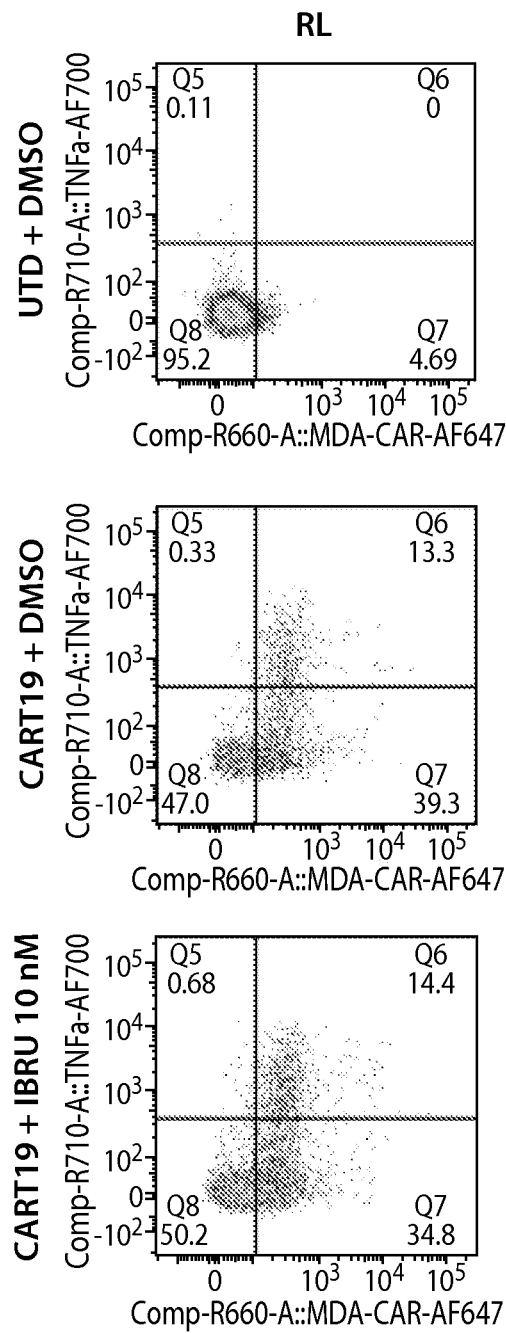
Figures 4, 13:
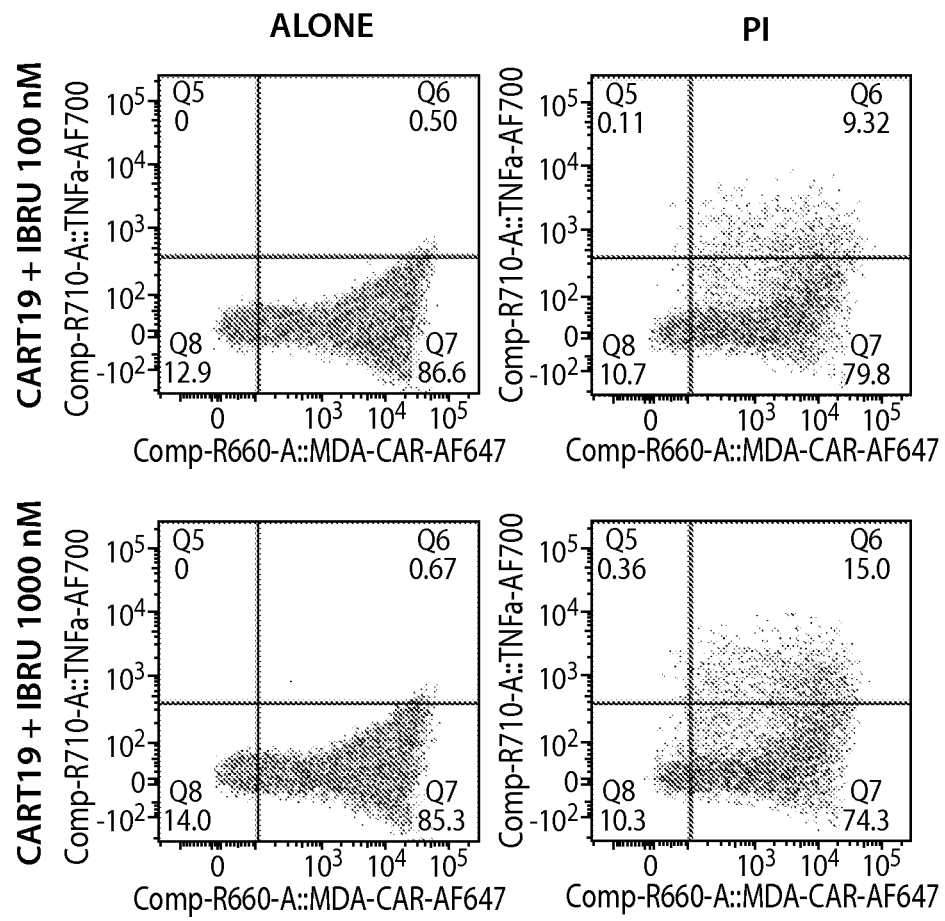
Figures 5, 13:
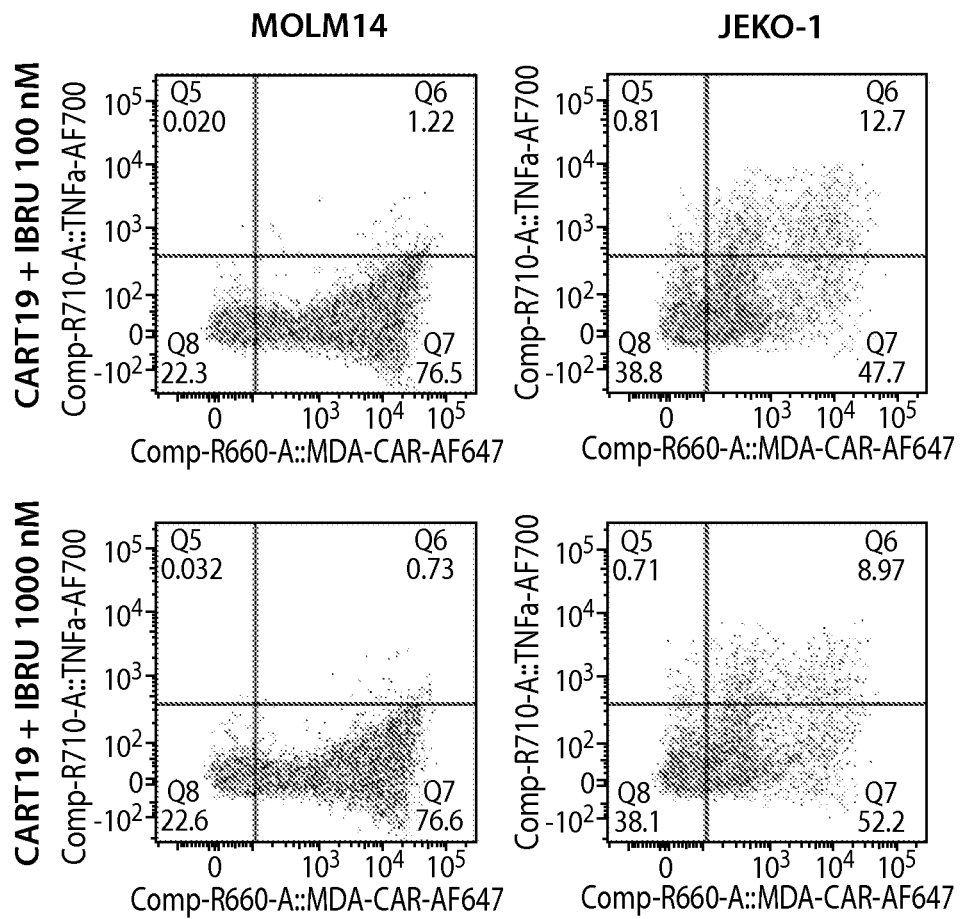
Figures 6, 13:
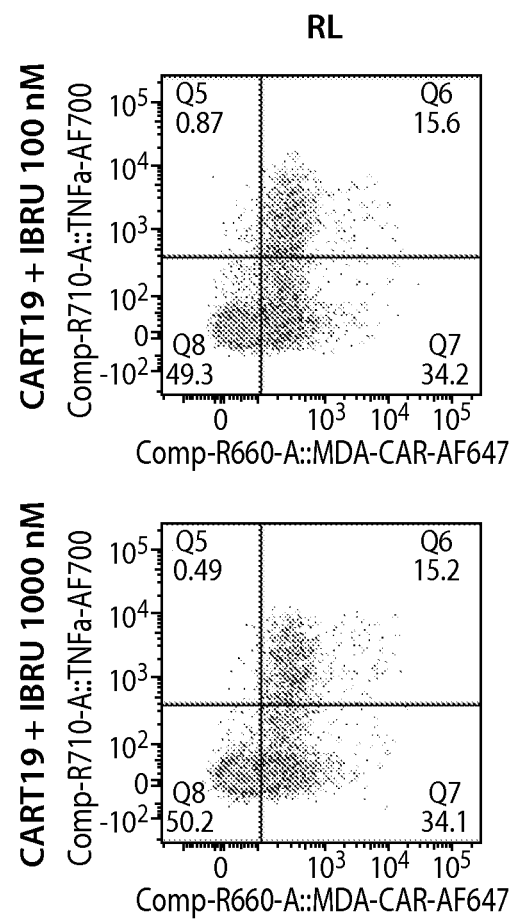
Figures 1, 14:
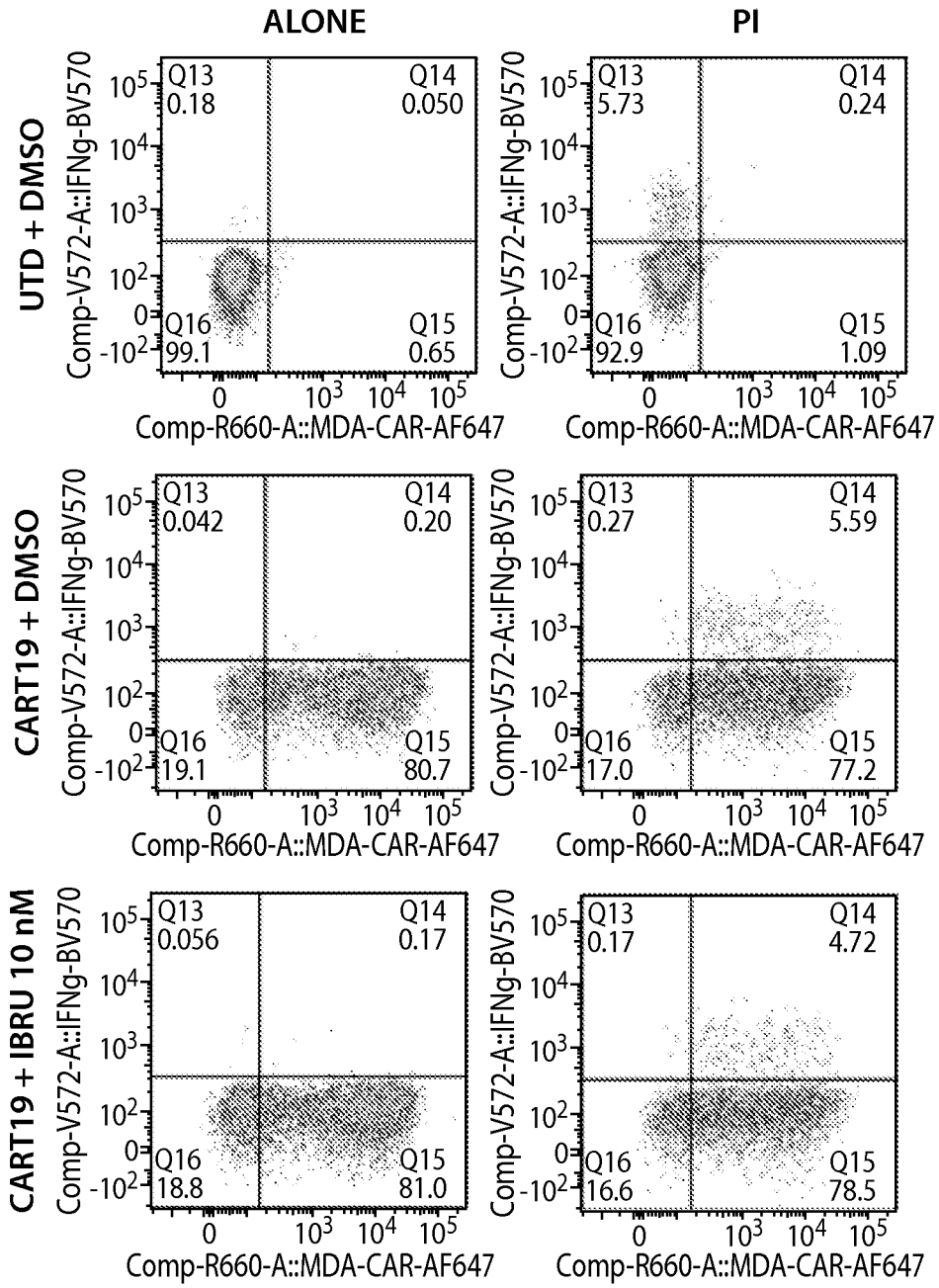
Figures 2, 14:
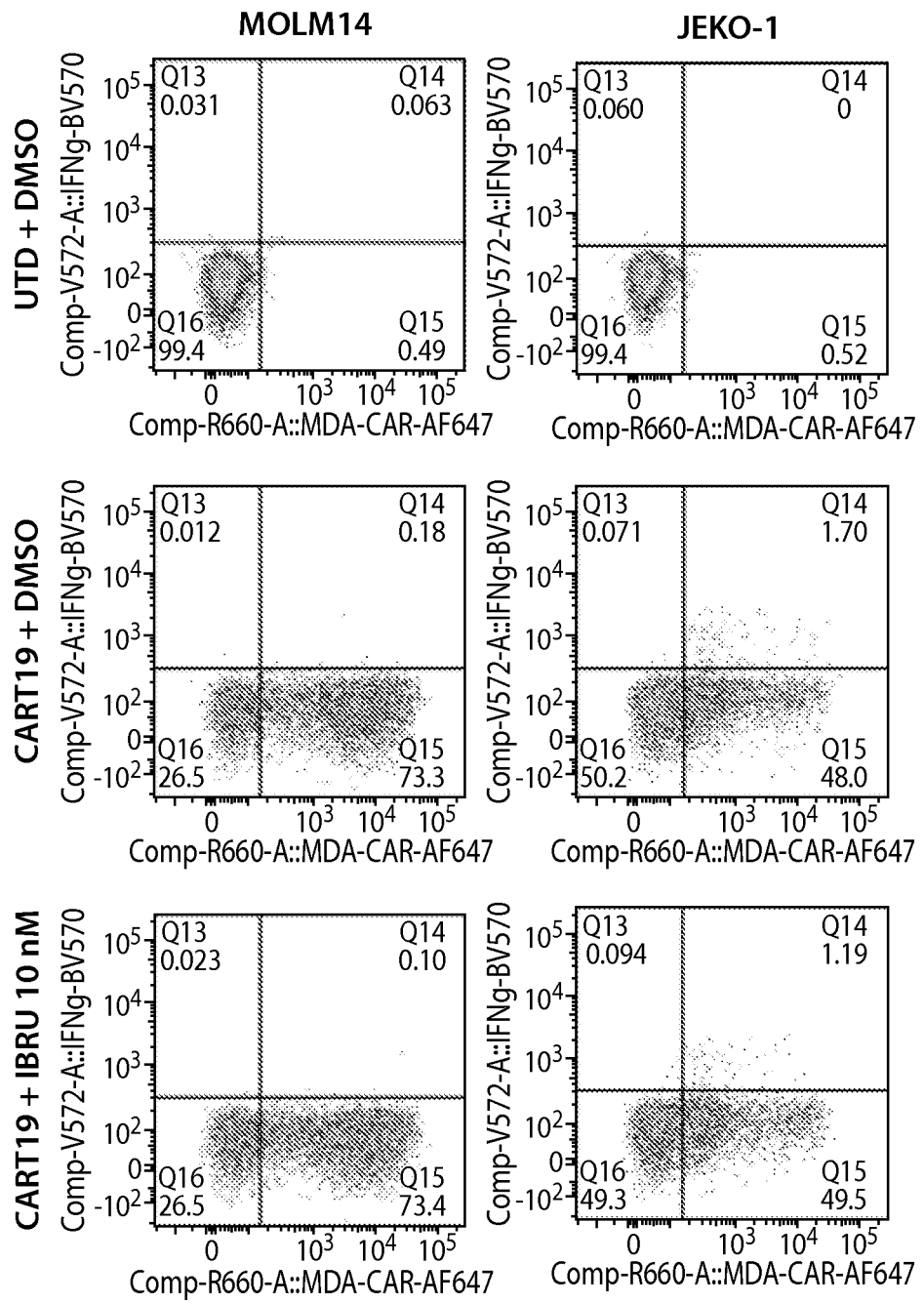
Figures 3, 14:
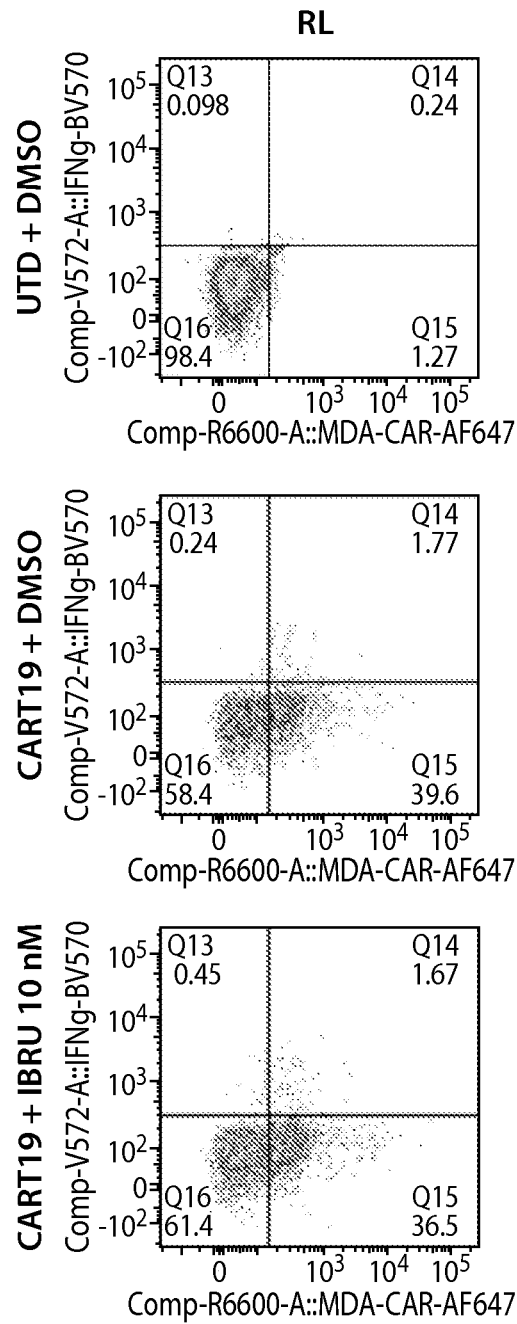
Figures 4, 14:
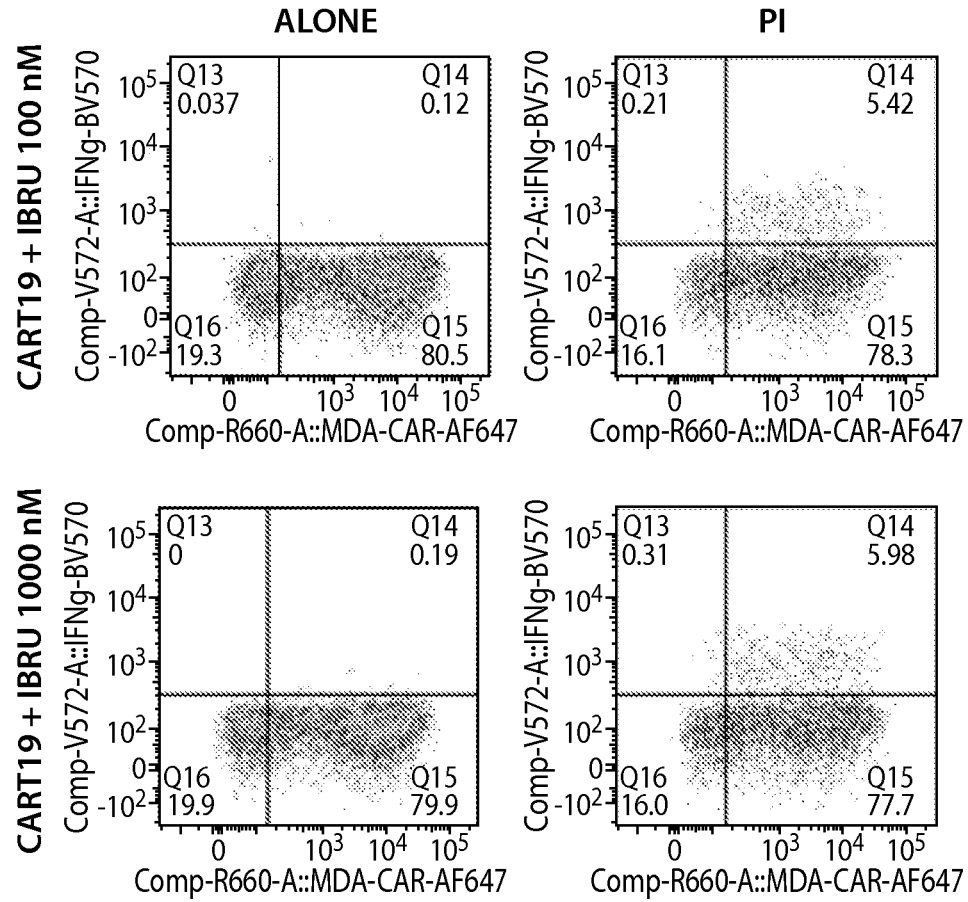
Figures 5, 14:
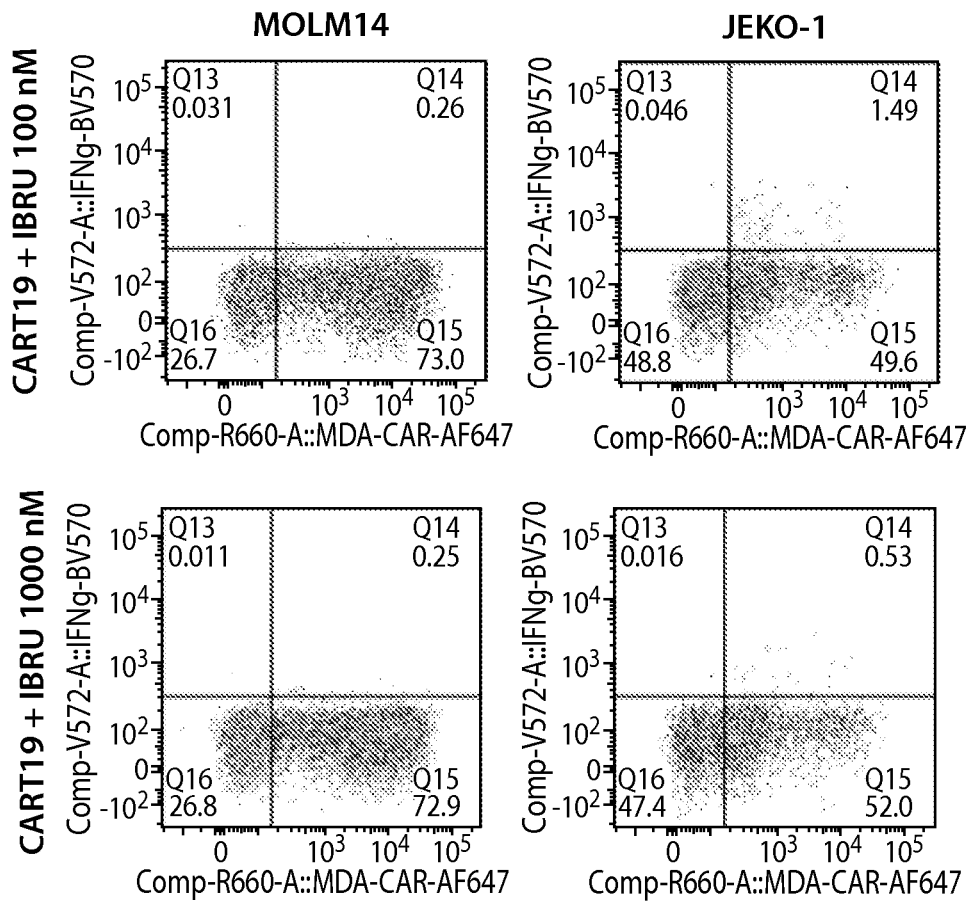
Figures 6, 14:
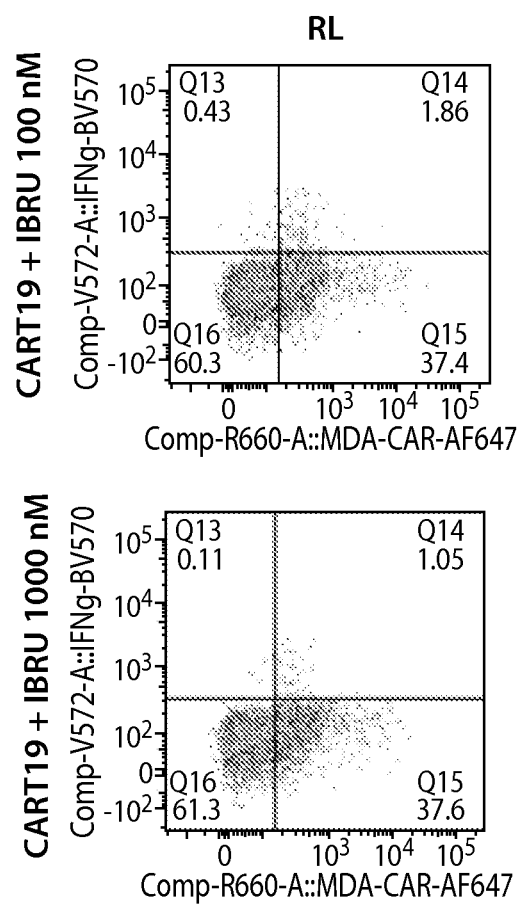
Figures 1, 54D:
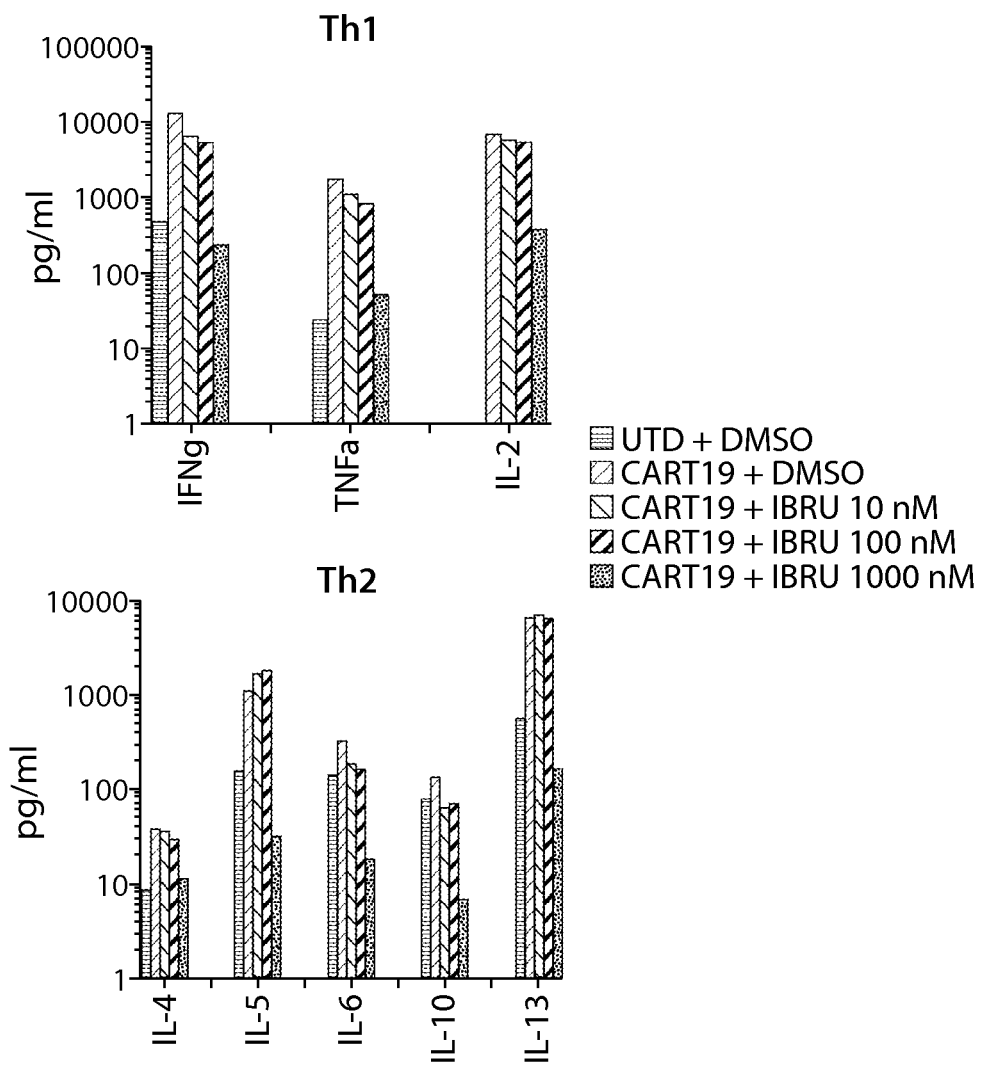
Figures 2, 54D:
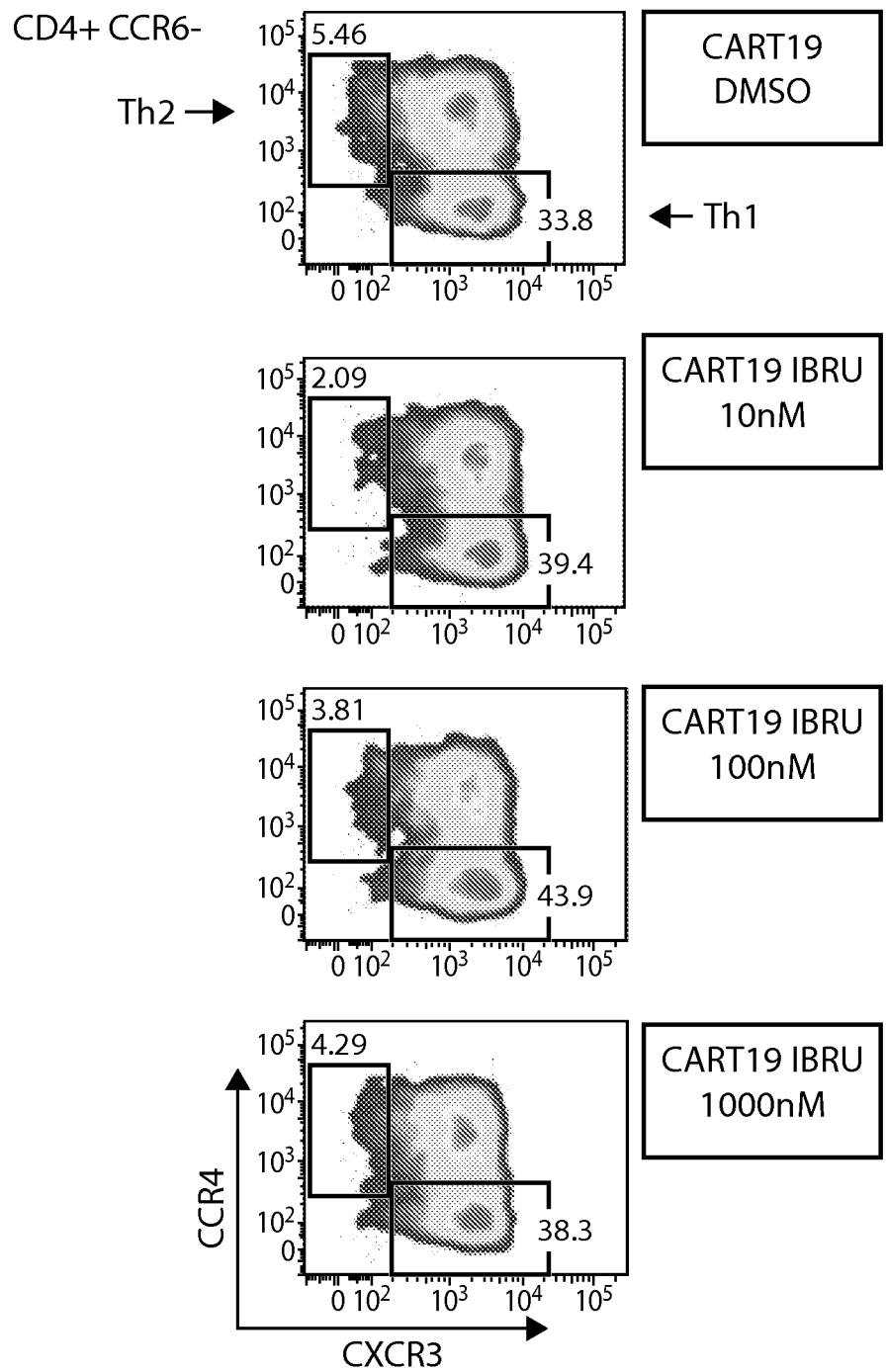

Also, experiments using two different techniques indicated that there were no differences in Th1/Th2 polarization between ibrutinib-exposed and ibrutinib-unexposed CART19 cells (FIGS. 54D-1 and 54D-2).

Figure 54E:
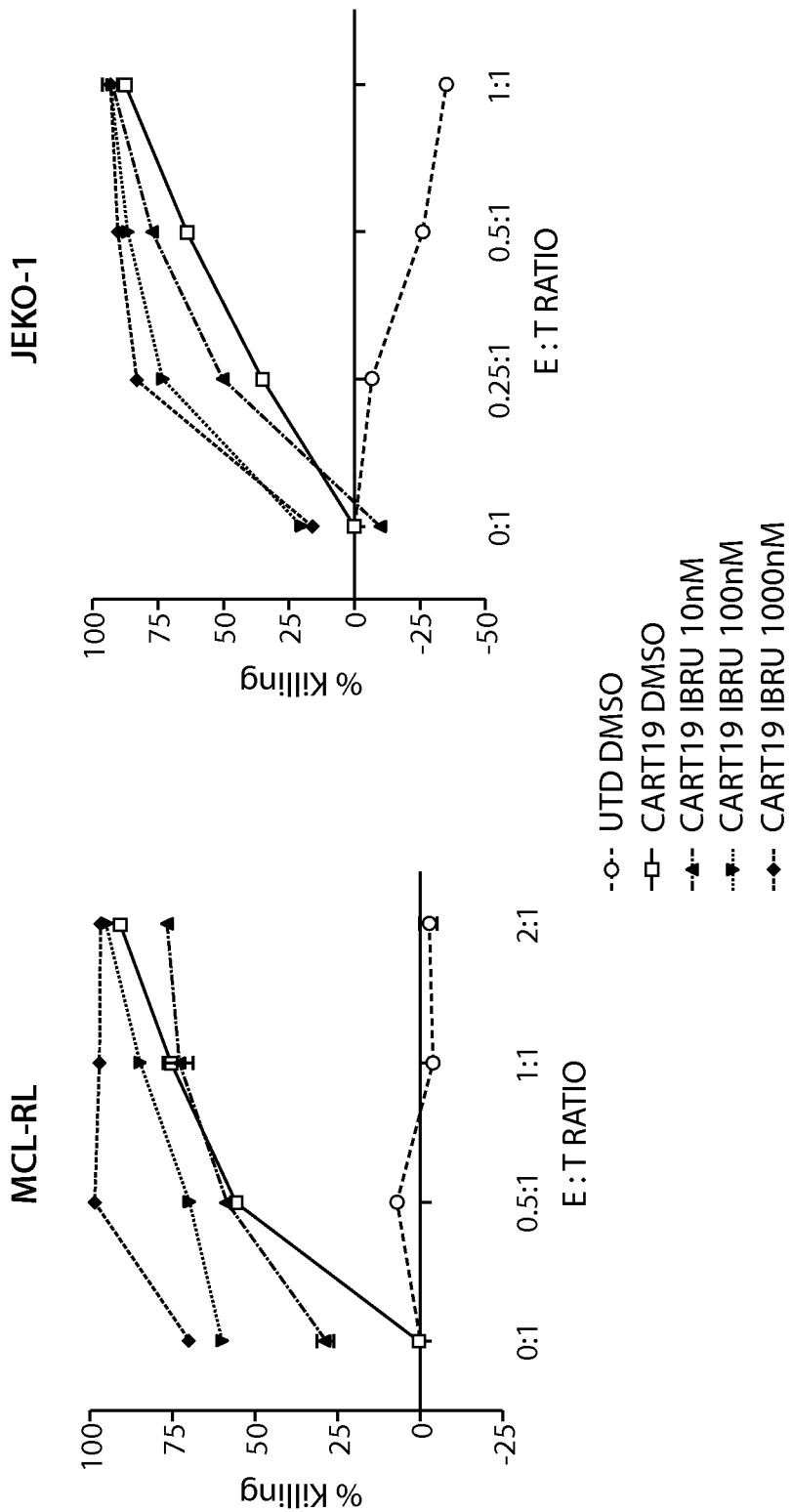
FIG. 54E is a set of graphs showing the percentage killing by CART19 cells of various MCL cell lines when combined with different concentrations of ibrutinib.
Figure 54F:
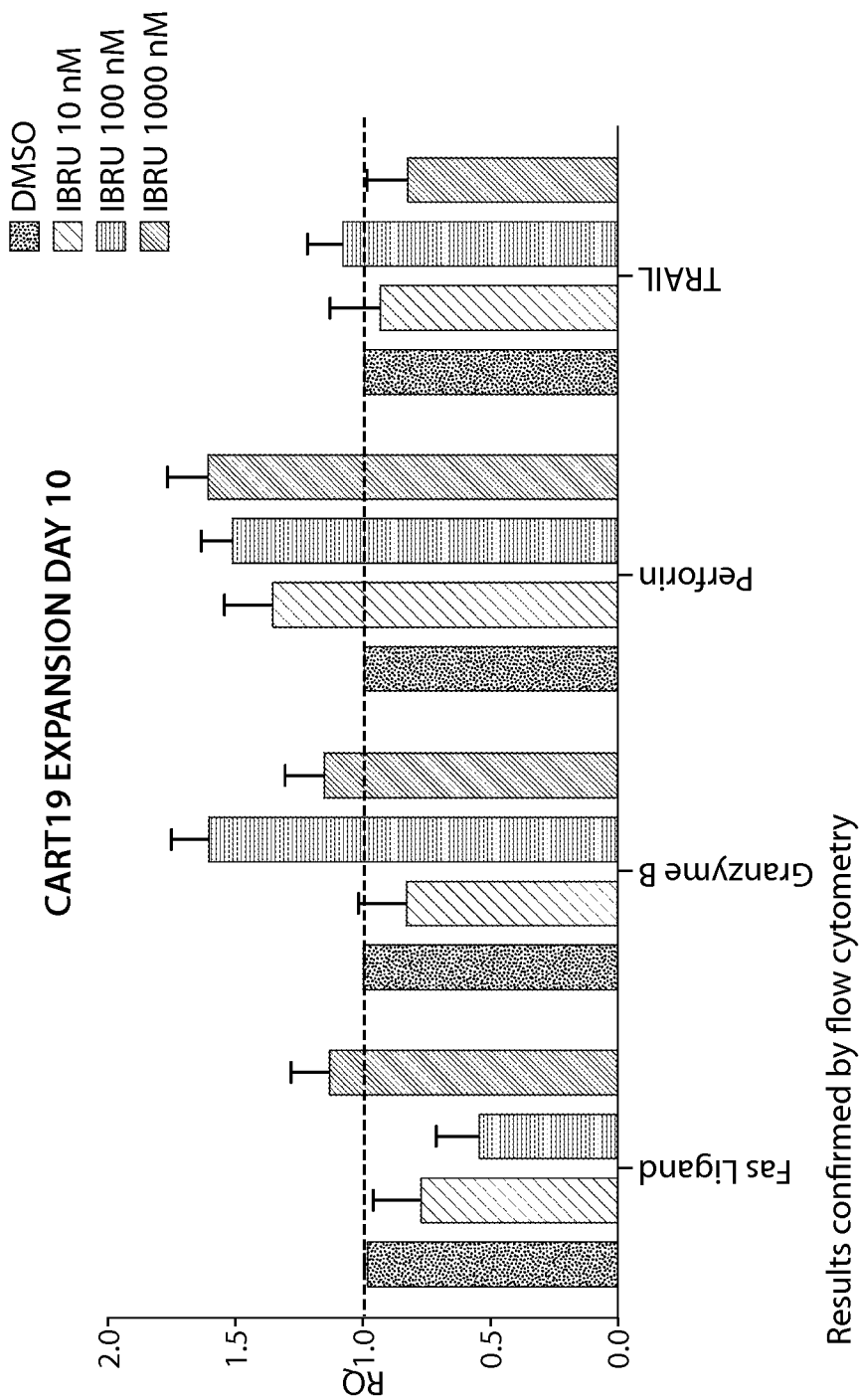
FIG. 54F is a bar graph showing the expression of various markers of intrinsic cytotoxic function of CART19 cells when combined with various concentrations of ibrutinib.

Killing of MCL cells by CART19 cells was augmented in the presence of ibrutinib, suggesting an at least additive effect from the combination (FIG. 54E). However, intrinsic cytotoxic function of CART19 cells was not augmented in the presence of ibrutinib. (FIG. 54F).

Figure 17A:
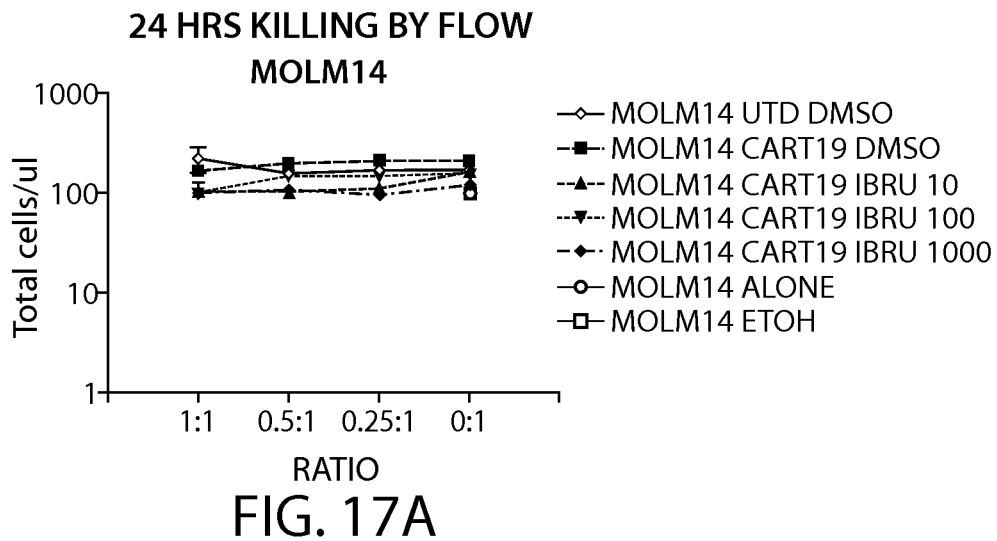
FIGS. 17A, 17B, and 17C are graphic representations of CART19 killing of tumor cells after 24 hours as measured by flow cytometry to count the total number of cells. Tumor cell lines MOLM14 (FIG. 17A), JEKO (FIG. 17B), and RL (FIG. 17C) were incubated with untransduced (UTD) or CART19 cells alone (ALONE), or in combination with varying concentrations of ibrutinib.
Figure 17B:
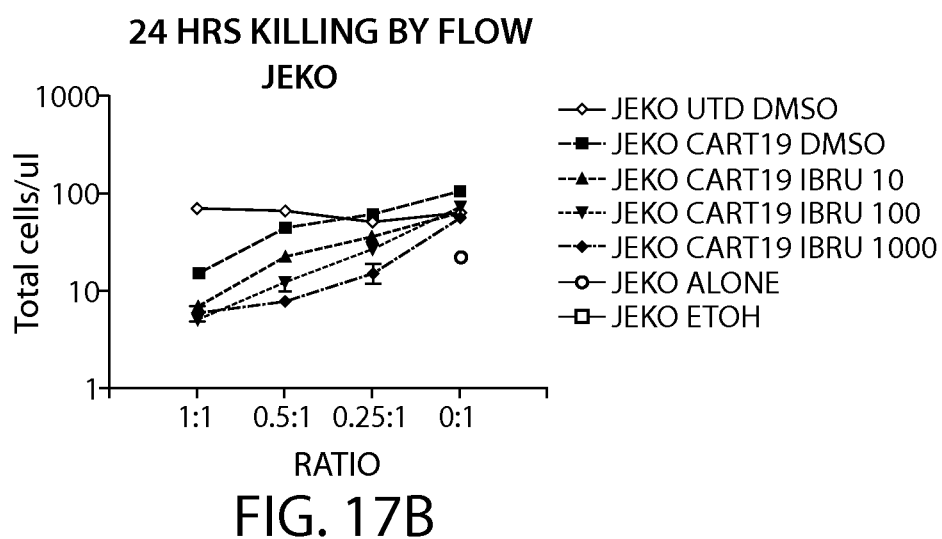
Figure 17C:
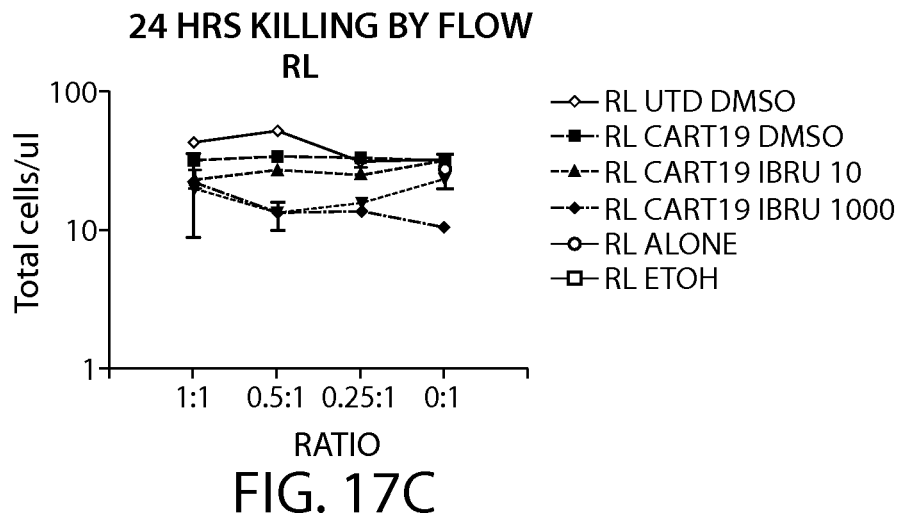

Additional bioluminescence assays were performed to assess CART19 cell killing of tumor cells. CART19 cells were plated with tumor cells MOLM14, JEKO-1, and RL carrying a luciferase reporter in varying ratios, such as 1:1; 1:0.5; 1:0.25; and 1:0 in a 96 well plate, in duplicate. After 24 hours, the bioluminescence was detected and quantified. Results indicated that bioluminescence in MOLM14 samples did not decrease after incubation with CART19 cells. However, for JEKO-1 and RL cells, the bioluminescence decreased in the presence of CART19 cells, indicating that CART19 cells mediated JEKO-1 and RL cell killing (FIGS. 16A, 16B, 16C, 16D, 16E, and 16F). There was a further decrease in bioluminescence when treated with ibrutinib, indicating that the combination of ibrutinib and CART19 caused increased JEKO-1 and RL cell killing than with CART19 treatment alone. Consistent with these results, calculation of total cells after each treatment showed that CART19 treatment of JEKO-1 and RL cells caused reduction in cell number and a further reduction when treated with CART19 and ibrutinib (FIGS. 17B and 17C), suggesting that the combination therapy was not only efficacious for killing MCL cells, but led to efficient killing of MCL cell lines.

Assessment of Ibrutinib/CART19 Treatment In Vivo

In these experiments, mouse models of mantle cell lymphoma were used to assess CART19 and ibrutinib combination therapy in vivo.

Figure 20:
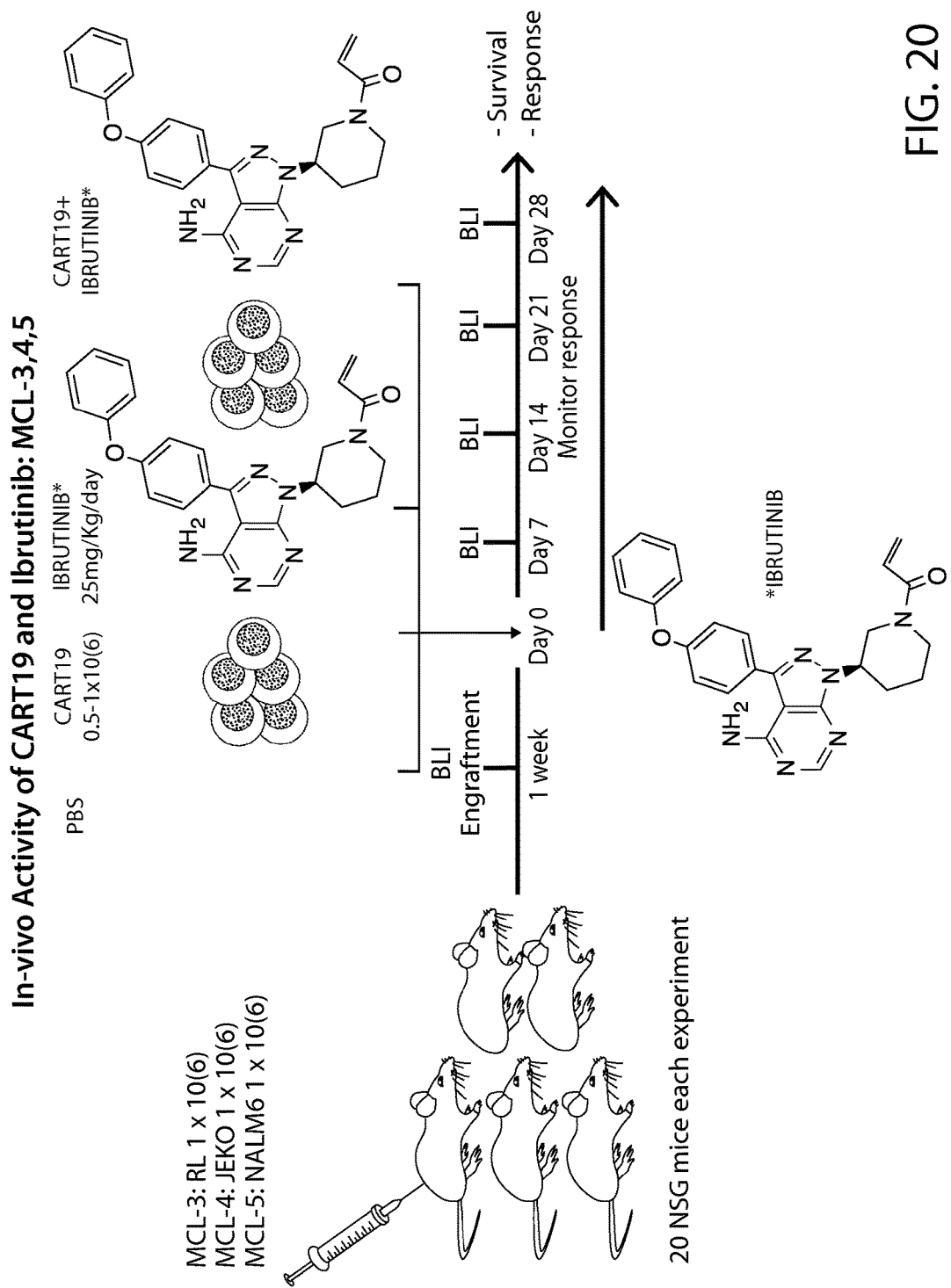
FIG. 20 is a schematic showing the protocol for administering and assessing CART19 and ibrutinib combination therapy in in vivo mouse models.
Figure 21A:
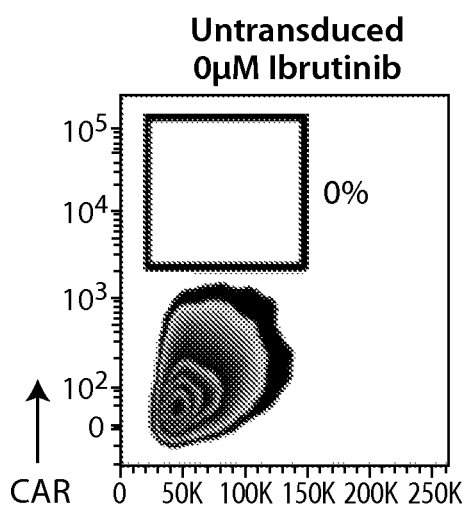
FIGS. 21A, 21B, 21C, and 21D is a graphic representation showing the transduction efficiency of PBMCs for generating CART19 T cells when cells are treated with ibrutinib prior to transduction. Untreated PBMCs were analyzed for CAR19 expression before transduction (FIG. 21A) and after transduction (FIG. 21C). Ibrutinib-treated PBMCs were analyzed for CAR19 expression before transduction (FIG. 21B) and after transduction (FIG. 21D).
Figure 21B:
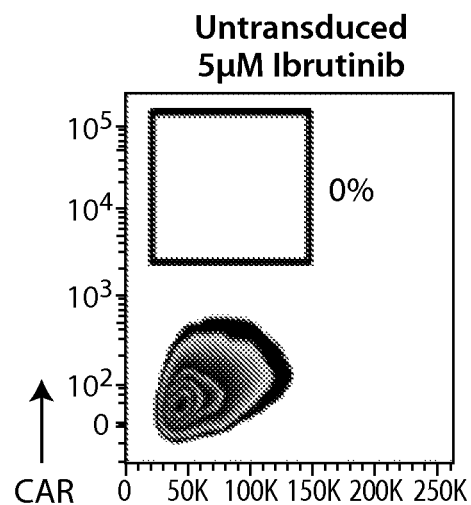
Figure 21C:
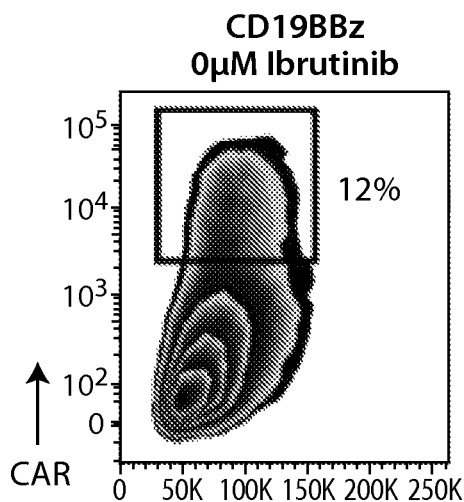
Figure 21D:
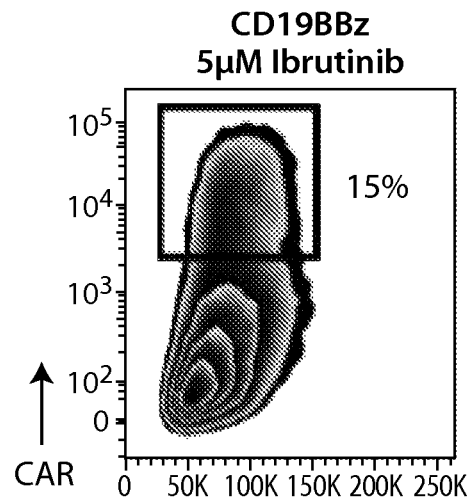
Figure 55:
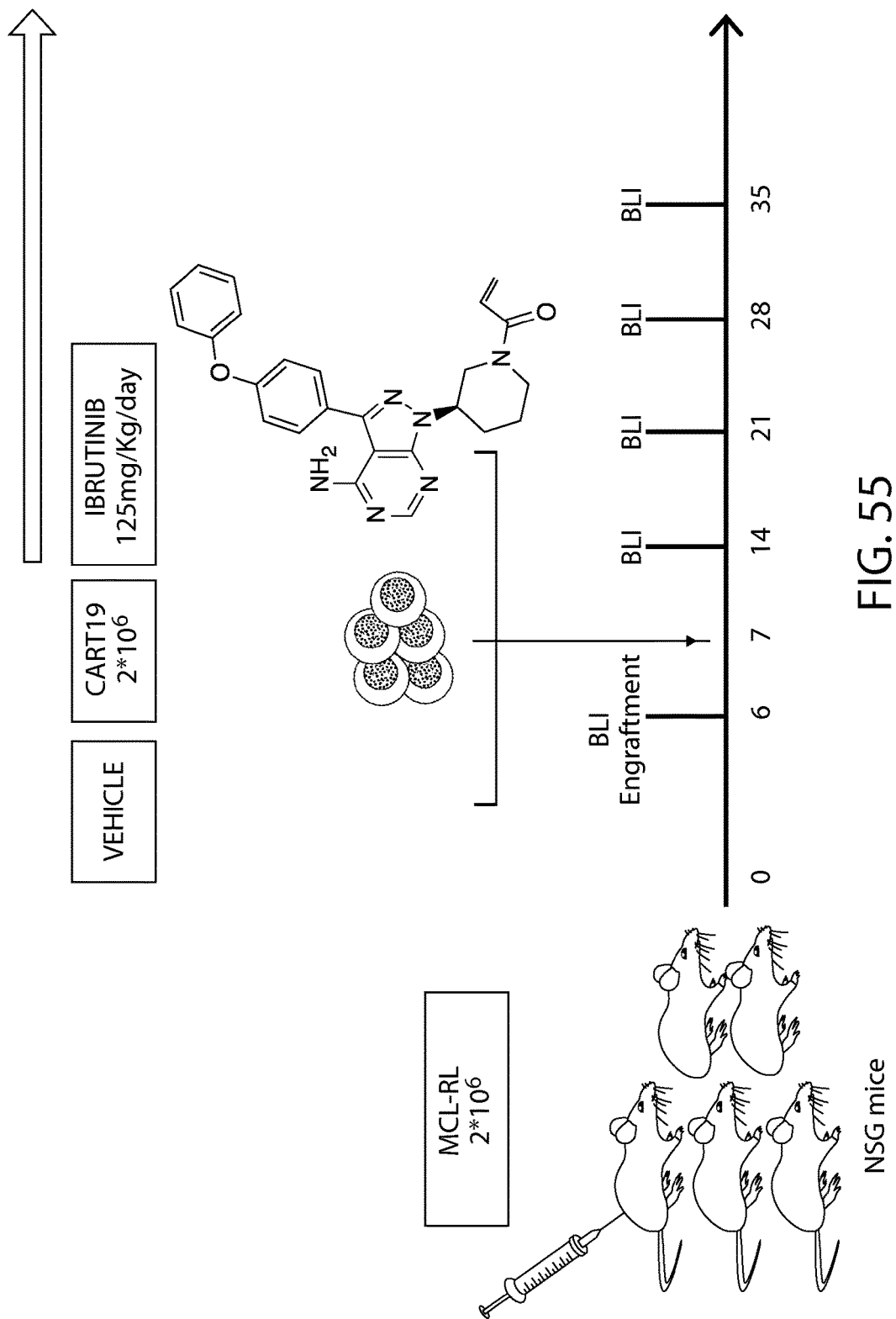
FIG. 55 is a schematic of an in vivo mouse model experimental setup to test the effect of CART19 and/or ibrutinib on MCL-RL-injected mice, with a readout being luminescence (a measure of the number of tumor cells).
Figure 56:
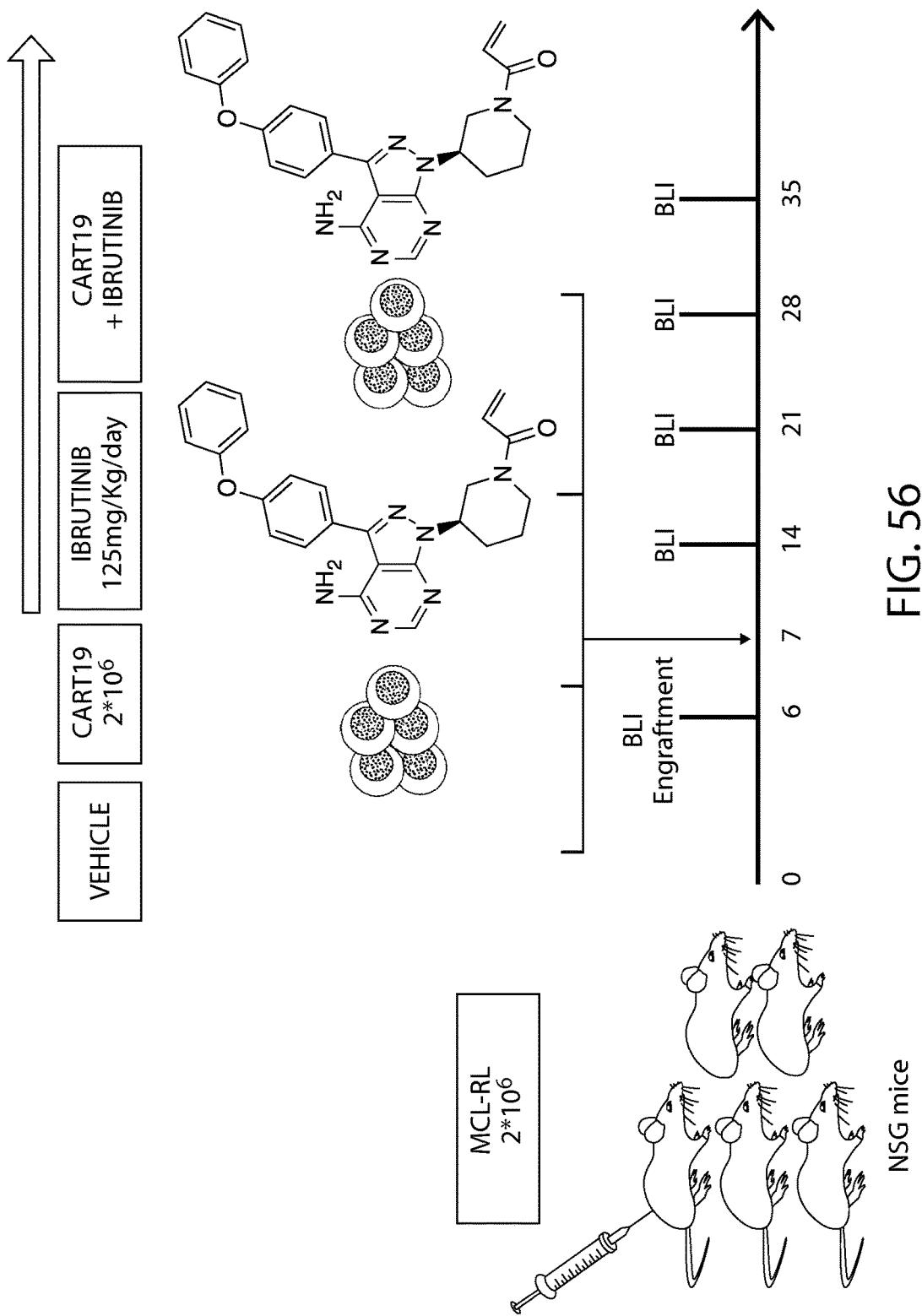
FIG. 56 is a schematic of an in vivo mouse model experimental setup to test the effect of CART19 and/or ibrutinib on MCL-RL-injected mice, with a readout being luminescence (a measure of the number of tumor cells).

Schematics such as those shown in FIGS. 20, 55, and 5A were used in this example. FIG. 20 shows a schematic of testing CART19/ibrutinib combination therapy in the in vivo mouse models of MCL. $1 \times 10^6$ cells from RL (MCL-3), JEKO-1 (MCL-4), and NALM6 (MCL-5) cell lines are injected in NSG mice (20 mice for each experiment). After 1 week to allow engraftment, treatment is initiated at Day 0, in which the treatment is: $0.5-1 \times 10^6$ CART19 cells (via injection), 25 mg/kg/day ibrutinib (oral gavage), or CART19+ ibrutinib treatment. At Day 7, Day 14, Day 21, and Day 28, the bioluminescence is imaged to monitor tumor size. Mice that are receiving ibrutinib treatment are continuously treated with ibrutinib. Survival of the mice is also monitored. FIGS. 55 and 56 show additional schematics of testing CART19/ibrutinib combination therapy in the in vivo mouse models of MCL. $2 \times 106$ MCL-RL cells are injected into NSG mice. After a week to allow engraftment (engraftment confirmed by bioluminescence imaging), treatment is initiated at Day 7 (after MCL-RL cell injection), in which treatment is: vehicle control, CART19 cells ($2 \times 10^6$ cells), and/or ibrutinib (125 mg/kg/day). At days 14, 21, 28, and 35 (after injection of MCL-RL cells), the bioluminescence is imaged to monitor tumor size.

Figure 32:
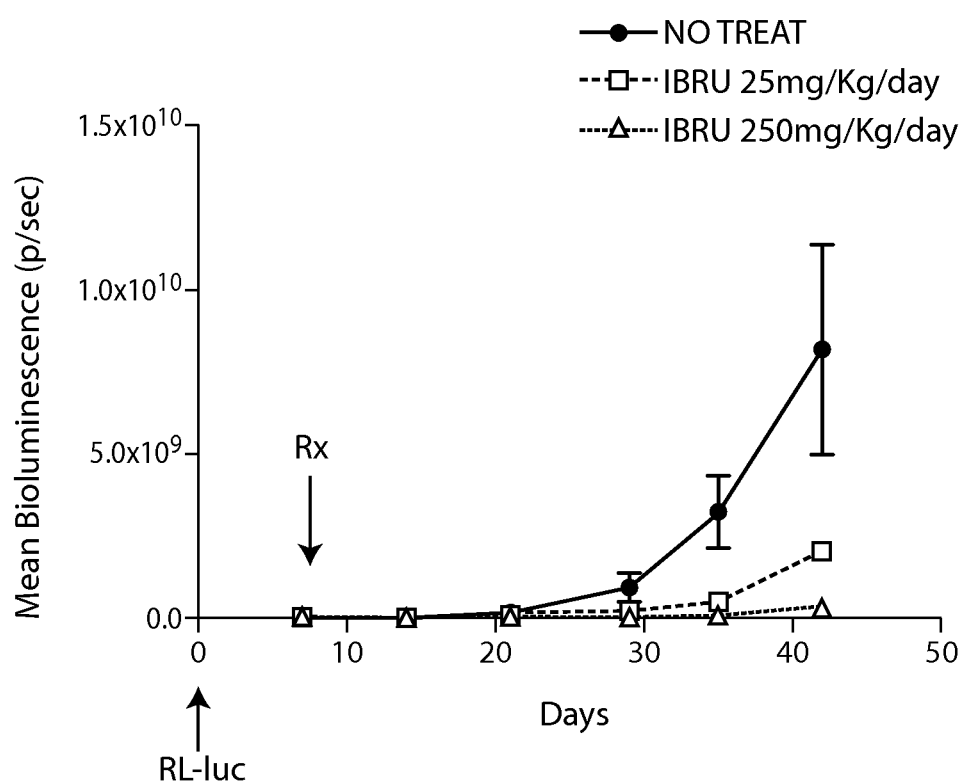
FIG. 32 is a graphic representation demonstrating the effect of ibrutinib treatment in an in vivo model of MCL.
Figure 57:
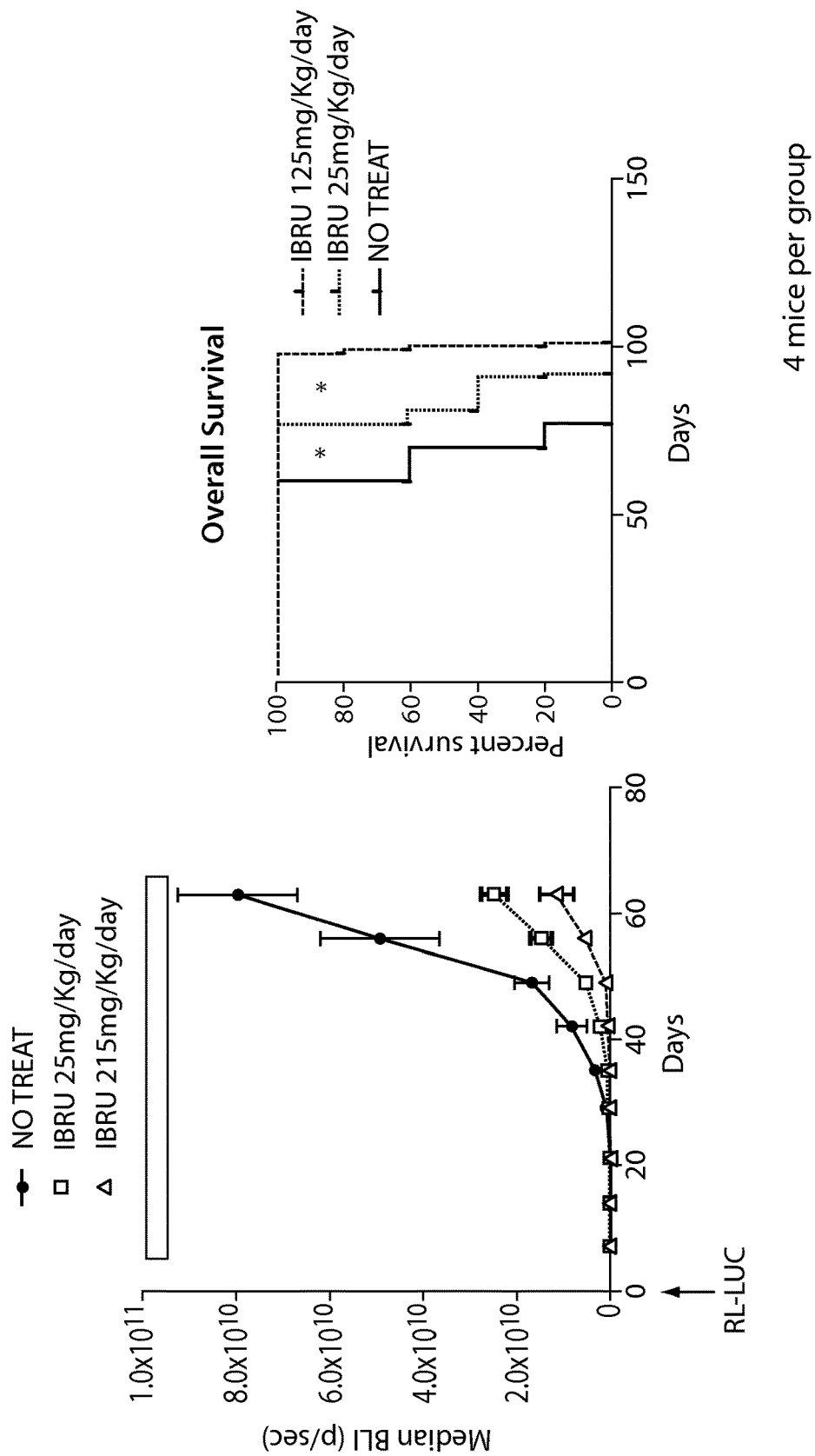
FIG. 57 is a set of graphs showing the luminescence (a measure of the measure of tumor cell number) in mice treated with ibrutinib at different concentrations and their overall survival after treatment.

The effect of ibrutinib treatment alone on an in vivo mouse model of MCL was examined. RL cells transfected with the GFP/luciferase gene were intravenously injected into immunodeficient NSG mice, resulting in 100% MCL engraftment in liver and spleen, with eventual spread into lymph nodes and bone marrow. Mice were treated with varying doses of ibrutinib, 25 mg/kg/day and 250 mg/kg/day. Mean bioluminescence, representing tumor growth, was assessed at various timepoints. As shown in FIG. 32, RL-derived tumors demonstrated dose-related sensitivity. Additional experiments titrating ibrutinib doses in RL cell-containing mice were performed and are shown in FIG. 57. A higher dose led to a better antitumor activity without increasing toxicity, in line with the higher dose of ibrutinib used in the clinic for MCL (Wang et al. NEJM 369.6 (2013):507-16).

Figure 18A:
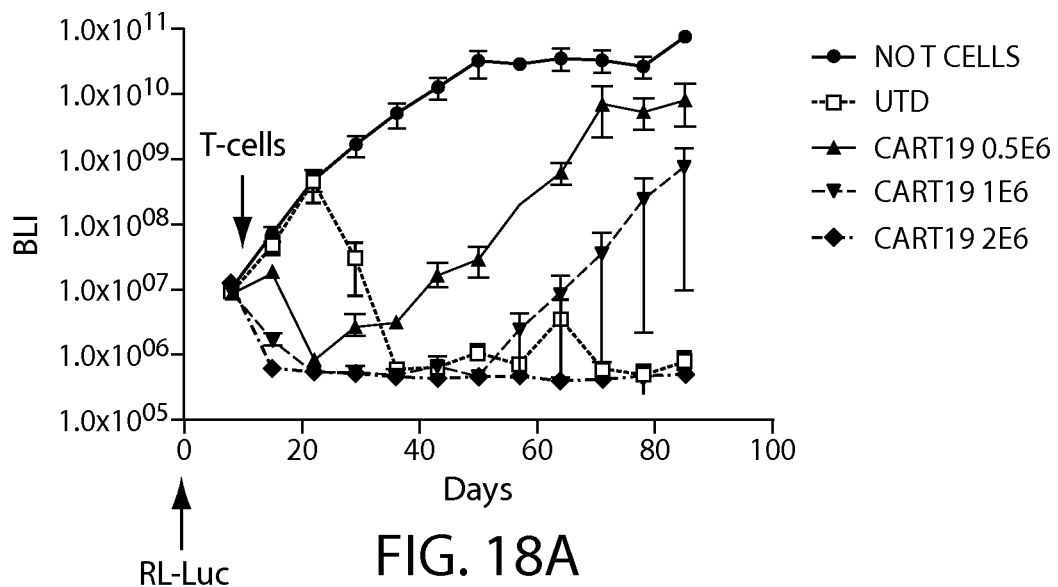
FIGS. 18A, 18B, 18C, and 18D are graphic representations of CART19 dose finding in the RL MCL mouse model. Tumor burden was monitored by bioluminescence imaging (BLI) over time (FIGS. 18A and 18B). Overall survival was monitored over time (FIG. 18C).
Figure 18B:
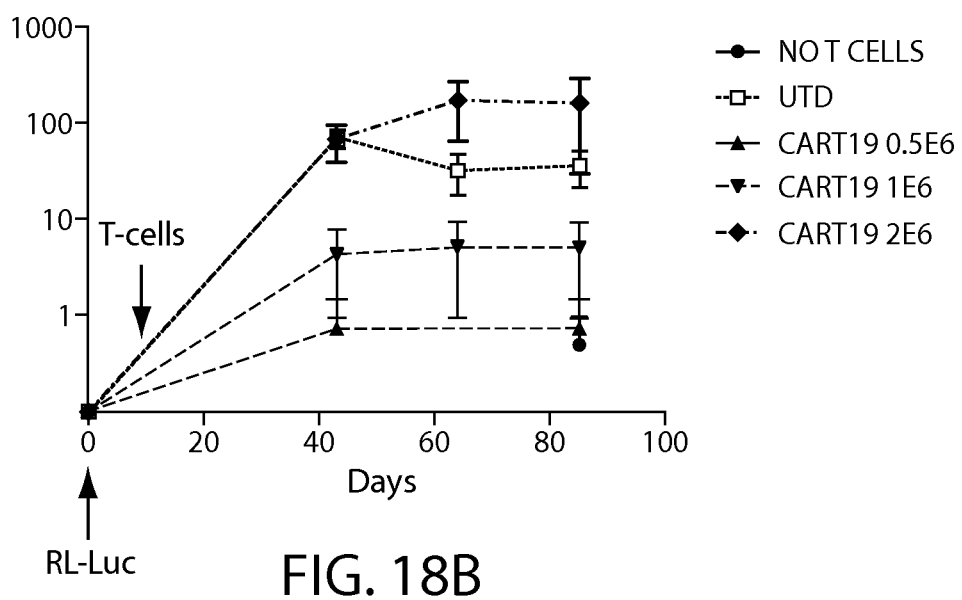
Figure 18C:
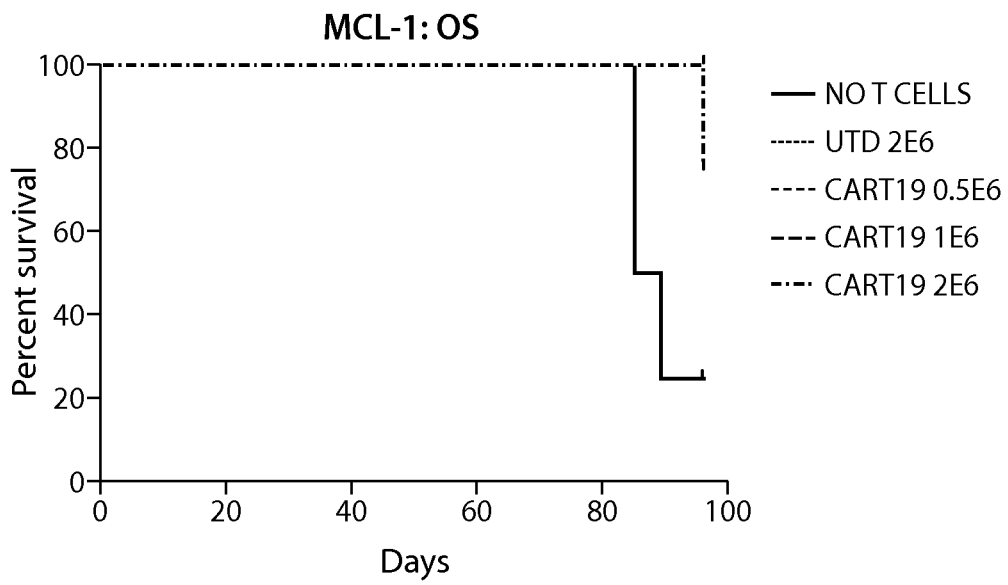
Figure 18D:
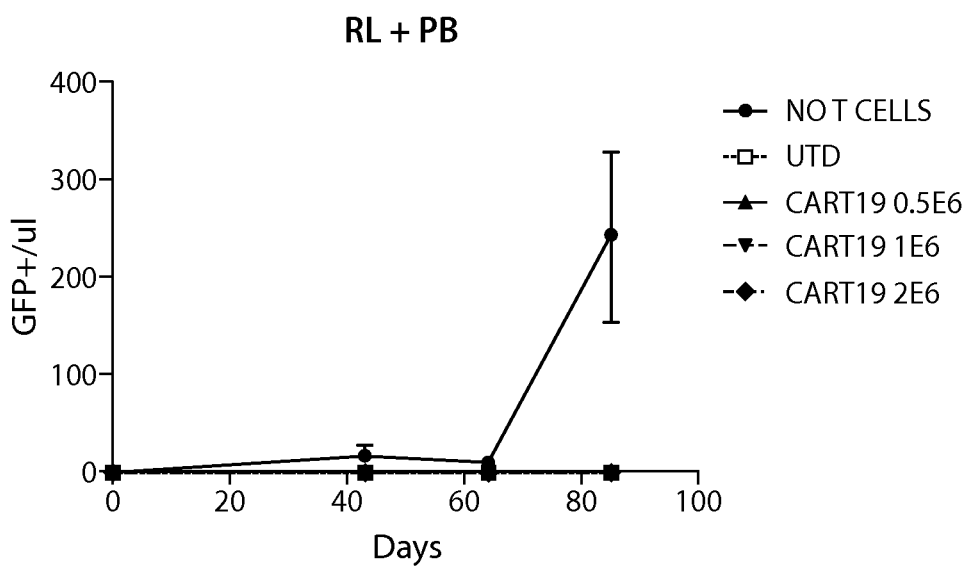
Figure 19B:
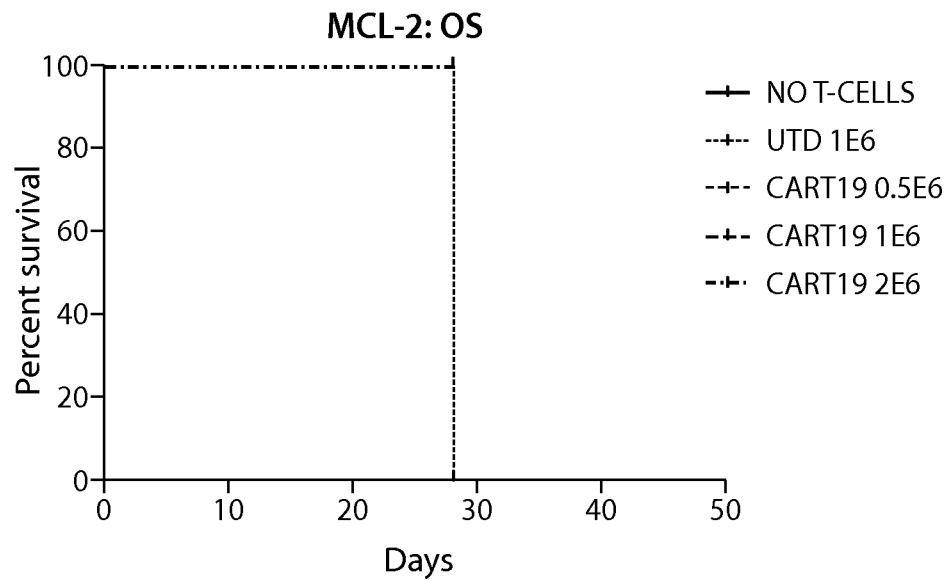

CART19 dose finding was also performed. Two MCL cell lines, RL (MCL-1) and JEKO-1 (MCL-2), carrying a GFP-luciferase reporter were injected into NSG mice at day 0. CART19 T cells were injected at day 7 at varying dosages, for example at 0.5×e6 cells, 1×e6 cells, or 2×e6 cells. Mice were monitored, for example, for 100 days. At various timepoints, the mice were monitored for tumor size (e.g., bioluminescence imaging) (FIGS. 18A and 18B, and FIG. 19A), and for overall survival (e.g., Kaplan-Meier survival curve) (FIG. 18C and FIG. 19B). Different doses of CART19 cells showing a dose-dependent anti-tumor efficacy, with $2 \times 10^6$ CART19 cells/mouse being the most effective dose (FIG. 19A).

Figure 58:
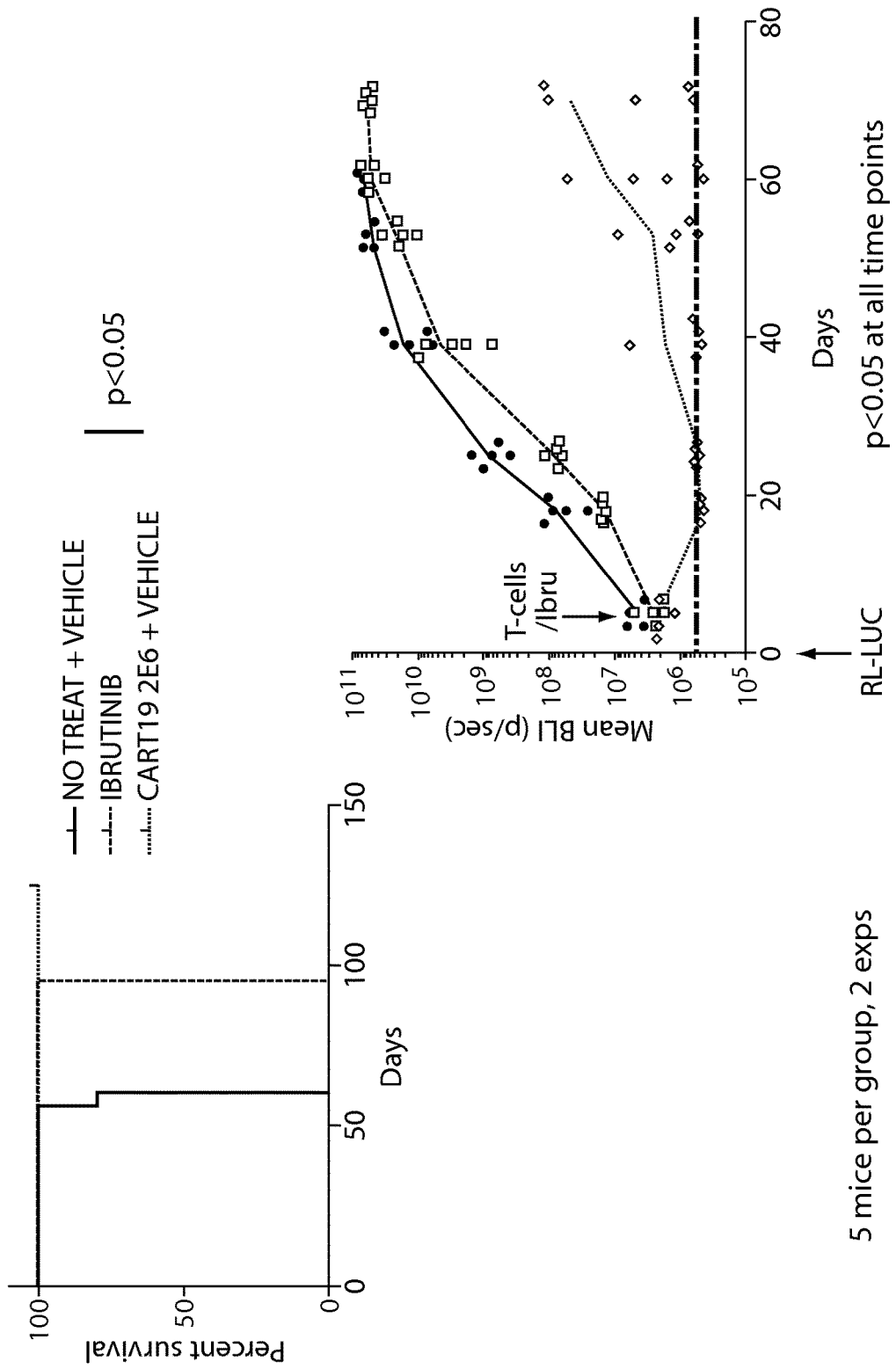
FIG. 58 is a set of graphs showing the luminescence (a measure of tumor cell number) in mice treated with ibrutinib or CART19 cells as well as their overall survival after treatment.
Figure 59:
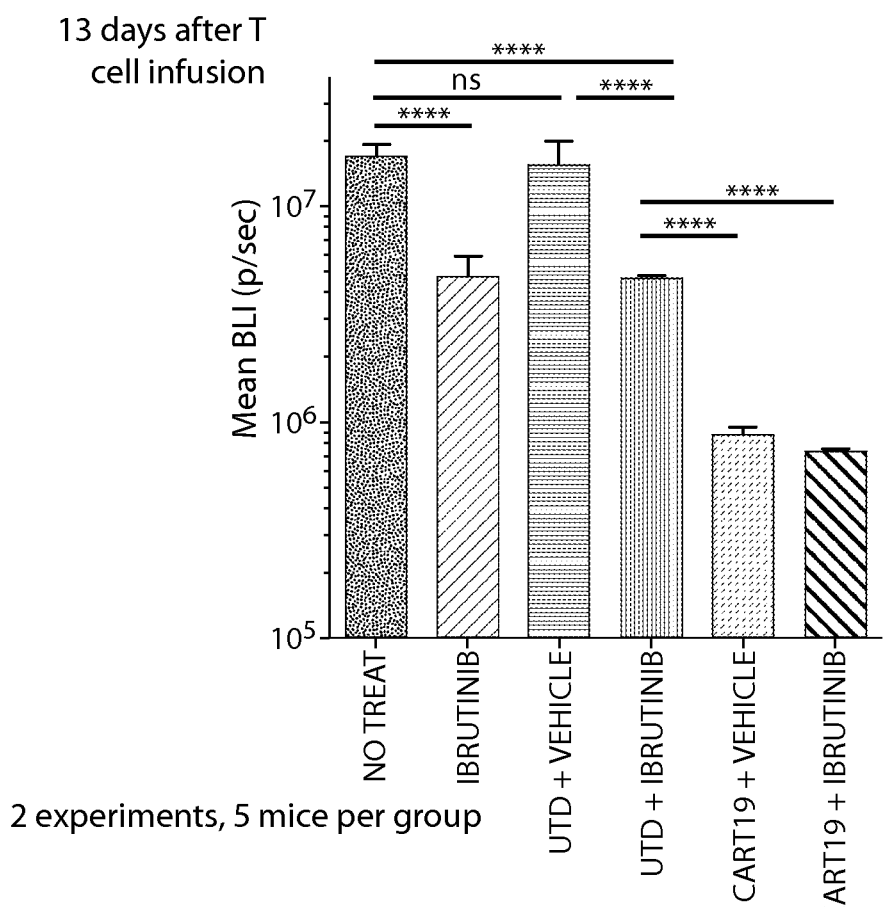
FIG. 59 is a graph showing the luminescence (a measure of tumor cell number) in mice after treatment with ibrutinib, untransduced T cells, ibrutinib with untransduced T cells, CART19 cells, and CART19 cells with ibrutinib.

These studies provided an opportunity to conduct a head-to-head comparison of the two of therapies for MCL. As shown in FIG. 58, long-term survival was achieved only in mice treated with CART-19 cells. There was no difference in anti-tumor effect when comparing untransduced T cells plus ibrutinib with ibrutinib alone. Therefore, in all subsequent experiments, the control groups were vehicle and ibrutinib alone (FIG. 59).

Figure 60:
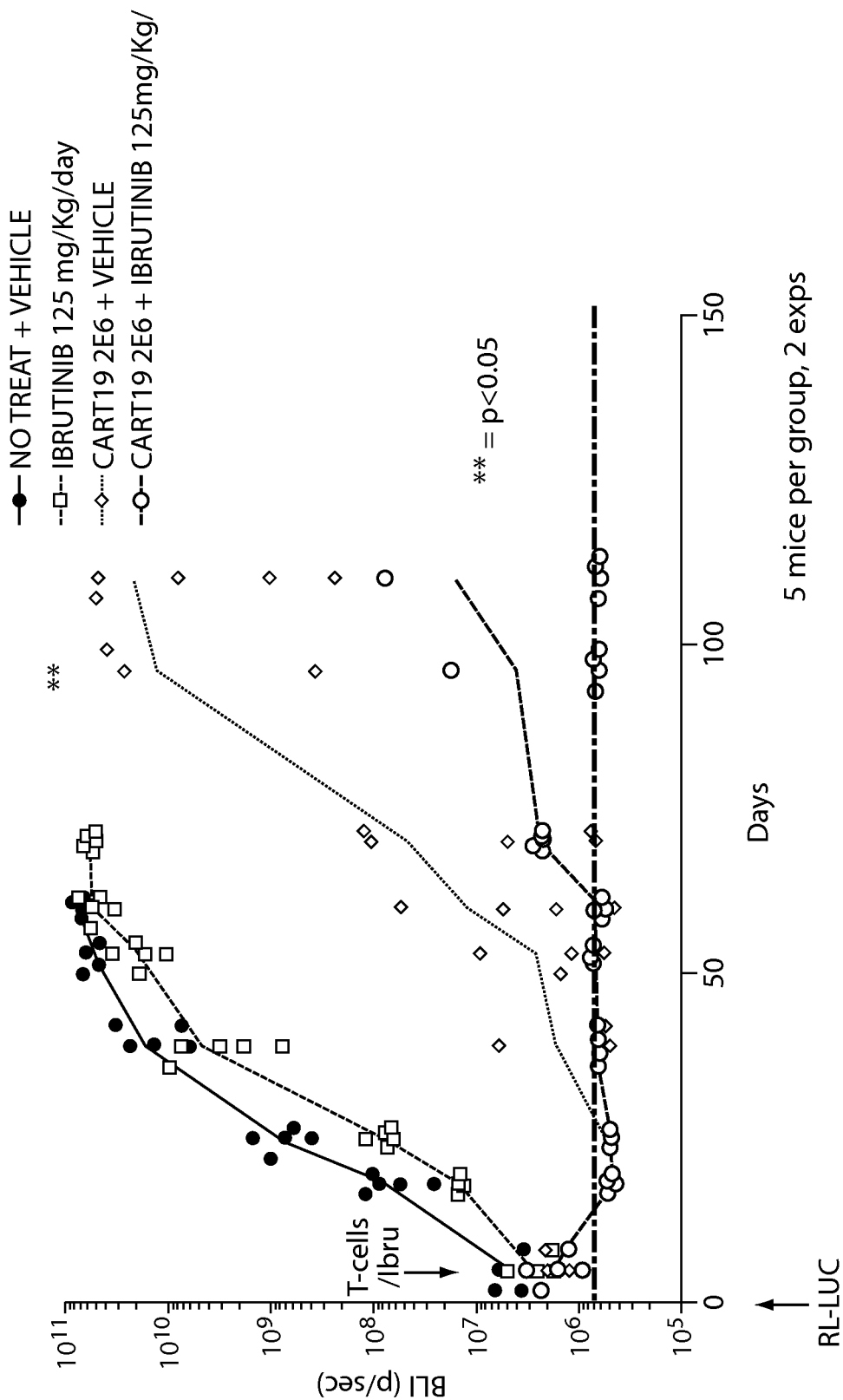
FIG. 60 is a graph showing the luminescence (a measure of tumor cell number) in mice after treatment with ibrutinib alone, CART19 cells alone, or the combination of ibrutinib with CART19 cells.

The addition of CART19 to ibrutinib was also tested, as detailed in the schematic in FIG. 56. Evaluation of the effect of ibrutinib on tumor burden indicated modestly delayed tumor growth at early time points. In contrast, CART19 cell therapy led to a clear decrease in tumor burden for several weeks. In mice receiving CART19 cells alone, this was followed by an indolent relapse beginning at Day 40, whereas mice that were treated with CART19 cells as well as ibrutinib had no detectable disease until Day 80 (FIG. 60). Histopathology of organs harvested at the end of the experiment showed persistence of disease in all control and ibrutinib treated mice with foci of tumor necrosis in the ibrutinib-treated. Most of the mice treated with CART19 alone showed indolent relapse at long term that was companied by the persistence of CART19 cells, while mice treated with CART19-ibrutinib showed clearance of the tumor and disappearance of CART19 from involved organs (data not shown).

Mechanism of Combined Effect of CART19 and Ibrutinib

The in vitro experiments herein indicated that ibrutinib neither impaired nor clearly augmented short-term CART19 effector functions. The in vivo studies showed that ibrutinib monotherapy had a modest anti-tumor effect. The results indicated that ibrutinib could significantly enhance the anti-tumor function of CART19 cells (FIG. 60). Therefore, experiments were performed to determine the mechanism for this effect.

Figure 61A:
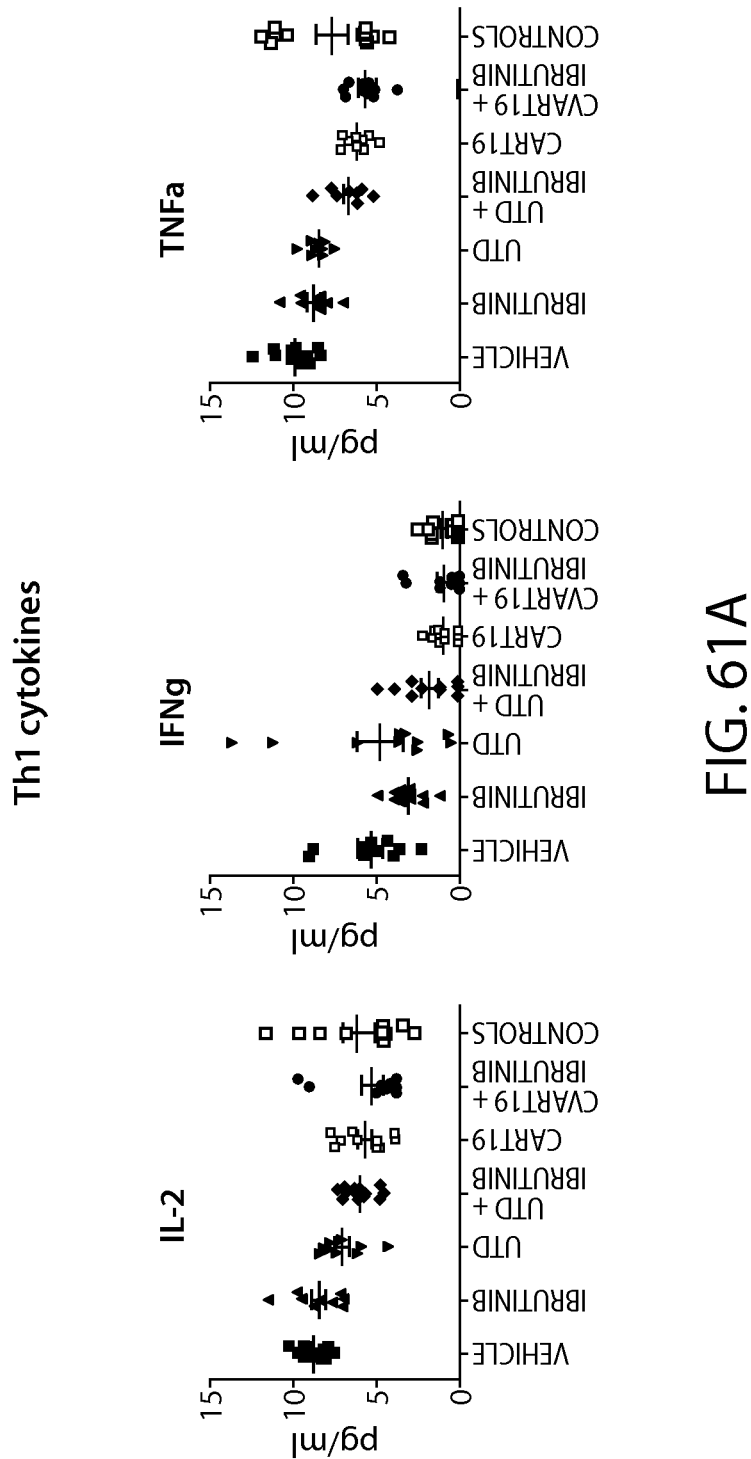
FIG. 61A is a set of graphs showing the level of Th1 cytokines produced in mice treated with ibrutinib and/or CART19 cells.
Figure 61B:
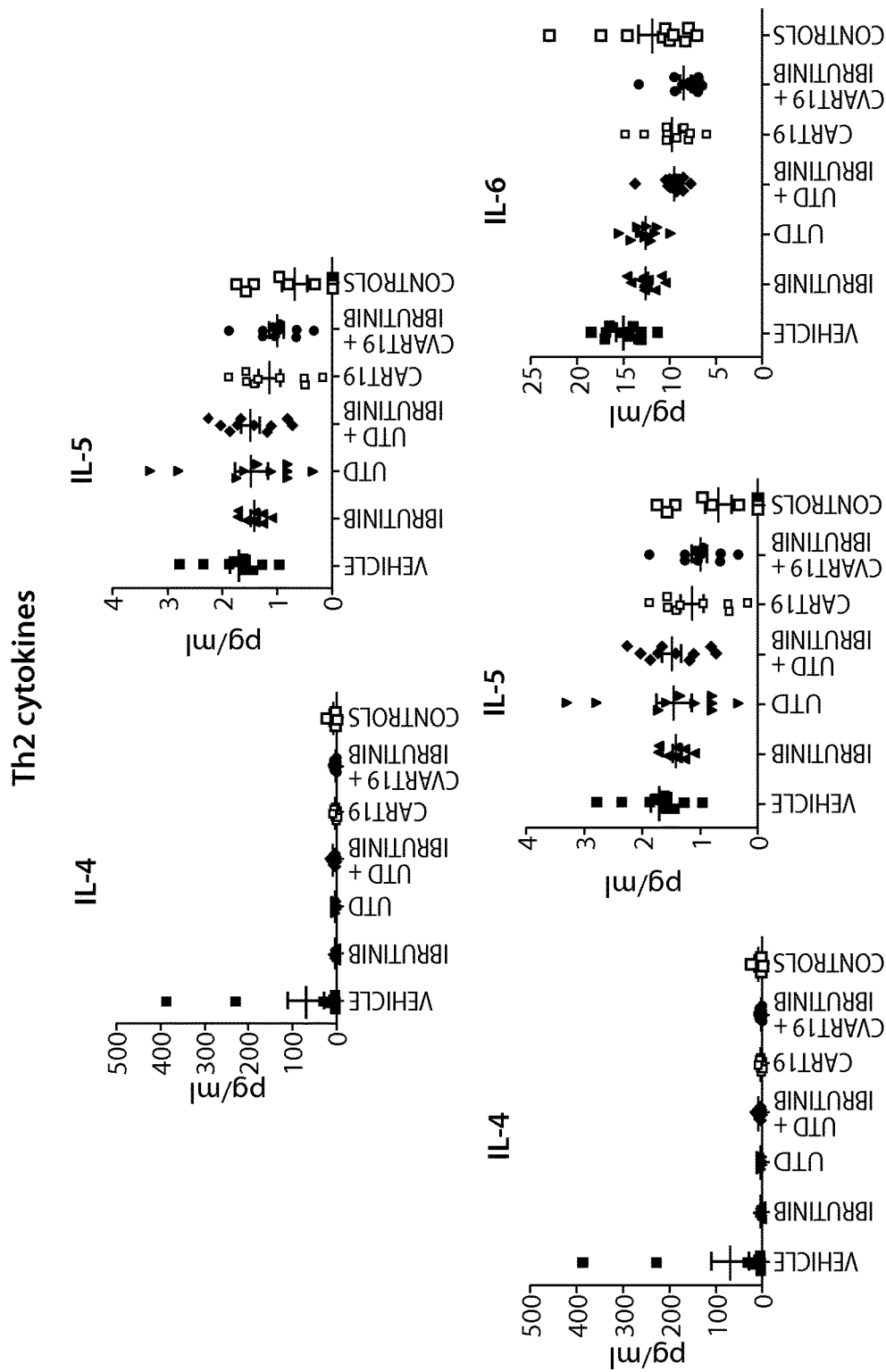
FIG. 61B is a set of graphs showing the level of Th2 cytokines produced in mice treated with ibrutinib and/or CART19 cells.
Figure 61C:
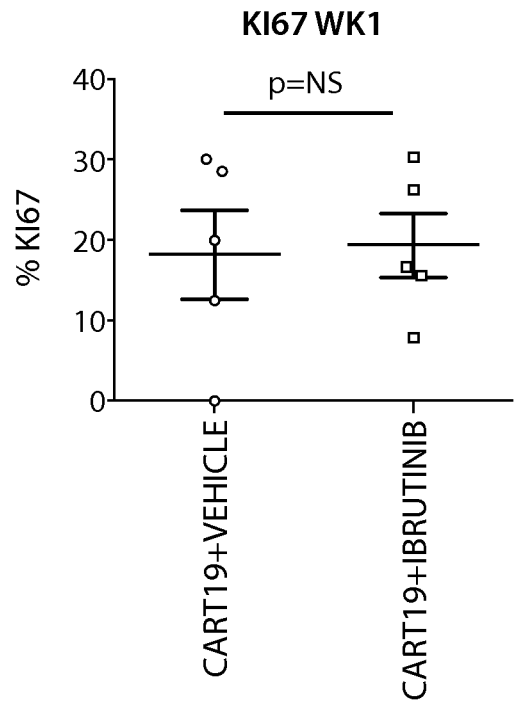
FIG. 61C is a graph showing the percentage of cells expressing the proliferation marker Ki67 in mice treated with CART19 cells or CART19 cells plus ibrutinib.
Figure 61D:
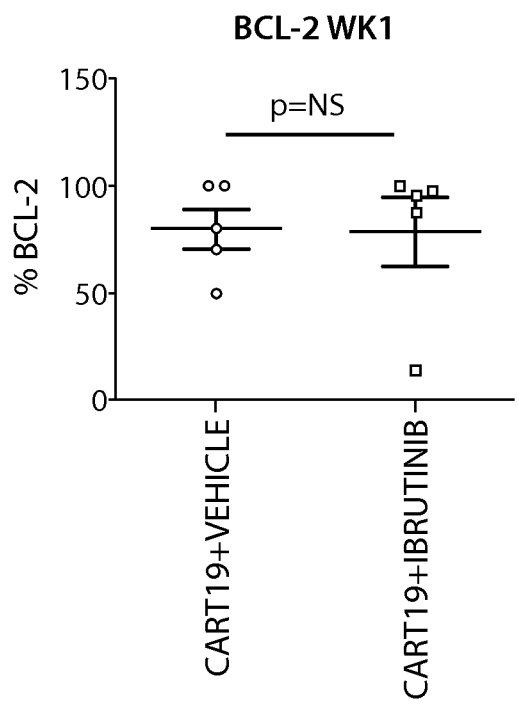
FIG. 61D is a graph showing the percentage of cells expressing the anti-apoptotic marker BCL-2 in mice treated with CART19 cells or CART19 cells plus ibrutinib.

Inhibition of ITK has been shown to inhibit Th2 polarization and skew towards a Th1 phenotype (Dubovsky et al. Blood 122.15 (2013):2539-49). In mice treated with CART19 cells and ibrutinib, an increase in Th1 cells when compared with CART19 cell monotherapy was not observed using this assay (FIG. 61A, 61B). However, exposure of mice to ibrutinib led to an increase in peripheral CART19 cells. There was no difference in the proliferation marker Ki67 between the treatment group and a control group (FIG. 61C), so this assay did not detect a difference in proliferation. Similarly, there was no difference in the anti-apoptotic marker Bcl2 or the apoptosis marker phosphotidyl serine, suggesting that the difference in CART cell numbers was not related to an impairment of apoptosis (FIG. 61D). As ibrutinib has been associated with peripheral lymphocytosis in patients, experiments were done to determine whether this was also found in mice treated with ibrutinib alone. One week after beginning ibrutinib, there were more circulating MCL cells and fewer nodal/organ MCL cells in ibrutinib-treated mice. Interestingly, this increase was observed in both ibrutinib-sensitive and -resistant in vivo model, as it was also observed in NSG mice engrafted with the acute leukemia cell line NALM-6 (data not shown).

In order to understand the role of ibrutinib in T cell expansion in vivo we engrafted NSG mice with MCL-RL WT cells and treated them with luciferase-positive T cells. Both CTL019 and CTL019-ibrutinib treated mice showed intense T cell expansion compared to UTD or UTD-ibrutinib (data not shown). We then investigated the frequency of different T cells subsets in vivo and did not see differences in PB T cells 1 week after T cells infusion. (data not shown). Since CXCR4 is involved in ibrutinib-driven B cell mobilization in humans, we checked the expression of CXCR4 in vivo in PB T cells of mice treated with CTL019 or CTL019-ibrutinib: CXCR4 level were similar in the 2 groups (data not shown). Lastly, expression of inhibitory/costimulatory receptor on PB of T cells of mice treated with CART19 and CART19-ibrutinib was analyzed. No difference in expression of TIM3, LAGS, CD137 or CTLA4 was evident, however a trend to a reduced PD-1 expression was noted in mice treated with CTL019 and UTD combined with ibrutinib.

Conclusions

Therapies for B-cell malignancies include small molecule inhibitors of BCR signaling and CD19-directed T cell based therapies. In the setting of relapsed MCL, the BTK inhibitor ibrutinib is now approved by the FDA and engenders high initial response rates. Unfortunately, these responses tend to be transient and require higher drug doses than those used for CLL. CART-19 leads to durable responses in patients with high-risk B-ALL, and it may be efficacious in other B-cell malignancies as well. Preliminary data suggest that the responses of mature B-cell malignancies to CART-19 may be lower than those of B-ALL, but the mechanism of this disparity has not yet been ascertained. This example investigated the impact of adding ibrutinib to CART19 in the treatment of MCL.

Different MCL cell lines with variable sensitivities to ibrutinib (IC50 ranging from 10 nM to 10 µM) were used for in vitro experiments. These different cell lines were used to model both ibrutinib-sensitive and ibrutinib-resistant MCL. At all but the highest doses of ibrutinib, CART19 cell function was unimpaired, with intact T cell expansion kinetics, tumor recognition and killing, and cytokine production. Furthermore, the results did not reveal a T helper polarization upon ibrutinib exposure. This finding may be due to a combination of factors, including the use of a mixed culture of CD4 and CD8 cells, in contrast to the model of CD4-only experimentation performed by Dubovksy et al. Blood 122.15 (2013):2539-49. Both ibrutinib-sensitive and ibrutinib-resistant cell lines strongly activated CART19 cells and induced killing, cytokine production and proliferation. Combination of CART19 and ibrutinib in vitro led to at least additive tumor killing. The results in this example show a superiority of CART19 over ibrutinib when each was used as monotherapy at clinically relevant doses and schedules of administration (single dose for CART19, continuous administration for ibrutinib).

A systemic xenograft MCL model was also generated in this example, using the MCL-RL cell line generated in a laboratory. Treatment of these mice with different doses of allogeneic CAR19 T cells led to a dose dependent anti-tumor effect. A similar dose response to CART-19 was also observed in the ibrutinib resistant JEKO-1 cell line. MCL-RL was treated in vivo with different doses (e.g., 0, 25 and 125 mg/kg/day) of Ibrutinib, leading to a median overall survival respectively of 70, 81 and 100 days (p<0.001). A direct in vivo comparison of the ibrutinib 125 mg/kg and CART19 showed a significantly improved tumor control for CART19 treated mice. Also, MCL-RL engrafted mice were treated with vehicle, ibrutinib, CART19 or the combination of CART19 and ibrutinib (iCART19). At clinically relevant doses, monotherapy of MCL with CART19 was superior over monotherapy with ibrutinib, and the combination of ibrutinib with CART19 led to an augmented anti-tumor effect. In particular, the iCART19 combination in vivo led to initially higher circulating levels of CART19 cells, followed by deep tumor responses, and relapses were significantly delayed when ibrutinib was added to CART19. The iCART19 combination resulted in an improved tumor control with 80% of mice reaching complete remission and long-term disease-free survival. Mechanistically, mice treated with ibrutinib had higher numbers of circulating CART19 cells without changes in Th1/Th2 or memory phenotype. Thus, the results herein show that ibrutinib can be combined with CART19 in a rational manner and suggest that the properties of each of these therapies may compensate for deficiencies of the other, thus leading to enhanced long-term anti-tumor effect. The experiments and results of combining BCR signaling inhibition with anti-CD19 directed T cell therapy pave the way to rational combinations of non-crossresistant therapies for B cell malignancies.

The kinetics of tumor response and relapse suggest that ibrutinib serves either to deepen the initial response achieved by CTL019 alone, or to enhance the long-term immunosurveillance capacity of CTL019 cells.

Example 9: Ibrutinib/CAR19 T-Cell Combined Therapy for Chronic Lymphocytic Leukemia Ibrutinib is also utilized for treatment of chronic lymphocytic leukemia (CLL). Ibrutinib has not demonstrated cytotoxic effects on T cells or NK cells. However, in CLL cells, ibrutinib promotes programmed cell death and inhibits tumor cell migration and adhesion. In this example, experiments were performed to examine: 1) the effect of ibrutinib on CART19 production from patients undergoing ibrutinib therapy; and 2) the optimal timing of treatment with ibrutinib in combination with CART19 for optimal in vivo function.

Effect of Ibrutinib on CART19 Production and Function

Normal donor PBMCs were obtained using apheresis as described herein, for example in Example 6. The PBMCs were incubated with 5 µM of ibrutinib for 30 minutes or were left untreated (for control), and then the cells were washed twice. The cells were then transduced with lentiviral constructs containing CAR19 to generate CART19 T cells using the methods described herein, for example, in Example 4. The number of CART19 T cells generated from ibrutinib-treated PBMCs FACs analysis was performed to determine the number of CART19 T cells generated from ibrutinib-treated PBMCs compared to untreated PBMCs. As shown in FIG. 21, 15% of the transduced ibrutinib-treated PBMCs expressed CAR19 and 12% of the transduced untreated PBMCs expressed CAR19. These results demonstrate that ibrutinib treatment does not affect lentiviral transduction efficiency or CART19 T cell production. Therefore, CART19 T cells can be manufactured from CLL patients undergoing ibrutinib treatment.

Further in vitro analysis was performed to determine the effect of ibrutinib on CART19 T cell proliferation, CART19 cytotoxicity, and the ratio of $T_H1:T_H2$ cytokine production.

For measuring cell proliferation, cells were stained with CFSE for detection of proliferating cells and analyzed by FACS, as described in Example 4. CART19 T cells were incubated with varying concentrations of ibrutinib (0.1 µM, 0.5 µM, 1 µM, and 5 µM), and were either stimulated with CD3/CD28 beads or were left unstimulated. In FIG. 22, histograms were overlayed to compare the unstimulated to the CD3/CD28 stimulated CART19 T cells at each concentration of ibrutinib. For each concentration of ibrutinib, CD3/CD28-stimulated T cell proliferation was observed, thereby demonstrating that ibrutinib treatment did not affect CART19 cell proliferation.

Figure 23:
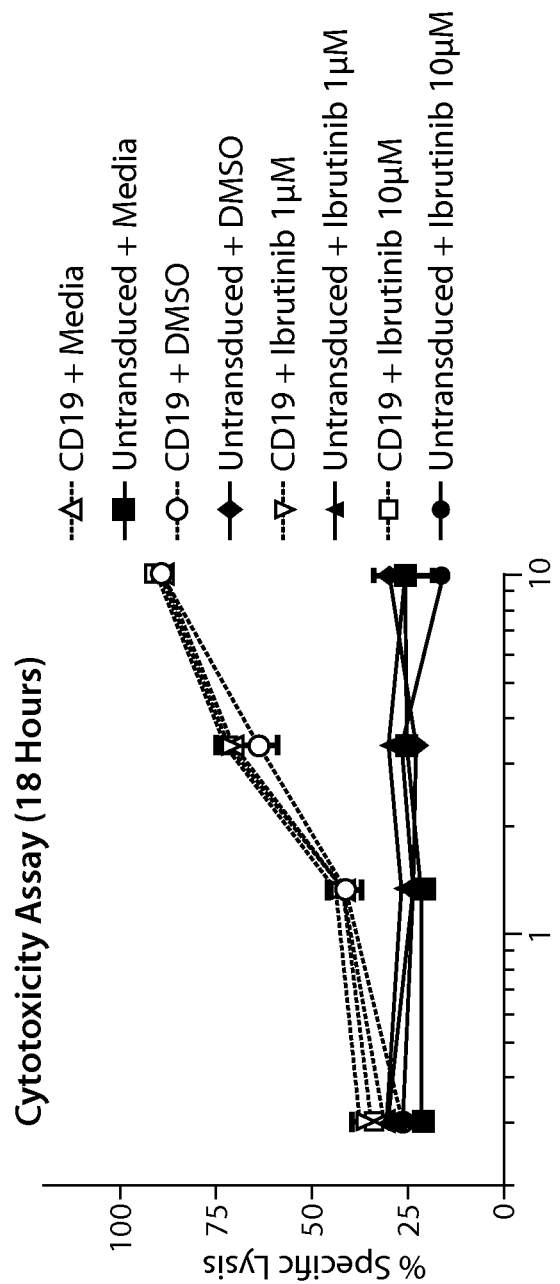
FIG. 23 is a graphic representation demonstrating that ibrutinib does not affect CART19 cytotoxicity.

The effect of ibrutinib on cytotoxicity of CART19 T cells was also assessed, using methods described in Example 4. Untransduced and CAR19-transduced T cells were treated with media, DMSO, or 1 µM ibrutinib. A flow-based killing assay was performed using titrating effector to target (E;T) ratios with effector CART19 cells (media, DMSO, or ibrutinib-treated) to determined specific cytotoxic activity against CD19-expressing target cells. As shown in FIG. 23, CART19 T cells treated with ibrutinib demonstrated the same percentage of specific cytotoxic activity against CD19-expressing target cells as controls (CART19 T cells treated with media or DMSO). Thus, ibrutinib treatment does not affect CART19 cytotoxicity.

Figure 24:
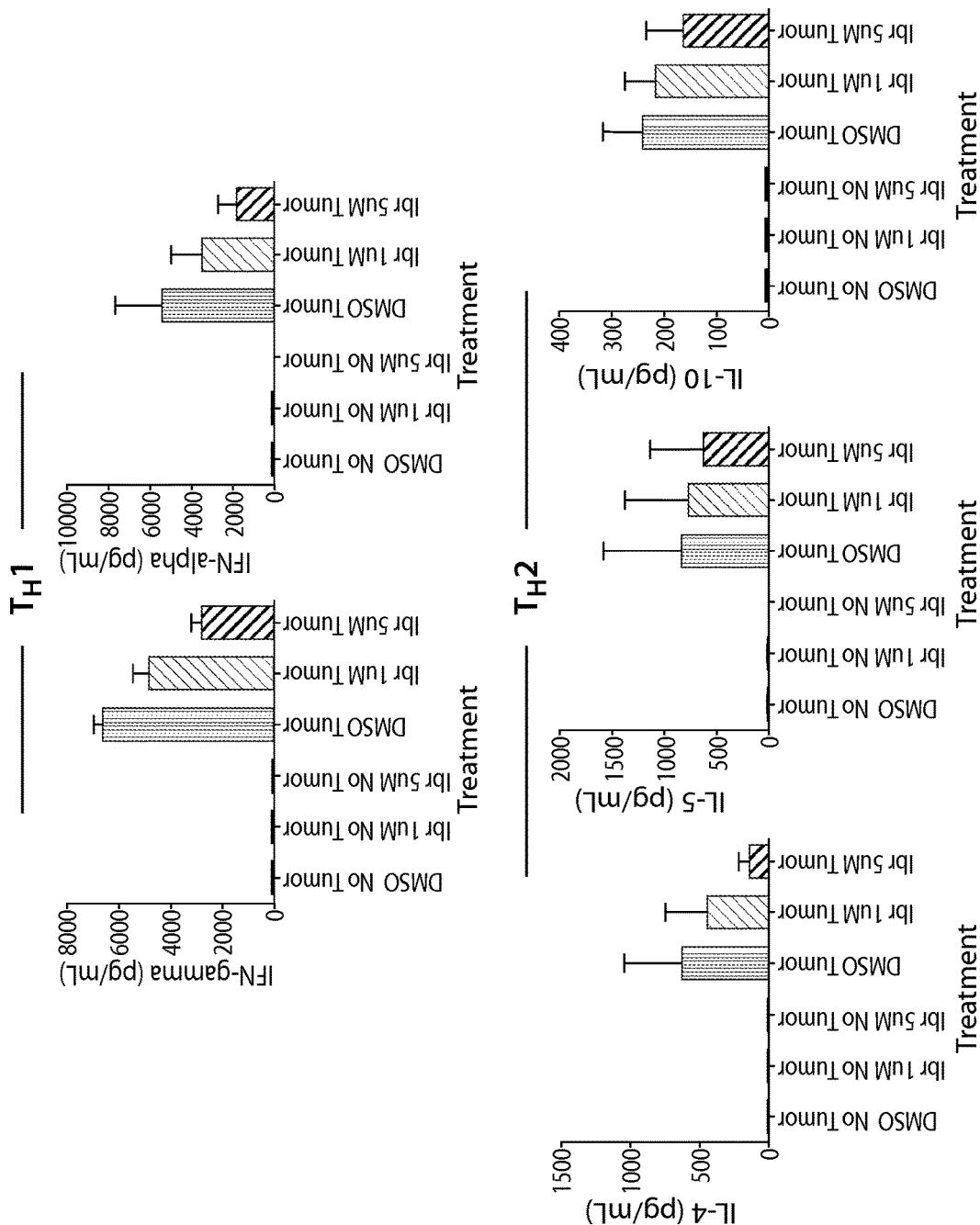
FIG. 24 is a series of graphic representations that demonstrate that ibrutinib treatment does not promote skewing of $T_H1/T_H2$ cytokines in CART19 cells.

Ibrutinib treatment can limit $T_H2$ activation, and therefore may promote $T_H1$ selective pressure in T cells and skew $T_H1/T_H2$ cytokines in human CLL patients. Assays were performed to measure $T_H1$ and $T_H2$ cytokine production in the presence or absence of ibrutinib or DMSO (control). As shown in FIG. 24, ibrutinib does not promote skewing of $T_H1$ and $T_H2$ cytokines in CART 19 cells.

Efficacy of Ibrutinib/CART19 Combination Treatment In Vivo

CART19 function was assessed in an in vivo mouse model. Nalm/6 cells (human acute lymphoblastic leukemia cell line) were implanted into NSG mice, and the mice were monitored daily for at least 50 days. The Nalm/6 tumor model produces tumors that are not sensitive to ibrutinib, and therefore allow analysis of CART19 function in vivo and efficacy in reducing tumor volume/treating cancer. Starting on day 7, mice were administered either DMSO (control) or ibrutinib daily by oral gavage. CART19 was administered on day 7 or day 9, or mice were left untreated (control). At days 4, 11, 18, 25 and 32, the number of Nalm/6 cells circulating in the mice were measured, e.g., by peripheral blood FACS analysis, to determine the efficacy of the CART19 for clearing Nalm/6 cells in the presence or absence of ibrutinib. For example, the cells were stained with anti-human CD19 antibody to determine the percent of human CD19+(Nalm/6) cells in the blood of the tumor-bearing NSG mice.

Figure 25A:
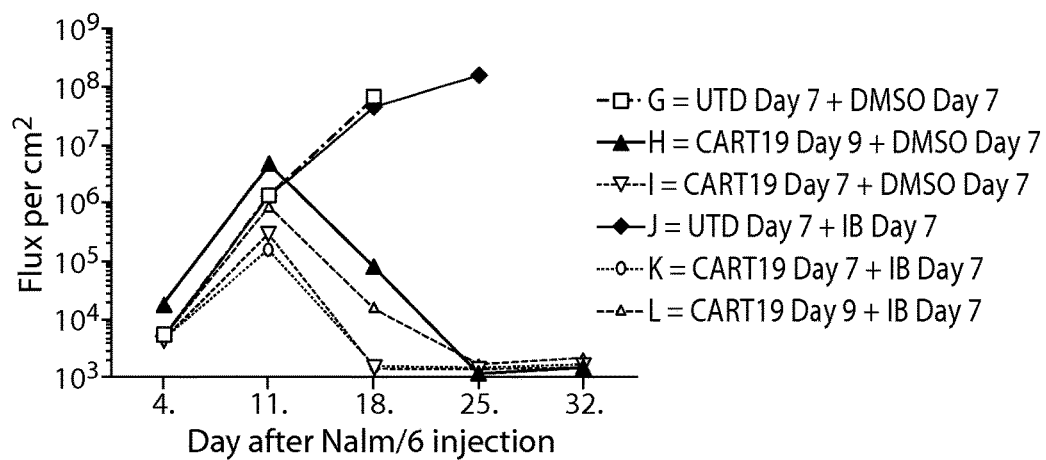
FIGS. 25A and 25B are graphic representations showing that continuous administration of ibrutinib does not affect CART19 function in clearing tumor cells in vivo.

As shown in FIG. 25A, mice that did not receive CART19 injections exhibited an increase in tumor Nalm/6 cells. However, mice that received CART19 injections in combination with daily administration of DMSO showed successful clearing (reduction) of Nalm/6 cells. Mice that received CART19 injections in combination with daily administration of ibrutinib also showed successful clearing of the Nalm/6 cells with the same kinetics and efficacy as the mice that received DMSO treatment. Therefore, these results demonstrate that ibrutinib treatment does not impair CART19 function in clearing Nalm/6 cells from this tumor model.

Figure 25B:
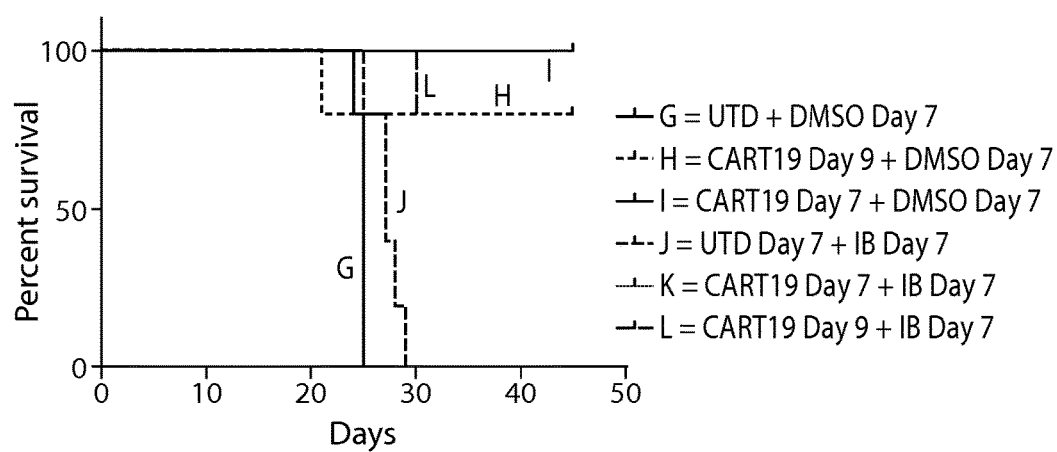

Health status of the mice were monitored for at least 50 days after injection of the Nalm/6 cells. The Kaplan-Meier survival curve of FIG. 25B shows that none of the mice that were untreated (did not receive CART19 T cells) and received either DMSO or ibrutinib survived greater than 30 days after injection of the Nalm/6 cells. However, treatment with CART19 T cells, with DMSO or with ibrutinib increased the survival of the mice. Thus, these results taken together with the tumor burden results from FIGS. 13-1, 13-2, 13-3, 13-4, 13-5, and 13-6 demonstrate that ibrutinib treatment does not impair CART19 function in clearing tumor cells from the in vivo NSG-Nalm/6 tumor model.

Optimal Timing of Ibrutinib/CART19 Combination Treatment in CLL Patients

The optimal time during ibrutinib treatment of CLL for administration of CART19 was assessed using samples from CLL patients who were undergoing ibrutinib treatment for one year. PBMC samples from 9 CLL patients (Patient 111330026, Patient 111330030, Patient 111330039, Patient 111330056, Patient 111330073, Patient 111330074, Patient 111330081, Patient 111330086, and Patient 111330111) were isolated at different cycles of the ibrutinib treatment and were used to manufacture CART19 T cells. The PBMC samples were collected before ibrutinib treatment to establish a baseline, and then collected during ibrutinib treatment at cycle 2, day 1, and cycle 12, day 1. Several different parameters of CART19 manufacturing were assessed, such as transduction, proliferation, cyotoxicity, and cytokine production. Other evaluations can include ex vivo immunophenotyping, such as assessment of memory, inhibitor molecules, and exhaustion.

FIG. 26 shows the results from flow cytometry analysis from CAR19 transduction of T cells from Patient 111330030, which was representative of the results obtained from the other 8 patients after CAR transduction. PBMCs were collected from the patients at the indicated times (baseline, e.g., before treatment; cycle 2 at day 1; and cycle 12 at day 1) and were transduced with lentiviral vectors containing CAR19, using methods as described, for example, in Example 4. The transduced PBMCs were then stained for annexin, CD3, CD4, and GAM (to detect CAR), and then analyzed by FACS analysis. The boxed region in the graphs in FIGS. 14-1, 14-2, 14-3, 14-4, 14-5, and 14-6 shows the percentage of cells that were GAM positive, and successfully transduced to CART19 T cells. The lower three graphs show that CAR19 was successfully transduced in about 23% of cells at baseline, 28% of cells at cycle 2, day 1, and 44% of cells at cycle 12, day 1.

Figures 1, 27:
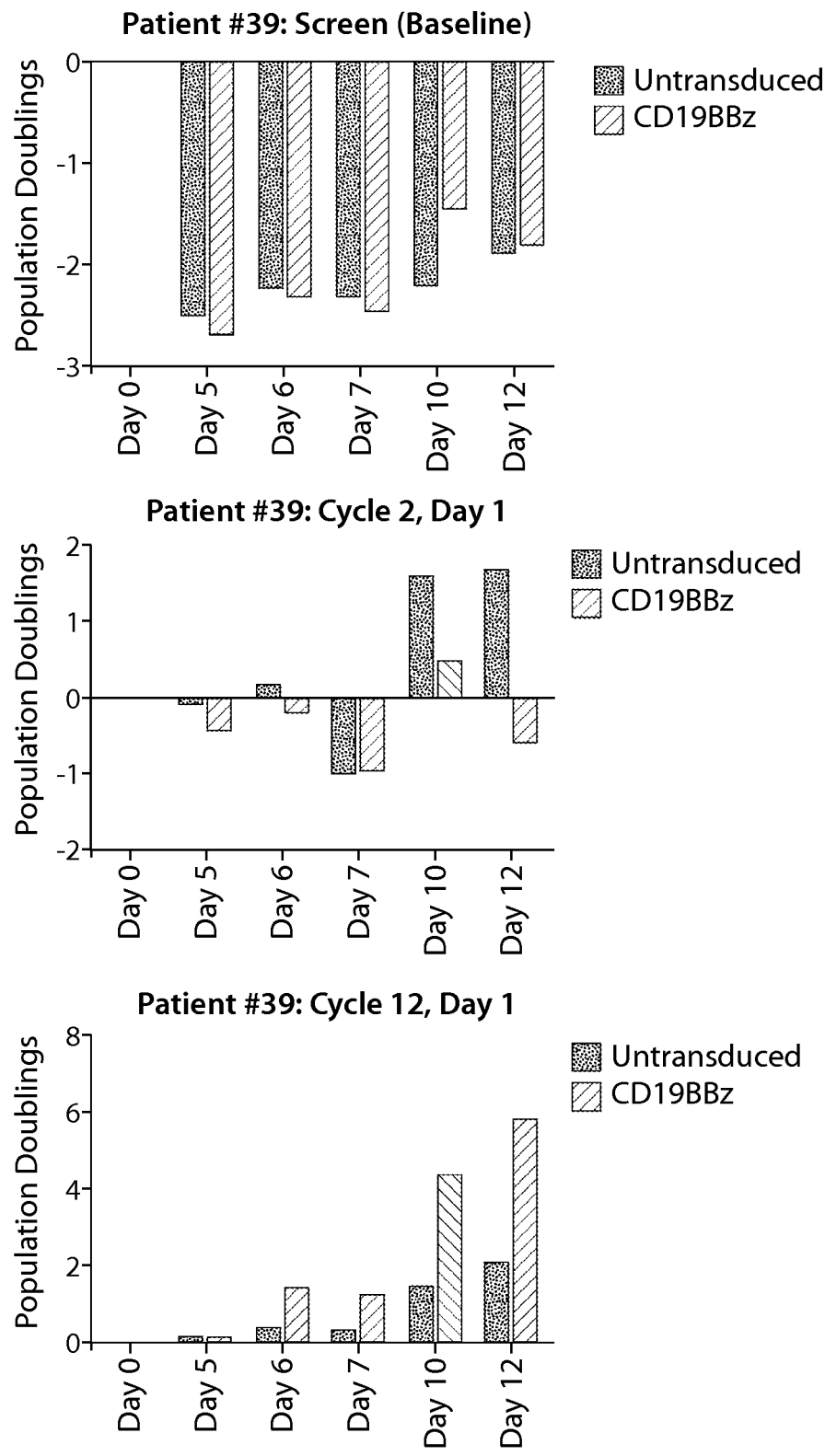
Figures 2, 27:
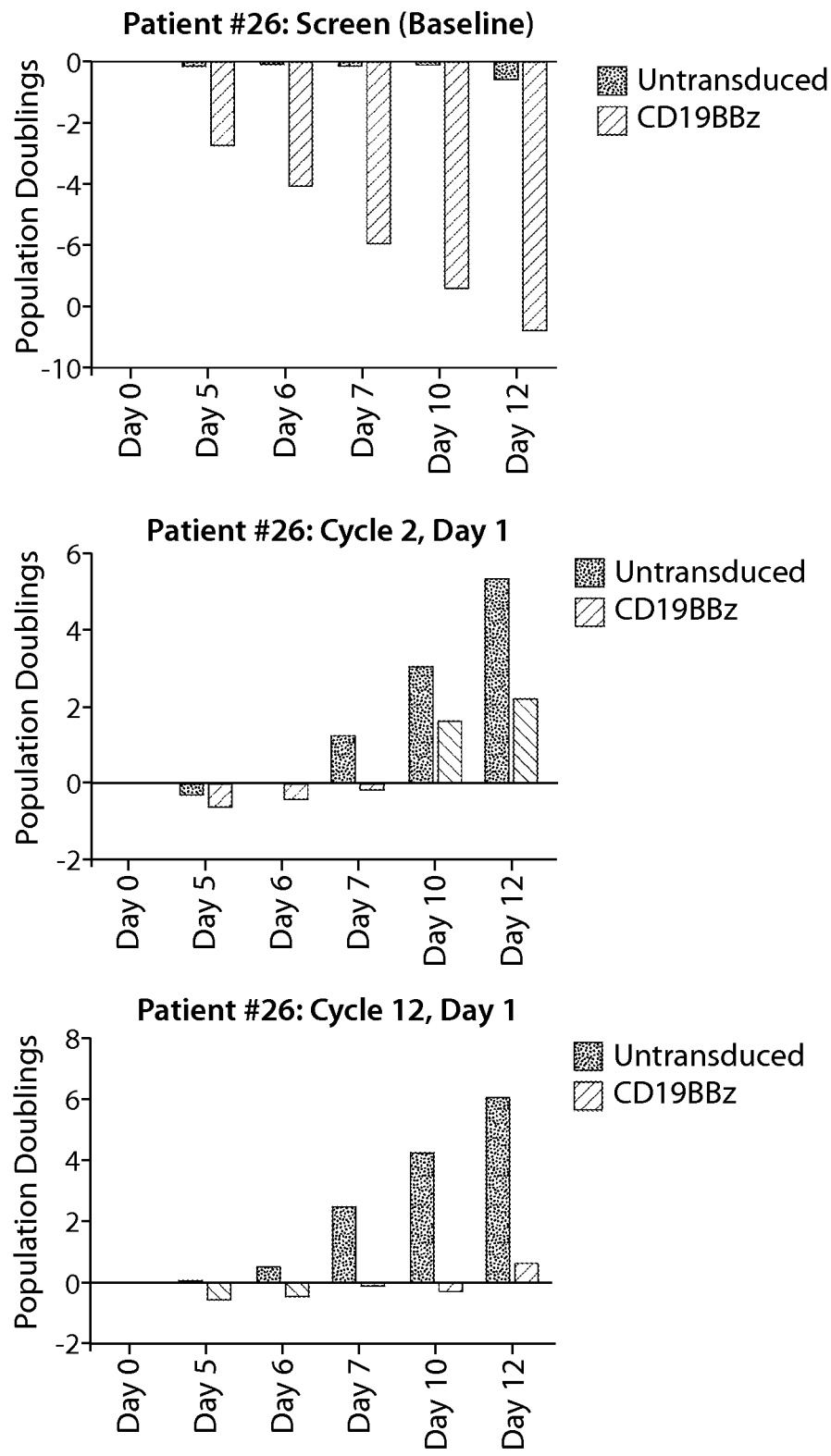
Figures 3, 27:
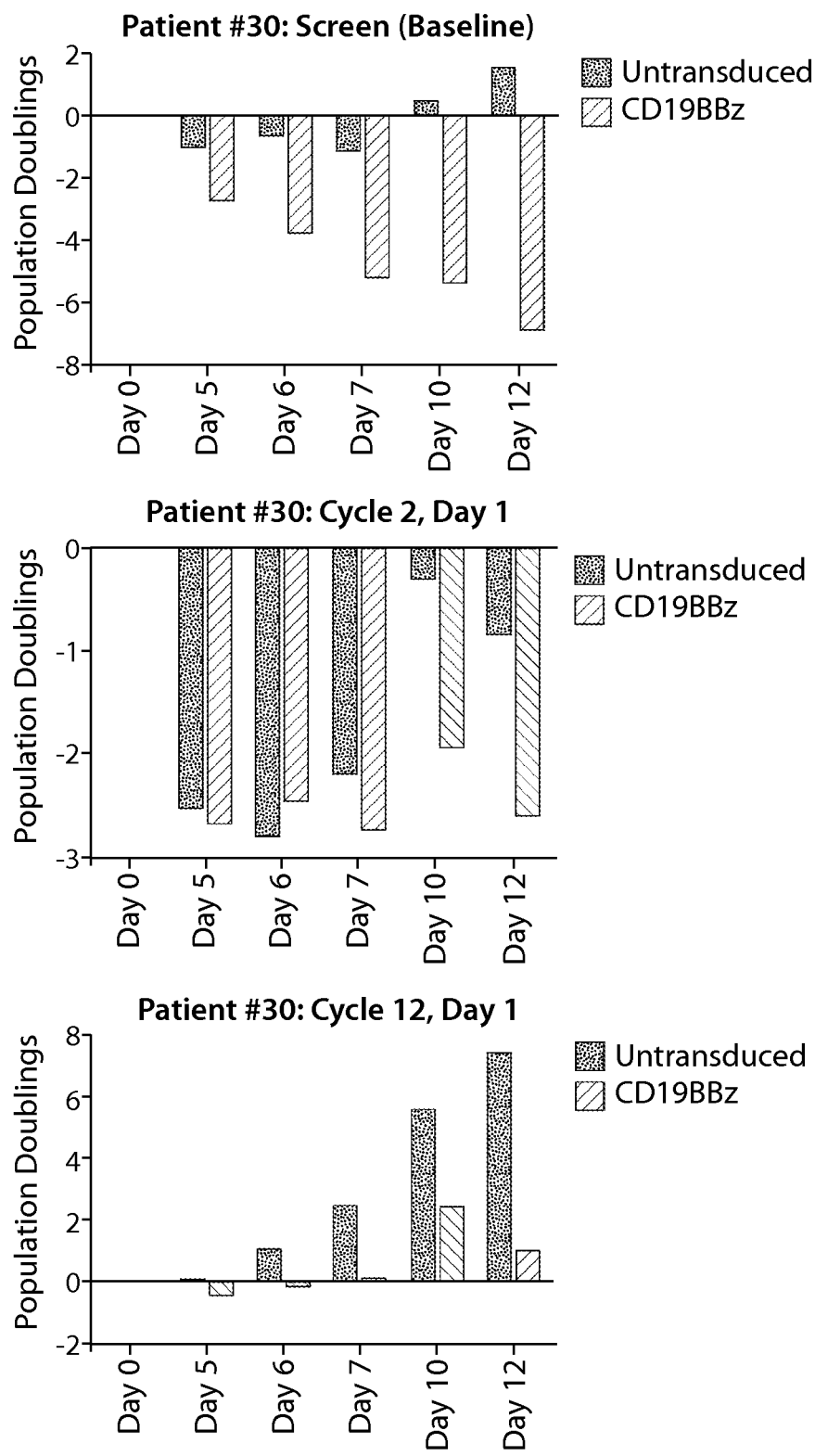

Next, the proliferation rate (or population doublings) of the CART19 cells or the untransduced cells (control) was assessed at each time point (baseline, cycle 2 at day 1, and cycle 12 at day 1) for 12 days. FIG. 27-1 through 27-3 shows the graphic representations of the population doublings over 12 days for three patients, Patient 111330039 (#39), Patient 111330026 (#26), and Patient 111330030 (#30). These results indicate that with regard to proliferation rate, PBMCs isolated between or at cycle 2, day 1 and cycle 12, day 1 are preferred for CAR transduction.

Potential Mechanisms for Ibrutinib Treatment Affecting CART19 Function

Various mechanisms of ibrutinib treatment that may affect CART19 function was assessed from CLL patient samples.

Figures 28A, 28B, 28C:
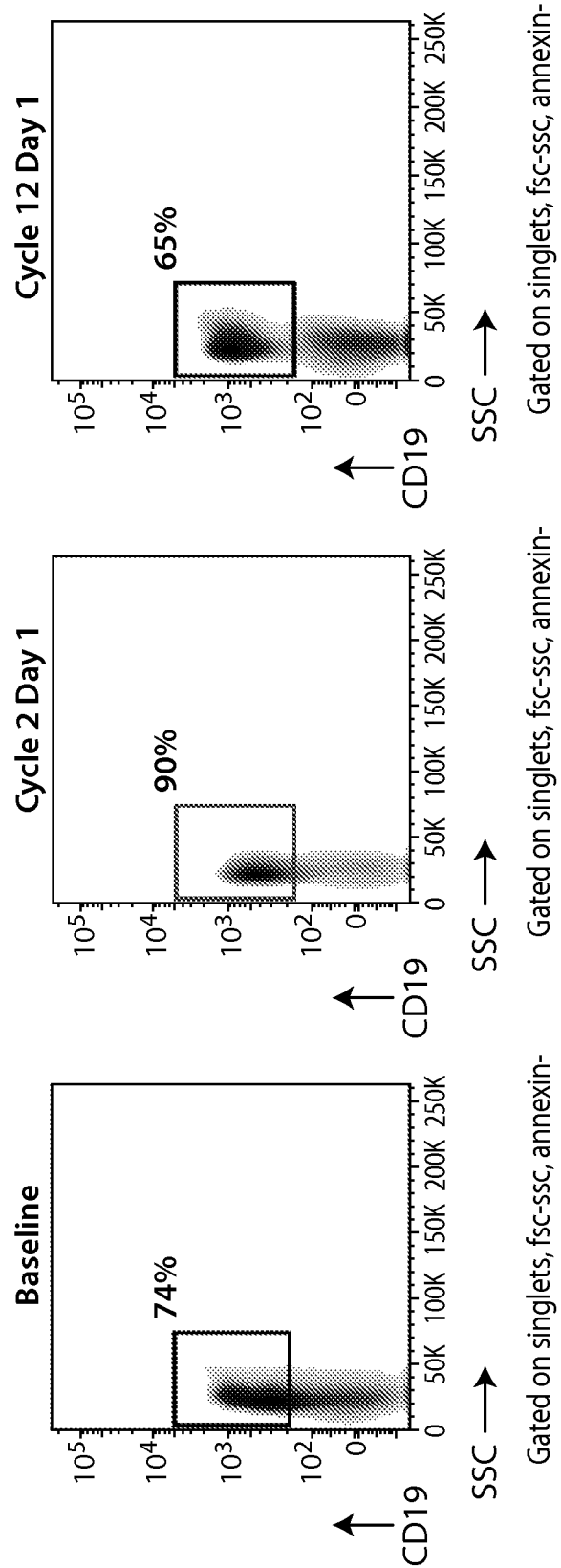
FIGS. 28A, 28B, and 28C are graphic representations demonstrating that ibrutinib treatment in CLL patients induces lymphocytosis. Cells from the patient were isolated at the indicated timepoints: baseline (FIG. 28A); cycle 2, day 1 (FIG. 28B); and cycle 12, day 1 (FIG. 28C).

Analysis of CD19-expressing (CD19+) cells was assessed by FACS analysis. PBMCs from a CLL patient undergoing ibrutinib treatment were isolated at baseline (before ibrutinib treatment), at cycle 2, day 1, and at cycle 12, day 1, and were subsequently stained for CD19. FACS analysis showed that ibrutinib causes a decrease in CD19-expressing cells (FIG. 28A, FIG. 28B, and FIG. 28C). Thus, these results indicate that ibrutinib treatment induces lymphocytosis.

Additional analysis was performed to examine CD200 expression on tumor cells over time during ibrutinib treatment. The immune-suppressive molecule CD200 is up-regulated on primary B cell CLL tumor cells. CD200 binds to its receptor, CD200R, which is expressed on cells of the monocyte/macrophage lineage and on T lymphocytes. Interaction of CD200 with its receptor delivers an inhibitory signal to the macrophage lineage altering cytokine profiles from $T_H1$ to $T_H2$ and results in the induction of regulatory T cells. Samples from Patients 111330030, 111330026, and 111330039 at baseline (screen), cycle 2, day 1, and cycle 12, day 1 were stained for annexin, CD19 (to sort for CD19-expressing tumor cells), and CD200 and analyzed by FACS. The histograms detecting CD200 expression on tumor cells from each timepoint was overlaid for each patient (FIGS. 29A, 29B, and 29C). Generally, CD200 expression on tumor cells decreased over time during ibrutinib treatment.

The frequency of PD1-expressing T cells during ibrutinib treatment was also assessed. Samples from patients were obtained at baseline, cycle 2, day 1, and cycle 12, day 1 and stained with annexin, CD3, CD8, and PD1. Cells that were negative for annexin and positive for CD3 were analyzed for CD8 and PD1 expression. The cells that express CD8 and PD1 are designated by the box in FIGS. 30A, 30B, and 30C. Comparison of FACS profiles of cells at baseline (FIG. 30A), cycle 2, day 1 (FIG. 30B), and cycle 12, day 1 (FIG. 30C), indicates that ibrutinib treatment decreases the frequency of PD1-expressing cells over time.

The data obtained from the experiments described above indicate that the optimal time for administering CART19 therapy to CLL patients receiving ibrutinib is between cycle 2 and cycle 12, or at cycle 12.

Example 10: CAR19 T Cell Therapy for Hodgkin Lymphoma

Figure 33:
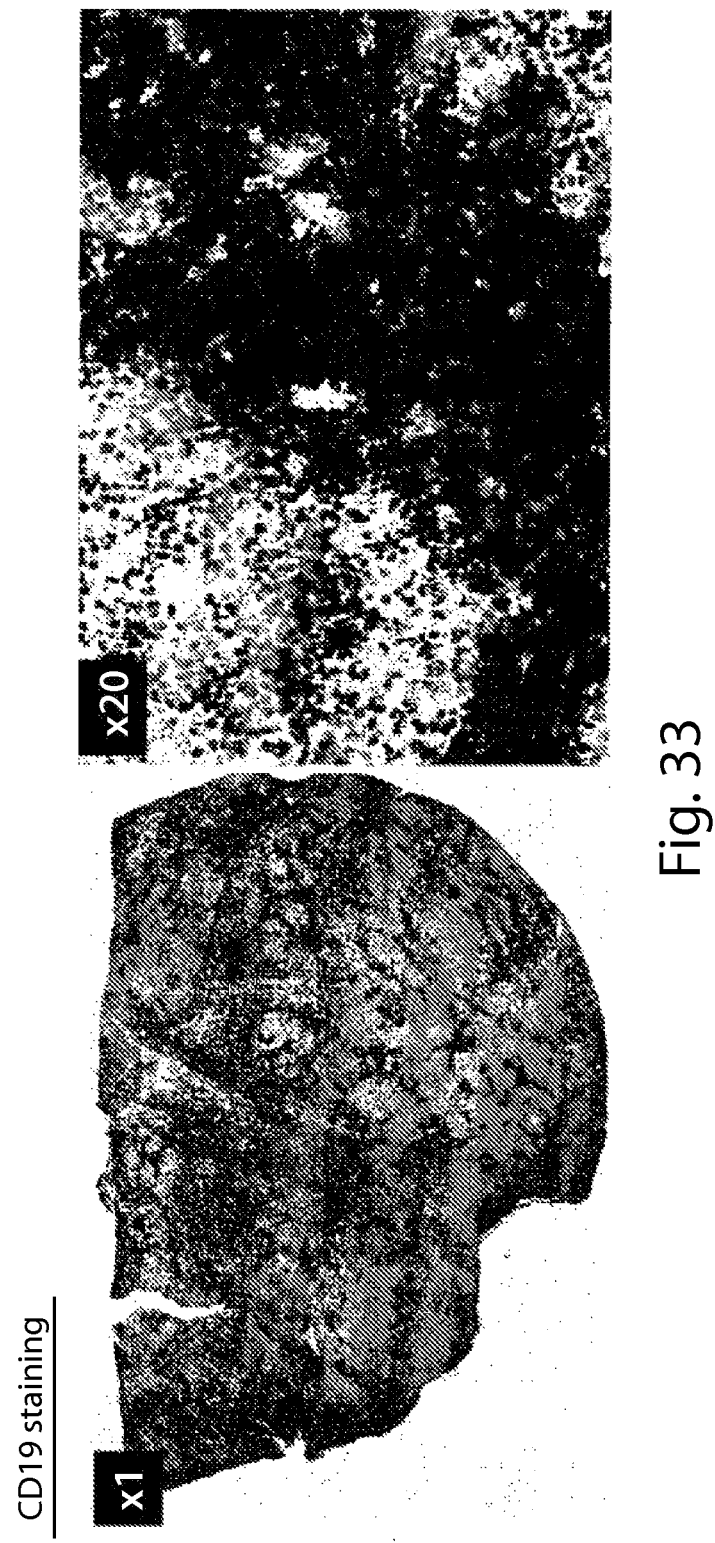
FIG. 33 (left panel and right panel) are images of immunohistochemical analysis of a Hogdkin's lymphoma showing CD19 expressing cells present in the tumor.

CAR19 T cell therapy can also be used to treat Hodgkin lymphoma (HL). Hodgkin lymphoma is characterized by the presence of malignant Hodgkin Reed-Sternberg (HRS) cells that are derived from clonal germinal center B cells. There are several factors that indicate the therapeutic efficacy of CAR19 T cell therapy for HL. CD19 staining of HL tumors shows CD19-expressing (CD19$^+$) cells within the tumor and tumor microenvironment (FIG. 33). A study has shown that a clonal B cell population (CD20$^+$CD27$^+$ALDH$^+$) that expresses CD19 is responsible for the generation and maintenance of Hodgkin lymphoma cell lines, and also circulates in the blood of most HL patients (Jones et al., Blood, 2009, 113(23):5920-5926). This clonal B cell population has also been suggested to give rise to or contribute to the generation of the malignant HRS cells. Thus, CART19 therapy would deplete this B cell population that contributes to tumorigenesis or maintenance of tumor cells. Another study showed that B cell depletion retards solid tumor growth in multiple murine models (Kim et al., J Immunotherapy, 2008, 31(5): 446-57). In support of the idea that depletion of B cells in the HL tumormicroenvironment results in some anti-tumor effect, current therapies, such as rituxan, are being clinically tested for targeting and depletion of tumoral B cells in HL (Younes et al., Blood, 2012, 119(18):4123-8). De novo carcinogenesis related to chronic inflammation has also been shown to be B-cell dependent (de Visser, et al., Cancer Cell, 2005, 7(5):411-23). The results from these studies indicate that targeting of the B cell population, particularly in the HL tumor microenvironment, would be useful for treating HL, by reducing or inhibiting disease progression or tumor growth.

In addition, normal CD19-expressing B cells also infiltrate the tumor microenvironment in HL. Previous studies with CART19 therapy in CLL and ALL (e.g., described in Examples 4 and 5) show that CART19 exposure to CD19+ targets leads to cytokine production and macrophage production. Thus, modulation of the HL tumor microenvironment from a pro-tumor microenvironment to an anti-tumor microenvironment can be achieved by infusing CART19 to interact with normal CD19+ B cells present in the HL. For example, CART19 exposure to CD19-expressing targets causes cytokine production, e.g., inflammatory cytokines, that promote anti-tumor activity through the expansion of cytotoxic T cells, activation of macrophages, and recruitment of other immune effector cells with various functions that inhibit tumor growth, such as leukocytes, macrophages, and antigen-presenting cells. Because the target CD19+ B cells may not be malignant (e.g., normally circulating B cells), a transient rather than protracted CART19 effect may be preferred for modulation of the tumor microenvironment.

Figure 34:
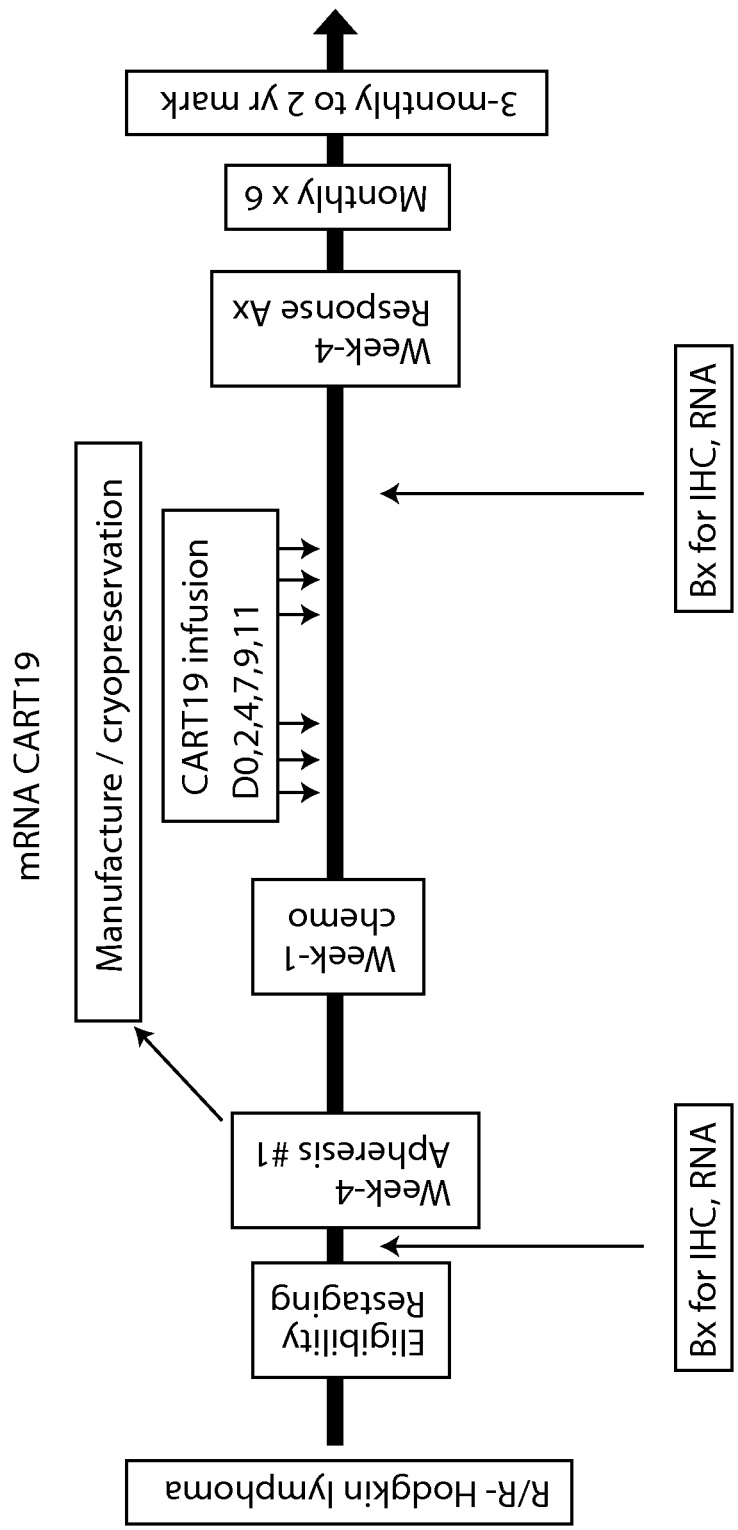
FIG. 34 is a schematic diagram of the experimental set-up for a study to assess the therapeutic efficacy of CART19 treatment in patients with Hodgkin lymphoma.

A study to examine the therapeutic efficacy of CART19 therapy in HL patients can be performed as described below (FIG. 34). The study will also assess the safety and tolerability of CART19 in HL subjects, and determine the effect of CART19 cells on the HL tumor microenvironment.

8 patients with classical HL are treated in this study. Patients are of all ages, though separate protocols for drug delivery can be established for pediatric and adult patients. Patients in this study have no available potentially curative treatment options (such as autologous (ASCT) or allogeneic stem cell transplantation), or are not suitable for such curative treatment options. For example, patients can be any of the following: PET+ after salvage chemotherapy, PET+ after treatment with brentuximab, or PET+ after ASCT with or without prior brentuximab exposure. The patients will have a limited prognosis (several months to less than or equal to 2 year expected survival) with currently available therapies. And finally, the patients will not have received anti-CD20 antibody therapy. Patients are excluded due to lack of feasibility, e.g., if the patient has insufficient numbers of T cells for 6 infusions of CART19.

An mRNA CAR19 is produced by in vitro transcription. The CAR19 mRNA is electroporated into donor T cells, and the resulting cells are expanded and stimulated by incubation with CD3/CD28 beads. Dosages containing $1 \times 10^8$-$5 \times 10^8$ RNA-electroporated CAR19 T cells are delivered to the patient three times a week for two weeks (e.g., at day 0, 2, 4, 7, 9 and 11). The overall response rate will be assessed by clinical, CT, and PET scanning at 1 month after treatment. Response and survival will be monitored monthly for the first 6 months, then every 3 months until 2 years after the first CART19 infusion (day 0). Monitoring techniques include biopsy of the tumor or lymph node (e.g., for immunohistochemical analysis and/or RNA for gene expression profiling) and PET scanning before and after CART19 treatment. For example, the effect of the CART19 cells on the HL tumor microenvironment are analyzed by comparing the results of gene expression profiling performed on accessible lymph node biopsies from selected patients before treatment and approximately one week after treatment (or the appropriate time after treatment to allow for alteration of cellular phenotype). To assess the safety and tolerability of CART19 treatment, the frequency and severity of adverse events are reported, including the frequency of cytokine release syndrome (CRS) and macrophage activation syndrome (MAS).

Chemotherapy may be administered concurrently with CART19 treatment. The first dose of CART19 can be preceded by lymphodepleting chemotherapy, e.g., cytoxan.

Example 11: Non-Responder Subset of CLL Patients Exhibit Increased Expression of Immune Checkpoint Inhibitor Molecules In this study, CART19 cells from clinical manufacture from 34 CLL patients were assessed for expression of immune checkpoint inhibitor molecules, such as PD-1, LAG3, and TIM3. The response of this cohort to CART19 was known and hence a correlation between response and biomarker expression patterns could be assessed.

Manufactured CART19 cells from CLL patients with different responses to CART therapy were analyzed by flow cytometry to determine the expression of CAR and the immune checkpoint inhibitor molecules PD-1, LAG3, and TIM3. The CART19 cells were from: healthy donors (HD) (n=2); CLL patients that responded to CART therapy (CR) (n=5); CLL patients that partially responded to CART therapy (PR) (n=8); CLL patients that did not respond to CART therapy (NR) (n=21). Cells were stained with fluorescently labeled antibodies that specifically recognize CD3, CD4, CD8, CD27, CD45RO, the CAR19 molecule, and immune checkpoint molecules PD-1, LAG3, and TIM3, according to standard methods for flow cytometry analysis known in the art. Expression of each marker, e.g., CD4+, CD8+, etc., was determined by flow cytometry analysis software, and subpopulations (e.g., CD4+ T cells, CD8+ T cells, or CAR19-expressing T cells) were further analyzed for the expression of immune checkpoint molecules PD-1, LAG3, and TIM3.

Figure 35C:
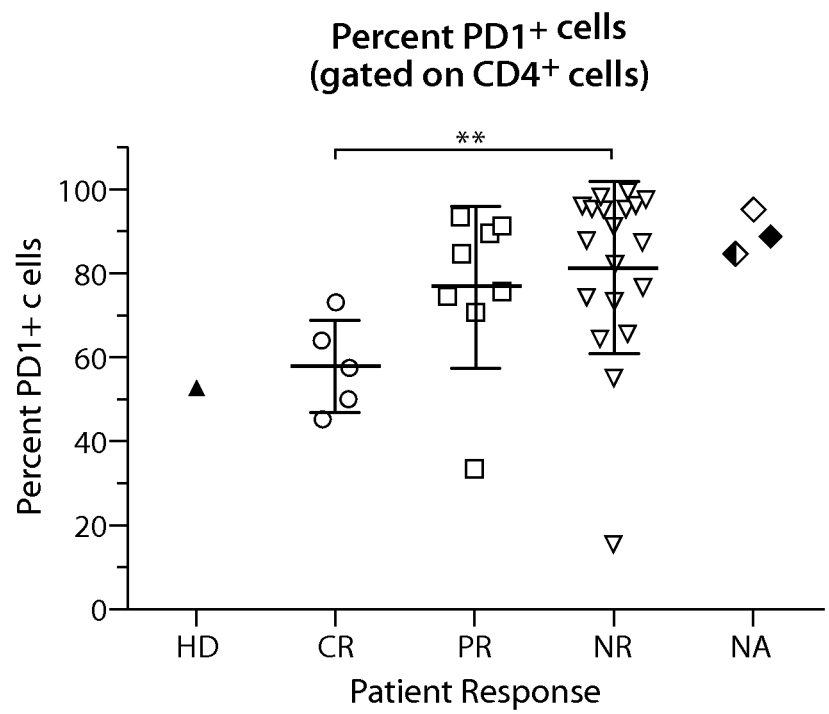

An example of the flow cytometry profiles analysis used to determine surface marker expression is shown in FIGS. 35A and 35B. T cells expressing CD4 were determined using flow cytometry, and were further analyzed for CAR19 and PD-1 expression, such that the x-axis of the profiles indicate CAR19 expression (the top left (Q5) and bottom left (Q8) quadrants show the CAR19-negative CD4+ cells, while the top right (Q6) and bottom right (Q7) quadrants show the CAR19-expressing CD4+ cells) and the y-axis shows PD-1 expression (the bottom left (Q8) and right (Q7) quadrants show the PD-1 negative CD4+ cells and the top left (Q5) and right (Q6) quadrants show the PD-1-expressing CD4+ cells). In the CD4+ population from a CART responder, 44.7% of the CD4+ cells overall expressed PD-1, and about 22.3% of the CAR19-expressing cells were PD-1 positive, while 27.2% of CAR19-expressing cells were PD-1 negative (FIG. 35A). In contrast, in the CD4+ population from a non-responder, there was a significant decrease in CAR19-expressing cells overall (about 15.3% compared to the 49.5% in CR), with 14.7% of the CAR19-expressing cells being PD-1 positive while only 0.64% were PD-1 negative (FIG. 35B). Comparison between the profiles in FIG. 35A and FIG. 35B shows that a much higher percentage of the CD4+ cells from a non-responder express PD-1 (about 92.9%) compared to the CART responder (about 44.7%).

Figure 35D:
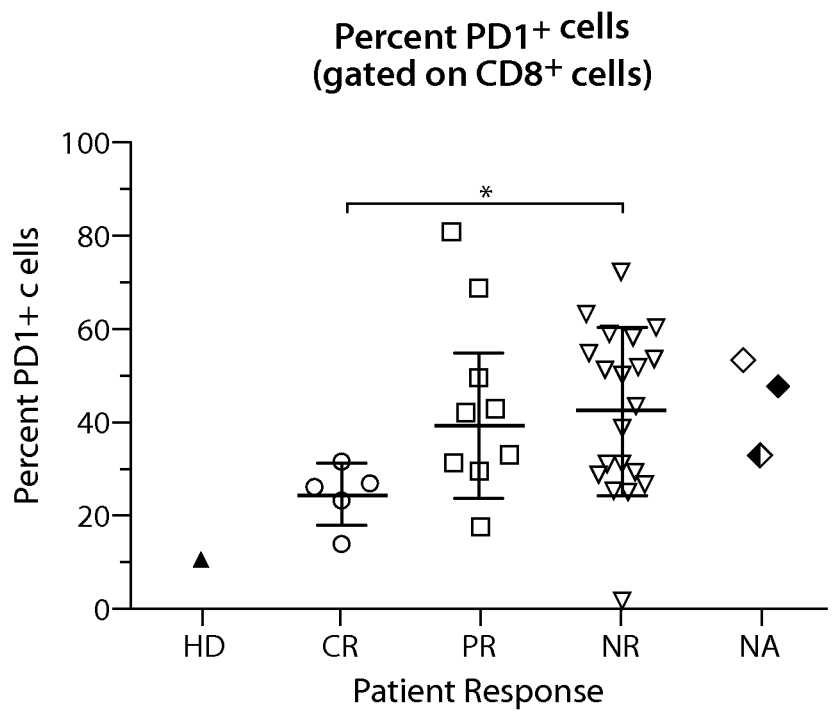

Using the methods and analysis described above, the percentage of PD-1 expressing (PD-1+) cells of the CD4+ population and the CD8+ population was determined for each patient in each response group. Non-responders were shown to have a greater percentage of PD-1+ cells in both the CD4+(FIG. 35C) and CD8+(FIG. 35D) populations compared to those that responded to CAR therapy (CR); the increase of average PD-1 percentage was statistically significant for both CD4+ and CD8+ populations. Partial responders (PR) exhibited higher percentages of PD-1+ cells than responders (CR) in both CD4+(FIG. 35C) and CD8+ (FIG. 35D) populations.

Figure 36A:
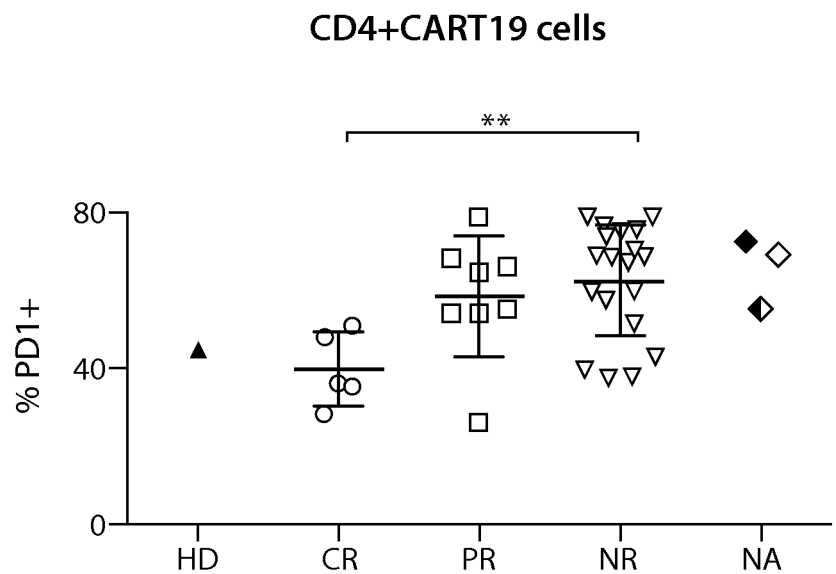
FIGS. 36A and 36B show the distribution of PD1 expression in CD4 and CAR19-expressing cells (FIG. 36A) or CD8 and CAR19-expressing cells (FIG. 36B) from groups of subjects with different responses to CART therapy.
Figure 36B:
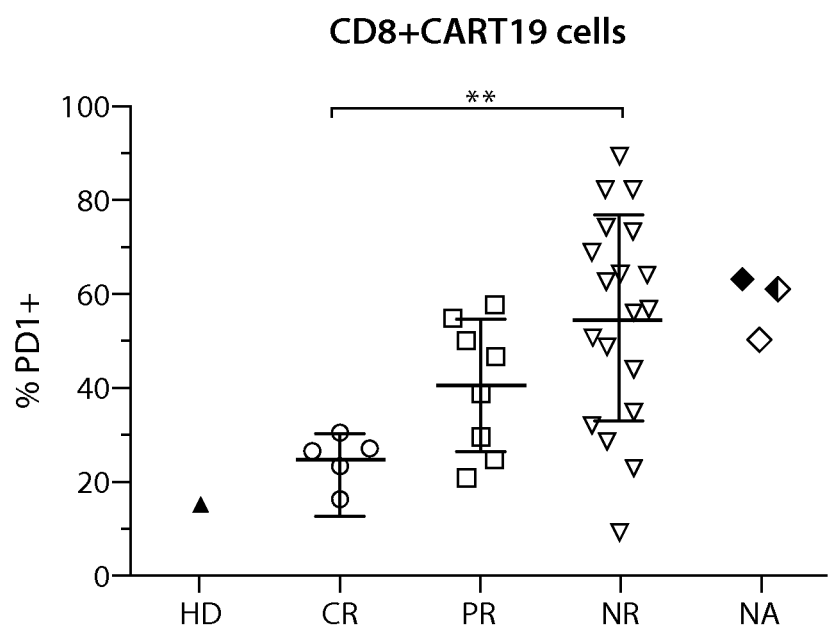

Next, the percentage of PD-1 expressing (PD-1+) cells of the CAR19-expressing CD4+ population and the CAR19-expressing CD8+ population was determined for each patient in each response group. Similar analysis was performed as above, with the additional step of analyzing the CD4+ and CD8+ cells for CAR19-expression, and after identification of the CAR19-expressing cells, determining the percentage of cells with PD-1 expression from the populations of CAR19-expressing cells. A similar trend as that observed in the CD4+ and CD8+ overall populations was observed for the CAR19 expressing CD4+ and CD8+ populations: non-responders were shown to have a greater percentage of PD-1+ cells in both the CD4+(FIG. 36A) and CD8+(FIG. 36B) populations compared to those that responded to CAR therapy (CR); the increase of average PD-1 percentage was statistically significant for both CD4+ and CD8+ populations. Partial responders (PR) exhibited higher percentages of PD-1+ cells than responders (CR) in both CD4+(FIG. 36A) and CD8+(FIG. 36B) populations.

Figure 37:
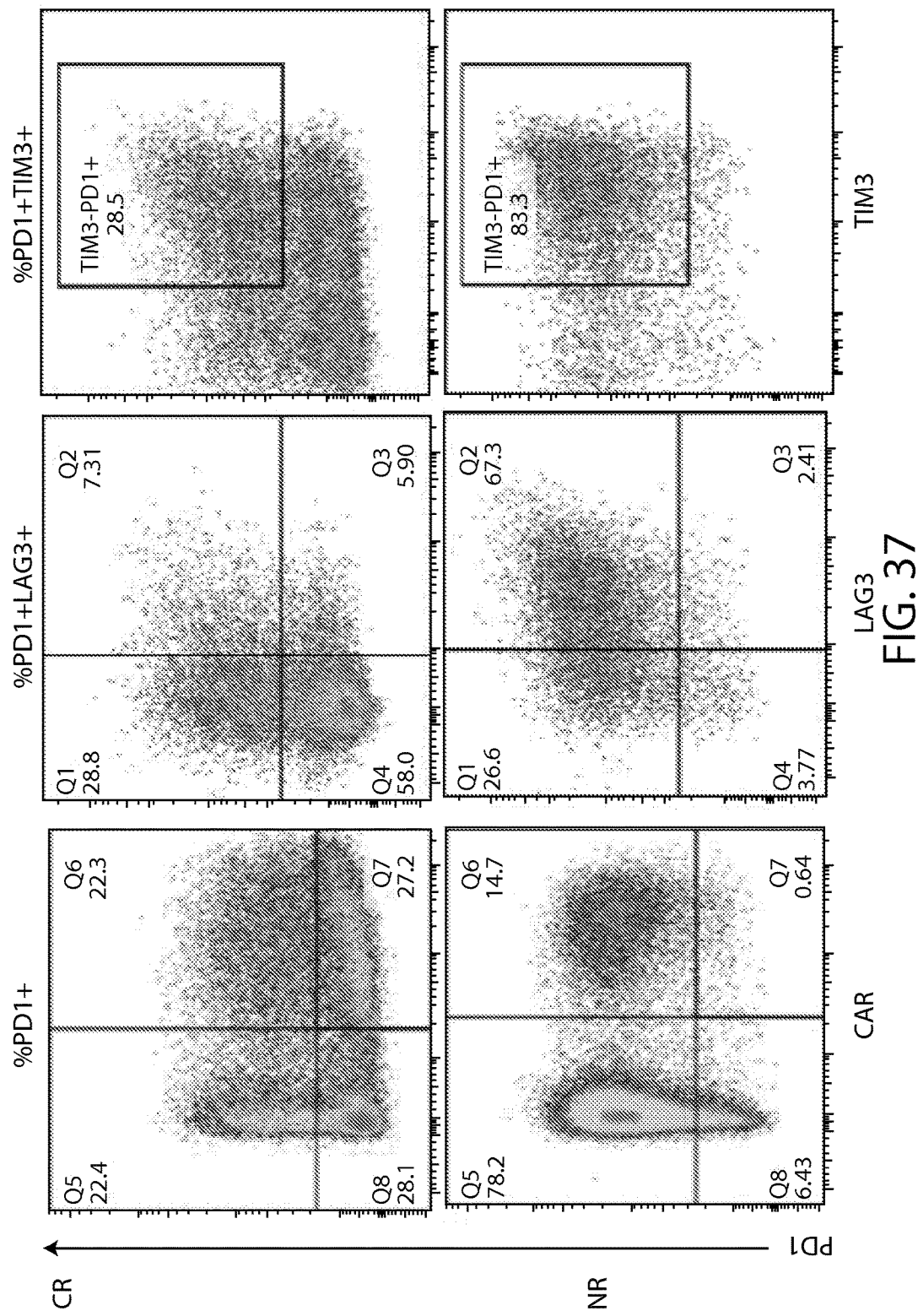
FIG. 37 shows flow cytometry analysis of PD1, CAR 19, LAG3, and TIM3 expression on T cells from subjects that are complete responders (CR) or non-responders (NR) to CART therapy.
Figure 38A:
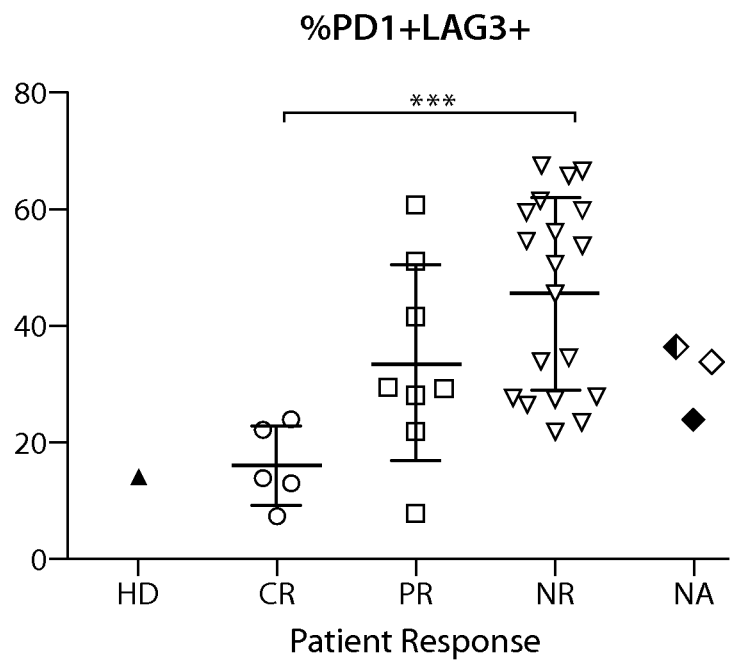
FIGS. 38A and 38B show the distribution of PD1 and LAG3 expression (FIG. 38A) or PD1 and TIM3 expression (FIG. 38B) from groups of subjects with different responses to CART therapy.
Figure 38B:
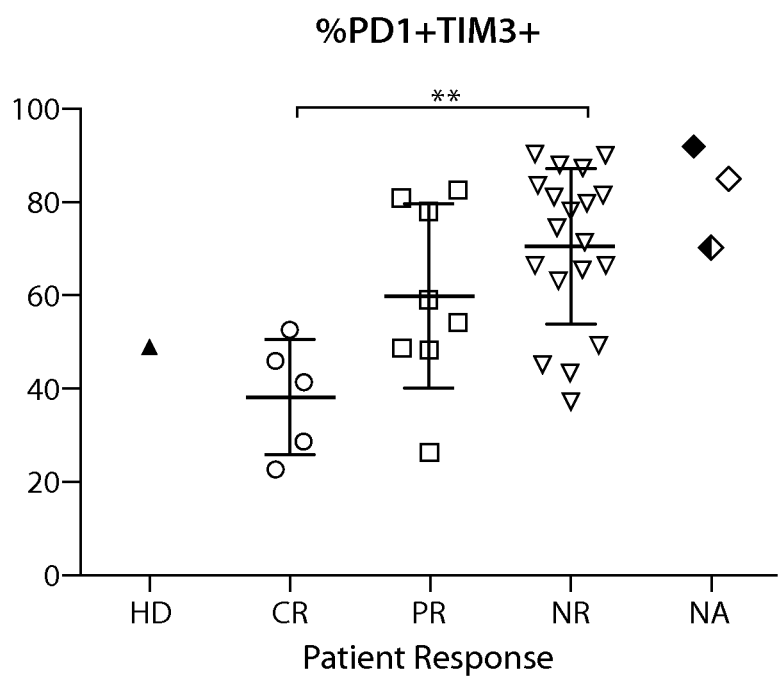

Further analysis was performed to determine the distribution of cells expressing PD-1, LAG3, and TIM3 from patients with different responses to CAR therapy. Representative cell profile analysis for PD-1, LAG3, and TIM3 expression in the CD4+ population is shown in FIG. 37. The cell populations were first analyzed for CD4+ and CD8+ expression. The CD4+ population (or CD8+ population, not shown) was then analyzed for PD-1 and CAR19 expression (FIG. 37, left profiles). As described previously, non-responders (NR) had a significantly increased percentage of cells that were PD-1+ overall compared to CART responders (CR) (about 92.9% PD-1 positive for NR compared to 44.7% PD-1 positive for CR). Moreover, in non-responders, CAR19-expressing cells were mostly PD-1 positive (14.7% PD-1 positive and CAR+ compared to 0.64% PD-1 negative and CAR+). Then the populations were analyzed for PD-1 and LAG3 co-expression (FIG. 37, middle profiles). Cells that expressed both PD-1 and LAG3 are shown in the top right quadrant (Q2). Non-responders had a significantly increased percentage of cells that expressed both immune checkpoint inhibitors, PD-1 and LAG3, compared to CART responders (67.3% compared to 7.31%). PD-1 expression was also analyzed with TIM3 expression. In FIG. 37, right profiles, the box indicates the cells that express both PD-1 and TIM3. Similar to the results obtained with PD-1 and LAG3, the non-responders had a significantly higher percentage of cells that expressed both immune checkpoint inhibitors, PD-1 and TIM3, compared to CART responders (83.3% compared to 28.5%). The percentage of PD-1 expressing cells (PD1+), PD-1 and LAG3-expressing cells (PD1+LAG3+), and PD-1 and TIM3-expressing cells (PD1+ TIM3+) was determined for each patient in each response group using the flow cytometry analysis as described above. Non-responders were shown to have an increased percentage of PD1+LAG3+ cells (FIG. 38A) and PD1+TIM3+ cells (FIG. 38B) compared to CART responders that was statistically significant for both cell populations. Partial responders also showed an increased percentage of both cell populations compared to CART responders, with the averages being decreased compared to the non-responders.

These results indicate that patients that do not respond to CAR therapy exhibit increased expression of immune checkpoint inhibitors (e.g., PD-1, LAG3, and TIM3) compared to patients that respond or partially respond to CAR therapy. Thus, these results show that agents that inhibit or decrease expression of immune checkpoint inhibitors, e.g., PD-1, LAG3, or TIM3, may be useful for administration to patients receiving CAR therapy to prevent immune suppression through immune checkpoint pathways (e.g., mediated by PD-1, LAG3, or TIM3), thereby increasing the efficacy of the CAR-expressing cells.

Example 12: Effects of mTOR Inhibition on Immunosenescence in the Elderly

One of the pathways most clearly linked to aging is the mTOR pathway. The mTOR inhibitor rapamycin has been shown to extend lifespan in mice and improve a variety of aging-related conditions in old mice (Harrison, D E et al. (2009) Nature 460:392-395; Wilkinson J E et al. (2012) Aging Cell 11:675-682; and Flynn, J M et al. (2013) Aging Cell 12:851-862). Thus, these findings indicate that mTOR inhibitors may have beneficial effects on aging and aging-related conditions in humans.

An age-related phenotype that can be studied in a short clinical trial timeframe is immunosenescence. Immunosenescence is the decline in immune function that occurs in the elderly, leading to an increased susceptibility to infection and a decreased response to vaccination, including influenza vaccination. The decline in immune function with age is due to an accumulation of immune defects, including a decrease in the ability of hematopoietic stem cells (HSCs) to generate naïve lymphocytes, and an increase in the numbers of exhausted PD-1 positive lymphocytes that have defective responses to antigenic stimulation (Boraschi, D et al. (2013) Sci. Transl. Med. 5:185ps8; Lages, C S et al. (2010) Aging Cell 9:785-798; and Shimatani, K et al., (2009) Proc. Natl. Acad. Sci. USA 106:15807-15812). Studies in elderly mice showed that 6 weeks of treatment with the mTOR inhibitor rapamycin rejuvenated HSC function leading to increased production of naïve lymphocytes, improved response to influenza vaccination, and extended lifespan (Chen, C et al. (2009) Sci. Signal. 2:ra75).

To assess the effects of mTOR inhibition on human aging-related phenotypes and whether the mTOR inhibitor RAD001 ameliorates immunosenescence, the response to influenza vaccine in elderly volunteers receiving RAD001 or placebo was evaluated. The findings presented herein suggest that RAD001 enhanced the response to influenza vaccine in elderly volunteers at doses that were well tolerated. RAD001 also reduced the percentage of programmed death (PD)-1 positive CD4 and CD8 T lymphocytes that accumulate with age. These results show that mTOR inhibition has beneficial effects on immunosenescence in elderly volunteers.

As described herein, a 6 week treatment with the mTOR inhibitor RAD001, an analog of rapamycin, improved the response to influenza vaccination in elderly human volunteers.

Methods

Study Population

Elderly volunteers >=65 years of age without unstable underlying medical diseases were enrolled at 9 sites in New Zealand and Australia. Exclusion criteria at screening included hemoglobin <9.0 g/dL, white blood cell count <3,500/mm$^3$, neutrophil count <2,000/mm$^3$, or platelet count <125,000/mm$^3$, uncontrolled diabetes, unstable ischemic heart disease, clinically significant underlying pulmonary disease, history of an immunodeficiency or receiving immunosuppressive therapy, history of coagulopathy or medical condition requiring long-term anticoagulation, estimated glomerular filtration rate <30 ml/min, presence of severe uncontrolled hypercholesterolemia (>350 mg/dL, 9.1 mmol/L) or hypertriglyceridemia (>500 mg/dL, 5.6 mmol/L).

Baseline demographics between the treatment arms were similar (Table 8). Of the 218 subjects enrolled, 211 completed the study. Seven subjects withdrew from the study. Five subjects withdrew due to adverse events (AEs), one subject withdrew consent, and one subject left the study as a result of a protocol violation.

TABLE 8

Demographic and Baseline characteristics of the Study Patients

| Population | | RAD001 0.5 mg daily N = 53 | RAD001 5 mg weekly N = 53 | RAD001 20 mg weekly N = 53 | Placebo pooled N = 59 | Total N = 218 |
|---|---|---|---|---|---|---|
| Age (Years) | Mean (SD) | 70.8 (5.0) | 72.0 (5.3) | 71.4 (5.2) | 71.1 (5.1) | 71.3 (5.2) |
| Gender | Male-n (%) | 34 (64%) | 27 (51%) | 32 (60%) | 31 (53%) | 124 (57%) |
| BMI* (kg/m2) | Mean (SD) | 27.4 (4.2) | 28.8 (5.0) | 28.0 (4.1) | 28.0 (4.2) | 28.0 (4.4) |
| Race-n (%) | Caucasian | 48 (91%) | 50 (94%) | 46 (87%) | 54 (92%) | 198 (91%) |
| | Other | 5 (9%) | 3 (6%) | 7 (13%) | 5 (8%) | 20 (9%) |

*The body-mass index is weight in kilograms divided by the square of the height in meters Study Design and Conduct From December 2011 to April 2012, 218 elderly volunteers were enrolled in a randomized, observer-blind, placebo-controlled trial. The subjects were randomized to treatment arms using a validated automated randomization system with a ratio of RAD001 to placebo of 5:2 in each treatment arm. The treatment arms were:

RAD001 0.5 mg daily or placebo
RAD001 5 mg weekly or placebo
RAD001 20 mg weekly or placebo The trial was observer-blind because the placebo in the RAD001 0.5 mg daily and 20 mg weekly cohorts differed slightly from the RAD001 tablets in those cohorts. The study personnel evaluating the subjects did not see the study medication and therefore were fully blinded. The treatment duration for all cohorts was 6 weeks during which time subjects underwent safety evaluations in the clinic every 2 weeks. After subjects had been dosed for 4 weeks, RAD001 steady state levels were measured pre-dose and at one hour post dose. After completing the 6 week course of study drug, subjects were given a 2 week drug free break to reverse any possible RAD001-induced immunosuppression, and then were given a 2012 seasonal influenza vaccination (Agrippal®, Novartis Vaccines and Diagnostics, Siena, Italy) containing the strains H1N1 A/California/07/2009, H3N2 A/Victoria/210/2009, B/Brisbane/60/2008. Four weeks after influenza vaccination, subjects had serum collected for influenza titer measurements. Antibody titers to the 3 influenza vaccine strains as well as to 2 heterologous strains (A/H1N1 strain A/New Jersy/8/76 and A/H3N2 strain A/Victoria/361/11) were measured by standard hemagglutination inhibition assay (Kendal, A P et al. (1982) *Concepts and procedures for laboratory-based influenza surveillance. Atlanta: Centers for Disease Control and Prevention* B17-B35). Levels of IgG and IgM specific for the A/H1N1/California/07/2009 were measured in serum samples taken before and 4 weeks after influenza vaccination as described previously (Spensieri, F. et al. (2013) *Proc. Natl. Acad. Sci. USA* 110:14330-14335). Results were expressed as fluorescence intensity.

All subjects provided written informed consent. The study was conducted in accordance with the principals of Good Clinical Practice and was approved by the appropriate ethics committees and regulatory agencies.

Safety

Adverse event assessment and blood collection for hematologic and biochemical safety assessments were performed during study visits. Adverse event information was also collected in diaries that subjects filled out at home during the 6 weeks they were on study drug. Data on all adverse events were collected from the time of informed consent until 30 days after the last study visit. Events were classified by the investigators as mild, moderate or severe.

Statistical Analysis

The primary analysis of geometric mean titer ratios was done using a normal Bayesian regression model with non-informative priors. This model was fitted to each antibody titer on the log scale. The primary outcome in each model was the Day 84 measurement. The Day 63 measurement was included in the outcome vector. The model fitted using SAS 9.2 proc mixed with the prior statement. The covariance structure of the matrix was considered as unstructured (option type=UN). A flat prior was used. For the secondary analysis of seroconversion rates, logistic regression was used.

The intention to treat population was defined as all subjects who received at least one full dose of study drug and who had no major protocol deviations impacting efficacy data. 199 out of the total of 218 subjects enrolled in the study were in the intention to treat population.

Immunophenotyping

Peripheral blood mononuclear cells were isolated from whole blood collected at 3 time points: baseline; after 6 weeks of study drug treatment; and at the end of study when subjects had been off study drug for 6 weeks and 4 weeks after influenza vaccination. Seventy-six PBMC subsets were analyzed by flow cytometry using 8-color immunophenotyping panels at the Human Immune Monitoring Center at Stanford University, Calif., USA as described previously (Maecker, H T et al. (2012) *Nat Rev Immunol.* 12:191-200). Seventy-six PBMC subsets were analyzed by flow cytometry using 8-color lyophilized immunophenotyping panels (BD Lyoplate, BD Biosciences, San Diego, Calif.). PBMC samples with viability >80% and yield of $2\times10^6$ cells or greater were included in the analysis.

Relative changes of the immunophenotypes from baseline to Week 6 of study drug treatment and from baseline to the end of study (Week 12) were calculated for each of the RAD001 dosing cohorts. Student T test was conducted to examine if the relative change of the immunophenotypes from baseline to the two blood sampling time points was significantly different from zero, respectively, within each dosing group after adjusting for placebo effect. Missing data imputation in treatment effect analysis was not conducted. Therefore if a patient has a missing phenotype data at baseline, this patient was not be included in the analysis for this phenotype. If a patient had a missing phenotype data at 6 or 12 weeks, then this patient did not contribute to the analysis of this phenotype for the affected timepoint.

608 tests in 76 phenotypes under 3 dosing groups were conducted to compare the treatment effect against the placebo effect. Stratified false discovery rate (FDR) control methodology was implemented to control the occurrence of false positives associated with multiple testing yet provide considerably better power. The cell type group was taken as the stratification factor and conducted FDR (q-value) calculation within each stratum respectively. All null-hypotheses were rejected at 0.05 significance level with corresponding q-value ≤0.1. The multiple testing adjustment strategy with rejecting at 0.05 significance level and corresponding q<0.1 ensured that less than 10% of the findings are false.

In a second analysis, the immunophenotype changes between pooled treatment and placebo groups, where all three RAD001 dosing groups were combined. To determine which immunophenotype changes differed between the treated and placebo groups, within-patient cell count ratios for each measured phenotype were calculated between baseline and Week 6 of study drug treatment and between baseline and the end of study (Week 12). The ratios were log transformed, and analyzed by analysis of covariance at each time point in order to detect a difference between the pooled treatment and placebo groups. 152 tests in 76 phenotypes were performed to compare the pooled treatment effect against the placebo effect. Stratified false discovery rate (FDR) control methodology was implemented to control the occurrence of false positives associated with multiple testing yet provide considerably better power (Benjamini, Y. et al. (1995) *J. Roy. Statist.* 57:289-300; and Sun, L. et al. (2006) *Genet. Epidemiol.* 30:519-530). The cell type group was taken as the stratification factor and FDR (q-value) calculation was conducted within each stratum respectively. All null-hypotheses at 0.05 significance level and q-value less than 20% were rejected. This can be interpreted as rejecting only those hypotheses with P values less than 0.05 and less than 20% probability that the each observed significant result is due to multiple testing.

Results

In general, RAD001 was well tolerated, particularly the 0.5 mg daily and 5 mg weekly dosing regimens. No deaths occurred during the study. Three subjects experienced four serious adverse events (SAEs) that were assessed as unrelated to RAD001. The 4 SAEs were retinal hemorrhage of the left eye with subsequent blindness in a subject with normal platelet counts who had completed a 6 week course of 5 mg weekly RAD001 6 weeks previously; severe back pain in a subject treated with placebo and severe gastroenteritis in a subject treated with placebo. A list of treatment-related adverse events (AEs) with an incidence >2% in any treatment group is provided in Table 9. The most common RAD001-related AE was mouth ulcer that, in the majority of cases, was of mild severity. Overall, subjects who received RAD001 had a similar incidence of severe AEs as those treated with placebo. Only one severe AE was assessed as related to RAD001 mouth ulcers in a subject treated with 20 mg weekly RAD001.

TABLE 9

Incidence of treatment-related AEs >2% in any treatment group by preferred term

| | RAD001 0.5 mg daily N = 53 n (%) | RAD001 5 mg weekly N = 53 n (%) | RAD001 20 mg weekly N = 53 n (%) | Placebo, pooled N = 59 n (%) | Total N = 218 n (%) |
|---|---|---|---|---|---|
| Total AE(s) | 35 | 46 | 109 | 21 | 211 |
| Patients with AE(s) | 22 (41.5%) | 20 (37.7%) | 27 (50.9%) | 12 (20.3%) | 81 (37.2%) |
| Mouth ulceration | 6 (11.3%) | 2 (3.8%) | 9 (17.0%) | 3 (5.1%) | 20 (9.2%) |
| Headache | 0 | 2 (3.8%) | 9 (17.0%) | 1 (1.7%) | 12 (5.5%) |
| Blood cholesterol increased | 2 (3.8%) | 2 (3.8%) | 2 (3.8%) | 0 | 6 (2.8%) |
| Diarrhea | 1 (1.9%) | 4 (7.5%) | 1 (1.9%) | 0 | 6 (2.8%) |
| Dyspepsia | 0 | 3 (5.7%) | 2 (3.8%) | 1 (1.7%) | 6 (2.8%) |
| Fatigue | 0 | 2 (3.8%) | 4 (7.5%) | 0 | 6 (2.8%) |
| Low density lipoprotein increased | 2 (3.8%) | 1 (1.9%) | 2 (3.8%) | 0 | 5 (2.3%) |
| Tongue ulceration | 3 (5.7%) | 1 (1.9%) | 0 | 1 (1.7%) | 5 (2.3%) |
| Insomnia | 1 (1.9%) | 2 (3.8%) | 1 (1.9%) | 0 | 4 (1.8%) |
| Dry mouth | 0 | 0 | 2 (3.8%) | 1 (1.7%) | 3 (1.4%) |
| Neutropenia | 0 | 0 | 3 (5.7%) | 0 | 3 (1.4%) |
| Oral pain | 0 | 2 (3.8%) | 1 (1.9%) | 0 | 3 (1.4%) |
| Pruritus | 0 | 2 (3.8%) | 1 (1.9%) | 0 | 3 (1.4%) |
| Conjunctivitis | 0 | 2 (3.8%) | 0 | 0 | 2 (0.9%) |
| Erythema | 0 | 2 (3.8%) | 0 | 0 | 2 (0.9%) |
| Limb discomfort | 0 | 2 (3.8%) | 0 | 0 | 2 (0.9%) |
| Mucosal inflammation | 0 | 0 | 2 (3.8%) | 0 | 2 (0.9%) |
| Paresthesia oral | 2 (3.8%) | 0 | 0 | 0 | 2 (0.9%) |
| Stomatitis | 0 | 0 | 2 (3.8%) | 0 | 2 (0.9%) |
| Thrombocytopenia | 0 | 0 | 2 (3.8%) | 0 | 2 (0.9%) |
| Urinary tract infection | 0 | 0 | 2 (3.8%) | 0 | 2 (0.9%) |

The ability of RAD001 to improve immune function in elderly volunteers was evaluated by measuring the serologic response to the 2012 seasonal influenza vaccine. The hemagglutination inhibition (HI) geometric mean titers (GMT) to each of the 3 influenza vaccine strains at baseline and 4 weeks after influenza vaccination are provided in Table 10. The primary analysis variable was the HI GMT ratio (4 weeks post vaccination/baseline). The study was powered to be able to demonstrate that in at least 2 out of 3 influenza vaccine strains there was 1) a ≥1.2-fold GMT increase relative to placebo; and 2) a posterior probability no lower than 80% that the placebo-corrected GMT ratio exceeded 1. This endpoint was chosen because a 1.2-fold increase in the influenza GMT ratio induced by the MF-59 vaccine adjuvant was associated with a decrease in influenza illness (Iob, A et al. (2005) *Epidemiol Infect* 133:687-693).

TABLE 10

HI GMTs for each influenza vaccine strain at baseline and at 4 weeks after influenza vaccination

| Influenza Vaccine Strain | | Time | RAD001 0.5 mg daily N = 50 | RAD001 5 mg weekly N = 49 | RAD001 20 mg weekly N = 49 | Placebo N = 55 |
|---|---|---|---|---|---|---|
| A/H1N1 | GMT (CV %) | Baseline | 102.8 (186.9) | 84.2 (236.4) | 90.1 (188.4) | 103.2 (219.7) |
| | | Week 4 | 190.2 (236.9) | 198.73 (195.6) | 129.7 (175.9) | 169.4 (259.8) |
| | GMT ratio (CV %) | | 2.6 (302.5) | 2.5 (214.3) | 1.8 (201.5) | 2.0 (132.7) |
| A/H3N2 | GMT (CV %) | Baseline | 106.8 (168.2) | 126.04 (162.6) | 137.1 (211.5) | 131.7 (162.3) |
| | | Week 4 | 194.4 (129.1) | 223.0 (118.8) | 223.0 (163.6) | 184.3 (153.2) |
| | GMT ratio (CV %) | | 2.1 (152.6) | 2.0 (189.2) | 2.1 (277.3) | 1.6 (153.6) |
| B | GMT (CV %) | Baseline | 44.2 (96.6) | 64.8 (87.3) | 58.0 (156.0) | 57.0 (112.6) |
| | | Week 4 | 98.4 (94.8) | 117.3 (99.9) | 99.2 (124.1) | 114.6 (136.7) |
| | GMT ratio (CV %) | | 2.5 (111.2) | 2.2 (112.8) | 2.1 (126.5) | 2.2 (109.2) |

Figure 40A:
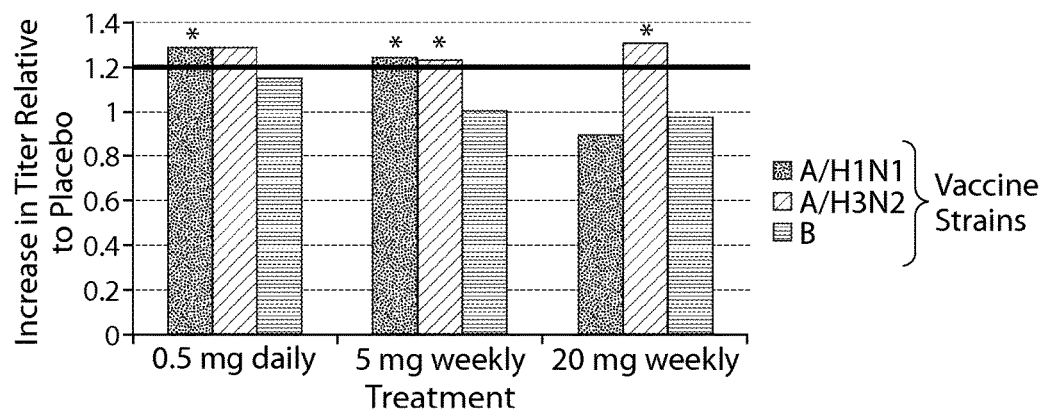
FIGS. 40A and 40B are graphs showing an increase in titers to influenza vaccine strains as compared to placebo.

Baseline indicates 2 weeks prior to influenza vaccination
Week 4 indicates 4 weeks after influenza vaccination
N is number of subjects per cohort
GMT is geometric mean titer
GMT ratio is the GMT at week 4 post vaccination/GMT at baseline
CV % indicates coefficient of variation In the intent-to-treat (ITT) population, the low, immune enhancing, dose RAD001 (0.5 mg daily or 5 mg weekly) cohorts but not higher dose (20 mg weekly) cohort met the primary endpoint of the study (FIG. 40A). This demonstrates that there is a distinct immunomodulatory mechanism of RAD001 at the lower doses, and that at the higher dose the known immunosuppressive effects of mTOR inhibition may come into play. Furthermore, the results suggest a trend toward improved immune function in the elderly after low, immune enhancing, dose RAD001 treatment.

Figure 40B:
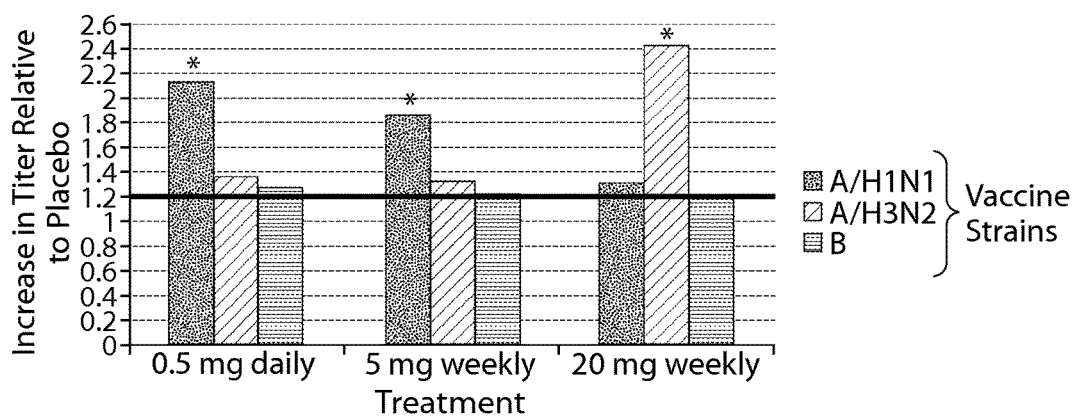

In a subgroup analysis, the subset of subjects with low baseline influenza titers (≤1:40) experienced a greater RAD001-associated increase in titers than did the ITT population (FIG. 40B). These data show that RAD001 is particularly effective at enhancing the influenza vaccine response of subjects who did not have protective (>1:40) titers at baseline, and therefore were at highest risk of influenza illness.

Figure 41:
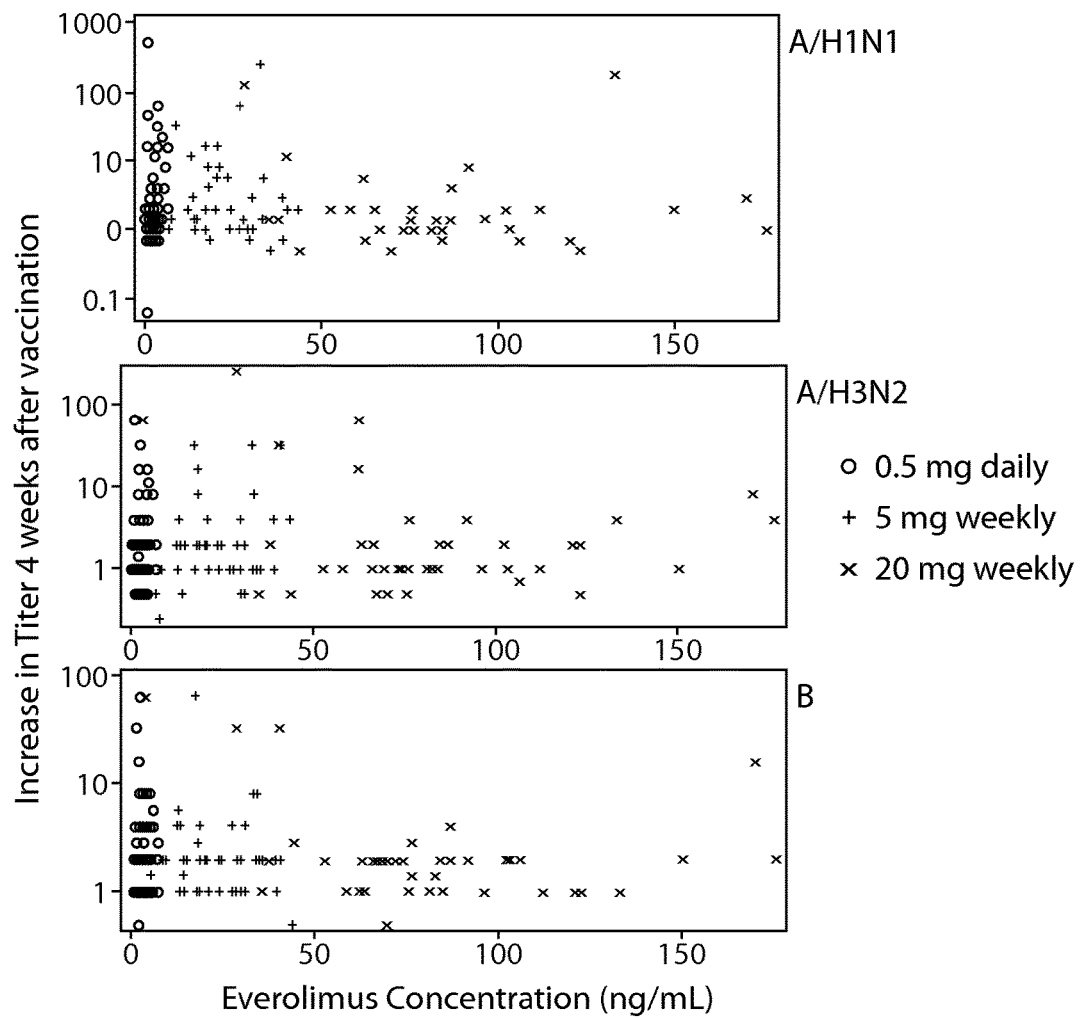
FIG. 41 shows a scatter plot of RAD001 concentration versus fold increase in geometric mean titer to each influenza vaccine strain 4 weeks after vaccination. RAD001 concentrations (1 hour post dose) were measured after subjects had been dosed for 4 weeks. All subjects who had pharmacokinetic measurements were included in the analysis set. The fold increase in geometric mean titers at 4 weeks post vaccination relative to baseline is shown on the y axis.

Scatter plots of RAD001 concentration versus increase in titer to each influenza vaccine strain show an inverse exposure/response relationship (FIG. 41). Modeling and simulation based on mTOR mediated phosphorylation of S6 kinase (S6K) predicts that the 20 mg weekly dosing regimen inhibits mTOR-mediated S6K activity almost completely, the 5 mg weekly dosing regimen inhibits S6K activity by over 50%, and the 0.5 mg daily dosing regiment inhibits S6K phosphorylation by approximately 38% during the dosing interval (Tanaka, C et al. (2008) *J. Clin. Oncol* 26:1596-1602). Thus, partial mTOR inhibition, e.g., mTOR-mediated S6K phosphorylation, with low, immune enhancing, dose RAD001 may be as, if not more effective, than near complete mTOR inhibition with high dose RAD001 at enhancing the immune response of the elderly.

Rates of seroconversion 4 weeks after influenza vaccination were also evaluated. Seroconversion was defined as the change from a negative pre-vaccination titer (i.e., HI titer <1:10) to post-vaccination HI titer ≥1:40 or at least 4-fold increase from a non-negative (≥1:10) pre-vaccination HI titer. In the intention-to-treat population, seroconversion rates for the H3N2 and B strains were increased in the RAD001 as compared to the placebo cohorts although the increases did not meet statistical significance (Table 11). In the subpopulation of subjects with baseline influenza titers <=1:40, RAD001 treatment also increased the rates of seroconversion to the H3N2 and B strains, and these results reached statistical significance for the B strain in the 0.5 mg daily dosing cohort. These data further show that RAD001 enhanced the serologic response to influenza vaccination in the elderly.

TABLE 11

Percent of subjects with seroconversion to influenza 4 weeks after vaccination

|  | Placebo N = 54 | 0.5 mg N = 48 | 5 mg N = 49 | 20 mg N = 48 |
|---|---|---|---|---|
| Intention to Treat Population | | | | |
| H1N1 | 24 | 27 | 27 | 17 |
| H3N2 | 17 | 27 | 24 | 25 |
| B | 17 | 27 | 22 | 19 |
| Subjects with Baseline Titers <=40 | | | | |
| H1N1 | 40 | 42 | 45 | 36 |
| H3N2 | 42 | 64 | 53 | 71 |
| B | 16 | 40* | 33 | 28 |

*Odds ratio for seroconversion between RAD001 and Placebo significantly different than 1 (two-sided p-value < 0.05 obtained by logistic regression with treatment as fixed effect)

Figure 42:
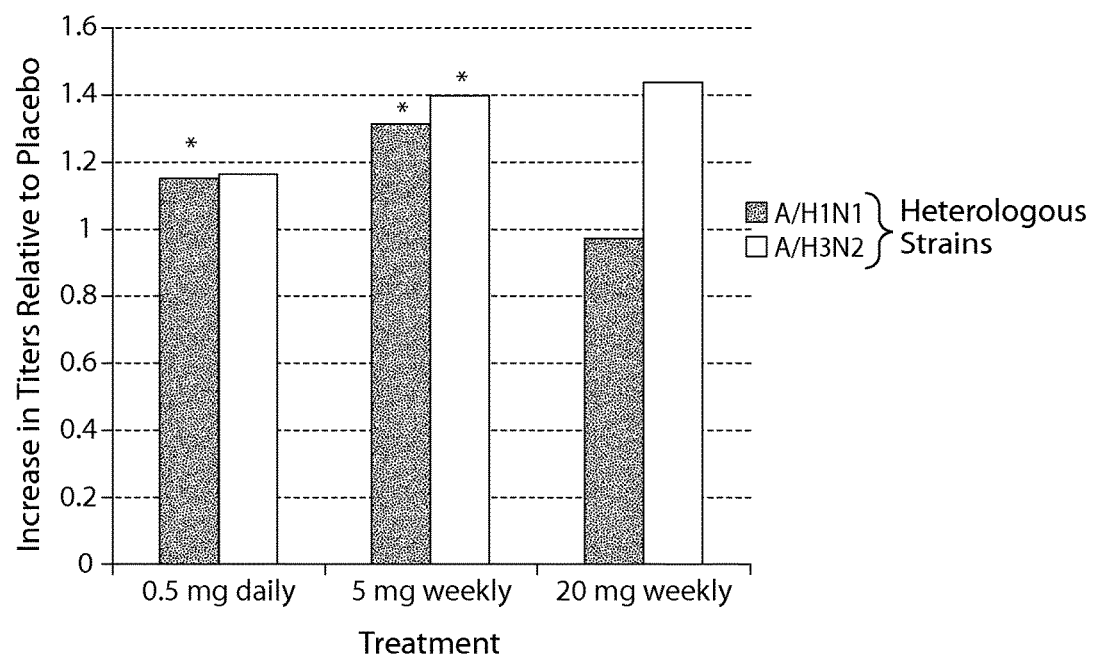
FIG. 42 is a graphic representation showing increase in titers to heterologous influenza strains as compared to placebo. The increase above baseline in influenza geometric mean titers to 2 heterologous influenza strains (A/H1N1 strain A/New Jersey/8/76 and A/H3N2 strain A/Victoria/361/11) not contained in the influenza vaccine relative to the increase in the placebo cohort 4 weeks after vaccination is shown for each of the RAD001 dosing cohorts in the intention to treat population. * indicates increase in titer relative to placebo exceeds 1 with a posterior probability of at least 80%.

Current seasonal influenza vaccines often provide inadequate protection against continuously emerging strains of influenza that present as variants of previously circulating viruses. However, mice vaccinated against influenza in the presence of the mTOR inhibitor rapamycin, as compared to placebo, developed a broader serologic response to influenza. The broader serologic response included antibodies to conserved epitopes expressed by multiple subtypes of influenza that provided protection against infection with heterologous strains of influenza not contained in the vaccine (Keating, R et al. (2013) *Nat Immunology* 14:2166-2178). To determine if RAD001 broadened the serologic response to influenza in the elderly volunteers, HI titers to 2 heterologous strains of influenza not contained in the influenza vaccine (A/H1N1 strain A/New Jersey/8/76 and A/H3N2 strain A/Victoria/361/11) were measured. The increase in the HI GMT ratios for the heterologous strains was higher in the RAD001 as compared to placebo cohorts (FIG. 42). In addition, seroconversion rates for the heterologous strains were higher in the RAD001 as compared to placebo cohorts. The increase in seroconversion rates in the 5 and 20 mg weekly RAD001 dosing cohorts was statistically significant for the H3N2 heterologous strain (Table 12). The H3N2 seroconversion rate for the pooled RAD001 cohorts was 39% versus 20% for the placebo cohort (p=0.007). The results presented herein suggest that mTOR inhibition broadens the serologic response of elderly volunteers to influenza vaccination, and increases antibody titers to heterologous strains of influenza not contained in the seasonal influenza vaccine.

Figure 43A:
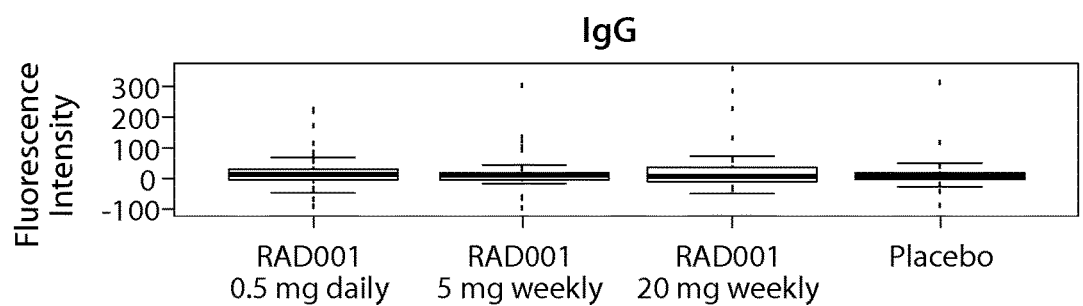
FIGS. 43A and 43B are graphic representations of IgG and IgM levels before and after influenza vaccination. Levels of anti-A/H1N1/California/07/2009 influenza IgG and IgM were measured in serum obtained from subjects before and 4 weeks post influenza vaccination. No significant difference in the change from baseline to 4 weeks post vaccination in anti-H1N1 influenza IgG and IgM levels were detected between the RAD001 and placebo cohorts (all p values >0.05 by Kruskal-Wallis rank sum test).
Figure 43B:
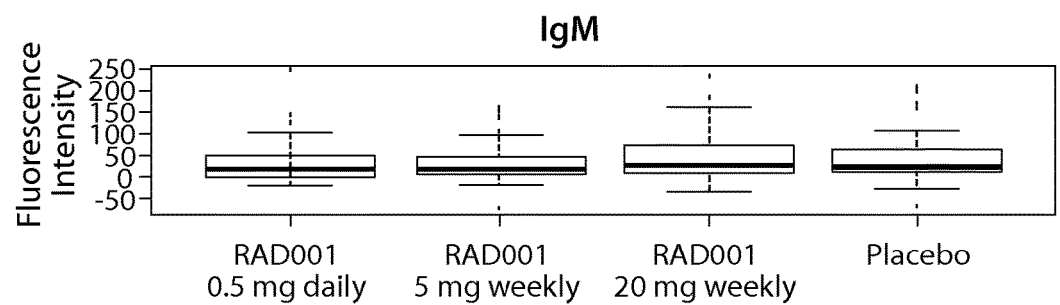

Broadened serologic response to heterologous strains of influenza in mice treated with rapamycin has been associated with an inhibition of class switching in B cells and an increase in anti-influenza IgM levels (Keating, R. et al. (2013) *Nat Immunol* 14:2166-2178). However, inhibition of class switching may not be involved in the broadened serologic response in humans treated with RAD001 because the post-vaccination anti-influenza IgM and IgG levels did not differ between RAD001 and placebo treated cohorts (FIG. 43).

TABLE 12

Percentage of subjects who seroconvert to heterologous strains of influenza 4 weeks after seasonal influenza vaccination

|  | Placebo, pooled | RAD001 0.5 mg daily | RAD001 5 mg weekly | RAD001 20 mg weekly |
|---|---|---|---|---|
| A/H1N1 strain: A/NewJersey/8/76 | 7% | 17% | 16% | 8% |
| A/H3N2 strain: A/Victoria/361/11 | 20% | 38% | 39%* | 40%* |

*Odds ratio for seroconversion between RAD001 and Placebo significantly different than 1 (two-sided p-value < 0.05 obtained by logistic regression with treatment as fixed effect)

Figure 44A:
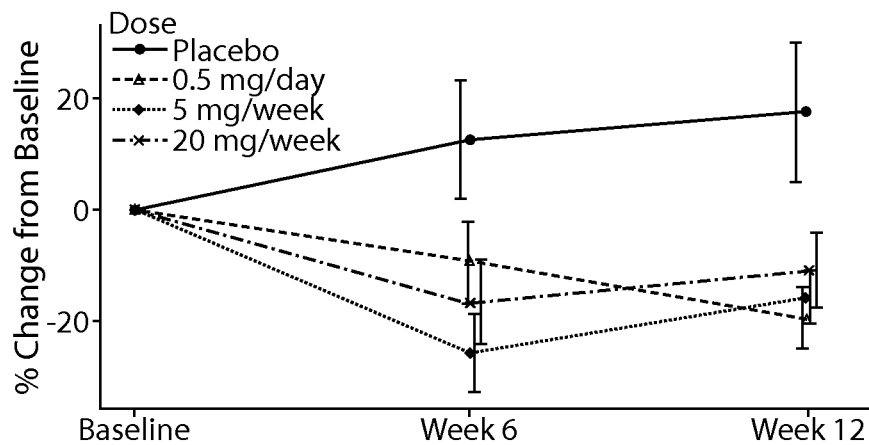
FIGS. 44A, 44B, and 44C are graphic representations of the decrease in percent of PD-1-positive CD4 and CD8 and increase in PD-1-negative CD4 T cells after RAD001 treatment. The percent of PD-1-positive CD4, CD8 and PD-1-negative CD4 T cells was determined by FACS analysis of PBMC samples at baseline, after 6 weeks of study drug treatment (Week 6) and 6 weeks after study drug discontinuation and 4 weeks after influenza vaccination (Week 12).
Figure 44B:
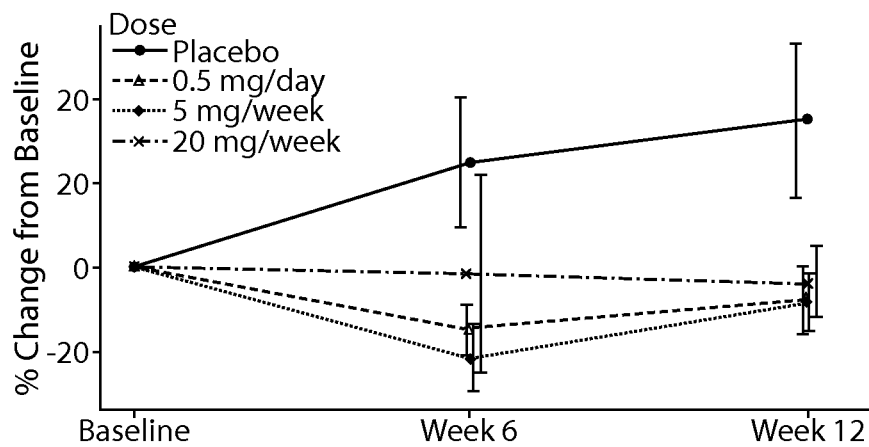
Figure 44C:
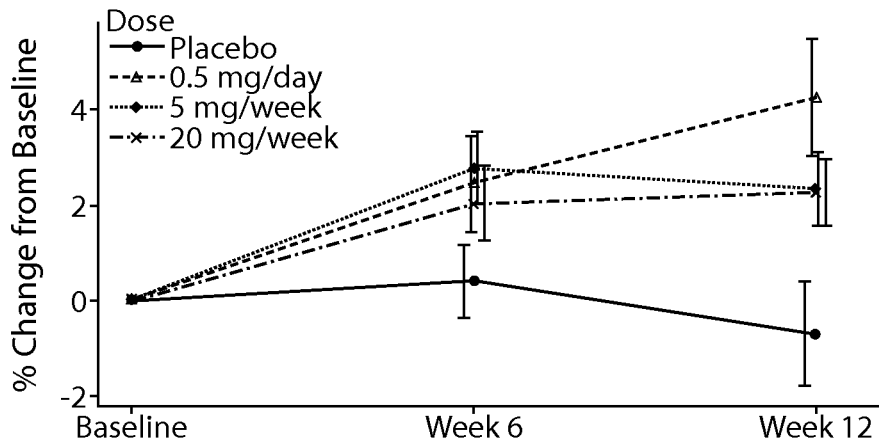

To address the mechanism by which RAD001 enhanced immune function in elderly volunteers, immunophenotyping was performed on PBMC samples obtained from subjects at baseline, after 6 weeks of study drug treatment and 4 weeks after influenza vaccination (6 weeks after study drug discontinuation). Although the percentage of most PBMC subsets did not differ between the RAD001 and placebo cohorts, the percentage of PD-1 positive CD4 and CD8 cells was lower in the RAD001 as compared to placebo cohorts (FIG. 44). PD-1 positive CD4 and CD8 cells accumulate with age and have defective responses to antigen stimulation because PD-1 inhibits T cell receptor-induced T cell proliferation, cytokine production and cytolytic function (Lages, C S et al. (2010) *Aging Cell* 9:785-798). There was an increase in percentage of PD-1 positive T cells over time in the placebo cohort. At week 12 (4 weeks post-vaccination) this increase may have been due to influenza vaccination since influenza virus has been shown to increase PD-1 positive T cells (Erikson, J J et al. (2012) *JCI* 122:2967-2982). However the percentage of CD4 PD-1 positive T cells decreased from baseline at week 6 and 12 in all RAD001 cohorts (FIG. 44A). The percentage of CD8 PD-1 positive cells also decreased from baseline at both week 6 and 12 in the two lower dose RAD001 cohorts (FIG. 44B). The percentage of PD-1 negative CD4 T cells was evaluated and increased in the RAD001 cohorts as compared to the placebo cohorts (FIG. 44C).

Figure 45A:
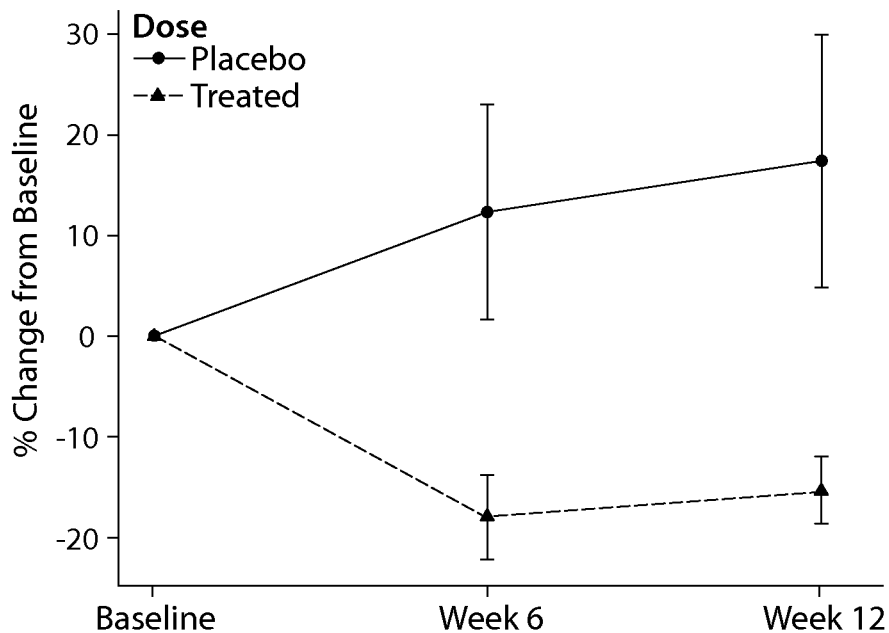
FIGS. 45A and 45B are graphic representations of the decrease in percent of PD-1-positive CD4 and CD8 and increase in PD-1-negative CD4 T cells after RAD001 treatment adjusted for differences in baseline PD-1 expression. The percent of PD-1-positive CD4, CD8 and PD-1-negative CD4 T cells was determined by FACS analysis of PBMC samples at baseline, after 6 weeks of study drug treatment (Week 6) and 6 weeks after study drug discontinuation and 4 weeks after influenza vaccination (Week 12).
Figure 45B:
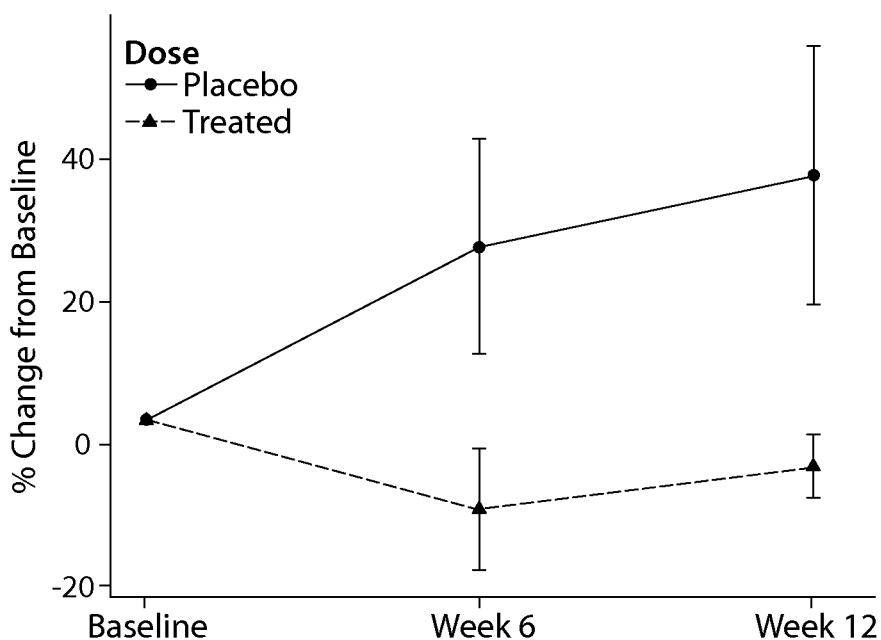

Under more stringent statistical analysis, where the results from the RAD001 cohorts were pooled and adjusted for differences in baseline PD-1 expression, there was a statistically significant decrease of 30.2% in PD-1 positive CD4 T cells at week 6 in the pooled RAD cohort (n=84) compared to placebo cohort (n=25) with p=0.03 (q=0.13) (FIG. 45A). The decrease in PD-1 positive CD4 T cells at week 12 in the pooled RAD as compared to the placebo cohort is 32.7% with p=0.05 (q=0.19). FIG. 45B shows a statistically significant decrease of 37.4% in PD-1 positive CD8 T cells at week 6 in the pooled RAD001 cohort (n=84) compared to placebo cohort (n=25) with p=0.008 (q=0.07). The decrease in PD-1 positive CD8 T cells at week 12 in the pooled RAD001 as compared to the placebo cohort is 41.4% with p=0.066 (q=0.21). Thus, the results from FIGS. 44 and 45 together suggest that the RAD001-associated decrease in the percentage of PD-1 positive CD4 and CD8 T cells may contribute to enhanced immune function.

Conclusion

In conclusion, the data presented herein show that the mTOR inhibitor RAD001 ameliorates the age-related decline in immunological function of the human elderly as assessed by response to influenza vaccination, and that this amelioration is obtained with an acceptable risk/benefit balance. In a study of elderly mice, 6 weeks treatment with the mTOR inhibitor rapamycin not only enhanced the response to influenza vaccination but also extended lifespan, suggesting that amelioration of immunosenescence may be a marker of a more broad effect on aging-related phenotypes.

Since RAD001 dosing was discontinued 2 weeks prior to vaccination, the immune enhancing effects of RAD001 may be mediated by changes in a relevant cell population that persists after discontinuation of drug treatment. The results presented herein show that RAD001 decreased the percentage of exhausted PD-1 positive CD4 and CD8 T cells as compared to placebo. PD-1 expression is induced by TCR signaling and remains high in the setting of persistent antigen stimulation including chronic viral infection. While not wishing to be bound by theory, is possible that RAD001 reduced chronic immune activation in elderly volunteers and thereby led to a decrease in PD-1 expression. RAD001 may also directly inhibit PD-1 expression as has been reported for the immunophilin cyclosporine A (Oestreich, K J et al. (2008) *J Immunol.* 181:4832-4839). A RAD001-induced reduction in the percentage of PD-1 positive T cells is likely to improve the quality of T cell responses. This is consistent with previous studies showing that mTOR inhibition improved the quality of memory CD8 T cell response to vaccination in mice and primates (Araki, K et al. (2009) *Nature* 460:108-112). In aged mice, mTOR inhibition has also been shown to increase the number of hematopoietic stem cells, leading to increased production of naïve lymphocytes (Chen, C et al. (2009) *Sci Signal* 2:ra75). Although significant differences in the percentages of naïve lymphocytes in the RAD001 versus placebo cohorts were not detected in this example, this possible mechanism may be further investigated.

The mechanism by which RAD001 broadened the serologic response to heterologous strains of influenza may be further investigated. Rapamycin has also been shown to inhibit class switching in B cells after influenza vaccination. As a result, a unique repertoire of anti-influenza antibodies was generated that promoted cross-strain protection against lethal infection with influenza virus subtypes not contained in the influenza vaccine (Keating, R et al. (2013) *Nat Immunol.* 14:2166-2178). The results described herein did not show that RAD001 altered B cell class switching in the elderly subjects who had discontinued RAD001 2 weeks prior to influenza vaccination. Although the underlying mechanism requires further elucidation, the increased serologic response to heterologous influenza strains described herein may confer enhanced protection to influenza illness in years when there is a poor match between the seasonal vaccine and circulating strains of influenza in the community.

The effect of RAD001 on influenza antibody titers was comparable to the effect of the MF59 vaccine adjuvant that is approved to enhance the response of the elderly to influenza vaccination (Podda, A (2001) *Vaccine* 19:2673-2680). Therefore, RAD001-driven enhancement of the antibody response to influenza vaccination may translate into clinical benefit as demonstrated with MF59-adjuvanted influenza vaccine in the elderly (Iob, A et al. (2005) *Epidemiol Infect.* 133:687-693). However, RAD001 is also used to suppress the immune response of organ transplant patients. These seemingly paradoxical findings raise the possibility that the immunomodulatory effects of mTOR inhibitors may be dose and/or antigen-dependent (Ferrer, I R et al. (2010) *J Immunol.* 185:2004-2008). A trend toward an inverse RAD001 exposure/vaccination response relationship was seen herein. It is possible that complete mTOR inhibition suppresses immune function through the normal cyclophilin-rapamycin mechanism, whereas partial mTOR inhibition, at least in the elderly, enhances immune function due to a distinct aging-related phenotype inhibition. Of interest, mTOR activity is increased in a variety of tissues including hematopoietic stem cells in aging animal models (Chen C. et al. (2009) *Sci Signal* 2:ra75 and Barns, M. et al. (2014) *Int J Biochem Cell Biol.* 53:174-185). Thus, turning down mTOR activity to levels seen in young tissue, as opposed to more complete suppression of mTOR activity, may be of clinical benefit in aging indications.

The safety profile of mTOR inhibitors such as RAD001 in the treatment of aging-related indications has been of concern. The toxicity of RAD001 at doses used in oncology or organ transplant indications includes rates of stomatitis, diarrhea, nausea, cytopenias, hyperlipidemia, and hyperglycemia that would be unacceptable for many aging-related indications. However, these AEs are related to the trough levels of RAD001 in blood. Therefore the RAD001 dosing regimens used in this study were chosen to minimize trough levels. The average RAD001 trough levels of the 0.5 mg daily, 5 mg weekly and 20 mg weekly dosing cohorts were 0.9 ng/ml, below 0.3 ng/ml (the lower limit of quantification), and 0.7 ng/ml, respectively. These trough levels are significantly lower than the trough levels associated with dosing regimens used in organ transplant and cancer patients. In addition, the limited 6 week course of treatment decreased the risk of adverse events. These findings suggest that the dosing regimens used in this study may have an acceptable risk/benefit for some conditions of the elderly. Nonetheless, significant numbers of subjects in the experiments described herein developed mouth ulcers even when dosed as low as 0.5 mg daily. Therefore the safety profile of low, immune enhancing, dose RAD001 warrants further study. Development of mTOR inhibitors with cleaner safety profiles than currently available rapalogs may provide better therapeutic options in the future for aging-associated conditions.

Example 13: Enhancement of Immune Response to Vaccine in Elderly Subjects

Immune function declines in the elderly, leading to an increase incidence of infection and a decreased response to vaccination. As a first step in determining if mTOR inhibition has anti-aging effects in humans, a randomized placebo-controlled trial was conducted to determine if the mTOR inhibitor RAD001 reverses the aging-related decline in immune function as assessed by response to vaccination in elderly volunteers. In all cases, appropriate patent consents were obtained and the study was approved by national health authorities.

The following 3 dosing regimens of RAD001 were used in the study:
20 mg weekly (trough level: 0.7 ng/ml)
5 mg weekly (trough level was below detection limits)
0.5 mg daily (trough level: 0.9 ng/ml)

These dosing regimens were chosen because they have lower trough levels than the doses of RAD001 approved for transplant and oncology indications. Trough level is the lowest level of a drug in the body. The trough level of RAD001 associated with the 10 mg daily oncology dosing regimen is approximately 20 ng/ml. The trough level associated with the 0.75-1.5 mg bid transplant dosing regimen is approximately 3 ng/ml. In contrast, the trough level associated with the dosing regimens used in our immunization study were 3-20 fold lower.

Since RAD001-related AEs are associated with trough levels, the 3 dosing regimens were predicted to have adequate safety for normal volunteers. In addition, the 3 doses were predicted to give a range of mTOR inhibition. P70 S6 Kinase (P70 S6K) is a downstream target that is phosphorylated by mTOR. Levels of P70 S6K phosphorylation serve as a measure of mTOR activity. Based on modeling and simulation of P70 S6K phosphorylation data obtained in preclinical and clinical studies of RAD001, 20 mg weekly was predicted to almost fully inhibit mTOR activity for a full week, whereas 5 mg weekly and 0.5 mg daily were predicted to partially inhibit mTOR activity.

Elderly volunteers >=65 years of age were randomized to one of the 3 RAD001 treatment groups (50 subjects per arm) or placebo (20 subjects per arm). Subjects were treated with study drug for 6 weeks, given a 2 week break, and then received influenza (Aggrippal, Novartis) and pneumoccal (Pneumovax 23, Merck), vaccinations. Response to influenza vaccination was assessed by measuring the geometric mean titers (GMTs) by hemagglutination inhibition assay to the 3 influenza strains (H1N1, H3N2 and B influenza subtypes) in the influenza vaccine 4 weeks after vaccination. The primary endpoints of the study were (1) safety and tolerability and (2) a 1.2 fold increase in influenza titers as compared to placebo in 2/3 of the influenza vaccine strains 4 weeks after vaccination. This endpoint was chosen because a 1.2 fold increase in influenza titers is associated with a decrease in influenza illness post vaccination, and therefore is clinically relevant. The 5 mg weekly and 0.5 mg daily doses were well tolerated and unlike the 20 mg weekly dose, met the GMT primary endpoint (FIG. 40A). Not only did RAD001 improve the response to influenza vaccination, it also improved the response to pneumococcal vaccination as compared to placebo in elderly volunteers. The pneumococcal vaccine contains antigens from 23 pneumococcal serotypes. Antibody titers to 7 of the serotypes were measured in our subjects. Antibody titers to 6/7 serotypes were increased in all 3 RAD cohorts compared to placebo.

The combined influenza and pneumococcal titer data suggest that partial (less than 80-100%) mTOR inhibition is more effective at reversing the aging-related decline in immune function than more complete mTOR inhibition.

Example 14: Low Dose mTOR Inhibition Increases Energy and Exercise

Figure 46:
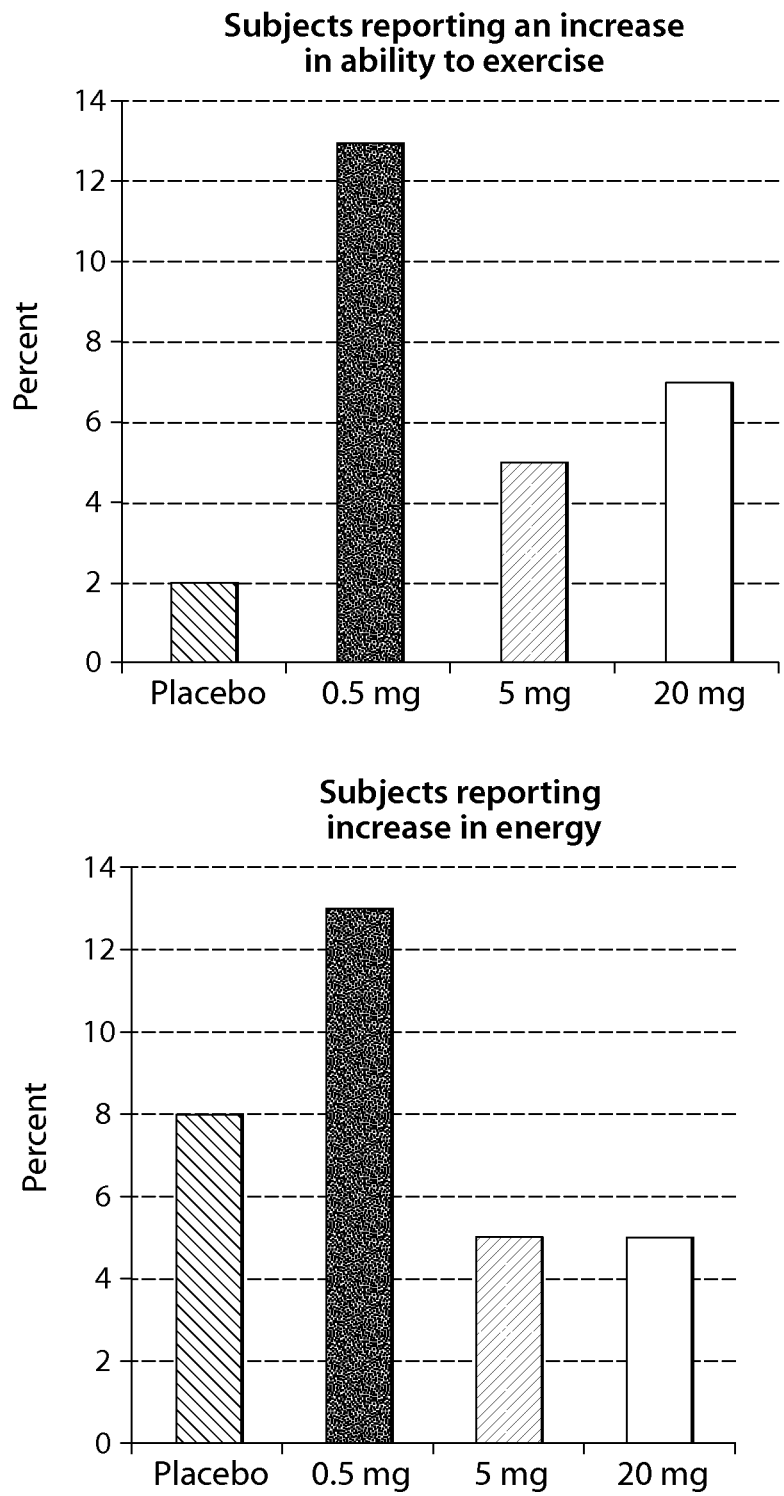
FIG. 46 depicts increases in exercise and energy in elderly subjects in response to RAD001.

In preclinical models, mTOR inhibition with the rapalog rapamycin increases spontaneous physical activity in old mice (Wilkinson et al. Rapamycin slows aging in mice. (2012) Aging Cell; 11:675-82). Of interest, subjects in the 0.5 mg daily dosing cohort described in Example 13 also reported increased energy and exercise ability as compared to placebo in questionnaires administered one year after dosing (FIG. 46). These data suggest that partial mTOR inhibition with rapalogs may have beneficial effects on aging-related morbidity beyond just immune function.

Example 15: P70 S6 Kinase Inhibition with RAD001

Figure 47A:
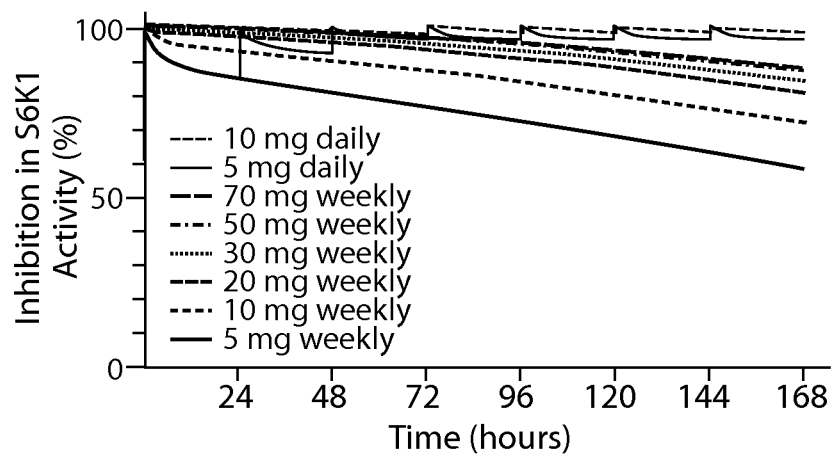
FIGS. 47A and 47B depict the predicted effect of RAD001 on P70 S6K activity in cells.
Figure 47B:
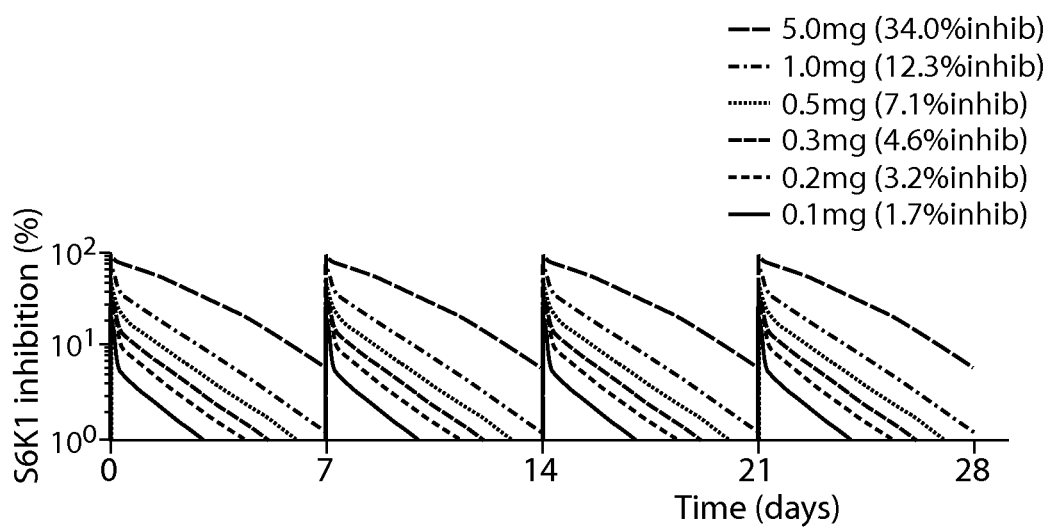

Modeling and simulation were performed to predict daily and weekly dose ranges of RAD001 that are predicted to partially inhibit mTOR activity. As noted above, P70 S6K is phosphorylated by mTOR and is the downstream target of mTOR that is most closely linked to aging because knockout of P70 S6K increases lifespan. Therefore modeling was done of doses of RAD001 that partially inhibit P70 S6K activity. Weekly dosing in the range of >=0.1 mg and <20 mg are predicted to achieve partial inhibition of P70 S6K activity (FIG. 47).

For daily dosing, concentrations of RAD001 from 30 pM to 4 nM partially inhibited P70 S6K activity in cell lines (Table 13). These serum concentrations are predicted to be achieved with doses of RAD001 >=0.005 mg to <1.5 mg daily.

TABLE 13

| Percent inhibition of P70 S6K activity in HeLa cells in vitro | | | | | | |
|---|---|---|---|---|---|---|
| RAD001 concentration | 0 | 6 pM | 32 pM | 160 pM | 800 pM | 4 nM | 20 nM |
| % P70 S6K inhibition | 0 | 0 | 18 | 16 | 62 | 90 | 95 |

Conclusion

Methods of treating aging-related morbidity, or generally enhancing an immune response, with doses of mTOR inhibitors that only partially inhibit P70 S6K. The efficacy of partial mTOR inhibition with low doses of RAD001 in aging indications is an unexpected finding. RAD001 dose ranges between >=0.1 mg to <20 mg weekly and >=0.005 mg to <1.5 mg daily will achieve partial mTOR inhibition and therefore are expected to have efficacy in aging-related morbidity or in the enhancement of the immune response.

Example 16: Exogenous IL-7 Enhances the Function of CAR T Cells

After adoptive transfer of CAR T cells, some patients experience limited persistence of the CAR T cells, which can result in suboptimal levels of anti-tumor activity. In this example, the effects of administration of exogenous human IL-7 is assessed in mouse xenograft models where an initial suboptimal response to CAR T cells has been observed.

Figure 48A:
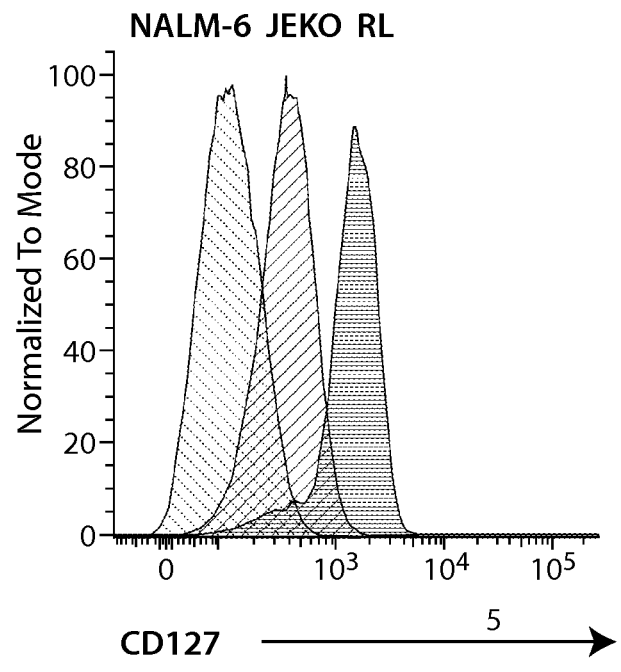
FIGS. 48A and 48B show IL-7 receptor (CD127) expression on cancer cell lines and CART cells. Expression of CD127 was measured by flow cytometry analysis in three cancer cell lines: RL (mantle cell lymphoma), JEKO (also known as Jeko-1, mantle cell lymphoma), and Nalm-6 (B-ALL) (FIG. 48A). CD127 expression was measured by flow cytometry analysis on CD3 positive (CART) cells that had been infused and circulating in NSG mice (FIG. 48B).
Figure 48B:
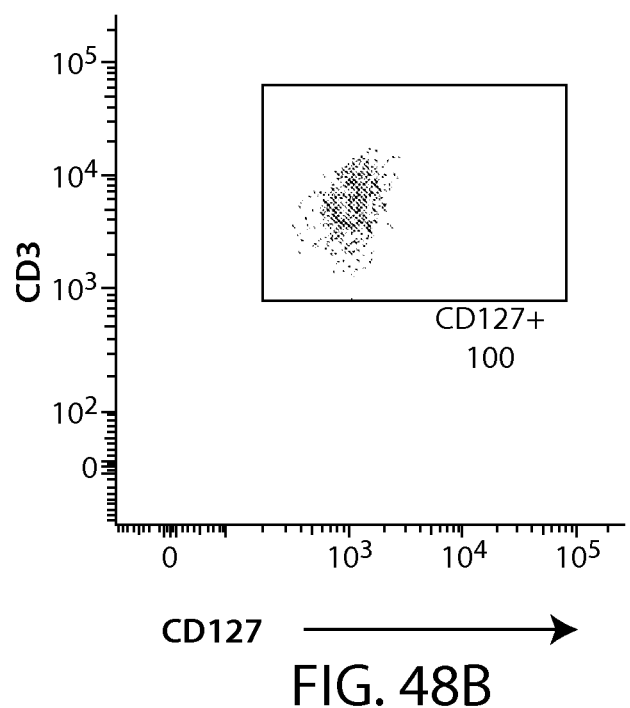

Expression of the IL-7 receptor CD127 was first assessed in different cancer cell lines and in CAR-expressing cells. Two mantle cell lymphoma cell lines (RL and Jeko-1) and one B-ALL cell line (Nalm-6) were analyzed by flow cytometry for CD127 expression. As shown in FIG. 48A, out of the three cancer cell lines tested, RL was shown to have the highest expression of CD127, followed by Jeko-1 and Nalm-6. CART19 cells were infused into NSG mice and CD127 expression was assessed on the circulating CART19 cells by flow cytometry. As shown in FIG. 48B, CD127 is uniformly expressed on all circulating CART19 cells.

Figure 49A:
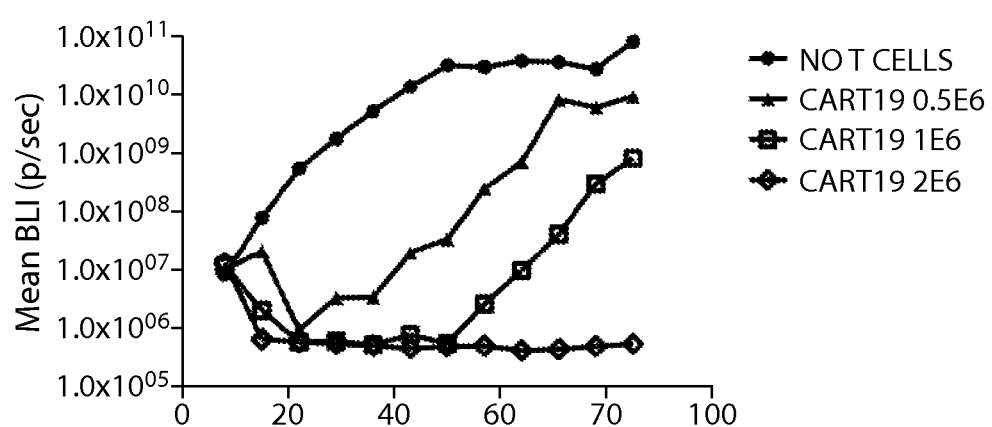
FIGS. 49A, 49B, and 49C show the anti-tumor response after CART19 treatment and subsequent IL-7 treatment. NSG mice engrafted with a luciferase-expressing mantle lymphoma cell line (RL-luc) at Day 0 were treated with varying dosages of CART19 cells at Day 6, and tumor burden was monitored. Mice were divided into 4 groups and received no CART19 cells, $0.5 \times 10^6$ CART19 cells (CART19 0.5E6), $1 \times 10^6$ CART19 cells (CART19 1E6), or $2 \times 10^6$ CART19 cells (CART19 2E6). Tumor burden after CART treatment was measured by detection of bioluminescence (mean BLI) (FIG. 49A). Mice receiving $0.5 \times 10^6$ CART19 cells (CART19 0.5E6) or $1 \times 10^6$ CART19 cells (CART19 1E6) were randomized to receive recombinant human IL-7 (rhIL-7) or not. Tumor burden, represented here by mean bioluminescence (BLI), was monitored for the three mice (#3827, #3829, and #3815, receiving the indicated initial CART19 dose) from FIG. 49A that were treated with IL-7 starting at Day 85 (FIG. 49B). IL-7 was administered through IP injection 3 times weekly. Tumor burden, represented here by mean bioluminescence (BLI) before Day 85 (PRE) and after Day 115 (POST) was compared between mice that did not receive IL-7 (CTRL) and mice that received IL-7 treatment (IL-7) (FIG. 49C).
Figure 49B:
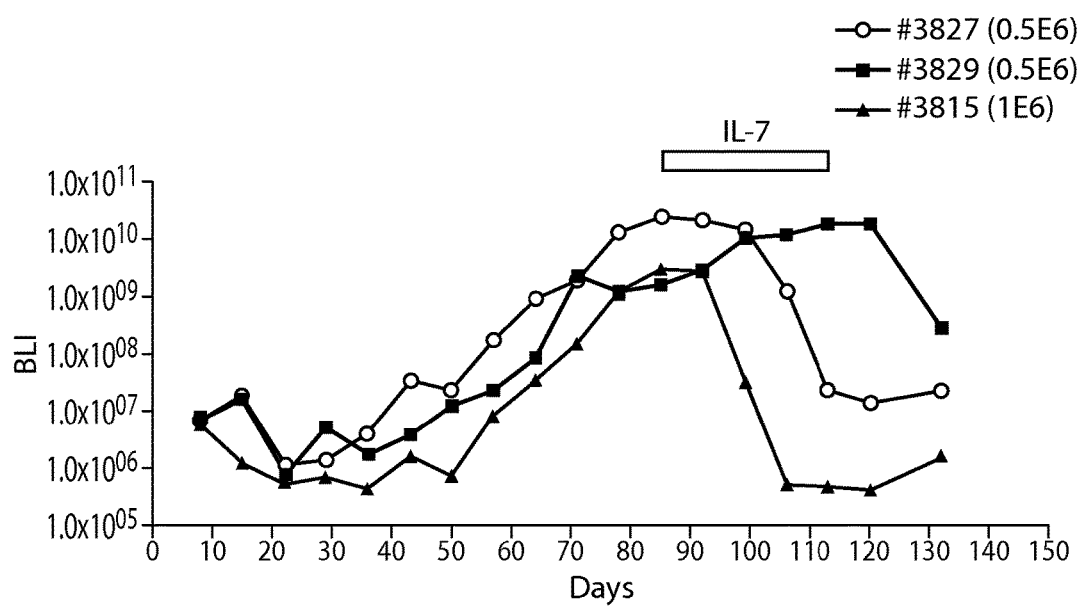
Figure 49C:
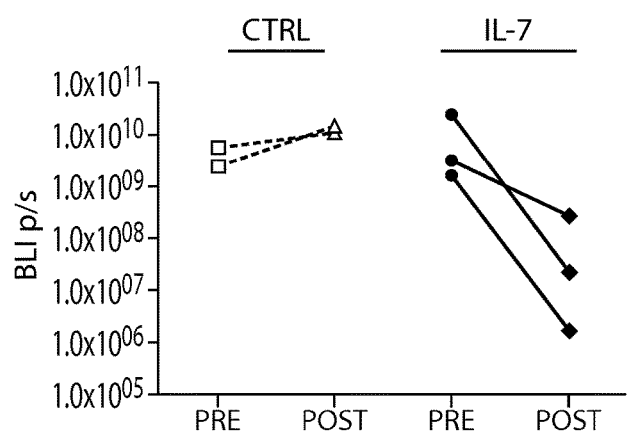

Next, the effect of exogenous IL-7 treatment on anti-tumor activity of CART19 cells was assessed in a lymphoma animal model. NSG mice were engrafted with a luciferase-expressing mantle cell line (RL luc) on Day 0 (D0), followed by treatment of CART19 cells on Day 6. The NSG mice were divided into groups, where one group received no CART19 cells, a second group received $0.5 \times 10^6$ CART19 cells, a third group received $1 \times 10^6$ CART19 cells, and a fourth group received $2 \times 10^6$ CART19 cells. Tumor size was monitored by measuring the mean bioluminescence of the engrafted tumors over more than 80 days. Only mice receiving $2 \times 10^6$ CART19 cells demonstrated rejection of the tumor and inhibition of tumor growth (FIG. 49A). Mice from the two groups receiving $0.5 \times 10^6$ CART19 cells or $1 \times 10^6$ CART19 cells were shown to s a suboptimal anti-tumor response. Mice from these two groups were then randomized, where three mice (mouse #3827 and #3829 which received $0.5 \times 10^6$ CART19 cells, and mouse #3815 which received $1 \times 10^6$ CART19 cells) received exogenous recombinant human IL-7 at a dosage of 200 ng/mouse by intraperitoneal injection three times weekly starting at Day 85, and two mice did not. The tumor burden of mice receiving exogenous IL-7 from Day 85-125, as detected by mean bioluminescence, is shown in FIG. 49B. All mice receiving IL-7 showed a dramatic response of 1-3 log reduction in tumor burden. Mice that originally received a higher dose of CART19 cells (mouse #3815 which received $1 \times 10^6$ CART19 cells) showed a more profound response. When comparing the tumor burden of mice that received IL-7 treatment to control, before and after IL-7 treatment, tumor reduction in tumor burden was only seen in the mice that had received IL-7 treatment (FIG. 49C).

Figure 50A:
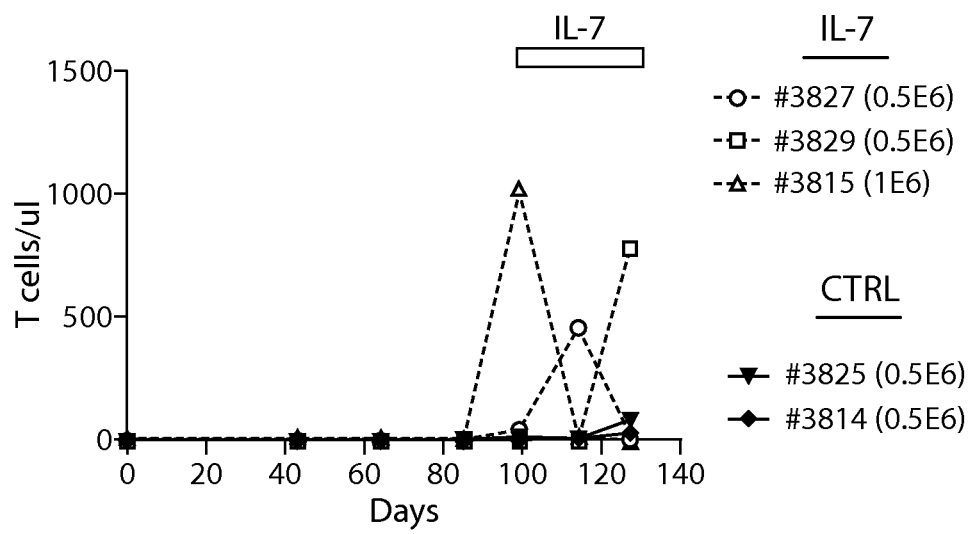
FIGS. 50A and 50B show the T cell dynamics after IL-7 treatment. The level of human T cells detected in the blood was monitored for each of the mice receiving IL-7 or control mice (FIG. 50A). The level of CART19 cells (CD3+ cells) detected in the blood was measured before (PRE) and 14 days after (Day 14) initiation of IL-7 treatment (FIG. 50B).
Figure 50B:
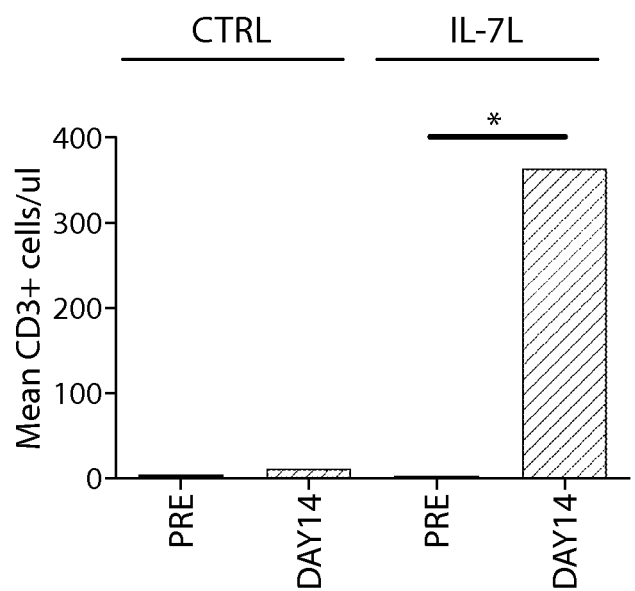
Figure 51:
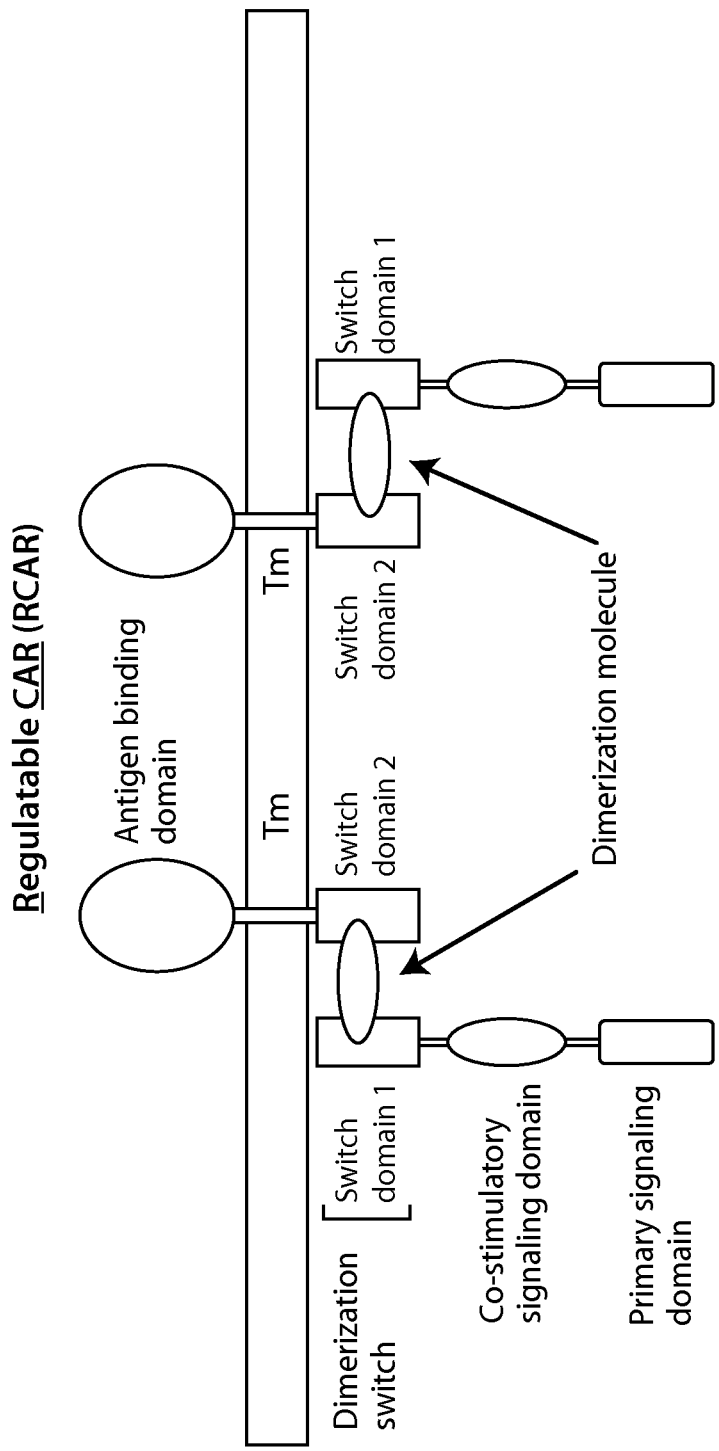
FIG. 51 depicts the structures of two exemplary RCAR configurations. The antigen binding members comprise an antigen binding domain, a transmembrane domain, and a switch domain. The intracellular binding members comprise a switch domain, a co-stimulatory signaling domain and a primary signaling domain. The two configurations demonstrate that the first and second switch domains described herein can be in different orientations with respect to the antigen binding member and the intracellular binding member. Other RCAR configurations are further described herein.

T cell dynamics following IL-7 treatment in the lymphoma animal model was also examined. Human CART19 cells were not detectable in the blood prior to IL-7 treatment. Upon treatment of IL-7, there was rapid, but variable increase in the numbers of T cells in the treated mice (FIG. 50A). The extent of T cell expansion observed in mice receiving the IL-7 also correlated with tumor response. The mouse with the highest number of T cells detected in the blood at peak expansion during IL-7 treatment (mouse #3815) had the most robust reduction in tumor burden (see FIG. 49B). Moreover, the time of peak expansion correlated with the T cell dose injected as baseline. The number/level CD3-expressing cells in the blood were also measured before and after IL-7 treatment. In control mice, very few CD3-expressing cells were detected, while IL-7-treated mice showed a significant increase in CD3+ cells after IL-7 treatment (FIG. 50B).

Together, the results in this example demonstrate that exogenous IL-7 treatment increases T cell proliferation and anti-tumor activity in vivo, indicating that use of IL-7 in patients with suboptimal results after CAR therapy can improve anti-tumor response in these patients.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

---

What is claimed is:

1. A method of treating a mammal having a leukemia or lymphoma associated with expression of CD19, comprising:
administering to the mammal an effective amount of a population of immune effector cells, wherein the immune effector cells comprise autologous T cells, that expresses a CAR polypeptide that binds CD19 (a CAR19-expressing cell population), in combination with ibrutinib,
wherein the CAR polypeptide comprises:
(i) an extracellular anti-CD19 binding domain that comprises: a light chain complementary determining region 1 (LC CDR1) of SEQ ID NO: 25, a light chain complementary determining region 2 (LC CDR2) of SEQ ID NO: 26, a light chain complementary determining region 3 (LC CDR3) of SEQ ID NO: 27, a heavy chain complementary determining region 1 (HC CDR1) of SEQ ID NO: 19, a heavy chain complementary determining region 2 (HC CDR2) of any of SEQ ID NO: 20-23, and a heavy chain complementary determining region 3 (HC CDR3) of SEQ ID NO: 24;
(ii) an intracellular signaling domain capable of stimulating the autologous T cells comprising the CAR polypeptide, wherein the intracellular signalling domain comprises:
(a) a primary signalling domain which comprises a CD3zeta domain, or a functional fragment thereof, and
(b) a costimulatory domain comprising an intracellular signaling domain of a protein selected from the group consisting of OX40, CD27, CD28, ICOS, and 4-1BB;
(iii) a transmembrane domain disposed between the anti-CD19 binding domain and the intracellular signalling domain, wherein the transmembrane domain is a transmembrane domain of a protein chosen from: the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 or CD154.

2. The method of claim 1, wherein ibrutinib and the CAR19-expressing cell population are administered to the mammal as a first line of therapy.

3. The method of claim 1, wherein the CAR19-expressing cell population is administered to the mammal after administration of ibrutinib.

4. The method of claim 1, wherein the mammal is, or is identified as being, a complete or partial responder to ibrutinib, or a complete or partial responder to the CAR19-expressing cell population.

5. The method of claim 1, wherein the method further comprises administering GDC-0834, RN-486, CGI-560, CGI-1764, HM-71224, CC-292, ONO-4059, CNX-774, or LFM-A13.

6. The method of claim 1, wherein ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, or 600 mg daily.

7. The method of claim 1, wherein the anti-CD19 binding domain comprises a murine light chain variable region of Table 7, a murine heavy chain variable region of Table 7, or both.

8. The method of claim 1, wherein the anti-CD19 binding domain comprises the amino acid sequence of SEQ ID NO:59, or a sequence with 95-99% identity thereto.

9. The method of claim 1, wherein the anti-CD19 binding domain is a humanized anti-CD19 binding domain.

10. The method of claim 9, wherein the humanized anti-CD19 binding domain comprises an amino acid sequence chosen from: SEQ ID NO:1, SEQ ID NO:2, SEQ ID NO:3, SEQ ID NO: 4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12, or a sequence with 95-99% identity thereto.

11. The method of claim 10, wherein the humanized anti-CD19 binding domain is a scFv that comprises a light chain variable region attached to a heavy chain variable via a linker, wherein the linker comprises the sequence of SEQ ID NO: 53.

12. The method of claim 1, wherein the transmembrane domain comprises the amino acid sequence of SEQ ID NO: 15, or a sequence with 95-99% identity thereto.

13. The method of claim 12, wherein the anti-CD19 binding domain is connected to the transmembrane domain by a hinge region, wherein the hinge region comprises the amino acid sequence of SEQ ID NO:14, or SEQ ID NO:45.

14. The method of claim 1, wherein the intracellular signaling domain further comprises a costimulatory domain that comprises the amino acid sequence of SEQ ID NO: 16, or SEQ ID NO:51.

15. The method of claim 1, wherein the intracellular signaling domain comprises the amino acid sequence of SEQ ID NO: 16, the amino acid sequence of SEQ ID NO:17, or both.

16. The method of claim 1, wherein CAR polypeptide comprises an amino acid sequence of SEQ ID NO:58, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, or SEQ ID NO:42.

17. The method of claim 1, further comprising administration of an agent which inhibits an immune inhibitory molecule chosen from: PD1, PD-L1, CTLA4, TIM3, CEACAM, LAG3, VISTA, BTLA, TIGIT, LAIR1, CD160, or 2B4.

18. The method of claim 1, wherein the leukemia or lymphoma is chosen from mantle cell lymphoma (MCL), chronic lymphocytic leukemia (CLL), acute lymphoid leukemia (ALL), diffuse large B cell lymphoma (DLBCL), small lymphocytic leukemia (SLL), acute myelogenous leukemia (AML), or multiple myeloma (MM).

19. The method of claim 1, further comprising administration of a cytokine chosen from IL-7, IL-15, or IL-21.

20. The method of claim 1 wherein remission of the hematological cancer is prolonged or relapse of the hematological cancer is delayed.

21. The method of claim 1, wherein the CAR19-expressing cell population is administered in combination a second kinase inhibitor, wherein the second kinase inhibitor is other than ibrutinib, when the mammal is, or is identified as being, a non-responder or relapser to ibrutinib, wherein second kinase inhibitor is chosen from one or more of GDC-0834, RN-486, CGI-560, CGI-1764, HM-71224, CC-292, ONO-4059, CNX-774, or LFM-A13, or a combination thereof.

22. The method of claim 1, wherein the mammal is, or is identified as being, a partial responder to ibrutinib, and the mammal is administered the CAR19-expressing cell population, alone or in combination with ibrutinib, during the period of partial response.

23. The method of claim 1, wherein ibrutinib is formulated for administration for 1, 2, 3, 4, 5, 6, 7, 8, 9, 10, 11, 12 or more cycles, wherein cycle length is 21 or 28 days.

24. The method of claim 1, which comprises performing a lymphocyte infusion with the CAR19-expressing cell population.

25. The method of claim 1, wherein the mammal has undergone lymphodepletion, wherein the lymphodepletion comprises administration of one or more of melphalan, cytoxan, cyclophosphamide, and fludarabine.

26. The method of claim 1, wherein the intracellular signaling domain comprises the amino acid sequence of SEQ ID NO:16, the amino acid sequence of SEQ ID NO:43, or both.

27. The method of claim 1, wherein the intracellular signaling domain comprises the amino acid sequence of SEQ ID NO: 51, the amino acid sequence of SEQ ID NO:17, or both.

28. The method of claim 1, wherein the intracellular signaling domain comprises the amino acid sequence of SEQ ID NO:51, the amino acid sequence of SEQ ID NO:43, or both.

29. The method of claim 1, wherein the leukemia or lymphoma is a relapsed or refractory leukemia or lymphoma.

30. The method of claim 1, wherein the leukemia or lymphoma is MCL.

31. The method of claim 1, wherein the leukemia or lymphoma is CLL.

32. The method of claim 1, wherein the CAR19-expressing cell population is administered to the mammal at least 1, at least 2, at least 3, at least 4, or at least 6 months after administration of ibrutinib was begun.

33. The method of claim 1, wherein the mammal experiences a reduction in PD1-expressing T cells after administration of ibrutinib.

34. The method of claim 1, wherein the anti-CD19 binding domain comprises a heavy chain variable domain and a light chain variable domain.

35. The method of claim 1, wherein the anti-CD19 binding domain comprises a sequence of SEQ ID NO: 2, or a sequence with 95-99% identity thereof.

36. The method of claim 1, wherein the mammal is a human.

37. A method of treating a human subject having a leukemia or lymphoma associated with expression of CD19, comprising: administering to the subject an effective amount of a population of immune effector cells, wherein the immune effector cells comprise autologous T cells, that express a CAR polypeptide that binds CD19 (a CAR19-expressing cell population), in combination with ibrutinib, wherein the CAR polypeptide comprises:
   (i) an extracellular anti-CD19 binding domain that comprises a HC CDR1 of SEQ ID NO: 19, a HC CDR2 of any of SEQ ID NOS: 20-23, a HC CDR3 of SEQ ID NO: 24, a LC CDR1 of SEQ ID NO: 25, a LC CDR2 of SEQ ID NO: 26, and a LC CDR3 of SEQ ID NO: 27,
   (ii) an intracellular signaling domain capable of stimulating the autologous T cell comprising the CAR polypeptide, wherein the intracellular signalling domain comprises a primary signalling domain which comprises a CD3zeta domain amino acid sequence of SEQ ID NO: 17 or SEQ ID NO: 43, and
   (iii) a transmembrane domain disposed between the anti-CD19 binding domain and the intracellular signalling domain, wherein the transmembrane domain comprises the amino acid sequence of SEQ ID NO: 15.

38. The method of claim 37, wherein the CAR polypeptide comprises the amino acid sequence of SEQ ID NO: 58.

39. The method of claim 37, wherein the CAR polypeptide comprises the amino acid sequence of SEQ ID NO: 32.

40. The method of claim 37, wherein the leukemia or lymphoma is selected from BALL, acute lymphoid leukemia (ALL), acute myelogenous leukemia (AML), multiple myeloma (MM), diffuse large B cell lymphoma (DLBCL), and mantle cell lymphoma (MCL).

41. The method of claim 37, wherein the leukemia or lymphoma is selected from CLL or SLL.

42. The method of claim 37, wherein the intracellular signaling domain further comprises a costimulatory domain comprising an intracellular signaling domain of a protein selected from the group consisting of OX40, CD27, CD28, ICOS, and 4-1BB.

43. The method of claim 42, wherein the costimulatory domain comprises the amino acid sequence of SEQ ID NO: 16, or the amino acid sequence of SEQ ID NO: 51.

44. A method of treating a human subject having CLL or SLL, comprising: administering to the subject an effective amount of a population of immune effector cells, wherein the immune effector cells comprise autologous T cells, that express a CAR polypeptide that binds CD19 (a CAR19-expressing cell population), in combination with ibrutinib, wherein the CAR polypeptide comprises:
  (i) an extracellular anti-CD19 binding domain that comprises a HC CDR1 of SEQ ID NO: 19, a HC CDR2 of any of SEQ ID NOS: 20-23, a HC CDR3 of SEQ ID NO: 24, a LC CDR1 of SEQ ID NO: 25, a LC CDR2 of SEQ ID NO: 26, and a LC CDR3 of SEQ ID NO: 27,
  (ii) an intracellular signaling domain comprising the amino acid sequence of SEQ ID NO: 17 or SEQ ID NO: 43, and SEQ ID NO: 16 or SEQ ID NO: 51; and
  (iii) a transmembrane domain comprising the amino acid sequence of SEQ ID NO: 15.

45. A method of treating a human subject having CLL or SLL, comprising: administering to the subject an effective amount of a population of immune effector cells, wherein the immune effector cells comprise autologous T cells, that express a CAR polypeptide that binds CD19 (a CAR19-expressing cell population), in combination with ibrutinib, wherein the CAR polypeptide comprises the amino acid sequence of SEQ ID NO:58, thereby treating the human subject.

* * * * *